US007070790B1

(12) United States Patent
Bukh et al.

(10) Patent No.: US 7,070,790 B1
(45) Date of Patent: Jul. 4, 2006

(54) NUCLEOTIDE AND DEDUCED AMINO ACID SEQUENCES OF THE ENVELOPE 1 AND CORE GENES OF ISOLATES OF HEPATITIS C VIRUS AND THE USE OF REAGENTS DERIVED FROM THESE SEQUENCES IN DIAGNOSTIC METHODS AND VACCINES

(75) Inventors: Jens Bukh, Bethesda, MD (US); Roger H. Miller, Rockville, MD (US); Robert H. Purcell, Boyds, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/084,691

(22) Filed: May 26, 1998

Related U.S. Application Data

(60) Division of application No. 08/290,665, filed on Aug. 15, 1994, now Pat. No. 5,882,852, which is a continuation-in-part of application No. 08/086,428, filed on Jun. 29, 1993, now Pat. No. 5,514,539.

(51) Int. Cl.
*A61K 39/29* (2006.01)
*C12Q 1/04* (2006.01)
*C07K 4/02* (2006.01)
*C07K 14/08* (2006.01)
*G01N 33/53* (2006.01)

(52) U.S. Cl. .............................. 424/228.1; 424/184.1; 424/186.1; 424/189.1; 424/204.1; 435/4; 435/5; 435/7.1; 530/300; 530/350

(58) Field of Classification Search ................... 435/5, 435/6, 7.1, 7.9, 7.91, 7.92, 7.93, 7.94, 7.95, 435/69.1, 69.3, 320.1; 530/300, 350, 387.1, 530/388.3, 389.1, 391.1, 391.3, 403, 389.4; 424/184.1, 185.1, 186.1, 189.1, 204.1, 228.1, 424/225.1; 514/2; 536/23.1, 23.7, 23.72
See application file for complete search history.

(56) References Cited

U.S. PATENT DOCUMENTS 4,870,026 A * 9/1989 Wands et al. .................. 435/5

(Continued)

FOREIGN PATENT DOCUMENTS

EP 489968 A1 * 6/1992

(Continued)

OTHER PUBLICATIONS

Definition "vaccine", The On-line Medical Dictionary, http://cancerweb.ncl.ac.uk/omd/.*

(Continued)

*Primary Examiner*—James C. Housel
*Assistant Examiner*—Zachariah Lucas
(74) *Attorney, Agent, or Firm*—Knobbe, Martens, Olson & Bear, LLP

(57) ABSTRACT

The nucleotide and deduced amino acid sequences of cDNAs encoding the envelope 1 genes and core genes of isolates of hepatitis C virus (HCV) are disclosed. The invention relates to the oligonucleotides, peptides and recombinant envelope 1 and core proteins derived from these sequences and their use in diagnostic methods and vaccines.

23 Claims, 135 Drawing Sheets

U.S. PATENT DOCUMENTS

| | | | |
|---|---|---|---|
| 5,298,410 A | * | 3/1994 | Phillips et al. .............. 435/188 |
| 5,350,671 A | | 9/1994 | Houghton et al. |
| 5,372,928 A | | 12/1994 | Miyamura et al. |
| 5,427,909 A | | 6/1995 | Okamoto et al. |
| 5,436,126 A | * | 7/1995 | Wang ............................ 435/5 |
| 5,645,983 A | * | 7/1997 | Liao et al. ..................... 435/5 |
| 5,856,437 A | * | 1/1999 | Miyamura et al. .......... 530/350 |
| 6,054,264 A | * | 4/2000 | Chien et al. ................... 435/5 |

FOREIGN PATENT DOCUMENTS

| | | |
|---|---|---|
| EP | 0 586 065 | 3/1994 |
| GB | 2 212 511 B | 1/1992 |
| JP | 05 068562 A | 3/1993 |
| WO | WO 92 19743 | 11/1992 |
| WO | WO 92 21759 | 12/1992 |
| WO | WO 94 01778 | 1/1994 |
| WO | WO 94 25601 | 11/1994 |
| WO | WO 94 27153 | 11/1994 |
| WO | WO 95 01442 | 1/1995 |
| WO | WO 95/12677 * | 5/1995 |

OTHER PUBLICATIONS

Definition "vaccine", Stedman's On-line Medical Dictionary, 27th Edition, http://www.stedmans.com.*
Ferroni et al., Journal of Clinical Microbiology, vol. 31 No. 6, pp. 1586-1591 (Jun. 1993).*
Shirai et al., Journal of Birology, vol. 68 No. 5, pp. 3334-3342 (May 1994).*
Isaguliants et al., Vaccine, vol. 22, pp. 1656-1665 (2004).*
Zein et al., Microbes and Infection, vol. 4, pp. 1237-1246 (2002).*
Koff, Raymond, International Journal for Parasitology, vol. 33, pp. 517-533 (2003).*
Seo-Hee Cho et al.: "Genomic typing of hepatitis C viruses from Korean patients: implications of genome variation in the E2/NS1 region." Biochemical and Biophysical Research Communications, vol. 196, No. 2, Oct. 29, 1993, pp. 780-788.
H.M. Müller et al.: "Genetic variability of German hepatitis C virus isolates" Journal of Medical Virology, vol. 40, 1993, pp. 291-306.
J.H. Han et al.: "Characterization of the terminal regions of hepititis C viral RNA: Identification of conserved sequences in the 5 -untranslated region and poly{A} tails at the 3' end." Proc. Natl. Acad. Sci. USA, vol. 88, No. 5, Mar. 1, 1991, pp. 1711-1715.
H. Okamoto et al.: "Characterization of the genomic sequences of type V {or 3a} hepatitis C virus isolates and PCR primers for specific detection" Journal of General Virology, vol. 74, 1993, pp. 2385-2390.
A. Machida et al.: "Two distinct subtypes of Hepatitis C virus defined by antibodies directed to the putative core protein." Hepatology, vol. 16, No. 4, Oct. 1992, pp. 886-891.
Simmonds P. et al., "Identification of genotypes of hepatitis C virus by sequence comparisons in the core, E1 and NS-5 regions," Journal of General Virology, 5:1053-1061 (1994).
Kao, J.H. et al., "Detection of divergent hepatitis C virus envelope sequences," Journal of Biomedical Science, 3:158-162 (1994).
Roggendorf, M. et al., "Variability of the envelope regions of HCV in European isolates and its significance as a diagnostic tool," Archives of Virology Supplementum, 7:27-39 (1993).
Li, Ji-Su et al., "Identification of the third major genotype of hepatitis C virus in France", Biochem. Biophys. Res. Commun., 1474-81 (1994).
Choo, O.L. et al. (1989) Science, 244:359-362.
Weiner, A. J. et al. (1990) Lancet, 335:1-3.
Kuo, G. et al. (1992) Science, 244:362-364.
Okamoto, H. et al. (1992) J. Gen. Virol, 73:673-679.
Bukh, J. et al. (1992) Proc. Natl. Acad. Sci. U.S.A., 89:187-191.
Bukh, J. et al. (1992) Proc. Natl. Acad. Sci. U.S.A., 89:4942-4946.
Cha, T. et al. (1992) Proc. Natl. Acad. Sci. U.S.A., 89:7144-148.
Chan S-W. et al. (1992) J. Gen. Virol., 73:1131-1141.
Lee, C-H. et al. (1992) J. Clin. Microbio, 30:1602-1604.
Choo, et al. (1991) Proc. Natl. Acad. Sci. U.S.A., 88:2451-2455.
Okamoto, et al. (1992) Virology, 188:331-341.
Inchauspe, et al. (1991) Proc. Natl. Acad. Sci. USA, 88:10292-10296.
Takamizawa, A. et al. (1991) J. Virol., 65:1105-1113.
Kato, N. et al. (1990) Proc. Natl. Acad. Sci. U.S.A., 87:9524-9528.
Okamoto, H. et al. (1992) Virology, 190:894-899.
Ogata, N. et al. (1991) Proc. Natl. Acad. Sci. U.S.A., 88:3392-3396.
Mori, S. et al. (1992) Biochem. Biophys. Res. Comm., 183:334-342.
Weiner, A.J. et al. (1991) Virology, 180:842-848.
Hijikata, M. et al. (1991) Biochem. Biophys. Res. Comm., 175:220-228.
Okamoto, H. et al. (1990) Japan. J. Exp. Med., 60:167-177.
Takeuchi, K. et al. (1990) J. Gen. Virol., 71:3027-3033.
Chen P. J. et al. (1992) Virology, 188:102-113.
Liu, K. et al. (1992) Gene, 114:245-250.
Tanaka, T. et al. (1992) Virus Research, 23:39-53.
Abe, K. et al. (1992) J. Gen. Virol., 73, 2725-2729.
Honda, M. et al. (1993) Arch. Virol., 128, 163-169.
Stuyver, L. et al. (1993) Biochem, Biophys. Res. Comm., 192:635-641.
Okamoto, H. et al. (1994) J. Gen. Virol., 75:629-635.
Bukh, J. et al. (1993) PNAS, 90:8234-8238.
Li, J., et al. (1991) Gene, 105:167-172.
Houghton, M. (1991) Hepatology, 14:381-388.
Machida, A. et al. (1992) Hepatology, 16:886-891.
Okamoto, H. et al. (1993) J. Gen. Virol., 74:2385-2390.
Simmonds, P., et al. (1993) J. Gen. Virol., 74:661-668.
Stuyver, L. et al. (1993) J. Gen. Virol., 74:1093-1102.
Widell, A. et al. (1994) J. Med. Virol., 44:272-279.
Qu D. et al. (1994) J. Gen. Virol., 75:1063-1070.
Simmonds, P. et al. (1994) J. Gen. Virol., 75:1053-1061.
Tokita, H., et al. (1994) J. Gen. Virol., 75:931-936.
Stuyver, L., et al. (1994) PNAS, 91:10134-10138.
Vlazow, S., et al. (1994) J. Virol. Meth., 48:81-92.
Simmonds, P., et al. (1993) J. Clin. Microbiol., 31:1493-1503.
Hayashi, N., et al. (1993) J. Hepatol., 17 (suppl 3) S94-S107.
Wang, Y., et al. (1993) J. Med. Viro., 40:254-260.
Tanaka, T., et al. (1994) Hepatology, 19:1347-1353.
Sakamoto, M., et al. (1994) J. Gen. Virol., 75:1761-1768.

* cited by examiner

FIGURE 1A-1

| SEQ ID NO: | Isolate | |
|---|---|---|
| 5 | S14 | 1 TACCAAGTGCGCAACTCCACGGGGCTTTACCATGTtACCAATGATTGCCCTAACTCGAGTA |
| 1 | DK7 | 1 TACCAAGTGCGCAACTCCACGGGGCTTTACCATGTCACCAATGATTGCCCTAACTCGAGTA |
| 8 | US11 | 1 TACCAAGTAcGCAACTCCACGGGGCTTTACCATGTCACCAATGATTGCCCTAACTCGAGTA |
| 4 | DR4 | 1 CACCAAGTGCGCAACTCTACAGGGCTTTACCATGTCACCAATGATTGCCCTAATTCGAGTA |
| 3 | DR1 | 1 CACCAAGTGCGCAACTCTACAGGGCTTTACCATGTCACCAATGATTGCCCTAATTCGAGTA |
| 2 | DK9 | 1 CACCAAGTACGCAACTCCTCGGGCCTCTACCATGTCACCAATGATTGCCCTAACTCGAGTA |
| 6 | S18 | 1 TACCAAGTACGCAACTCCaCGGGGCCTTTACCATGTCACCAATGACTGCCCTAACTCGAGcA |
| 7 | SW1 | 1 TACCAAGTACGCAACTCCtCGGGCCTTTACCATGTCACCAATGAtTGCCCTAACTCGAGtA |
| 1-8 | consensus | tACCAAGT-CGCAACTCcaCgGGgCTTtACCATGTCACCATGATTGCCCTAAcTCGAGtA |

| SEQ ID NO: | Isolate | |
|---|---|---|
| 5 | S14 | 62 TtGTGTACGAGaCaGCtGATGCtATCCtAcACAcGcTtCCGGGaTGTGTCCCCTtGCgTTCGtGA |
| 1 | DK7 | 62 TcGTGTACGAGaGAGCGGCCGATGCCGATCCTGCACACTCCGCACGTGTCCCTTGCGTTCGCGA |
| 8 | US11 | 62 TTGTGTACGAGAGCGGCCGATGCCGATCCTGCACACTCCGGACGTGTGTCCTTGCGTTCGCGA |
| 4 | DR4 | 62 TTGTGTACGAGAGCGGCCGATGCCGATCCTGCACACCTGCACACGCCGGGTGTGTCCCTTGCGTTCGCGA |
| 3 | DR1 | 62 TTGTGTACGAGAGCGGCCGATGCCGATCCTGCACACCTGCACGCGCCGGGTGTGTCCCTTGCGTTCGCGA |
| 2 | DK9 | 62 TTGTGTACGAGAGCGGCCGATGCCGATCCTGCAtTCTCCaGGGTGTGTCCCTTGCGTTCGCGA |
| 6 | S18 | 62 TTGTGTACGAGACGGCCGATaCCATCCTACACACTCTCCgGGGTGTGTCCCTTGCGTTCGCGA |
| 7 | SW1 | 62 TTGTGTACGAGACGGCCGATgCCATtCTACACTCTCCAGGGGTGTGTCCCTTGCGTTCGCGA |
| 1-8 | consensus | TtGTGTACGAGgCgGCcGATgCcATcCTgCAc-CtCCgGGgTGTGTCCCTTGCGTTCGCGA |

FIGURE 1A-2

| SEQ ID NO: | Isolate | | |
|---|---|---|---|
| 5 | S14 | 123 | GGGTAACAcCTCGAGGTGTTGGGTGGCGATGACCCCCACGGTGGCCACCAGGGACGGCAAA |
| 1 | DK7 | 123 | GGGTAACGCtTCGAGGTGTTGGGTGGCGATGACCCCCACGGTGGCCACCAGGGAtGGCAAA |
| 8 | US11 | 123 | GGGTAACGCttCGAGGTGTTGGGTGGCGATGACCCCCACGGTGGCCACCAGGGACGGCAAA |
| 4 | DR4 | 123 | GGGTAACAcCCTCGAGGTGTGGGTGGCGGTGACCCCCACGGTGCCACCAGGACGGCAAA |
| 3 | DR1 | 123 | GGGTAACGCCTCGAGGTGTGGGTGGCGGTGACCCCCACGGTGCCACCAGGACGGCAAA |
| 2 | DK9 | 123 | GGGTAACGCCTCGAaATGTTGGGTGGCGGTGCCCCCACGGTGCCACCAGGACGGCAAg |
| 6 | S18 | 123 | GGGTAACGCCTCGAcATGTTGGGTGcCGGTGGCCCGGTGCCCCACAGTtGCCACCAGGACGGCAAA |
| 7 | SW1 | 23 | GGaTggCGCccGAagTGTTGGGTGgCGGTGgCGGTGACCCCACAGTcGCCACTaGGGACGGCAAA |
| 1-8 | consensus | | GGgTaaCgcctCGAggTGTtGGGTGgCGgTgaCCCCcACGgTgGCCACcAGGGAcGGCAAa |

| SEQ ID NO: | Isolate | | |
|---|---|---|---|
| 5 | S14 | 184 | CTCCCCgCAacCGaCGGCAGCTtCGACGTtACATCGATCTGCTtGTCGGGAGcGCCACCCTCTGTT |
| 1 | DK7 | 184 | CTCCCCACAgCGACGGCAGCTTCGACGTCACATCGATCTGCTcGTCGGGAGtGCCACCCTCTGTT |
| 8 | US11 | 184 | CTCCCCACAACGCAacTTCGACGCAGCTTCGACGTCACATCGATCTGCTCGTCGGGAGCGCCACCCTCTGTT |
| 4 | DR4 | 184 | CTCCCCACAACGCAGCAGCTTCGACGTcCGACGTCACATCGACCTGCTGCTTGTCGGGAGCGCCACCCTCTGCT |
| 3 | DR1 | 184 | CTCCCCACAACGCAGCAGCTTCGACGTCACATCGATCTGCTGCTTGTCGGGAGCGCCACCCTCTGCT |
| 2 | DK9 | 184 | CTCCCCCACAACGCAGCAGCTTCGACGTCACATCGACGTCACATCGACCTGCTGCTTGTCGGGAGCGCCACCCTCTGCT |
| 6 | S18 | 184 | CTCCCCCGCAACGCAGCAGCTTCGACGTCACATCGATCTGCTGCTTGTCGGGAGCGCCACCCTCTGCT |
| 7 | SW1 | 184 | CTCCCtGCAACGCAGCAGCTTCGACGTCACATCGATCTGCTTGTtGGGAGCGCCACCCTCTGCT |
| 1-8 | consensus | | CTCCCC--CAaCGCAgCTtCGACGTCACATCGAtCTGCTtGTcGGgAGcGCCACCCTCTGcT |

FIGURE 1A-3

| SEQ ID NO: | Isolate | | |
|---|---|---|---|
| 5 | S14 | 245 | CGGCCCTCTACGTGGGGACtGTGTGCGGGTCTGTCTTCTTGTCGGTCAGCTGTTACCTT |
| 1 | DK7 | 245 | CGGCCCTCTACGTGGGGACCTGTGCGGGTCTGTCTTCTTGTCGGTCAACTGTTACCTT |
| 8 | S11 | 245 | CGGCCCTCTACGTGTGCGGGGACCTGTGCGGGTCTGTCTTTCTTGTCGGTCAACTGTTACCTT |
| 4 | DR4 | 245 | CGGCCCTCTACGTGGGGACtTGTGCGGGTCTGTCTTCCTTGTCGGTCAACTGTCACCTT |
| 3 | DR1 | 245 | CGGCCCCTCTACGTGGGGGACCTGTGCGGGTCTGTCTTCCTTGTCGGTCAACTGTCACCTT |
| 2 | DK9 | 245 | CGGCCCCTCTACGTGGGGGACCTGTGCGGGTCTGTCTTCCTTGTCGGCCAACTGTCACCTT |
| 6 | S18 | 245 | CGGCCCTCTATGTGGGGGACCTGTGCGGGTCTGTTCTTGTCAGCCAGCTGTCACtaT |
| 7 | SW1 | 245 | CGGCCCTCTAcGTGGGGGACtTGTGCGGGTCTGTCCTTCTcGTCAGtCAacTGTTCACgtT |
| 1-8 | consensus | | CGGCCCTCTAcGTGGGGGAC-TGTGCGGGTCTGTCTTcCTtGTcGgtCAacTGTcACctT |

| SEQ ID NO: | Isolate | | |
|---|---|---|---|
| 5 | S14 | 306 | CTCTCCCAGGCGCCtCTGGACGCGACGCAAGaCTGCAATTGTTCTATCTATCCGGCCATATA |
| 1 | DK7 | 306 | CTCTCCCAGaGCGCACTGGACGACGACGCAAGGCAAGCAAGCAATTGTTCTATCTATCCGGCCATATA |
| 8 | S11 | 306 | CTCTCCCAGaCGCCACTGGACGACGCAgGGCTGCAATTGTTCTATCTATCCGGCCATATA |
| 4 | DR4 | 306 | CTCTCCCAGGCCaCCACTGGACAACGCAAGACTGCAATTGTTCCATCTATCCGGCCATATA |
| 3 | DR1 | 306 | CTCTCCCAGGCGCCACTGGACAACGCAAGACTGCAATTGTTCTATCTATCCGGCCATATA |
| 2 | DK9 | 306 | tTCTCCCAGGCGCCACTGGACAACGCAAGACTGCAATTGTTCTATCTATCCGGCCATATA |
| 6 | S18 | 306 | CTCCCCCAGaCGCCACTGGACAACGCAAGACTGCAACTGTTCTATCTACCCGGCCATATt |
| 7 | SW1 | 306 | CTCCCCCAGGCGCCACTGGACAACGCAAGACTGCAACTGTTCTATCTACCCGGCCATATA |
| 1-8 | consensus | | cTcTcCCAGgCgCCaCTGGaCaACGCAagaCTGcAAtTGTTcTAtCTAtCCcGGCCAtATa |

| SEQ ID NO: | Isolate | | |
|---|---|---|---|
| 5 | S14 | 489 | AGTCCTaGCGGGCATAGCGTATTTcTCCATGGTGGGaAACTGGGCGAAGGTCCTaGTGGTG |
| 1 | DK7 | 489 | AGTCCTgGCGGGCATAGCGTATTTtTCCATGGTGGGAACTGGGCGAAGGTCCTGGTAGTG |
| 8 | S11 | 489 | AGTCCTAGCGGGCATAGCGTATTTCTCCATGGTGGGAACTGGGCGAAGGTCCTGGTAGTG |
| 4 | DR4 | 489 | AGTCCTAGCGGGCATAGCGTATTTCTCCATGGTGGGAACTGGGCGAAGGTCCTGGTAGTG |
| 3 | DR1 | 489 | AGTCCTAGCGGGCATAGCGTATTTCTCCATGGTGGGAACTGGGCGAAGGTCGTGGTAGTG |
| 2 | DK9 | 489 | AGTCCTAGCGGGCATAGCGTATTTCTCCATGGTGGGAACTGGGCGAAGGTCGTGGTgGTa |
| 6 | S18 | 489 | AGTCCTAGCGGGCATAGCGTATTTCTCCATGGGGGGAACTGGGCGAAGGTCCTGcTAGTG |
| 7 | SW1 | 489 | AGTCCTAGCGGGCATAGCGTATTTCTCCATGGcGGGGAACTGGGCGAAGGTCCTGaTAGTG |
| 1-8 | consensus | | AGTCCTaGCGGGCATAGCGTATTTCTCCATGgtGGGgAACTGGGCGAAGGTCCTggTaGTg |

| SEQ ID NO: | Isolate | | |
|---|---|---|---|
| 5 | S14 | 550 | CTGCTGCTATTcGCCGGCGTtGACGCG |
| 1 | DK7 | 550 | CTGCTGCTATTTGCCGGCGTCGACGCG |
| 8 | US11 | 550 | CTGCTGCTATTTGCCGGCGTCGACGCG |
| 4 | DR4 | 550 | CTGTTGCTGTTTGCCGGCGTTGATGCG |
| 3 | DR1 | 550 | CTGTTGCTGTTTGCCGGCGTTGATGCG |
| 2 | DK9 | 550 | CTGTTGCTGTTTaCCGGCGTCGATGCG |
| 6 | S18 | 550 | CTGTTGCTGTTTgCCGGCGTCGATGCG |
| 7 | SW1 | 550 | CTGTTGCTGTTTtCCGGCGTCGATGCG |
| 1-8 | consensus | | CTGtTGCTgTTTgCCGGCGTcGAtGCG |

FIGURE 1B-1

| SEQ ID NO: | Isolate | Sequence |
|---|---|---|
| 11 | DK1 | TATGAAGTGCGCAACGTGTCCGGGgTGTACCAcGTCACaAaCGACTGCTCCAACTCAAGCA |
| 24 | T10 | TATGAAGTGCGCAACGTGTCCGGGaTGTACCAtGTCACgAACGACTGCTCCAACTCAAGCA |
| 10 | D3 | TATGAAGTGCGCAACGTGTCCGGGGTGTACCAGTCACAatGACTGTTCCAACTCGAGCA |
| 9 | D1 | TATGAAGTGCGCAACGTGTCCGGGGTGTACCATGTCACAaGTCACGAACGACTGTTCCAACTCGAGCA |
| 14 | HK5 | TATGAAGTGCGCAACGTGTCCGGGTATACCATGTCACGAACGACTGCTCCAACTtAAGCA |
| 15 | HK8 | TATGAAGTGCGCAACGTGTCCGGGATATACCATGTCACGAACGACTGCTCCAACTCAAGCA |
| 12 | HK3 | TATGAAGTGCGCAACGTGTCCGGGATATACCATGTCACGAACGACTGCTCCAACTCAAGCg |
| 23 | T3 | TACGAAGTGCGCAACGTGTCCGGGGTGTACtATGTCACGAACGACTGTTCCAACTCAAGCA |
| 22 | SW2 | TATGAAGTGCGCAACGTGTCCGGGGTGTAtCATGTCACGAACGACTGTTCCAACTCAAGCA |
| 17 | IND8 | TATGAGgTGCGCAACGTGTCCGGGGTGTACCATGTCACGAACGACTGCTCCAACTCAAGTA |
| 16 | IND5 | TATGAAGTGCGCAACGTGTCCGGGGTGTACCATGTCACAaGAACGACTGCTCCAACTCAAGTA |
| 21 | SA10 | TATGAAGTGCGCAACGTGTCCGGGaTGTACCATGTCACGAACGACTGCTCCAACTCAAGCA |
| 20 | S45 | TATGAAGTGCGCAACGTGTCCGGGgcGTACCATGTCACGAACGACTGCTCCAACTCAAGCA |
| 25 | US6 | TATGAAGTGCGCAACGTGTCCGGGATGTACCATGTCACGAACGACTGCTCCAACTCAAGCA |
| 13 | HK4 | cATGAAGTGCaCAACGTaTCCGGGATcTACCATGTCACGAACGACTGCTCCAACTCAAGTA |
| 18 | P10 | TATGAAGTGCGCAACGTgTCCGGGTGTACCATGTCACGAACGACTGCTCCAACTCAAGTA |
| 19 | S9 | TATGAAGTGCGCAACGTaTCCGGGGCGTACCATGTCACGAACGACTGCTCCAACTCAAGTA |
| 9-25 | consensus | tAtGAaGTGCgCAACGTgTCCGGGgtgTAccATGTCACgAAcGACTGcTCCAACTcaAGca |

FIGURE 1B-2

| SEQ ID NO: | Isolate | | |
|---|---|---|---|
| 11 | DK1 | 62 | TcGTGTaTGAGGCAGtGGACgTGATCATgCAtACCCCaGGGTGCGTGCCCTGCGTTCGGGA |
| 24 | T10 | 62 | TtGTGTtTGAGGCAGCGGACtTGATCATGCACACCCCCGGGTGCGTGCCCTGCGTTCGGGA |
| 10 | D3 | 62 | TcGTGTATGAGACAGCGGACATGATCATGCACACCCCCGGGTGCGTGCCCTGCGTTCGGGA |
| 9 | D1 | 62 | TtGTGTATGAGACAGCGGACATGATCATGCACACCCCCGGGTGCGTGCCCTGCGTTCGGGA |
| 14 | HK5 | 62 | TCGTGTAcGAGACAaCGGACATGATCATGCACACCCCCTGGGTGCGTGCCCTGCGTTCGGGA |
| 15 | HK8 | 62 | TCGTGTATGAaACAGCGGACATGATtATGCATACCCCTGGATGCaTGCCCTGCGTTCGGGA |
| 12 | HK3 | 62 | TCGTGTATGAGACAGCaGACATGATCATGCATACCCCTGGATGCGTGCCCTGCGTaCGGGA |
| 23 | T3 | 62 | TtGTGTATGAGACAGCGGACATGATCATGCACACCCCTGGGTGCGTGCCCTGCGTTCGGGA |
| 22 | SW2 | 62 | TtGTGTATGAGACAGCGGACATGATCATGCACACCCCCGGGTGCGTGCCCTGCGTTCGGGA |
| 17 | IND8 | 62 | TTGTGTATGAGGCAGCGGACATGATCATGCACACCCCCGGGTGCGTGCCCTGCGTTCGGGA |
| 16 | IND5 | 62 | TTGTGTATGAGGCAGCGGACATGATCATGCACACtCCCGGGTGCGTGCCCTGCGTTCGGGA |
| 21 | SA10 | 62 | TTGTGTATGAGGCAGCGGACATGATCATGCACACCCCCGGGTGCGTGCCCTGCGTTCGGGA |
| 20 | S45 | 62 | TTGTGTATGAGGCAGtGGACgTGATCcTGCACACCCCCtGGGTGCGTGCCCTGCGTTCGGGA |
| 25 | US6 | 62 | TTGTGTATGAGGCAGCGGACATGATCATGCACACCCCACTCCCGGGTGCGTGCCCTGtGTTCGGGA |
| 13 | HK4 | 62 | TTGTGTATGAGGCAGCGGACATGATCATgCAtACCCCCGGGTGCGTGCCCTGCGTcCGGGA |
| 18 | P10 | 62 | TTGTGTATGAGGCAGCGGACATGAtAaTGCAcACCCCCGGGTGCGTGCCCTGtGTTCGGGA |
| 19 | S9 | 62 | TTGTGTAcGAGGCAGCGGACgTGATcATGCAtACCCCCGGGTGtGTaCCCTGCGTTCaGGA |
| 9-25 | consensus | | TtGTGTatGAggCAgcgGACAtGATcaTGCAcACCCCgGGgTGcgTgCCCTGcgTtCgGGA |

FIGURE 1B-3

| SEQ ID NO: | Isolate | | |
|---|---|---|---|
| 11 | DK1 | 123 | GaacCAACcaCTCCcGtTGCTGGGTAGcGCTCACcCCCACGCTCGCGGCCAGGAACgCCAGC |
| 24 | T10 | 123 | GGgCAACTCCTCCCGCTGCTGGGTAGcGCTCACTCCCACGCTCGCGGCCAGGAACACCAGC |
| 10 | D3 | 123 | GGACAACTCCTCTCGCTGCTGGGTAGcGCTCACCCCCACGCTCGCGGCTAGGAATAGCAGC |
| 9 | D1 | 123 | GGACAACTCCTCCGCTGCTGGGTAGCGCTCACCCCCACGCTCGCGGCTAGGAATAGCAGC |
| 14 | HK5 | 123 | GGACAACTCCTCCCGCTGCTGGGTAGCGCTCgCCCCCACGCTCGCGGCTAGGAATGGCAaC |
| 15 | HK8 | 123 | aACAACTCCTCCCGTTGtGGGTAGCGCTCgCCCCCACGCTCGCGGCCAGGAACGCCAGC |
| 12 | HK3 | 123 | GAACAACTCCTCCCGTTGcTGGGTgGCGCTCACTCCCACGCTCGCGGCTAGGAtGTCAGC |
| 23 | T3 | 123 | GAACAACTCCTCCCGCTGtTGGGTAGcGCTCACTCCCACGCTCGCGGCCAGGAACGTCAGC |
| 22 | SW2 | 123 | GAgCAAtTCCTCCCGCTGCTGGGTAGcGCTtACTCCCACGCTCGCGGCCAGGAACGCCAGC |
| 17 | IND8 | 123 | GGcCAACTCCTCCCGCTGCTGGGTAGCGCTCACTCCCACGCTaGCaGCCAGGAACaCCAGC |
| 16 | IND5 | 123 | GGGCAACTtCTCTaGtTGCTGGGTAGCGCTCACTCCACTCTCGCGGCtAGGAACGCCAGC |
| 21 | SA10 | 123 | GGGCAACTCCTCCCGCTGCTGGGTAGcGCTCACTCCCACTCTCGCGGCCAGGAACGCCAGC |
| 20 | S45 | 123 | GAACAACTCCTCCCGCTGCTGGGTAGCGCTCACTCCCACGCTCGCGGCCAGGAACTCCAGC |
| 25 | US6 | 123 | GAACAACTCCTCCGtTGCTGGGTgGCGCTCACTCCCACGCTCGCGGCCAGGAACTCCAGC |
| 13 | HK4 | 123 | GAACAAtTCCTCCCGcTGCTGGGTAGCGCTCACTCCCACGCTCGCGGCCAGGAACGCtAGC |
| 18 | P10 | 123 | GAACAACTCCTCCGCTGCTGGGTAGcGCTCACTCCACaCTCGCGGCtAGGAAttCCAGC |
| 19 | S9 | 123 | GggtAACTCCTCCCaaTGCTGGGTgGCGCTCACcCCCACGcTCGCGGCCAGGAACgCtAcC |
| 9-25 | consensus | | gaacAActcCTCccgcTGcTGGGTaGCGCTcaCtCCCAcGcTcGcGgCCAGGAAcgccAgC |

FIGURE 1B-4

| SEQ ID NO: | Isolate | | |
|---|---|---|---|
| 11 | DK1 | 184 | aTCCCCACTACGACaATACGACGCCATGTCGATTTGCTTCGTTGGGGGGCTGCTTTCTGCT |
| 24 | T10 | 184 | GTCCCCACTACGACgATACGACGCCATGTCGATTTGCTTCGTTGGGGCGGCTGCTTTCTGCT |
| 10 | D3 | 184 | GTCCCCACTACGACaATACGAGGCCACGTCGATTTGCTTCGTTGGGGCGGCTGCTTCTGCT |
| 9 | D1 | 184 | GTCCCCACTACGGCgATACGACCGCCACGTCGATTTGCTTCGTTGGGGCGGCTGCTTCTGCT |
| 14 | HK5 | 184 | GTCCCCACCACCGACGGCAATACGACGCCACGTCGACTTGCTTCGTTGGGGCGGCTGCTTTCTGCT |
| 15 | HK8 | 184 | GTCCCCACTACGACAATACGACGCCACGTCGACTCGATTTGCTTCGTTGGGGCGGCTGCTTTCTGCT |
| 12 | HK3 | 184 | GTCCCCACCACGACGTCACGTCACGTCAGGTCGATTTGCTTCGTTGGGGCGGCTGCTTTCTGCG |
| 23 | T3 | 184 | GTCCCCACTAaGACAATACGACGTCACGTCGATTTGCTTCGTTGGGGCGGCTGCTTTCTGCT |
| 22 | SW2 | 184 | GTCCCCACTACGACAATACGAGCGCCACGTCGACGTCGATTTGCTTCGTTGGGGCGGCTGCTTTCTGCT |
| 17 | IND8 | 184 | GTCCCCACCACGACAATACGACGCCACGTCGATTTGCTTCGTTGGGGCGGCTGCTTTCTGTT |
| 16 | IND5 | 184 | GTCtCCACCACGACGACACCAACGCGCCACGTCGATTTGCTTCGTTGGGGCGGCTGCTTTCTGCT |
| 21 | SA10 | 184 | GTCCCCACTACGACAATACGACGCCACGTCGATTTGCTTCGTTGGGGCGGCTGCTTTCTGCT |
| 20 | S45 | 184 | GTCCCCACTACGACAATACGACGtCACGTCGATTTGCTtCACGTCGATTTGCTTCGTTGGGGCGGCTGCTTTCTGCT |
| 25 | US6 | 184 | GTCCCCACTACGACAATACGACGCCACGTCGATTTGCTCGATTTGCTTCGTTGGGGCGGCTGCTaCTTTCTGCT |
| 13 | HK4 | 184 | aTCCCCACTACGACAATACGACAACGCCATGTCGAcTTGCTCCATGTCGATTTGCTTCGTTGGGGCGGCTGCTTTCTGCT |
| 18 | P10 | 184 | GTCCCaACTACGgCAATACGACGCCATGTCGATTTGCTTCGTTGGGGCGGCTGCTTTCTGCT |
| 19 | S9 | 184 | GTCCCCACCACGaCAATACGACGtCATGTCGATTTGCTCGTTGCTCGTTGGGGCGGCTGtTTGTTTTCTGCT |
| 9-25 | consensus | | gTCcCCACTAcGaCaATACGAcGcCAcGTCGAtTTGCTCGTTGGGGCGGCTGctTTTCTGCT |

FIGURE 1B-5

| SEQ ID NO: | Isolate | | |
|---|---|---|---|
| 11 | DK1 | 245 | CCGCTATGTAcGTGGGgGACCTCTGCGTCCGTTTCCTCCGTCTCTCAGCTGTTCACCTT |
| 24 | T10 | 245 | CCGCTATGTAtGTGGGaGACCTCTGCGTCTCCGTCTCTCAGCTGTTCACCTT |
| 10 | D3 | 245 | CCGCCATGTACGTGGGGGATCTtTGCGGATCTCTGCGTCTCCGTCTCCAGCTGTTCACCTT |
| 9 | D1 | 245 | CCGCCATGTACGTGGGGATCTCTGCGGATCTCTGCGTCTCCATCTCCCAGCTGTTCACCcT |
| 14 | HK5 | 245 | CCGCTATGTACGTGGGGATCTCTGCGGATCTCTGCGTTTCCTCCGTCTCCCAGCTGTTCACCTT |
| 15 | HK8 | 245 | CCGCTATGTACGTGGGGATCTCTGCGGATCTCTGCGTTTTCCTCCGTCTCCCAGCTGTTCACCTT |
| 12 | HK3 | 245 | CCGCTATGTACGTGGGGATCTCTGCGGATCTCTGCGTTTTCCTCGTCTCCCAGCTGTTCACCTT |
| 23 | T3 | 245 | CCGCTATGTACGTGGGGATCTCTGCGGATCTCTGCGTTTCCTCCGTCTCCCAGCTGTTCACTTT |
| 22 | SW2 | 245 | CCGtTATGTACGTGGGGATCTCTGCGGATCTCTGCGTTTCCTCCGTCTCGTCTCCAGCTGTTCACTTT |
| 17 | IND8 | 245 | CCGCTATGTACGTGGGGATCTCTGCGGATCTCTGCGTTTCCTCCGTCTCGTCTCCCAGCTGTTCACCTT |
| 16 | IND5 | 245 | CCGCTATGTACGTGGGGATCTCTGCGGATCTaTGCGTTTCCTCCGTCTCCCAGCTGTTCACCTT |
| 21 | SA10 | 245 | CCGCCATGTACGTGGGGGGAcCTCTGCGGATCTCTGCGTTTCCTCCTTGTCTCCCAGCTGTTCACCTT |
| 20 | S45 | 245 | CCGCTATGTACGTGGGGGATcCTCGCGGATCTCGCGTCCGTTTCCTCCTTGTCTCCCAGCTGTTCACCTT |
| 25 | US6 | 245 | CCGCTATGTACGTGGGGGACcCTCTGCGTCGCGGTCCGTTTCCTCCATCTCCCAGCTGTTCACCTT |
| 13 | HK4 | 245 | CCGCCATGTACGTGGGaGAGATCTCCGCGGATCTCtGCGTCTTCCTCTTCCTCGTCTCCCAGtTGTTCACCTT |
| 18 | P10 | 245 | CCGCTATGTACGTGGGGATCTCTGCGGATCTCTTGCGTGTcTCCTCCTCGTCTCCCAGCTGTTCACCTT |
| 19 | S9 | 245 | CCGCTATGTACGTGGGGGACCTgTGCGGATCTCTGCGGATCTCGTTTCCTCCATCTCCCAGCTGTTCACCaT |
| 9-25 | consensus | | CCGctATGTACgTGGGgGATCTCTGCGgaTCTCTgCGTCTgTttTCCTcgTcTCccAGcTGTTCAccttT |

FIGURE 1B-6

| SEQ ID NO: | Isolate | | |
|---|---|---|---|
| 11 | DK1 | 306 | tTCaCCTCGCCGGCATGAGACagcacaCAGGACTGCAACTGCTCAATCTATCCGGCCAcgTt |
| 24 | T10 | 306 | CTCGCCTCGCCGGCATGAGACActtTgCAGGACTGCAACTGCTCAATCTATCCGGCCAtcTG |
| 10 | D3 | 306 | CTCGCCTCGCCGGCATGAGACaCAGGAaTGTAACTGCTCAATCTATCCGGCCACGTG |
| 9 | D1 | 306 | CTCGCCTCGCCGGCATGAGACGGTACAGGAGTGTAAtTGCTCAATCTATCCGGCCACGTG |
| 14 | HK5 | 306 | CTCGCCTCGCCGACACGAGACGGTACAGGACTGCAACTGCTCAATCTATCCGGCCACGTA |
| 15 | HK8 | 306 | CTCGCCTCGCCGACACGAGACGGTACAGGACTGCAACTGCTCAATCTATCCGGCCACGTA |
| 12 | HK3 | 306 | tTCGCCTCGCCGGCATGAGACACAGGACTACAGGACTGCAACTGCTCAATCTATCCGGCCACGTA |
| 23 | T3 | 306 | CTCGCCTCGCCGGCACGAGACAGTACAGGACTACAGGACTGCAACTGCTCACTCTATCCGGCCACGTA |
| 22 | SW2 | 306 | tTCACCTCGCCGGCATGAGACACGAGACAGTACAGGACTGCAACTGCTCAATCTATCCGGCCACGTA |
| 17 | IND8 | 306 | CTCACCGCGCCGGCATGAGACATGAGACAGTACAGGACTGCAATTGCTCCATCTATCCGGCCACGTA |
| 16 | IND5 | 306 | CTCACCGCGCCGGCATGAGACATGAGACAGTACAGGACTGCAATTGCTCCATCTATCCGGCCACGTA |
| 21 | SA10 | 306 | CTCGCCTCGCCGGCGtATGAGACAGTACAGGACTGCAATTGCTCAATCTATCCGGCCGCGTA |
| 20 | S45 | 306 | CTCGCCTCGCCGGCATGAGACAGTACAGGACTGCAAcTGTTCAATCTATCCGGCCACGTA |
| 25 | US6 | 306 | CTCGCCTCGTCaGCATGAGACATGAGACAGTACAGGACTGCAATTGTTCAATCTATCCGGCCACGTA |
| 13 | HK4 | 306 | CTCGCCTCGCCGGCATTgaGACATGAGACgGTACAGTACAGGACTGCAATTGcTCAATCTATCCGGCCACGTA |
| 18 | P10 | 306 | CTCaCCTCGCCGGCATgaGACATGAGACAGTACAGGACTGCAATTGtCAATCTATCCtGGCCACGTA |
| 19 | S9 | 306 | CTCgCCccCGtCGGCATgaGACATGAGaCAGTACAGGaACTACAGaACTGCAATTGCTCAATCTATCCGGaCACGTg |
| 9-25 | consensus | | cTCgCCTcCGcCggcAtgaGACagtaCAGgACTGCTCaaTCTATCCgGcCacgTa |

FIGURE 1B-7

| SEQ ID NO: | Isolate | | |
|---|---|---|---|
| 11 | DK1 | 367 | TCAGGTCACCGCATGGCTTGGGAtATGATGATGAAACTGGTCaCCTACAACAGCcCTAGTGc——————— |
| 24 | T10 | 367 | TCAGGTCACCGCATGGCTTGGGACATGATGATGATGAAACTGGTCGCCTACAACAGCtCTAGTGG——————— |
| 10 | D3 | 367 | ACAGGTCACCGCATGGCTTGGGATATGATGATGATGAAACTGGTCGCCTACAGCAGCCCTAGTGG——————— |
| 9 | D1 | 367 | ACAGGTCACCGtATGGCTTGGGATATGATGATGATGAAACTGGTCACCTACAACAGCCtTAGTGG——————— |
| 14 | HK5 | 367 | ACAGGTCACCGCATGGCTTGGGATATGATGATGATGAAACTGGTCACCTACAACAGCCCTAGTGG——————— |
| 15 | HK8 | 367 | TCAGGTCACCGCATGGCTTGGGATATGATGATGATGAAACTGGTCACCTACAACAGCCCTAGTGG——————— |
| 12 | HK3 | 367 | TCAGGTCACCGCATGGCTTGGGATATGATGATGATGAAACTGGTCgCCCACACAGCCCTAGTGG——————— |
| 23 | T3 | 367 | aCAGGTCACCGtATGGCTTGGGATATGATGATGATGAAACTGGTCCCCtACAgCAGCCCTAGTGG——————— |
| 22 | SW2 | 367 | TCAGGTCACCGCATGGCTTGGGACATGATGATGATGAAACTGGTCACCTACAGCAGCCCTgGTGG——————— |
| 17 | IND8 | 367 | TCAGGTCACCGCATGGCTTGGGATATGATGATGATGAAACTGGTCACCTACAGCAGCgCCTAGTGG——————— |
| 16 | IND5 | 367 | TCAGGTCACCGCATGGCCtGGGATATGATGATGATGAAACTGGTCACCTACAGCAGCCCTAGTGG——————— |
| 21 | SA10 | 367 | ACAGGTCACCGCATGGCTTGGGATATGATGATGATGAAACTGGTCACCTACAGCAGCtCTAGTaG——————— |
| 20 | S45 | 367 | ACAGGTCACCGCATGGCTTGGGATATGATGATGATGAAACTGGTCgCCTACAGCAGCCtTAGTGG——————— |
| 25 | US6 | 367 | TCAGGTCACCGCATGGCTTGGGATATGATGATGATGAAACTGGTCACCTACAGCAGCCCTAGTG

FIGURE 1B-8

| SEQ ID NO: | Isolate | | |
|---|---|---|---|
| 11 | DK1 | 428 | TaTCGCAGTTACTCCGaATCCCACAAGCTGTCgTGGACATGGTGgCggGGGCCCACTGGGG |
| 24 | T10 | 428 | TgTCGCAGTTACTCCGGATCCCACAAGCTGTCaTGGACATGGTGaCaGGGGCCCACTGGGG |
| 10 | D3 | 428 | TATCGCAGTTACTCCGGATCCCACAAGCTGTCgTGGACATGGTGCGGGGGCCCACTGGGG |
| 9 | D1 | 428 | TATCGCAGTTACTCCGGATCCCACAAGCTGTCaTGGACATGGTGCGGGGGCCCACTGGGG |
| 14 | HK5 | 428 | TGTCGCAGTTACTCCGGATCCCGCAAGCTGTCGTGGACATGGTGCGGGGGCCCACTGGGG |
| 15 | HK8 | 428 | TGTCGCAGTTACTCCGGATCCCGCAAGCTaTCGTGGACATGGTGCGGGGGCCCACTGGGG |
| 12 | HK3 | 428 | TGTCGCAaATTACTCCGGATCCCGCAAGCTGTCGTGGACATGGTGCGGGGGCCCACTGGGG |
| 23 | T3 | 428 | TGTCGCAGTTgCTCCGGATCCCACAAGCTGTCGTGGACATGGTaGCGGGGGCCCACTGGGG |
| 22 | SW2 | 428 | TATCGCAGTTaCTCCGGATCCCACAAGCTGTCGTGGACATGGTaGCGGGGGCCCACTGGGG |
| 17 | IND8 | 428 | TATCGCAGTTgCTCCGGATCCCACAAGCTGTCGTGGATATGGTGCGGGGGCCCACTGGGG |
| 16 | IND5 | 428 | TATCGCAGTTgCTCCGGATCCCACAAGCTGTCGTGGATATGGTGCGGGGGCCCACTGGGG |
| 21 | SA10 | 428 | TATCGCAGTTACTTACTCCGGATCCCACAAGCTaTCGTGGACATGGTGCGGGGGCCCACTGGGG |
| 20 | S45 | 428 | TATCGCAGTTACTCCGGATCCCACAAGCTGTCaTGGACATGGTGCGGGGGCCCACTGGGG |
| 25 | US6 | 428 | TATCGCAGTTACTCCGGATCCCACAAGCTGTCaTGGACATGGTGCGGGaGCCCACTGGGG |
| 13 | HK4 | 428 | TATCGCAGTTACTCCGacTCCCACAAGCTaTCtTGGATgTGGTGCGGGGGCCCACTGGGG |
| 18 | P10 | 428 | TgTCGCAGCTACTCCGGATCCCACAAGCTaTCtTGGATgTGGTGCGGGGGCCCACTGGGG |
| 19 | S9 | 428 | TaTCGCAGCTACTCCGGATCCCACAAGCTgTCaTGGATaTGGTGCGGGGGCCCACTGGGG |
| 9-25 | consensus | | TaTCGCAgtTaCTCCGgaTCCCaCAAGCTgTCgTGGAcaTGGTggCgGGgGCCCACTGGGG |

FIGURE 1B-9

| SEQ ID NO: | Isolate | | |
|---|---|---|---|
| 11 | DK1 | 489 | AGTCCTGGGCGGGCCTcGCCTACTAcTCCATGGCGGGGAACTGGGCCAAGGTTTTAATTGTG |
| 24 | T10 | 489 | ::::::::::::::::::::::::::::::::::::::::::::::::::::::::::::: |
| 10 | D3 | 489 | AGTCCTGGGCGGCCCTtGCCTACTATTCCATGGCGGGGAACTGGGCTAAGGTTTTAATTGTG |
| 9 | D1 | 489 | GGTCCTGGGCGGGCCTGCCTACTATTCCATGGTGGGGAACTGGGCTAAGGTTTTGATTGTG |
| 14 | HK5 | 489 | GGTCCTGGGCGGGCCTTGCCTACTATTCCATGGTGGGGAACTGGGCTAAGGTTTTGATTGTG |
| 15 | HK8 | 489 | GGTCCTGGGCGGGCCTTGCCTACTATTCCATGGTGGGaAACTGGGCTAAGGTTTTGATTGTG |
| 12 | HK3 | 489 | AGTCCTAGCGGGCCCTTGCCTACTATTCCATGGTGGCAACTGGGCTAAGGTTTTGATTGTG |
| 23 | T3 | 489 | AGTCCTAGCGGGCCCTTGCCTACTATTCCATGGTGGGaAACTGGGCTAAGGTTTTGATTGTG |
| 22 | SW2 | 489 | AGTCCTGGGCGGGCCTTGCCTACTATTCCATGGTGGGGAACTGGGCTAAGGTTTTGATTGTG |
| 17 | IND8 | 489 | AGTCCTGGGCGGGCCTTGCaTACTACTATTCCATGGTGGGGAACTGGGCTAAGGTTTTGATTGTG |
| 16 | IND5 | 489 | AATCCTGGCGGGCCTTGCCTACTATTCCATGGTAGGGAACTGGGCTAAGGTTTTGATTGTG |
| 21 | SA10 | 489 | AATCCTGGCGGGCCTTGCCTACTATTCCATGGTAGGGAACTGGGCTAAGGTTTTGATTGTG |
| 20 | S45 | 489 | AGTCCTGGGCGGGCCTTGCCTACTATTCCATGGTGGGGAACTGGGCTAAGGTTCTGATTGTG |
| 25 | US6 | 489 | AGTCCTGGGCGGGCCTTGCCTACTATTCCATGGTGGGGAACTGGGCTAAGGTTCTGATTGTG |
| 13 | HK4 | 489 | AGTCCTaGCGGGCCTTGCtCTACTATTCCATGGTGGGGAACTGGGCCAAGGTTTTGATTGTG |
| 18 | P10 | 489 | AGTCCTGGCGGGCCTTGCCTACTATTCCATGGTGGGGAACTGGGCTAAGGTcTTGATTGTG |
| 19 | S9 | 489 | AGTCCTGGCGGGCCTCGCCTACTATTCCATGGTGGGGAACTGGGCTAAGGTTTTGATTGTG |
| 9-25 | consensus | | agTCCTgGCGGGCCTtGCcTACTAtTCCATGgTgGGgAACTGGGCtAAGGTttTgATTGTg |

FIGURE 1B-10

| SEQ ID NO: | Isolate | | |
|---|---|---|---|
| 11 | DK1 | 550 | tTGCTACTCTTTGCCGGCGTTGATGGG |
| 24 | T10 | 550 | ATGCTACTCTTTGCCGGCGTTGATGGG |
| 10 | D3 | 550 | ATGCTACTCTTTGCTGGCGTcGACGGC |
| 9 | D1 | 550 | ATGCTACTCTTTGCTGGCGTTGACGGC |
| 14 | HK5 | 550 | ATGCTACTtTTTGCCGGCGTTGATGGG |
| 15 | HK8 | 550 | ATGCTACTgTTTGCCGGCGTTGATGGG |
| 12 | HK3 | 550 | ATGCTACTtTTTGCCGGCGTTGATGGG |
| 23 | T3 | 550 | cTGCTACTCTTTGCCGGCGTTGATGGG |
| 22 | SW2 | 550 | ATGCTACTCTTTGCtGGCGTTGACGGG |
| 17 | IND8 | 550 | ATGCTACTCTTTGCCGGCGTTGACGGG |
| 16 | IND5 | 550 | ATGCTACTCTTTGCCGGCGTTGACGGG |
| 21 | SA10 | 550 | ATGCTACTCTTTGCCGGCGTTGACGGG |
| 20 | S45 | 550 | ATGCTACTCTTTGCCGGCGTTGACGGG |
| 25 | US6 | 550 | tTGCTACTCTTTGCCGGCCGTTGACGGG |
| 13 | HK4 | 550 | ATGCTACTCTTTGCCGGCGTTGACGGG |
| 18 | P10 | 550 | ATGCTACTCTTTGCCGGCGTTGACGGa |
| 19 | S9 | 550 | ATGCTACTtTTTGCtGGtGTTGACGGg |
| 9-25 | consensus | | aTGCTACTcTTTGCcGGcGTtGAcGGg |

FIGURE 1C-1

| SEQ ID NO: | Isolate | | |
|---|---|---|---|
| 26 | T2 | 1 | GCcCAAGTGAgGAACACCAgccgCgtTACATGGTGACtAACGACTGTTCcAATGAGAGCA |
| 27 | T4 | 1 | GCaCAAGTGAAGAAACACCACTAaCAGCTACATGGTGACCAACGACTGTTCtAATGACAGCA |
| 28 | T9 | 1 | GCCgAAGTGAAGAACACCAGTACCAGCTACATGGTGACaAATGACTGTTCCAACGACAGCA |
| 29 | US10 | 1 | GtCcAAGTGAAaAAACACCAGTACCAGCTATATGGTGACCAATGACTGCTCCAACGACAGCA |
| 26-29 | consensus | | GcccAAGTGAagAACACCAgtacCaGcTACATGGTGACcAA-GACTGtTCcAA-GAcAGCA |

| SEQ ID NO: | Isolate | | |
|---|---|---|---|
| 26 | T2 | 62 | TCACCTGGCAGCTCCAaGCCGCGGTtCTCCACGTCCCCGGGTGTaTCCCGTGtGAGAggct |
| 27 | T4 | 62 | TCACtTGGCAGCTCCAGGCCGCGGTCCTCCACGTCCCCGGGTGTGTCCCGTGGAGAaAac |
| 28 | T9 | 62 | TCACCTGGCAACTCCAGGCCGCGGTCCTCCACGTCCCCGGGTGcGTCCCGTGCGAGAgAGT |
| 29 | US10 | 62 | TCACtTGGCAACTtgAGGCtGCGGTCCTCCACGTtCCCGGGTGTGTCCCGTGCGAGAaAGT |
| 26-29 | consensus | | TCAC-TGGCA-CTccAgGCCGCGGTcCTCCACGTcCCCGGGTGtgTCCCGTgCGAGA-agt |

| SEQ ID NO: | Isolate | | |
|---|---|---|---|
| 26 | T2 | 123 | GGGAAATACATCcCGaTGCTGGATACCGGTCaCACCAAACGTGGCCGTGCGGCAGCCCGGC |
| 27 | T4 | 123 | GGGAAATACATCtCGGTGCTGGATACCGGTtTCACCAAACGTGGCCGTGCGGCAGCCCGGC |
| 28 | T9 | 123 | tGGAAAcGTGCGGTGCTGGATACCGGTCTCgCCAAACGTaGCtGTGCAGCGGCCTGGC |
| 29 | US10 | 123 | gGGAAAtaCaTCtCGGTGCTGGATACCGGTCTCaCCAAAtGTGGCCGTGCAGCGGCCTGGC |
| 26-29 | consensus | | gGGAAAtaCaTCtCGgTGCTGGATACCGGTctCaCCAAAcGTGGCcGTGC-GC-GCC-GGC |

FIGURE 1C-2

| SEQ ID NO: | Isolate | | |
|---|---|---|---|
| 26 | T2 | 184 | GCtCTtACGCAGGGCTTGCGGACGCACATcGACACATGGTTGTGATGTCCGCCACGCTCTGCT |
| 27 | T4 | 184 | GCCCTCACGCAGGGCTTGCGGACGCACATtGACACATGGTTGTGATGTCCGCCACGCTCTGCT |
| 28 | T9 | 184 | GCCCTCACGCAGGGCTTGCGGACGCACATCGACACATGGTTGTGATGTCCGCCACGCTCTGCT |
| 29 | US10 | 184 | GCCCTCACGCAGGGCTTGCGGACtCACATCGACACATGGTcGTGATGTCCGCCACGCTCTGCT |
| 26-29 | consensus | | GCcCTcACGCAGGGCTTGCGGACgCACATcGACACATGGTtGTGATGTCCGCCACGCTCTGCT |

| SEQ ID NO: | Isolate | | |
|---|---|---|---|
| 26 | T2 | 245 | CTGCCCTCTACGTGGGGACCTCTGCGCGGGTGAATGCTCGCAGCCCAGATGTTCATtGT |
| 27 | T4 | 245 | CTGCTCTtTACGTGGGGACCTCTGCGCGGGTGAATGCTCGCAGCCCAGATGTTCATcGT |
| 28 | T9 | 245 | CCGCTCTcTACGTGGGGAtCTCTGCGCGGGGTaATGCTCGCcGCtCAGATGTTCATTaT |
| 29 | US10 | 245 | CCGCTCTtTACGTGGGGActTCTGCGGtGGGaTgATGCTCGCaGCcCAaATGTTCATTgT |
| 26-29 | consensus | | C-GCtCT-TACGTGGGGAccTCTGCGGcGGGgTgATGCTCGCaGCcCAgATGTTCATtgT |

| SEQ ID NO: | Isolate | | |
|---|---|---|---|
| 26 | T2 | 306 | CTTCGCCCGgACGcCACTGGTTTGTGCAAGAaTGCAATTGCTCGATCTACCCcGGtACCATC |
| 27 | T4 | 306 | CTTCGCCCGCAACAtCACTGGTTTTGTGCAAGACTGCAATTGCTCtATCTACCCTGcACCATC |
| 28 | T9 | 306 | CTTCGCCCGCAgCACCACTGGTTTGTGCAGGAATGCAACTGCTCCATtTACCCTGTACCATC |
| 29 | US10 | 306 | CTTCGCCCGcgCCACCACTCGTTTGTGCAGGAATGCAACTGCTCCATcTACCCcGGTACCATC |
| 26-29 | consensus | | CTTCGCCCGC-aCacCACTggTTTGTGCA-GAaTGCAA-TGCTCcATcTACCC-GGtACCATC |

FIGURE 1C-3

| SEQ ID NO: | Isolate |  |  |
|---|---|---|---|
| 26 | T2 | 367 | ACTGGACACCGTATGGCATGGGAcATGATGATGAACTGGTCGCCCACaGCCACCATGATCC |
| 27 | T4 | 367 | ACTGGACACCGTATGGCATGGGAtATGATGATGAACTGGTCGCCCACgGCCACCATGATCC |
| 28 | T9 | 367 | ACTGGACACCGTATGGCATGGGACATGATGATGAACTGGTCGCCCACaaCCACCATGATCt |
| 29 | US10 | 367 | ACcGGgCACCGTATGGCATGGGACATGATGATGAACTGGTCGCCCACggCCACttTGATCc |
| 26-29 | consensus |  | ACtGGaCACCGTATGGCATGGGaCATGATGATGAACTGGTCGCCCAC-gCCACcaTGATCc |

| SEQ ID NO: | Isolate |  |  |
|---|---|---|---|
| 26 | T2 | 428 | TGGCGTACGCGATGCGCGTTCCCGAGGTCATCaTaGACATCaTcggCGGGGGCtCACTGGGG |
| 27 | T4 | 428 | TGGCGTACGCGATGCGCGTTCCCGAGGTCATCtTAGACATCgTtAGCGGGGGCaCACTGGGG |
| 28 | T9 | 428 | TGGCGTACGCGATGCGCGTTCCCGAGGTCATCATAGACATCATcAGCGGaGCtCACTGGGG |
| 29 | US10 | 428 | TGGCGTACGtGATGCGCGTTCCCGAGGTCATCATAGACATCATtAGCGGGGGCgCAtTGGGG |
| 26-29 | consensus |  | TGGCGTACGcGATGCGCGTTCCcGAGGTCATCaTAGACATCaT-aGCGGgGCtCACTGGGG |

| SEQ ID NO: | Isolate |  |  |
|---|---|---|---|
| 26 | T2 | 489 | CGTCATGTTtGGCTTGGCCTACTTCTCTATGCAGGGAGCGTGGGCGAAgGTCATTGTCATC |
| 27 | T4 | 489 | CGTCATGTTcGGCTTGGCCtACTTCTCTATGCAGGGAGCGTGGGCGAAaGTCGTTGTCATC |
| 28 | T9 | 489 | CGTCATGTTCGGCcTAGCCTACTTCTCTATGCAGGGAGCGTGGGCGAAgGTCGTTGTCATC |
| 29 | US10 | 489 | CGTCtTGTTCGGCtTAGCCTACTTCTCTATGCAGGGAGCGTGGGCGAAaGTCGTTGTCATC |
| 26-29 | consensus |  | CGTCaTGTTcGGCtT-GCCTACTTCTCTATGCAGGGAGCGTGGGCGAA-GTCgTTGTCATC |

FIGURE 1C-4

| SEQ ID NO: | Isolate | | |
|---|---|---|---|
| 26 | T2 | 550 | CTctTGCTGGCtGCTGGGGTGGACGCG |
| 27 | T4 | 550 | CTtcTGCTGGCCGCTGGGGTGGACGCG |
| 28 | T9 | 550 | CTgtTGCTcaCCGCTGGcGTGGACGCG |
| 29 | US10 | 550 | CTtcTGCTagCCGCTGGggGTGGACGCG |
| 26-29 | consensus | | CTt-TGCTggCCGCTGGGgGTGGACGCG |

FIGURE 1D-1

| SEQ ID NO: | Isolate | | |
|---|---|---|---|
| 33 | T8 | 1 | GTGGAAGTtAGaAaACaCCAGTTttAGCTACTACGCCACCAATGATTGCTgAACAACAGCA |
| 30 | DK8 | 1 | GTGGAAGTcAGGAACATCAGTTCcAGCTACTACGCCACCAATGATTGCTCAAACAACAGCA |
| 32 | SW3 | 1 | GTGGAAGTcAGGAACATCAGTTCTAGCTACTAtGCCACCAATGATTGCTCAAACAgCAGCA |
| 31 | DK11 | 1 | GTGGAAGTCAGGAACAcCAGTTCTAGtTACTAcGCCACCAATGATTGCTCAAACAaCAGCA |
| 30-33 | consensus | | GTGGAAGTcAGgAACA-CAGTTctAGcTACTAcGCCACCAATGATTGCTcaaACaaCAGCA |

| SEQ ID NO: | Isolate | | |
|---|---|---|---|
| 33 | T8 | 62 | TCACCTGGCAgCTCACCaaCGCAGTTCTCCACCTTCCCGGATGCGTCCCATGTGAGAATGA |
| 30 | DK8 | 62 | TCACCTGGCAACTCACCgACGCAGTTCTCCACCTTCCCGGATGCGTCCCATGTGAGAATGA |
| 32 | SW3 | 62 | TCACCTGGCAACTCACCAAcGCAGTcCTCCACCTTCCCGGATGCGTCCCgTGTGAGAATGA |
| 31 | DK11 | 62 | TCACCTGGCAACTCACCAACGCAGTtCTCCACCTTCCCGGATGCGTCCCaTGTGAGAATGA |
| 30-33 | consensus | | TCACCTGGCAacTCACCaaCGCAGTtCTCCACCTTCCCGGATGCGTCCCaTGTGAGAATGA |

| SEQ ID NO: | Isolate | | |
|---|---|---|---|
| 33 | T8 | 123 | CAATGGCACCtTGCGCTGCTGGATACAAGTaACACCTAATGTGGCTGTGAAACCGtGGGC |
| 30 | DK8 | 123 | CAATGGCACCCTGCGCTGCTGGATACAAGTGACACCTAATGTGGCTGTGAAACACCGCGGC |
| 32 | SW3 | 123 | CAATGGCACCCTGCACTGCTGGATACAAGTGACACCTAATGTGGCTGTGAAACACCGCGGC |
| 31 | DK11 | 123 | tAATGGCACCCTGCACTGCTGGATACAAGTGACACCTAATGTGGCTGTGAAACACCGCGGC |
| 30-33 | consensus | | cAATGGCACCCTGC-CTGCTGGATACAAGTgACACCTAATGTGCTGTGAAACACCGCGGC |

FIGURE 1D-2

| SEQ ID NO: | Isolate | | |
|---|---|---|---|
| 33 | T8 | 184 | GCACTcACTCACAACCTGCGAACgCAtGTCGACGTGATCGTAATGGCAGCTACGGTCTGCT |
| 30 | DK8 | 184 | GCACTtACTCAtAACCTGCGAACACAGTCGACGTGATCGTAATGGCAGCTACGGTCTGCT |
| 32 | SW3 | 184 | GCgCTCACTCACACAACCTGCGAGCACAGTCGACGTGATATGATCGTAATGGCAGCTACGGTCTGCT |
| 31 | DK11 | 184 | GCaCTCACTCACAACCTGCGAGCACACAtaTaGATATGATtGTAATGGCAGCTACGGTCTGCT |
| 30-33 | consensus | | GCACTcACTCAcAACCTGCGA-CaCA-gTcGA--TGATcGTAATGGCAGCTACGGTCTGCT |

| SEQ ID NO: | Isolate | | |
|---|---|---|---|
| 33 | T8 | 245 | CGGCCTTGTATGTGGGgGACGTgTGCGGGGGCCGTGATGATaGcGTCGCAGGCTtTCATAAT |
| 30 | DK8 | 245 | CGGCCCTTGTATGTGGGAGAGACGTaTGCGGGGGCCGTGATGATCGTCGTGTCGCAGGCTCTCATAAT |
| 32 | SW3 | 245 | CGGCCTTGTATGTGGGAGAGACAtGTGCGGGCCGTGATGATCGTGTCGCAGGCTTTCATAAT |
| 31 | DK11 | 245 | CGGCCTTGTATGTGGGAGACGTGTGCGGGGCCGTGATGATCGTGTCGCAGGCTtTCATAgT |
| 30-33 | consensus | | CGGCCTTGTATGTGGaGACGTgTGCGGGGGCCGTGATGATCGTGTCGCAGGCTtTCATAaT |

| SEQ ID NO: | Isolate | | |
|---|---|---|---|
| 33 | T8 | 306 | ATCGCCagaACGCCACAACTTcACCCAGGAGTGCAACTGTTCCATCTACCAAGGTCATATC |
| 30 | DK8 | 306 | ATCGCCtGAACGCCACAACTTtACCCAGGAGTGCAACTGTTCCATCTACCAAGGTCATATC |
| 32 | SW3 | 306 | ATCGCCAGAACGCCACAACTTtACCCAAGAGTGCAACTGTTCCATCTACCAAGGTCgTATC |
| 31 | DK11 | 306 | ATCGCCAGAACaCCCAcACTTtACCcACACTTTACCCAAGAGTGCAACTGTTCCATCTACCAAGGTCacATC |
| 30-33 | consensus | | ATCGCCagAACgCCACaACTTtACCCA-GAGTGCAACTGTTCCATCTACCAAGGTCatATC |

FIGURE 1D-3

| SEQ ID NO: | Isolate | | |
|---|---|---|---|
| 33 | T8 | 367 | ACCGGCCACCGCATGGCATGGGACATGATGCTgAACTGGTCACCAACTCTcACCATGATCC |
| 30 | DK8 | 367 | ACCGGCCACCGCATGGCATGGGACATGATGCTAAACTGGTCACCAACTCTTACCATGATCC |
| 32 | SW3 | 367 | ACCGGCCACCCGCATGGCgTGGGACATGATGCTAAACTGGTCACCAACTCTTACCATGATCC |
| 31 | DK11 | 367 | ACCGGCCACCGCATGGCATGGGACATGATGCTtAACTGGTCACCAACTCTcACCATGATCC |
| 30-33 | consensus | | ACCGGCCACCGCATGGCATGGGACATGATGCTaAACTGGTCACCAACTCT-ACCATGATCC |

| SEQ ID NO: | Isolate | | |
|---|---|---|---|
| 33 | T8 | 428 | TCGCCTAcGCtGCTCGTGTgCCTGAaCTAGtCCTtgAaGTTGTCTTCGGCGGCCATTGGGG |
| 30 | DK8 | 428 | TCGCCTATGCCGCtCGTGTTCCTGAGCTAGcCCTtccAgGTTGTCTTCGGCGGCCATTGGGG |
| 32 | SW3 | 428 | TtGCCTATGCCGCtCGTGTTCCTGAGCTAGTCCTTGAAGTTGTCTTCGGCGGCCATTGGGG |
| 31 | DK11 | 428 | TcGCCTATGCCGCcCGTGTTCCTGAGCTAGTCCTTGAAGTCGTCTTCGGtGGtCATTGGGG |
| 30-33 | consensus | | TcGCCTAtGCcGCtCGTGTcCCTGAGcTAGtCCTtgAaGTtGTCTTCGGcGGCCATTGGGG |

| SEQ ID NO: | Isolate | | |
|---|---|---|---|
| 33 | T8 | 489 | CGTGGTGTGTTTGGCTTGGCCTATTTCTCCATGCAaGGAGAGCGTGGGCCAAAGTCATcGCCATC |
| 30 | DK8 | 489 | CGTGGTGTGTTTGGCTTGGCCTATTTCTCCATGCAgGGAGAGCGTGGGCCAAAGTCATTGCCATC |
| 32 | SW3 | 489 | CGTGGTGTGTTTGGCTTGGCCTATTTCTCCATGCAaGGAGAGCGTGGGCCAAGGTCATTGCCATC |
| 31 | DK11 | 489 | CGTGGTGTGTTTGGCTTGGCCTATTTCTCCATGCAgGGAGAGCGTGGGCCAAGGTCATTGCCATC |
| 30-33 | consensus | | cGTGGTGTTTGGCTTGGCCTATTTCTCCATGCA-GGAGCGTGGGCCAA-GTCATtGCCATC |

FIGURE 1D-4

| SEQ ID NO: | Isolate | | |
|---|---|---|---|
| 33 | T8 | 550 | CTCCTcCTTGTCGCAGGAGTGGAcGCA |
| 30 | DK8 | 550 | CTCCTtCTTGTCGCAGGAGTGGATGCA |
| 32 | SW3 | 550 | CTCCTgCTTGTCGCAGGAGTGGATGCA |
| 31 | DK11 | 550 | CTCCTtCTTGTaGCAGGAGTGGATGCA |
| 30-33 | consensus | | CTCCTtCTTGTCGCAGGAGTGGAtGCA |

FIGURE 1E-1

| SEQ ID NO: | Isolate | | |
|---|---|---|---|
| 35 | DK12 | 1 | tTAGAGTGGCGGAATGTGTCCGGCCTCTAcGTCCTTAcCAACGACTGTtCCAATAGCAGTA |
| 36 | HK10 | 1 | CTAGAGTGGCGGAATGTGTCTGGCCTCTATGTCCTTACCAACGACTGTcCCAATAGCAGTA |
| 37 | S2 | 1 | CTAGAGTGGCGGAATACGTCTCGGCCTCTATGTCCTCACCAACGACTGTTCCAATAGCAGTA |
| 39 | S54 | 1 | CTAGAGTGGCGGAATACGTCTCGGCCTCTCTATAtCCTTACCAACGACTGTTCCAATAGCAGTA |
| 38 | S52 | 1 | CTAGAGTGGCGGAATACGTCTGGCCCTCTATGtCCTTACCAACGACTGTtCCAATAGCAGTA |
| 35-39 | consensus | | cTAGAGTGGCGGAATacGTCtGGCCTCTATgtCCTtACCAACGACTGTtCCAATAGCAGTA |

| SEQ ID NO: | Isolate | | |
|---|---|---|---|
| 35 | DK12 | 62 | TcGTGTATGAGGCCGATGACGTCATTCTGCACACACCTGGCTGTGTACCTTGTGTTCAGGA |
| 36 | HK10 | 62 | TTGTGTATGAGGCCGATGACGTCATTCTGCACACACCTGGCTGTGTACCTTGTGTTCAGGA |
| 37 | S2 | 62 | TTGTGTATGAGGCCGATGACGTtATTCTGCACACACCTGGCTGTGTACCTTGTGTTCAGGA |
| 39 | S54 | 62 | TTGTGTATGAGGCCGATGACGTCATTCTGCACACACCCGGCTGTGTACCTTGTGTTCAGGA |
| 38 | S52 | 62 | TTGTGTATGAGGCCGATGACGTCATTCTGCACACACCCGGCTGTGTACCTTGTGTTCAGGA |
| 35-39 | consensus | | TtGTGTATGAGGCCGATGACGTCATTCTGCACACACCtGGCTGTGTACCTTGTGTTCAGGA |

FIGURE 1E-2

| SEQ ID NO: | Isolate | | |
|---|---|---|---|
| 35 | DK12 | 123 | CGGCAATACATCtACGTGCTGGACCTCaGTGACgCCTACAGTGGCAGTCAGTACGTCGGA |
| 36 | HK10 | 123 | CGGCAATACATCCACGTGCTGGACCTCgTGACACCTACAGTGGCAGTCAGTACGTCGGA |
| 37 | S2 | 123 | CGGtAATACATCCACGTGCTGGACCCCAGTGACACCTACAGTGGCAGTCAGTAtGTCGGA |
| 39 | S54 | 123 | CGGCAATACATCCACGTGCTGGACCCCAGTGACACCTACGGTGGCAGTCAGTACGTCGGA |
| 38 | S52 | 123 | CGGCAATACATCCAtGTGCTGGACCCCAGTGACACCTACGGTGGCAGTCAGTACGTCGGA |
| 35-39 | consensus | | CGGcAATACATCcACgTGCTGGACCCcAGTGACaCCTACaGTGgCAGTCAGTAcGTCGGA |

| SEQ ID NO: | Isolate | | |
|---|---|---|---|
| 35 | DK12 | 184 | GCAACCACCGCtTCGATACGCAGTCATGTGGACCTGcTAGTGGGCGGCCACGATGTGCT |
| 36 | HK10 | 184 | GCAACCACCGCcTCGATACGCAGTCATGTGGACCTGTTAGTGGGCGGCCACGATGTGCT |
| 37 | S2 | 184 | GCAACCACCGCTTCGATACGCAGTCATGTGGACCTATTgGTGGGCGGCCACtATGTGCT |
| 39 | S54 | 184 | GCAACCACCGCTTCGATACGCAGTCATGTGGACCTATTAGTGGGCGGCCACGCTGTGCT |
| 38 | S52 | 184 | GCAACCACCGCTTCGATACGCAGTCATGTGGACCTATTAGTGGGCGGCCACGCTGTGCT |
| 35-39 | consensus | | GCAACCACCGCTTCGATACGCAGTCATGTGGACCTatTagTGGGCGGCCACgaTGTGCT |

FIGURE 1E-3

| SEQ ID NO: | Isolate | | |
|---|---|---|---|
| 35 | DK12 | 245 | CTGCGCTCTACGTGGGtGATgTGTGTGGGGCGTCTTCCTtGTGGGACAAGCCTTCACGTT |
| 36 | HK10 | 245 | CTGCGCTCTACGTGGGCGATATGTGTGGGGCCGTCTTCCTCGTGGGACAAGCCTTCACGTT |
| 37 | S2 | 245 | CTGCGCTCTACGTGGGTGATATGTGTGGGGCCGTCTTCTCGTGGGACAAGCCTTCACGTT |
| 39 | S54 | 245 | CTGCGCTCTATGTGGGTGATATGTGTGGGGCCGTCTCTTCTCGTGGGACAAGCCTTCACGTT |
| 38 | S52 | 245 | CTGCGCTCTATGTGGGTGATATGTGTGGGGCCGTCTCTTTCTCGTGGGACAAGCCTTCACGTT |
| 35-39 | consensus | | CTGCGCTCTAcGTGGtGATgTGTGGGGCCGTCTcTTtCTcGTGGGACAAGCCTTCACGTT |

| SEQ ID NO: | Isolate | | |
|---|---|---|---|
| 35 | DK12 | 306 | CAGACCTcGTCGCCATCAAACaGTCCAGACCTGTAACTGCTCGCTGTACCCAGGCCAtCTT |
| 36 | HK10 | 306 | CAGACCgCGTCGCCATCAAACGGTCCAGACCTGTAACTGCTCGCTGTACCCAGGCCAcCTT |
| 37 | S2 | 306 | CAGACCTCGTCGCCATCAAACGGTCCAGACCTGTAACTGCTCGCTGTACCCAGGCCATCTT |
| 39 | S54 | 306 | CAGACCTCGTCGCCATCAAACGGTCCAGACCTGTAACTGCTCGCTGTACCCAGGCCATCTT |
| 38 | S52 | 306 | CAGACCTCGTCGCCATCAAACGGTCCAGACCTGTAACTGCTCGCTGTACCCAGGCCATgTT |
| 35-39 | consensus | | CAGACCtCGTCGCCATCAAACgGTCCAGACCTGTAACTGCTCGCTGTACCCAGGCCAtcTT |

FIGURE 1E-4

| SEQ ID NO: | Isolate | | |
|---|---|---|---|
| 35 | DK12 | 367 | TCAGGACATCGAATGGCTTGGGATATGATGATGAATTGGTCCCCCGCtGTGGGTATGGTGG |
| 36 | HK10 | 367 | TCAGGACATCGAATGGCTTGGGATATGATGATGAATTGGTCCCCGCcGTGGGTATGGTGG |
| 37 | S2 | 367 | TCAGGACATCGCATGGCTTGGGATATGATGATGAATTGGTCCCCCGCTGTGGGTATGGTGG |
| 39 | S54 | 367 | TCAGGACATCGAATGGCTTGGGATATGATGATGAATTGGTCCCCCGCTGTGGGTATGGTGG |
| 38 | S52 | 367 | TCAGGACATCGAATGGCTTGGGATATGATGATGAATTGGTCCCCCGCTGTGGGTATGGTGG |
| 35-39 | consensus | | TCAGGACATCGaATGGCTTGGGATATGATGATGAATTGGTCCCCCGCtGTGGGTATGGTGG |

| SEQ ID NO: | Isolate | | |
|---|---|---|---|
| 35 | DK12 | 428 | TaGCGCACGTCCTGCGtcTGCCCCAGAGACCTTGTTCGACATAATAGCtGGGGCCCATTGGGG |
| 36 | HK10 | 428 | TGGCGCACGTCCTGCGgTTGCCCCAGAGACCTTGTTCGACATAATAGCCGGGGCCCATTGGGG |
| 37 | S2 | 428 | TGGCGCACGTtCTGCGtTTGCCCCAGAGACCgTGTTCGACATAATAGCCGGGGCCCATTGGGG |
| 39 | S54 | 428 | TGGCGCACATCCTGCGATTGCCCCAGAGACCTTGTTTGACATACTGGCCGGGGCCCATTGGGG |
| 38 | S52 | 428 | TGGCGCACATCCTGCGATTGCCCCAGAGACCTTGTTTGACATACTGGCCGGGGCCCATTGGGG |
| 35-39 | consensus | | TgGCGCACgTcCTGCG-tTGCCCCAGAGACCtTGTTcGACATAaTaGCCGGGGCCCATTGGGG |

FIGURE 1E-5

| SEQ ID NO: | Isolate | |
|---|---|---|
| 35 | DK12 | 489 CATCaTGGCgGGCCTAGCCTATTACTCCATGCAGGGCAACTGGGCCAAGGTCGCTATCATC |
| 36 | HK10 | 489 CATCTTGGCaGGCCTAGCCTATTACTCCATGCAGGGCAACTGGGCCAAGGTCGCTATCATC |
| 37 | S2 | 489 CATCTTGGCGGGGCCTAGCCTATTACTCCATGCAaGGCAACTGGGCCAAGGTCGCTATCATC |
| 39 | S54 | 489 CATCTTGGCGGGCCTAGCCTATTATTCTATGCAGGGCAACTGGGCCAAGGTCGCTATCATC |
| 38 | S52 | 489 CATCTTGGCGGGCCTAGCCTATTATTCTATGCAGGGCAACTGGGCCAAGGTCGCTATtgTC |
| 35-39 | consensus | CATCtTGGCgGGCCTAGCCTATTACTcCATGCAGGGCAACTGGGCCAAGGTCGCTATCaTC |

| SEQ ID NO: | Isolate | |
|---|---|---|
| 35 | DK12 | 550 ATGGTTATGTTTCAGGaGTCGATGCC |
| 36 | HK10 | 550 ATGGTTATGTTTCAGGGGTCGATGCC |
| 37 | S2 | 550 ATGGTTATGTTTCAGGGGTCGAcGCC |
| 39 | S54 | 550 ATGGTTATGTTTCAGGGGTCGATGCC |
| 38 | S52 | 550 ATGATTATGTTTCAGGGGTCGATGCC |
| 35-39 | consensus | ATGgTTATGTTTCAGGgGTCGAtGCC |

FIGURE 1F-1

```
SEQ ID NO:   Isolate
     43         Z7    1  GTcAACTATCaCAATGCCTCGGGCGTCTATCACATCACCAACGACTGCCCGAACTCGAGCA
                         |||||||||| |||||||||||||||||||||||||||| ||||||||||||||||||||
     42         Z6    1  GTtAACTATCgCAATGCCTCGGGCGTCTATCACGTCACGTCACCAACGACTGCCCGAACTCGAGCA 42-43 consensus (Z6)    GTtAACTATCgCAATGCCTCGGGCGTCTATCACgTCACCAACGACTGCCCGAACTCGAGCA SEQ ID NO:   Isolate
     43         Z7   62  TAaTGTATGAGGCCGAACACCACCATCCTACACCTCCCAGGGTGCGTACCCTGTGTGAGGGa
                         || ||||||||||||||||||| ||||||| ||||||||||||||||   |||||||||| 
     42         Z6   62  TAGTGTATGAGGCCGAACACCAgATCTTACACCTCCCAGGGTGCtTgCCCTGTGTGAGGGt 42-43 consensus (Z6)    TAgTGTATGAGGCCGAACACCAgATCtTACACCTCCCAGGGTGCtTgCCCTGTGTGAGGGt SEQ ID NO:   Isolate
     43         Z7  123  gGGGAACCAGTCACGCTGCTGGGTGGCCCTTACTCCCACCGTGGGCGgCCTTATATCGGT
                         ||||| | ||||||||||||||||||||||||||||||||||||||   |||||||||||
     42         Z6  123  tGGGAAtCAGTCACGCTGCTGGGTGGCCCTTACTCCCACCGTGGtGtCTTATATCGGT 42-43 consensus (Z6)    tGGGAAtCAGTCACGCTGCTGGGTGGCCCTTACTCCCACCGTGGCGtCTTATATCGGT SEQ ID NO:   Isolate
     43         Z7  184  GCaCCGGCTTGAatCCatCCGGAGACATGTGGACCTGATGGTAGGCGCTGCTACAGTGTGCT
                         || ||||||||| | ||| ||||||||||||||||||||| ||||||||||||| |||||
     42         Z6  184  GCTCCGGCTTGACTCCCTCCGGAGACATGTGGACCTGATGGTGGGCGCCGCTACTGTaTGCT 42-43 consensus (Z6)    GCtCCGGCTTGACTCCCTCCGGAGACATGTGGACCTGATGGTGGGCGCCGCTACTGTaTGCT SEQ ID NO:   Isolate
     43         Z7  245  CcGCtCTCTACaTTGGGGACCTGTGCGGTGGCGGTaTTtTTGGTTGGtCAGATGTTtTCTTT
                         |  |||||||| ||||| ||||| ||||||||||| ||| |||||||||||||| |||||
     42         Z6  245  CtGCCCCTCTACgTTGgAgAtCTGTGCGGTGGtGCATTCTTGGTTGGCCAGATGTTCTCCTT 42-43 consensus (Z6)    CtGCCCTCTACgTTGgaGAtCTGTGcGGTGGtGcATTCTTGGTTGGcCAGATGTTcTCcTT
```

FIGURE 1F-2

```
SEQ ID NO:   Isolate
    43          Z7      306  CCAGCCGCGACGCCACTGGACTACGCAGGACTGCAATTGTTCCATCTAtCgCGGGCAcgTt
                              |||||||||||||||||||||||||||||||||||||||||||| || ||||| ---
    42          Z6      306  CCAGCCGCGACGCCACTGGACTACGCAGGACTGCAATTGTTCtATCTACGCAGGGCATATC 42-43 consensus (Z6)         CCAGCCGCGACGCCACTGGACTACGCAGGACTGCAATTGTTCtATCTAcGCaGGGCAtaTc SEQ ID NO:   Isolate
    43          Z7      367  ACaGGCCACAGaATGGCATGGACATGATGATGAACTGGAGTCCCACACCACCtTGgTCC
                              ||  |||||||| |||||||||||||||||||||||||||||||||||||||| || --
    42          Z6      367  ACgGGCCACAGgATGGCATGGACATGATGATGAACTGGAGTCCCACAACCACCCTGcTtC 42-43 consensus (Z6)         ACgGGCCACAGgATGGCATGGACATGATGATGAACTGGAGTCCCACAACCACCCTGcTtC SEQ ID NO:   Isolate
    43          Z7      428  TCGCCCAGGTtATGAGGATCCCTAGCACTCTGGTgACCTACTCaCTGGAGGGCACTGGGG
                              |||||||||| ||||||||||||||||||||| |||||||| ||||||||||||||||
    42          Z6      428  TCGCCCAGGTcATGAGGATCCCTAGCACTCTGGTaGAtCTACTCGCTGGAGGGCACTGGGG 42-43 consensus (Z6)         TCGCCCAGGTcATGAGGATCCCTAGCACTCTGgTaGAtCTACTCgCTGGAGGGCACTGGGG SEQ ID NO:   Isolate
    43          Z7      489  taTCCTTaTcGGGgTGGCaTACTTCtGCATGCAAGCTAATTGGGCCAAGGTCATtCTGGTC
                              |  |||| |  |||| |||| ||||| || |||||||||||||||| |||| ||||||
    42          Z6      489  CgTCCTTGTtGGGtTGGCGTACTTCAGtATGCAAGCTAATTGGGCCAAaGTCATCCTGGTC 42-43 consensus (Z6)         cgTCCTTgTtGGGtTGGCgTACTTCAGtATGCAAGCTAATTGGGCCAAaGTCATcCTGGTC SEQ ID NO:   Isolate
    43          Z7      550  CTTTTCCTtCTaCGCTGGAGTTGATGCC
                              |||| ||||||| ||||||||||||||
    42          Z6      550  CTTTTCCTCTTCGCTGGAGTTGATGCC 42-43 consensus (Z6)         CTTTTCCTcTtCGCTGGAGTTGATGCC
```

FIGURE 1G-1

| SEQ ID NO: | Isolate | |
|---|---|---|
| 45 | SA1 | 1   GTtCCCTACCGgAATGCCTCTGGGGTTTACCATGTCACCAATGAcTGCCCAAACTCcTCCA |
| 47 | SA5 | 1   GTCCCCTACCGgAAATGCCTCTGGGGTTTATCATGTCACCAATGATTGCCCAAACTCTTCCA |
| 49 | SA7 | 1   GTCCCCTACCGgAAATGCCTCTCGGGGTTTATCATGTCACCAATGATTGCCgAACTCTTCCA |
| 46 | SA4 | 1   GTCCCCTACCGAAAcGCCTCTGGGGTTTATCATGTCACCAATGATTGCCCAAACTCTTCCA |
| 50 | SA13 | 1   GTTCCCTACCGAAATGCCTCTGGGGTTTATCATGTCACCAATGATTGCCCAAACTCTTCCA |
| 48 | SA6 | 1   GTTCCtTACCGgAATGCCTCTGGGGTgTATCATGTtACCAATGATTGCCCAAACTCTTCCA |
| 45-50 | consensus | GTcCCTACCGaAATGCCTCTgGGGGTtTAtCATGTCACCAATGAtTGCCaAACTCtTCCA |

| SEQ ID NO: | Isolate | |
|---|---|---|
| 45 | SA1 | 62  TAGTCTACGAGGCTGATAgCCTGATCtTGCACGCACCTGGcCTGCCGTGCCCTGTGTCAgGcA |
| 47 | SA5 | 62  TAGTCTACGAGAGCTGATAACCTGATTCTGCACGCACCTGGTTGCGTGCCCTGTGTCAaGgA |
| 49 | SA7 | 62  TAGTCTAtGAGGCTGAcAACCTGATCCTGCACGCACCTGGTTGCGTGCCCTGTGTCAgACA |
| 46 | SA4 | 62  TAGTCTACGAGGCTGATAACCTGATCTTGCAtGCACCTGGTTGCGTGCCtTGTGTCAGGCA |
| 50 | SA13 | 62  TCGTCTACGAGGCTGATGACCTGACCTGATCTTACACGCACCTGGTTGCGTGCCCTGTGTtAGGCA |
| 48 | SA6 | 62  TaGTCTAtGAGGCTGATGACCTGATGACCTGATGATCCTACACGCACCTGGcCTGCGTGCCCTGTGTccGGaA |
| 45-50 | consensus | TaGTcTAcGAGGCTGAtaaCCTGATc-TgCAcGCACCTGGtTGCCGTGCCCTGTGTcaggcA |

FIGURE 1G-2

| SEQ ID NO: | Isolate | | |
|---|---|---|---|
| 45 | SA1 | 123 | AGaTAAATGTCAGTAGGTGCTGGGTCCAAATCACCCCCACACTGTCAGCCCCGAcCTTCGGA |
| 47 | SA5 | 123 | AGgTAAATGTCAGTAGGTGCTGGGTCCAAATCACCCCCACATTGTCAGCCCCGAAACCTCGGA |
| 49 | SA7 | 123 | AaATAAATGTCAGTAGGTGCTGGGTCCAAATCACCCCCACATTGTCAGCCCCGAACCTCGGA |
| 46 | SA4 | 123 | AGATAAATGTCAGTAaGTGCTGGGTCCAAATCACCCCCACGTTGTCAGCCCCGAAtCTCGGA |
| 50 | SA13 | 123 | GGaTAAATGTCAGTAGGTGCTGGGTCCAgATCACCCCCACACTGTCAGCCCCGAGCCTCGGA |
| 48 | SA6 | 123 | GGaTAAATGTCAGTAGaTGCTGGGTtCAtATCACCCCCACTaTCAGCCCCGAGCCTCGGA |
| 45-50 | consensus | | agaTAAATGTCAGTAggTGCTGGGTCCAaATCACCCCCACa-TgTCAGCCCCGAaccTCGGA |

| SEQ ID NO: | Isolate | | |
|---|---|---|---|
| 45 | SA1 | 184 | GCGGTCACGGCTCCTCTTCGGAGGGCCGTTGACTACTTAGCGGGAGGaGCTGCtCTCTGCT |
| 47 | SA5 | 184 | GCGGTCACGGCTCCTCTTCGGAGGGtCGTTGACTACTTAGCGGGAGGGGCTGCCCTCTGCt |
| 49 | SA7 | 184 | GCGGTCACGGCTCCTCTTCGGAGGGCCGTTGACTACcTAGCGGGAGGGGCTGCCCTCTGCT |
| 46 | SA4 | 184 | GCGGTCACGGCTCCTCTTCGGAGGGCCGTTGACTACTTAGCGGGAGGGGCTGCCCTCTGCT |
| 50 | SA13 | 184 | GCGGTCACGGCTCCTCTTCGGAGGGCCGTTGACTACTTAGCGGGAGGGGCTGCCCTtTGCT |
| 48 | SA6 | 184 | GCGGTCACGGCTCCTCTTCGGAGGGCCGTTGAtTACTTgGCGGGaGGGGCGCCCTgTGCT |
| 45-50 | consensus | | GCGGTCACGGCTCCTCTTCGGAGGGCcGTTGAcTACtTAGCGGGaGGGGCtGCCCTcTGCT |

FIGURE 1G-3

| SEQ ID NO: | Isolate | | |
|---|---|---|---|
| 45 | SA1 | 245 | CCGCACTATACGTCGGcGACGCGTGCCGGGGGCAGTGTTcCTGGTAGGCCAAATGTTCACCTA |
| 47 | SA5 | 245 | CCGCACTATACGTCGGGGACGCGTGCCGGGGGCAGTGTTcCTGGTAGGCCAAATGTTCACCTA |
| 49 | SA7 | 245 | CCGCGCTATACGTCGGGGACGCGTGCCGGGGGCAGTGTTTTTGGTAGGCCAgATGTTCAgCTA |
| 46 | SA4 | 245 | CCGCaCTATACGTCGGGGACGCGTGCCGGGGGCAGTGTTTTTGGTAGGCCAAATGTTCACCTA |
| 50 | SA13 | 245 | CCGCGTTATACGTCGGAGAGACGCGTGCGGGGGCAGTGTTTTTGGTAGtCAAATGTTCACCTA |
| 48 | SA6 | 245 | CCGCGTTATACCGTCGGAGAGACGTGTGCGGGGCATTGTTTTTTGGTAGGCCAAAATGTTCACCTA |
| 45-50 | consensus | | CCGC-cTATACGTCGGgGACGcGTGCGGGGGCAgTGTTcttGGTAGGCCAaATGTTCaccTA |

| SEQ ID NO: | Isolate | | |
|---|---|---|---|
| 45 | SA1 | 306 | TAGGCCTTCGCCAGCATACCACAGTGCAGGACTGCAACTGTTCCATTTACAGtGGCCATATC |
| 47 | SA5 | 306 | TAGGCCTTCGCCAGCATACTACGGTGCAGGACTGCAACTGTTCCATTTACAGcGGCCATATC |
| 49 | SA7 | 306 | TAGGCCTTCGCCAGCACACTACGGTGCAGGACTGCAACTGTTCCATTTACAGTGGCCATATC |
| 46 | SA4 | 306 | TAGGCCTTCGCCAGCACACTACGGTGCAAGACTGCAAtTGcTCtATTTACAGTGGCCATATC |
| 50 | SA13 | 306 | TAGGCCCTCGCCggCATAaTgttGTGCAGGACTGCAACTGtTCCATTTACAGTGGCCACATC |
| 48 | SA6 | 306 | TAGgCCCTCGCCAGCATgcTacgGTaCAGGACTGCAACTGCTCCATTTACAGTGGCCALATC |
| 45-50 | consensus | | TAGgCCTTCGCCAGCAtactacgGTgCAggACTGCAAcTGtTCcATTTACAGtGGCCAtATC |

FIGURE 1G-4

| SEQ ID NO: | Isolate | | |
|---|---|---|---|
| 45 | SA1 | 367 | ACCGGCCACCGgATGGCtTGGGACATGATGATGAATTGGTCACCTACGACACAGCCTTGCTGA |
| 47 | SA5 | 367 | ACCGGCCACCGAATGGCATGGACATGATGATGAATTGGTCACCTACGACACAGCCTTGGTGA |
| 49 | SA7 | 367 | ACCGGCCACCGAATGCATGGACATGATGATGAATTGGTCACCTACGACACAGCCTTGGTGA |
| 46 | SA4 | 367 | ACCGGCCACCGGATGGCATGGACATGATGATGAATTGGTCACCTACGACGGCCTTGCTGA |
| 50 | SA13 | 367 | ACCGGCCACCGGATGGCATGGACATGATGATGAATTGGTCACCTACAaACAGCtTTGGTGA |
| 48 | SA6 | 367 | ACtGGCCACCGGATGGCATGGACATGATGATGAATTGGTCACCgCgACAGCcTTGGTGA |
| 45-50 | consensus | | ACcGGCCACCGgATGGCaTGGGACATGATGATGAATTGGTCACCtaCgACaGCCTTGgTGA |

| SEQ ID NO: | Isolate | | |
|---|---|---|---|
| 45 | SA1 | 428 | TGGCCCAGaTGCTACGGATcCCCCAgGTGGTCATaGACATCATaGCCGGGGCCACTGGGG |
| 47 | SA5 | 428 | TGGCCCAGaGTTGCTACGGATTCCCCAaGTGGTCATtGACATCATtGCCGGGGCCACTGGGG |
| 49 | SA7 | 428 | TGGCCCAGAGTTGCTACGGATTCCCCAGTGGTCATGACATCATTGCCGGGGCCACTGGGG |
| 46 | SA4 | 428 | TGGCCCAGAGTTGCTACGGATTCCCCAGTGGTCATCGACATCATTGCCGGGGCCACTGGGG |
| 50 | SA13 | 428 | TGGCCCAGTTGtTACGGATTCCCCAGTGGTCATTGACATCATTGCCGGGCCCACTGGGG |
| 48 | SA6 | 428 | TGGCCCAaaTGCTACGGATTCCCCAGTGGTCATTGACATCATTGCCGGGgCCACTGGGG |
| 45-50 | consensus | | TGGCCCAgtTGCTACGGATtCCCCAgtGTGGTCATtGACATCATtGCCGGGGCCACTGGGG |

FIGURE 1G-5

| SEQ ID NO: | Isolate | | |
|---|---|---|---|
| 45 | SA1 | 489 | GGTCTTGTTGCCGccGCATACTTtGCGTCgGCCGCCAACTGGGCTAAGGTaGTGCTGGTt |
| 47 | SA5 | 489 | GGTCTTGTTCGCCGtCGCATACTTCGCGTCAGCGGCTAAACTGGGCTAAGGTTGTGCTGGTC |
| 49 | SA7 | 489 | GGTCTTGTTCGCCGCCGCATATATTCGCGTCAGCGGCTAAACTGGGCTAAGGTTGTGCTGGTC |
| 46 | SA4 | 489 | GGTCTTGTTCGCCGCCGCATATATTCGCGTCAGCGGCTAAACTGGGCTAAGGTTGTGCTGGTC |
| 50 | SA13 | 489 | GGTCTTGTTCGCCGCCGCATACTaCGCGTCGGCGGCTAAACTGGGCTAAGGTTaTaCTGGTC |
| 48 | SA6 | 489 | GGTCTTGTTCGCCGCtGCATACTtCGCGTCGGCGGCTAAACTGGGCCAAGGTTGTGCTGGTC |
| 45-50 | consensus | | GGTCTTGTTcGCCGccGCATAcTtcGCGTC-GCgGCtAACTGGGCtAAGGTTgTgCTGGTc |

| SEQ ID NO: | Isolate | | |
|---|---|---|---|
| 45 | SA1 | 550 | CTGTTcCTGTTTGCGGGGGTCGATGGC |
| 47 | SA5 | 550 | CTGTTTCTGTTTGCGGGGGTCGATGGC |
| 49 | SA7 | 550 | TTGTTTCTGTTTGCGGGGGTCGATGCC |
| 46 | SA4 | 550 | TTGTTTCTGTTTGCGGGGGTCGATGCC |
| 50 | SA13 | 550 | cTGTTTCTGTTTGCGGGGGTCGATGCC |
| 48 | SA6 | 550 | tTGTTTCTGTTTGCGGGGGTtGATGCC |
| 45-50 | consensus | | -TGTTtCTGTTTGCGGGGGTcGATGcC |

FIGURE 1H-1

| SEQ ID NO: | Genotype | | |
|---|---|---|---|
| 30-33 | (IV/2b) | 1 | GTGGAAGTcAGgAACAtCAGTtCtaGCtACTAcGCCACCAATGATTGCTCaAACaACAGCA |
| 34 | (2c) | 1 | GTGGAGGTCAAGACACGGCGACTCCTACATGCCGACCAACGATTGCTCCAACTCTAGTA |
| 26-29 | (III/2a) | 1 | GccCAAGTGGCGAAgAGAACACCAgtaCCaGcTACAATGGTGACCAACGACTGtTCCAATGACAGCA |
| 35-39 | (V/3a) | 1 | cTAGAGTGGCGGAATAcGTCTGGCCTCTAtGTCCTtACCAACGACTGTtCCAATAGCAGTA |
| 9-25 | (II/1b) | 1 | tAtGAaGTGCgCAAGTGTgTCCGGGgtgTAccAtGTCACgAAcGACTGCTCCAACTcaAGca |
| 1-8 | (I/1a) | 1 | tACCAAGTgCGCAACTCcaCgGgCTTtTACCATGTCACCAATGAtTGCCCTAAcTCGAGtA |
| 40 | (4a) | 1 | GAGCACTACCGGAATGCTTCGGGCATCTATCACATCACCAATGATTGTCCGAATTCCAGTA |
| 42-43 | (4c) | 1 | GTtAACTATCgCAATGCCTCGGGCGTCTATCACgTCACCAACGACTGCCCGAACTCGAGCA |
| 44 | (4d) | 1 | TACAACTATCGCAACAGTCGGGCTGTCTACCATGTCACCAACGATTGCCCTAACACCAGCA |
| 41 | (4b) | 1 | GTGCACTACCGGAATGCTTCGGGCGTCTATCATGTCACCAATGATTGCCCAaAACTCtTCCA |
| 45-50 | (5a) | 1 | GTtCCcTACCGaAAtGCCTCtGGGGTtTAtCATGTCACCAATGATTGCCCAACTCCAGCA |
| 51 | (6a) | 1 | CTTACCTACGGCAACTCCAGTGGGCTATACCATCTCACAAATGATTGCCCAACTCCAGCA |

1-51 consensus                                    A           TA              AC AA GA TG    C  AA

| SEQ ID NO: | Genotype | | |
|---|---|---|---|
| 30-33 | (IV/2b) | 62 | TCACCTGGCCAaCTCACCaACGCAGTtCTCCACCTTCCCGATGCGTCCaTGTGAGAATGA |
| 34 | (2c) | 62 | TCGTTTGGCAGCTTGAAGAGCAGTGCTTCATATCTGGATGCGTCCTTGTGAGCGTAC |
| 26-29 | (III/2a) | 62 | TCACcTGGCAaCTccAgCccAgTccAgTcCACCTCCCGGGTGtGTCCGTGCGAGAagt |
| 35-39 | (V/3a) | 62 | TtGTGTATGAGGCCGATGACGTcATTCTGCACACACCtGGCTGCTGTACCTTGTGTTCAGGA |
| 9-25 | (II/1b) | 62 | TtGTGTATGAGGCAgcgGACaTGACaTGATcaTGCAcAccCCGGTGcgTgCCTGcGTtCgGGA |
| 1-8 | (I/1a) | 62 | TtGTGTACGAGGCGCGCCATgCCATcCTgCAcaCtCCgGGTGTGTCcCTTGCGTTCgCGA |
| 40 | (4a) | 62 | TAGTCTATGAAGCTGACCATCACATCCTACACTTGCCGGGTGCGTACCCTGTGTGATGAC |
| 42-43 | (4c) | 62 | TAgTGTATGAGGCCGAAACCGATTACCACATCTACACCTTACACCTCCCGGGATGCGTCTTGCGTGAGGGt |
| 44 | (4d) | 62 | TAGTCTATGAAACCGATTACCACATCTTACACCTTACACCTCCCGGGATGCGTTCCTTGCGTGAGGGA |
| 41 | (4b) | 62 | TAGTGTACGAGACGGAGCACCACATCACTTGCCAGGTGTGTCCCCTGTGCGAC |
| 45-50 | (5a) | 62 | TaGTcTAcGAGGCTGAtaaCCTGATcTTgCAcGCACCTGGtTGCGCCTGTGTcaggcA |
| 51 | (6a) | 62 | TCGTGCTGGAGGCGGATGCTATGATGTCATTTGCATTTGCCTGGATGCTTGCCTTGTGTGAGGGT |

1-51 consensus   T    A         T  T CA           CC GG TG   T CC  TG    G

FIGURE 1H-2

| SEQ ID NO: | Genotype | |
|---|---|---|
| 30-33 | (IV/2b) | 123 cAATGGCACCcTGCgCTGCTGGATACAAGTgACACCTAATGTGGCTGTGAAACACCGcGGC |
| 34 | (2c) | 123 CGCCAACGTCTCTCGATgTTGGGTGCCGGTTGCCCCCAATCTCGCCATAAGTCAACCTGGC |
| 26-29 | (III/2a) | 123 gGGAAAtaCaTCtCGgTGCTGGATACCGGTctCaCCAAAcGTGGcGTGCaGCaGCCCGGC |
| 35-39 | (V/3a) | 123 CGGCAATACATCcAcGTGCTGGACCcCagTGACACCTACAgTGACGTCAGTACGTCGGA |
| 9-25 | (II/1b) | 123 gaacAActcCTCccgcTGCTGGGTaGGCTcactCCCACgtCtCGggCTcGgCAGGAAacgccAgC |
| 1-8 | (I/1a) | 123 GGgTaaCgcctCGAggTGTTGGGTGgCGgTGaCCCCCACgGTGgCCACcAGGGAcGGCAAa |
| 40 | (4a) | 123 TGGGAACACATGCGTTGCTGCTGGACGCCGGTGACGCCTACAGTGGCTGTGCACACCGGGC |
| 42-43 | (4c) | 123 tGGGAAtCAGTCACGCTGCTGCTGGGTGGGCCCTTACTCCACCGTGGcGgtCTTATATCGGT |
| 44 | (4d) | 123 AGGGAACAAGTCTACATGCTGGGTGTCTCTCACCCCACCGTGGCTGCGCAACATCTGAAT |
| 41 | (4b) | 123 GGAGAATACTTCTCGCTGCTGCTGGGTGCCCTTGACCCCCACTGTGGCCGCGCCTATCCAAC |
| 45-50 | (5a) | 123 agaTAATGTCAGTAggTGCTGGGTcCAaaATCACCCCACatTgTCAGCCCGAaccTCGGA |
| 51 | (6a) | 123 CGATGATCGGTCCACCTGTTGGCATGCTGTGACCCCACCCTGGCCATACCAAATGCTTCC |

1-51 consensus            TG TGG     T C CC A   T C

| SEQ ID NO: | Genotype | |
|---|---|---|
| 30-33 | (IV/2b) | 184 GCaCTcACTCACaAACCTGCGAaCaCAtgTcGAcaTGATCGTAATGGCAGCTACGGTCTGCT |
| 34 | (2c) | 184 GCTCTCACTAAGGCCTGCCTGGAGCACACACATCGATATCATCGTGATGTCTGTACGGTCTGTT |
| 26-29 | (III/2a) | 184 GCcCTcACGCAGGCTTGCGGACGCACATGACATGGTTGTGATGTCCGCAGCTCTGCT |
| 35-39 | (V/3a) | 184 GCAACCACCGCTTCGATACGCAGCTCATGTGACCTCATGTGGACCTCaTTaGTGGGCGGCCACGaTGTGCT |
| 9-25 | (II/1b) | 184 gTCcCACTAcGaCaATACGACGCCACGTCGATTGCTCGTCGTTGGGGCCTTgctTTCTGCT |
| 1-8 | (I/1a) | 184 CTCCCgCAAcGCAgcTTcGACGTtCGACGTCACATGCATGGGACTTGTCGgGAGcGCCACCCTCTGcT |
| 40 | (4a) | 184 GCTCCGCTTGAGTCGTTCCGGCGACATGTGGACTTAATGTAGGCGCGGCCCACTTTGTGTT |
| 42-43 | (4c) | 184 GCtCCGCTTGACTCCcTCCGGAGACCTTGACCTGATGGTGCCGCCGCTACTGTaTGCT |
| 44 | (4d) | 184 GCTCCGCTTGAGTCTTTGAGACTGCCAGCACGTAGACCTGACCTGATGGTGGGGCGCCCACTCTCTGCT |
| 41 | (4b) | 184 GCACCGTTAGAGTCCATGCGCAGGCATGTAGACGTTGACTACTAGCCGGaGGGGTCGCCCTCTGCT |
| 45-50 | (5a) | 184 GCGGTCACGGCTCCCTTCTTCGGAGGCGCGGTTGACTACTAGCCGGaGGGGTCGCCCGCCGAGTGTTGCT |
| 51 | (6a) | 184 ACGCCCGCAACGGGGATTCCGCAGGCATGTGGATCTTCTGCGGCCGCCAGTGTTTGCT |

1-51 consensus         T G     T GA     T G     GC     T TG T

FIGURE 1H-3

| SEQ ID NO: | Genotype | | |
|---|---|---|---|
| 30-33 | (IV/2b) | 245 CGGCCTTGTATGTGGaGaACgTgTGCGGGGCCGTGATGATcGtGTGCGAGGCTtTCATAaT |
| 34 | (2c) | 245 CTGCCCTTTATGTGGGGACGTGTGTGGCGCGCGGGGtgATGCTGGCGCGTCAGTGTCGTCGT |
| 26-29 | (III/2a) | 245 CcGCtCTTtACGTGGGGGGAccTCTGCGCGGCCGGtgATGCTCGCaGCCCAgATGTTCATtgT |
| 35-39 | (V/3a) | 245 CTGCGCTCTACGTGGGtGATATGTGTGGGCCGTCTGTtCTcGTGGGACAAGCCTTCACGTT |
| 9-25 | (II/1b) | 245 CCGctATGTACGTGGGGGAtCTCTGCGGaTCTGTCTgTtCTCCTcgTcTCCAGCTGTTCACcTT |
| 1-8 | (I/1a) | 245 CGGCCCTTCTACGTGGGGGACtTGTGCGGGTCTGTCTgTtCTgCTgtCAaCTGTTCACcTT |
| 40 | (4a) | 245 CTGCCCTCTATGTTGGGGACCTCTGCGGAGTGCCTTCCTGATGGGCAGATGATCACTTT |
| 42-43 | (4c) | 245 CtgCCCTCTACgTTGGaGAtCTGTGCGGTGGtGcATTCTTGGTTGGcCAGATGTTcTCTT |
| 44 | (4d) | 245 CCGCCCTCTACATCGGAGACGTGTGTGGGGTGTCTCTCCTAGTGGGCCAGCTGTTGACTT |
| 41 | (4b) | 245 CCGCCCTTCTACATTGGAGATCTGTGTGGGAGGCGTCTTCCTAGTGGGCCAGCTGTTGACTT |
| 45-50 | (5a) | 245 CCGCgCTATACGTCGGGGACGCGTGCGGCAGtGTTtTGGTAGGcCAaATGTTCAcCTA |
| 51 | (6a) | 245 CATCCCTGTACATCGGGGACCCTGTGCTCTCTCTTTTGGCGGGACAACTATTCACCTT |
| 1-51 | consensus | C T TA T GG GA TG GG T T CA T |

| SEQ ID NO: | Genotype | | |
|---|---|---|---|
| 30-33 | (IV/2b) | 306 ATCGCCaGAAACgCCAcAACTTtACCCaaGAGTGCAACTGTTCCATCTACCAAGGTCatATC |
| 34 | (2c) | 306 GTCGCCACACAACATACGTTTGTCCAGGAATGCAACTGTTCCATATACCCGGGCCGCATT |
| 26-29 | (III/2a) | 306 CTCGCCGCaaCacCACTgGTTGTTGTGCAAcACCTGCAATGCTCCATCCAtCtGGtACCATC |
| 35-39 | (V/3a) | 306 CAGACCTCGTCGCCGCCATCAAACgGTCCAGACCTGTAACTGCTGCTGTACCAGGCCATcTT |
| 9-25 | (II/1b) | 306 cTTCGCTCCGcCGgcATgAGACagtaCAGgACTGCAAcAACTGCAAATGTTCTaTCCgGcCacgTa |
| 1-8 | (I/1a) | 306 cTTCtCCCAGgCgCCACTGGACAACGCAAgACTGCAAGAGTGCAATTGTTCTaTCtATCCgGCCATATa |
| 40 | (4a) | 306 TCGGCCGCCGTCGCCGACGCCACTGGACTACGCCAGGACTGCAATTGCTCATCTACACTGGCCATATC |
| 42-43 | (4c) | 306 CCAGCCGCGGACGCCACTGGACTACGCCAGGACTGCAATTGCTCATCTAcgCaGgGCATaCATATC |
| 44 | (4d) | 306 CCAACCTCGCCGCCGGACCACCCAAGACTGCAATTGTCCATCTACACAGGACATATC |
| 41 | (4b) | 306 CCGACCGCGCCGGACTGGACTGGACGATTGCAACTGCTCCATCTATCCTGTCACGTC |
| 45-50 | (5a) | 306 TAGgCCTTCGCCaGCATactacgGTgCAGGACTGCAACTGtCTCCATTTACAGtGGCCATATC |
| 51 | (6a) | 306 TCAGCCCCGCCGTCATTGGACTGTGCAAGACTGCAACTGCTCCATCTATACAGGCCACGTC |
| 1-51 | consensus | CA TG AA TG TC T TA GG T |

FIGURE 1H-4

| SEQ ID NO: | Genotype | | |
|---|---|---|---|
| 30-33 | (IV/2b) | 367 | ACCGGCCACCGCATGGCatGGACATGATGCTaAACTGGTCACCAACTCTtACCATGATCC |
| 34 | (2c) | 367 | ACGGGaCACCGCATGGCTTGGATATGATGATGATGAACTGGTCGCCACTACCACCATGCTCC |
| 26-29 | (III/2a) | 367 | ACtCGGaCACCGTATGGCATGGACACATGATGATGATGATGAACTGGTCGCCACGgCCACcatGATCc |
| 35-39 | (V/3a) | 367 | TCAGGACATCACCGCATGGCTTGGATATGATGATGATGAATTGGTCCCCCGCtGTGGGTATGGTGG |
| 9-25 | (II/1b) | 367 | tCAGGTCACcCGCATGGCTCaTGGACATGGATATGATGATGAACTGTCACTCACAgCaGCccTaGTgg |
| 1-8 | (I/1a) | 367 | ACGGtCAcCGCATGGCaTGGCaTGGATATGATGATGATGAACTGTCCCCTACgaCgCgCgCTGTag |
| 40 | (4a) | 367 | ACCGGCCACAGGATGCGTGGACATGGACATGATGATGAACTGGACCCTACCACCACTCTGCTCC |
| 42-43 | (4c) | 367 | ACgGGCCACCAGAtGCATGGCATGCATGCATGGACATGATGATGAACTGGAGCCTCCACAACCCTgCTtC |
| 44 | (4d) | 367 | ACAGGACACAGAATGGCTTGGACATGGACATGATGATGATGAATTGGAGCCCCACTGCGACGCTGGTCC |
| 41 | (4b) | 367 | TCGGGCCACAGGATGGCCTGGACATGGACATGATGATGATGAACTGGAGCCTACCAGCGCGCTGATTA |
| 45-50 | (5a) | 367 | ACCGGCCACCGcATGGCgATGGCATGGCTTGGACATGATGATGATGAACTGGTCACtaCgAcaGcCTTgGTGA |
| 51 | (6a) | 367 | ACCGGCCACAGGATGCTTGGACATGGACATGATGATGATGAACTGGTCACCCACCAACCACTCTGGTCC |
| 1-51 | consensus | | C GG CA G ATGGC TGGGA ATGATG T AA TGG CC C T T |

| SEQ ID NO: | Genotype | | |
|---|---|---|---|
| 30-33 | (IV/2b) | 428 | TcGCCTAtGCcGCtCGTGTtCCTGagCTAgtCCTgAaGTtGTCTtCGGcGGcCATTGGGG |
| 34 | (2c) | 428 | TGGCGTACTTGGTGCGCATCCGGAAGTCATCTTGGATATTGTTACAGGAGTCATTGGGG |
| 26-29 | (III/2a) | 428 | TGGCGTACGcGATGCGTTCCCGAGGTCATCATAGACATCATtaGCGGGgCCTACtCGGGG |
| 35-39 | (V/3a) | 428 | TgGCGCACgTCCTGCGTtTGCCCCAGACCtGTTCGACATAaTaGCCGGGCCCATTGGGG |
| 9-25 | (II/1b) | 428 | TaTCGCAgtTaCTCCGgaTCCaCAAGCTgTCgTGGAcaTGGTggCgGGgGCCCACTGGGG |
| 1-8 | (I/1a) | 428 | TaGCtCAGCTGCTCcGaTCCgCAagCCaTCTTGGACATGATGCGTTGCCGGAGGCACTGGGG |
| 40 | (4a) | 428 | TCGCCCAGATCATGAGGGTCCCACACTCTTCTGGTaGAtCTACTCgCTGGAGGGCACTGGGG |
| 42-43 | (4c) | 428 | TCGCCCAGTcATGAGGATCCTAGAGCGCCATGGTCGACCTGCTTGCTGCAGGCGGCACTGGGG |
| 44 | (4d) | 428 | TCGCCCAACTTATGAGGATCCCAGGCGCCATGTCGACCTGGTGACTGGTCACTGGGG |
| 41 | (4b) | 428 | TGGCTCAGATCTTACGGATCCCCTATCCTAGGTGACTTGCTCACCGGGGTCACTGGGG |
| 45-50 | (5a) | 428 | TGGCCCAgtTGcTACGGATcCCCAGGTGGTCATtGACATCATtGCCGGGGgCCACTGGGG |
| 51 | (6a) | 428 | TATCTAGCATCTTGAGGGTACTACCTGAGATTTGTGCGAGTGTGATATTTGGTGGCCATTGGGG |
| 1-51 | consensus | | T C G T CC T T GG G CA TGGGG |

FIGURE 1H-5

| SEQ ID NO: | Genotype | | |
|---|---|---|---|
| 30-33 | (IV/2b) | 489 | cGTGGtGTGTTTGGCTTGCCTATTTCTCCATGCAggGAGCGTGGGCCAAaGTCATgCCATC |
| 34 | (2c) | 489 | TGTAAtGTTTGGCCTCGCTTACTTCTCCATGCAGGATCGTGGGCGAAGGTCATCGTTATc |
| 26-29 | (III/2a) | 489 | CGTCaTGTTcGGCttaGCCTAGCCTACTTCTCTAGGAGCGTGGGCGAAaGTCgTTGTCATC |
| 35-39 | (V/3a) | 489 | CATCtTGGCgGGCGGGGGCCTtGCCTAGCCTATTACTCCATGCAgGCAACTGGCCAAGGTCGCTATcaTC |
| 9-25 | (II/1b) | 489 | agTCCTggCGGGGCCTtGCCTACTATtCCATGGtgGGgAACTGGGCtAAGGTtTgATTGTg |
| 1-8 | (I/1a) | 489 | AGTCCTaGCGGGGCATAGCGTATTtCTCCATGCATGGTGGGgAACTGGGCGAAGGTCcTggTaGTg |
| 40 | (4a) | 489 | CGTCCTCGCGGGCTTGGCGTACTTCAGCATGCAAGGCAATTGGGCCAAGGTAGTCCTGGTC |
| 42-43 | (4c) | 489 | cgTCCTTgTtGGGtTGGCgTACTTCagTATGCAAGCTAATTGGGCCAAaGTCATCCTGGTC |
| 44 | (4d) | 489 | CATTCTGGTTGGCATAGCGTACTTCAGCATGCAAGCTAATTGGGCCAAGGTTATCCTGGTC |
| 41 | (4b) | 489 | AGTTCTTGCTGGTCTAGCTTTCTTCAGCATGCAGAGTAACTGGGCGAAGGTCATCCTGGTC |
| 45-50 | (5a) | 489 | GGTCTTGTTCGCCGCCATACTtcGCGTCgGCTAACTGGGCtAAGGTtgTgCTGGTc |
| 51 | (6a) | 489 | GATACTACTAGCCGTTGCCTACTTGGCATGCTGGCAACTGGCTAAAAGTTCTGGCTGTT |

| 1-51 | consensus | T T G GC T T TGG AA GT T |

| SEQ ID NO: | Genotype | | |
|---|---|---|---|
| 30-33 | (IV/2b) | 550 | CTCCTtCTTGTcGCAGGAGTGGAtGCA |
| 34 | (2c) | 550 | CTCCCTGCTGACTGCTGGGGTGGAGGCG |
| 26-29 | (III/2a) | 550 | CTttTGCTggCcGCTGGgGTGGACGCG |
| 35-39 | (V/3a) | 550 | ATGgTTATGTTTTCAGgGGTCGAtGCC |
| 9-25 | (II/1b) | 550 | aTGCTACTcTTTGCcggCGTtGAcGGg |
| 1-8 | (I/1a) | 550 | CTGtTGCTgTTtgCCGGCGTcGAtGCG |
| 40 | (4a) | 550 | CTTTTCCTCTTGCTGGGGTAGACGCC |
| 42-43 | (4c) | 550 | CTGTTCCTCTCGCTGGAGTTGATGCC |
| 44 | (4d) | 550 | CTGTTCCTCTTTGCCGGGGTCGACGCT |
| 41 | (4b) | 550 | CTATTCCTCTTTGCCGGGGTCGAGGGA |
| 45-50 | (5a) | 550 | tTGTTTCTGTTTGCGGGGGTCGATGcC |
| 51 | (6a) | 550 | CTGTTCCTATTTGCAGGGGTTGAAGCA |

| 1-51 | consensus | T T T C GG GT GA G |

FIGURE 2A-1

| SEQ ID NO: | Isolate | |
|---|---|---|
| 56 | S14 | 1 YQVRNSTGLYHVTNDCPNSSIVYEtADAILHaPGCVPCVREGNtSRCWVAMTPTVATRDGK |
| 52 | DK7 | 1 YQVRNSTGLYHVTNDCPNSSIVYEAADAILHTPGCVPCVREGNvSRCWVAMTPTVATRDGK |
| 59 | US11 | 1 YQVRNSTGLYHVTNDCPNSSIVYEAADAILHTPGCVPCVREGNaSRCWVAMTPTVATRDGK |
| 55 | DR4 | 1 YQVRNSTGLYHVTNDCPNSSIVYEAADAILHTPGCVPCVREGNtSRCWVAVTPTVATRDGK |
| 54 | DR1 | 1 HQVRNSTGLYHVTNDCPNSSIVYEAADAILHaPGCVPCVREGNASRCWVAVTPTVATRDGK |
| 53 | DK9 | 1 HQVRNSSGLYHVTNDCPNSSIVYEAADAILHSPGCVPCVREGNASKCWVAVAPTVATRDGK |
| 58 | SW1 | 1 YQVRNSSGLYHVTETADAILHSPGCVPCVREdgApKCWVAVAPTVATRDGK |
| 57 | S18 | 1 YQVRNStGLYHVTNDCPNSSIVYETADtILHSPGCVPCVREgnAsrCWVpVAPTVATRDGK |
| 52-59 | consensus | yQVRNStGLYHVTNDCPNSSIVYEaAdAILH-PGCVPCVREgnasrCWVavtPTVATRDGK |

| SEQ ID NO: | Isolate | |
|---|---|---|
| 56 | S14 | 62 LPatQLrRRyIDLLVGSATLCSALYVGDLCGSVFLVGQLFTFSPRRlWTTQDCNCSIYPGHI |
| 52 | DK7 | 62 LPTaQLRRHIDLLVGSATLCSALYVGDLCGSVFLVGQLFTFSPRRHWTTQGCNCSIYPGHI |
| 59 | US11 | 62 LPTTQLRRHIDLLVGSATLCSALYVGDLCGSVFLVGQLFTFSPRRHWTTQDCNCSIYPGHI |
| 55 | DR4 | 62 LPTTQLRRHIDLLVGSATLCSALYVGDLCGSVFLVGQLFTFSPRhHWTTQDCNCSIYPGHI |
| 54 | DR1 | 62 LPTTQLRRHIDLLVGSATLCSALYVGDLCGSVFLVGQLFTFSPRRHWTTQDCNCSIYPGHI |
| 53 | DK9 | 62 LPATQLRRHIDLLVGSATLCSALYVGDLCGSVFLVGQLFTFSPRRHWTTQDCNCSIYPGHI |
| 58 | SW1 | 62 LPATQLRRHIDLLVGSATLCSALYVGDLCGSVFLVSQLFTFSPRRHWTTQDCNCSIYPGHI |
| 57 | S18 | 62 LPATQLRRHIDLLVGSATLCSALYVGDLCGSVFLVSQLFTiSPRRHWTTQdCNCSIYPGHI |
| 52-59 | consensus | LP-tQLRRHIDLLVGSATLCSALYVGDLCGSVFLVgQLFTfSPRrhWTTQdCNCSIYPGHI |

FIGURE 2A-2

| SEQ ID NO: | Isolate | | |
|---|---|---|---|
| 56 | S14 | 123 | TGHRMAWDMMMNWSPTTALVVAQLLRIPQAILDMIAGAHWGVLAGIAYFSMVGNWAKVLVV |
| 52 | DK7 | 123 | TGHRMAWDMMMNWSPTTALVVAQLLRIPQAILDMIAGAHWGVLAGIAYFSMVGNWAKVLVV |
| 59 | US11 | 123 | TGHRMAWDMMMNWSPTaALVVAQLLRIPQAILDMIAGAHWGVLAGIAYFSMVGNWAKVLVV |
| 55 | DR4 | 123 | TGHRMAWDMMMNWSPTTALVVAQLLRIPQAILDMIAGAHWGVLAGIAYFSMVGNWAKVLVV |
| 54 | DR1 | 123 | TGHRMAWDMMMNWSPTTALVVAQLLRIPQAILDMIAGAHWGVLAGIAYFSMVGNWAKVLVV |
| 53 | DK9 | 123 | TGHRMAWDMMMNWSPTaALVMAQLLRIPQAILDMIAGAHWGVLAGIAYFSMVGNWAKVVVV |
| 58 | SW1 | 123 | TGHRMAWDMMMNWSPTTALVvAQLLRIPQAVLDMIAGAHWGVLAGIAYFSMVGNWAKVLiV |
| 57 | S18 | 123 | TGHRMAWDMMMNWSPTTALViAQLLRvPQAVLDMIAGAHWGVLAGIAYFSMaGNWAKVL1V |
| 52-59 | consensus | | TGHRMAWDMMMNWSPTtALVvAQLLRiPQAiLDMIAGAHWGVLAGIAYFSMvGNWAKVlvV |

| SEQ ID NO: | Isolate | | |
|---|---|---|---|
| 56 | S14 | 184 | LLLFAGVDA |
| 52 | DK7 | 184 | LLLFAGVDA |
| 59 | US11 | 184 | LLLFAGVDA |
| 55 | DR4 | 184 | LLLFAGVDA |
| 54 | DR1 | 184 | LLLFAGVDA |
| 53 | DK9 | 184 | LLLFtGVDA |
| 58 | SW1 | 184 | LLLFsGVDA |
| 57 | S18 | 184 | LLLFaGVDA |
| 52-59 | consensus | | LLLFaGVDA |

FIGURE 2B-1

| SEQ ID NO: | Isolate | | |
|---|---|---|---|
| 75 | T10 | 1 | YEVRNVSGmYHVTNDCSNSSIVfEAaDlIMHTPGCVPCVREgNsSRCWVALTPTLAARNtS |
| 62 | DK1 | 1 | YEVRNVSGvYHVTNDCSNSSIVYEAvDvIMHTPGCVPCVRENNhSRCWVALTPTLAARNAS |
| 64 | HK4 | 1 | hEVhNVSGiYHVTNDCSNSSIVYEAADMIMHTPGCVPCVRENNSSRCWVALTPTLAARNAS |
| 76 | US6 | 1 | YEVRNVSGmYHVTNDCSNSSIVYEAADMIMHTPGCVPCVRENNSSRCWVALTPTLAARNAS |
| 68 | IND8 | 1 | YEVRNVSGVYHVTNDCSNSSIVYEAAADMIMHTPGCVPCVREGNfSsCWVALTPTLAARNAS |
| 67 | IND5 | 1 | YEVRNVSGVYHVTNDCSNSSIVYEAADMIMHTPGCVPCVREGNSSRCWVALTPTLAARNAS |
| 73 | SW2 | 1 | YEVRNVSGVYHVTNDCSNSSIVYETADMIMHTPGCVPCVREaNSSRCWVALTPTLAARNtS |
| 63 | HK3 | 1 | YEVRNVSGVYHVTNDCSNSSIVYETADMIMHTPGCVPCVRENNSSRCWVALTPTLAARNVS |
| 66 | HK8 | 1 | YEVRNVSGIYHVTNDCSNSSIVYETADMIMHTPGCVPCVRENNSSRCWVALTPTLAARNVS |
| 61 | D3 | 1 | YEVRNVSGVYqVTNDCSNSsvVYETADMIMHTPGCmPCVRENNSSRCWVALTPTLAARNsS |
| 74 | T3 | 1 | YEVRNVSGVYyVTNDCSNSSIVYETADMIMHTPGCVPCVRESNSSRCWVALTPTLAARNAS |
| 65 | HK5 | 1 | YEVRNVSGVYHVTNDCSN1SIVYEttDMIMHTPGCVPCVRENNSSRCWVALTPTLAARNAS |
| 71 | S45 | 1 | YEVRNVSGaYHVTNDCSNSSIVYEAvDvIlHTPGCVPCVRENNSSRCWVALaPTLAARNSS |
| 72 | SA10 | 1 | YEVRNVSGmYHVTNDCSNSSIVYEAADMIMHTPGCVPCVRENNSSRCWVALTPTLAARNSS |
| 69 | P10 | 1 | YEVRNVSGVYHVTNDCSNSSIVYEAADMIMHTPGCVPCVREdNSSRCWVALTPTLAARNSS |
| 60 | D1 | 1 | YEVRNVSGVYHVTNDCSNSSIVYEtADMIMHTPGCVPCVRENNSSRCWVALTPTLAARNgm |
| 70 | S9 | 1 | YEVRNVSGaYHVTNDCSNSSIVYEaADvIMHTPGCVPCVqEgNSSqCWVALTPTLAARNat |

60-76 consensus yEVrNVSGvYhVTNDCSNsSiVyEaaDmImHTPGCvPCVrEnNsSrCWVALtPTLAARNas

FIGURE 2B-2

| SEQ ID NO: | Isolate | | Sequence |
|---|---|---|---|
| 75 | T10 | 62 | vPTTTIRrHVDLLVGAAAFCSAMYVGDLCGSVFLVSQLFTFSPRRHET1QDCNCSIYPGH1 |
| 62 | DK1 | 62 | IPTTTIRRHVDLLVGAAAFCSAMYVGDLCGSVFLVSQLFTFSPRRHETaQDCNCSIYPGHV |
| 64 | HK4 | 62 | IPTTTIRRHVDLLVGAAAFCSAMYVGDLCGSVFLVSQLFTFSPRRHETVQDCNCSIYPGHV |
| 76 | US6 | 62 | VPTTTIRRHVDLLVGAAtFCSAMYVGDLCGSVFLiSQLFTFSPRqHETVQDCNCSIYPGHV |
| 68 | IND8 | 62 | IPTTTIRRHVDLLVGAAAFCSAMYVGDLCGSVFLVSQLFTFSPRRHETVQDCNCSIYPGHV |
| 67 | IND5 | 62 | VsTTTIRhHVDLLVGAAAFCSAMYVGDLCGSVFLVSQLFTFSPRRHETVQDCNCSIYPGHV |
| 73 | SW2 | 62 | VPTTTIRRHVDLLVGAAAFCSAMYVGDLCGSVFLVSQLFTFSPRRHETVQDCNCSIYPGHV |
| 63 | HK3 | 62 | VPTTTIRRHVDLLVGAAAFCSvMYVGDLCGSVFLVSQLFTFSPRRHETVQDCNCSIYPGHV |
| 66 | HK8 | 62 | VPTTTIRRHVDLLVGAAAFCSAMYVGDLCGSVFLVSQLFTFSPRRHETVQDCNCSIYPGHV |
| 61 | D3 | 62 | VPTTTIRRHVDLLVGAAAFCSAMYVGDLCGSVFLVSQLFTFSPRRHETVQeCNCSIYPGHV |
| 74 | T3 | 62 | VPTtKTIRRHVDLLVGAAAFCSAMYVGDLCGSVFLVSQLFTFSPRRHETVQDCNCSIYPGHV |
| 65 | HK5 | 62 | VPTTaIRRHVDLLVGAAAFCSAMYVGDLCGSVFLVSQLFTFSPRRHETVQDCNCSIYPGHV |
| 71 | S45 | 62 | VPTTTIRRHVDLLVGAAAFCSAMYVGDLCGSVFLVSQLFTFSPRRHETVQDCNCSIYPGHV |
| 72 | SA10 | 62 | VPTTTIRRHVDLLVGAAAFCSAMYVGDLCGSVFLVSQLFTFSPRRyETVQDCNCSIYPGrV |
| 69 | P10 | 62 | VPTTAIRRHVDLLVGAAAFCSAMYVGDLCGSV1LVSQLFTFSPRRHwTVQDCNCSIYPGHV |
| 60 | D1 | 62 | VPTTAIRRHVDLLVGAAvFCSAMYVGDLCGSVFLISQLFT1SPRRHETVQeCNCSIYPGHV |
| 70 | S9 | 62 | VPTTtIRRHVDLLVGAAAFCSAMYVGDLCGSVFLISQLFTiSPRRHETVQnCNCSIYPGHV |
| 60-76 | consensus | | vpTttIRrHVDLLVGAAaFCSaMYVGDLCGSVFLvSQLFTfSPRrheTvQdCNCSiYPGhv |

FIGURE 2B-3

| SEQ ID NO: | Isolate | | |
|---|---|---|---|
| 75 | T10 | 123 | SGHRMAWDMMMNWSPTTALVvSQLLRIPQAVmDMVtGAHWGVLAGLAYYSMAGNWAKVLIV |
| 62 | DK1 | 123 | SGHRMAWDMMMNWSPTTALV1SQLLRIPQAVvDMVAGAHWGVLAGLAYYSMAGNWAKVLIV |
| 64 | HK4 | 123 | SGHRMAWDMMMNWSPTTAALVVSQLLRIPQAVMDMVAGAHWGVLAGLAYYSMVGNWAKVLIV |
| 76 | US6 | 123 | SGHRMAWDMMMNWSPTTAALVVSQLLRIPQAVMDMVAGAHWGVLAGLAYYSMVGNWAKVLIV |
| 68 | IND8 | 123 | SGHRMAWDMMMNWSPTAALVVSQLLRIPQAVVDMVAGAHWGILAGLAYYSMVGNWAKVLIV |
| 67 | IND5 | 123 | SGHRMAWDMMMNWSPTAALVVSQLLRIPQAVVDMVAGAHWGILAGLAYYSMVGNWAKVLIV |
| 73 | SW2 | 123 | SGHRMAWDMMMNWSPTAALVVSQLLRIPQAVVDMVAGAHWGVLAGLAYYSMVGNWAKVLIV |
| 63 | HK3 | 123 | SGHRMAWDMMMNWSPTAALVVSQLLRIPQAVVDMVAGAHWGVLAGLAYYSMVGNWAKVLIV |
| 66 | HK8 | 123 | SGHRMAWDMMMNWSPTTALVVSQLLRIPQAiVDMVAGAHWGVLAGLAYYSMVGNWAKVLIV |
| 61 | D3 | 123 | TGHRMAWDMMMNWSPTAALVVSQLLRIPQAVVDMVAGAHWGVLAGLAYYSMVGNWAKVLIV |
| 74 | T3 | 123 | TGHRMAWDMMMNWSPTAALVVSQLLRIPQAVVDMVAGAHWGVLAGLAYYSMVGNWAKVLIV |
| 65 | HK5 | 123 | TGHRMAWDMMMNWSPTAALVVSQLLRIPQAVVDMVAGAHWGVLAGLAYYSMVGNWAKVLIV |
| 71 | S45 | 123 | TGHRMAWDMMMNWSPTAALVVSQLLRIPQAVVDMVAGAHWGVLAGLAYYSMVGNWAKVLIV |
| 72 | SA10 | 123 | TGHRMAWDMMMNWSPTtALVVSQLLRIPQAVVDMVAGAHWGVLAGLAYYSMVGNWAKVLIV |
| 69 | P10 | 123 | sGHRMAWDMMMNWSPTaALVVSQLLRIPQAVVDMVAGAHWGVLAGLAYYSMVGNWAKVLIV |
| 60 | D1 | 123 | TGHRMAWDMMMNWSPTAALVVSQLLRIPQAIlDvVAGAHWGVLAGLAYYSMVGNWAKVLIV |
| 70 | S9 | 123 | TGHRMAWDMMMNWSPTAALVVSQLLRIPQAVMDMVAGAHWGVLAGLAYYSMVGNWAKVLIV |
| 60-76 | consensus | | sGHRMAWDMMMNWSPTaALVvSQLLRiPQAvvDmVaGAHWGvLAGLAYYSmVGNWAKVLIV |

FIGURE 2B-4

| SEQ ID NO: | Isolate | | |
|---|---|---|---|
| 75 | T10 | 184 | mLLFAGVDG |
| 62 | DK1 | 184 | lLLFAGVDG |
| 64 | HK4 | 184 | mLLFAGVDG |
| 76 | US6 | 184 | lLLFAGVDG |
| 68 | IND8 | 184 | MLLFAGVDG |
| 67 | IND5 | 184 | MLLFAGVDG |
| 73 | SW2 | 184 | MLLFAGVDG |
| 63 | HK3 | 184 | MLLFAGVDG |
| 66 | HK8 | 184 | MLLFAGVDG |
| 61 | D3 | 184 | MLLFAGVDG |
| 74 | T3 | 184 | lLLFAGVDG |
| 65 | HK5 | 184 | MLLFAGVDG |
| 71 | S45 | 184 | MLLFAGVDG |
| 72 | SA10 | 184 | MLLFAGVDG |
| 69 | P10 | 184 | MLLFAGVDG |
| 60 | D1 | 184 | MLLFAGVDG |
| 70 | S9 | 184 | MLLFAGVDG |
| 60-76 | consensus | | mLLFAGVDG |

FIGURE 2C-1

| SEQ ID NO: | Isolate | | |
|---|---|---|---|
| 77 | T2 | 1 | AQVrNTsrgYMVTNDCSNeSITWQLQAAVLHVPGCiPCErlGNTSRCWIPVtPNVAVRQPG |
| 78 | T4 | 1 | AQVKNTtnSYMVTNDCSNDSITWQLQAAVLHVPGCVPCEktGNTSRCWIPVSPNVAVRQPG |
| 79 | T9 | 1 | AeVKNTSTSYMVTNDCSNDSITWQLQAAVLHVPGCVPCErVGNaSRCWIPVSPNVAVRPG |
| 80 | US10 | 1 | vqVKNTSTSYMVTNDCSNDSITWQLeAAVLHVPGCVPCEkVGNtSRCWIPVSPNVAVQRPG |
| 77-80 | consensus | | aqVkNTstsYMVTNDCSNdSITWQLqAAVLHVPGCvPCE-vGNtSRCWIPVsPNVAV--PG |

| SEQ ID NO: | Isolate | | |
|---|---|---|---|
| 77 | T2 | 62 | ALTQGLRTHIDMVVMSATLCSALYVGDLCGGVMLAAQMFIVSPrrHWFVQeCNCSIYPGTI |
| 78 | T4 | 62 | ALTQGLRTHIDMVVMSATLCSALYVGDLCGGVMLAAQMFIVSPQHHWFVQdCNCSIYPGTI |
| 79 | T9 | 62 | ALTQGLRTHIDMVVMSATLCSALYVGDLCGGVMLAAQMFIiSPQHHWFVQECNCSIYPGTI |
| 80 | US10 | 62 | ALTQGLRTHIDMVVMSATLCSALYVGDfCGGmMLAAQMFIVSPrHHsFVQECNCSIYPGTI |
| 77-80 | consensus | | ALTQGLRTHIDMVVMSATLCSALYVGDlCGGvMLAAQMFIvsp-hHwFVQeCNCSIYPGTI |

| SEQ ID NO: | Isolate | | |
|---|---|---|---|
| 77 | T2 | 123 | TGHRMAWDMMNWSPTATMILAYAMRVPEVIiDIigGAHWGVMFGLAYFSMQGAWAKViVI |
| 78 | T4 | 123 | TGHRMAWDMMNWSPTATMILAYAMRVPEVIlDIvSGAHWGVMFGLAYFSMQGAWAKVVVI |
| 79 | T9 | 123 | TGHRMAWDMMNWSPTcTMILAYAMRVPEVIIDIISGAHWGVMFGLAYFSMQGAWAKVVVI |
| 80 | US10 | 123 | TGHRMAWDMMNWSPTaTllILAY-vMRVPEVIIDIiSGAHWGVlFGLAYFSMQGAWAKVVVI |
| 77-80 | consensus | | TGHRMAWDMMNWSPTaTmILAYaMRVPEVIiDIisGAHWGVmFGLAYFSMQGAWAKVvVI |

FIGURE 2C-2

| SEQ ID NO: | Isolate | | |
|---|---|---|---|
| 77 | T2 | 184 | LLLAAGVDA |
| 78 | T4 | 184 | LLLAAGVDA |
| 79 | T9 | 184 | LLLtAGVDA |
| 80 | US10 | 184 | LLLaAGVDA |
| 77-80 | consensus | | LLLaAGVDA |

FIGURE 2D-1

| SEQ ID NO: | Isolate | | |
|---|---|---|---|
| 82 | DK11 | 1 | VEVRNtSSSYYATNDCSNnSITWQLTNAVLHLPGCVPCENDNGTLHCWIQVTPNVAVKHRG |
| 83 | SW3 | 1 | VEVRNiSSSYYATNDCSNsSITWQLTNAVLHLPGCVPCENDNGTLHCWIQVTPNVAVKHRG |
| 84 | T8 | 1 | VEVRNtSfSYYATNDCSNNSITWQLTNAVLHLPGCVPCENDNGTLRCWIQVTPNVAVKHRG |
| 81 | DK8 | 1 | VEVRNiSsSYYATNDCSNNSITWQLTdAVLHLPGCVPCENDNGTLRCWIQVTPNVAVKHRG |
| 81-84 | consensus | | VEVRN-SsSYYATNDCSNnSITWQLTnAVLHLPGCVPCENDNGTL-CWIQVTPNVAVKHRG |

| SEQ ID NO: | Isolate | | |
|---|---|---|---|
| 82 | DK11 | 62 | ALTHNLRAHiDMIVMAATVCSALYVGDvCGAVMIVSQAFIvSPEhhhFTQECNCSIYQGhI |
| 83 | SW3 | 62 | ALTHNLRAHVDMIVMAATVCSALYVGDVCGAVMIVSQAFIISPERHNFTQECNCSIYQGHI |
| 84 | T8 | 62 | ALTHNLRTHVDVIVMAATVCSALYVGDVCGAVMIaSQAFIISPERHNFTQECNCSIYQGHI |
| 81 | DK8 | 62 | ALTHNLRTHVDVIVMAATVCSALYVGDVCGAVMIvSQAlIISPERHNFTQECNCSIYQGHI |
| 81-84 | consensus | | ALTHNLR-HvD-IVMAATVCSALYVGDvCGAVMIvSQAfIiSPErHnFTQECNCSIYQGhI |

| SEQ ID NO: | Isolate | | |
|---|---|---|---|
| 82 | DK11 | 123 | TGHRMAWDMMLNWSPTLTMILAYAARVPELVLEVVFGGHWGVVFGLAYFSMQGAWAKVIAI |
| 83 | SW3 | 123 | TGHRMAWDMMLNWSPTLTMILAYAARVPELVLEVVFGGHWGVVFGLAYFSMQGAWAKVIAI |
| 84 | T8 | 123 | TGHRMAWDMMLNWSPTLTMILAYAARVPELVLEVVFGGHWGVVFGLAYFSMQGAWAKVIAI |
| 81 | DK8 | 123 | TGHRMAWDMMLNWSPTLTMILAYAARVPELaLqVVFGGHWGVVFGLAYFSMQGAWAKVIAI |
| 81-84 | consensus | | TGHRMAWDMMLNWSPTLTMILAYAARVPELvLeVVFGGHWGVVFGLAYFSMQGAWAKVIAI |

FIGURE 2D-2

| SEQ ID NO: | Isolate | | |
|---|---|---|---|
| 82 | DK11 | 184 | LLLVAGVDA |
| 83 | SW3 | 184 | LLLVAGVDA |
| 84 | T8 | 184 | LLLVAGVDA |
| 81 | DK8 | 184 | LLLVAGVDA |
| 81-84 | consensus | | LLLVAGVDA |

FIGURE 2E-1

| SEQ ID NO: | Isolate | |
|---|---|---|
| 86 | DK12 | 1 LEWRNVSGLYVLTNDCsNSSIVYEADDVILHTPGCVPCVQDGNTSTCWTSVTPTVAVRYVG |
| 87 | HK10 | 1 LEWRNVSGLYVLTNDCpNSSIVYEADDVILHTPGCVPCVQDGNTSTCWTSVTPTVAVRYVG |
| 88 | S2 | 1 LEWRNTSGLYVLTNDCSNSSIVYEADDVILHTPGCVPCVQDGNTSTCWTPVTPTVAVRYVG |
| 90 | S54 | 1 LEWRNTSGLYiLTNDCSNSSIVYEADDVILHTPGCVPCVQDGNTSTCWTPVTPTVAVRYVG |
| 89 | S52 | 1 LEWRNTSGLYVLTNDCSNSSIVYEADDVILHTPGCVPCVQDGNTSmCWTPVTPTVAVRYVG |
| 86-90 | consensus | LEWRNtSGLYvLTNDCsNSSIVYEADDVILHTPGCVPCVQDGNTStCWTpVTPTVAVRYVG |

| SEQ ID NO: | Isolate | |
|---|---|---|
| 86 | DK12 | 62 ATTASIRSHVDLLVGAATMCSALYVGDvCGAVFLVGQAFTFRPRRHQTVQTCNCSLYPGHL |
| 87 | HK10 | 62 ATTASIRSHVDLLVGAATMCSALYVGDMCGAVFLVGQAFTFRPRRHQTVQTCNCSLYPGHL |
| 88 | S2 | 62 ATTASIRSHVDLLVGAATMCSALYVGDMCGAVFLVGQAFTFRPRRHQTVQTCNCSLYPGHL |
| 90 | S54 | 62 ATTASIRSHVDLLVGAATLCSALYVGDMCGAVFLVGQAFTFRPRRHQTVQTCNCSLYPGHL |
| 89 | S52 | 62 ATTASIRSHVDLLVGAATLCSALYVGDMCGAVFLVGQAFTFRPRRHQTVQTCNCSLYPGHv |
| 86-90 | consensus | ATTASIRSHVDLLVGAATmCSALYVGDmCGAVFLVGQAFTFRPRRHQTVQTCNCSLYPGHl |

FIGURE 2E-2

| SEQ ID NO: | Isolate | | |
|---|---|---|---|
| 86 | DK12 | 123 | SGHRMAWDMMMNWSPAVGMVVAHvLRLPQTLFDIIAGAHWGImAGLAYYSMQGNWAKVAII |
| 87 | HK10 | 123 | SGHRMAWDMMMNWSPAVGMVVAHVLRLPQTLFDIIAGAHWGILAGLAYYSMQGNWAKVAII |
| 88 | S2 | 123 | SGHRMAWDMMMNWSPAVGMVVAHVLRLPQTLFDIIAGAHWGILAGLAYYSMQGNWAKVAII |
| 90 | S54 | 123 | SGHRMAWDMMMNWSPAVGMVVAHVLRLPQTvFDIIAGAHWGILAGLAYYSMQGNWAKVAII |
| 89 | S52 | 123 | SGHRMAWDMMMNWSPAVGMVVAHILRLPQTLFDILAGAHWGILAGLAYYSMQGNWAKVAII |
| 86-90 | consensus | | SGHRMAWDMMMNWSPAVGMVVAHvLRLPQTlFDIiAGAHWGIlAGLAYYSMQGNWAKVAIv |

| SEQ ID NO: | Isolate | | |
|---|---|---|---|
| 86 | DK12 | 184 | MVMFSGVDA |
| 87 | HK10 | 184 | MVMFSGVDA |
| 88 | S2 | 184 | MVMFSGVDA |
| 90 | S54 | 184 | MIMFSGVDA |
| 89 | S52 | 184 | MIMFSGVDA |
| 86-90 | consensus | | MvMFSGVDA |

FIGURE 2F

```
SEQ ID NO:   Isolate
    94         Z7       1  VNYhNASGVYHiTNDCPNSSImYEAEHHILHLPGCVPCVReGNQSRCWVALTPTVAAPYIG
                           ||| |||||||| |||||||||| |||||| ||||||||| |||||| |||||||| |||
    93         Z6       1  VNYrNASGVYHvTNDCPNSSIvYEAEHqILHLPGClPCVRvGNQSRCWVALTPTVAvsYIG 93-94 consensus (Z6)       VNYrNASGVYHvTNDCPNSSIvYEAEHqILHLPGClPCVRvGNQSRCWVALTPTVAvsYIG SEQ ID NO:   Isolate
    94         Z7      62  APLESiRRHVDLMVGAATVCSALYIGDLCGGVFLVGQMFSFQPRRHWTTQDCNCSIYAGHV
                           |||| | |||||||||||||||||| |||| ||||||||||||||||||||||||||||
    93         Z6      62  APLdSLRRHVDLMVGAATVCSALYvGDLCGGaFLVGQMFSFQPRRHWTTQDCNCSIYAGHI 93-94 consensus (Z6)       APLdSlRRHVDLMVGAATVCSALYvGDLCGGaFLVGQMFSFQPRRHWTTQDCNCSIYAGHi SEQ ID NO:   Isolate
    94         Z7     123  TGHRMAWDMMMNWSPTTTIvLAQVMRIPSTLVDLLTGGHWGiLiGvAYFcMQANWAKVILV
                           |||||||||||||||||| ||||||||||||||| ||||||| | || ||| |||||||
    93         Z6     123  TGHRMAWDMMMNWSPTTTLlLAQVMRIPSTLVDLLaGGHWGvLVGlAYFsMQANWAKVILV 93-94 consensus (Z6)       TGHRMAWDMMMNWSPTTTLlLAQVMRIPSTLVDLLaGGHWGvLvGlAYFsMQANWAKVILV SEQ ID NO:   Isolate
    94         Z7     184  LFLyAGVDA
                           ||| |||||
    93         Z6     184  LFLfAGVDA 93-94 consensus (Z6)       LFLfAGVDA
```

FIGURE 2G-1

| SEQ ID NO: | Isolate | |
|---|---|---|
| 98 | SA5 | 1 VPYRNASGVYHVTNDCPNSSIVYEADNLILHAPGCVPCVKegNVSRCWVQITPTLSAPNLG |
| 100 | SA7 | 1 VPYRNASGVYHVTNDCPNSSIVYEADNLILHAPGCVPCVRCWVQITPTLSAPNLG |
| 97 | SA4 | 1 VPYRNASGVYHVTNDCPNSSIVYEADNLILHAPGCVPCVRQnNVSRCWVQITPTLSAPNLG |
| 96 | SA1 | 1 VPYRNASGVYHVTNDCPNSSIVYEADsLILHAPGCVPCVRQDNVSkCWVQITPTLSAPNLG |
| 99 | SA6 | 1 VPYRNASGVYHVTNDCPNSSIVYEADDLILHAPGCVPCVRQDNVSRCWVQITPTLSAPtfG |
| 101 | SA13 | 1 VPYRNASGVYHVTNDCPNSSIVYEADDLILHAPGCVPCVRkDNVSRCWVhITPTLSAPSLG |
| 96-101 | consensus | VPYRNASGVYHVTNDCPNSSIVYEADnLILHAPGCVPCVRqgNVSrCWVqITPTLSAPnlG |

| SEQ ID NO: | Isolate | |
|---|---|---|
| 98 | SA5 | 62 AVTAPLRRavDYLAGGAALCSALYVGDACGAvFLVGQMFtYRPRQHTtVQDCNCSIYSGHI |
| 100 | SA7 | 62 AVTAPLRRAVDYLAGGAALCSALYVGDACGAVFLVGQMFtYRPRQHTTVQDCNCSIYSGHI |
| 97 | SA4 | 62 AVTAPLRRAVDYLAGGAALCSALYVGDACGAVFLVGQMFsYRPRQHTTVQDCNCSIYSGHI |
| 96 | SA1 | 62 AVTAPLRRAVDYLAGGAALCSALYVGDACGAVFLVGQMFTYRPRQHTTVQDCNCSIYSGHI |
| 99 | SA6 | 62 AVTAPLRRAVDYLAGGAALCSALYVGDvCGAIFLVGQMFTYRPRQHaTVQDCNCSIYSGHI |
| 101 | SA13 | 62 AVTAPLRRAVDYLAGGAALCSALYVGDaCGAvFLVGQMFTYsPRrHnvVQDCNCSIYSGHI |
| 96-101 | consensus | AVTAPLRRaVDYLAGGAALCSALYVGDaCGAvFLVGQMFtYrPRqHttVQDCNCSIYSGHI |

FIGURE 2G-2

| SEQ ID NO: | Isolate | | |
|---|---|---|---|
| 98 | SA5 | 123 | TGHRMAWDMMMNWSPTTALVMAQvLRIPQVVIDIIAGGHWGVLFAvAYFASAANWAKVVLV |
| 100 | SA7 | 123 | TGHRMAWDMMMNWSPTTALVMAQLLRIPQVVIDIIAGGHWGVLFAAAYFASAANWAKVVLV |
| 97 | SA4 | 123 | TGHRMAWDMMMNWSPTTALVMAQLLRIPQVVIDIIAGGHWGVLFAAAYFASAANWAKViLV |
| 96 | SA1 | 123 | TGHRMAWDMMMNWSPTTALLMAQLLRIPQVVIDIIAGGHWGVLFAAAYFASAANWAKVVLV |
| 99 | SA6 | 123 | TGHRMAWDMMMNWSPaTALVMAQMLRIPQVVIDIIAGGHWGVLFAAAYFASAANWAKVVLV |
| 101 | SA13 | 123 | TGHRMAWDMMMNWSPtTALVMAQllRIPQVVIDIIAGaHWGVLFAaAYfASAANWAKVVLV |
| 96-101 | consensus | | TGHRMAWDMMMNWSPtTALvMAQlLRIPQVVIDIIAGgHWGVLFAaAYfASAANWAKVvLv |

| SEQ ID NO: | Isolate | | |
|---|---|---|---|
| 98 | SA5 | 184 | LFLFAGVDg |
| 100 | SA7 | 184 | LFLFAGVDA |
| 97 | SA4 | 184 | LFLFAGVDA |
| 96 | SA1 | 184 | LFLFAGVDg |
| 99 | SA6 | 184 | LFLFAGVDA |
| 101 | SA13 | 184 | LFLFAGVDA |
| 96-101 | consensus | | LFLFAGVDa |

FIGURE 2H-1

```
SEQ ID NO:  Genotype
 81-84      (IV/2b)    1 VEVRNiSsSYYATNDCSNnSITWQLTnAVLHLPGCVPCENDNGTLrCWIQVTPNVAVKHRG
    85        (2c)     1 VEVKDTGDSYMPTNDCSNSSIVWQLEGAVLHTPGCVPCERTANVSRCWVPVAPNLAISQPG
 77-80     (III/2a)    1 aqVkNTstsYMVTNDCSNdSITWQLqAAVLHVPGCvPCEkvGNtSRCWIPVsPNVAVqqPG
 86-90       (V/3a)    1 LEWRNtSGLYvLTNDCsNSSIVYEADDVILHTPGCVPCVQDGNTStCWTpVTPTVAVRYVG
 60-76      (II/1b)    1 yEVrNVSGvYhVTNDCSNsSiVyEaaDmImHTPGCvPCVrEnNsSrCWVALtPTLAARNas
 52-59       (I/1a)    1 yQVRNStGLYHVTNDCPNSSIVYEaADaILHsPGCVPCVREgnasrCWVavtPTVATRDGK
    91         (4a)    1 EHYRNASGIYHITNDCPNSSIVYEADHHILHLPGCVPCVMTGNTSRCWTPVTPTVAVAHPG
 93-94         (4c)    1 VNYrNASGVYHvTNDCPNSSIvYEAEHqILHLPGClPCVRvGNQSRCWVALTPTVAvsYIG
    95         (4d)    1 YNYRNSSGVYHVTNDCPNSSIVYETDYHILHLPGCVPCVREGNKSTCWVSLTPTVAAQHLN
    92         (4b)    1 VHYRNASGVYHVTNDCPNTSIVYETEHHIMHLPGCVPCVRTENTSRCWVPLTPTVAAPYPN
96-101         (5a)    1 VPYRNASGVYHVTNDCPNSSIVYEADnLILHAPGCVPCVrqdNVSrCWVqITPTLSAPnlG
   102         (6a)    1 LTYGNSSGLYHLTNDCPNSSIVLEADAMILHLPGCLPCVRVDDRSTCWHAVTPTLAIPNAS 52-102     consensus             Y  TNDC N S          H PGC PC        CW    P SEQ ID NO:  Genotype
 81-84      (IV/2b)   62 ALTHNLRtHvDmIVMAATVCSALYVGDvCGAVMIvSQAfIiSPErHnFTQECNCSIYQGhI
    85        (2c)    62 ALTKGLRAHIDIIVMSATVCSALYVGDVCGALMLAAQVVVVSPQHHTFVQECNCSIYPGRI
 77-80     (III/2a)   62 ALTQGLRTHIDMVVMSATLCSALYVGDlCGGvMLAAQMFIvSPqhHwFVQeCNCSIYPGTI
 86-90       (V/3a)   62 ATTASIRSHVDLLVGAATmCSALYVGDmCGAVFLVGQAFTFRPRRHQTVQTCNCSLYPGHl
 60-76      (II/1b)   62 vpTttIRrHVDLLVGAAaFCSaMYVGDLCGSVfLvSQLFTfSPRrheTvQdCNCSiYPGhv
 52-59       (I/1a)   62 LPatQLRRhIDLLVGSATLCSALYVGDLCGSVFLVgQLFTfSPRrhWTTQdCNCSIYPGHI
    91         (4a)   62 APLESFRRHVDLMVGAATLCSALYVGDLCGGAFLMGQMITFRPRRHWTTQECNCSIYTGHI
 93-94         (4c)   62 APLdSlRRHVDLMVGAATVCSALYvGDLCGGaFLVGQMFSFQPRRHWTTQDCNCSIYAGHi
    95         (4d)   62 APLESLRRHVDLMVGGATLCSALYIGDVCGGVFLVGQLFTFQPRRHWTTQDCNCSIYTGHI
    92         (4b)   62 APLESMRRHVDLMVGAATMCSAFYIGDLCGGVFLVGQLFDFRPRRHWTTQDCNCSIYPGHV
96-101         (5a)   62 AVTAPLRRaVDYLAGGAALCSALYVGDaCGAvFLVGQMFtYrPRqHttVQDCNCSIYSGHI
   102         (6a)   62 TPATGFRRHVDLLAGAAVVCSSLYIGDLCGSLFLAGQLFTFQPRRHWTVQDCNCSIYTGHV
52-102     consensus          R   D     A  CS  Y GD CG      Q     P      Q CNCS Y G
```

FIGURE 2H-2

| SEQ ID NO: | Genotype | | |
|---|---|---|---|
| 81-84 | (IV/2b) | 123 | TGHRMAWDMMLNWSPTLTMILAYAARVPELvLeVVFGGHWGVVFGLAYFSMQGAWAKVIAI |
| 85 | (2c) | 123 | TGHRMAWDMMMNWSPTTMLLAYLVRIPEVILDIVTGGHWGVMFGLAYFSMQGSWAKVIVI |
| 77-80 | (III/2a) | 123 | TGHRMAWDMMMNWSPTaTmILAyaMRVPEViiDIisGAHWGVmFGLAYFSMQGAWAKVvVI |
| 86-90 | (V/3a) | 123 | SGHRMAWDMMMNWSPAVGMVVAHvLRLPQTlFDIiAGAHWGIlAGLAYYSMQWAKVAIi |
| 60-76 | (II/1b) | 123 | SGHRMAWDMMMNWSPTaALvvSQLLRiPQAvvDmVaGAHWGvLAGLAYYSMvGNWAKVLIV |
| 52-59 | (I/1a) | 123 | TGHRMAWDMMMNWSPTtALvvAQLLRiPQAiLDMIAGAHWGVLAGIAYFSMvGNWAKVlvV |
| 91 | (4a) | 123 | TGHRMAWDMMMNWSPTTTLLLAQIMRVPTAFLDMVAGGHWGVLAGLAYFSMQGNWAKVVLV |
| 93-94 | (4c) | 123 | TGHRMAWDMMMNWSPTTLllAQVMRIPSTLVDLLaGGHWGvLvGlAYFsMQANWAKVILV |
| 95 | (4d) | 123 | TGHRMAWDMMMNWSPTATlVLAQLMRIPGAMVDLLAGGHWGILvGIAYFSMQANWAKVILV |
| 92 | (4b) | 123 | SGHRMAWDMMMNWSPTSALIMAQILRIPSILGDLLTGGHWGVLAGLAFFSMQSNWAKVILV |
| 96-101 | (5a) | 123 | TGHRMAWDMMMNWSPtTALvMAQlLRIPQVVIDIIAGgHWGVLFAaAYfASAANWAKVvLV |
| 102 | (6a) | 123 | TGHRMAWDMMMNWSPTTTLvLSSILRVPEICASVIFGGHWGILLAVAYFGMAGNWLKVLAV |
| 52-102 | consensus | | GHRMAWDMM NWSP      R P       G HWG       A       W KV |

| SEQ ID NO: | Genotype | | |
|---|---|---|---|
| 81-84 | (IV/2b) | 184 | LLLVAGVDA |
| 85 | (2c) | 184 | LLLTAGVEA |
| 77-80 | (III/2a) | 184 | LLLaAGVDA |
| 86-90 | (V/3a) | 184 | MvMFSGVDA |
| 60-76 | (II/1b) | 184 | mLLFAGVDG |
| 52-59 | (I/1a) | 184 | LLLFAGVDA |
| 91 | (4a) | 184 | LFLFAGVDA |
| 93-94 | (4c) | 184 | LFLfAGVDA |
| 95 | (4d) | 184 | LFLFAGVDA |
| 92 | (4b) | 184 | LFLFAGVEG |
| 96-101 | (5a) | 184 | LFLFAGVDa |
| 102 | (6a) | 184 | LFLFAGVEA |
| 52-102 | consensus | | GV |

| SEQ ID NO: | ISOLATE | |
|---|---|---|
| 108 | DR4 | 1 ATGAGCACGAATCCTAAACCTCAAAGAAAAACCAAACGTAACACCAACCGTCGCCCACAGG |
| 103 | DK7 | 1 ATGAGCACGAATCCTAAACCTCAAAGAAAAACCAAACGTAACACCAACCGTCGCCCACAGG |
| 104 | US11 | 1 ATGAGCACGAATCCTAAACCTCAAAGAAAAACCAAACGTAACACCAACCGTCGCCCACAGG |
| 105 | S14 | 1 ATGAGCACGAATCCTAAACCTCAAAGAAAAACCAAACGTAACACCAACCGTCGCCCACAGG |
| 106 | SW1 | 1 ATGAGCACGAATCCTAAACCTCAAAGAAAAACCAAACGTAACACCAACCGTCGCCCACAGG |
| 107 | S18 | 1 ATGAGCACGAATCCTAAACCTCAAAGAAAAACCAAACGTAACACCAACCGTCGCCCACAGG |
| 103-108 | consensus | ATGAGCACgAATCCTAAACCTCAAAGAAAAACCAAACGTAACACCAACCGTCGCCCACAGG |

| SEQ ID NO: | ISOLATE | |
|---|---|---|
| 108 | DR4 | 62 ACGTCAAGTTCCCGGGTGGCGGTCAGATCGTTGGTGGAGTTTACTTGTTGCCGCGCAGGGG |
| 103 | DK7 | 62 ACGTCAAGTTCCCGGGTGGCGGTCAGATCGTTGGTGGAGTTTACTTGTTGCCGCGCAGGGG |
| 104 | US11 | 62 ACGTCAAGTTCCCGGGTGGCGGTCAGATCGTTGGTGGAGTTTACTTGTTGCCGCGCAGGGG |
| 105 | S14 | 62 ACGTCAAGTTCCCGGGTGGCGGTCAGATCGTTGGTGGAGTTTACTTGTTGCCGCGCAGGGG |
| 106 | SW1 | 62 ACGTCAAGTTCCCGGGTGGCGGTCAGATCGTTGGTGGAGTTTACTTGTTGCCGCGCAGGGG |
| 107 | S18 | 62 ACGTtAAGTTCCCGGGTGGCGGTCAGATCGTTGGTGGAGTTTACTTGTTGCCGCGCAGGGG |
| 103-108 | consensus | ACGTCAAGTTCCCGGGTGGCGGTCAGATCGTTGGTGGAGTTTACTTGTTGCCGCGCAGGGG |

| SEQ ID NO: | ISOLATE | |
|---|---|---|
| 108 | DR4 | 123 CCCTAGATTGGGTGTGCGCGCGaCGAGGAAGACTTCCGAGCGGTCGCAACCTCGAGGTAGA |
| 103 | DK7 | 123 CCCTAGATTGGGTGTGCGCGCGACGAGGAAGACTTCCGAGCGGTCGCAACCTCGAGGTAGA |
| 104 | US11 | 123 CCCTAGATTGGGTGTGCGCGCGACGAGGAAGACTTCCGAGCGGTCGCAACCTCGAGGTAGA |
| 105 | S14 | 123 CCCTAGATTGGGTGTGCGCGCGACGAGGAAGACTTCCGAGCGGTCGCAACCTCGAGGTAGA |
| 106 | SW1 | 123 CCCTAGATTGGGTGTGCGCGCGACGAGGAAGACTTCCGAGCGGTCGCAACCTCGAGGTAGA |
| 107 | S18 | 123 CCCTAGATTGGGTGTGCGCGCGACGAGGAAGACTTCCGAGCGGTCGCAACCTCGAGGTAGA |
| 103-108 | consensus | CCCTAGATTGGGTGTGCGCGCGaCGAGGAAGACTTCCGaGCGGTCGCAACCTCGaGGTAGA |

FIGURE 6A-2

| SEQ ID NO: | ISOLATE | | |
|---|---|---|---|
| 108 | DR4 | 184 | CGTCAGCCTATCCCCAAGGCgCGTCGGCCCGAGGGCAGGACCTGGGCTCAGCCCGGGTACC |
| 103 | DK7 | 184 | CGTCAGCCTATCCCCAAGGCACGTCGGCCCGAGGGCAGGACCTGGGCTCAGCCCGGGTACC |
| 104 | US11 | 184 | CGTCAGCCTATCCCCAAGGCACGTCGGCCCGAGGGCAGGACCTGGGCTCAGCCCGGGTACC |
| 105 | S14 | 184 | CGTCAGCCTATCCCCAAGGCTCGGCCCGAGGGCAGGACCTGGGCTCAGCCCGGGTATC |
| 106 | SW1 | 184 | CGTCAGCCTATCCCCAAGGCGCGTCGGCCCGAGGGCAGGACCTGGGCTCAGCCCGGGTATC |
| 107 | S18 | 184 | CGTCAGCCTATCCCCAAGGCGCGTCGGCCCGAGGGCAGGACCTGGGCTCAGCCCGGGTACC |

103-108 consensus  CGTCAGCCTATCCCCAAGGC-CGTCGGCCCGAGGGCAGGACCTGGGCTCAGCCCGGGTAcC

| SEQ ID NO: | ISOLATE | | |
|---|---|---|---|
| 108 | DR4 | 245 | CTTGGCCCCTCTATGGCAATGAGGGCTGCGGGTGGGCGGGATGGCTCCTGTCcCCCGTGG |
| 103 | DK7 | 245 | CTTGGCCCCTCTATGGCAATGAGGGCTGCGGGTGGGCGGGATGGCTCCTGTCCTCCCGTGG |
| 104 | US11 | 245 | CTTGGCCCCTCTATGGCAATGAGGGCTGCGGGTGGGCGGGATGGCTCCTGTCTCCCGTGG |
| 105 | S14 | 245 | CTTGGCCCCTCTATGGCAATGAGGGCTGCGGGTGGGCGGGATGGCTCCTGTCTCTCCGTGG |
| 106 | SW1 | 245 | CTTGGCCCCTCTATGGCAATGAGGGCTGCGGATGGGCGGGATGGCTCCTGTCCTCCCGTGG |
| 107 | S18 | 245 | CTTGGCCCCTCTATGGCAATGAGGGCTGCGGGTGGGCGGGATGGCTCCTGTCCTCCCCGTGG |

103-108 consensus  CTTGGCCCCTCTATGGCAATGAGGGCTGCGGGTGGGCGGGATGGCTCCTGTC-CCCCGTGG

| SEQ ID NO: | ISOLATE | | |
|---|---|---|---|
| 108 | DR4 | 306 | CTCTCGGCCTAGCTGGGCCCCCGGCGtAGGTCGCGCAATTTGGGTAAgGTC |
| 103 | DK7 | 306 | CTCTCGGCCTAGCTGGGCCCCACAGACCCCCGGCGCAGTTGCGCAATTTGGGTAAaGTC |
| 104 | US11 | 306 | CTCTCGGCCTAGCTGGGCCCCACAGACCCCCGGCGACCCCGGCGTAGTTCGCGCAATTTGGGTAAGGTC |
| 105 | S14 | 306 | CTCTCGGCCTAGCTGGGCCCCACAGACCCCCGGCGCCCGGCGTAGTTCGCGCAATTTGGGTAAGGTC |
| 106 | SW1 | 306 | CTCTCGGCCTAGCTGGGCCCCACAGACCCCCGGCGCCCGGCGTAGTTCGCGCAATTTGGGTAAGGTC |
| 107 | S18 | 306 | CTCcGGCCTAGCTGGGCCCCACAGACCCCCGGCGCCCGGCGTAGTTCGCGCAATTTGGCAAGGTC |

103-108 consensus  CTTCtCGGCCTAGCTGGGCCCCCACaGACCCCCGGCGtAGGTCGCGCAATTTGGGtAAgGTC

FIGURE 6A-3

| SEQ ID NO: | ISOLATE | | |
|---|---|---|---|
| 108 | DR4 | 367 | ATCGAcACCCTcACGTGcGGCTTGCGCCGACCTCATGGGTACATcCCGCTCGTCGGCGCCC |
| 103 | DK7 | 367 | ATCGATACCCTTACGTGCGGCTTGCGCCGACCTCATGGGTACATACCGCTCGTCGGCGCCC |
| 104 | US11 | 367 | ATCGATACCCTTACGTGCGGCTTGCGCCGACCTCATGGGTACATACCGCTCGTCGGCGCCC |
| 105 | S14 | 367 | ATCGATACCCTCACGTGCGGCTTGCGCCGACCTCATGGGTACATACCGCTCGTCGGCGCCC |
| 106 | SW1 | 367 | ATCGATACCCTCACGTGCGGCTTGCGCCGACCTCATGGGTACATTCCGCTCGTCGGCGCCC |
| 107 | S18 | 367 | ATCGATACCCTCACGTGCGGCTTGCGCCGACCTCATGGGTACATTCCGCTCGTCGGCGCCC |

103-108  consensus      ATCGAtACCCTcACGTGCGGCTTCGCCGACCTCATGGGTACATaCCGCTCGTCGGCGCCC

| SEQ ID NO: | ISOLATE | | |
|---|---|---|---|
| 108 | DR4 | 428 | CcCTTGGgGGCGCTGCCAGGGCCCTGGCGCATGGCGTCCGaGTTCTGAAGACGGCGTGAA |
| 103 | DK7 | 428 | CTCTTGGAGGCGCTGCCAGGGCCCTGGCGCATGGCGTCCGGGTTCTGAAGACGGCGTGAA |
| 104 | US11 | 428 | CTCTCGGAGGCGCTGCCAGGGCCCTGGCGCATGGCGTCCGGGTTCTGAAGACGGCGTGAA |
| 105 | S14 | 428 | CcCTCGGgGGCGCTGCCAGGGCCCTGGCGCATGGCGTCCGGGTTCTGAAGACGGCGTGAA |
| 106 | SW1 | 428 | CTCTtGGAGGCGCTGCCAGGGCCCTGGCGCATGGCGTCCGGGTTCTGAAGACGGCGTGAA |
| 107 | S18 | 428 | CTCTcGGAGGCGCTGCCAGGGCCCTGGCGCATGGCGTCCGgGTTCTGAAGACGGCGTGAA |

103-108  consensus      CtCT-GGaGGCGCTGCCAGGGCCCTGGCGCATGGCGTCCGgGTTCTGAAGACGGCGTGAA

| SEQ ID NO: | ISOLATE | | |
|---|---|---|---|
| 108 | DR4 | 489 | CTATGCAACAGGGAAtCTTCCTGGTTGCTCTTTCTCTATCTTCCTTTTGGCttTGCTCTCT |
| 103 | DK7 | 489 | CTATGCAACAGGGAACCTTCCTGGTTGCTCTTTCTCTATCTCCTTTTGGCCCCTGCTCTCT |
| 104 | US11 | 489 | CTATGCAACAGGGAACCTTCCTGGTTGCTCTTTCTCTATCTTCCTTCTGGCCCCTGCTCTCT |
| 105 | S14 | 489 | CTATGCAACAGGGAACCTTCCTGGTTGCTCTTTCTCTATCTCCTTCTGGCCCCTGCTTTCT |
| 106 | SW1 | 489 | CTATGCAACAGGGAACCTTCCTGGTTGCTCTTTCTCTATCTCCTaGCCTCTGGCCCCTGCTTTCT |
| 107 | S18 | 489 | CTATGCAACAGGGAACCTTCCTGGTTGCTCTTTCTCTATCTCCTTCTGGCCCCTGCTTTCT |

103-108  consensus      CTATGCAACAGGGAACCTTCCTGGTTGCTCTTTCTCTATCTtCCTtcTgCcCCTGCTcTCT

FIGURE 6A-4

| SEQ ID NO: | ISOLATE | | |
|---|---|---|---|
| 108 | DR4 | 550 | TGCtTGACCGTGCCCGCaTCGGCC |
| 103 | DK7 | 550 | TGCCTGACCGTGCCCGCTTCGGCC |
| 104 | US11 | 550 | TGCCTGACTGTGCCCGCTTCAGCC |
| 105 | S14 | 550 | TGCCTGACTGTGCCCGCTTCAGCC |
| 106 | SW1 | 550 | TGCCTGACaGTGCCCGCGTCAGCC |
| 107 | S18 | 550 | TGtCTGACtGTGCCCGGTCAGCt |

103-108 consensus    TGccTGActGTGCCCGCtTCaGCc

FIGURE 6B-1

| SEQ ID NO: | ISOLATE | |
|---|---|---|
| 119 | S9 | 1 ATGAGCACGAATCCTAAACCTCAAAGAAAAACCAAACGTAACACCAACCGCGCCCACAGG |
| 117 | IND3 | 1 ATGAGCACGAATCCTAAACCTCAAAGAAAAACCAAACGTAACACCAACCGCGCCCACAGG |
| 118 | IND8 | 1 ATGAGCACGAATCCTAAACCTCAAAGAAAAACCAAACGTAACACCAACCGCGCCCACAGG |
| 111 | D1 | 1 ATGAGCACGAATCCTAAACCTCAAAGAAAAACCAAACGTAACACCAACCGCGCCCACAGG |
| 112 | US6 | 1 ATGAGCACGAATCCTAAACCTCAAAGAAAAACCAAACGTAACACCAACCGCGCCCACAGG |
| 113 | P10 | 1 ATGAGCACGAATCCTAAACCTCAAAGAAAAACCAAACGTAACACCAACCGCGCCCACAGG |
| 114 | DK1 | 1 ATGAGCACGAATCCTAAACCTCAAAGAAAAACCAAACGTAACACCAACCGCGCCCACAGG |
| 115 | T10 | 1 ATGAGCACGAATCCTAAACCTCAAAGAAAAACCAAACGTAACACCAACCGCGCCCACAGG |
| 116 | SW2 | 1 ATGAGCACGAATCCTAAACCTCAAAGAAAAACCAAACGTAACACCAACCGCGCCCACAGG |
| 122 | HK4 | 1 ATGAGCACGAATCCTAAACCTCAAAGAAAAgACCAAACGTAACACCAACCGCGCCCACAGG |
| 109 | SA10 | 1 ATGAGCACGAATCCTAAACCTCAAAGAAGAAACCAAACGTAACACCAACCGCGCCCACAGG |
| 110 | S45 | 1 ATGAGCACGAATCCTAAACCTCAAAGAcAAAACCAAACGTAACACCAACCGCGCCCACAGG |
| 123 | P8 | 1 ATGAGCACGAcTCCTAAACCTCAAAGAAAAACCAAACGTAACACCACCAgCCGCGCCCACAGG |
| 124 | T3 | 1 ATGAGCACGAATCCTAAACCTCAAAGAAAAACCAAACGTAACACCAACCGCGCCCACAGG |
| 120 | HK3 | 1 ATGAGCACGAATCCTAAACCTCAAAGAAAAACCAAACGTAACACCAACCGCGCCCACAGG |
| 121 | HK5 | 1 ATGAGCACGAATCCTAAACCTCAAAGAAAAACCAAACGTAACACCAACCGCGCCCACAGG |

109-124 consensus ATGAGCACGAaTCCTAAACCTCAAAGAaAaACCAAACGTAACACCAaCCGCGCCCACAGG

FIGURE 6B-2

| SEQ ID NO: | ISOLATE | | |
|---|---|---|---|
| 119 | S9 | 62 | ACGTtAAGTTCCCGGGCGGTGGTCAGATCGTCGGTGGAGTTTACCTGTTGCCGCGCAGGGG |
| 117 | IND3 | 62 | ACGTCAAGTTCCCGGGCGGTGGTCAGATCGTTGGTGGAGTTTACCTGTTGCCGCGCAGGGG |
| 118 | IND8 | 62 | ACGTCAAGTTCCCGGGCGGTGGTCAGATCGTTGGTGGAGTTTACCTGTTGCCGCGCAGGGG |
| 111 | D1 | 62 | ACGTCAAGTTCCCGGGCGGTGGTCAGATCGTCGGTGGAGTTTACCTGTTGCCGCGCAGGGG |
| 112 | US6 | 62 | ACGTCAAGTTCCCGGGCGGTGGTCAGATCGTTGGTGGAGTTTACCTGTTGCCGCGCAGGGG |
| 113 | P10 | 62 | ACGTCAAGTTCCCGGGCGGTGGTCAGATCGTTGGTGGAGTTTACCTGTTGCCGCGCAGGGG |
| 114 | DK1 | 62 | ACGTCAAGTTCCCGGGCGGTGGTCAGATCGTTGGTGGAGTTTACCTGTTGCCGCGCAGGGG |
| 115 | T10 | 62 | ACGTCAAGTTCCCGGGCGGTGGTCAGATCGTTGGTGGAGTTTACCTGTTGCCGCGCAGGGG |
| 116 | SW2 | 62 | ACGTCAAGTTCCCGGGCGGTGGCCAGATCGTTGGTGGAGTTTACCTGTTGCCGCGCAGGGG |
| 122 | HK4 | 62 | ACGTtAAGTTCCCGGGCGGTGGCCAGATCGTCGGTGGAGTTTACCTGTTGCCGCGCAGGGG |
| 109 | SA10 | 62 | ACGTCAAGTTCCCGGGCGGTGGTCAGATCGTTGGTGGAGTcTAtCTGTTGCCGCGCAGGGG |
| 110 | S45 | 62 | ACGTCAAGTTCCCGGGtGGcGGTGGTCAGATCGTTGGTGGAGTTTACCTGTTGCCGCGCAGGGG |
| 123 | P8 | 62 | ACGTTAAGTTCCCGGGCGGTGGTCAGATCGTTGGTGGAGTTTACCTGTTGCCGCGCAGGGG |
| 124 | T3 | 62 | ACGTTAAGTTCCCGGGCGGCGGTGGTCAGATCGTTGGTGGAGTTTACCTGTTGCCGCGCAGGGG |
| 120 | HK3 | 62 | ACGTCAAGTTCCCGGGCGGCGGTGGTCAGATCGTTGGTGGAGTTTACCTGTTGCCGCGCAGGGG |
| 121 | HK5 | 62 | ACGTCAAGTTCCCGGGCGGTGGTCAGATCGTTGGTGGAGTTTACCTGTTGCCGCGCAGGGG |

| | | |
|---|---|---|
| 109-124 | consensus | ACGTCAAGTTCCCGGGcGGtGGtCAGATCGTtGGTGGAGTtTACCTGTTGCCGCGCAGGGG |

FIGURE 6B-3

| SEQ ID NO: | ISOLATE | | |
|---|---|---|---|
| 119 | S9 | 123 | CCCCAGGTTGGGTGTGCGCGCaACTAGGAAGAGACTTCCGAGCGGTCGCAACCTCGTGGAAGG |
| 117 | IND3 | 123 | CCCCAGGTTGGGTGTGCGCGCGACTAGGAAGAGACTTCCGAGCGGTCGCAACCTCGTGGAAGG |
| 118 | IND8 | 123 | CCCCAGGTTGGGTGTGCGCGCGACTAGGAAGAGACTTCCGAGCGGTCGCAACCTCGTGGAAGG |
| 111 | D1 | 123 | CCCCAGGTTGGGTGTGCGCGCGACTAGGAAGAGACTTCCGAGCGGTCGCAACCTCGTGGAAGG |
| 112 | US6 | 123 | CCCCAGGTTGGGTGTGCGCGCGACTAGGAAGAGACTTCCGAGCGGTCGCAACCTCGTGGAAGG |
| 113 | P10 | 123 | CCCCAGGTTGGGTGTGCGCGCGACTAGGAAGAGACTTCCGAGCGGTCGCAACCTCGTGGAAGG |
| 114 | DK1 | 123 | CCCCAGGTTGGGTGTGCGCGCGACTAGGAAGAGACTTCCGAGCGGTCGCAACCTCGTGGAAGG |
| 115 | T10 | 123 | CCCCAGGTTGGGTGTGCGCGCGACTAGGAAGAGACTTCCGAGCGGTCGCAACCTCGTGGAAGG |
| 116 | SW2 | 123 | CCCCgGGTTGGGTGTGCGCGCGACTAGGAAGAGACTTCCGAGCGGTCGCAACCTCGTGGAAGG |
| 122 | HK4 | 123 | CCCCAGGTTGGGTGTGCGCGCGACTAGGAAGAGACTTCCGAGCGGTCGCAACCTCGTGGAAGG |
| 109 | SA10 | 123 | CCCCAGGTTGGGTGTGCGCGCGACgAGGAAGAGACTTCCGAGCGGTCGCAACCTCGTGGAAGG |
| 110 | S45 | 123 | CCCCAGGTTGGGTGTGCGCGCGACTAGGAAGAGACTTCCGAGCGGTCGCAACCTCGTGGAcGG |
| 123 | P8 | 123 | CCCCAGGTTGGGTGTGCGCGCGACTAGGAAGAGACTTCCGAGCGGTCaCAACCTCGTGGAAGG |
| 124 | T3 | 123 | CCCCAGGTTGGGTGTGCGCGCGACTAGGAAGAGACTTCCGAGCGGaTCGCAACCTCGTGGcAGG |
| 120 | HK3 | 123 | CCCCAGGTTGGGTGTGCGCGCGACCAGGAAGAGACTTCaGAGCGGTCGCAACCTCGTGGAAGG |
| 121 | HK5 | 123 | CCCCAGGTTGGGTGTGCGCGCGACCAGGAGAGAGACTTCCGAGCGGTCGCAACCTCGTGGAAGG |

| 109-124 | consensus | CCCCaGGTTGGGTGTGCGCGCGgACTAGGAAGAGACTTCCGAGCGgTCgCAACCTCGTGGAaGG |

FIGURE 6B-4

| SEQ ID NO: | ISOLATE | | |
|---|---|---|---|
| 119 | S9 | 184 | CGACAACCTATCCCCAAGGCTCGCCatCCCGAGGGcAGGGCCTGGGCTCAGCCCGGGTACC |
| 117 | IND3 | 184 | CGACAACCTATCCCCAAGGCTCGCCGCCGAGGGTAGGCCTGGGCTCAGCCCGGGTACC |
| 118 | IND8 | 184 | CGACAACCTATCCCCAAGGCTCGCCGCCGAGGGTAGGGCCTGGGCTCAGCCCGGcACC |
| 111 | D1 | 184 | CGACAACCTATCCCCAAGGCTCGCCGCCGAGGGTAGGGCCTGGGCTCAGCCCGGGTACC |
| 112 | US6 | 184 | CGACAACCTATCCCCAAGGCTCGCCGCCGAGGGCAGGGCCTGGGCTCAGCCCGGGTACC |
| 113 | P10 | 184 | CGACAACCTATCCCCAAGGCTCGCCGCCGAGGGCAGGGCCTGGGCTCAGCCCGGGTACC |
| 114 | DK1 | 184 | CGACAACCTATCCCCAAGGCTCGCCGCCGAGGGCAGGGCCTGGGCTCAGCCCGGGTACC |
| 115 | T10 | 184 | CGACAACCTATCCCCAAGGCTCGCCAGCCCGAGGGCAGGGCCTGGGCTCAGCCCGGGTACC |
| 116 | SW2 | 184 | CGACAgCCTATCCCCAAGGCTCGCCAGCCCGAGGGCAGGGCCTGGGCTCAGCtGGGTACC |
| 122 | HK4 | 184 | CGACAACCTATCCCCAAGGCTCGCCAGCCCGAGGGCAGGGCCTGGGCTCAGCCCGGGTACC |
| 109 | SA10 | 184 | CGACAACCTATCCCCAAGGCTCGCCGCCAaCCCGAGGGCAGGACCTGGGCCCAGCCCGGGTACC |
| 110 | S45 | 184 | CGACAACCTATCCCCAAGGCTCGCCGCCGCAGCCCGAGGGCAGGACCTGGGCCCAGCCCGGGCATC |
| 123 | P8 | 184 | CGACAACCTATCCCCAAGGCTCGCCGCCGCCGAGCCCGAGGGCAGGACCTGGGCCTGGGCTCAGCCCGGGCACC |
| 124 | T3 | 184 | CGACAACCTATCCCCAAGGCTCGCCGCCGAGCCCGAGGGTAGGGCCTGGGCTCAGCCCGGGTACC |
| 120 | HK3 | 184 | CGACAACCTATCCCCAAGGCTCGCCGCCaACCCGAGGGCAGGACCGAGGACCTGGGCTCAGCCCGGGTATC |
| 121 | HK5 | 184 | CGACAACCTATCCCCAAGGCTCGCCGCCGACCCGAGGGCAGGACCTGGGCTCAGCCCGGGTATC |
| 109-124 | consensus | | CGACAaCcTTATCCCCAAGGCTCGCCGCCggCCCGAGGGcAGGgCCTGGGCtCAGCCCGGGtAcC |

FIGURE 6B-5

| SEQ ID NO: | ISOLATE | | |
|---|---|---|---|
| 119 | S9 | 245 | CTTGGCCCCCTCTACGGCAATGAGGGCTTGGGGTGGGCAGGATGGCTCCTGTCACCCGtGG |
| 117 | IND3 | 245 | CTTGGCCCCCTCTATGGCAATGAGGGCTTGGGGTGGGCAGGATGGCTCCTGTCACCCGCGG |
| 118 | IND8 | 245 | CTTGGCCCCCTCTATGGCAATGAGGGCTTGGGGTGGGCAGGATGGCTCCTGTCACCCGCGG |
| 111 | D1 | 245 | CTTGGCCCCCTCTATGGCAACGAGGGCTTGGGGTGGGCAGGATGGCTCCTGTCACCCGCGG |
| 112 | US6 | 245 | CTTGGCCCCCTCTATGGCAACGAGGGCATGGGGTGGGCAGGATGGCTCCTGTCACCCGTGG |
| 113 | P10 | 245 | CTTGGCCCCCTCTATGGCAATGAGGGCTtGGGGTGGGCAGGATGGCTCCTGTCACCCGTGG |
| 114 | DK1 | 245 | CTTGGCCCCCTCTATGGCAATGAGGGCATGGGGTGGGCAGGATGGCTCCTGTCACCCGcGG |
| 115 | T10 | 245 | CTTGGCCCCCTCTATGGCAATGAGGGCATGGGGTGGGCAGGATGGCTCCTGTCACCCGtGG |
| 116 | SW2 | 245 | CcTGGCCCCCTCTATGGCAATGAGGGCATGGaTGGGCAGGATGGCTCCTGTCcCCCGCGG |
| 122 | HK4 | 245 | CTTGGCCCCCTCTATGGCAATGAGGGCATGGGGTGGGCAGGATGGCTCCTGTCACCCGCGG |
| 109 | SA10 | 245 | CTTGGCCCCCTCTATGGCAATGAGGGCATGGGGTGGGCAGGATGGCTCCTGTCACCCGTGG |
| 110 | S45 | 245 | CTTGGCCCCCTCTATGGCAATGAGGGCTTGGGGTGGGCAGGATGGCTCCTGTCACCCGTGG |
| 123 | P8 | 245 | CTTGGCCCCCTCTATGGCgACGAGGGCATGGGGTGGGCgGGATGGCTCCTGTCACCCGCGG |
| 124 | T3 | 245 | CTTGGCCCCCTCTATGGCAACGAGGGCATGGGGTGGGCAGGATGGCTCCTGTCACCCGCGG |
| 120 | HK3 | 245 | CTTGGCCCCCTCTATGGCAACGAGGGCATGGGGTGGGCAGGATGGCTCCTGTCACCCGCGG |
| 121 | HK5 | 245 | CTTGGCCCCCTCTATGGCAATGAGGGCATGGGGTGGGCAGGATGGCTCCTGTCACCCCatGG |

| | | |
|---|---|---|
| 109-124 | consensus | CtTGGCCCCCTCTAtGgCaAtGAGGGC-TGGGgTGGGCAGGATGGCTCCTGTCaCCCgcGG |

FIGURE 6B-6

| SEQ ID NO: | ISOLATE | | |
|---|---|---|---|
| 119 | S9 | 306 | cTCTCGGCCTAGTTGGGCCCCAatGACCCCCGGCGTAGGTCGCGTAATTGGGTAAgGTC |
| 117 | IND3 | 306 | tTCTCGGCCTAGTTGGGCCCCACAGACCCCCGGCGTAGGTCGCGTAATTGGGTAAaGTC |
| 118 | IND8 | 306 | CTCTCGGCCTAGTTGGGCCCCACAGACCCCCGGCGTAGGTCGCGTAATTGGGTAAGGTC |
| 111 | D1 | 306 | CTCCCGGCCTAGTTGGGCCCCACGACCCCCGGCGTAGGTCGCGTAATTTGGGTAAGGTC |
| 112 | US6 | 306 | CTCCCGGCCTAGTTGGGCCCCACGGACCCCCGGCGTAGGTCGCGTAATTTGGGTAAGGTC |
| 113 | P10 | 306 | CTCTCGGCCTAGTTGGGCCCCACGGACCCCCGGCGTAGGTCGCGTAATTTGGGTAAGGTC |
| 114 | DK1 | 306 | CTCTCGGCCTAGTTGGGCCCCAaCGACCCCCGGCGTAGGTCGCGTAATTTGGGTAAGGTC |
| 115 | T10 | 306 | CTCcCGGCCTAGTTGGGCCCCACaGACCCCCGGCGTAGGTCGCGTAATTTGGGTAAGGTC |
| 116 | SW2 | 306 | CTCTCGGCCTAGTTGGGCCCCACtGACCCCCGGCGTAGGTCGCGTAATTTGGGTAAGGTC |
| 122 | HK4 | 306 | CTCTCGGCCTAGTTGGGCCCCACGGACCCCCGGCGTAGGTCGCGCAATTTGGGTAAGGTC |
| 109 | SA10 | 306 | CTCTCGGCCTAGTTGGTTGGGCCCCACGGACCCCCGGCGTAGGTCGCGtAATTTGGGTAAGGTC |
| 110 | S45 | 306 | CTCCCGGCCTAGTTGGGCCCCACGACCCCCGGCGTAGGTCGCGCAATTTGGGTAAGGTC |
| 123 | P8 | 306 | CTCCCGGCCTAGTTGGGCCCCACGGACCCCCGGCGTAGGTCGCGCAATTTGGGTAAGGTC |
| 124 | T3 | 306 | CTCCCGGCCTAAtTGGGCCCCACaGACCCCCGGCGTAGGTCGCGtAATcTGGGTAAGGTC |
| 120 | HK3 | 306 | CTCTCGGCCTAATTGGGCCCCACGGACCCCCGGCGTAGGTCGCGCAATTTGGGTAAGGTC |
| 121 | HK5 | 306 | CTCTCGGCCTAGTTGGGCCCCACGGACCCCCGGCGTAGGTCGCGtAATTTGGGTAAGGTC |
| 109-124 | consensus | | cTCtCGGCCTAgTTGGGCCCCAcgGACCCCCGGCGTAGGTCGCGtAAtTGGGTAAgGTC |

FIGURE 6B-7

| SEQ ID NO: | ISOLATE | | |
|---|---|---|---|
| 119 | S9 | 367 | ATCGATACCCTCACATGCGGCTTtGCCGACCTCATGGGGTACATtCCGCTCGTCGGCGCCC |
| 117 | IND3 | 367 | ATCGATACCCTCACATGCGGCTTCGCCGACCTCATGGGTACATCCCGCTCGTCGGCGCCC |
| 118 | IND8 | 367 | ATCGATACCCTCACATGCGGCTTCGCCGACCTCATGGGTACATCCGCTCGTCGGCGCCC |
| 111 | D1 | 367 | ATCGATACCCTCACATGCGGCTTCGCCGACCTCATGGGTACATCCGCTCGTCGGCGCCC |
| 112 | US6 | 367 | ATCGATACCCTCACATGCGGCTTCGCCGACCTCATGGGTACATCCGCTCGTCGGCGCCC |
| 113 | P10 | 367 | ATCGATACCCTCACATGCGGCTTCGCCGACCTCATGGGTACATtCCGCTCGTCGGCGCCC |
| 114 | DK1 | 367 | ATCGATACCCTCACATGCGGCTTCGCCGACCTCATGGGTACATtCCGCTCGTCGGCGCCC |
| 115 | T10 | 367 | ATCGATACCCTCACATGCGGCTTCGCCGACCTCATGGGTACATtCCGCTCGTCGGCGCCC |
| 116 | SW2 | 367 | ATCGATACCCTCACATGCGGCTTCGCCGACCTCATGGGTACATtCCGCTCGTCGGCGCCC |
| 122 | HK4 | 367 | ATCGATACCCTCACATGCGGCTTCGCCGACCTCATGGGTACATtCCGCTCGTCGGCGCCC |
| 109 | SA10 | 367 | ATCGATACCCTCACgTGCGGCTTCGCCGACCTCATGGGTACATtCCGCTCGTCGGCGCCC |
| 110 | S45 | 367 | ATCGATACCCTCACATGCGGCTTCGCCGACCTCATGGGTACATtCCGCTCGTCGGCGCCC |
| 123 | P8 | 367 | ATCGATACCCTCACATGCGGCTTCGCCGACCTCATGGGTACATtCCGCTCGTCGGCGgCC |
| 124 | T3 | 367 | ATCGATACCCTCACATGCGGCTTCGCCGACCTCATGGGTACATtCCGCTCGTCGGCGCtC |
| 120 | HK3 | 367 | ATCGATACCCTCACgTGCGGCGTGCCGACCTCATGGGTACATCCGCTCGTCGGtGCCC |
| 121 | HK5 | 367 | ATCGATACCCTCACgTGCGGCTTCGCCGACCTCATGGGTACATCCCGCTCGTCGGCGCCC |

| 109-124 | consensus | ATCGATACCCTCACatGCGGCTTcGCCGACCTCATGGGTACAttCCGCTCGTCGGcGccC |

FIGURE 6B-8

| SEQ ID NO: | ISOLATE | | |
|---|---|---|---|
| 119 | S9 | 428 | CCCTAGGGGCGCTGCCAGGGCtCTGGCGCATGGCGTCCGGGTtCTGGAGGACGGCGTGAA |
| 117 | IND3 | 428 | CCCTAGGGGCGCTGCCAGGCCCTGGCGCATGGCGTCCGGGTCCTGGAGGACGGCGTGAA |
| 118 | IND8 | 428 | CCCTAGGGGGTGCTGCCAGGCCCTGGCGCATGGCGTCCGGGTCCTGGAGGACGGCGTGAA |
| 111 | D1 | 428 | CCCTAGGGGGTGCTGCCAGGCCCTGGCGCATGGCGTCCGGGTTCTGGAGGACGGCGTGAA |
| 112 | US6 | 428 | CCCTAGGGGCGCTGCCAGGCCCTtGGCGCATGGCGTCCGGGTTCTGGAGGACGGCGTGAA |
| 113 | P10 | 428 | CCCTAGGGGCGCTGCCAGGGCCCTGGCGCATGGCGTCCGGGTCCTGGAGGACGGCGTGAA |
| 114 | DK1 | 428 | CCCTAGGGGCGCTGCCAGGCCCTGGCGCATGGCGTCCGGGTCCTGGAGGACGGCGTGAA |
| 115 | T10 | 428 | CCCTAGGGGCGCTGCCAGGCtCTGGCaCATGGtGTCCGGGTTCTGGAGGACGGCGTGAA |
| 116 | SW2 | 428 | CCCTAGGGGCGCTGCCAGGCCCTGGCgCATGGCGTCCGGGTCCTGGAGGACGGCGTGAA |
| 122 | HK4 | 428 | CCTTAGGGGCGTGCCTGCCAGaGCCTTGGCGCATGGCaCATGGtGTCCGGGTTgTGGAGGACGGCGTGAA |
| 109 | SA10 | 428 | CtTTAGGGGCGCTGCCTGCCAGaGCCTTGGCGCATGGCGTCCGGGTTCTGGAaGACGGCGTGAA |
| 110 | S45 | 428 | CCCTAGGGGCGCTGCCAGaGCCTTGGCGCATGGCGTCCGGGTTCTGGAGGACGGCGTGAA |
| 123 | P8 | 428 | CCCTAGGGGCGTTGCCAGGCCCTGGCGCATGGCGTCCGGGTTgTGGAGGACGGCGTGAA |
| 124 | T3 | 428 | CCtTAGGGGCGTTGCCAGGCCCTGGCGCATGGCGTCCGGGTTCTGGAGGACGGCGTGAA |
| 120 | HK3 | 428 | CCCTAGGGGCGCGTTGCCAGAGCCttGGCACATGTGTCCGGGTTCTGGAGGACGGCGTGAA |
| 121 | HK5 | 428 | CCCTAGGGGCGTGCCAGAGCCTGCCACACGTGTCCGGGCACACGGTGTCCGGGTTCTGGAGGACGGCGTGAA |
| 109-124 | consensus | | CccTAGGGGcGCTGCCAGgCccTGGCgCATGGCGTCCGGGTtcTGGAgGACGGCGTGAA |

FIGURE 6B-9

| SEQ ID NO: | ISOLATE | | |
|---|---|---|---|
| 119 | S9 | 489 | CTATGCAACAGGGAACcTcCCCGGTTGCTCTTTCTCTATCTTCCTTcTgGCTTTgCTgTCC |
| 117 | IND3 | 489 | CTATGCAACAGGGAACTTGCCCGGTTGCTCTTCTCTATCTTCCTTCTCTTTTaGCTTTgCTATCC |
| 118 | IND8 | 489 | CTATGCAACAGGGAACTTGCCCGGTTGCTCTTCTCTATCTTCCTTTCTTTGCTTTGCTATCC |
| 111 | D1 | 489 | tTATGCAACAGGGAAtTGCCCGGTTGCTCTTCTCTATCTTCCTCTTCCTTGGCTTTGCTGTCC |
| 112 | US6 | 489 | CTATGCAACAGGGAACTTGCCCGGTTGCTCTTCTCTATCTTCCTCTTCCTTGGCTTTGCTGTCC |
| 113 | P10 | 489 | CTATGCAACAGGGAATCTGCCCGGTTGCTCTTCTCTATCTTCCTCTTGGCTTTGCTGTCC |
| 114 | DK1 | 489 | CTAcGCAACAGGGAATTTGCCCGGTTGCTCTTCTCTATCTTCCTCTTGGCTTGCTGTCC |
| 115 | T10 | 489 | CTATGCAACAGGGAATTTGCCCGGTTGCTCTTCTCTATCTTCCTCTTGGCTCtGtCTGTCC |
| 116 | SW2 | 489 | CTATGCAACAGGGAATcTGCCCGGTTGCTCTTCTCTTTCTCTATCTTCCTCTTGGCTCTCGTCC |
| 122 | HK4 | 489 | CTATGCAACAGGGAATTTGCCCGGTTGCTCTTCTCTATCTTCCTCTTGGCTtTGCTGTCC |
| 109 | SA10 | 489 | CTATGCAACAGGGAATTTGCCCGGTTGCTCCTTCTCTATCTTCCTCTTGGCTcTGCTGTCC |
| 110 | S45 | 489 | CTATGCAACAGGGAATCTGCCCGGTTGCCCTTCTCTATCTTCCTCTTGGCTcTCGTGTCC |
| 123 | P8 | 489 | CTATGCAACAGGGAATCTGCCTGGTTGCTCTTCTCTATCTTCCTCTTtTGGCTTTGCTGTCt |
| 124 | T3 | 489 | tTAcGCAACAGGGAATTTGCCTGGTTGCTCTTCTCTATCTTCCTCTTGGCTTTGCTGTCC |
| 120 | HK3 | 489 | CTAtGCAACAGGGAATTTACCCGGTTGCTCTTCTCTATCTTCCTCTTGGCTTGCTGTCC |
| 121 | HK5 | 489 | CTAcGCAACAGGGAATaTACCCGGTTGCTCTTTCTCTATCTTCCTCTTtTGGCTTGCTGTCC |

| 109-124 | consensus | cTAtGCAACAGGGAAttTgCCcGGTTGCtCtTTcTCTATcTTCcTctTgGCTtTgcTgTCc |

FIGURE 6B-10

| SEQ ID NO: | ISOLATE | | |
|---|---|---|---|
| 119 | S9 | 550 | TGTTTGACCATCCCAGCTTCCGCT |
| 117 | IND3 | 550 | TGTTTGACCATCCCAGCTTCCGCT |
| 118 | IND8 | 550 | TGTTTGACCgTCCCAGCTTCCGCT |
| 111 | D1 | 550 | TGTTTGACCATCCCAGCTTCCGCT |
| 112 | US6 | 550 | TGTTTGACCATtCCAGCTTCCGCT |
| 113 | P10 | 550 | TGccTGACCATCCCAGCTTCCGCT |
| 114 | DK1 | 550 | TGTTGACCATCCCAGCgTCCGCT |
| 115 | T10 | 550 | TGTtTGACCATCCCAGCTTCCGCc |
| 116 | SW2 | 550 | TGTCTGACCATCCCAGCTTCCGCT |
| 122 | HK4 | 550 | TGTTTGACCATCCCAGCTTCCGCT |
| 109 | SA10 | 550 | TGTTaACCATCCCAGCTTCCGCT |
| 110 | S45 | 550 | TGcTTGACCATCCCAGCTTCCGCT |
| 123 | P8 | 550 | TGtcTGACCATCCCAGCTTCCGCT |
| 124 | T3 | 550 | TGCTTGACCATCCCAGCTTCCGCT |
| 120 | HK3 | 550 | TGCTTGACCACCCCAGCTTCCGCT |
| 121 | HK5 | 550 | TGtcTGACCACCCCAGtTTCCGCT |

| 109-124 | consensus | TGttTgACCatcCCAgCTTCCGCt |

FIGURE 6C-1

| SEQ ID NO: | ISOLATE | | |
|---|---|---|---|
| 119 | S9 | 1 | ATGAGCACGAATCCTAAACCTCAAAGAAAAACCAAACGTAACACCAACCGCCGCCCACAGG |
| 117 | IND3 | 1 | ATGAGCACGAATCCTAAACCTCAAAGAAAAACCAAACGTAACACCAACCGCCGCCCACAGG |
| 118 | IND8 | 1 | ATGAGCACGAATCCTAAACCTCAAAGAAAAACCAAACGTAACACCAACCGCCGCCCACAGG |
| 111 | D1 | 1 | ATGAGCACGAATCCTAAACCTCAAAGAAAAACCAAACGTAACACCAACCGCCGCCCACAGG |
| 112 | US6 | 1 | ATGAGCACGAATCCTAAACCTCAAAGAAAAACCAAACGTAACACCAACCGCCGCCCACAGG |
| 113 | P10 | 1 | ATGAGCACGAATCCTAAACCTCAAAGAAAAACCAAACGTAACACCAACCGCCGCCCACAGG |
| 114 | DK1 | 1 | ATGAGCACGAATCCTAAACCTCAAAGAAAAACCAAACGTAACACCAACCGCCGCCCACAGG |
| 115 | T10 | 1 | ATGAGCACGAATCCTAAACCTCAAAGAAAAACCAAACGTAACACCAACCGCCGCCCACAGG |
| 116 | SW2 | 1 | ATGAGCACGAATCCTAAACCTCAAAGAAAAACCAAACGTAACACCAACCGCCGCCCACAGG |
| 122 | HK4 | 1 | ATGAGCACGAATCCTAAACCTCAAAGAAAAACCAAACGTAACACCAACCGCCGCCCACAGG |
| 109 | SA10 | 1 | ATGAGCACGAATCCTAAACCTCAAAGAgAAAACCAAACGTAACACCAACCGCCGCCCACAGG |
| 110 | S45 | 1 | ATGAGCACGAATCCTAAACCTCAAAGACAAAACCAAACGTAACACCAACCGCCGCCCACAGG |
| 123 | P8 | 1 | ATGAGCACGACTCCTAAACCTCAAAGAAAAACCAAACGTAACACCAgCCGCCGCCCACAGG |
| 124 | T3 | 1 | ATGAGCACGAATCCTAAACCTCAAAGAAAAACCAAACGTAACACCAACCGCCGCCCACAGG |
| 120 | HK3 | 1 | ATGAGCACGAATCCTAAACCTCAAAGAAAAACCAAACGTAACACCAACCGCCGCCCACAGG |
| 121 | HK5 | 1 | ATGAGCACGAATCCTAAACCTCAAAGAAAAACCAAACGTAACACCAACCGCCGCCCACAGG |
| 108 | DR4 | 1 | ATGAGCACGAATCCTAAACCTCAAAGAAAAACCAAACGTAACACCAACCGTCGCCCACAGG |
| 104 | US11 | 1 | ATGAGCACGAATCCTAAACCTCAAAGAAAAACCAAACGTAACACCAACCGTCGCCCACAGG |
| 105 | S14 | 1 | ATGAGCACGAATCCTAAACCTCAAAGAAAAACCAAACGTAACACCAACCGTCGCCCACAGG |
| 106 | SW1 | 1 | ATGAGCACGAATCCTAAACCTCAAAGAAAAACCAAACGTAACACCAACCGTCGCCCACAGG |
| 107 | S18 | 1 | ATGAGCACGAATCCTAAACCTCAAAGAAAAACCAAACGTAACACCAACCGTCGCCCACAGG |
| 103 | DK7 | 1 | ATGAGCACGaATCCTAAACCTCAAAGAAAAACCAAACGTAACACCAACCGTCGCCCACAGG |

| 103-124 | consensus | ATGAGCACGaAtCCTAAACCTCAAAGAaAaACCAAACGTAACACCAaCCGcCGCCCACAGG |

FIGURE 6C-2

| SEQ ID NO: | ISOLATE | | |
|---|---|---|---|
| 119 | S9 | 62 | ACGTtAAGTTCCCGGGCGGTGGtCAGATCGTcGGTGGAGTTtACCTGTTGCCGCGCAGGGG |
| 117 | IND3 | 62 | ACGTCAAGTTCCCGGGCGGTGGCCAGATCGTTGGTGGAGTTTACCTGTTGCCGCGCAGGGG |
| 118 | IND8 | 62 | ACGTCAAGTTCCCGGGCGGTGGCCAGATCGTTGGTGGAGTTTACCTGTTGCCGCGCAGGGG |
| 111 | D1 | 62 | ACGTCAAGTTCCCGGGCGGTGGCCAGATCGTTGGTGGAGTTTACCTGTTGCCGCGCAGGGG |
| 112 | US6 | 62 | ACGTCAAGTTCCCGGGCGGTGGTGTCAGATCGTTGGTGGAGTTTACCTGTTGCCGCGCAGGGG |
| 113 | P10 | 62 | ACGTCAAGTTCCCGGGCGGTGGTCAGATCGTTGGTGGAGTTTACCTGTTGCCGCGCAGGGG |
| 114 | DK1 | 62 | ACGTCAAGTTCCCGGGCGGTGGTCAGATCGTTGGTGGAGTTTACCTGTTGCCGCGCAGGGG |
| 115 | T10 | 62 | ACGTCAAGTTCCCGGGCGGTGGTCAGATCGTTGGTGGAGTTTACCTGTTGCCGCGCAGGGG |
| 116 | SW2 | 62 | ACGTCAAGTTCCCGGGCGGCGGTGGCCAGATCGTTGGTGGAGTTTACCTGTTGCCGCGCAGGGG |
| 122 | HK4 | 62 | ACGTtAAGTTCCCGGGCGGTGGCCAGATCGTcGGTGGAGTTTACCTGTTGCCGCGCAGGGG |
| 109 | SA10 | 62 | ACGTCAAGTTCCCGGGCGGTGGCCAGATCGTTGGTGGAGTCtATCTGTTGCCGCGCAGGGG |
| 110 | S45 | 62 | ACGTCAAGTTCCCGGGtGGCGGTGGTCAGATCGTTGGTGGAGTTTACCTGTTGCCGCGCAGGGG |
| 123 | P8 | 62 | ACGTtAAGTTCCCGGGCGGTGGTCAGATCGTTGGTGGAGTTTACCTGTTGCCGCGCAGGGG |
| 124 | T3 | 62 | ACGTtAAGTTCCCGGGCGGCGGTGGTCAGATCGTTGGTGGAGTTTACCTGTTGCCGCGCAGGGG |
| 120 | HK3 | 62 | ACGTCAAGTTCCCGGGCGGTGGCGGTCAGATCGTTGGTGGAGTTTACCTGTTGCCGCGCAGGGG |
| 121 | HK5 | 62 | ACGTCAAGTTCCCGGGCGGTGGCGGTCAGATCGTTGGTGGAGTTTACCTGTTGCCGCGCAGGGG |
| 108 | DR4 | 62 | ACGTCAAGTTCCCGGGCGGTGGCGGTCAGATCGTTGGTGGAGTTTACTTGTTGCCGCGCAGGGG |
| 104 | US11 | 62 | ACGTCAAGTTCCCGGGCGGTGGTGGCGGTCAGATCGTTGGTGGAGTTTACTTGTTGCCGCGCAGGGG |
| 105 | S14 | 62 | ACGTCAAGTTCCCGGGCGGTGGTGGCGGTCAGATCGTTGGTGGAGTTTACTTGTTGCCGCGCAGGGG |
| 106 | SW1 | 62 | ACGTCAAGTTCCCGGGCGGTGGTGGCGGTCAGATCGTTGGTGGAGTTTACTTGTTGCCGCGCAGGGG |
| 107 | S18 | 62 | ACGTtAAGTTCCCGGGCGGTGGTGGCGGTCAGATCGTTGGTGGAGTTTACTTGTTGCCGCGCAGGGG |
| 103 | DK7 | 62 | ACGTcAAGTTCCCGGGCGGTGGCGGTCAGATCGTTGGTGGAGTTTACTTGTTGCCGCGCAGGGG |

| 103-124 | consensus | ACGTCAAGTTCCCGGGCGGtGGtCAGATCGTtGGTGGAGTtTAccTGTTGCCGCGCAGGGG |

FIGURE 6C-3

| SEQ ID NO: | ISOLATE | | |
|---|---|---|---|
| 119 | S9 | 123 | CCCCAGGTTGGGTGTGCGCGCaACTAGGAAGACTTCCGAGCGGTCGCAACCTCGTGGAAGG |
| 117 | IND3 | 123 | CCCCAGGTTGGGTGTGCGCGCGCGACTAGGAAGACTTCCGAGCGGTCGCAACCTCGTGAAGG |
| 118 | IND8 | 123 | CCCCAGGTTGGGTGTGCGCGCGCGACTAGGAAGACTTCCGAGCGGTCGCAACCTCGTGAAGG |
| 111 | D1 | 123 | CCCCAGGTTGGGTGTGCGCGCGCGACTAGGAAGACTTCCGAGCGGTCGCAACCTCGTGAAGG |
| 112 | US6 | 123 | CCCCAGGTTGGGTGTGCGCGCGCGACTAGGAAGACTTCCGAGCGGTCGCAACCTCGTGAAGG |
| 113 | P10 | 123 | CCCCAGGTTGGGTGTGCGCGCGCGACTAGGAAGACTTCCGAGCGGTCGCAACCTCGTGAAGG |
| 114 | DK1 | 123 | CCCCAGGTTGGGTGTGCGCGCGCGACTAGGAAGACTTCCGAGCGGTCGCAACCTCGTGAAGG |
| 115 | T10 | 123 | CCCCAGGTTGGGTGTGCGCGCGCGACTAGGAAGACTTCCGAGCGGTCGCAACCTCGTGAAGG |
| 116 | SW2 | 123 | CCCCcGGTTGGGTGTGCGCGCGCGACTAGGAAGACTTCCGAGCGGTCGCAACCTCGTGAAGG |
| 122 | HK4 | 123 | CCCCAGGTTGGGTGTGCGCGCGCGACTAGGAAGACTTCCGAGCGGTCGCAACCTCGTGAAGG |
| 109 | SA10 | 123 | CCCCAGGTTGGGTGTGCGCGCGCGACgAGGAAGACTTCCGAGCGGTCGCAACCTCGTGAAGG |
| 110 | S45 | 123 | CCCCAGGTTGGGTGTGCGCGCGCGACTAGGAAGACTTCCGAGCGGTCaCAACCTCGTGGACGG |
| 123 | P8 | 123 | CCCCAGGTTGGGTGTGCGCGCGCGACTAGGAAGACTTCCGAGCGaTCGCAACCTCGTGGcAGG |
| 124 | T3 | 123 | CCCCAGGTTGGGTGTGCGCGCGCGACTAGGAAGACTTCCGAGCGGTCGCAACCTCGTGAAGG |
| 120 | HK3 | 123 | CCCCAGGTTGGGTGTGCGCGCGCGACCAGGAAGACTTCaGAGCGGTCGCAACCTCGTGAAGG |
| 121 | HK5 | 123 | CCCCAGGTTGGGTGTGCGCGCGCGACCAGGAAGACTTCCGAGCGGTCGCAACCTCGTGAAGG |
| 108 | DR4 | 123 | CCCTAGATTGGGTGTGCGCGCGCGACGAGGAAGACTTCCGAGCGGTCGCAACCTCGAGGTAGA |
| 104 | US11 | 123 | CCCTAGATTGGGTGTGCGCGCGCGACGAGGAAGACTTCCGAGCGGTCGCAACCTCGAGGTAGA |
| 105 | S14 | 123 | CCCTAGATTGGGTGTGCGCGCGCGACGAGGAAGACTTCCGAGCGGTCGCAACCTCGAGGTAGA |
| 106 | SW1 | 123 | CCCTAGATTGGGTGTGCGCGCGCGACGAGGAAGACTTCCGAGCGGTCGCAACCTCGAGGTAGA |
| 107 | S18 | 123 | CCCTAGATTGGGTGTGCGCGCGCGACGAGGAAGACTTCCGAGCGGTCGCAACCTCGAGGTAGA |
| 103 | DK7 | 123 | CCCTAGATTGGGTGTGCGCGCGCcGAGGAAGACTTCCGAGCGGTCGCAACCTCGAGGTAGA |

| 103-124 | consensus | | CCCcaGgTTGGGTGTGCGCGCGgacTAGGAAGACTTCcGAGCGgTCgCAACCTCGtGGaaGg |

FIGURE 6C-4

| SEQ ID NO: | ISOLATE | | |
|---|---|---|---|
| 119 | S9 | 184 | CGACAACCTATCCCCAAGGCTCGCCatCCCGAGGGCAGGGCCTGGGCTCAGCCCGGGTACC |
| 117 | IND3 | 184 | CGACAACCTATCCCCAAGGCTCGCCGGCCCGAGGGCCTAGGGCCTGGGCTCAGCCCGGGTACC |
| 118 | IND8 | 184 | CGACAACCTATCCCCAAGGCTCGCCGGCCCGAGGGCCTAGGGCCTGGGCTCAGCCCGGCACC |
| 111 | D1 | 184 | CGACAACCTATCCCCAAGGCTCGCCGGCCCGAGGGCCTAGGGCCTGGGCTCAGCCCGGGTACC |
| 112 | US6 | 184 | CGACAACCTATCCCCAAGGCTCGCCGGCCCGAGGGCCAGGGCCTGGGCTCAGCCCGGGTACC |
| 113 | P10 | 184 | CGACAACCTATCCCCAAGGCTCGCCGGCCCGAGGGCCAGGGCCTGGGCTCAGCCCGGGTACC |
| 114 | DK1 | 184 | CGACAACCTATCCCCAAGGCTCGCCGGCCCGAGGGCCAGGGCCTGGGCTCAGCCCGGGTACC |
| 115 | T10 | 184 | CGACAACCTATCCCCAAGGCTCGCCAGCCCGAGGGCCAGGGCCTGGGCTCAGCCCGGGTACC |
| 116 | SW2 | 184 | CGACAgCCTATCCCCAAGGCTCGCCAGCCCGAGGGCCAGGGCCTGGGCTCAGCCCGGGTACC |
| 122 | HK4 | 184 | CGACAACCTATCCCCAAGGCTCGCCAGCCCGAGGGCCAGGGCCTGGGCTCAGCCCGGGTACC |
| 109 | SA10 | 184 | CGACAACCTATCCCCAAGGCTCGCCAaCCCAGCCCGAGGGCCAGGGCCAGGACCTGGGCTCAGCCCGGGTACC |
| 110 | S45 | 184 | CGACAACCTATCCCCAAGGCTCGCCGGCCCAGCCCGAGGGCCAGGACCTGGGCTCAGCCCGGGTACC |
| 123 | P8 | 184 | CGACAACCTATCCCCAAGGCTCGCCGGCCCGAGGGCCAGGACCTGGGCCCAGCCCGGGCACC |
| 124 | T3 | 184 | CGACAACCTATCCCCAAGGCTCGCCGGCCCGAGGGCCAGGGCCAGGACCTGGGCTCAGCCCGGGTACC |
| 120 | HK3 | 184 | CGACAACCTATCCCCAAGGCTCGCCGGCCCAACCCGAGGGCTAGGGCCAGGACCTGGGCTCAGCCCGGGTATC |
| 121 | HK5 | 184 | CGACAACCTATCCCCAAGGCTCGCCGGCCCGACCCGAGGGCCAGGACCTGGGCTCAGCCCGGGTATC |
| 108 | DR4 | 184 | CGTCAGCCTATCCCCAAGGCgCGTCGGCCCGAGGGCCAGGACCTGGGCTCAGCCCGGGTACC |
| 104 | US11 | 184 | CGTCAGCCTATCCCCAAGGCACGTCGGCCCGAGGGCCAGGACCTGGGCTCAGCCCGGGTACC |
| 105 | S14 | 184 | CGTCAGCCTATCCCCAAGGCACGTCGGCCCGAGGGCCAGGACCTGGGCTCAGCCCGGGTATC |
| 106 | SW1 | 184 | CGTCAGCCTATCCCCAAGGCGCGTCGGCCCGAGGGCCAGGACCTGGGCTCAGCCCGGGTATC |
| 107 | S18 | 184 | CGTCAGCCTATCCCCAAGGCGCGTCGGCCCGAGGGCCAGGACCTGGGCTCAGCCCGGGTACC |
| 103 | DK7 | 184 | CGTCAGCCTATCCCCAAGGCaCGTCGGCCCGAGGGCCAGGACCTGGGCTCAGCCCGGGTACC |

| 103-124 | consensus | CGaCAaCCTATCCCCAAGGCtCGcCggCCCGAGGGCAGGgCCTGGGCtCAGCCCGGGtAcC |

FIGURE 6C-5

| SEQ ID NO: | ISOLATE | | |
|---|---|---|---|
| 119 | S9 | CTTGGCCCCTCTACGGCAATGAGGGCTTGGGGTGGGCAGGATGGCTCCTGTCACCCGtGG | 245 |
| 117 | IND3 | CTTGGCCCCTCTATGGCAATGAGGGCTTGGGGTGGGCAGGATGGCTCCTGTCACCCGCGG | 245 |
| 118 | IND8 | CTTGGCCCCTCTATGGCAATGAGGGCTTGGGGTGGGCAGGATGGCTCCTGTCACCCGCGG | 245 |
| 111 | D1 | CTTGGCCCCTCTATGGCAACGAGGGCTTGGGGTGGGCAGGATGGCTCCTGTCACCCGCGG | 245 |
| 112 | US6 | CTTGGCCCCTCTATGGCAACGAGGGCaTGGGGTGGGCAGGATGGCTCCTGTCACCCGTGG | 245 |
| 113 | P10 | CTTGGCCCCTCTATGGCAATGAGGGCtTGGGGTGGGCAGGATGGCTCCTGTCACCCGTGG | 245 |
| 114 | DK1 | CTTGGCCCCTCTATGGCAATGAGGGCATGGGGTGGGCAGGATGGCTCCTGTCACCCGcGG | 245 |
| 115 | T10 | CTTGGCCCCTCTATGGCAATGAGGGCATGGGGTGGGCAGGATGGCTCCTGTCACCCGtGG | 245 |
| 116 | SW2 | CcTGGCCCCTCTATGGCAATGAGGGCATGGaTGGGCAGGATGGCTCCTGTCcCCCGCGG | 245 |
| 122 | HK4 | CTTGGCCCCTCTATGGCAATGAGGGCATGGGGTGGGCAGGATGGCTCCTGTCACCCGCGG | 245 |
| 109 | SA10 | CTTGGCCCCTCTATGGCAATGAGGGCTTGGGGTGGGCAGGATGGCTCCTGTCACCCGTGG | 245 |
| 110 | S45 | CTTGGCCCCTCTATGGCAATGAGGGCTTGGGGTGGGCAGGATGGCTCCTGTCACCCGTGG | 245 |
| 123 | P8 | CTTGGCCCCTCTATGcCAATGAGGGCTTGGGGTGGGCGGGATGGCTCCTGTCACCCGCGG | 245 |
| 124 | T3 | CTTGGCCCCTCTATGGCgACGAGAGGGCATGGGGTGGGCAGGATGGCTCCTGTCACCCGCGG | 245 |
| 120 | HK3 | CTTGGCCCCTCTATGGCAATGAGGGCATGGGGTGGGCAGGATGGCTCCTGTCACCCGCGG | 245 |
| 121 | HK5 | CTTGGCCCCTCTATGGCAATGAGGGCATGGGGTGGGCAGGATGGCTCCTGTCACCCGTGG | 245 |
| 108 | DR4 | CTTGGCCCCTCTATGGCAATGAGGGCTGCGGGGTGGGCAGGATGGCTCCTGTCACCCaTGG | 245 |
| 104 | US11 | CTTGGCCCCTCTATGGCAATGAGGGCTGCGGGGTGGGCGGGATGGCTCCTGTCcCCCGTGG | 245 |
| 105 | S14 | CTTGGCCCCTCTATGGCAATGAGGGCTGCGGGGTGGGCGGGATGGCTCCTGTCTCCCGTGG | 245 |
| 106 | SW1 | CTTGGCCCCTCTATGGCAATGAGGGCTGCGGaTGGGCGGGATGGCTCCTGTCTCCCGTGG | 245 |
| 107 | S18 | CTTGGCCCCTCTATGGCAATGAGGGCTGCGGGGTGGGCGGGATGGCTCCTGTCTCCCGTGG | 245 |
| 103 | DK7 | CTTGGCCCCTCTATGGCAATGAGGGCTGCGGGGTGGGCGGGATGGCTCCTGTctCCCGTGG | 245 |

103-124 consensus   ctTGGCCCCTCTAtGgCaAtGAGGGCttgGGgTGGGCaGGATGGCTCCTGTCaCCCGtGG

FIGURE 6C-6

| SEQ ID NO: | ISOLATE | | |
|---|---|---|---|
| 119 | S9 | 306 | cTCTCGGCCTAGTTGGGGCCCCAatGACCCCCGGCGTAGGTCGCGTAATTGGGTAAgGTC |
| 117 | IND3 | 306 | tTCTCGGCCTAGTTGGGGCCCCACACAGACCCCCGGCGTAGGTCGCGTAATTGGGTAAaGTC |
| 118 | IND8 | 306 | CTCTCGGCCTAGTTGGGGCCCCACAGACCCCCGGCGTAGGTCGCGTAATTGGGTAAGGTC |
| 111 | D1 | 306 | CTCCCGGCCTAGTTGGGGCCCCACCGACCCCCGGCGTAGGTCGCGTAATTGGGTAAGGTC |
| 112 | US6 | 306 | CTCCCGGCCTAGTTGGGGCCCCACGGACCCCCGGCGTAGGTCGCGTAATTGGGTAAGGTC |
| 113 | P10 | 306 | CTCTCGGCCTAGTTGGGGCCCCACGGACCCCCGGCGTAGGTCGCGTAATTGGGTAAGGTC |
| 114 | DK1 | 306 | CTCTCGGCCTAGTTGGGGCCCCAacGACCCCCGGCGTAGGTCGCGTAATTGGGTAAGGTC |
| 115 | T10 | 306 | CTCcCGGCCTAGTTGGGGCCCCACAGACCCCCGGCGTAGGTCGCGTAATTGGGTAAGGTC |
| 116 | SW2 | 306 | CTCTCGGCCTAGTTGGGGCCCCACtGACCCCCGGCGTAGGTCGCGTAATTGGGTAAGGTC |
| 122 | HK4 | 306 | CTCTCGGCCTAGTTGGGGCCCCACGGACCCCCGGCGTAGGTCGCGTAATTGGGTAAGGTC |
| 109 | SA10 | 306 | CTCTCGGCCTAGTTGGGGCCCCACGGACCCCCGGCGTAGGTCGCGCAATTGGGTAAGGTC |
| 110 | S45 | 306 | CTCTCGGCCTAGTTGGGGCCCCACGGACCCCCGGCGTAGGTCGCGCAATTGGGTAAGGTC |
| 123 | P8 | 306 | CTCCCGGCCTAATTGGGGCCCCACGGACCCCCGGCGTAGGTCGCGCAATTGGGTAAGGTC |
| 124 | T3 | 306 | CTCCCGGCCTAATTGGGGCCCCACACAGACCCCCGGCGTAGGTCGGtAATcTGGGTAAGGTC |
| 120 | HK3 | 306 | CTCTCGGCCTAGTTGGGGCCCCACGGACCCCCGGCGTAGGTCGCGCAATTGGGTAAGGTC |
| 121 | HK5 | 306 | CTCTCGGCCTAGTTGGGGCCCCACGGACCCCCGGCGTAGGTCGCGtAATTGGGTAAGGTC |
| 108 | DR4 | 306 | CTCTCGGCCTAGCTGGGGCCCCACAGACCCCCGGCGTAGGTCGCGCAATTGGGTAAGGTC |
| 104 | US11 | 306 | CTCTCGGCCTAGCTGGGGCCCCACGGACCCCCGGCGTAGGTCGCGCAATTGGGTAAGGTC |
| 105 | S14 | 306 | CTCTCGGCCTAGCTGGGGCCCCACAGACCCCCGGCGTAGGTCCGCGCAATTTGGGTAAGGTC |
| 106 | SW1 | 306 | CTCTCGGCCTAGCTGGGGCCCCACAGACCCCCGGCGTAGGTCGCGCAATTGGGTAAGGTC |
| 107 | S18 | 306 | CTCcCGGCCTAGCTGGGGCCCTACAGACCCCCGGCGTAGGTCGCGCAATTGGGCAAAGTC |
| 103 | DK7 | 306 | CTCtCGGCCTAGCTGGGGCCCCACAGACCCCCGGCGCAGGTCGCGCAATTGGGtAAAGTC |

| 103-124 | consensus | | cTCtCGGCCTAgtTGGGGCCCCAc-GACCCCCGGCGtAGGTCGCGtAAttTGGGtAAgGTC |

FIGURE 6C-7

| SEQ ID NO: | ISOLATE | | |
|---|---|---|---|
| 119 | S9 | 367 | ATCGATACCCTCACATGCGGCTTtGCCGACCTCATGGGTACAttCCGCTCGTCGGCGCCC |
| 117 | IND3 | 367 | ATCGATACCCTCACATGCGGCTTCGCCGACCTCATGGGTACATCCGCTCGTCGGCGCCC |
| 118 | IND8 | 367 | ATCGATACCCTCACATGCGGCTTCGCCGACCTCATGGGTACATCCGCTCGTCGGCGCCC |
| 111 | D1 | 367 | ATCGATACCCTCACATGCGGCTTCGCCGACCTCATGGGTACATCCGCTCGTCGGCGCCC |
| 112 | US6 | 367 | ATCGATACCCTCACATGCGGCTTCGCCGACCTCATGGGTACATTCCGCTCGTCGGCGCCC |
| 113 | P10 | 367 | ATCGATACCCTCACATGCGGCTTCGCCGACCTCATGGGTACATTCCGCTCGTCGGCGCCC |
| 114 | DK1 | 367 | ATCGATACCCTCACATGCGGCTTCGCCGACCTCATGGGTACATTCCGCTCGTCGGCGCCC |
| 115 | T10 | 367 | ATCGATACCCTCACATGCGGCTTCGCCGACCTCATGGGTACATTCCGCTCGTCGGCGCCC |
| 116 | SW2 | 367 | ATCGATACCCTCACATGCGGCTTCGCCGACCTCATGGGTACATTCCGCTCGTCGGCGCCC |
| 122 | HK4 | 367 | ATCGATACCCTCACATGCGGCTTCGCCGACCTCATGGGTACATTCCGCTCGTCGGCGCCC |
| 109 | SA10 | 367 | ATCGATACCCTCACATGCGGCTTCGCCGACCTCATGGGTACATTCCGCTCGTCGGCGCCC |
| 110 | S45 | 367 | ATCGATACCCTCACgTGCGGCTTCGCCGACCTCATGGGTACATTCCGCTCGTCGGCGCCC |
| 123 | P8 | 367 | ATCGATACCCTCACATGCGGCTTCGCCGACCTCATGGGTACATTCCGCTCGTCGGCGCCC |
| 124 | T3 | 367 | ATCGATACCCTCACATGCGGCTTCGCCGACCTCATGGGTACATTCCGCTCGTCGGCGctc |
| 120 | HK3 | 367 | ATCGATACCCTCACgTGCGGCTTCGCCGACCTCATGGGTACATCCGCTCGTCGGtGCCC |
| 121 | HK5 | 367 | ATCGATACCCTCACgTGCGGCTTCGCCGACCTCATGGGTACATCCGCTCGTCGGCGCCC |
| 108 | DR4 | 367 | ATCGAcACCCTCACgTGCGGCTTCGCCGACCTCATGGGTACATCCGCTCGTCGGCGCCC |
| 104 | US11 | 367 | ATCGATACCCTtACgTGCGGCTTCGCCGACCTCATGGGTACATACCGCTCGTCGGCGCCC |
| 105 | S14 | 367 | ATCGATACCCTCACgTGCGGCTTCGCCGACCTCATGGGTACATACCGCTCGTCGGCGCCC |
| 106 | SW1 | 367 | ATCGATACCCTCACgTGCGGCTTCGCCGACCTCAtGGGTACATTCCGCTCGTCGGCGCCC |
| 107 | S18 | 367 | ATCGATACCCTCACgTGCGGCTTCGCCGACCTCATGGGTACATTCCGCTCGTCGGCGCCC |
| 103 | DK7 | 367 | ATCGATACCCTtACgTGCGGCTTCGCCGACCTCATGGGTACATaCCGCTCGTCGGCGccc |

| 103-124 | consensus | ATCGAtACCCTcACaTGCGGCTTCGCCGACCTCATGGGTACATtCCGCTCGTCGGcGccc |

FIGURE 6C-8

| SEQ ID NO: | ISOLATE | | |
|---|---|---|---|
| 119 | S9 | 428 | CCCTAGGGGCGCTGCCAGGGCtCTGGCGCATGGCGTCCGGGTtCTGGAGGACGGCGTGAA |
| 117 | IND3 | 428 | CCCTAGGGGGCGCTGCCAGGCCCTGGCGCATGGCGTCCGGGTCCTGGAGGACGGCGTGAA |
| 118 | IND8 | 428 | CCCTAGGGGGTGCTGCCAGGCCCTGGCGCATGGCGTCCGGGTCCTGGAGGACGGCGTGAA |
| 111 | D1 | 428 | CCCTAGGGGGTGCTGCCAGGCCCTGGCGCATGGCGTCCGGGTTCTGGAGGACGGCGTGAA |
| 112 | US6 | 428 | CCCTAGGGGGCGCTGCCAGGCCtTGGCGCATGGCGTCCGGGTTCTGGAGGACGGCGTGAA |
| 113 | P10 | 428 | CCCTAGGGGGCGCTGCCAGGGCCTGGCGCATGGCGTCCGGGTTCTGGAGGACGGCGTGAA |
| 114 | DK1 | 428 | CCCTAGGGGGCGCTGCCAGGCCCTGGCGCATGGCGTCCGGGTTCTGGAGGACGGCGTGAA |
| 115 | T10 | 428 | CCCTAGGGGGCGCTGCCAGGGCtCTGGCaCATGGCGTCCGGGTTCTGGAGGACGGCGTGAA |
| 116 | SW2 | 428 | CCCTAGGGGGCGCTGCCAGGCCCTGGCgCATGgtGTCCGGGTCtCCGAGGACGGCGTGAA |
| 122 | HK4 | 428 | CCCTAGGGGCGtGCCAGaGCCCTGGCgCATGgtGTCCGGGTTgTGGAGGACGGCGTGAA |
| 109 | SA10 | 428 | CCtTAGGGGCGtGCTGCCAGGCCCTtGGCGCATGGCGTCCGGGTTCTGGAaGACGGCGTGAA |
| 110 | S45 | 428 | CCCTAGGGGGCGCTGCCAGgCCCTGGCGCATGGCGTCCGGGTTCTGGAGGACGGCGTGAA |
| 123 | P8 | 428 | CCCTAGGGGGCGCGTTGCCAGgCCCTGGCGCATGGCGTCCGGGTTgTGGAGGACGGCGTGAA |
| 124 | T3 | 428 | CCtTAGGGGGCGCGGTTGCCAGGCCCTGGCGCATGGCGTCCGGGTTCTGGAGGACGGCGTGAA |
| 120 | HK3 | 428 | CCCTAGGGGGCGCGTTGCCAGAGCCTTGGCACATGTGTCCGGGTTCTGGAGGACGGCGTGAA |
| 121 | HK5 | 428 | CCCTAGGGGGCGCGTTGCCAGAGCCCTGGCACACATGGCGTCCGGGTTCTGGAGGACGGCGTGAA |
| 108 | DR4 | 428 | CCCTtGGGGaGCCGTTGCCAGGCCCTGGCGCATGGCGTCCGaGTTCTGGAGGACGGCGTGAA |
| 104 | US11 | 428 | CtCTCGGaGGCGGCCGTTGCCAGGCCCTGGCGCATGGCGTCCGGGTTCTGGAAGACGGCGTGAA |
| 105 | S14 | 428 | CCCTCGGggGGCCGTTGCCAGGCCCTGGCGCATGGCGTCCGGGTTCTGGAAGACGGCGTGAA |
| 106 | SW1 | 428 | CtCTtGGAGGCCGTTGCCAGGCCCTGGCGCATGGCGTCCGGGTTCTGGAAGACGGCGTGAA |
| 107 | S18 | 428 | CTCTCGGAGGCCGCTGCCAGGCCCTGGCGCATGGCGTCCGGGTTCTGGAAGACGGCGTGAA |
| 103 | DK7 | 428 | CTCTtGGAGGCGGCTGCCAGGCCCTGGCGCATGGCGTCCGGGTTCTGGAAGACGGCGTGAA |

103-124 consensus CccTaGgGgCgGcTGCCAggGCCcCTGGCgCAtGGcGTCCggGTtcTGGAgGACGGCGTGAA

FIGURE 6C-9

| SEQ ID NO: | ISOLATE | | |
|---|---|---|---|
| 119 | S9 | 489 | CTATGCAACAGGGAACCTcCCCGGTTGCTCTTCTCTATCTTCCTCTgGCTTTGCTTgTCC |
| 117 | IND3 | 489 | CTATGCAACAGGGAACTTGCCCGGTTGCTCTTCTCTATCTTCCTCTTTaGCTTTGCTATCC |
| 118 | IND8 | 489 | CTATGCAACAGGGAACTTGCCCGGTTGCTCTTCTCTATCTTCCTCTTTGGCTTTGCTATCC |
| 111 | D1 | 489 | tTATGCAACAGGGAAtTTGCCCGGTTGCTCTTCTCTATCTTCCTCTTGGCTTTGCTGTCC |
| 112 | US6 | 489 | CTATGCAACAGGGAACTTGCCCGGTTGCTCTTCTCTATCTTCCTCTTGGCTTTGCTGTCC |
| 113 | P10 | 489 | CTATGCAACAGGGAATcTGCCCGGTTGCTCTTCTCTATCTTCCTCTTGGCTTTGCTGTCC |
| 114 | DK1 | 489 | CTACGCAACAGGGAATTTGCCCGGTTGCTCTTCTCTATCTTCCTCTTGGCTCTgTtGTCC |
| 115 | T10 | 489 | CTATGCAACAGGGAATTTGCCCGGTTGCTCTTTTCTATCTTCCTCTTGGCTCTGCTGTCC |
| 116 | SW2 | 489 | CTATGCAACAGGGAATcTGCCCGGTTGCTCCTCTCTATCTTCCTCTTGGCTtTGCTGTCC |
| 122 | HK4 | 489 | CTATGCAACAGGGAATTTGCCCGGTTGCCCTTCTCTATCTTCCTCTGCTGCTGCTGTCC |
| 109 | SA10 | 489 | CTATGCAACAGGGAATTTGCCCGGTTGCcCTTTCTCTATCTTCCTCTTGGCTTGCTGTCC |
| 110 | S45 | 489 | CTATGCAACAGGGAATCTGCCCGGTTGCTCTTCTCTATCTTCCTCTTGGCTTGCTGTCC |
| 123 | P8 | 489 | CTATGCAACAGGGAATCTGCCCGGTTGCTCTGGTTGCTCTTCTCTATCTTCCTCTTTGGCTTTGCTGTCt |
| 124 | T3 | 489 | tTAcGCAACAGGGAATCTGCCCGGTTGCTCTTCTCTATCTTCCTCTTGGCTTTGCTGTCC |
| 120 | HK3 | 489 | CTATGCAACAGGGAATTTACCCGGTTGCTCTTCTCTATCTTCCTCTTTGGCTTTGCTGTCC |
| 121 | HK5 | 489 | CTAcGCAACAGGGAATaTACCCGGTTGCTCTTCTCTATCTTCCTCTTGGCTTTGCTGTCC |
| 108 | DR4 | 489 | CTATGCAACAGGGAATCTTCCTGGTTGCTCTTCTCTATCTTCCTTTTGGCTTTGCTCTCT |
| 104 | US11 | 489 | CTATGCAACAGGGAACCTTCCTGGTTGCTCTTCTCTATCTTCCGGCCCTGCTCTCT |
| 105 | S14 | 489 | CTATGCAACAGGGAACCTTCCTGGTTGCTCTTCTCTATCTTCCTCTAGCCCTGCTTTCT |
| 106 | SW1 | 489 | CTATGCAACAGGGAACCTTCCTGGTTGCTCTTCTCTATCTTCCTCTTGGCCCTGCTCTCT |
| 107 | S18 | 489 | CTATGCAACAGGGAACCTTCCTGGTTGCTCTTCTCTATCTTCCTCTTGGCCCTGCTCTCT |
| 103 | DK7 | 489 | CTATGCAACAGGGAACCTTCCTGGTTGCTCTTCTCTATCTTCCTCTTGGCCCTGCTCTCT |

103-124  consensus  cTAtGCAACAGGGAAtcTgCCcGGTTGCtCtTTcTCTATCTTCCtCtTggCttTgCTgTcc

FIGURE 6C-10

| SEQ ID NO: | ISOLATE | | |
|---|---|---|---|
| 119 | S9 | 550 | TGTTTGACCATCCCAGCTTCCGCT |
| 117 | IND3 | 550 | TGTTTGACCATCCCAGCTTCCGCT |
| 118 | IND8 | 550 | TGTTTGACCgTCCCAGCTTCCGCT |
| 111 | D1 | 550 | TGTTTGACCATCCCAGCTTCCGCT |
| 112 | US6 | 550 | TGTTTGACCATtCCAGCTTCCGCT |
| 113 | P10 | 550 | TGccTGACCATCCCAGCgTCCGCT |
| 114 | DK1 | 550 | TGTTTGACCATCCCAGCTTCCGCc |
| 115 | T10 | 550 | TGTCTGACCATCCCAGCTTCCGCT |
| 116 | SW2 | 550 | TGTCTGACCATCCCAGCTTCCGCT |
| 122 | HK4 | 550 | TGTCTGACCATCCCAGCTTCCGCT |
| 109 | SA10 | 550 | TGTTTGACCATCCCAGCTTCCGCT |
| 110 | S45 | 550 | TGTTTaACCATCCCAGCTTCCGCT |
| 123 | P8 | 550 | TGcTGACCATCCCAGCTTCCGCT |
| 124 | T3 | 550 | TGtcTGACCATCCCAGCTTCCGCT |
| 120 | HK3 | 550 | TGCTTGACCATCCCAGCTTCCGCT |
| 121 | HK5 | 550 | TGtcTGACCACCCCAGCTTCCGCT |
| 108 | DR4 | 550 | TGCtTGACCACCCCAGtTTCCGCT |
| 104 | US11 | 550 | TGCCTGACCGTGCCCGCaTgGCC |
| 105 | S14 | 550 | TGCCTGACTGTGCCCGCTTCAGCC |
| 106 | SW1 | 550 | TGCCTGACTGTGCCCGCTTCAGCC |
| 107 | S18 | 550 | TGCCTGACaGTGCCCGGTCAGCC |
| 103 | DK7 | 550 | TGCCTGACGTGCCCGCTTCGgCc |

103-124 consensus TGttTgACcatcCCaGcTTCcGCt

FIGURE 6D-1

| SEQ ID NO: | ISOLATE | | |
|---|---|---|---|
| 128 | T2 | 1 | ATGAGCACAAttCCTAAACCTCAAAGAAAAACCAAAAGAAACACTAACCGTTCGCCCACAaG |
| 125 | T4 | 1 | ATGAGCACAAATCCTAAACCTCAAAGAAAAACCAAAAGAAACACCAACCGTCGCCCACAgG |
| 126 | US10 | 1 | ATGAGCACAAATCCTAAACCTCAAAGAAAAACCAAAAGAAACACTAACCGTCGCCCACAaG |
| 127 | T9 | 1 | ATGAGCACAAATCCAaAACCcAAAGAAAAACCAtAAGAAACACCAACCGTCGCCCACAgG |

125-128 consensus ATGAGCACAAaTCCtAAACCtCAAAGAAAAACCAaAAGAAACAC-AACCGTCGCCCACA-G

| SEQ ID NO: | ISOLATE | | |
|---|---|---|---|
| 128 | T2 | 62 | ACGTTAAGTTtCCGGGCGGCGCCCAGATCGTTGGCGGAGTATACTTGcTGCCGCGCAGGGG |
| 125 | T4 | 62 | ACGTTAAGTTcCCGGGCGGCGCCCAGATCGTTGGCGGAGTATACTTGTTGCCGCGCAGGGG |
| 126 | US10 | 62 | ACGTTAAGTTtCCGGGCGGCGCCCAGATCGTTGGCGGAGTATACTTGTTGCCGCGCAGGGG |
| 127 | T9 | 62 | ACGTTAAGTTCCGGGGCGGCGCCCAGATCGTTGGCGGAGTATACTTGTTGCCGCGCAGGGG |

125-128 consensus ACGTTAAGTT-CCGGGCGGCGCCCAGATCGTTGGCGGAGTATACTTGtTGCCGCGCAGGGG

| SEQ ID NO: | ISOLATE | | |
|---|---|---|---|
| 128 | T2 | 123 | CCCCAGGTTGGGTGTGCGCGCGACAAGGAAGAGACTTCGGAGCGgTCCCAGCCtCGTGGaAGG |
| 125 | T4 | 123 | CCCCAGGTTGGGTGTGCGCGCGACAAGGAAGAGACTTCGGAGCGaTCCCAGCCACGTGGAGG |
| 126 | US10 | 123 | CCCCAGGTTGGGTGTGCGCGCGACAAGGAAGAGACTTCGGAGCGGTCCCAGCCACGTGGAGG |
| 127 | T9 | 123 | CCCtAGGTTGGGTGTGCGaCGACAAGGAAGAGACTTCGGAGCGGTCCCAGCCACGTGGAGG |

125-128 consensus CCCCAGGTTGGGTGTGCGcGACAAGGAAGAGACTTCGGAGCCGTCCCAGCCaCGTGGgAGG

| SEQ ID NO: | ISOLATE | | |
|---|---|---|---|
| 128 | T2 | 184 | CGCCAGCCCATCCCAAAGATCGGCGCTCCACTGGCAAGTCCTGGGGAAAACCAGGATAcC |
| 125 | T4 | 184 | CGCCAGCCCATCCCAAAGATCGGCGCTCCACTGGCAAGTCCTGGGAAAACCAGGATAtC |
| 126 | US10 | 184 | CGCCAGCCCATCCCAAAGATCGGCGCGCCCACTGGCAAGTCCTGGGAAAACCAGGATACC |
| 127 | T9 | 184 | CGCCAGCCCATCCCAAAGATCGGCGCtCCACTGGCAAGTCCTGGGAAAACCAGGATACC |

125-128 consensus CGCCAGCCCATCCCAAAGATCGGCGCtCCACTGGCAAGTCCTGGGAAAACCAGGATAcC

FIGURE 6D-2

| SEQ ID NO: | ISOLATE | | |
|---|---|---|---|
| 128 | T2 | 245 | CCTGGCCCCTGTATGGGAATGAGGgCTCGGCTGGGCAGGATGGCTCCTGTCCCCCGAGG |
| 125 | T4 | 245 | CCTGGCCCCTGTATGGGAATGAGGGACTCGGCTGGGCAGGATGGCTCCTGTCCCCCGAGG |
| 126 | US10 | 245 | CtTGGCCCCTATATGGGAATGAGGGACTCGGCTGGGCAGGATGGCTCCTGTCCCCCGAGG |
| 127 | T9 | 245 | CcTGGCCtCTATATGGGAATGAGGGACTCGGCTGGGCGGGATGGCTCCTGTCCCCCGAGG |
| 125-128 | consensus | | CcTGGCCcCT-TATGGGAATGAGGGaCTCGGCTGGGCaGGATGGCTCCTGTCCCCCGAGG |

| SEQ ID NO: | ISOLATE | | |
|---|---|---|---|
| 128 | T2 | 306 | TTCtCGTCCCTCtTGGGGCCCCAATGACCCCGGCATAGTCGCGCAAtGTGGGTAAaGTC |
| 125 | T4 | 306 | TTCCCGTCCCTCCTCtGGGGCCCCAATGACCCCGGCATAGTCGCGCAACGTGGGTAAGGTC |
| 126 | US10 | 306 | TTCCCGTCCCCTCTTGGGGCCCCAcTGAtCCCGGCATAGTCGCGCAACGTGGGTAAGGTC |
| 127 | T9 | 306 | TTCCCGTCCCTCTTGGGGCCCCAgTGACCCCGGCATAGTCGCGCAACGTGGGTAAGGTC |
| 125-128 | consensus | | TTCCCGTCCCTCtTGGGGCCCCAaTGACCCCGGCATAGTCGCGCAAcGTGGGTAAgGTC |

| SEQ ID NO: | ISOLATE | | |
|---|---|---|---|
| 128 | T2 | 367 | ATCGATACCCTAACGTGCgGCtTTGCCGACCTCATGGGGTACaTCCCCGTCGTAGGCGcCC |
| 125 | T4 | 367 | ATCGATACCCTAACGTGCAGCcTTGCCGACCTCATGGGTACgTCCCCGTCGTAGGCGcGCC |
| 126 | US10 | 367 | ATCGATACCCTAACGTGCGGCTTTGCCGACCTCATGGGaTACATCCCCGTCgTgGGCGCtC |
| 127 | T9 | 367 | ATCGATACCCTAACGTGCGGCTTTGCCGACCTCATGGGgTACATCCCCGTCGTaGGCGCcC |
| 125-128 | consensus | | ATCGATACCCTAACGTGCgGCtTTGCCGACCTCATGGGgTACaTCCCCGTCGTaGGCGcCC |

| SEQ ID NO: | ISOLATE | | |
|---|---|---|---|
| 128 | T2 | 428 | CGcTtGGTGGtGTCGCCAGAGCTCTtGCGCATGGCGTGAGAGTCCTGGAGGACGGaGTTAA |
| 125 | T4 | 428 | CGtTgGGTGGCGTCGCCAGAGCTCTCGCGCATGGCGTCTCGAGAGTCCTGGAGGACGGGGTTAA |
| 126 | US10 | 428 | CGCTTGGTGGCGTCGCCAGAGCTCTCGCGCATGGCGTGAGGGTCCTGGAGGACGGGGTTAA |
| 127 | T9 | 428 | CGCTTGGTGGCGTtGCCAGAGCTCTCGCGCACGGCGTGAGAGTCCTGGAGGACGGGGTTAA |
| 125-128 | consensus | | CGcTtGGTGGcGTcGCCAGAGCTCtCGCGCAtGGCGTGAGaGTCCTGGAGGACGGgGTTAA |

FIGURE 6D-3

| SEQ ID NO: | ISOLATE | | |
|---|---|---|---|
| 128 | T2 | 489 | TTATGCAACAGGtAACTtACCcGGTTGCTCCtTTTCTATcTTCTTGCTaGCCCTgCTGTCC |
| 125 | T4 | 489 | TTATGCAACAGGaAACTtACCtGGTTGCTCCtCCTTTCTATtTTCTTGCTGGCCCTACTGTCC |
| 126 | US10 | 489 | TTATGCAACAGGGAACTtACCcGGTTGCTCCCCCTTTCTATCTTCTTGCTGGCCTTACTGTCC |
| 127 | T9 | 489 | TTATGCAACAGGGAACcTACCtGGTTGCTCCtCCTCTTTTCTATCTTCTTGCTGGCCcTACTGTCC |
| 125-128 | consensus | | TTATGCAACAGGgAACtTACC-GGTTGCTCCcTTTCTATcTTCTTGCTgGCCcTaCTGTCC |

| SEQ ID NO: | ISOLATE | | |
|---|---|---|---|
| 128 | T2 | 550 | TGCATCACtATTCCggTtTCaGCT |
| 125 | T4 | 550 | TGCATCACCATTCCAGTCTCCGCT |
| 126 | US10 | 550 | TGCATCACCATTCCAGTCTCTGCT |
| 127 | T9 | 550 | TGCATCACCAcTCCgGcCTCTGCT |
| 125-128 | consensus | | TGCATCACcAtTCC-GtcTCtGCT |

FIGURE 6E-1

| SEQ ID NO: | ISOLATE | | |
|---|---|---|---|
| 131 | DK11 | 1 | ATGAGCACAAATCCTAAACCTCAAAGAAAACCAAAAGAAATACAAACCGCGCCCACAGG |
| 132 | SW3 | 1 | ATGAGCACAAATCCTAAACCTCAAAGAAAAGAAAACCAAAAGAAATACAAACCGCGCCCACAGG |
| 133 | DK8 | 1 | ATGAGCACAAATCCTAAACCTCAAAGAAAACAAACCAAAAGAAAACACAAACCGCGCCCACAGG |
| 129 | T8 | 1 | ATGAGCACAAATCCTAAACCTCAAAGAAAAACAAACCAAAAGAAAACAAAACCGCGCCCACAGG |
| 130 | US1 | 1 | ATGAGCACAAATCCTAAACCTCAAAGAAAACAAACCAAAAGAAACACAAACCGCGCCCACAGG |
| 129-133 | consensus | | ATGAGCACAAATCCTAAACCTCAAAGAAAACAAACCAAAAGAAACACAAACCGCCCCCACAGG |

| SEQ ID NO: | ISOLATE | | |
|---|---|---|---|
| 131 | DK11 | 62 | ACGTTAAGTTCCCGGGTGGCGCGGCCAGATCGTTGGCGGAGTTTACTTGCTGCCGCCAGGGG |
| 132 | SW3 | 62 | ACGTTAAGTTCCCGGGTGGCGCGGCCAGATCGTTGGCGGAGTTTACTTGCTGCCGCCAGGGG |
| 133 | DK8 | 62 | ACGTTAAGTTCCCGGGTGGCGCGGCCAGATCGTTGGCGGAGTTTACTTGCTGCCGCCAGGGG |
| 129 | T8 | 62 | ACGTCAAGTTCCCGGGTGGCGCGGCCAGATCGTTGGCGGAGTTTACTTGCTGCCGCCAGGGG |
| 130 | US1 | 62 | ACGTCAAGTTCCCGGGTGGCGCGGtCAGATCGTTGGCGCCAGATCGTTGGCGGAGTTTACTTGCTGCCGCCAGGGG |
| 129-133 | consensus | | ACGTtAAGTTCCCGGGTGGCGGCCAGATCGTTGGCGGAGTTTACTTGCTGCCGCCAGGGG |

| SEQ ID NO: | ISOLATE | | |
|---|---|---|---|
| 131 | DK11 | 123 | CCCCAGGTTGGGTGTGCGCAcCGACAAGGAAGACTTCCGAGCGATCCCAGCCGCGTGGGAGA |
| 132 | SW3 | 123 | CCCCAGGTTGGGTGTGCGCGCGACAAGGAAGACTTCCGAGCGATCCCAGCCGCGTGGGAGA |
| 133 | DK8 | 123 | CCCCAGGTTGGGTGTGCGCGCGACAAGGAAGACTTCCGAGCGATCCCAGCCGCGTGGGAGA |
| 129 | T8 | 123 | CCCtAGGTTGGGTGTGCGCGCGACAAGGAAGtCTTCCGAGCGATCCCAGCCGCGTGGGAGg |
| 130 | US1 | 123 | CCCcAGGTTGGGTGTGCGCGCGACAAGGAAGACTTCCGAGCGATCCCAGCCGCGTGGGAGA |
| 129-133 | consensus | | CCCcAGGTTGGGTGTGCGCgCGACAAGGAAGaCTTCCGAGCGATCCCAGCCGCGTGGGAGa |

FIGURE 6E-2

| SEQ ID NO: | ISOLATE | | |
|---|---|---|---|
| 131 | DK11 | 184 | CGCCAGCCCATCCCGAAAGATCGGCGCTCCACCGGCAAGcCCTGGGAAAGCCAGGATATC |
| 132 | SW3 | 184 | CGCCAGCCCATCCCGAAAGATCGGCGCTCCACCGGCAAGTCCTGGGAAAGCCAGGATATC |
| 133 | DK8 | 184 | CGCCAGCCCATCCCGAAAGATCGGCGCTCCACCGGCAAGTCCTGGGAAAACCGGATATC |
| 129 | T8 | 184 | CGCCAGCCCATCCCGAAAGATCGGCGCTCCACCGGCAAGTCTGGGAAAACCAGGATATC |
| 130 | US1 | 184 | CGCCAGCCCATCCCGAAAGATCGGCGCTCCACCGGCAAGTCCTGGGAAAAgCCAGGATATC |
| 129-133 | consensus | | CGCCAGCCCATCCCGAAAGATCGGCGCTCCACCGGCAAGtCCTGGGAAAgCCaGGATATC |

| SEQ ID NO: | ISOLATE | | |
|---|---|---|---|
| 131 | DK11 | 245 | CTTGGCCCCTGTATGAAACGAGGGCTGCGGCTGGGCAGGTTGGCTCCTGTCCCCGCGG |
| 132 | SW3 | 245 | CTTGGCCCCTGTATGAAACGAGGGCTGCGCTGGGCAGGTTGGCTCCTGTCCCCCGCGG |
| 133 | DK8 | 245 | CTTGGCCCCTGTATGAAACGAGGGCTGCGGCTGGGCAGGTTGGCTCCTGTCCCCGCGG |
| 129 | T8 | 245 | CTTGGCCTCTtGTACGAAACGAGGGCTGCGGCGGtTGGGCAGGTTGGCTCCTGTCCCCGCGG |
| 130 | US1 | 245 | CTTGGCCTCTgTACGAAACGAGGGCTGCGCTGGGCAGGTTGGCTCCTGTCCCCCGCGG |
| 129-133 | consensus | | CTTGGCCcctgTAtGAaACGAGGGCTGCGGCtGGGCAGGTTGGCTCCTGTCCCCGCGG |

| SEQ ID NO: | ISOLATE | | |
|---|---|---|---|
| 131 | DK11 | 306 | GTCTCATCCTAATTGGGGCCCCCACTGACCCCCGGCATAaATCACGCAATTTGGtAAAGTC |
| 132 | SW3 | 306 | GTCTCATCCTAATTGGGGCCCCCACTGACCCCCGGCATAGATCACGCAATTTGGCAAAGTC |
| 133 | DK8 | 306 | GTCTCGTCCTACTTGGGGCCCCCACTGACCCCCGGCATAGATCACGCAATTTGGCAAAGTC |
| 129 | T8 | 306 | GTCTCGTCCTACTTGGGGCCCCCACTGACCCCCGGCATAGATCACGTAATTTGGCAgAGTC |
| 130 | US1 | 306 | GTCTCGTCCTACTTGGGGCCCCCACTGACCCCCGGCACAGATCACGTAACTTGGCAgAGTC |
| 129-133 | consensus | | GTCTCgTCCTaCTTGGGGCCCCCACTGACCCCCGGCAtAgATCACGCAaaTTTGGCAaaGTC |

FIGURE 6E-3

| SEQ ID NO: | ISOLATE | | |
|---|---|---|---|
| 131 | DK11 | 367 | ATCGACACCATTACGTGTGGTTTTGCCGACCTCATGGGGTACATCCCTGTCGGCGCCC |
| 132 | SW3 | 367 | ATCGACACCATTACGTGTGTGGTTTTGCCGACCTCATGGGGTACATCCCTGTCGGCGCCC |
| 133 | DK8 | 367 | ATCGACACCATTACGTGTGTGGTTTTGCCGACCTCATGGGGTACATCCCTGTTGGCGCCC |
| 129 | T8 | 367 | ATCGATACCATTACATGTGGTTTTGCCGACCTCATGGGGTACATCCCTGTTGGCGCCC |
| 130 | US1 | 367 | ATCGATACCATTACGTGTGGTTTTGCCGACCTCATGGGGTACATCCCTGTTGGCGCCC |
| 129-133 | consensus | | ATCGAcACCATTACgTGTGTGGTTTTGCCGACCTCATGGGGTACATCCCTGTcGGCGCCC |

| SEQ ID NO: | ISOLATE | | |
|---|---|---|---|
| 131 | DK11 | 428 | CGGTCGGAGGCGTCGCCAGAGCTCTGGCACACGGTGTTAGAGTCCTGGAAGACGGGATAAA |
| 132 | SW3 | 428 | CGGTCGGAGGCGTCGCCAGAGCTCTGGCACACGGTGTTAGAGTCCTGGAAGACGGGATAAA |
| 133 | DK8 | 428 | CGGTtGGAGGCGTCGCCAGAGCTCTGGCACACGGTGTTAGGGTCCTGGAAGACGGGATAAA |
| 129 | T8 | 428 | CGGTCGGAGGCGTCGCCAGAGCTCTGGCACAtGGTGTTAGGGTCCTGGAAGACGGGATAAA |
| 130 | US1 | 428 | CGGTCGGAGGCGTCGCCAGAGCTCTGGCACACGGTGTTAGGGTCCTGGAAGACGGGATAAA |
| 129-133 | consensus | | CGGTcGGAGGCGTCGCCAGAGCTCTGGCACAcGGTGTTAGgGTCCTGGAAGACGGGATAAA |

| SEQ ID NO: | ISOLATE | | |
|---|---|---|---|
| 131 | DK11 | 489 | TTACGCAACAGGGAATCTGCCTGGTTGCTCTTTTCTATCTTCTTACTTGCTCTTCTGTCa |
| 132 | SW3 | 489 | TTACGCAACAGGGAATCTGCCTGGTTGCTCCTTGCTCTTCTTCTATCTTCTTACTTGCTCTTCTGTCG |
| 133 | DK8 | 489 | TTACGCAACAGGGAATTTGCCTGGTTGCTCCTTGCTCTTCTTCTATCTTCTTACTTGCTCTTCTGTCG |
| 129 | T8 | 489 | cTAtGCAACAGGGAATTGCCTGGTTGCTCCTTTTCTATCTTCTTACTTGCTCTTCTGTCa |
| 130 | US1 | 489 | tTAcGCAACAGGGAATCTGCCTGGTTGCTCCTTTCTATCTTCTTACTTGCTCTTCTGTCg |
| 129-133 | consensus | | tTAcGCAACAGGGAATcTGCCTGGTTGCTCtTTTTCTATCTTCTTacTTGCTCTTCTGTCg |

FIGURE 6E-4

| SEQ ID NO: | ISOLATE | | |
|---|---|---|---|
| 131 | DK11 | 550 | TGCTgCACAGTGCCAGTGTCTGCG |
| 132 | SW3 | 550 | TGCTtCACAGTGCCAGTGTCTGCG |
| 133 | DK8 | 550 | TGCTgCACAGTGCCAGTGTCTGCG |
| 129 | T8 | 550 | TGCTtCACAGTGCCAGTGTCTGCA |
| 130 | US1 | 550 | TGCgcCACggTGCCggTGTCTGCA |
| 129-133 | consensus | | TGCt-CACagTGCCagTGTCTGCg |

FIGURE 6F-1

| SEQ ID NO: | ISOLATE | | |
|---|---|---|---|
| 131 | DK11 | 1 | ATGAGCACAAATCCTAAACCTCAAAGAAAAACCAAAGAAATACAAACCGCCGCCCACAGG |
| 132 | SW3 | 1 | ATGAGCACAAATCCTAAACCTCAAAGAAAAACCAAAGAAATACAAACCGCCGCCCACAGG |
| 133 | DK8 | 1 | ATGAGCACAAATCCTAAACCTCAAAGAAAAACCAAAGAAAACACAAACCGCCGCCCACAGG |
| 129 | T8C | 1 | ATGAGCACAAATCCTAAACCTCAAAGAAAAACCAAAGAAAACAAACCGCCGCCCACAGG |
| 130 | US1 | 1 | ATGAGCACAAATCCTAAACCTCAAAGAAAAACCAAAGAAAACACAAACCGCCGCCCACAGG |
| 125 | T4 | 1 | ATGAGCACAAATCCTAAACCTCAAAGAAAAACCAAAGAAACACCAACCGTCGCCCACAGG |
| 126 | US10 | 1 | ATGAGCACAAATCCTAAACCTCAAAGAAAAACCAAAGAAACACTAACCGTCGCCCACAaG |
| 127 | T9 | 1 | ATGAGCACAAATCCaAAACCtCAAAGAAAAACCAtAAGAAAAACCAACCGCCCACAgG |
| 128 | T2 | 1 | ATGAGCACACAAtTCCTAAACCTCAAAGAAAAACCAAAGAAAACACTAACCGTCGCCCACAaG |
| 134 | S83 | 1 | ATGAGCACAaTCCTAAACCTCAAAGAAAAACCAAAGAAAACACTAACCGCcGCCCACAgG |
| 125-134 | consensus | | ATGAGCACAAaTCCtAAACCtCAAAGAAAAACCAaAAGAAAcACaAACCGcCGCCCACAgG |

| SEQ ID NO: | ISOLATE | | |
|---|---|---|---|
| 131 | DK11 | 62 | ACGTTAAGTTCCCGGGTGGCGGCCAGATCGTTGGCGGAGTTTACTTGCTGCCGCAGGGG |
| 132 | SW3 | 62 | ACGTTAAGTTCCCGGGTGGCGGCCAGATCGTTGGCGGAGTTTACTTGCTGCCGCAGGGG |
| 133 | DK8 | 62 | ACGTTAAGTTCCCGGGTGGCGGCCAGATCGTTGGCGGAGTTTACTTGCTGCCGCAGGGG |
| 129 | T8 | 62 | ACGTCAAGTTCCCGGGTGGCGGCCAGATCGTTGCGGAGTTTACTTGCTGCCGCAGGGG |
| 130 | US1 | 62 | ACGTCAAGTTCCCGGGTGGCGGtCAGATCGTTGGCGGAGTTTACTTGCTGCCGCAGGGG |
| 125 | T4 | 62 | ACGTCAAGTTCCCGGGCGGCGGCCAGATCGTTGGCGGAGTATACTTGTTGCCGCAGGGG |
| 126 | US10 | 62 | ACGTTAAGTTtCCGGGCGGCGGCCAGATCGTTGGCGGAGTATACTTGTTGCCGCAGGGG |
| 127 | T9 | 62 | ACGTTAAGTTcCCGGGCGGCGGCCAGATCGTTGGCGGAGTATACTTGCTGCCGCAGGGG |
| 128 | T2 | 62 | ACGTTAAGTTtCCGGGCGGCGGCCAGATCGTTGGCGGAGTATACTTGCTGCCGCAGGGG |
| 134 | S83 | 62 | ACGTCAAGTTCCCGGGCGGtGGCCAGATCGTTGGCGGAGTATACTTGCTGCCGCAGGGG |
| 125-134 | consensus | | ACGTtAAGTTCCCGGG-GGcGGCCAGATCGTTGGCGGAGT-TACTTGcTGCCGCAGGGG |

FIGURE 6F-2

| SEQ ID NO: | ISOLATE | | |
|---|---|---|---|
| 131 | DK11 | 123 | CCCCAGGTTGGGTGTGCGCaCGACAAGGAAGACTTCCGAGCGATCCCAGCCGCTGGGAGA |
| 132 | SW3 | 123 | CCCCAGGTTGGGTGTGCGCGCGACAAGGAAGAAGACTTCCGAGCGATCCCAGCCGCTGGGAGA |
| 133 | DK8 | 123 | CCCCAGGTTGGGTGTGCGCGCGACAAGGAAGAAGACTTCCGAGCGATCCCAGCCGCGTGGAGg |
| 129 | T8 | 123 | CCCtAGGTTGGGTGTGCGCGCGACAAGGAAGAAGACTTCCGAGCGATCCCAGCCGCGTGGAGA |
| 130 | US1 | 123 | CCCCAGGTTGGGTGTGCGCGCGACAAGGAAGAAGACTTCCGAGCGATCCCAGCCGCGTGGAGA |
| 125 | T4 | 123 | CCCCAGGTTGGGTGTGCGCGCGACAAGGAAGAAGACTTCGGAGCGATCCCAGCCACGTGGAGG |
| 126 | US10 | 123 | CCCCAGGTTGGGTGTGCGCGCGACAAGGAAGAAGACTTCGGAGCGGTCCCAGCCACGTGGAGG |
| 127 | T9 | 123 | CCCtAGGTTGGGTGTGCGCaCGACAAGGAAGAAGACTTCGGAGCGGTCCCAGCCACGTGGAGG |
| 128 | T2 | 123 | CCCCAGGTTGGGTGTGCGCGCGACAAGGAAGAAGACTTCGGAGCGGTCCCAGCCtCGTGGAAGG |
| 134 | S83 | 123 | CCCgAGGTTGGGTGTGCGCGCGACGAGGAAAaACTTCcGAaCGGTCCACGTGGgAGG |

125-134 consensus CCCcAGgTTGGGTGTGCgCgCgACaAGGAAgaCTTCcGAgCGaTCCCAGCCgCGTGGgAGg

| SEQ ID NO: | ISOLATE | | |
|---|---|---|---|
| 131 | DK11 | 184 | CGCCAGCCCCATCCCGAAAGATCGGGCGCTCCACCGGCAAGcCCTGGGGAAAGCCAGGATATC |
| 132 | SW3 | 184 | CGCCAGCCCCATCCCGAAAGATCGGGCGCTCCACCGGCAAGTCCTGGGGAAAGCCAGGATATC |
| 133 | DK8 | 184 | CGCCAGCCCCATCCCGAAAGATCGGGCGCTCCACCGGCAAGTCCTGGGGAAAACCAGGATATC |
| 129 | T8 | 184 | CGCCAGCCCCATCCCGAAAGATCGGGCGCTCCACCGGCAAGTCCTGGGGAAAACCgGATATC |
| 130 | US1 | 184 | CGCCAGCCCCATCCCGAAAGATCGGGCGCTCCACCGGCAAGTCCTGGGGAAAgCCAGGATATC |
| 125 | T4 | 184 | CGCCAGCCCCATCCCGAAAGATCGGGCGCTCCACTGGCAAGTCCTGGGGAAAACCAGGATATC |
| 126 | US10 | 184 | CGCCAGCCCCATCCCCAAAGATCGGGCGCCCCACTGGCAAGTCCTGGGGAAAACCAGGATACC |
| 127 | T9 | 184 | CGCCAGCCCCATCCCCAAAGATCGGGCGCTCCACTGGCAAGTCCTGGGGAAAACCAGGATACC |
| 128 | T2 | 184 | CGCCAGCCCCATCCTAAAGATCGGGCGCTCCACTGGCAAGTCCTGGGGAAAACCAGGATACC |
| 134 | S83 | 184 | CGCCAGCCCCATCCCTAAAGATCGGGCGCaCCACTGGCAAGgCCTGGGGAAggCCAGGATACC |

125-134 consensus CGCCAGCCCCATCCCgAAAGATCGGGCGCtCCAC-GGCAAGtCCTGGGGAAAaCCaGGATAtC

FIGURE 6F-3

| SEQ ID NO: | ISOLATE | | |
|---|---|---|---|
| 131 | DK11 | CTTGGCCCCTGTATGGAAACGAGGGCTGCGGCTGGGCAGGTTGGCTCCTGTCCCCGCGG | 245 |
| 132 | SW3 | CTTGGCCCCTGTATGAAACGAGGGCTGCGCGCTGGGCAGGTTGGCTCCTGTCCCCGCGG | 245 |
| 133 | DK8 | CTTGGCCCCTGTATGAAACGAGGGCTGCGGCTGGGCAGGTTGGCTCCTGTCCCCGCGG | 245 |
| 129 | T8 | CTTGGCCTCTtTACGGAAACGAGGGCTGCGTTGGGCAGGTTGGCTCCTGTCCCCGCGG | 245 |
| 130 | US1 | CTTGGCCTCTGTACGGAAACGAGGGCTGCGCGCTGGGCAGGTTGGCTCCTGTCCCCGCGG | 245 |
| 125 | T4 | CcTGGCCCCTGTATGGAATGGGAATGAGGGACTCGGCTGGCAGGATGGCTCCTGTCCCCGAGG | 245 |
| 126 | US10 | CtTGGCCCCTATATGGGAATGGGAATGAGGGACTCGGCTGGCAGGATGGCTCCTGTCCCCGAGG | 245 |
| 127 | T9 | CCTGGCCtCTATATGGGAATGGGAATGAGGGACTCGGCTGGGCGGGATGGCTCCTGTCCCCGAGG | 245 |
| 128 | T2 | CCTGGCCCCTGTATGGGAATGGGAATGAGGGCTCGGCTGGGCAGGATGGCTCCTCTGTCCCCGAGG | 245 |
| 134 | S83 | CtTGGCCCCTGTATGGGAATGAGGGCTTGGGCTGGGCAGGgTGGGCTCCTGTCCCCGCGG | 245 |

125-134 consensus CtTGGCCcCTgTAtGG-AA-GAGGGc--CGGcTGGGCaGGtTGGCTCCTGTCCCCCGCGG

| SEQ ID NO: | ISOLATE | | |
|---|---|---|---|
| 131 | DK11 | GTCTCATCCTAATTGGGGCCCCCACTGACCCCCGGCATAaATCACGCAATTTGGtAAAGTC | 306 |
| 132 | SW3 | GTCTCATCCTAATTGGGGCCCCCACTGACCCCCGGCATAGATCACGCAATTTGGGCAAAGTC | 306 |
| 133 | DK8 | GTCTCGTCCTACTTGGGGCCCCCACTGACCCCCGGCATAGATCACGCAATTTGGGCAAAGTC | 306 |
| 129 | T8 | GTCTCGTCCTACTTGGGGCCCCCACTGACCCCCGGCATAGATCACGTAATTTGGCAgAGTC | 306 |
| 130 | US1 | GTCTCGTCCTACTTGGGGCCCCCACTGACCCCCGGCACAGATCACGTAACTTGGGCAAGGTC | 306 |
| 125 | T4 | TTCCCGTCCCTCTGGGGCCCCCACCCCCAatGACTGACCCCCGGCATAGGTCGCGCAACGTGGGTAAGGTC | 306 |
| 126 | US10 | TTCCCGTCCCTCTTGGGGCCCCCAcTGAtCCCCGGCATAGGTCGCGCAACGTGGGTAAGGTC | 306 |
| 127 | T9 | TTCTCGTCCTCTTGGGGCCCCCAgTGACCCCCAaTGACCCCCGGCATAGGTCGCGCAACGTGGGTAAGGTC | 306 |
| 128 | T2 | TTCTCGTCCTCTTGGGGCCCCCAaTGACCCCCGGCATAGGTCGCGCAATGTGGGTAAaGTC | 306 |
| 134 | S83 | TTCCGcCCTTCaTGGGGCCCCACcGACCCCCGGCATAaaTCGCGCAAcTTGGGTAAgGTC | 306 |

125-134 consensus -TCtCgtCCt-ctTGGGGCCCCActGAcCCCCGGCAtAgaTC-CGcAA-tTGGGtAa-GTC

FIGURE 6F-4

| SEQ ID NO: | ISOLATE | | |
|---|---|---|---|
| 131 | DK11 | 367 | ATCGACACCATTACGTGTGTTTGCCGACCTCATGGGGTACATCCCTGTCGTCGGCGCCC |
| 132 | SW3 | 367 | ATCGACACCATTACGTGTGTTTGCCGACCTCATGGGTACATCCCTGTCGTTGGCGCCC |
| 133 | DK8 | 367 | ATCGACACCATTACGTGTGTTTGCCGACCTCATGGGTACATCCCTGTCGTTGGCGCCC |
| 129 | T8 | 367 | ATCGATACCATTACaTGTGTTTGCCGACCTCATGGGTACATCCCTGTCGTTGGCGCCC |
| 130 | US1 | 367 | ATCGATACCATTACGTGTGTTTGCCGACCTCATGGGTACATCCTGTCGTTGGCGCCC |
| 125 | T4 | 367 | ATCGATACCCTAACGTGCAgCCTTGCCGACCTCATGGGTACgTCCCGTCGTaGGCGgCC |
| 126 | US10 | 367 | ATCGATACCCTAACGTGCGGCTTTGCCGACCTCATGGaTACATCCCCGTCGTaGGCGCtC |
| 127 | T9 | 367 | ATCGATACCCTAACGTGCGGCTTTGCCGACCTCATGGGTACATCCCCGTCGTgGGCGCtC |
| 128 | T2 | 367 | ATCGATACCCTAACGTGCGGCTTTGCCGACCTCATGGGTACATCCCGTCGTAGGCGCCC |
| 134 | S83 | 367 | ATCGATACCCTAACGTGCGGtTTTGCCGACCTCATGGGTACATaCCCGTCGTgGGCGtC |
| 125-134 | consensus | | ATCGatACC-T-ACgTG-ggtTTTGCCGACCTCATGGGtACaTcCC-GTCGTtGGCGccC |

| SEQ ID NO: | ISOLATE | | |
|---|---|---|---|
| 131 | DK11 | 428 | CGGTCGGAGGCGTCGCCAGAGCTCTGGCACACGGTGTTAGAGTCCTTAGAGACGGGATAAA |
| 132 | SW3 | 428 | CGGTCGGAGGCGTCGCCAGAGCTCTGGCACACGGTGTGTTAGAGTCCTGGAAGACGGGATAAA |
| 133 | DK8 | 428 | CGGTCGGAGGCGTCGCCAGAGCTCTGGCACACGGTGTGTTAGAGTCCTTAGAGACGGGATAAA |
| 129 | T8 | 428 | CGGTtGGAGGCGTCGCCAGAGCTCTGGCACACGGTGTTAGGTCCTTAGGGTCCTGGAAGACGGGATAAA |
| 130 | US1 | 428 | CGGTCGGAGGCGTCGCCAGAGCTCTGGCACAtGGTGTTAGGGTCCTGGAAGACGGGATAAA |
| 125 | T4 | 428 | CGGTCGGAGGCGTCGCCAGAGCTCTGGCACACGGTGTTAGGGTCCTGGAGACGGGATAAA |
| 126 | US10 | 428 | CGtTgGGTGGTGGCGTCGCCAGAGCTCTCGCGCATGGCGTGAGAGTCCTGGAGACGGGGTTAA |
| 127 | T9 | 428 | CGCTTGGTGGCGTCGCCAGAGCTCTCGCGCATGGCGTGAGGTCCTGGAGGACGGGGTTAA |
| 128 | T2 | 428 | CGCTTGGTGGCGTtGCCAGAGCTCTGCGCACGGCTCTGCGCATGGCGTGAGAGTCCTGGAGGACGGGGTTAA |
| 134 | S83 | 428 | CGCTTGGTGGtGTcGCGGCGTtGCCAGAGCTCTtGCGCATGGCGTGAGAGTCCTGGAGGACGGaGTTAA |
| 125-134 | consensus | | CggTtGGaGGcGTcGCCAGAGctCTgGCaCA-GGtGT-AG-GTcCTGGA-GACGGgaTaAA |

FIGURE 6F-5

| SEQ ID NO: | ISOLATE | | |
|---|---|---|---|
| 131 | DK11 | 489 | TTACGCAACAGGGAATCTGCCTGGTTGCTCTTTTCTATCTTCTTACTTGCTCTTCTGTCa |
| 132 | SW3 | 489 | TTACGCAACAGGGAATCTGCCTGGTTGCTCTTTTCTATCTTCTTACTTGCTCTTCTGTCG |
| 133 | DK8 | 489 | TTACGCAACAGGGAATTTGCCTGGTTGCTCTTTTCTATCTTCTTGTTGCTCTTCTGTCG |
| 129 | T8 | 489 | cTAtGCAACAGGGAATCTGCCTGGTTGCTCTTTTCTATCTTCTTGCTTGCTCTTCGTCa |
| 130 | US1 | 489 | TTAcGCAACAGGGAATcTGCCTGGTTGCTCTTTTCTATCTTCTTaCTTGCTCTTCGTCg |
| 125 | T4 | 489 | TTATGCAACAGGGAACTTACCTGGTTGCTCTTATtTCTTGTtGCCCTACTGTCC |
| 126 | US10 | 489 | TTATGCAACAGGGAACTTACCcGGTTGCTCTTGTCTTCTTGCTGGCCtTACTGTCC |
| 127 | T9 | 489 | TTATGCAACAGGGAACCtACCTACCTGGTTGCTCTCATTCTTCTTGTTGCTGGCCCTACTGTCC |
| 128 | T2 | 489 | TTATGCAACAGGtAACTTACCCGGTTGCTCTTGTCTTCTTGCTaGCCCTgCTGTCC |
| 134 | S83 | 489 | TTATGCAACgGGgAATTTgCCCGGTTGCTCTTCTTcTCtTgGCCCTctTGTCt |

125-134 consensus    tTAtGCAAcAgGGaAAttTgCCtGGtTGCTcTCtTTCTATcTTctTgcTtgC--cTtcTGTCc

| SEQ ID NO: | ISOLATE | | |
|---|---|---|---|
| 131 | DK11 | 550 | TGCTgCACAGTGCCAGTGTCTGCG |
| 132 | SW3 | 550 | TGCTtCACAGTGCCAGTGTCTGCG |
| 133 | DK8 | 550 | TGCTgCACAGTGCCAGTGTCTGCG |
| 129 | T8 | 550 | TGCTtCACAGTGCCAGTGTCTGCA |
| 130 | US1 | 550 | TGCgcCACgTGCCgTGTCTGCA |
| 125 | T4 | 550 | TGCATCACCATTCCAGTCTCCgCT |
| 126 | US10 | 550 | TGCATCACCATTCCAGTCTCTGCT |
| 127 | T9 | 550 | TGCATCACCAcTCCGGcCTTCTGCT |
| 128 | T2 | 550 | TGCATCACTATTCCGGTTTCaGCT |
| 134 | S83 | 550 | TGCATCtCTgTgCCAgTTTCCGCc |

125-134 consensus    TGCatCaCagtgCCaGtgTCtGCt

FIGURE 6G-1

| SEQ ID NO: | ISOLATE | | |
|---|---|---|---|
| 138 | DK12 | 1 | ATGAGCACACTTCCTAAACCTCAAAGAAAAACCAAAAGAAACACCATCCGTCGCCCACAGG |
| 135 | HK10 | 1 | ATGAGCACACTTCCTAAACCTCAAAGAAAAACCAAAAGAAACACCATCCGTCGCCCACAGG |
| 136 | S52 | 1 | ATGAGCACACTTCCTAAACCTCAAAGAAAAACAAAAGAAACACCATCCGTCGCCCACAGG |
| 137 | S2 | 1 | ATGAGCACACTTCCTAAACCTCAAAGAAAAACAAAAGAAACACCATCCGTCGCCCACAGG |

135-138 consensus    ATGAGCACACTTCCTAAACCTCAAAGAAAAACCAAAAGAAACACCATCCGTCGCCCACAGG

| SEQ ID NO: | ISOLATE | | |
|---|---|---|---|
| 138 | DK12 | 62 | ACGTcAAGTTCCCGGGTGGCGGACAGATCGTTGGTGAGTATACGTGTTGCCGCGCAGGGG |
| 135 | HK10 | 62 | ACGTTAAGTTCCCGGGTGGCGGACAGATCGTTGGTGAGTATACGTGTTGCCGCGCAGGGG |
| 136 | S52 | 62 | ACGTTAAGTTCCCGGGTGGCGGACAGATCGTTGGTGAGTATACGTGTTGCCGCGCAGGGG |
| 137 | S2 | 62 | ACaTcAAGTTCCCGGGTGGCGGACAGATCGTTGGTGAGTATACGTGTTGCCGCGCAGGGG |

135-138 consensus    ACgT-AAGTTCCCGGGTGGCGGACAGATCGTTGGTGAGTATACGTGTTGCCGCGCAGGGG

| SEQ ID NO: | ISOLATE | | |
|---|---|---|---|
| 138 | DK12 | 123 | CCCACGATTGGGTGTGCGCGCGACGCGTAAAACTTCTGAACGGTCaCAGCCTCGCGGACGg |
| 135 | HK10 | 123 | CCCACGATTGGGTGTGCGCGCGACGCGTAAAACTTCTGAACGGTCgCAGCCTCGCGGACGA |
| 136 | S52 | 123 | CCCACGATTGGGTGTGCGCGCGACGCGTAAAACTTCTGAACGGTCACAGCCTCGCGGACGA |
| 137 | S2 | 123 | CCCACGATTGGGTGTGCGCGCGACGCGTAAAACTTCTGAACGGTCACAGCCTCGCGGACGg |

135-138 consensus    CCCACGATTGGGTGTGCGCGCGACGCGTAAAACTTCTGAACGGTCaCAGCCTCGCGGACG-

| SEQ ID NO: | ISOLATE | | |
|---|---|---|---|
| 138 | DK12 | 184 | CGACAGCCTATCCCCAAGGCGCGTCGGAGCGAAGGCCGGTCCTGGGCTgGGTACC |
| 135 | HK10 | 184 | CGACAGCCTATCCCCAAGGCGCGTCGGAGCGAAGGCCGGTCCTGGGCTCCAGCCCGGGTACC |
| 136 | S52 | 184 | CGACAGCCTATCCCCAAGGCGCGTCGGAGCGAAGGCCGGTCCTGGGCTCCAGCCCGGGTACC |
| 137 | S2 | 184 | CGACAGCCTATCCCCAAGGCGCGTCGGAGCGAAGGCCGaTCCTGGGCTCCAGCCCGGGTACC |

135-138 consensus    CGACAGCCTATCCCCAAGGCGCGTCGGAGCGAAGGCCGgTCCTGGGCTCCAGCCcGGGTACC

FIGURE 6G-2

| SEQ ID NO: | ISOLATE | | |
|---|---|---|---|
| 138 | DK12  | 245 | CTTGGCCCCCTCTATGTAACGAGGGCTGCGGGTGGGCAGGGTGGCTCCTGTCCCACGCGG |
| 135 | HK10  | 245 | CTTGGCCCCCTCTATGTAACGAGGGCTGCGGGTGGGCAGGaTGGCTCCTGTCCCACGCGG |
| 136 | S52   | 245 | CTTGGCCCCCTCTATGTAAtGAGGGCTGCGGGTGGGCAGGGTGGCTCCTGTCCCACGCGG |
| 137 | S2    | 245 | CTTGGCCCCCTCTATGTAACGAGGGCTGCGGGTGGGCAGGGTGGCTCCTGTCCCACGCGG |

135-138 consensus        CTTGGCCCCCTCTATGTAAcGAGGGCTGCGGGTGGGCAGGGTGGCTCCTGTCCCACGCGG

| SEQ ID NO: | ISOLATE | | |
|---|---|---|---|
| 138 | DK12  | 306 | CTCCCGTCCATCTTGGGGCCCAAACGACCCCGGCGgaGGTCCCGCAATTTGGGTAAgGTC |
| 135 | HK10  | 306 | CTCCCGTCCATCTTGGGGCCCAAACGACCCCGGCGGGacGGTCCCGCAATTTGGGTAAAGTC |
| 136 | S52   | 306 | CTCCCGTCCATCTTGGGGCCCAAACGACCCCGGCGGGGAGGTCCCGCAATTTGGGTAAAGTC |
| 137 | S2    | 306 | CTCCCGTCCATCTTGGGGCCCAAAtGACCCCGGCGGGAGGTCCCGCAATTTGGGTAAAGTC |

135-138 consensus        CTCCCGTCCATCTTGGGGCCCAAAcGACCCCGGCGgaGGTCCCGCAATTTGGGTAAgGTC

| SEQ ID NO: | ISOLATE | | |
|---|---|---|---|
| 138 | DK12  | 367 | ATCGATACCCTCACGTGCGGATTCGCCGACTTCATGGGTACATCCGCTCGTCGGCGCTC |
| 135 | HK10  | 367 | ATCGATACCCTTACGTGCGGATTCGCCGACTTCATGGGTACATCCGCTCGTCGGCGCTC |
| 136 | S52   | 367 | ATCGATACCCTTACGTGCGGCTTCGCCGACTTCATGGGTACATCCGCTCGTCGGCGCTC |
| 137 | S2    | 367 | ATCGATACCCTTACGTGCGGCTTCGCCGACTTCATGGGTACATCCGCTCGTCGGCGCTC |

135-138 consensus        ATCGATACCCTtACGTGCGGaTTCGCCGACTTCATGGGTACATCCGCTCGTCGGCGCTC

| SEQ ID NO: | ISOLATE | | |
|---|---|---|---|
| 138 | DK12  | 428 | CtGTAGGgGGCGTCGCAAGAGCCCTCGGCGATGCCGTGAGGGCCCTTGAAGACGGATAAA |
| 135 | HK10  | 428 | CCGTAGGAGGCGTCGCAAGAGCCCTCGGCGATGCCGTGAGGGCCCTTGAAGACGGATAAA |
| 136 | S52   | 428 | CCGTAGGAGGCGTCGCAAGAGCCCTCGGCGATGCCGTGAGGGCCCTTGAAGACGGATAAA |
| 137 | S2    | 428 | CCGTAGGAGGCGTCGCAAGAGCCCTCGGCGATGCCGTGAGGGCCCTTGAAGACGGATAAA |

135-138 consensus        CcGTAGGaGGCGTCGCAAGAGCCCTCGGCGATGCCGTGAGGGCCCTTGAAGACGGATAAA

FIGURE 6G-3

| SEQ ID NO: | ISOLATE | | |
|---|---|---|---|
| 138 | DK12 | 489 | TTTCGCAACAGGGAACTTGCCCGGTTGCTCCTTTTCTATCTTCCTTCTGCTCTGTTCTCT |
| 135 | HK10 | 489 | TTTCGCAACAGGGAACTTGCCCGGTTGCTCCTTTTCTATCTTCCTTCTTGCTCTGTTCTCT |
| 136 | S52 | 489 | TTTTGCAACAGGGAACTTGCCCGGTTGCTCCTTCTCTTTCTATCTTCCTTCTGCTCTGTTCTCT |
| 137 | S2 | 489 | TTTTGCAACAGGGAACTTGCCCGGTTGCTCCTTTTCTTTCTATCTTCCTTCTTGCCCTGTTCTCc |

135-138 consensus TTT-GCAACAGGGAACTTGCCCGGTTGCTCCTTTTCTATCTTCCTTCTGCTCTGTTCTCt

| SEQ ID NO: | ISOLATE | | |
|---|---|---|---|
| 138 | DK12 | 550 | TGCcTAATTCATTCATCCAGCAGCAGCTAGT |
| 135 | HK10 | 550 | TGCTTAATTCATCATCCAGCAGCAGCTAGT |
| 136 | S52 | 550 | TGCTTAgTTCATCCtGCAGCTAGT |
| 137 | S2 | 550 | TGCTTAaTTCATCCAGCAGCAGCTAGT |

135-138 consensus TGCtTAaTTCATCCaGCAGCTAGT

FIGURE 6H-1

| SEQ ID NO: | ISOLATE | | |
|---|---|---|---|
| 145 | DK13 | 1 | ATGAGCACGAATCCTAAACCTCAAAGAAAAACCAAACGTAACACCAACCGCCGCCCAATGG |
| 143 | Z6 | 1 | ATGAGCACGAATCCTAAACCTCAAAGAAAAACCAAACGTAACACCAACCGCCGCCCCATGG |
| 144 | Z7 | 1 | ATGAGCACGAATCCTAAACCTCAAAGAAAAACCAAACGTAACACCAACCGCCGCCCCATGG |
| 140 | Z8 | 1 | ATGAGCACGAATCCTAAACCTCAAAGAAAAACCAAACGTAACACCAACCGCCGCCCCtATGG |
| 139 | Z4 | 1 | ATGAGCACGAATCCTAAACCTCAAAGAAAAACCAAACGTAACACCAACCGCCGCCCCATGG |
| 142 | Z5 | 1 | ATGAGCACGAATCCTAAACCTCAAAGAAAAACCAAACGTAACACCAACCGCCGCCCCATGG |
| 141 | Z1 | 1 | ATGAGCACGAATCCTAAACCTCAAAGAAAAACCAAACGTAACACCAACCGtCGCCCCATGG |

139-145 consensus    ATGAGCACgAATCCTAAACCTCAAAGAAAAACCAAACGTAACACCAACCGcCGCCCCATGG

| SEQ ID NO: | ISOLATE | | |
|---|---|---|---|
| 145 | DK13 | 62 | ACGTTAAGTTCCCGGGTGGCGGCCAGATCGTTGGCGGAGTTTACTTGTTGCCGCGCAGGGG |
| 143 | Z6 | 62 | ACGTTAAGTTCCCGGGTGGCGGCCAGATCGTTGGCGGAGTTTACTTGTTGCCGCGCAGGGG |
| 144 | Z7 | 62 | ACGTTAAGTTCCCGGGTGGCGGCCAGATCGTTGGCGGAGTTTACTTGTTGCCGCGCAGGGG |
| 140 | Z8 | 62 | AtGTAAAaTTCCCaGGCGGCGGCCAGATCGTTGGCGGAGTTTACTTGTTGCCGCGCAGGGG |
| 139 | Z4 | 62 | AcGTAAAgTTCCCGGGTGGCGGTGGtCAGATCGTTGGCGGAGTTTACTTGTTGCCGCGCAGGGG |
| 142 | Z5 | 62 | ATGTAAAATTCCCGGGCGGCGGCCAGATCGTTGGCGGAGTTTACTTGTTGCtGCCGCGCAGGGG |
| 141 | Z1 | 62 | ATGTgAAATTCCCGGGCGGCGGCCAGATCGTTGGCGGAGTTTACTTGtTGCCGCGCAGGGG |

139-145 consensus    AcGT-AAgTTCCCgGGtGGtGGcCAGATCGTTGGCGGAGTTTACTTGtTGCCGCGCAGGGG

| SEQ ID NO: | ISOLATE | | |
|---|---|---|---|
| 145 | DK13 | 123 | CCCtAGaTTGGGTGTGCGCGCGACTAGGAAGACTTCGGAGCGGTCGCAACCTCGTGGGAGg |
| 143 | Z6 | 123 | CCCCAGGTTGGGTGTGCGCGCGACTAGGAAGACTTCGGAGCGGTCGCAACCTCGTGGGAGA |
| 144 | Z7 | 123 | CCCCAGaTTGGGTGTGCGCaCaACTAGGAAGACTTCGGAGCGGTCGCAACCTCGTGGGAGA |
| 140 | Z8 | 123 | CCCCAGGTTGGGTGTGCGCGCGACTCGGAAGACTTCGGAGCGGTCGCAACCTCGTGGCAGG |
| 139 | Z4 | 123 | CCCCAGGTTGGGTGTGCGCGCGACTCGaAAGACTTCGGAGCGGTCGCAACCTCGTGGCAGG |
| 142 | Z5 | 123 | CCCCAGGTTGGGTGTGCGCGCGACTCGGAAGACTTCGGAGCGGTCGCAACCTCGCGGCAGG |
| 141 | Z1 | 123 | CCCCcGGTTGGGTGTGCGCGCGACTCagCGGAAGACTTCGGAAGACTTCGGAGCGGTCaCAACCTCGtGGCAGG |

139-145 consensus    CCCcaGgTTGGGTGTGCGCgGCgGaCTcCgAAGACTTCGGAGCGGTCgCAACCTCgtGgCAGg

FIGURE 6H-2

| SEQ ID NO: | ISOLATE | | |
|---|---|---|---|
| 145 | DK13 | 184 | CGCCAGCCTATCCCCAAGGCgGcCaActcGAGGGtAGGTCCTGGGCTCAGCCTGGGTATC |
| 143 | Z6 | 184 | CGCCAGCCTATCCCCAAGGCACGTCGATCTGAGGGAAGGTCCTGGGCTCAGCCCGGGTATC |
| 144 | Z7 | 184 | CGTCAGCCTATCCCCAAGGCACGTCGATCTGAGGGAAGGTCCTGGGCTCAaCCGGGTACC |
| 140 | Z8 | 184 | CGTCAGCCTATCCCCAAGGCACGTCGGTCCGAGGGtAGGTCCTGGGCTCAGCCCGGGTACC |
| 139 | Z4 | 184 | CGTCAaCCTATCCCCAAGGCgCgCcAGcCaGaGAGGGCAGaTCCTGGGCgCAGCCGGGTACC |
| 142 | Z5 | 184 | CGTCAGCCTATCCCCAGGCaCGtCGGTCCGAGGGCAGTCCTGGGCTCAGCCCGGGTACC |
| 141 | Z1 | 184 | CGTCAGCCTATCCCCAAGGCgCgCcGGTCCGCCGGTCCGAGGGCAGTCCTGGGCTCAGCCCGGGTACC |
| 139-145 | consensus | | CGtCAgCCTATCCCCAaGGCaCGtCggtccGAGGGCAGtTCCTGGGCtCAgCCCGGGTAcC |

| SEQ ID NO: | ISOLATE | | |
|---|---|---|---|
| 145 | DK13 | 245 | CtTGGCCCCCTTTACGGCAATGAGGGCTGCGGGTGGCGGGATGGCTCCTGTCACCCCGTGG |
| 143 | Z6 | 245 | CATGGCCTCTCTTTACGGTAATGAGGGTTGCGGGTGGCGCGGGATGGCTCCTGTCACCCCGTGG |
| 144 | Z7 | 245 | CATGGCCTCTCTTTACGGTAACGAGGGTTGCGGGTGGCAGGATGGCTCtGTCACCCCGTGG |
| 140 | Z8 | 245 | CATGGCCTCTCTTTACGGTAATGAaGGCTGtGGGTGGCGGGTGGCTGGCTCCTGTCCCCCGCGG |
| 139 | Z4 | 245 | CTTGGCCCCCTCTATGCAATGAGGGCTGCGGGTGGGGTGCAGGTGGCTCCTGTCtCCtCGCGG |
| 142 | Z5 | 245 | CTTGGCCtCTTTATGCAATGAGGGCTGCGGGTGTGGGTGGCAGGTGGCTCCTGTCCCCCGCGG |
| 141 | Z1 | 245 | CTTGGCCCCTTTTACGCAATGAGGGCTGTGGGTGGCAGGTGGCTCCTGTCCCCCGCGG |
| 139-145 | consensus | | CtTGGCCtCTtTAcGGcAAtGAGGGCTGcGGGGTGGGCaGG-TGGCTCcTGTC-CCcCGcGG |

| SEQ ID NO: | ISOLATE | | |
|---|---|---|---|
| 145 | DK13 | 306 | CTCTCGgCGCCGTCTTGGGGCCCgAATGATCCCCGGCGgAGGTCCCGCAACTTGGGTAAGGTC |
| 143 | Z6 | 306 | CTCTCGACCGTCTTGGGGtCCAAATGATCCCCGGCGCGAAGGTCCCGCAACTTGGGTAAGGTC |
| 144 | Z7 | 306 | CTCTCGACCGTCTTGGGGCCCAAATGATCCCCGGCGCGAAGGTCCCGCAACTTGGGTAAGGTC |
| 140 | Z8 | 306 | CTCTCGACCGTCTTGGGGCCCAAATGATCCCCGGCGCGAGGTCCGCGCAATTGGGTAAGGTC |
| 139 | Z4 | 306 | CTCTCGGCCATCTTGGGGCCCAAATGATCCCCGGCGCGAGaTCGGCGAATCTGGGTAAGGTC |
| 142 | Z5 | 306 | CTCTCGGCCATCTTGGGGCCCaAAATGATCCCCGGCGTAGTCCCGCAATCTGGGTAAGGTC |
| 141 | Z1 | 306 | aTCTCGGCCATCTTGGGGCCCaAAATGATCCCCGGCGTAGTCCCGtAATCTGGGTAAaGTC |
| | | | tTCcaGGCCGTCTTGGGGCCCcAATGATCCCCGGCGAGTCCCGcAAttTGGGTAAgGTC |
| 139-145 | consensus | | cTCtcGCCGTCTTGGGGCCcaAATGATCCCCGGCGAGTCCGcAAtTGGGTAAgGTC |

FIGURE 6H-3

| SEQ ID NO: | ISOLATE | | |
|---|---|---|---|
| 145 | DK13 | 367 | ATCGATAccCTAACTTGCGGcTTCGCCGAcCTCATGGATACATCCCGgTCGTAGGCGCCC |
| 143 | 26 | 367 | ATCGATActCTAACTTGCGGtTTCGCCGAtCTCATGGATACATCCCGCTCGTAGGCGCCC |
| 144 | 27 | 367 | ATCGATACCCTAACCTGCGGCTTtGCCGACCTCATGGATACATCCCGCTCGTAGGCGCCC |
| 140 | 28 | 367 | ATCGATACCCTcACGTGCGGCTTCGCCGACCTCATGGATACATCCCGCTCGTGGGCGCCC |
| 139 | 24 | 367 | ATCGATACCCTGACGTGCGGCTTCGCCGACCTCATGGATACATCCCGaTCGTGGGCGCCC |
| 142 | 25 | 367 | ATCGATACCCTGACGTGTGGCTTCGCCGACCTCATGGATACATTCCGCTCGTcGGGCGCCC |
| 141 | 21 | 367 | ATCGATACCCTGACGTGTGGCTTCGCCGACCTCATGGATACATTCCGCTCGTaGGCGCCC |

139-145 consensus ATCGATACccT-ACgTGcGGCTTcGCCGAcCTCATGGATACATCCCGCTCGTaGGCGCCC

| SEQ ID NO: | ISOLATE | | |
|---|---|---|---|
| 145 | DK13 | 428 | CCGTGGGtGGCGTCGCCAGaGCCCTGGCGCATGGCGTCAGGcTTCTGGAGGACGGGgTCAA |
| 143 | 26 | 428 | CCGTGGGCGGCGTCGCCAGGGCCCTGGCaCATGGCGTGTTAGGGCTgTGGAGGACGGGATCAA |
| 144 | 27 | 428 | CCGTGGGCGGCGTCGCCAGGGCCCTaGCGCATGGCGTTAGGGCTCTGGAGGACGGGATAA |
| 140 | 28 | 428 | CaGTaGGaGGCGTCGCCAGaGCCCTGGCGCATGGCGTCAGGGCTGTGGAGGACGGGATCAA |
| 139 | 24 | 428 | CcGTgGGgGGCGTCGCCAGGGCtCTGGCGCATGGCGTCAGGGCTGTGGAGGACGGGATtAA |
| 142 | 25 | 428 | CaGTaGGTGGCGTCGCCAGGGCCtTGGCGCATGGCGTCAGGGCCtGGAGGACGGGAATCAA |
| 141 | 21 | 428 | CtGTgGGTGGCGTCGCCAGGGCCCTGGCGCATGGCGTCAGGGCCGtGGAGGACGGGAATtAA |

139-145 consensus CcGTgGGtGGCGTCGCCAGGGCccTgGCgCATGGCGtCAGGgctgTGGAGGACGGgaTcAA

| SEQ ID NO: | ISOLATE | | |
|---|---|---|---|
| 145 | DK13 | 489 | TTATGCAACAGGGAATCTTCCGGTTGCTCTTTCTCTATCTTCCCTTGGCACTgCTcTCG |
| 143 | 26 | 489 | TTATGCAACAGGGAATCTTCCGGTTGCTCTTTCTCTATCTTCCTTGGCACTTCTTTCG |
| 144 | 27 | 489 | TTATGCAACAGGGAATCTTCCGGTTGCTCTTTtCTCTATCTTCCCTTGGCACTTCTTTCG |
| 140 | 28 | 489 | CTATGCAACAGGGAACCTTCCGGTTCCTGGTTGCTCTTTCTCTATCTTCCTTGGCACTTCTCTCG |
| 139 | 24 | 489 | CTATGCAACAGGGAATCTTCCGGTTCCTGGTTGCTCTTTCTCTATCTTCCTTtTGGCACTTCTTTCG |
| 142 | 25 | 489 | CTATGCAACAGGGAATCTTCCTTCCTGGTTGCTCcTTtCTCTATCTTCCTaCTTGCACTTtTCTCG |
| 141 | 21 | 489 | CTAcGCAACAGGGAACCTTCCTTGCTGGTTGCTCTCTTCTCTATCTTCTCTTGCACTTTCTCTCG |

139-145 consensus cTAtGCAACAGGGAAtCTTCCcGGTTGCTCTtTcTCTATCTTcCTtGCACTtcTCTCG

FIGURE 6H-4

| SEQ ID NO: | ISOLATE | | |
|---|---|---|---|
| 145 | DK13 | 550 | TGCCTgACTGTTCCCgCtTCGGCC |
| 143 | Z6 | 550 | TGCCTaACTGTTCCCaCCTCGGCC |
| 144 | Z7 | 550 | TGCCTgACTGTTCCCgCCTCGGCC |
| 140 | Z8 | 550 | TGCCTaACcGTcCCAGCCGTtGCT |
| 139 | Z4 | 550 | TGCCTcACtGTtCCAGCGTcGGCT |
| 142 | Z5 | 550 | TGCtTGACAACACCggGCATCCGT |
| 141 | Z1 | 550 | TGCcTGACAACACCagGCATcGCc |

139-145 consensus  TGCcTgACtgttCC-gC-TCgGCc

FIGURE 6I-1

| SEQ ID NO: | ISOLATE | | |
|---|---|---|---|
| 153 | SA11 | 1 | ATGAGCACGAATCCTAAACCTCAAAGAAAAACCaAAAGAAAACACCAACCGCCGCCCACAGG |
| 152 | SA6 | 1 | ATGAGCACGAATCCTAAACCTCAAAGAAAAACCaAAAGAAAACACCAACCGCCGCCCACAGG |
| 146 | SA4 | 1 | ATGAGCACGAATCCTAAACCTCAAAGAAAAACAAAAGAAAACACCAACCGCCGCCCACAGG |
| 147 | SA5 | 1 | ATGAGCACGAATCCTAAACCTCAAAGAAAAACAAAAGAAAACACCAACCGCCGCCCACAGG |
| 148 | SA7 | 1 | ATGAGCACGAATCCTAAACCTCAAAGAAAAACAAAAGAAAACACCAACCGCCGCCCACAGG |
| 149 | SA1 | 1 | ATGAGCACGAATCCTAAACCTCAAAGAAAAACAAAAGAAAACACCAACCTCCGCCCACAGG |
| 150 | SA3 | 1 | ATGAGCACGAATCCTAAACCTCAAAGAAAAACAAAAGAAAACACCAACCGCGCCCACAGG |
| 151 | SA13 | 1 | ATGAGCACGAATCCTAAACCTCAAAGAAAAACAAAAGAAAACACCAACCGCCGCCCACAGG |
| 146-153 | consensus | | ATGAGCACGAATCCTAAACCTCAAAGAAAACCaAAAGAAAACACCAACCgCCGCCCACAGG |

| SEQ ID NO: | ISOLATE | | |
|---|---|---|---|
| 153 | SA11 | 62 | ACGTCAAGTTCCCGGGCGGTGCGTCAGATCGTTGGTGGAGTTTACTTGTTGCCGCGCAGGGG |
| 152 | SA6 | 62 | ACGTCAAGTTCCCGGGCGGTGCGTCAGATCGTTGGTGGAGTTTACTTGTTGCCGCGCAGGGG |
| 146 | SA4 | 62 | ACGTtAAGTTCCCGGGCGGTGCGTCAGATCGTTGGTGGAGTcTACTTGTTGCCGCGCAGGGG |
| 147 | SA5 | 62 | ACGTCAAGTTCCCGGGCGGTGCGTCAGATCGTTGGTGGAGTTTACTTGTTGCCGCGCAGGGG |
| 148 | SA7 | 62 | ACGTCAAGTTCCCGGGCGGTGCGTCAGATCGTTGGTGGAGTTTACTTGTTGCCGCGCAGGGG |
| 149 | SA1 | 62 | ACGTCAAGTTCCCGGGCGGTGCGTCAGATCGTTGGTGGAGTTTACTTGTTGCCGCGCAGGGG |
| 150 | SA3 | 62 | ACGTCAAGTTCCCGGGCGGTGCGTCAGATCGTTGGTGGAGTTTACTTGTTGCCGCGCAGGGG |
| 151 | SA13 | 62 | ACGTCAAGTTCCCGGGCGGTGCGTCAGATCGTTGGTGGAGTTTACTTGTTGCCGCGCAGGGG |
| 146-153 | consensus | | ACGTCAAGTTCCCGGGCGGTGCGTCAGATCGTTGGTGGAGTtTACTTGTTGCCGCGCAGGGG |

| SEQ ID NO: | ISOLATE | | |
|---|---|---|---|
| 153 | SA11 | 123 | CCCTaGgtTGGGTGTGCGCGCgACTCGGAAGACTTCaGAACGGTCGCAACCCCGTGGgCGG |
| 152 | SA6 | 123 | CCCTcGtaTGGGTGTGCGCGCgACTCGGAAGACTTCgGAACGGTCGCAACCCCGTGGaCGG |
| 146 | SA4 | 123 | CCCTAGgTTGGGTGTGCGCGCgACTCGGAAGACTTCAGAACGGTCGCAACCCCGTGGGCGG |
| 147 | SA5 | 123 | CCCTAGaTTGGGTGTGCGCGCgACTCGGAAGACTTCAGAACGGTCGCAACCCCGTGGGCGG |
| 148 | SA7 | 123 | CCCTAGGTTGGGTGTGCGCGCgACTCGGAAGACTTCAGAACGGTCGCAACCCCGTGGGCGG |
| 149 | SA1 | 123 | CCCCAGGTTGGGTGTGCGCGCgACTCGGAAGACTTCgGAACGGTCGCAACCCCGTGGGCGG |
| 150 | SA3 | 123 | CCCCAGGTTGGGTGTGCGCGCaACTCGGAAGACTTCAGAACGGTCGCAACCCCGTGAACGG |
| 151 | SA13 | 123 | CCCtAGGTTGGGTGTGCGCGCgACTCGGAAGACTTCAGAACGGTCGCAACCCCGTGAACGG |
| 146-153 | consensus | | CCCtaGgtTGGGTGTGCGCGCgACTCGGAAGACTTCaGAACGGTCGCAACCCCGTGGgCGG |

FIGURE 6I-2

| SEQ ID NO: | ISOLATE | | |
|---|---|---|---|
| 153 | SA11 | 184 | CGTCAGCCTATTCCCAAGGCGCGCCAAcCaCAGGGcCGGTCCTGGGGTCAACCCGGGTACC |
| 152 | SA6 | 184 | CGTCAGCCTATTCCCAAGGCGCGCCAAtCcGcGGGtCGGTCCTGGGGTCAACCCGGGTACC |
| 146 | SA4 | 184 | CGCCAGCCTATTCCCAAGGCGCGCCAACCCACGGGCCGGTCCTGGGGTCAACCCGGGTACC |
| 147 | SA5 | 184 | CGCCAGCCTATTCCCAAGGCGCGCCAACCCACGGGCCGGTCCTGGGGTCAACCCGGGTACC |
| 148 | SA7 | 184 | CGCCAGCCTATTCCCAAGGCGCGCCAACCCACGGGCCGGTCCTGGGGTCAACCCGGGTACC |
| 149 | SA1 | 184 | CGCCAGCCTATTCCCAAGGCGCGCCAACCCACGGGCCGGTCCTGGGGTCAACCCGGGTACC |
| 150 | SA3 | 184 | CGCCAGCCTATTCCCAAGGCtCGCCAGCCCACGGGCCGGTCCTGGGGTCAACCCGGGTACC |
| 151 | SA13 | 184 | CGtCAGCCTATcCCCAAGGCgCgCCAGCCCACGGGCCGGTCCTGGGGTCAACCCGGGTACC |

146-153 consensus  CGcCAGCCTATtCCCAAGGCgCgCCAacCcaCaGGGcCGGTCCTGGGGTCAACCCGGGTACC

| SEQ ID NO: | ISOLATE | | |
|---|---|---|---|
| 153 | SA11 | 245 | CTTGGCCCtTTTAcGCCAATGAGGGCCTCGGGTGGGCAGGGTGGcTGCTCTCCCtCGAGG |
| 152 | SA6 | 245 | CTTGGCCCCTTTTACGCCAATGAGGGCCTCGGGTGGGCAGGGTGGTTGCTCTCTCCCCGAGG |
| 146 | SA4 | 245 | CTTGGCCCCTTTTACGCCAATGAGGGCCTCGGGTGGGCAGGGTGGTTGCTCTCTCCCCGAGG |
| 147 | SA5 | 245 | CTTGGCCCCTTTTACGCCAATGAGGGCCTCGGGTGGGCAGGGTGGTTGCTCTCTCCCCGAGG |
| 148 | SA7 | 245 | CTTGGCCCCTTTTACGCCAATGAGGGCCTCGGGTGGGCAGGGTGGTTGCTCTCTCCCCGAGG |
| 149 | SA1 | 245 | CTTGGCCCCTTTTACGCCAATGAGGGCCTCGGGTGGGCAGGGTGGTTGCTCTCTCCCCGAGG |
| 150 | SA3 | 245 | CTTGGCCCCCTTTACGCCAATGAGGGCCTCGgTTGGGCAGGGTGGTTGCTCTCTCCCCGAGG |
| 151 | SA13 | 245 | CTTGGCCCCTTTAtGCCAATGAGGGCCTCGgTTGGGCAGGGTGGTTGCTCTCTCCCCGAGG |

146-153 consensus  CTTGGCCCcTTTAcGCCAATGAGGGCCTCGgGTGGGCAGGGTGGtTGCTCTCTCCCcGAGG

| SEQ ID NO: | ISOLATE | | |
|---|---|---|---|
| 153 | SA11 | 306 | CTTCTCGGCCTAACTGGGCCCCAATGACCCCGGCGAAgATCGCGCAATTTGGcAAGGTC |
| 152 | SA6 | 306 | CTTCTCGGCCTAATTGGGGCCCCCAATGACCCCGGCGAAAATCGCGCAATTTGGTAAGGTC |
| 146 | SA4 | 306 | CTTCTCGGCCTAATTGGGGCCCCCAATGACCCCGGCGAAATCGCGCAATTTGGGTAAGGTC |
| 147 | SA5 | 306 | CTTCTCGGCCTAATTGGGGCCCCCAATGACCCCGGCGAAAgTCGCGCAATTTGGGTAAGGTC |
| 148 | SA7 | 306 | CTTCTCGGCCTAATTGGGGCCCCCAATGACCCCGGCGAAAATCGCGCAATTTGGGTAAGGTC |
| 149 | SA1 | 306 | CTTCTCGGCCTAATTGGGGCCCCCAATGACCCCGGCGAAAGTCGCGGAAGTCGCGCAATTTGGGTAAGGTC |
| 150 | SA3 | 306 | CTTCTCGGCCTAgTTGGGGCCCCCAAcGACCCCGGGGAAATCGCGCAATTTGGGTAAGGTC |
| 151 | SA13 | 306 | CTTCTCGGCCTAaTTGGGGCCCCAAtGACCCCGGGGAAATCGCGCAACTTGGGTAAGGTC |

146-153 consensus  CTTCTCGGCCTAatTGGGGCCCCAAtGACCCCGGCGAaTCGCGCAatTGGGtAAGGTC

FIGURE 6I-3

| SEQ ID NO: | ISOLATE | | |
|---|---|---|---|
| 153 | SA11 | 367 | ATCGATACCCTAACGTGCGGATTCGCCGACCTCATGGGTACATCCCGCTCGTAGGCGGCC |
| 152 | SA6 | 367 | ATCGATACCCTAACGTGCGGATTCGCCGACCTCATGGGTACATCCCGCTCGTAGGCGGCC |
| 146 | SA4 | 367 | ATCGATACCCTAACGTGCGGATTCGCCGACCTCATGGGTACATCCCGCTCGTAGGCGGCC |
| 147 | SA5 | 367 | ATCGATACCCTAACGTGCGGATTCGCCGACCTCATGGGTACATCCCGCTCGTAGGCGGCC |
| 148 | SA7 | 367 | ATCGATACCCTAACGTGCGGATTCGCCGACCTCATGGGTACATCCCGCTCGTAGGCGGCC |
| 149 | SA1 | 367 | ATCGAcACCCTAACaTGCGGATTCGCCGACCTCATGGGTACATCCCGCTCGTAGGCGGCC |
| 150 | SA3 | 367 | ATCGATACCCTAACGTGCGGATTCGCCGAtCTCATGGGTACATCCCGCTCGTAGGCGGCC |
| 151 | SA13 | 367 | ATCGATACCCTgACGTGCGGATTCGCCGAcCTCATGGGTACATCCCGCTCGTAGGCGGCC |

146-153 consensus ATCGAtACCCTaAcGtGCGGATTCGCCGAcCTCATGGGTACATCCCGCTCGTAGGCGGCC

| SEQ ID NO: | ISOLATE | | |
|---|---|---|---|
| 153 | SA11 | 428 | CCGTTGGGGGCGTCGCAAGGGCcCTCGCACACGGTGTGAGaGcTCTTGAGGACGGGGTAAA |
| 152 | SA6 | 428 | CCGTTGGGGGCGTCGCAAGGGCtCTCGCACACGGTGTGAGGGTTCTTGAGGACGGGGTAAA |
| 146 | SA4 | 428 | CCGTTGGGGGCGTCGCAAGGGCCCTtGCACATGGTGTGAGGGTTCTTGAGGACGGGGTAAA |
| 147 | SA5 | 428 | CCGTTGGGGGCGTCGCAAGGGCCCTCGCACATGGTGTGAGGGTTCTTGAGGACGGGGTAAA |
| 148 | SA7 | 428 | CCGTTGGGGGCGTCGCAAGGGCTCTCGCACACGGTGTGAGGGTTCTTGAGGACGGGGTAAA |
| 149 | SA1 | 428 | CCGTTGGGGGCGTCGCAAGGGCTCTCGCACACGGTGTGAGGGTTCTTGAGGACGGGGTAAA |
| 150 | SA3 | 428 | CCGTTGGGGGCGTCGCAAGGGCTCGCAAtGGTGTGAGGGTTCTTGAGGACGGGGTAAA |
| 151 | SA13 | 428 | CCGTTGGGGGCGTCGCAAGGGCTCTCGCACAcGGTGTGAGGGTCCTTGAGGACGGGGTAAA |

146-153 consensus CCGTTGGGGGCGTCGCAAGGGCtCTcGCACACGGTGTGAGgGttCTTGAGGACGGGGTAAA

| SEQ ID NO: | ISOLATE | | |
|---|---|---|---|
| 153 | SA11 | 489 | tTATGCAACaGGGAATtTtCCCGGTTGCTCTTTCTCcATCTTTaTCCTTGCACTTCTCTCG |
| 152 | SA6 | 489 | CTATGCAACAGGGAATTTGCCCGGTTGCTCTTTCTCTCTATCTTTgTCCTTGCACTTCTCTCG |
| 146 | SA4 | 489 | CTATGCAACgGGGAATTTGCCCGGTTGCTCTTTCTCTCTATCTTTATCCTTGCACTTCTCTCG |
| 147 | SA5 | 489 | CTATGCAACAGGGAATTTGCCCGGTTGCTCTTTCTCTCTATCTTTATCCTTGCACTTCTCTCG |
| 148 | SA7 | 489 | CTATGCAACAGGGAATCTGCCCGGTTGCTCTTTCTCTCTATCTTTATCCTTGCACTTCTCTCG |
| 149 | SA1 | 489 | tTACGCAACAGGGAATTTGCCCGGTTGCTCTTTCTCTCTATCTTTATCCTTGCACTTCTTTCC |
| 150 | SA3 | 489 | CTACGCAACAGGGAATTTACCCGGTTGCTCTTTCTCTCTATCTTTATCCTTGCACTTCTTTCA |
| 151 | SA13 | 489 | CTAtGCAACAGGGAATTTACCCGGTTGCTCTTTCTCTCTATCTTTATCCTTGCACTTCTTTCA |

146-153 consensus cTAtGCAACaGGGAATtTgCCCGGTTGCTCTTTCTCtATCTTTaTCCTTGCACTTCtCTCg

FIGURE 6I-4

| SEQ ID NO: | ISOLATE | | |
|---|---|---|---|
| 153 | SA11 | 550 | TGCtTgACCGTCCCggCCaCTGCA |
| 152 | SA6  | 550 | TGCCTaACCGTCCCtgCCTCTGCA |
| 146 | SA4  | 550 | TGCCTGACCGTCCCggCCTCTGCA |
| 147 | SA5  | 550 | TGCtTGACCGTCCCAGCCTCTGCA |
| 148 | SA7  | 550 | TGCCTGACCGTCCCAGCCTCTGCA |
| 149 | SA1  | 550 | TGtCTGAtCaTCCCGGCCTCTGCA |
| 150 | SA3  | 550 | TGCCTGACCGTCCCGGCCTCTGCA |
| 151 | SA13 | 550 | TGCCTGACtGTCCCGaCCTCTGCc |

| 146-153 | consensus | TGccTgAccgTCCCggCCtCtGCa |

FIGURE 6J-1

| SEQ ID NO: | Genotype | | |
|---|---|---|---|
| 103-154 | cons. | 1 | ATGAGCACgaaTCCtAAACCtCAAAGAaAaACCaaAcGtAAcACCaAcCgcCGcCGCCCacagG |
| 103-124 | 1 | 1 | ATGAGCACgAaTCCtAAACCTCAAAGAaAaACCaAAcGTAACACCaACCgCGCCCACAGG |
| 125-134 | 2 | 1 | ATGAGCACaAaTCCtAAACCTCAAAGAaGAaAACCaAAcACAACGcGCCCACAgg |
| 135-138 | 3 | 1 | ATGAGCACACTTCCTAAACCTCAAAGAaAAAACCaAAAGAaAACACCATCCGTCGCCACAGG |
| 139-145 | 4 | 1 | ATGAGCACgAaTCCTAAACCTCAAAGAaAAAAGAaAACgTAACACCgCGCCCCATGG |
| 146-153 | 5 | 1 | ATGAGCACgAATCCTAAACCTCAAAGAaAAAACCaAAAGAaAACACCAACgCCGCCACAGG |
| 154 | 6 | 1 | ATGAGCACACTTCCAAAACCCAAAGAAAACCAAAGAaAACACCAACGTCGCCCAACGG |

| SEQ ID NO: | Genotype | | |
|---|---|---|---|
| 103-154 | cons. | 62 | AcgTcAAgTTcCCgGgGcGgTgGtCAGATCGTtGgtGGAGTtTActTgTtGCCgCgCAGGGG |
| 103-124 | 1 | 62 | ACGTCAAGTTCCCGGGcGgTgGtCAGATCGTtGGTGGAGTtTAccTGTTGCCGCGCAGGGG |
| 125-134 | 2 | 62 | ACGTtAAGTTCCCGGGcGgCGgCAGATCGTTGGCGGAGTACTTGCTGCCGCGCAGGGG |
| 135-138 | 3 | 62 | ACGTcAAGTTCCCGGGTGGCGGACAGATCGTTGGTGGAGTATACGTGTTGCCGCGCAGGGG |
| 139-145 | 4 | 62 | ACgTcAAGTTCCCgGgTGGtGgCAGATCGTTGGCGGAGTTTACTTGTtGCCGCGCAGGGG |
| 146-153 | 5 | 62 | ACGTaAAgTTCCCGGGCGTGTCGGTCAGATCGTTCAGATCGTTGGTGGAGTTTACTTGTTGCCGCGCAGGGG |
| 154 | 6 | 62 | ACGTCAAGTTCCCGGGTGGCGGTCAGATCGTTGGCGGAGTTTACTTGTTGCCGCGCAGGGG |

| SEQ ID NO: | Genotype | | |
|---|---|---|---|
| 103-154 | cons. | 123 | CCCcaGgTTGGGTGTGCGCgCgaCtaGgAAgaCTTCCgAgcCGgTCgCAaCCtcGtGgaaGg |
| 103-124 | 1 | 123 | CCCCAGgTTGGGTGTGCGCGCGgaCtAGGAAGAAGACTTCCGAGGAAGACTTCGCAACCTCGtGGaaGg |
| 125-134 | 2 | 123 | CCCCAgTTGGGTGTGCGCGCgCGACAAGGAAgaCTTCCgAgCGaTCCAGCCgTGGgAGg |
| 135-138 | 3 | 123 | CCCACGATTGGGTGTGCGCGCGCGACGCGTAAAACTTCTGAACGGTCaCAGCCTCGCGGACGa |
| 139-145 | 4 | 123 | CCCCAGgTTGGGTGTGCGCGCgaCTCGgAAGACTTCGGAGCCTTCGCAACCTCGtGgCAGg |
| 146-153 | 5 | 123 | CCCtaGgTTGGGTGTGCGCGCGCGCGAACTCgGAAGACTTCaGAACGGTCGCAACCCCGTGGgCGG |
| 154 | 6 | 123 | CCCCGGTTGGGTGTGCGGCGCGAGAGAAAGACTTCCGAGCGATCCGAGCCCAGAGGCAGG |

FIGURE 6J-2

| SEQ ID NO: | Genotype | | |
|---|---|---|---|
| 103-154 | cons. | 184 | CGaCAgCCtATcCCcaAgGctCGcCggcccgagGGcaggtcCTGGGCtcagCCcGGgtAcC |
| 103-124 | 1 | 184 | CGaCAaCCTATCCCCAAGGCtCGcCggCCCGAGGGcAGGgCCTGGGCtCAGCCcGGGtACC |
| 125-134 | 2 | 184 | CGCCAGCCCATCCCgAAAAGATCGGCGCtCCACTgGCAAGtCCTGGGGAAaaCCaGGATAtC |
| 135-138 | 3 | 184 | CGACAGCCTATCCCCAAGGCGCGTCGAGCGGAAGGCCGgTCCTgGGCTCAGCCCGGGTACC |
| 139-145 | 4 | 184 | CGtCAgCCTATCCCcAaGGCaCGtCggtccGAGGGcAGtCCTgGGCtCAgCCcGGGTAcC |
| 146-153 | 5 | 184 | CGcCAGCCTATtCCCAAGGcGcGCCAacCCacGGGcCGGTCCTgGGGTCAACCCGGGTACC |
| 154 | 6 | 184 | CGCCAACCTATACCAAAGGCGCGCCAGCCCAGGGcAGGCACTGGGCTCAGCCCGGATACC |

| SEQ ID NO: | Genotype | | |
|---|---|---|---|
| 103-154 | cons. | 245 | CtTGGCCccTcTAtGgcaAtGAgGGCttcGggTGGGCaGGaTGGCTccTgTcCcCCgcGG |
| 103-124 | 1 | 245 | CtTGGCCCCCtCTAtGgCaAtGAgGGGCttgGgTGGGCaGGATGGCTCCTGTCaCCCCgtGG |
| 125-134 | 2 | 245 | CtTGGCCCcCCTgTAtGGgAAtGAGGAGGgcctCGGCTGGCAGgtCGGCTtGCTCCCCCCCGCGG |
| 135-138 | 3 | 245 | CTTGGCCCCCTCTAtGGTAAcGAGAGGCTGCGGGTGGCAGGGtGGCTCCTGTCCTCCCCACGCGG |
| 139-145 | 4 | 245 | CtTGGCCtCTttAcGGcAAtGAggGCtGcGGGGtGGCtGCAggGTGGCTCCTGTCCtGTCccCGcGG |
| 146-153 | 5 | 245 | CTTGGCCccTTTAcGCCAATGAGGGCCTCGgtTGGCAGGGCCTGCTCTCCCcGAGG |
| 154 | 6 | 245 | CTTGGCCTCTTTATGGAAACGAGGGCTGTGGGTGGCAGGTTGGCTCCTGTCCCCCGCGG |

| SEQ ID NO: | Genotype | | |
|---|---|---|---|
| 103-153 | cons. | 306 | cTTctcggCCtagtTGGGGcccActgAcCCCcGGCgtaggTCgCGcAAttTGGGtAagtTC gCGcAAtTGGGtAagGTC |
| 103-124 | 1 | 306 | CTTcTCGGCCTAgtTGGGGCCCCAcaGACCCCCGGCGGtAGGTCGCGtAATtTGGGtAAgTC |
| 125-134 | 2 | 306 | tTCtCgtCCttcctTGGGGCCCCActGACCCCCGGCAtAgaTCgCaActTGGGtAagGTC |
| 135-138 | 3 | 306 | CTCCCGTCCATCTTGGGCCCAAAcGACCCCCGGCGgaGAGTCCGCAATTTGGGTAaAgTC |
| 139-145 | 4 | 306 | CTCtcGgcCGTCTTGGGCccaaATGATCCCGGCGAGtCcCgcAAttTGGGTAAgGTC |
| 146-153 | 5 | 306 | CTCTCGGCCTAatTGGGCCCCAATgACCCCCGGCGaAaaTCGCGAAtTGGGtAAGGTC |
| 154 | 6 | 306 | CTCCCGGCCACATTGGGGCCCAATGACCCCCGGCGTCGATCCGAATTTGGGTAAGGTC |

FIGURE 6J-3

| SEQ ID NO: | Genotype | | |
|---|---|---|---|
| 103-154 | cons. | 367 | ATCGAtACccTcACgTGcgGctTcGCCGAcCTCATGGGgTACaTcCCgcTCgTcGgCgCccC |
| 103-124 | 1 | 367 | ATCGAtACCCTcACaTGCGGCTTcGCCGACCTCATGGGGTACaTtCCGCTCGTCGGcGccC |
| 125-134 | 2 | 367 | ATCGAtACCcTaACgTGcGgtTtGCCGACCTCATGGGgTACaTcCCGTCGTtGGcGccC |
| 135-138 | 3 | 367 | ATCGATACCCTtACgTGcGATTcGCCGACCTCATGGGGTACATCCCGCTCGTcGGCGCTC |
| 139-145 | 4 | 367 | ATCGATACccTgACgTGcGgCTTcGCCGAcCTCATGGGATACATCCCGCTCGTaGGCGCCC |
| 146-153 | 5 | 367 | ATCGAtACCcTaACgTGCGGATTCGCCGAcCTCATGGGTACATCCCGCTCGTAGGCGGCC |
| 154 | 6 | 367 | ATCGATACCCTaACCCTAACGTGTGGGTTCGCCGATCTCATGGGTACATTCCCGTCGTGGGCGCGC |

| SEQ ID NO: | Genotype | | |
|---|---|---|---|
| 103-154 | cons. | 428 | CcgTaGGGgGcGtcGCcaggGCccTgGCgCAtGGcGTcaGggttcTgAgGaGGACGGgTgAA |
| 103-124 | 1 | 428 | CccTaGGgGGcG-GcTGCCAGgGCccTgGCgCATgGCgTCCGgGTtcTGGAgGACGGCGTGAA |
| 125-134 | 2 | 428 | CggTtGGaGGcGTcGCCAGAGCcTgGCaCATgGTGTgAGGgTCTGGAgAGACGGgaTaAA |
| 135-138 | 3 | 428 | CCGTAGGaGGCGTCGCAAGAGCCCTCGCGCATGGCCTgGAGGCGTGAGGCCCTgAAGACGGGATAAA |
| 139-145 | 4 | 428 | CCGTgGGtGGCGTCGCCAGgGCcCTgGCgCATgGCgTcAGGgctgTGGAGGACGGgaTcAA |
| 146-153 | 5 | 428 | CCGTTGGGGGCGTCGCCAAGGGCTCTCgCACAcGGTGTGAGgtTCTTGAGgACGGGTAAA |
| 154 | 6 | 428 | CTTTGGGCGCGGCCGGCTCGCGCTGCGCTGCACATGGCGTGAGGCGCAATCGAGACGGACGGATCAA |

| SEQ ID NO: | Genotype | | |
|---|---|---|---|
| 103-154 | cons. | 489 | cTatgCAAcCaGggAAtTgCCcGgTTgCtCtTTcTcTAtCTTccTccTgcTcTgcTgTCc |
| 103-124 | 1 | 489 | cTAtGCAACaGGgAAtcTgCCcGgTTgCtCtTTgCtCtTTcTcTAtCTTcCtCtTgCttTgCtTGcTgTCc |
| 125-134 | 2 | 489 | tTAtGCAACaGgGAAtTgCCtGGTTgCTCtTTgCTCtTTTcTATcTtTcTgCccTTcTGTCc |
| 135-138 | 3 | 489 | TTTcGCAACaGGGAACTTGCCCGGTTGCCCGgTTGCtCtCCtTTTcTATCTTcTATcTTcTGtTTGcTCTGTTCTCt |
| 139-145 | 4 | 489 | cTAtGCAAcAGGgAAtCTTCCcGGTTgCtCtTTcTcTATcTTcCtTgGCACTtcTcTCG |
| 146-153 | 5 | 489 | cTAtGCAAcAGGGAATtTgCCcGGTTgCtCCCCGGTTgCtCCTATCTTTaTCCTTgCACTTcTCTCg |
| 154 | 6 | 489 | TTATGCAACAGGGAATCTCCCCGgTTgCTCtTTcTcTATcTTcTATCTTCCTTTGGCACTACTCTCG |

FIGURE 6J-4

| SEQ ID NO: | Genotype | | |
|---|---|---|---|
| 103-154 | cons. | 550 | TGcctgaccgtcCCagcttCtgct |
| 103-124 | 1 | 550 | TGtTTgACcatcCCaGctTCcGCt |
| 125-134 | 2 | 550 | TGCatCaCagtgCCaGtgTCtGCt |
| 135-138 | 3 | 550 | TGCtTAaTTCATCCaGCAGCTAGT |
| 139-145 | 4 | 550 | TGCcTgACtgtCCagCgTCgGCc |
| 146-153 | 5 | 550 | TGccTgAccgTCCCggCCtctGCa |
| 154 | 6 | 550 | TGCCTCACAACGCCAGCTTCGGCT |

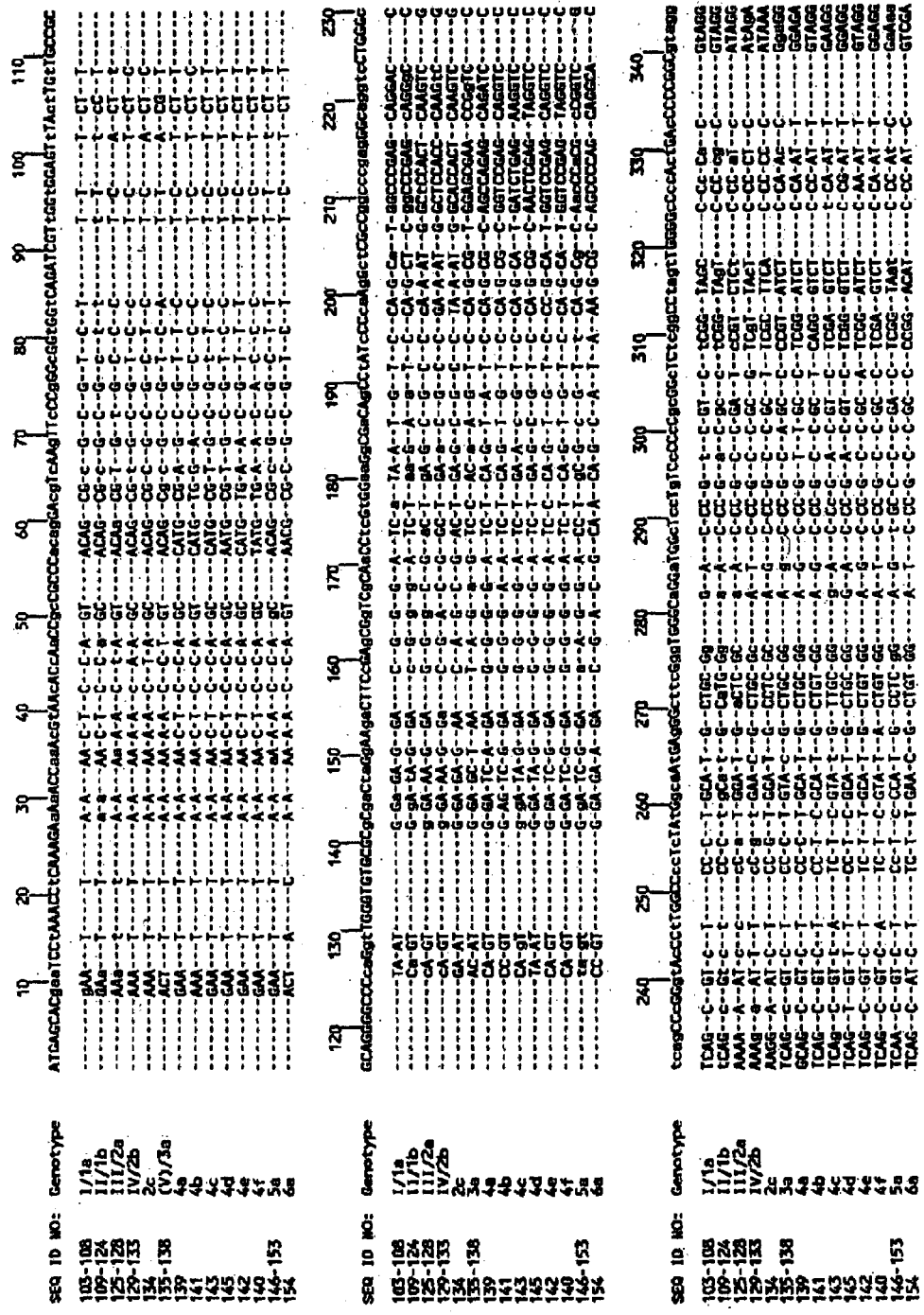

FIGURE 7A-1

| SEQ ID NO: | ISOLATE | | |
|---|---|---|---|
| 156 | US11 | 1 | MSTNPKPQRKTKRNTNRRPQDVKFPGGGQIVGGVYLLPRRGPRLGVRATRKTSERSQPRGR |
| 157 | S14 | 1 | MSTNPKPQRKTKRNTNRRPQDVKFPGGGQIVGGVYLLPRRGPRLGVRATRKTSERSQPRGR |
| 158 | SW1 | 1 | MSTNPKPQRKTKRNTNRRPQDVKFPGGGQIVGGVYLLPRRGPRLGVRATRKTSERSQPRGR |
| 159 | S18 | 1 | MSTNPKPQRKTKRNTNRRPQDVKFPGGGQIVGGVYLLPRRGPRLGVRATRKTSERSQPRGR |
| 160 | DR4 | 1 | MSTNPKPQRKTKRNTNRRPQDVKFPGGGQIVGGVYLLPRRGPRLGVRATRKTSERSQPRGR |
| 155 | DK7 | 1 | MSTNPKPQRKTKRNTNRRPQDVKFPGGGQIVGGVYLLPRRGPRLGVRApRKTSERSQPRGR |

155-160 consensus     MSTNPKPQRKTKRNTNRRPQDVKFPGGGQIVGGVYLLPRRGPRLGVRAtRKTSERSQPRGR

| SEQ ID NO: | ISOLATE | | |
|---|---|---|---|
| 156 | US11 | 62 | RQPIPKARRPEGRTWAQPGYPWPLYGNEGCGWAGWLLSPRGSRPSWGPTDPRRRSRNLGKV |
| 157 | S14 | 62 | RQPIPKARRPEGRTWAQPGYPWPLYGNEGCGWAGWLLSPRGSRPSWGPTDPRRRSRNLGKV |
| 158 | SW1 | 62 | RQPIPKARRPEGRTWAQPGYPWPLYGNEGCGWAGWLLSPRGSRPSWGPTDPRRRSRNLGKV |
| 159 | S18 | 62 | RQPIPKARRPEGRTWAQPGYPWPLYGNEGCGWAGWLLSPRGSRPSWGPTDPRRRSRNLGKV |
| 160 | DR4 | 62 | RQPIPKARRPEGRTWAQPGYPWPLYGNEGCGWAGWLLSPRGSRPSWGPTDPRRRSRNLGKV |
| 155 | DK7 | 62 | RQPIPKARRPEGRTWAQPGYPWPLYGNEGCGWAGWLLSPRGSRPSWGPTDPRRRSRNLGKV |

155-160 consensus     RQPIPKARRPEGRTWAQPGYPWPLYGNEGCGWAGWLLSPRGSRPSWGPTDPRRRSRNLGKV

| SEQ ID NO: | ISOLATE | | |
|---|---|---|---|
| 156 | US11 | 123 | IDTLTCGFADLMGYIPLVGAPLGGAARALAHGVRVLEDGVNYATGNLPGCSFSIFLLALLS |
| 157 | S14 | 123 | IDTLTCGFADLMGYIPLVGAPLGGAARALAHGVRVLEDGVNYATGNLPGCSFSIFLLALLS |
| 158 | SW1 | 123 | IDTLTCGFADLMGYIPLVGAPLGGAARALAHGVRVLEDGVNYATGNLPGCSFSIFLLALLS |
| 159 | S18 | 123 | IDTLTCGFADLMGYIPLVGAPLGGAARALAHGVRVLEDGVNYATGNLPGCSFSIFLLALLS |
| 160 | DR4 | 123 | IDTLTCGFADLMGYIPLVGAPLGGAARALAHGVRVLEDGVNYATGNLPGCSFSIFLLALLS |
| 155 | DK7 | 123 | IDTLTCGFADLMGYIPLVGAPLGGAARALAHGVRVLEDGVNYATGNLPGCSFSIFLLALLS |

155-160 consensus     IDTLTCGFADLMGYIPLVGAPLGGAARALAHGVRVLEDGVNYATGNLPGCSFSIFLLALLS

FIGURE 7A-2

| SEQ ID NO: | ISOLATE | | |
|---|---|---|---|
| 156 | US11 | 184 | CLTVPASA |
| 157 | S14 | 184 | CLTVPASA |
| 158 | SW1 | 184 | CLTVPASA |
| 159 | S18 | 184 | CLTVPASA |
| 160 | DR4 | 184 | CLTVPASA |
| 155 | DK7 | 184 | CLTVPASA |
| 155-160 | consensus | | CLTVPASA |

FIGURE 7B-1

| SEQ ID NO: | ISOLATE | |
|---|---|---|
| 175 | P8 | 1 MSTtPKPQRKTKRNTsRRPQDVKFPGGGQIVGGVYLLPRRGPRLGVRATRKTSERSQPRGR |
| 170 | IND8 | 1 MSTNPKPQRKTKRNTNRRPQDVKFPGGGQIVGGVYLLPRRGPRLGVRATRKTSERSQPRGR |
| 162 | S45 | 1 MSTNPKPQRKTKRNTNRRPQDVKFPGGGQIVGGVYLLPRRGPRLGVRATRKTSERSQPRGR |
| 171 | S9 | 1 MSTNPKPQRqTKRNTNRRPQDVKFPGGGQIVGGVYLLPRRGPRLGVRATRKTSERSQPRGR |
| 163 | D1 | 1 MSTNPKPQRKTKRNTNRRPQDVKFPGGGQIVGGVYLLPRRGPRLGVRATRKTSERSQPRGR |
| 165 | P10 | 1 MSTNPKPQRKTKRNTNRRPQDVKFPGGGQIVGGVYLLPRRGPRLGVRATRKTSERSQPRGR |
| 169 | IND3 | 1 MSTNPKPQRKTKRNTNRRPQDVKFPGGGQIVGGVYLLPRRGPRLGVRATRKTSERSQPRGR |
| 164 | US6 | 1 MSTNPKPQRKTKRNTNRRPQDVKFPGGGQIVGGVYLLPRRGPRLGVRATRKTSERSQPRGR |
| 166 | DK1 | 1 MSTNPKPQRKTKRNTNRRPQDVKFPGGGQIVGGVYLLPRRGPRLGVRATRKTSERSQPRGR |
| 167 | T10 | 1 MSTNPKPQRKTKRNTNRRPQDVKFPGGGQIVGGVYLLPRRGPRLGVRATRKTSERSQPRGR |
| 168 | SW2 | 1 MSTNPKPQRKTKRNTNRRPQDVKFPGGGQIVGGVYLLPRRGPRLGVRATRKTSERSQPRGR |
| 161 | SA10 | 1 MSTNPKPQRKTKRNTNRRPQDVKFPGGGQIVGGVYLLPRRGPRLGVRATRKTSERSQPRGR |
| 174 | HK4 | 1 MSTNPKPQRKTKRNTNRRPQDVKFPGGGQIVGGVYLLPRRGPRLGVRATRKTSERSQPRGR |
| 172 | HK3 | 1 MSTNPKPQRKTKRNTNRRPQDVKFPGGGQIVGGVYLLPRRGPRLGVRATRKTSERSQPRGR |
| 176 | T3 | 1 MSTNPKPQRKTKRNTNRRPQDVKFPGGGQIVGGVYLLPRRGPRLGVRATRKTSERSQPRGR |
| 173 | HK5 | 1 MSTNPKPQRKTKRNTNRRPQDVKFPGGGQIVGGVYLLPRRGPRLGVRATRKTSERSQPRGR |

161-176 consensus   MSTnPKPQRKTKRNTnRRPQDVKFPGGGQIVGGVYLLPRRGPRLGVRATRKTSERSQPRGR

| SEQ ID NO: | ISOLATE | |
|---|---|---|
| 175 | P8 | 62 RQPIPKARRPEGRAWAQPGHPWPLYaNEGLGWAGWLLSPRGSRPSWGPTDPRRRSRNLGKV |
| 170 | IND8 | 62 RQPIPKARRPEGRAWAQPGHPWPLYGNEGLGWAGWLLSPRGSRPSWGPTDPRRRSRNLGKV |
| 162 | S45 | 62 RQPIPKARRPEGRAWAQPGHPWPLYGNEGLGWAGWLLSPRGSRPSWGPTDPRRRSRNLGKV |
| 171 | S9 | 62 RQPIPKARhPEGRAWAQPGYPWPLYGNEGLGWAGWLLSPRGSRPSWGPnDPRRRSRNLGKV |
| 163 | D1 | 62 RQPIPKARRPEGRAWAQPGYPWPLYGNEGLGWAGWLLSPRGSRPSWGPTDPRRRSRNLGKV |
| 165 | P10 | 62 RQPIPKARRPEGRAWAQPGYPWPLYGNEGLGWAGWLLSPRGSRPSWGPTDPRRRSRNLGKV |
| 169 | IND3 | 62 RQPIPKARRPEGRAWAQPGYPWPLYGNEGLGWAGWLLSPRGSRPSWGPTDPRRRSRNLGKV |
| 164 | US6 | 62 RQPIPKARRPEGRAWAQPGYPWPLYGNEGMGWAGWLLSPRGSRPSWGPTDPRRRSRNLGKV |
| 166 | DK1 | 62 RQPIPKARRPBGRAWAQPGYPWPLYGNEGMGWAGWLLSPRGSRPSWGPnDPRRRSRNLGKV |
| 167 | T10 | 62 RQPIPKARQPEGRAWAQPGYPWPLYGNEGMGWAGWLLSPRGSRPSWGPTDPRRRSRNLGKV |
| 168 | SW2 | 62 RQPIPKARQPEGRTWAQPGYPWPLYGNEGMGWAGWLLSPRGSRPSWGPTDPRRRSRNLGKV |
| 161 | SA10 | 62 RQPIPKARQPEGRTWAQPGYPWPLYGNEGlGWAGWLLSPRGSRPSWGPTDPRRRSRNLGKV |
| 174 | HK4 | 62 RQPIPKARQPEGRTWAQPGYPWPLYGNEGMGWAGWLLSPRGSRPNWGPTDPRRRSRNLGKV |
| 172 | HK3 | 62 RQPIPKARRPEGRAWAQPGYPWPLYGdEGMGWAGWLLSPRGSRPNWGPTDPRRRSRNLGKV |
| 176 | T3 | 62 RQPIPKARRPEGRtWAQPGYPWPLYGnEGMGWAGWLLSPhGSRPsWGPtDPRRRSRNLGKV |
| 173 | HK5 | 62 RQPIPKARRPEGRtWAQPGYPWPLYGnEG-GWAGWLLSPrGSRPsWGPtDPRRRSRNLGKV |

161-176 consensus   RQPIPKARrPEGRaWAQPGyPWPLYgnEG-GWAGWLLSPrGSRPsWGPtDPRRRSRNLGKV

FIGURE 7B-2

| SEQ ID NO: | ISOLATE | | |
|---|---|---|---|
| 175 | P8 | 123 | IDTLTCGFADLMGYIPLVGgPLGGvARALAHGVRVvEDGVNYATGNLPGCSFSIFLLALLS |
| 170 | IND8 | 123 | IDTLTCGFADLMGYIPLVGAPLGGAARALAHGVRVLEDGVNYATGNLPGCSFSIFLLALLS |
| 162 | S45 | 123 | IDTLTCGFADLMGYIPLVGAPLGGAARALAHGVRVLEDGVNYATGNLPGCSFSIFLLALLS |
| 171 | S9 | 123 | IDTLTCGFADLMGYIPLVGAPLGGAARALAHGVRVLEDGVNYATGNLPGCSFSIFLLALLS |
| 163 | D1 | 123 | IDTLTCGFADLMGYIPLVGAPLGGAARALAHGVRVLEDGVNYATGNLPGCSFSIFLLALLS |
| 165 | P10 | 123 | IDTLTCGFADLMGYIPLVGAPLGGAARALAHGVRVLEDGVNYATGNLPGCSFSIFLLALLS |
| 169 | IND3 | 123 | IDTLTCGFADLMGYIPLVGAPLGGAARALAHGVRVLEDGVNYATGNLPGCSFSIFLLALLS |
| 164 | US6 | 123 | IDTLTCGFADLMGYIPLVGAPLGGAARALAHGVRVLEDGVNYATGNLPGCSFSIFLLALLS |
| 166 | DK1 | 123 | IDTLTCGFADLMGYIPLVGAPLGGAARALAHGVRVLEDGVNYATGNLPGCSFSIFLLALLS |
| 167 | T10 | 123 | IDTLTCGFADLMGYIPLVGAPLGGAARALAHGVRVLEDGVNYATGNLPGCSFSIFLLALLS |
| 168 | SW2 | 123 | IDTLTCGFADLMGYIPLVGAPLGGAARALAHGVRVLEDGVNYATGNLPGCSFSIFLLALLS |
| 161 | SA10 | 123 | IDTLTCGFADLMGYIPLVGAPLGGVARALAHGVRVLEDGVNYATGNLPGCSFSIFLLALLS |
| 174 | HK4 | 123 | IDTLTCGFADLMGYIPLVGAPLGGVARALAHGVRVvEDGVNYATGNLPGCSFSIFLLALLS |
| 172 | HK3 | 123 | IDTLTCGFADLMGYIPLVGAPLGGVARALAHGVRVLEDGVNYATGNLPGCpFSIFLLALLS |
| 176 | T3 | 123 | IDTLTCGFADLMGYIPLVGAPLGGVARALAHGVRVLEDGVNYATGNLPGCSFSIFLLALLS |
| 173 | HK5 | 123 | IDTLTCGFADLMGYIPLVGAPLGGVARALAHGVRVLEDGVNYATGNiPGCSFSIFLLALLS |

161-176 consensus IDTLTCGFADLMGYIPLVGaPLGGaARALAHGVRVlEDGVNYATGNlPGCsFSIFLLALLS

| SEQ ID NO: | ISOLATE | | |
|---|---|---|---|
| 175 | P8 | 184 | CLTiPASA |
| 170 | IND8 | 184 | CLTvPASA |
| 162 | S45 | 184 | CLTIPASA |
| 171 | S9 | 184 | CLTIPASA |
| 163 | D1 | 184 | CLTIPASA |
| 165 | P10 | 184 | CLTIPASA |
| 169 | IND3 | 184 | CLTIPASA |
| 164 | US6 | 184 | CLTIPASA |
| 166 | DK1 | 184 | CLTIPASA |
| 167 | T10 | 184 | CLTIPASA |
| 168 | SW2 | 184 | CLTIPASA |
| 161 | SA10 | 184 | CLTIPASA |
| 174 | HK4 | 184 | CLTIPASA |
| 172 | HK3 | 184 | CLTtPASA |
| 176 | T3 | 184 | CLTtPvSA |
| 173 | HK5 | 184 | CLTtPASA |

161-176 consensus CLTiPaSA

FIGURE 7C-1

| SEQ ID NO: | ISOLATE | |
|---|---|---|
| 173 | HK5 | 1 MSTNPKPQRKTKRNTNRRPQDVKFPGGGQIVGGVYLLPRRGPRLGVRATRKTSERSQPRGR |
| 176 | T3 | 1 MSTNPKPQRKTKRNTNRRPQDVKFPGGGQIVGGVYLLPRRGPRLGVRATRKTSERSQPRGR |
| 172 | HK3 | 1 MSTNPKPQRKTKRNTNRRPQDVKFPGGGQIVGGVYLLPRRGPRLGVRATRKTSERSQPRGR |
| 174 | HK4 | 1 MSTNPKPQRKTKRNTNRRPQDVKFPGGGQIVGGVYLLPRRGPRLGVRATRKTSERSQPRGR |
| 161 | SA10 | 1 MSTNPKPQRKTKRNTNRRPQDVKFPGGGQIVGGVYLLPRRGPRLGVRATRKTSERSQPRGR |
| 168 | SW2 | 1 MSTNPKPQRKTKRNTNRRPQDVKFPGGGQIVGGVYLLPRRGPRLGVRATRKTSERSQPRGR |
| 167 | T10 | 1 MSTNPKPQRKTKRNTNRRPQDVKFPGGGQIVGGVYLLPRRGPRLGVRATRKTSERSQPRGR |
| 166 | DK1 | 1 MSTNPKPQRKTKRNTNRRPQDVKFPGGGQIVGGVYLLPRRGPRLGVRATRKTSERSQPRGR |
| 164 | US6 | 1 MSTNPKPQRKTKRNTNRRPQDVKFPGGGQIVGGVYLLPRRGPRLGVRATRKTSERSQPRGR |
| 169 | IND3 | 1 MSTNPKPQRKTKRNTNRRPQDVKFPGGGQIVGGVYLLPRRGPRLGVRATRKTSERSQPRGR |
| 165 | P10 | 1 MSTNPKPQRKTKRNTNRRPQDVKFPGGGQIVGGVYLLPRRGPRLGVRATRKTSERSQPRGR |
| 163 | D1 | 1 MSTNPKPQRKTKRNTNRRPQDVKFPGGGQIVGGVYLLPRRGPRLGVRATRKTSERSQPRGR |
| 156 | US11 | 1 MSTNPKPQRKTKRNTNRRPQDVKFPGGGQIVGGVYLLPRRGPRLGVRATRKTSERSQPRGR |
| 157 | S14 | 1 MSTNPKPQRKTKRNTNRRPQDVKFPGGGQIVGGVYLLPRRGPRLGVRATRKTSERSQPRGR |
| 158 | SW1 | 1 MSTNPKPQRKTKRNTNRRPQDVKFPGGGQIVGGVYLLPRRGPRLGVRATRKTSERSQPRGR |
| 159 | S18 | 1 MSTNPKPQRKTKRNTNRRPQDVKFPGGGQIVGGVYLLPRRGPRLGVRATRKTSERSQPRGR |
| 160 | DR4 | 1 MSTNPKPQRKTKRNTNRRPQDVKFPGGGQIVGGVYLLPRRGPRLGVRATRKTSERSQPRGR |
| 155 | DK7 | 1 MSTNPKPQRKTKRNTNRRPQDVKFPGGGQIVGGVYLLPRRGPRLGVRApRKTSERSQPRGR |
| 170 | IND8 | 1 MSTNPKPQRKTKRNTNRRPQDVKFPGGGQIVGGVYLLPRRGPRLGVRATRKTSERSQPRGR |
| 162 | S45 | 1 MSTNPKPQRqTKRNTNRRPQDVKFPGGGQIVGGVYLLPRRGPRLGVRATRKTSERSQPRGR |
| 171 | S9 | 1 MSTNPKPQRKTKRNTsRRPQDVKFPGGGQIVGGVYLLPRRGPRLGVRATRKTSERSQPRGR |
| 175 | P8 | 1 MSTtPKPQRKTKRNTKRNTsRRPQDVKFPGGGQIVGGVYLLPRRGPRLGVRATRKTSERSQPRGR |

155-176 consensus

MSTnPKPQRKTKRNThRRPQDVKFPGGGQIVGGVYLLPRRGPRLGVRATRKTSERSQPRGR

FIGURE 7C-2

| SEQ ID NO: | ISOLATE | | |
|---|---|---|---|
| 173 | HK5 | 62 | RQPIPKARRPEGRtWAQPGYPWPLYGnEGMWAGWLLSPhGSRPsWGPTDPRRRSRNLGKV |
| 176 | T3 | 62 | RQPIPKARRPEGRaWAQPGYPWPLYGdEGMGWAGWLLSPRGSRPNWGPTDPRRRSRNLGKV |
| 172 | HK3 | 62 | RQPIPKARQPEGRTWAQPGYPWPLYGNEGMGWAGWLLSPRGSRPNWGPTDPRRRSRNLGKV |
| 174 | HK4 | 62 | RQPIPKARQPEGRTWAQPGYPWPLYGNEGMGWAGWLLSPRGSRPSWGPTDPRRRSRNLGKV |
| 161 | SA10 | 62 | RQPIPKARQPEGRTWAQPGYPWPLYGNEGlGWAGWLLSPRGSRPSWGPTDPRRRSRNLGKV |
| 168 | SW2 | 62 | RQPIPKARQPEGRAWAQPGYPWPLYGNEGMGWAGWLLSPRGSRPSWGPTDPRRRSRNLGKV |
| 167 | T10 | 62 | RQPIPKARQPEGRAWAQPGYPWPLYGNEGMGWAGWLLSPRGSRPSWGPTDPRRRSRNLGKV |
| 166 | DK1 | 62 | RQPIPKARRPEGRAWAQPGYPWPLYGNEGMGWAGWLLSPRGSRPSWGPTDPRRRSRNLGKV |
| 164 | US6 | 62 | RQPIPKARRPEGRAWAQPGYPWPLYGNEGMGWAGWLLSPRGSRPSWGPmDPRRRSRNLGKV |
| 169 | IND3 | 62 | RQPIPKARRPEGRAWAQPGYPWPLYGNEGMGWAGWLLSPRGSRPSWGPTDPRRRSRNLGKV |
| 165 | P10 | 62 | RQPIPKARRPEGRAWAQPGYPWPLYGNEGLGWAGWLLSPRGSRPSWGPTDPRRRSRNLGKV |
| 163 | D1 | 62 | RQPIPKARRPEGRAWAQPGYPWPLYGNEGLGWAGWLLSPRGSRPSWGPTDPRRRSRNLGKV |
| 156 | US11 | 62 | RQPIPKARRPEGRAWAQPGYPWPLYGNEGLGWAGWLLSPRGSRPSWGPTDPRRRSRNLGKV |
| 157 | S14 | 62 | RQPIPKARRPEGRAWAQPGYPWPLYGNEGCGWAGWLLSPRGSRPSWGPTDPRRRSRNLGKV |
| 158 | SW1 | 62 | RQPIPKARRPBGRTWAQPGYPWPLYGNEGCGWAGWLLSPRGSRPSWGPTDPRRRSRNLGKV |
| 159 | S18 | 62 | RQPIPKARRPEGRTWAQPGYPWPLYGNEGCGWAGWLLSPRGSRPSWGPTDPRRRSRNLGKV |
| 160 | DR4 | 62 | RQPIPKARRPEGRTWAQPGYPWPLYGNEGCGWAGWLLSPRGSRPSWGPTDPRRRSRNLGKV |
| 155 | DK7 | 62 | RQPIPKARRPEGRTWAQPGYPWPLYGNEGLGWAGWLLSPRGSRPSWGPTDPRRRSRNLGKV |
| 170 | IND8 | 62 | RQPIPKARRPEGRAWAQPGHPWPLYGNEGLGWAGWLLSPRGSRPSWGPTDPRRRSRNLGKV |
| 162 | S45 | 62 | RQPIPKARRPEGRAWAQPGHPWPLYGNEGLGWAGWLLSPRGSRPSWGPTDPRRRSRNLGKV |
| 171 | S9 | 62 | RQPIPKARhPEGRAWAQPGYPWPLYGNEGLGWAGWLLSPRGSRPSWGPTDPRRRSRNLGKV |
| 175 | P8 | 62 | RQPIPKARrPEGRAWAQPGhPWPLYaNEGLGWAGWLLSPRGSRPSWGPtDPRRRSRNLGKV |

155-176 consensus     RQPIPKARrPEGRaWAQPGyPWPLYgnEG--GWAGWLLSPrGSRPsWGPtDPRRRSRNLGKV

FIGURE 7C-3

| SEQ ID NO: | ISOLATE | | |
|---|---|---|---|
| 173 | HK5 | 123 | IDTLTCGFADLMGYIPLVGAPLGGVARALAHGVRVLEDGVNYATGNiPGCSFSIFLLALLS |
| 176 | T3 | 123 | IDTLTCGFADLMGYIPLVGAPLGGVARALAHGVRVLEDGVNYATGNLPGCSFSIFLLALLS |
| 172 | HK3 | 123 | IDTLTCGFADLMGYIPLVGAPLGGVARALAHGVRVLEDGVNYATGNLPGCSFSIFLLALLS |
| 174 | HK4 | 123 | IDTLTCGFADLMGYIPLVGAPLGGVARALAHGVRVvEDGVNYATGNLPGCSFSIFLLALLS |
| 161 | SA10 | 123 | IDTLTCGFADLMGYIPLVGAPLGGVARALAHGVRVLEDGVNYATGNLPGCpFSIFLLALLS |
| 168 | SW2 | 123 | IDTLTCGFADLMGYIPLVGAPLGGAARALAHGVRVLEDGVNYATGNLPGCSFSIFLLALLS |
| 167 | T10 | 123 | IDTLTCGFADLMGYIPLVGAPLGGAARALAHGVRVLEDGVNYATGNLPGCSFSIFLLALLS |
| 166 | DK1 | 123 | IDTLTCGFADLMGYIPLVGAPLGGAARALAHGVRVLEDGVNYATGNLPGCSFSIFLLALLS |
| 164 | US6 | 123 | IDTLTCGFADLMGYIPLVGAPLGGAARALAHGVRVLEDGVNYATGNLPGCSFSIFLLALLS |
| 169 | IND3 | 123 | IDTiLTCGFADLMGYIPLVGAPLGGAARALAHGVRVLEDGVNYATGNLPGCSFSIFLLALLS |
| 165 | P10 | 123 | IDTLTCGFADLMGYIPLVGAPLGGAARALAHGVRVLEDGVNYATGNLPGCSFSIFLLALLS |
| 163 | D1 | 123 | IDTLTCGFADLMGYIPLVGAPLGGAARALAHGVRVLEDGVNYATGNLPGCSFSIFLLALLS |
| 156 | US11 | 123 | IDTLTCGFADLMGYIPLVGAPLGGAARALAHGVRVLEDGVNYATGNLPGCSFSIFLLALLS |
| 157 | S14 | 123 | IDTLTCGFADLMGYIPLVGAPLGGAARALAHGVRVLEDGVNYATGNLPGCSFSIFLLALLS |
| 158 | SW1 | 123 | IDTLTCGFADLMGYIPLVGAPLGGAARALAHGVRVLEDGVNYATGNLPGCSFSIFLLALLS |
| 159 | S18 | 123 | IDTLTCGFADLMGYIPLVGAPLGGAARALAHGVRVLEDGVNYATGNLPGCSFSIFLLALLS |
| 160 | DR4 | 123 | IDTLTCGFADLMGYIPLVGAPLGGAARALAHGVRVLEDGVNYATGNLPGCSFSIFLLALLS |
| 155 | DK7 | 123 | IDTLTCGFADLMGYIPLVGAPLGGAARALAHGVRVLEDGVNYATGNLPGCSFSIFLLALLS |
| 170 | IND8 | 123 | IDTLTCGFADLMGYIPLVGAPLGGAARALAHGVRVLEDGVNYATGNLPGCSFSIFLLALLS |
| 162 | S45 | 123 | IDTLTCGFADLMGYIPLVGAPLGGAARALAHGVRVLEDGVNYATGNLPGCSFSIFLLALLS |
| 171 | S9 | 123 | IDTLTCGFADLMGYIPLVGgPLGGvARALAHGVRVvEDGVNYATGNLPGCSFSIFLLALLS |
| 175 | P8 | 123 | IDTLTCGFADLMGYIPLVGgPLGGvARALAHGVRVLEDGVNYATGNLPGCSFSIFLLALLS |

| 155-176 | consensus | | IDTLTCGFADLMGYIPLVGaPLGGaARALAHGVRVlEDGVNYATGNlPGCsFSIFLLALLS |

FIGURE 7C-4

| SEQ ID NO: | ISOLATE | | |
|---|---|---|---|
| 173 | HK5 | 184 | CLTtPvSA |
| 176 | T3 | 184 | CLTiPASA |
| 172 | HK3 | 184 | CLTtPASA |
| 174 | HK4 | 184 | CLTIPASA |
| 161 | SA10 | 184 | CLTIPASA |
| 168 | SW2 | 184 | CLTIPASA |
| 167 | T10 | 184 | CLTIPASA |
| 166 | DK1 | 184 | CLTIPASA |
| 164 | US6 | 184 | CLTIPASA |
| 169 | IND3 | 184 | CLTIPASA |
| 165 | P10 | 184 | CLTIPASA |
| 163 | D1 | 184 | CLTIPASA |
| 156 | US11 | 184 | CLTVPASA |
| 157 | S14 | 184 | CLTVPASA |
| 158 | SW1 | 184 | CLTVPASA |
| 159 | S18 | 184 | CLTVPASA |
| 160 | DR4 | 184 | CLTVPASA |
| 155 | DK7 | 184 | CLTVPASA |
| 170 | IND8 | 184 | CLTVPASA |
| 162 | S45 | 184 | CLTIPASA |
| 171 | S9 | 184 | CLTIPASA |
| 175 | P8 | 184 | CLTIPASA |
| 155-176 | consensus | | CLTiPaSA |

FIGURE 7D

```
SEQ ID NO:   ISOLATE
179          T9        1    MSTNPKPQRKTiRNTNRRPQDVKFPGGGQIVGGVYLLPRRGPRLGVRtTRKTSERSQPRGR
178          US10      1    MSTNPKPQRKTKRNTNRRPQDVKFPGGGQIVGGVYLLPRRGPRLGVRATRKTSERSQPRGR
180          T2        1    MSTiPKPQRKTKRNTNRRPQDVKFPGGGQIVGGVYLLPRRGPRLGVRATRKTSERSQPRGR
177          T4        1    MSTnPKPQRKTKRNTNRRPQDVKFPGGGQIVGGVYLLPRRGPRLGVRaTRKTSERSQPRGR 177-180      consensus       MSTnPKPQRKTKRNTNRRPQDVKFPGGGQIVGGVYLLPRRGPRLGVRaTRKTSERSQPRGR SEQ ID NO:   ISOLATE
179          T9        62   RQPIPKDRRsTGKSWGKPGYPWPLYGNEGLGWAGWLLSPRGSRPSWGPsDPRHRSRNVGKV
178          US10      62   RQPIPKDRRpTGKSWGKPGYPWPLYGNEGLGWAGWLLSPRGSRPSWGPtDPRHRSRNVGKV
180          T2        62   RQPIPKDRRSTGKSWGKPGYPWPLYGNEGLGWAGWLLSPRGSRPSWGPNDPRHRSRNVGKV
177          T4        62   RQPIPKDRRSTGKSWGKPGYPWPLYGNEGLGWAGWLLSPRGSRPSWGPNDPRHRSRNVGKV 177-180      consensus       RQPIPKDRRsTGKSWGKPGYPWPLYGNEGLGWAGWLLSPRGSRPSWGPnDPRHRSRNVGKV SEQ ID NO:   ISOLATE
179          T9        123  IDTLTCGFADLMGYIPVVGAPLGGVARALAHGVRVLEDGVNYATGNLPGCSFSIFLLALLS
178          US10      123  IDTLTCGFADLMGYIPVVGAPLGGVARALAHGVRVLEDGVNYATGNLPGCSFSIFLLALLS
180          T2        123  IDTLTCGFADLMGYIPVVGAPLGGVARALAHGVRVLEDGVNYATGNLPGCSFSIFLLALLS
177          T4        123  IDTLTCsLADLMGYvPVVGgPLGGVARALAHGVRVLEDGVNYATGNLPGCSFSIFLLALLS 177-180      consensus       IDTLTCgfADLMGYiPVVGaPLGGVARALAHGVRVLEDGVNYATGNLPGCSFSIFLLALLS SEQ ID NO:   ISOLATE
179          T9        184  CITTtPaSA
178          US10      184  CITIPVSA
180          T2        184  CITIPVSA
177          T4        184  CITIPVSA 177-180      consensus       CITiPvSA
```

FIGURE 7E

| SEQ ID NO: | ISOLATE | | |
|---|---|---|---|
| 183 | DK11 | 1 | MSTNPKPQRKTKRNTNRRPQDVKFPGGGQIVGGVYLLPRRGPRLGVRtTRKTSERSQPRGR |
| 184 | SW3 | 1 | MSTNPKPQRKTKRNTNRRPQDVKFPGGGQIVGGVYLLPRRGPRLGVRATRKTSERSQPRGR |
| 181 | T8 | 1 | MSTNPKPQRKTKRNTNRRPQDVKFPGGGQIVGGVYLLPRRGPRLGVRATRKTSERSQPRGR |
| 182 | US1 | 1 | MSTNPKPQRKTKRNTNRRPQDVKFPGGGQIVGGVYLLPRRGPRLGVRATRKTSERSQPRGR |
| 185 | DK8 | 1 | MSTNPKPQRKTKRNTNRRPQDVKFPGGGQIVGGVYLLPRRGPRLGVRATRKsSERSQPRGR |

181-185 consensus  MSTNPKPQRKTKRNTNRRPQDVKFPGGGQIVGGVYLLPRRGPRLGVRaTRKtSERSQPRGR

| SEQ ID NO: | ISOLATE | | |
|---|---|---|---|
| 183 | DK11 | 62 | RQPIPKDRRSTGKpWGKPGYPWPLYGNEGCGWAGWLLSPRGSHPNWGPTDPRHkSRNLGKV |
| 184 | SW3 | 62 | RQPIPKDRRSTGKSWGKPGYPWPLYGNEGCGWAGWLLSPRGSHPNWGPTDPRHRSRNLGKV |
| 181 | T8 | 62 | RQPIPKDRRSTGKSWGKPGYPWPLYGNEGCGWAGWLLSPRGSRPTWGPTDPRHRSRNLGKV |
| 182 | US1 | 62 | RQPIPKDRRSTGKSWGKPGYPWPLYGNEGCGWAGWLLSPRGSRPTWGPTDPRHRSRNLGrV |
| 185 | DK8 | 62 | RQPIPKDRRSTGKSWGKPGYPWPLYGNEGCGWAGWLLSPRGSRPTWGPTDPRHRSRNLGKV |

181-185 consensus  RQPIPKDRRSTGKsWGKPGYPWPLYGNEGCGWAGWLLSPRGSrPtWGPTDPRHrSRNLGkV

| SEQ ID NO: | ISOLATE | | |
|---|---|---|---|
| 183 | DK11 | 123 | IDTITCGFADLMGYIPVVGAPVGGVARALAHGVRVLEDGINYATGNLPGCSFSIFLLALLS |
| 184 | SW3 | 123 | IDTITCGFADLMGYIPVVGAPVGGVARALAHGVRVLEDGINYATGNLPGCSFSIFLLALLS |
| 181 | T8 | 123 | IDTITCGFADLMGYIPVVGAPVGGVARALAHGVRVLEDGINYATGNLPGCSFSIFLLALLS |
| 182 | US1 | 123 | IDTITCGFADLMGYIPVVGAPVGGVARALAHGVRVLEDGINYATGNLPGCSFSIFLLALLS |
| 185 | DK8 | 123 | IDTITCGFADLMGYIPVVGAPVGGVARALAHGVRVLEDGINYATGNLPGCSFSIFLLALLS |

181-185 consensus  IDTITCGFADLMGYIPVVGAPVGGVARALAHGVRVLEDGINYATGNLPGCSFSIFLLALLS

| SEQ ID NO: | ISOLATE | | |
|---|---|---|---|
| 183 | DK11 | 184 | CcTVPVSA |
| 184 | SW3 | 184 | CFTVPVSA |
| 181 | T8 | 184 | CFTVPVSA |
| 182 | US1 | 184 | CaTVPVSA |
| 185 | DK8 | 184 | CcTVPVSA |

181-185 consensus  C-TVPVSA

FIGURE 7F-1

| SEQ ID NO: | ISOLATE | | |
|---|---|---|---|
| 183 | DK11 | 1 | MSTNPKPQRKTKRNTNRRPQDVKFPGGGQIVGGVYLLPRRGPRLGVRtTRKTSERSQPRGR |
| 184 | SW3 | 1 | MSTNPKPQRKTKRNTNRRPQDVKFPGGGQIVGGVYLLPRRGPRLGVRATRKTSERSQPRGR |
| 181 | T8 | 1 | MSTNPKPQRKTKRNTNRRPQDVKFPGGGQIVGGVYLLPRRGPRLGVRATRKTSERSQPRGR |
| 182 | US1 | 1 | MSTNPKPQRKTKRNTNRRPQDVKFPGGGQIVGGVYLLPRRGPRLGVRATRKTSERSQPRGR |
| 185 | DK8 | 1 | MSTNPKPQRKTKRNTNRRPQDVKFPGGGQIVGGVYLLPRRGPRLGVRATRKsSERSQPRGR |
| 186 | S83 | 1 | MSTNPKPQRKTKRNTNRRPQDVKFPGGGQIVGGVYLLPRRGPRLGVRATRKTSERSQPRGR |
| 178 | US10 | 1 | MSTNPKPQRKTKRNTNRRPQDVKFPGGGQIVGGVYLLPRRGPRLGVRATRKTSERSQPRGR |
| 180 | T2 | 1 | MSTiPKPQRKTKRNTNRRPQDVKFPGGGQIVGGVYLLPRRGPRLGVRtTRKTSERSQPRGR |
| 179 | T9 | 1 | MSTNPKPQRKTiRNTNRRPQDVKFPGGGQIVGGVYLLPRRGPRLGVRtTRKTSERSQPRGR |
| 177 | T4 | 1 | MSTNPKPQRKTKRNTNRRPQDVKFPGGGQIVGGVYLLPRRGPRLGVRaTRKtSERSQPRGR |

177-186 consensus MSTnPKPQRKTkRNTNRRPQDVKFPGGGQIVGGVYLLPRRGPRLGVRaTRKtSERSQPRGR

| SEQ ID NO: | ISOLATE | | |
|---|---|---|---|
| 183 | DK11 | 62 | RQPIPKDRRsTGKpWGKPGYPWPLYGNEGCGWAGWLLSPRGSHPNWGPTDPRHkSRNLGKV |
| 184 | SW3 | 62 | RQPIPKDRRSTGKSWGKPGYPWPLYGNEGCGWAGWLLSPRGSHPNWGPTDPRHRSRNLGKV |
| 181 | T8 | 62 | RQPIPKDRRSTGKSWGKPGYPWPLYGNEGCGWAGWLLSPRGSRPTWGPTDPRHRSRNLGrV |
| 182 | US1 | 62 | RQPIPKDRRSTGKSWGKPGYPWPLYGNEGCGWAGWLLSPRGSRPTWGPTDPRHRSRNLGKV |
| 185 | DK8 | 62 | RQPIPKDRRSTGKSWGKPGYPWPLYGNEGCGWAGWLLSPRGSRPTWGPTDPRHRSRNLGKV |
| 186 | S83 | 62 | RQPIPKDRRtTGKSWGrPGYPWPLYGNEGLGWAGWLLSPRGSRPSWGPTDPRHkSRNLGKV |
| 178 | US10 | 62 | RQPIPKDRRpTGKSWGKPGYPWPLYGNEGLGWAGWLLSPRGSRPSWGPTDPRHRSRNVGKV |
| 180 | T2 | 62 | .RQPIPKDRRSTGKSWGKPGYPWPLYGNEGLGWAGWLLSPRGSRPSWGPnDPRHRSRNVGKV |
| 179 | T9 | 62 | RQPIPKDRRSTGKSWGKPGYPWPLYGNEGLGWAGWLLSPRGSRPSWGPsDPRHRSRNVGKV |
| 177 | T4 | 62 | RQPIPKDRRSTGKSWGKPGYPWPLYGNEGLGWAGWLLSPRGSRPSWGPnDPRHRSRNVGKV |

177-186 consensus RQPIPKDRRsTGKsWGKPGYPWPLYGNEG-GWAGWLLSPRGSrPsWGPtDPRHrSRNlGkV

FIGURE 7F-2

| SEQ ID NO: | ISOLATE | | |
|---|---|---|---|
| 183 | DK11 | 123 | IDTITCGFADLMGYIPVVGAPVGGVARALAHGVRVLEDGINYATGNLPGCSFSIFLLAALLS |
| 184 | SW3 | 123 | IDTITCGFADLMGYIPVVGAPVGGVARALAHGVRVLEDGINYATGNLPGCSFSIFLLAALLS |
| 181 | T8 | 123 | IDTITCGFADLMGYIPVVGAPVGGVARALAHGVRVLEDGINYATGNLPGCSFSIFLLAALLS |
| 182 | US1 | 123 | IDTITCGFADLMGYIPVVGAPVGGVARALAHGVRVLEDGINYATGNLPGCSFSIFLLAALLS |
| 185 | DK8 | 123 | IDTITCGFADLMGYIPVVGAPVGGVARALAHGVRVLEDGINYATGNLPGCSFSIFLLAALLS |
| 186 | S83 | 123 | IDTITCGFADLMGYIPVVGAPVGGVARALAHGVRVLEDGINYATGNLPGCSFSIFLLAALLS |
| 178 | US10 | 123 | IDTLTCGFADLMGYIPVVGAPVGGVARALAHGVRVLEDGVNYATGNLPGCSFSIFLLAALLS |
| 180 | T2 | 123 | IDTLTCGFADLMGYIPVVGAPVGGVARALAHGVRVLEDGVNYATGNLPGCSFSIFLLAALLS |
| 179 | T9 | 123 | IDTLTCGFADLMGYIPVVGAPLGGVARALAHGVRVLEDGVNYATGNLPGCSFSIFLLAALLS |
| 177 | T4 | 123 | IDTLTCsLADLMGYvPVVGgPLGGVARALAHGVRVLEDGiNYATGNLPGCSFSIFLLAALLS |

177-186 consensus   IDT-TCgfADLMGYiPVVGaPvGGVARALAHGVRVLEDGiNYATGNLPGCSFSIFLLAALLS

| SEQ ID NO: | ISOLATE | | |
|---|---|---|---|
| 183 | DK11 | 184 | CcTVPVSA |
| 184 | SW3 | 184 | CFTVPVSA |
| 181 | T8 | 184 | CFTVPVSA |
| 182 | US1 | 184 | CaTVPVSA |
| 185 | DK8 | 184 | CcTVPVSA |
| 186 | S83 | 184 | CIsVPVSA |
| 178 | US10 | 184 | CITiPVSA |
| 180 | T2 | 184 | CITIPVSA |
| 179 | T9 | 184 | CITtPaSA |
| 177 | T4 | 184 | CITiPvSA |

177-186 consensus   CitvPvSA

FIGURE 7G

| SEQ ID NO: | ISOLATE | | |
|---|---|---|---|
| 189 | S2 | 1 | MSTLPKPQRKTKRNTIRRPQDiKFPGGGQIVGGVYVLPRRGPRLGVRATRKTSERSQPRGR |
| 187 | HK10 | 1 | MSTLPKPQRKTKRNTIRRPQDVKFPGGGQIVGGVYVLPRRGPRLGVRATRKTSERSQPRGR |
| 190 | DK12 | 1 | MSTLPKPQRKTKRNTIRRPQDVKFPGGGQIVGGVYVLPRRGPRLGVRATRKTSERSQPRGR |
| 188 | S52 | 1 | MSTLPKPQRKTKRNTIRRPQDVKFPGGGQIVGGVYVLPRRGPRLGVRATRKTSERSQPRGR |

187-190 consensus  MSTLPKPQRKTKRNTIRRPQDVKFPGGGQIVGGVYVLPRRGPRLGVRATRKTSERSQPRGR

| SEQ ID NO: | ISOLATE | | |
|---|---|---|---|
| 189 | S2 | 62 | RQPIPKARRSEGRSWAQPGYPWPLYGNEGCGWAGWLLSPRGSRPSWGPNDPRRRSRNLGKV |
| 187 | HK10 | 62 | RQPIPKARRSEGRSWAQPGYPWPLYGNEGCGWAGWLLSPRGSRPSWGPNDPRRRSRNLGKV |
| 190 | DK12 | 62 | RQPIPKARRSEGRSWAQPGYPWPLYGNEGCGWAGWLLSPRGSRPSWGPNDPRRRSRNLGKV |
| 188 | S52 | 62 | RQPIPKARRSEGRSWAQPGYPWPLYGNEGCGWAGWLLSPRGSRPSWGPNDPRRRSRNLGKV |

187-190 consensus  RQPIPKARRSEGRSWAQPGYPWPLYGNEGCGWAGWLLSPRGSRPSWGPNDPRRRSRNLGKV

| SEQ ID NO: | ISOLATE | | |
|---|---|---|---|
| 189 | S2 | 123 | IDTLTCGFADLMGYIPLVGAPVGGVARALAHGVRALEDGINFATGNLPGCSFSIFLLALFS |
| 187 | HK10 | 123 | IDTLTCGFADLMGYIPLVGAPVGGVARALAHGVRALEDGINFATGNLPGCSFSIFLLALFS |
| 190 | DK12 | 123 | IDTLTCGFADLMGYIPLVGAPVGGVARALAHGVRALEDGINFATGNLPGCSFSIFLLALFS |
| 188 | S52 | 123 | IDTLTCGFADLMGYIPLVGAPVGGVARALAHGVRALEDGINFATGNLPGCSFSIFLLALFS |

187-190 consensus  IDTLTCGFADLMGYIPLVGAPVGGVARALAHGVRALEDGINFATGNLPGCSFSIFLLALFS

| SEQ ID NO: | ISOLATE | | |
|---|---|---|---|
| 189 | S2 | 184 | CLiHPAAS |
| 187 | HK10 | 184 | CLiHPAAS |
| 190 | DK12 | 184 | CLiHPAAS |
| 188 | S52 | 184 | CLvHPAAS |

187-190 consensus  CLiHPAAS

FIGURE 7H-1

| SEQ ID NO: | ISOLATE | | |
|---|---|---|---|
| 194 | Z5 | 1 | MSTNPKPQRKTKRNTNRRPMDVKFPGGGQIVGGVYLLPRRGPRLGVRAtRKTSERSQPRGR |
| 193 | Z1 | 1 | MSTNPKPQRKTKRNTNRRPMDVKFPGGGQIVGGVYLLPRRGPRLGVRAaRKTSERSQPRGR |
| 192 | Z8 | 1 | MSTNPKPQRKTKRNTNRRPMDVKFPGGGQIVGGVYLLPRRGPRLGVRATRKTSERSQPRGR |
| 195 | Z6 | 1 | MSTNPKPQRKTKRNTNRRPMDVKFPGGGQIVGGVYLLPRRGPRLGVRATRKTSERSQPRGR |
| 196 | Z7 | 1 | MSTNPKPQRKTKRNTNRRPMDVKFPGGGQIVGGVYLLPRRGPRLGVRtTRKTSERSQPRGR |
| 191 | Z4 | 1 | MSTNPKPQRKTKRNTNRRPMDVKFPGGGQIVGGVYLLPRRGPRLGVRATRKTSERSQPRGR |
| 197 | DK13 | 1 | MSTNPKPQRKTKRNTNRRPMDVKFPGGGQIVGGVYLLPRRGPRLGVRATRKTSERSQPRGR |

191-197 consensus   MSTNPKPQRKTKRNTNRRPMDVKFPGGGQIVGGVYLLPRRGPRLGVRAtRKTSERSQPRGR

| SEQ ID NO: | ISOLATE | | |
|---|---|---|---|
| 194 | Z5 | 62 | RQPIPqARRSEGRSWAQPGYPWPLYGNEGCGWAGWLLSPRGSRPSWGqNDPRRRSRNLGKV |
| 193 | Z1 | 62 | RQPIPKARRSEGRSWAQPGYPWPLYGNEGCGWAGWLLSPRGSRPSWGPNDPRRRSRNLGKV |
| 192 | Z8 | 62 | RQPIPKARRSEGRSWAQPGYPWPLYGNEGCGWAGWLLSPRGSRPSWGPNDPRRRSRNLGKV |
| 195 | Z6 | 62 | RQPIPKARRSEGRSWAQPGYPWPLYGNEGCGWAGWLLSPRGSRPSWGPNDPRRRSRNLGKV |
| 196 | Z7 | 62 | RQPIPKARRSEGRSWAQPGYPWPLYGNEGCGWAGWLLSPRGSRPSWGPNDPRRRSRNLGKV |
| 191 | Z4 | 62 | RQPIPKARQpEGRSWAQPGYPWPLYGNEGCGWAGWLLSPRGSRPSWGPNDPRRRSRNLGKV |
| 197 | DK13 | 62 | RQPIPKARQlEGRSWAQPGYPWPLYGNEGCGWAGWLLSPRGSRPSWGPNDPRRRSRNLGKV |

191-197 consensus   RQPIPKARrsEGRSWAQPGYPWPLYGNEGCGWAGWLLSPRGSRPSWGpNDPRRRSRNLGKV

FIGURE 7H-2

```
SEQ ID NO:   ISOLATE
194          Z5       123 IDTLTCGFADLMGYIPLVGAPVGGVARALAHGVRALEDGINYATGNLPGCSFSIFLLALfS
193          Z1       123 IDTLTCGFADLMGYIPLVGAPVGGVARALAHGVRAVEDGINYATGNLPGCSFSIFLLALLS
192          Z8       123 IDTLTCGFADLMGYIPLVGAPVGGVARALAHGVRAVEDGINYATGNLPGCSFSIFLLALLS
195          Z6       123 IDTLTCGFADLMGYIPLVGAPVGGVARALAHGVRAVEDGINYATGNLPGCSFSIFLLALLS
196          Z7       123 IDTLTCGFADLMGYIPLVGAPVGGVARALAHGVRALEDGINYATGNLPGCSFSIFLLALLS
191          Z4       123 IDTLTCGFADLMGYIPiVGAPVGGVARALAHGVRAvEDGINYATGNLPGCSFSIFLLALLS
197          DK13     123 IDTLTCGFADLMGYIPvVGAPVGGVARALAHGVRllEDGvNYATGNLPGCSFSIFLLALLS 191-197    consensus      IDTLTCGFADLMGYIPlVGAPVGGVARALAHGVRavEDGiNYATGNLPGCSFSIFLLAL1S SEQ ID NO:   ISOLATE
194          Z5       184 CLTTPASA
193          Z1       184 CLTTPASA
192          Z8       184 CLTVPASA
195          Z6       184 CLTVPtSA
196          Z7       184 CLTVPASA
191          Z4       184 CLTVPASA
197          DK13     184 CLTVPASA 191-197    consensus      CLTvPaSA
```

FIGURE 7I-1

| SEQ ID NO: | ISOLATE | | |
|---|---|---|---|
| 205 | SA11 | 1 | MSTNPKPQRKTKRNTNRRPQDVKFPGGGQIVGGVYLLPRRGPRLGVRATRKTSERSQPRGR |
| 202 | SA3 | 1 | MSTNPKPQRKTKRNTNRRPQDVKFPGGGQIVGGVYLLPRRGPRLGVRATRKTSERSQPRGR |
| 198 | SA4 | 1 | MSTNPKPQRKTKRNTNRRPQDVKFPGGGQIVGGVYLLPRRGPRLGVRATRKTSERSQPRGR |
| 199 | SA5 | 1 | MSTNPKPQRKTKRNTNRRPQDVKFPGGGQIVGGVYLLPRRGPRLGVRATRKTSERSQPRGR |
| 200 | SA7 | 1 | MSTNPKPQRKTKRNTNRRPQDVKFPGGGQIVGGVYLLPRRGPRLGVRATRKTSERSQPRGR |
| 203 | SA13 | 1 | MSTNPKPQRKTKRNTNRRPQDVKFPGGGQIVGGVYLLPRRGPRLGVRATRKTSERSQPRGR |
| 201 | SA1 | 1 | MSTNPKPQRKTKRNTN1RPQDVKFPGGGQIVGGVYLLPRRGPRLGVRATRKTSERSQPRGR |
| 204 | SA6 | 1 | MSTNPKPQRKTqRNTNrRPQDVKFPGGGQIVGGVYLLPRRGPRmGVRATRKTSERSQPRGR |
| 198-205 | consensus | | MSTNPKPQRKTkRNTNrRPQDVKFPGGGQIVGGVYLLPRRGPRLGVRATRKTSERSQPRGR |

| SEQ ID NO: | ISOLATE | | |
|---|---|---|---|
| 205 | SA11 | 62 | RQPIPKARQPTGRSWGQPGYPWPfYANEGLgWAGWLLSPRGSRPnWGPNDPRRrSRNLGKV |
| 202 | SA3 | 62 | RQPIPKARQPTGRSWGQPGYPWPLYANEGLGWAGWLLSPRGSRPNWGPNDPRRKSRNLGKV |
| 198 | SA4 | 62 | RQPIPKARQPTGRSWGQPGYPWPLYANEGLeWAGWLLSPRGSRPsWGPNDPRRKSRNLGKV |
| 199 | SA5 | 62 | RQPIPKARQPTGRSWGQPGYPWPLYANEGLGWAGWLLSPRGSRPNWGPNDPRRKSRNLGKV |
| 200 | SA7 | 62 | RQPIPKARQPTGRSWGQPGYPWPLYANEGLGWAGWLLSPRGSRPNWGPNDPRRKSRNLGKV |
| 203 | SA13 | 62 | RQPIPKARQPTGRSWGQPGYPWPLYANEGLGWAGWLLSPRGSRPNWGPNDPRRKSRNLGKV |
| 201 | SA1 | 62 | RQPIPKARQPTGRSWGQPGYPWPLYANEGLGWAGWLLSPRGSRPNWGPNDPRRKSRNLGKV |
| 204 | SA6 | 62 | RQPIPKARQsaGRSWGQPGYPWPLYANEGLGWAGWLLSPRGSRPNWGPNDPRRKSRNLGKV |
| 198-205 | consensus | | RQPIPKARQptGRSWGQPGYPWPlYANEGLGWAGWLLSPRGSRPnWGPNDPRRkSRNLGKV |

FIGURE 71-2

| SEQ ID NO: | ISOLATE | | |
|---|---|---|---|
| 205 | SA11 | 123 | IDTLTCGFADLMGYIPLVGGPVGGVARALAHGVRaLEDGVNYATGNLPGCSFPSIFILALLS |
| 202 | SA3 | 123 | IDTLTCGFADLMGYIPLVGGPVGGVARALAHGVRVLEDGVNYATGNLPGCSFPSIFILALLS |
| 198 | SA4 | 123 | IDTLTCGFADLMGYIPLVGGPVGGVARALAHGVRVLEDGVNYATGNLPGCSFSIFILALLS |
| 199 | SA5 | 123 | IDTLTCGFADLMGYIPLVGGPVGGVARALAHGVRVLEDGVNYATGNLPGCSFSIFILALLS |
| 200 | SA7 | 123 | IDTLTCGFADLMGYIPLVGGPVGGVARALAHGVRVLEDGVNYATGNLPGCSFSIFILALLS |
| 203 | SA13 | 123 | IDTLTCGFADLMGYIPLVGGPVGGVARALAHGVRVLEDGVNYATGNLPGCSFSIFILALLS |
| 201 | SA1 | 123 | IDTLTCGFADLMGYIPLVGGPVGGVARALAHGVRVLEDGVNYATGNLPGCSFSIFILALLS |
| 204 | SA6 | 123 | IDTLTCGFADLMGYIPLVGGPVGGVARALAHGVRvLEDGVNYATGNLPGCSFSIFvLALLS |
| 198-205 | consensus | | IDTLTCGFADLMGYIPLVGGPVGGVARALAHGVRvLEDGVNYATGNLPGCSFSIFiLALLS |

| SEQ ID NO: | ISOLATE | | |
|---|---|---|---|
| 205 | SA11 | 184 | CLTVPAtA |
| 202 | SA3 | 184 | CLTVPASA |
| 198 | SA4 | 184 | CLTVPASA |
| 199 | SA5 | 184 | CLTVPASA |
| 200 | SA7 | 184 | CLTVPASA |
| 203 | SA13 | 184 | CLTVPtSA |
| 201 | SA1 | 184 | CLiiPASA |
| 204 | SA6 | 184 | CLtvPASA |
| 198-205 | consensus | | CLtvPasA |

FIGURE 7J

| SEQ ID NO: 155-206 | Genotype cons. | 1 | MSThPKPQRKTKRNThrRPqDvKFPGGGQIVGGVYLLPRRGPRLGVRatRKtSERSQPRGRRQPIPkaRrpeGrsWaqPGyPWPlYgmRGcgWAGW |
|---|---|---|---|
| 155-176 | type 1 | | MSThPKPQRKTKRNThRRPQDVKFPGGGQIVGGVYLLPRRGPRLGVRALRKTSERSQPRGRRQPIPKARrPEGRaWAQPGyPWPLYgnRG-GWAGW |
| 177-186 | type 2 | | MSThPKPQRKTKRNNRRPQDVKFPGGGQIVGGVYLLPRRGPRLGVRaTRKTSERSQPRGRRQPIPKDRRsTGKWGKPGYPWPLYGNRGlGWAGW |
| 187-190 | type 3 | | MSTLPKPQRKTKSNTLRRPQDVKFPGGGQIVGGVYVLPRRGPRLGVRATRKTSERSQPRGRRQPIPKAARSEGRSWAQPGYPWPLYGNRGCGWAGW |
| 191-197 | type 4 | | MSTNPKPQRKTKRNTNRRPMDVKFPGGGQIVGGVYLLPRRGPRLGVRatRKTSERSQPRGRRQPIPKARrsEGRsWAQPGYPWPLYGnRGCGWAGW |
| 198-205 | type 5 | | MSTNPKPQRKTKRNTNrRPQDVKFPGGGQIVGGVYLLPRRGPRLGVRATRKTSERSQPRGRRQPIPKARQptGRsWGQPGYPWPlYANEGLgWAGW |
| 206 | type 6 | | MSTLPKPQRKTKRNTNRRPTDVKFPGGGQIVGGVYLLPRRGPRLGVRATRKTSERSQPRGRRQPIPKAaRPQGRHWAQPGYPWPLYGNEGCGWAGW |

| SEQ ID NO: 155-206 | Genotype cons. | 97 | LLSPrGSrPsWGptDPRrrSRNlGKVIDTlTCgfADLMGYiPlVGaPlGVArALAHGVRvlEDGvNyATGNlPCCsFSIFlLALLSCltvPasa |
|---|---|---|---|
| 155-176 | type 1 | | LLSPrGSRPsWQPtDPRRRSRNLGKVIDTLTCgfADLMGYIPlVGaPLGGaARRALAHGVRVlEDGVNYATGNlPCCsFSIFlLALLSCLTiPaSA |
| 177-186 | type 2 | | LLSPRGSrPsWgPtDPRHlrSRNlGKVIDTlTCgfADLMGYiPVVGaPvGGVARALAHGVRVlEDGlNYATGNLPGCSFSIFlLALLSCltvPvGA |
| 187-190 | type 3 | | LLSPRGSRPSWGpNDPRRRSRNlGKVIDTlLTCgFADLMGYiPlVGaPVGGaPVGGVARALAHGVRALAHGVRaVEDGlNYATGNLPGCSFSIFLLALFSCLiHPAAS |
| 191-197 | type 4 | | LLSPRGSRPSWGpAlDPRrRSRNlGKVIDTlLTCgFADLMGYiPlVGaPVGGPVGGVARAPRALAHGVRavEDGlNYATGNLPGCSFSIFLLALLSCLTvAPaSA |
| 198-205 | type 5 | | LLSPRGSRPnWGPnDPRDPrkSRNlGKVIDTlLTCgFADLMGYIPlVNGGPVGGPVGGVARAPRALAHGVRvLEDGVNYATGNLPGCSFSIFLLALLSCltvPaSA |
| 206 | type 6 | | LLSPRGSSRPEWGPRDPRRRSRNlGPNDPRRRSRNlGKVIDTlLTCgFADLMGYIPVVGAPLGGVAAALAHGVRAlEDGlNYATGNLPGCSFSIFLLALLSCLTTPASA |

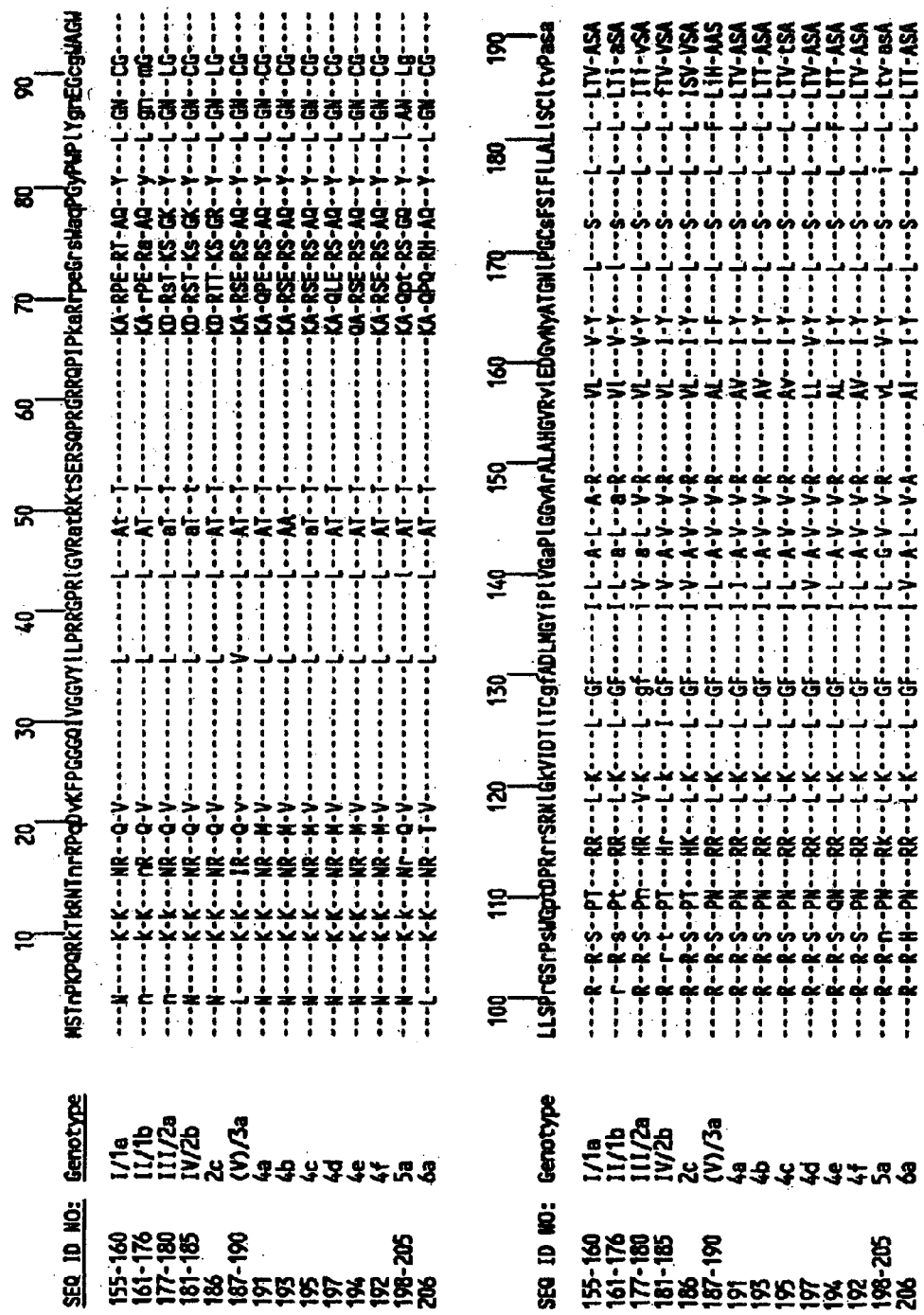

SEQUENCE LISTING

<160> NUMBER OF SEQ ID NOS: 274

<210> SEQ ID NO 1
<211> LENGTH: 576
<212> TYPE: DNA
<213> ORGANISM: Homo sapiens
<220> FEATURE:
<223> OTHER INFORMATION: Individual Isolate: DK7

<400> SEQUENCE: 1
taccaagtgc gcaactccac ggggctttac catgtcacca atgattgccc taactcgagt 60
atcgtgtacg aggcggccga tgccatcctg cacactccgg ggtgtgtccc ttgcgttcgc 120
gagggtaacg tctcgaggtg ttgggtggcg atgaccccca cggtggccac cagggatggc 180
aaactcccca cagcgcagct tcgacgtcac atcgatctgc tcgtcgggag tgccaccctc 240
tgttcggccc tctacgtggg ggacctgtgc gggtctgtct ttcttgtcgg tcaactgttt 300
accttctctc ccaggcgcca ctggacgacg caaggctgca attgttctat ctatcctggc 360
catataacgg gtcaccgcat ggcgtgggat atgatgatga actggtcccc taccacggcg 420
ttggtagtag ctcagctgct ccggatcccg caagccatct tggacatgat cgctggtgct 480
cactggggag tcctggcggg catagcgtat ttttccatgg tggggaactg ggcgaaggtc 540
ctggtagtgc tgctgctatt tgccggcgtc gacgcg 576

<210> SEQ ID NO 2
<211> LENGTH: 576
<212> TYPE: DNA
<213> ORGANISM: Homo sapiens
<220> FEATURE:
<223> OTHER INFORMATION: Individual Isolate: DK9

<400> SEQUENCE: 2
taccaagtac gcaactcctc gggcctctac catgtcacca atgattgccc taactcgagt 60
attgtgtacg aggcggccga tgccatcctg cattctccag ggtgtgtccc ttgcgttcgc 120
gagggtaacg cctcgaaatg ttgggtggcg gtggccccca cggtggccac cagggacggc 180
aagctccccg caacgcagct tcgacgtcac atcgatctgc ttgtcgggag cgccaccctc 240
tgctcggccc tctatgtggg ggacttgtgc gggtctgtct tccttgtcgg ccaactgttc 300
accttctccc ccagacgcca ctggacaacg caagactgca actgttctat ctaccccggc 360
catattacgg gtcatcgcat ggcgtgggat atgatgatga actggtcccc tacagcagcg 420
ctggtaatgg cgcagctgct caggatcccg caggccatct tggacatgat cgctggtgcc 480

```
cactggggag tcctagcggg catagcgtat ttctccatgg tggggaactg ggcgaaggtc    540
gtggtggtac tgttgctgtt taccggcgtc gatgcg                              576

<210> SEQ ID NO 3
<211> LENGTH: 576
<212> TYPE: DNA
<213> ORGANISM: Homo sapiens
<220> FEATURE:
<223> OTHER INFORMATION: Individual Isolate: DR1

<400> SEQUENCE: 3
caccaagtgc gcaactctac agggctttac catgtcacca atgattgccc taattcgagt    60
attgtgtacg aggcggccga tgccatcctg cacgcgccgg ggtgtgtccc ttgcgttcgc    120
gagggtaacg cctcgaggtg ttgggtggcg gtgaccccca cggtggccac cagggacggc    180
aaactcccca caacgcagct tcgacgtcac atcgacctgc ttgtcgggag cgccaccctc    240
tgctcggccc tctacgtggg ggacctgtgc gggtctgtct tccttgtcgg tcaactgttc    300 acctttctc ccaggcgcca ctggacaacg caagactgca attgttctat ctatcccggc    360
catataacgg gacaccgtat ggcatgggat atgatgatga actggtcccc tacgacagcg    420
ctggtaatgg ctcagctgct ccggatccca caagccatct tggacatgat cgctggagcc    480
cactggggag tcctagcggg catagcgtat ttctccatgg tggggaactg ggcgaaggtc    540
gtggtagtgc tgttgctgtt tgccggcgtt gatgcg                              576

<210> SEQ ID NO 4
<211> LENGTH: 576
<212> TYPE: DNA
<213> ORGANISM: Homo sapiens
<220> FEATURE:
<223> OTHER INFORMATION: Individual Isolate: DR4

<400> SEQUENCE: 4
caccaagtgc gcaactctac agggctttac catgtcacca atgattgccc taattcgagt    60
attgtgtacg aggcggccga tgccatcctg cacacgccgg ggtgtgtccc ttgcgttcgc    120
gagggtaaca cctcgaggtg ttgggtggcg gtgaccccca cggtggccac cagggacggc    180
aaactcccca caacgcagct ccgacgtcac atcgacctgc ttgtcgggag cgccaccctc    240
tgctcggccc tctacgtggg ggacttgtgc gggtctgtct tccttgtcgg tcaactgttc    300
accttctctc ccaggcacca ctggacaacg caagactgca attgttccat ctatcccggc    360
catataacgg gccaccgcat ggcgtgggat atgatgatga actggtcccc tacgacagcg    420
ctggtagtag ctcagctgct ccggatccca caagccatct tggacatgat cgctggtgcc    480
cactggggag tcctagcggg catagcgtat ttctccatgg tggggaactg ggcgaaggtc    540
ctggtagtgc tgttgctgtt tgccggcgtt gatgcg                              576

<210> SEQ ID NO 5
<211> LENGTH: 576
<212> TYPE: DNA
<213> ORGANISM: Homo sapiens
<220> FEATURE:
<223> OTHER INFORMATION: Individual Isolate:  S14

<400> SEQUENCE: 5
taccaagtgc gcaactccac ggggctttac catgttacca atgattgccc taactcgagt    60
attgtgtacg agacagctga tgctatccta cacgctccgg gatgtgtccc ttgcgttcgt    120
```

```
gagggtaaca cctcgaggtg ttgggtggcg atgaccccca cggtggccac cagggacggc    180
aaactccccg caacgcagct tcgacgttac atcgatctgc ttgtcgggag cgccaccctc    240
tgttcggccc tctacgtggg ggacttgtgc gggtctgtct ttcttgtcgg tcagctgttt    300
accttctctc ccaggcgcct ctggacgacg caagactgca attgttctat ctatcccggc    360
catataacgg gtcatcgcat ggcatgggat atgatgatga actggtcccc tacgacggca    420
ctggtagtag ctcagctgct ccggatccca caagccatct tggatatgat cgctggtgct    480
cactggggag tcctagcggg catagcgtat ttctccatgg tgggaaactg ggcgaaggtc    540
ctagtggtgc tgctgctatt cgccggcgtt gacgcg                              576

<210> SEQ ID NO 6
<211> LENGTH: 576
<212> TYPE: DNA
<213> ORGANISM: Homo sapiens
<220> FEATURE:
<223> OTHER INFORMATION: Individual Isolate: S18

<400> SEQUENCE: 6
taccaagtac gcaactccac gggcctttac catgtcacca atgactgccc taactcgagc     60
attgtgtacg agacggccga taccatccta cactctccgg ggtgtgtccc ttgcgttcgc    120
gagggtaacg cctcgagatg ttgggtgccg gtggcccccca cagttgccac cagggacggc    180
aaactccccg caacgcagct tcgacgtcac atcgatctgc ttgttgggag cgccaccctc    240
tgctcggccc tctatgtggg ggacctgtgc gggtctgtct ttcttgtcag ccagctgttc    300
actatctccc ccaggcgcca ctggacaacg caagactgca actgttctat ctaccccggc    360
catataacgg gtcaccgtat ggcatgggat atgatgatga actggtcccc tacaacggcg    420
ttggtaatag ctcagctgct cagggtcccg caagccgtct tggacatgat cgctggtgcc    480
cactggggag tcctagcggg catagcgtat ttctccatgg cggggaactg ggcgaaggtc    540
ctgctagtgc tgttgctgtt tgccggcgtc gatgcg                              576

<210> SEQ ID NO 7
<211> LENGTH: 576
<212> TYPE: DNA
<213> ORGANISM: Homo sapiens
<220> FEATURE:
<223> OTHER INFORMATION: Individual Isolate: SW1

<400> SEQUENCE: 7
taccaagtac gcaactcctc gggcctttac catgtcacca atgattgccc taactcgagt     60
attgtgtacg agacggccga tgccattcta cactctccag ggtgtgtccc ttgcgttcgc    120
gaggatggcg ccccgaagtg ttgggtggcg gtggcccccca cagtcgccac tagggacggc    180
aaactccctg caacgcagct tcgacgtcac atcgatctgc ttgtcggaag cgccaccctc    240
tgctcggccc tctacgtggg ggacttgtgc gggtctgtct ttctcgtcag tcaactgttc    300
acgttctccc ccaggcgcca ctggacaacg caagactgta actgttctat ctatcccggc    360
cacataacgg gtcaccgcat ggcatgggat atgatgatga actggtcccc cacaacagcg    420
ctggtagtag ctcagctgct caggatcccg caagccgtct tggacatgat cgctggtgcc    480
cactggggag tcctagcggg catagcgtat ttctccatgg tgggaaactg ggcgaaggtc    540
ctgatagtgc tgttgctgtt ttccggcgtc gatgcg                              576

<210> SEQ ID NO 8
<211> LENGTH: 576
```

```
<212> TYPE: DNA
<213> ORGANISM: Homo sapiens
<220> FEATURE:
<223> OTHER INFORMATION: Individual Isolate:  US11

<400> SEQUENCE: 8
taccaagtac gcaactccac ggggctttac catgtcacca atgattgccc taactcgagt      60
attgtgtacg aggcggccga tgccatcctg cacactccgg ggtgtgttcc ttgcgttcgc     120
gagggtaacg cttcgaggtg ttgggtggcg atgaccccca cggtggccac cagggacggc     180
aaactcccca caacgcaact tcgacgtcac atcgatctgc ttgtcgggag cgccaccctc     240
tgttcggccc tctacgtggg ggacctgtgc gggtctgtct ttcttgtcgg tcaactgttt     300
accttctctc ccagacgcca ctggacgacg cagggctgca attgttctat ctatcccggc     360
catataacgg gtcaccgcat ggcatgggat atgatgatga actggtcccc tacggcggcg     420
ttggtggtag ctcagctgct ccggatccca caagccatct tggacatgat cgctggtgct     480
cactggggag tcctagcggg catagcgtat ttctccatgg tggggaactg ggcgaaggtc     540
ctggtagtgc tgctgctatt tgccggcgtc gacgcg                               576

<210> SEQ ID NO 9
<211> LENGTH: 576
<212> TYPE: DNA
<213> ORGANISM: Homo sapiens
<220> FEATURE:
<223> OTHER INFORMATION: Individual Isolate:  D1

<400> SEQUENCE: 9
tatgaagtgc gcaacgtgtc cggggtgtac catgtcacga acgactgttc caactcgagc      60
attgtgtatg agacagcgga catgatcatg cacacccccg ggtgcgtgcc ctgcgttcgg     120
gaggacaact cctctcgctg ctgggtagcg ctcaccccca cgctcgcggc taggaatggc     180
aacgtcccca ctacggcgat acgacgccac gtcgatttgc tcgttggggc ggctgctttc     240
tgctccgcca tgtacgtggg ggatctctgc ggatctgttt cctcatctc ccagctgttc      300 accctctcgc ctcgccggca tgagacggta caggagtgta attgctcaat ctatcccggc     360
cacgtgacag gtcaccgtat ggcttgggat atgatgatga actggtcacc tacaacagcc     420
ttagtggtat cgcagttact ccggatccca caagctgtca tggacatggt ggcgggggcc     480
cactgggggg tcctggcggg cctcgcctac tattccatgg tggggaactg ggctaaggtt     540
ttgattgtga tgctactctt tgctggcgtt gacggc                               576

<210> SEQ ID NO 10
<211> LENGTH: 576
<212> TYPE: DNA
<213> ORGANISM: Homo sapiens
<220> FEATURE:
<223> OTHER INFORMATION: Individual Isolate:  D3

<400> SEQUENCE: 10
tatgaagtgc gcaacgtgtc cggggtgtac caagtcacca atgactgttc caactcgagc      60
atcgtgtatg agacagcgga catgatcatg cacacccccg ggtgcgtgcc ctgcgttcgg     120
gaggacaact cctctcgctg ctgggtagcg ctcaccccca cgctcgcggc taggaatagc     180
agcgtcccca ctacgacaat acgacgccac gtcgatttgc tcgttggggc ggctgctttc     240
tgctccgcca tgtacgtggg ggatctttgc ggatctgttt cctcgtctc ccagctgttc      300 accttctcgc ctcgccggca tgagacagta caggaatgta actgctcaat ctatcccggc     360
```

```
cacgtgacag gtcaccgcat ggcttgggat atgatgatga actggtcgcc tacagcagcc    420
ctagtggtat cgcagttact ccggatccca caagctgtcg tggacatggt ggcgggggcc    480 cactggggggg tcctggcggg cctcgcctac tattccatgg tggggaactg ggctaaggtt   540
ttgattgtga tgctactctt tgctggcgtc gacggc                              576

<210> SEQ ID NO 11
<211> LENGTH: 576
<212> TYPE: DNA
<213> ORGANISM: Homo sapiens
<220> FEATURE:
<223> OTHER INFORMATION: Individual Isolate:  DK1

<400> SEQUENCE: 11
tatgaagtgc gcaacgtgtc cggggtgtac cacgtcacaa acgactgctc caactcaagc    60
atcgtgtatg aggcagtgga cgtgatcatg cataccccag ggtgcgtgcc ctgcgttcgg    120
gagaacaacc actcccgttg ctgggtagcg ctcacccccca cgctcgcggc caggaacgcc   180
agcatcccca ctacgacaat acgacgccat gtcgatttgc tcgttggggc ggctgctttc    240
tgctccgcta tgtacgtggg ggacctctgc ggatccgttt cctcgtctc tcagctgttc     300 accttttcac ctcgccggca tgagacagca caggactgca actgctcaat ctatcccggc    360
cacgtttcag gtcaccgcat ggcttgggat atgatgatga actggtcacc tacaacagcc    420
ctagtgctat cgcagttact ccgaatccca caagctgtcg tggacatggt ggcgggggcc    480
cactggggag tcctggcggg cctcgcctac tactccatgg cggggaactg ggccaaggtt    540
ttaattgtgt tgctactctt tgccggcgtt gatggg                              576

<210> SEQ ID NO 12
<211> LENGTH: 576
<212> TYPE: DNA
<213> ORGANISM: Homo sapiens
<220> FEATURE:
<223> OTHER INFORMATION: Individual Isolate:  HK3

<400> SEQUENCE: 12
tatgaagtgc gcaacgtgtc cgggatatac catgtcacga acgactgctc caactcaagc    60
gtcgtgtatg agacagcaga catgatcatg cataccccctg gatgcgtgcc ctgcgtacgg   120
gagaacaact cctcccgctg ttgggtagcg ctcactccca cgctcgcggc caggaacgtc    180
agcgtcccca ccacgacaat acgacgtcac gtcgacttgc tcgttggggc ggctgccttc    240
tgctccgcta tgtacgtggg ggatctctgc ggatctgttt ccttgtctc ccagctgttc     300 accttctcgc ctcgccgaca cgagacagta caggactgca actgctcact ctatcccggc    360
cacgtatcag gtcaccgcat ggcttgggat atgatgatga actggtcccc tacagcagcc    420
ctagtggtgt cgcaattact ccggatcccg caagctgtcg tggacatggt ggcgggggcc    480
cactggggag tcctagcggg ccttgcctac tattccatgg tgggaaactg ggctaaggtt    540
ttgattgtga tgctacttttt tgccggcgtt gatggg                             576

<210> SEQ ID NO 13
<211> LENGTH: 576
<212> TYPE: DNA
<213> ORGANISM: Homo sapiens
<220> FEATURE:
<223> OTHER INFORMATION: Individual Isolate:  HK4

<400> SEQUENCE: 13
catgaagtgc acaacgtatc cgggatctac catgtcacga acgactgctc caactcaagt    60
```

-continued

```
attgtgtatg aggcagcgga catgatcatg catacccccg ggtgcgtgcc ctgcgtccgg      120
gagaacaact cctcccgttg ctgggtagcg ctcactccca cgctcgcggc caggaacgcc      180
agcatcccca ctacgacaat acgacgccat gtcgacttgc tcgttggggc ggctgctttc      240
tgctccgcca tgtacgtggg agatctctgc ggatctgtct tcctcgtctc ccagttgttc      300
accttctcgc ctcgccggca tgagacggta caggactgca attgctcaat ctatcccggc      360
cacgtatcag gtcaccgcat ggcttgggat atgatgatga actggtcacc tacagcagcc      420
ctagtggtat cgcagttact ccgactccca caagctgtca tggacatggt ggcgggagcc      480
cactggggag tcctagcggg ccttgcttac tattccatgg tggggaactg ggccaaggtt      540
ttgattgtga tgctactctt tgccggcgtt gacggg                                576
```

<210> SEQ ID NO 14
<211> LENGTH: 576
<212> TYPE: DNA
<213> ORGANISM: Homo sapiens
<220> FEATURE:
<223> OTHER INFORMATION: Individual Isolate: HK5

<400> SEQUENCE: 14

```
tatgaagtgc gcaacgtgtc cggggtatac catgtcacga acgactgctc caacttaagc       60
atcgtgtacg agacaacgga catgatcatg cacacccctg ggtgcgtgcc ctgcgttcgg      120
gaaaacaact cctcccgttg ttgggtagcg ctcgccccca cgctcgcggc caggaacgcc      180
agcgtcccca ccacggcaat acgacgccac gtcgacttgc tcgttggggc ggctgctttc      240
tgctccgcta tgtacgtggg ggatctttgc ggatctgttt tcctcgtctc ccagctgttc      300
accttctcgc ctcgccgaca cgagacggta caggactgca actgctcaat ctatcccggc      360
cacgtaacag gtcaccgcat ggcttgggat atgatgatga actggtcacc tacaacagcc      420
ctagtggtgt cgcagttact ccggatcccg caagctgtcg tggacatggt agcgggggcc      480
cactgggggg tcctggcggg ccttgcctac tattccatgg tgggaaactg gctaaggtt      540 ttgattgtga tgctactttt tgccggcgtt gatggg                                576
```

<210> SEQ ID NO 15
<211> LENGTH: 576
<212> TYPE: DNA
<213> ORGANISM: Homo sapiens

<400> SEQUENCE: 15

```
tatgaagtgc gcaacgtgtc cgggatatac catgtcacga acgactgctc caactcaagc       60
atcgtgtatg aaacagcgga catgattatg catacccctg gatgcatgcc ctgcgttcgg      120
gagaacaact cctcccgttg ctgggtggcg ctcactccca cgctcgcggc taggaatgtc      180
agcgtcccca ctacgacaat acgacgccac gtcgacttgc tcgttggggc ggctgctttc      240
tgctccgcta tgtacgtggg ggatctctgc ggatctgttt tcctcgtctc ccagctgttc      300
accttttcgc ctcgccgaca cgagacggta caggactgca actgctcaat ctatcccggc      360
cacgtatcag gtcaccgcat ggcttgggat atgatgatga actggtcgcc cacaacagcc      420
ctagtggtgt cgcagttact ccggatcccg caagctatcg tggacatggt ggcgggggcc      480
cactggggag tcctagcggg ccttgcctac tattccatgg tgggcaactg gctaaggtt      540 ttgattgtga tgctactgtt tgccggcgtt gatggg                                576
```

<210> SEQ ID NO 16

```
<211> LENGTH: 576
<212> TYPE: DNA
<213> ORGANISM: Homo sapiens
<220> FEATURE:
<223> OTHER INFORMATION: Individual Isolate:  IND5

<400> SEQUENCE: 16
tatgaagtgc gcaacgtgtc cggggtgtac catgtcacga acgactgctc caactcaagt    60
attgtgtatg aggcagcgga catgatcatg cacactcccg ggtgcgtgcc ctgcgttcgg   120
gagggcaact cctctcgctg ctgggtagcg ctcactccca ctctcgcggc caggaacgcc   180
agcgtctcca ccacgacaat acgacaccac gtcgatttgc tcgttggggc ggctgctttc   240
tgttccgcta tgtacgtggg ggatctatgc ggatctgttt tcctcgtctc ccagctgttc   300
accttctcac cgcgccggca tgagacagta caggactgca attgctccat ctatcccggc   360
cacgtatcag gtcaccgcat ggcctgggat atgatgatga actggtcacc tacagcagcc   420
ctagtggtat cgcagttgct ccggatccca caagctgtcg tggatatggt ggcgggggcc   480
cactggggaa tcctggcggg ccttgcctac tattccatgg tagggaactg gctaaggtt    540
ttgattgtga tgctactctt tgccggcgtt gacggg                             576

<210> SEQ ID NO 17
<211> LENGTH: 576
<212> TYPE: DNA
<213> ORGANISM: Homo sapiens
<220> FEATURE:
<223> OTHER INFORMATION: Individual Isolate:  IND8

<400> SEQUENCE: 17
tatgaggtgc gcaacgtgtc cggggtgtac catgtcacga acgactgctc caactcaagt    60
attgtgtatg aggcagcgga catgatcatg cacaccccg ggtgcgtgcc ctgcgttcgg    120
gagggcaact tctctagttg ctgggtagcg ctcactccca ctctcgcggc taggaacgcc   180
agcgtcccca ccacgacaat acgacgccac gtcgatttgc tcgttggggc ggctgctttc   240
tgttccgcta tgtacgtggg ggatctctgc ggatctgttt tccttgtctc ccagctgttc   300
accttctcac cgcgccggca tgagacagta caggactgca attgctccat ctatcccggc   360
cacgtatcag gtcaccgcat ggcttgggat atgatgatga actggtcacc tacagcggcc   420
ctagtggtat cgcagttgct ccggatccca caagctgtcg tggatatggt ggcgggggcc   480
cactggggaa tcctggcggg ccttgcctac tattccatgg tagggaactg gctaaggtt    540
ttgattgtga tgctactctt tgccggcgtt gacggg                             576

<210> SEQ ID NO 18
<211> LENGTH: 576
<212> TYPE: DNA
<213> ORGANISM: Homo sapiens
<220> FEATURE:
<223> OTHER INFORMATION: Individual Isolate:  P10

<400> SEQUENCE: 18
tatgaagtgc gcaacgtgtc cggggtgtac catgtcacga acgactgctc caactcaagt    60
attgtgtatg aggcagcgga catgataatg cacaccccg ggtgcgtgcc ctgtgttcgg    120
gagaacaact cctcccgctg ctgggtagcg ctcactccca cactcgcggc taggaattcc   180
agcgtcccaa ctacggcaat acgacgccat gtcgatttgc tcgttggggc ggctgctttc   240
tgctccgcta tgtacgtggg ggatctctgc ggatctgttc tcctcgtctc ccagctgttc   300
accttctcac ctcgccggca ttgagacagta caggactgca attgttcaat ctatcctggc  360
```

```
cacgtatcag gtcaccgcat ggcttgggat atgatgatga actggtcgcc cacagcagcc    420
ctagtggtgt cgcagctact ccggatccca caagctatct tggatgtggt ggcgggggcc    480
cactggggag tcctggcggg ccttgcctac tattccatgg tggggaactg ggctaaggtc    540
ttgattgtga tgctactctt tgccggcgtt gacgga                              576
```

<210> SEQ ID NO 19
<211> LENGTH: 576
<212> TYPE: DNA
<213> ORGANISM: Homo sapiens
<220> FEATURE:
<223> OTHER INFORMATION: Individual Isolate: S9

<400> SEQUENCE: 19

```
tatgaagtgc gcaacgtatc cggggcgtac catgtcacga acgactgctc caactcaagt    60
attgtgtacg aggcagcgga cgtgatcatg cataccccg  gtgtgtacc  ctgcgttcag   120 gagggtaact cctcccaatg ctgggtggcg ctcaccccca cgctcgcggc caggaacgct   180
accgtcccca ccacgacaat acgacgtcat gtcgatttgc tcgttggggc ggctgttttc   240
tgctccgcta tgtacgtggg ggacctgtgc ggatctgttt cctcatctc  ccagctgttc   300 accatctcgc cccgtcggca tgagacagta cagaactgca attgctcaat ctatcccgga   360
cacgtgacag gtcatcgcat ggcctgggat atgatgatga actggtcgcc tacaacagcc   420
ctagtggtat cgcagctact ccggatccca caagctgtca tggatatggt ggcgggggcc   480
cactggggag tcctggcggg cctcgcctac tattccatgg tggggaactg ggctaaggtt   540
ttgattgtga tgctacttttt tgctggtgtt gacggg                             576
```

<210> SEQ ID NO 20
<211> LENGTH: 576
<212> TYPE: DNA
<213> ORGANISM: Homo sapiens
<220> FEATURE:
<223> OTHER INFORMATION: Individual Isolate: S45

<400> SEQUENCE: 20

```
tatgaagtgc gcaacgtgtc cggggcgtac catgtcacga acgactgctc caactcaagc    60
attgtgtatg aggcagtgga cgtgatcctg cacaccccctg gtgcgtgcc  ctgcgttcgg   120 gagaacaact cctcccgttg ctgggtggcg ctcactccca cgctcgcggc caggaactcc   180
agcgtcccca ctacgacaat acgacgtcac gtcgatttgc tcgttggggc ggctgctttc   240
tgctccgcta tgtacgtggg ggatctctgc ggatctgttt tccttgtttc ccagctgttc   300
accttctcgc ctcgtcggca tgagacagta caggactgca actgttcaat ctatcccggc   360
cacgtaacag gtcaccgcat ggcttgggat atgatgatga actggtcgcc tacagcagcc   420
ttagtggtat cgcagttact ccggatccca caagctgtcg tggacatggt ggcgggggcc   480
cactggggag tcctggcggg ccttgcctac tattccatgg tggggaactg ggctaaggtt   540
ctgattgtga tgctactctt tgccggcgtt gacggg                              576
```

<210> SEQ ID NO 21
<211> LENGTH: 576
<212> TYPE: DNA
<213> ORGANISM: Homo sapiens
<220> FEATURE:
<223> OTHER INFORMATION: Individual Isolate: SA10

<400> SEQUENCE: 21

```
tatgaagtgc gcaacgtgtc cgggatgtac catgtcacga acgactgctc caactcaagc    60
attgtgtatg aggcagcgga catgatcatg cacaccccg ggtgcgtgcc ctgcgttcgg    120
gagaacaact cctcccgctg ctgggtagcg ctcactccca cgctcgcggc caggaactcc    180
agcgtcccca ctacgacaat acgacgccac gtcgatttgc tcgttggggc ggctgctttc    240
tgctccgcca tgtacgtggg ggacctctgc ggatctgttt tccttgtctc ccagctgttc    300
accttctcgc ctcgccggta tgagacagta caggactgca attgctcaat ctatcccggc    360
cgcgtaacag gtcaccgcat ggcttgggat atgatgatga actggtcacc tacaacagct    420
ctagtagtat cgcagttact ccggatccca caagctatcg tggacatggt ggcgggggcc    480
cactggggag tcctagcggg ccttgcctac tattccatgg tggggaactg ggctaaggtt    540
ttgattgtta tgctactctt tgccggcgtt gacggg                              576
```

<210> SEQ ID NO 22
<211> LENGTH: 576
<212> TYPE: DNA
<213> ORGANISM: Homo sapiens
<220> FEATURE:
<223> OTHER INFORMATION: Individual Isolate: SW2

<400> SEQUENCE: 22

```
tatgaagtgc gcaacgtgtc cggggtgtat catgtcacga acgactgttc caactcaagc    60
attgtgtatg agacagcgga catgatcatg cataccccg ggtgcgtgcc ctgcgttcgg    120
gaggccaact cctcccgctg ctgggtagcg ctcactccca cgctagcagc caggaacacc    180
agcgtcccca ctacgacaat acgacgccac gtcgatttgc tcgttggggc ggctgctttc    240
tgctccgtta tgtacgtggg ggatctctgc ggatctgttt tcctcgtctc ccagctgttc    300 acttttcac ctcgccggca cgagacagta caggactgca actgttccat ctatcccggc    360
cacgtatcag gtcaccgcat ggcttgggac atgatgatga actggtcacc tacagcagcc    420
ctggtggtat cgcagttact ccggatccca caagctgtcg tggacatggt agcgggggcc    480
cactggggag tcctggcggg ccttgcatac tattccatgg tggggaactg ggctaaggtt    540
ttgattgtga tgctactctt tgctggcgtt gacggg                              576
```

<210> SEQ ID NO 23
<211> LENGTH: 576
<212> TYPE: DNA
<213> ORGANISM: Homo sapiens
<220> FEATURE:
<223> OTHER INFORMATION: Individual Isolate: T3

<400> SEQUENCE: 23

```
tacgaagtgc gcaacgtgtc cggggtgtac tatgtcacga acgactgttc caactcaagc    60
attgtgtatg agacagcgga catgatcatg cacaccctg ggtgcgtgcc ctgcgttcgg    120
gagagcaatt cctcccgctg ctgggtagcg cttactccca cgctcgcggc caggaacgcc    180
agcgtcccca ctaagacaat acgacgtcac gtcgacttgc tcgttggggc ggctgctttc    240
tgttccgcta tgtacgtggg ggatctctgc ggatctgttt tcctcgtctc ccagctgttc    300
actttctcgc ctcgccggca tgagacagta caggactgca actgctcaat ctatcccggc    360
cacgtaacag gtcaccgtat ggcttgggat atgatgatga actggtcgcc cacaacggca    420
ctagtggtgt cgcagttgct ccggatccca caagctgtcg tggacatggt ggcgggggcc    480
cactggggag tcctggcggg ccttgcctac tattccatgg tggggaactg ggctaaggtt    540
ttgattgtgc tgctactctt tgccggcgtt gatggg                              576
```

<210> SEQ ID NO 24
<211> LENGTH: 576
<212> TYPE: DNA
<213> ORGANISM: Homo sapiens
<220> FEATURE:
<223> OTHER INFORMATION: Individual Isolate: T10

<400> SEQUENCE: 24

```
tatgaagtgc gcaacgtgtc cgggatgtac catgtcacga acgactgctc caactcaagc      60
attgtgtttg aggcagcgga cttgatcatg cacaccccg ggtgcgtgcc ctgcgttcgg      120
gagggcaact cctcccgctg ctgggtagcg ctcactccca cgctcgcggc caggaacacc      180
agcgtcccca ctacgacgat acgacgccat gtcgatttgc tcgttggggc ggctgctttc      240
tgctccgcta tgtatgtggg agacctctgc ggatctgttt tcctcgtctc tcagctgttc      300
accttctcgc ctcgccggca tgagactttg caggactgca actgctcaat ctatcccggc      360
catctgtcag gtcaccgcat ggcttgggac atgatgatga actggtcgcc tacaacagct      420
ctagtggtgt cgcagttact ccggatccca caagctgtca tggacatggt gacaggggcc      480
cactggggag tcctggcggg ccttgcctac tattccatgg cggggaactg ggctaaggtt      540
ttaattgtga tgctactctt tgccggcgtt gatggg                               576
```

<210> SEQ ID NO 25
<211> LENGTH: 576
<212> TYPE: DNA
<213> ORGANISM: Homo sapiens
<220> FEATURE:
<223> OTHER INFORMATION: Individual Isolate: US6

<400> SEQUENCE: 25

```
tatgaagtgc gcaacgtgtc cgggatgtac catgtcacga acgactgctc caactcaagc      60
attgtgtatg aggcagcgga catgatcatg cacactcccg ggtgcgtgcc ctgtgttcgg      120
gagaacaatt cctcccgctg ctgggtagcg ctcactccca cgctcgcggc caggaacgct      180
agcgtcccca ctacgacaat acgacgccac gtcgatttgc tcgttggggc ggctactttc      240
tgctccgcta tgtacgtggg ggacctctgc gggtccgttt tcctcatctc ccagctgttc      300
accttctcgc ctcgtcagca tgagacagta caggactgca attgttcaat ctatcccggc      360
cacgtatcag gtcaccgcat ggcttgggat atgatgatga attggtcacc tacagcagcc      420
ctagtggtat cgcagttact ccggatccca caagctgtca tggacatggt ggcggggcc       480
cactggggag tcctggcggg ccttgcctac tattccatgg tggggaactg ggctaaggtt      540
ctgattgtgt tgctactctt tgccggcgtt gacggg                               576
```

<210> SEQ ID NO 26
<211> LENGTH: 576
<212> TYPE: DNA
<213> ORGANISM: Homo sapiens
<220> FEATURE:
<223> OTHER INFORMATION: Individual Isolate: T2

<400> SEQUENCE: 26

```
gcccaagtga ggaacaccag ccgcggttac atggtgacta acgactgttc caatgagagc      60
atcacctggc agctccaagc cgcggttctc cacgtccccg ggtgtatccc gtgtgagagg      120
ctgggaaata catcccgatg ctggataccg gtcacaccaa acgtggccgt gcggcagccc      180
ggcgctctta cgcagggctt gcggacgcac atcgacatgg ttgtgatgtc cgccacgctc      240
```

```
tgctctgccc tctacgtggg ggacctctgc ggcggggtga tgctcgcagc ccagatgttc      300
attgtctcgc cgcgacgcca ctggtttgtg caagaatgca attgctccat ctaccccggt      360
accatcactg acaccgtat ggcatgggac atgatgatga actggtcgcc cacagccacc       420
atgatcctgg cgtacgcgat gcgcgttccc gaggtcatca tagacatcat cggcgggct      480 cactggggcg tcatgtttgg cttggcctac ttctctatgc agggagcgtg ggcgaaggtc      540
attgtcatcc tcttgctggc tgctggggtg gacgcg                                576
```

<210> SEQ ID NO 27
<211> LENGTH: 576
<212> TYPE: DNA
<213> ORGANISM: Homo sapiens
<220> FEATURE:
<223> OTHER INFORMATION: Individual Isolate: T4

<400> SEQUENCE: 27

```
gcacaagtga agaacaccac taacagctac atggtgacca cgactgttc taatgacagc       60 atcacttggc agctccaggc cgcggtcctc cacgtccccg ggtgtgtccc gtgcgagaaa      120
acgggaaata catctcggtg ctggataccg gtttcaccaa acgtggccgt gcggcagccc      180
ggcgccctca cgcagggctt gcggacgcac attgacatgg ttgtgatgtc cgccacgctc      240
tgctctgctc tttacgtggg ggacctctgc ggcggggtga tgctcgcagc ccagatgttc      300
atcgtctcgc cgcaacatca ctggtttgtg caagactgca attgctctat ctaccctggc      360
accatcactg acaccgtat ggcatgggat atgatgatga actggtcgcc cacggccacc       420
atgatcctgg cgtacgcgat gcgcgttccc gaggtcatct tagacatcgt tagcggggca      480
cactggggcg tcatgttcgg cttggcctac ttctctatgc agggagcgtg ggcgaaagtc      540
gttgtcatcc ttctgctggc cgctggggtg gacgcg                                576
```

<210> SEQ ID NO 28
<211> LENGTH: 576
<212> TYPE: DNA
<213> ORGANISM: Homo sapiens
<220> FEATURE:
<223> OTHER INFORMATION: Individual Isolate: T9

<400> SEQUENCE: 28

```
gccgaagtga agaacaccag taccagctac atggtgacaa atgactgttc caacgacagc      60
atcacctggc aactccaggc cgcggtcctc cacgtccccg ggtgcgtccc gtgcgagaga      120
gttggaaacg cgtcgcggtg ctggataccg gtctcgccaa acgtagctgt gcagcggcct     180
ggcgccctca cgcagggctt gcggacgcac atcgacatgg ttgtgatgtc cgccacgctc      240
tgctccgctc tctacgtggg ggatctctgc ggcggggtaa tgctcgccgc tcagatgttc      300
attatctcgc cgcagcacca ctggtttgtg caggaatgca actgctccat ttaccctggt      360
accatcactg acaccgtat ggcatgggac atgatgatga actggtcgcc cacaaccacc       420
atgatcttgg cgtacgcgat gcgcgttccc gaggtcatca tagacatcat cagcggagct      480
cactggggcg tcatgttcgg cctagcctac ttctctatgc agggagcgtg ggcgaaggtc      540
gttgtcatcc tgttgctcac cgctggcgtg gacgcg                                576
```

<210> SEQ ID NO 29
<211> LENGTH: 576
<212> TYPE: DNA
<213> ORGANISM: Homo sapiens
<220> FEATURE:
<223> OTHER INFORMATION: Individual Isolate: US10

<400> SEQUENCE: 29

| | | |
|---|---|---|
| gtccaagtga aaaacaccag taccagctat atggtgacca atgactgctc caacgacagc | 60 |
| atcacttggc aacttgaggc tgcggtcctc cacgttcccg ggtgtgtccc gtgcgagaaa | 120 |
| gtgggaaata catctcggtg ctggataccg gtctcaccaa atgtggccgt gcagcggcct | 180 |
| ggcgccctca cgcagggctt gcggactcac atcgacatgg tcgtgatgtc cgccacgctc | 240 |
| tgctccgctc tttacgtggg ggacttctgc ggtgggatga tgctcgcagc ccaaatgttc | 300 |
| attgtctcgc cgcgccacca ctcgtttgtg caggaatgca actgctccat ctaccccggt | 360 |
| accatcaccg ggcaccgtat ggcatgggac atgatgatga actggtcgcc cacggccact | 420 |
| ttgatcctgg cgtacgtgat gcgcgttccc gaggtcatca tagacatcat tagcggggcg | 480 |
| cattggggcg tcttgttcgg cttagcctac ttctctatgc agggagcgtg ggcgaaagtc | 540 |
| gttgtcatcc ttctgctagc cgctggggtg gacgcg | 576 |

<210> SEQ ID NO 30
<211> LENGTH: 576
<212> TYPE: DNA
<213> ORGANISM: Homo sapiens
<220> FEATURE:
<223> OTHER INFORMATION: Individual Isolate: DK8

<400> SEQUENCE: 30

| | | |
|---|---|---|
| gtggaagtca ggaacatcag ttccagctac tacgccacca atgattgctc aaacaacagc | 60 |
| atcacctggc aactcaccga cgcagttctc caccttcccg gatgcgtccc atgtgagaat | 120 |
| gacaatggca ccctgcgctg ctggatacaa gtgacaccta atgtggctgt gaaacaccgc | 180 |
| ggcgcactta ctcataacct gcgaacacac gtcgacgtga tcgtaatggc agctacggtc | 240 |
| tgctcggcct tgtatgtggg agacgtatgc ggggccgtga tgatcgtgtc gcaggctctc | 300 |
| ataatatcgc ctgaacgcca caactttacc caggagtgca actgttccat ctaccaaggt | 360 |
| catatcaccg gccaccgcat ggcatgggac atgatgctaa actggtcacc aactcttacc | 420 |
| atgatcctcg cctatgccgc tcgtgttcct gagctagccc tccaggttgt cttcggcggc | 480 |
| cattggggcg tggtgtttgg cttggcctat ttctccatgc agggagcgtg ggccaaagtc | 540 |
| attgccatcc tccttcttgt cgcaggagtg gatgca | 576 |

<210> SEQ ID NO 31
<211> LENGTH: 576
<212> TYPE: DNA
<213> ORGANISM: Homo sapiens
<220> FEATURE:
<223> OTHER INFORMATION: Individual Isolate: DK11

<400> SEQUENCE: 31

| | | |
|---|---|---|
| gtggaagtca ggaacaccag ttctagttac tacgccacca atgattgctc aaacaacagc | 60 |
| atcacctggc aactcaccaa cgcagttctc caccttcccg gatgcgtccc atgtgagaat | 120 |
| gacaatggca ccctgcactg ctggatacaa gtgacaccta atgtggctgt gaaacaccgc | 180 |
| ggcgcactca ctcacaacct gcgagcacat atagatatga ttgtaatggc agctacggtc | 240 |
| tgctcggcct tgtatgtggg agacgtgtgc ggggccgtga tgatcgtgtc gcaggctttc | 300 |
| atagtatcgc cagaacacca ccactttacc caagagtgca actgttccat ctaccaaggt | 360 |
| cacatcaccg gccaccgcat ggcatgggac atgatgctta actggtcacc aactctcacc | 420 |
| atgatcctcg cctatgccgc ccgtgttcct gagctagtcc ttgaagtcgt cttcggtggt | 480 | cattggggtg tggtgtttgg cttggcctat ttctccatgc agggagcgtg ggccaaggtc      540 attgccatcc tccttcttgt agcaggagtg gatgca                                576

<210> SEQ ID NO 32
<211> LENGTH: 576
<212> TYPE: DNA
<213> ORGANISM: Homo sapiens
<220> FEATURE:
<223> OTHER INFORMATION: Individual Isolate: SW3

<400> SEQUENCE: 32
gtggaagtca ggaacatcag ttctagctac tatgccacca atgattgctc aaacagcagc      60
atcacctggc aactcaccaa cgcagtcctc caccttcccg gatgcgtccc gtgtgagaat     120
gataatggca ccctgcactg ctggatacaa gtgacaccta atgtggctgt gaaacaccgc     180
ggcgcgctca ctcacaacct gcgagcacac gtcgatatga tcgtaatggc agctacggtc     240
tgctcggcct tgtatgtggg agacatgtgc ggggccgtga tgatcgtgtc gcaggctttc     300
ataatatcgc cagaacgcca caactttacc caagagtgca actgttccat ctaccaaggt     360
cgtatcaccg gccaccgcat ggcgtgggac atgatgctaa actggtcacc aactcttacc     420
atgatccttg cctatgccgc tcgtgttcct gagctagtcc ttgaagttgt cttcggcggc     480
cattggggcg tggtgtttgg cttggcctat ttctccatgc aaggagcgtg gccaaggtc      540 attgccatcc tcctgcttgt cgcaggagtg gatgca                                576

<210> SEQ ID NO 33
<211> LENGTH: 576
<212> TYPE: DNA
<213> ORGANISM: Homo sapiens
<220> FEATURE:
<223> OTHER INFORMATION: Individual Isolate: T8

<400> SEQUENCE: 33
gtggaagtta gaaacaccag ttttagctac tacgccacca atgattgctc gaacaacagc      60
atcacctggc agctcaccaa cgcagttctc caccttcccg gatgcgtccc atgtgagaat     120
gacaatggca ccttgcgctg ctggatacaa gtaacaccta atgtggctgt gaaacaccgt     180
ggcgcactca ctcacaacct gcgaacgcat gtcgacgtga tcgtaatggc agctacggtc     240
tgctcggcct tgtatgtggg ggacgtgtgc ggggccgtga tgatagcgtc gcaggctttc     300
ataatatcgc cagaacgcca caacttcacc caggagtgca actgttccat ctaccaaggt     360
catatcaccg gccaccgcat ggcatgggac atgatgctga actggtcacc aactctcacc     420
atgatcctcg cctacgctgc tcgtgtgcct gaactagtcc ttgaagttgt cttcggcggc     480
cattggggcg tggtgtttgg cttggcctat ttctccatgc aaggagcgtg ggccaaagtc     540
atcgccatcc tcctccttgt cgcaggagtg gacgca                                576

<210> SEQ ID NO 34
<211> LENGTH: 576
<212> TYPE: DNA
<213> ORGANISM: Homo sapiens
<220> FEATURE:
<223> OTHER INFORMATION: Individual Isolate: S83

<400> SEQUENCE: 34
gtggaggtca aggacaccgg cgactcctac atgccgacca acgattgctc caactctagt      60
atcgtttggc agcttgaagg agcagtgctt catactcctg gatgcgtccc ttgtgagcgt     120
accgccaacg tctctcgatg ttgggtgccg gttgccccca atctcgccat aagtcaacct     180

```
ggcgctctca ctaagggcct gcgagcacac atcgatatca tcgtgatgtc tgctacggtc    240
tgttctgccc tttatgtggg ggacgtgtgt ggcgcgctga tgctggccgc tcaggtcgtc    300
gtcgtgtcgc cacaacacca tacgtttgtc caggaatgca actgttccat atacccgggc    360
cgcattacgg gacaccgcat ggcttgggat atgatgatga actggtcgcc cactaccacc    420
atgctcctgg cgtacttggt gcgcatcccg gaagtcatct tggatattgt tacaggaggt    480
cattggggtg taatgtttgg cctcgcttac ttctccatgc agggatcgtg ggcgaaggtc    540
atcgttatcc tcctgctgac tgctggggtg gaggcg                             576

<210> SEQ ID NO 35
<211> LENGTH: 576
<212> TYPE: DNA
<213> ORGANISM: Homo sapiens
<220> FEATURE:
<223> OTHER INFORMATION: Individual Isolate:  DK12

<400> SEQUENCE: 35
ttagagtggc ggaatgtgtc cggcctctac gtccttacca acgactgttc caatagcagt     60
atcgtgtatg aggccgatga cgtcattctg cacacacctg gctgtgtacc ttgtgttcag    120
gacggcaata catctacgtg ctggacctca gtgacgccta cagtggcagt caggtacgtc    180
ggagcaacca ccgcttcgat acgcagtcat gtggacctgc tagtgggcgc ggccacgatg    240
tgctctgcgc tctacgtggg tgatgtgtgt ggggccgtct tccttgtggg acaagccttc    300
acgttcagac ctcgtcgcca tcaaacagtc cagacctgta actgctcgct gtacccaggc    360
catctttcag gacatcgaat ggcttgggat atgatgatga attggtcccc cgctgtgggt    420
atggtggtag cgcacgtcct gcgtctgccc cagaccttgt tcgacataat agctggggcc    480
cattggggca tcatggcggg cctagcctat tactccatgc agggcaactg gccaaggtc     540 gctatcatca tggttatgtt ttcaggagtc gatgcc                             576

<210> SEQ ID NO 36
<211> LENGTH: 576
<212> TYPE: DNA
<213> ORGANISM: Homo sapiens
<220> FEATURE:
<223> OTHER INFORMATION: Individual Isolate:  HK10

<400> SEQUENCE: 36
ctagagtggc ggaatgtgtc tggcctctat gtccttacca acgactgtcc caatagcagt     60
attgtgtatg aggccgatga cgtcattctg cacacacctg gctgtgtacc ttgtgttcag    120
gacggcaata catccacgtg ctggacctcg gtgacaccta cagtggcagt caggtacgtc    180
ggagcaacca ccgcctcgat acgcagtcat gtggacctgt tagtgggcgc ggccacgatg    240
tgctctgcgc tctacgtggg cgatatgtgt ggggccgtct tcctcgtggg acaagccttc    300
acgttcagac cgcgtcgcca tcaaacggtc cagacctgta actgctcgct gtacccaggc    360 caccttttcag gacatcgaat ggcttgggat atgatgatga attggtcccc cgccgtgggt    420
atggtggtgg cgcacgtcct gcggttgccc cagaccttgt tcgacataat agccggggcc    480
cattggggca tcttggcagg cctagcctat tactccatgc agggcaactg gccaaggtc     540 gctatcatca tggttatgtt ttcagggtc gatgcc                              576

<210> SEQ ID NO 37
<211> LENGTH: 576
<212> TYPE: DNA
```

```
<213> ORGANISM: Homo sapiens
<220> FEATURE:
<223> OTHER INFORMATION: Individual Isolate: S2

<400> SEQUENCE: 37
ctagagtggc ggaatacgtc tggcctctat gtcctcacca acgactgttc caatagcagt      60
attgtgtatg aggccgatga cgttattctg cacacacctg gctgtgtacc ttgtgttcag     120
gacggtaata catccacgtg ctggacccca gtgacaccta cagtggcagt caggtatgtc     180
ggagcaacca ccgcttcgat acgcagtcat gtggacctat tggtgggcgc ggccactatg     240
tgctctgcgc tctacgtggg tgatatgtgt ggggccgtct ttctcgtggg acaagccttc     300
acgttcagac ctcgtcgcca tcaaacggtc cagacctgta actgctcgct gtacccaggc     360
catctttcag gacatcgcat ggcttgggat atgatgatga attggtcccc cgctgtgggt     420
atggtggtgg cgcacgttct gcgtttgccc cagaccgtgt tcgacataat agccggggcc     480
cattgggcca tcttggcggg cctagcctat tactccatgc aaggcaactg gccaaggtc     540 gctatcatca tggttatgtt ttcaggggtc gacgcc                               576

<210> SEQ ID NO 38
<211> LENGTH: 576
<212> TYPE: DNA
<213> ORGANISM: Homo sapiens
<220> FEATURE:
<223> OTHER INFORMATION: Individual Isolate: S52

<400> SEQUENCE: 38
ctagagtggc ggaatacgtc tggcctctat gtccttacca acgactgttc caatagcagt      60
attgtgtatg aggccgatga cgtcattctg cacacacccg gctgtgtacc ttgtgttcag     120
gacggcaata catccatgtg ctggacccca gtgacaccta cggtggcagt caggtacgtc     180
ggagcaacca ccgcttcgat acgcagtcat gtggacctat tagtgggcgc ggccacgctg     240
tgctctgcgc tctatgtggg tgatatgtgt ggggccgtct ttctcgtggg acaagccttc     300
acgttcagac ctcgtcgcca tcaaacggtc cagacctgta actgctcgct gtacccaggc     360
catgtttcag gacatcgaat ggcttgggat atgatgatga attggtcccc cgctgtgggt     420
atggtggtgg cgcacatcct gcgattgccc cagaccttgt ttgacatact ggccggggcc     480
cattgggcca tcttggcggg cctagcctat tattctatgc agggcaactg gccaaggtc     540 gctattgtca tgattatgtt ttcaggggtc gatgcc                               576

<210> SEQ ID NO 39
<211> LENGTH: 576
<212> TYPE: DNA
<213> ORGANISM: Homo sapiens
<220> FEATURE:
<223> OTHER INFORMATION: Individual Isolate: S54

<400> SEQUENCE: 39
ctagagtggc ggaatacgtc tggcctctat atccttacca acgactgttc caatagcagt      60
attgtgtatg aggccgatga cgtcattctg cacacacccg gctgtgtacc ttgtgttcag     120
gacggcaata catccacgtg ctggacccca gtgacaccta cggtggcagt caggtacgtc     180
ggagcaacca ccgcttcgat acgcagtcat gtggacctat tagtgggcgc ggccacgctg     240
tgctctgcgc tctatgtggg tgatatgtgt ggggccgtct ttctcgtggg acaagccttc     300
acgttcagac ctcgtcgcca tcaaacggtc cagacctgta actgctcgct gtacccaggc     360
catctttcag gacatcgaat ggcttgggat atgatgatga attggtcccc cgctgtgggt     420
```

```
atggtggtgg cgcacatcct gcgattgccc cagaccttgt ttgacatact ggccgggcc      480 cattggggca tcttggcggg cctagcctat tattctatgc agggcaactg ggccaaggtc      540
gctatcatca tgattatgtt ttcaggggtc gatgcc                                576

<210> SEQ ID NO 40
<211> LENGTH: 576
<212> TYPE: DNA
<213> ORGANISM: Homo sapiens
<220> FEATURE:
<223> OTHER INFORMATION: Individual Isolate: Z4

<400> SEQUENCE: 40
gagcactacc ggaatgcttc gggcatctat cacatcacca atgattgtcc gaattccagt      60
atagtctatg aagctgacca tcacatccta cacttgccgg ggtgcgtacc ctgtgtgatg      120
actgggaaca catcgcgttg ctggacgccg gtgacgccta cagtggctgt cgcacacccg      180
ggcgctccgc ttgagtcgtt ccggcgacat gtggacttaa tggtaggcgc ggccactttg      240
tgttctgccc tctatgttgg ggacctctgc ggaggtgcct tcctgatggg gcagatgatc      300
acttttcggc cgcgtcgcca ctggaccacg caggagtgca attgttccat ctacactggc      360
catatcaccg gccacaggat ggcgtgggac atgatgatga actggagccc taccaccact      420
ctgctcctcg cccagatcat gagggtcccc acagcctttc tcgacatggt tgccggaggc      480
cactggggcg tcctcgcggg cttggcgtac ttcagcatgc aaggcaattg ggccaaggta      540
gtcctggtcc ttttcctctt tgctggggta gacgcc                               576

<210> SEQ ID NO 41
<211> LENGTH: 576
<212> TYPE: DNA
<213> ORGANISM: Homo sapiens
<220> FEATURE:
<223> OTHER INFORMATION: Individual Isolate: Z1

<400> SEQUENCE: 41
gtgcactacc ggaatgcttc gggcgtctat catgtcacca atgattgccc taacaccagc      60
atagtgtacg agacggagca ccacatcatg cacttgccag ggtgtgtccc ctgtgtgcgg      120
acggagaata cttctcgctg ctgggtgccc ttgaccccca ctgtggccgc gccctatccc      180
aacgcaccgt tagagtccat gcgcaggcat gtagacctga tggtgggtgc ggctactatg      240
tgttccgcct tctacattgg agatctgtgt ggaggcgtct tcctagtggg ccagctgttc      300
gacttccgac cgcgccggca ctggaccacc caggattgca actgctccat ctatcctggt      360
cacgtctcgg gccacaggat ggcctgggac atgatgatga actggagccc taccagcgcg      420
ctgattatgg ctcagatctt acggatcccc tctatcctag gtgacttgct caccgggggt      480
cactggggag ttcttgctgg tctagctttc ttcagcatgc agagtaactg ggcgaaggtc      540
atcctggtcc tattcctctt tgccggggtc gaggga                               576

<210> SEQ ID NO 42
<211> LENGTH: 576
<212> TYPE: DNA
<213> ORGANISM: Homo sapiens
<220> FEATURE:
<223> OTHER INFORMATION: Individual Isolate: Z6

<400> SEQUENCE: 42
gttaactatc gcaatgcctc gggcgtctat cacgtcacca acgactgccc gaactcgagc      60
```

```
atagtgtatg aggccgaaca ccagatctta cacctcccag ggtgcttgcc ctgtgtgagg      120
gttgggaatc agtcacgctg ctgggtggcc cttactccca ccgtggcggt gtcttatatc      180
ggtgctccgc ttgactccct ccggagacat gtggacctga tggtgggcgc cgctactgta      240
tgctctgccc tctacgttgg agatctgtgc ggtggtgcat tcttggttgg ccagatgttc      300
tccttccagc cgcgacgcca ctggactacg caggactgca attgttctat ctacgcaggg      360
catatcacgg gccacaggat ggcatgggac atgatgatga actggagtcc cacaaccacc      420
ctgcttctcg cccaggtcat gaggatccct agcactctgg tagatctact cgctggaggg      480
cactggggcg tccttgttgg gttggcgtac ttcagtatgc aagctaattg gccaaagtc       540 atcctggtcc ttttcctctt cgctggagtt gatgcc                               576
```

<210> SEQ ID NO 43
<211> LENGTH: 576
<212> TYPE: DNA
<213> ORGANISM: Homo sapiens
<220> FEATURE:
<223> OTHER INFORMATION: Individual Isolate: Z7

<400> SEQUENCE: 43

```
gtcaactatc acaatgcctc gggcgtctat cacatcacca acgactgccc gaactcgagc      60
ataatgtatg aggccgaaca ccacatccta cacctcccag ggtgcgtacc ctgtgtgagg      120
gaggggaacc agtcacgctg ctgggtggcc cttactccca ccgtggcggc gccttatatc      180
ggtgcaccgc ttgaatccat ccggagacat gtggacctga tggtaggcgc tgctacagtg      240
tgctccgctc tctacattgg ggacctgtgc ggtggcgtat ttttggttgg tcagatgttt      300
tctttccagc cgcgacgcca ctggactacg caggactgca attgttccat ctatgcgggg      360
cacgttacag gccacagaat ggcatgggac atgatgatga actggagtcc cacaaccacc      420
ttggtcctcg cccaggttat gaggatccct agcactctgg tggacctact cactggaggg      480
cactggggta tccttatcgg ggtggcatac ttctgcatgc aagctaattg gccaaggtc       540 attctggtcc ttttcctcta cgctggagtt gatgcc                               576
```

<210> SEQ ID NO 44
<211> LENGTH: 576
<212> TYPE: DNA
<213> ORGANISM: Homo sapiens
<220> FEATURE:
<223> OTHER INFORMATION: Individual Isolate: DK13

<400> SEQUENCE: 44

```
tacaactatc gcaacagctc gggtgtctac catgtcacca acgattgccc gaactcgagc      60
atagtctatg aaaccgatta ccacatctta cacctcccgg gatgcgttcc ttgcgtgagg      120
gaagggaaca agtctacatg ctgggtgtct ctcaccccca ccgtggctgc gcaacatctg      180
aatgctccgc ttgagtcttt gagacgtcac gtggatctga tggtgggcgg cgccactctc      240
tgctccgccc tctacatcgg agacgtgtgt ggggtgtgt tcttggtcgg tcaactgttc      300
accttccaac ctcgccgcca ctggaccacc caagactgca attgttccat ctacacagga      360
catatcacag gacacagaat ggcttgggac atgatgatga attggagccc cactgcgacg      420
ctggtcctcg cccaacttat gaggatccca ggcgccatgt cgacctgct tgcaggcggc       480 cactggggca ttctggttgg catagcgtac ttcagcatgc aagctaattg gccaaggtt       540 atcctggtcc tgtttctctt tgctggagtc gacgct                               576
```

-continued

```
<210> SEQ ID NO 45
<211> LENGTH: 576
<212> TYPE: DNA
<213> ORGANISM: Homo sapiens
<220> FEATURE:
<223> OTHER INFORMATION: Individual Isolate:  SA1

<400> SEQUENCE: 45
gttccctacc ggaatgcctc tggggtttac catgtcacca atgactgccc aaactcctcc      60
atagtctacg aggctgatag cctgatcttg cacgcacctg gctgcgtgcc ctgtgtcagg     120
caagataatg tcagtaggtg ctgggtccaa atcaccccca cactgtcagc cccgaccttc     180
ggagcggtca cggctcctct tcggagggcc gttgactact tagcgggagg agctgctctc     240
tgctccgcac tatacgtcgg cgacgcgtgc ggggcagtgt ttctggtagg ccaaatgttc     300
acctataggc ctcgccagca taccacagtg caggactgca actgttccat ttacagtggc     360
catatcaccg gccaccggat ggcttgggac atgatgatga attggtcacc tacgacagcc     420
ttgctgatgg cccagatgct acggatcccc caggtggtca tagacatcat agccgggggc     480
cactgggggg tcttgtttgc cgccgcatac tttgcgtcgg ccgccaactg ggctaaggta     540
gtgctggttc tgttcctgtt tgcggggggtc gatggc                              576

<210> SEQ ID NO 46
<211> LENGTH: 576
<212> TYPE: DNA
<213> ORGANISM: Homo sapiens
<220> FEATURE:
<223> OTHER INFORMATION: Individual Isolate:  SA4

<400> SEQUENCE: 46
gttccctacc gaaacgcctc tggggtttat catgtcacca atgattgccc aaactcttcc      60
atagtttacg aggctgataa cctgatcttg catgcacctg gttgcgtgcc ttgtgtcagg     120
caagataatg tcagtaagtg ctgggtccaa atcaccccca cgttgtcagc cccgaatctc     180
ggagcggtca cggctcctct tcggagggcc gttgactact tagcgggagg ggctgccctc     240
tgctccgcac tatacgtcgg ggacgcgtgc ggggcagtgt ttttggtagg ccaaatgttc     300
acctataggc ctcgccagca cactacggtg caagactgca attgctctat ttacagtggc     360
catatcaccg gccaccggat ggcatgggac atgatgatga attggtcacc tacgacggcc     420
ttgctgatgg cccagttgct acggattccc caggtggtca tcgacatcat tgccggggcc     480
cactgggggg tcttgtttgc cgccgcatat ttcgcgtcag cggctaactg ggctaaggtt     540
atactggtct tgtttctgtt tgcggggggtc gatgcc                              576

<210> SEQ ID NO 47
<211> LENGTH: 576
<212> TYPE: DNA
<213> ORGANISM: Homo sapiens
<220> FEATURE:
<223> OTHER INFORMATION: Individual Isolate:  SA5

<400> SEQUENCE: 47 gtccctacc gaaatgcctc tggggtttat catgtcacca atgattgccc aaactcttcc       60
atagtctacg aggctgataa cctgattctg cacgcacctg gttgcgtgcc ctgtgtcaag     120
gaaggtaatg tcagtaggtg ctgggtccaa atcaccccca cattgtcagc cccgaacctc     180
ggagcggtca cggctcctct tcggagggtc gttgactact tagcgggagg ggctgccctc     240
tgctccgcac tatacgtcgg ggacgcgtgc ggggcagtgt tcttggtagg ccaaatgttc     300
```

```
acctataggc ctcgccagca tactacggtg caggactgca actgttccat ttacagcggc    360
catatcaccg gccaccgaat ggcatgggac atgatgatga attggtcacc tacgacagcc    420
ttggtgatgg cccaggtgct acggattccc aagtggtca ttgacatcat tgccggggc      480 cactgggggg tcttgttcgc cgtcgcatac ttcgcgtcag cggctaactg gctaaggtt     540 gtgctggtcc tgtttctgtt tgcggggggtc gatggc                             576
```

<210> SEQ ID NO 48
<211> LENGTH: 576
<212> TYPE: DNA
<213> ORGANISM: Homo sapiens

<400> SEQUENCE: 48

```
gttccttacc ggaatgcctc tggggtgtat catgttacca atgattgccc aaactcttcc    60
atagtctatg aggctgatga cctgatccta cacgcacctg gctgcgtgcc ctgtgtccgg   120
aaggataatg tcagtagatg ctgggttcat atcaccccca cactatcagc cccgagcctc   180
ggagcggtca cggctcctct tcggagggcc gttgattact ggcgggagg ggccgccctg    240 tgctccgcgt tatacgtcgg agacgtgtgc ggggcattgt ttttggtagg ccaaatgttc   300
acctataggc ctcgccagca tgctacggta caggactgca actgctccat ttacagtggc   360
catatcactg gccaccggat ggcatgggac atgatgatga attggtcacc cgcgacagcc   420
ttggtgatgg cccaaatgct acggattccc caggtggtca ttgacatcat tgccggggc    480 cactgggggg tcttgttcgc cgctgcatac ttcgcgtcgg cggctaactg gctaaggtt    540 gtgctggtct tgtttctgtt tgcgggggtt gatgcc                             576
```

<210> SEQ ID NO 49
<211> LENGTH: 576
<212> TYPE: DNA
<213> ORGANISM: Homo sapiens
<220> FEATURE:
<223> OTHER INFORMATION: Individual Isolate: SA7

<400> SEQUENCE: 49

```
gtcccctacc gaaatgcctc cggggtttat catgtcacca atgattgccc gaactcttcc    60
atagtctatg aggctgacaa cctgatcctg cacgcacctg gttgcgtgcc ctgtgtcaga   120
caaaataatg tcagtaggtg ctgggtccaa atcaccccca cattgtcagc cccgaacctc   180
ggagcggtca cggctcctct tcggagggcc gttgactacc tagcgggagg ggctgccctc   240
tgctccgcgc tatacgtcgg ggacgcgtgc ggggcagtgt ttttggtagg ccagatgttc   300
agctataggc ctcgccagca cactacggtg caggactgca actgttccat ttacagtggc   360
catatcaccg gccaccgaat ggcatgggac atgatgatga attggtcacc tacgacagcc   420
ttggtgatgg cccagttgct acggattccc caggtggtca tcgacatcat tgccggggc    480 cactgggggg tcttgttcgc cgccgcatat ttcgcgtcag cggctaactg gctaaggtt    540 gtgctggtct tgtttctgtt tgcggggggtc gatgcc                            576
```

<210> SEQ ID NO 50
<211> LENGTH: 576
<212> TYPE: DNA
<213> ORGANISM: Homo sapiens
<220> FEATURE:
<223> OTHER INFORMATION: Individual Isolate: SA13

<400> SEQUENCE: 50

```
gttccctacc gaaatgcctc tggggtttat catgtcacca atgattgccc aaactcttcc    60
```

-continued

```
atcgtctacg aggctgatga cctgatctta cacgcacctg gttgcgtgcc ctgtgttagg    120
cagggtaatg tcagtaggtg ctgggtccag atcaccccca cactgtcagc cccgagcctc    180
ggagcggtca cggctcctct tcggagggcc gttgactact tagcgggggg ggctgccctt    240
tgctccgcgt tatacgtcgg agacgcgtgc ggggcagtgt ttttggtagg tcaaatgttc    300
acctatagcc ctcgccggca taatgttgtg caggactgca actgtccat ttacagtggc     360 cacatcaccg gccaccggat ggcatgggac atgatgatga attggtcacc tacaacagct    420
ttggtgatgg cccagttgtt acggattccc caggtggtca ttgacatcat tgccggggcc    480
cactgggggg tcttgttcgc cgccgcatac tacgcgtcgg cggctaactg ggccaaggtt    540
gtgctggtcc tgtttctgtt tgcggggggtc gatgcc                             576
```

```
<210> SEQ ID NO 51
<211> LENGTH: 576
<212> TYPE: DNA
<213> ORGANISM: Homo sapiens
<220> FEATURE:
<223> OTHER INFORMATION: Individual Isolate: HK2

<400> SEQUENCE: 51
```

```
cttacctacg gcaactccag tgggctatac catctcacaa atgattgccc caactccagc     60
atcgtgctgg aggcggatgc tatgatcttg catttgcctg gatgcttgcc ttgtgtgagg    120
gtcgatgatc ggtccacctg ttggcatgct gtgaccccca ccctggccat accaaatgct    180
tccacgcccg caacgggatt ccgcaggcat gtggatcttc ttgcgggcgc cgcagtggtt    240
tgctcatccc tgtacatcgg ggacctgtgt ggctctctct ttttggcggg acaactattc    300
acctttcagc cccgccgtca ttggactgtg caagactgca actgctccat ctatacaggc    360
cacgtcaccg gccacaggat ggcttgggac atgatgatga actggtcacc cacaaccact    420
ctggtcctat ctagcatctt gagggtacct gagatttgtg cgagtgtgat atttggtggc    480
cattggggga tactactagc cgttgcctac tttggcatgg ctggcaactg gctaaaagtt    540
ctggctgttc tgttcctatt tgcaggggtt gaagca                              576
```

```
<210> SEQ ID NO 52
<211> LENGTH: 192
<212> TYPE: PRT
<213> ORGANISM: Homo sapiens
<220> FEATURE:
<223> OTHER INFORMATION: Individual Isolate: DK7

<400> SEQUENCE: 52
```

```
Tyr Gln Val Arg Asn Ser Thr Gly Leu Tyr His Val Thr Asn Asp Cys
 1               5                  10                  15

Pro Asn Ser Ser Ile Val Tyr Glu Ala Ala Asp Ala Ile Leu His Thr
                20                  25                  30

Pro Gly Cys Val Pro Cys Val Arg Glu Gly Asn Val Ser Arg Cys Trp
            35                  40                  45

Val Ala Met Thr Pro Thr Val Ala Thr Arg Asp Gly Lys Leu Pro Thr
        50                  55                  60

Ala Gln Leu Arg Arg His Ile Asp Leu Leu Val Gly Ser Ala Thr Leu
    65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
               100                 105                 110
```

```
Cys Asn Cys Ser Ile Tyr Pro Gly His Ile Thr Gly His Arg Met Ala
            115                 120                 125

Trp Asp Met Met Met Asn Trp Ser Pro Thr Thr Ala Leu Val Val Ala
        130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190

<210> SEQ ID NO 53
<211> LENGTH: 192
<212> TYPE: PRT
<213> ORGANISM: Homo sapiens
<220> FEATURE:
<223> OTHER INFORMATION: Individual Isolate: DK9

<400> SEQUENCE: 53

Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu His Ser
            20                  25                  30

Pro Gly Cys Val Pro Cys Val Arg Glu Gly Asn Ala Ser Lys Cys Trp
        35                  40                  45

Val Ala Val Ala Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
            100                 105                 110

Cys Asn Cys Ser Ile Tyr Pro Gly His Ile Thr Gly His Arg Met Ala
            115                 120                 125

Trp Asp Met Met Met Asn Trp Ser Pro Thr Ala Ala Leu Val Met Ala
        130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Val Val Leu Leu Leu Phe Thr Gly Val Asp Ala
            180                 185                 190

<210> SEQ ID NO 54
<211> LENGTH: 192
<212> TYPE: PRT
<213> ORGANISM: Homo sapiens
<220> FEATURE:
<223> OTHER INFORMATION: Individual Isolate: DR1

<400> SEQUENCE: 54

His Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Ala
            20                  25                  30

Pro Gly Cys Val Pro Cys Val Arg Glu Gly Asn Ala Ser Arg Cys Trp
```

```
                35                  40                  45
Val Ala Val Thr Pro Thr Val Ala Thr Arg Asp Gly Lys Leu Pro Thr
 50                  55                  60

Thr Gln Leu Arg Arg His Ile Asp Leu Leu Val Gly Ser Ala Thr Leu
 65                  70                  75                  80

Cys Ser Ala Leu Tyr Val Gly Asp Leu Cys Gly Ser Val Phe Leu Val
                 85                  90                  95

Gly Gln Leu Phe Thr Phe Ser Pro Arg Arg His Trp Thr Thr Gln Asp
                100                 105                 110

Cys Asn Cys Ser Ile Tyr Pro Gly His Ile Thr Gly His Arg Met Ala
                115                 120                 125

Trp Asp Met Met Met Asn Trp Ser Pro Thr Thr Ala Leu Val Met Ala
130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Val Val Leu Leu Leu Phe Ala Gly Val Asp Ala
                180                 185                 190
```

<210> SEQ ID NO 55
<211> LENGTH: 192
<212> TYPE: PRT
<213> ORGANISM: Homo sapiens
<220> FEATURE:
<223> OTHER INFORMATION: Individual Isolate: DR4

<400> SEQUENCE: 55

```
His Gln Val Arg Asn Ser Thr Gly Leu Tyr His Val Thr Asn Asp Cys
 1                   5                  10                  15

Pro Asn Ser Ser Ile Val Tyr Glu Ala Ala Asp Ala Ile Leu His Thr
                 20                  25                  30

Pro Gly Cys Val Pro Cys Val Arg Glu Gly Asn Thr Ser Arg Cys Trp
             35                  40                  45

Val Ala Val Thr Pro Thr Val Ala Thr Arg Asp Gly Lys Leu Pro Thr
 50                  55                  60

Thr Gln Leu Arg Arg His Ile Asp Leu Leu Val Gly Ser Ala Thr Leu
 65                  70                  75                  80

Cys Ser Ala Leu Tyr Val Gly Asp Leu Cys Gly Ser Val Phe Leu Val
                 85                  90                  95

Gly Gln Leu Phe Thr Phe Ser Pro Arg His His Trp Thr Thr Gln Asp
                100                 105                 110

Cys Asn Cys Ser Ile Tyr Pro Gly His Ile Thr Gly His Arg Met Ala
                115                 120                 125

Trp Asp Met Met Met Asn Trp Ser Pro Thr Thr Ala Leu Val Val Ala
130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
                180                 185                 190
```

<210> SEQ ID NO 56
<211> LENGTH: 192
<212> TYPE: PRT

```
<213> ORGANISM: Homo sapiens
<220> FEATURE:
<223> OTHER INFORMATION: Individual Isolate: S14

<400> SEQUENCE: 56

Tyr Gln Val Arg Asn Ser Thr Gly Leu Tyr His Val Thr Asn Asp Cys
 1               5                  10                  15

Pro Asn Ser Ser Ile Val Tyr Glu Thr Ala Asp Ala Ile Leu His Ala
                20                  25                  30

Pro Gly Cys Val Pro Cys Val Arg Glu Gly Asn Thr Ser Arg Cys Trp
            35                  40                  45

Val Ala Met Thr Pro Thr Val Ala Thr Arg Asp Gly Lys Leu Pro Ala
    50                  55                  60

Thr Gln Leu Arg Arg Tyr Ile Asp Leu Val Gly Ser Ala Thr Leu
 65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg Leu Trp Thr Thr Gln Asp
                100                 105                 110

Cys Asn Cys Ser Ile Tyr Pro Gly His Ile Thr Gly His Arg Met Ala
            115                 120                 125

Trp Asp Met Met Met Asn Trp Ser Pro Thr Thr Ala Leu Val Val Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
                180                 185                 190

<210> SEQ ID NO 57
<211> LENGTH: 192
<212> TYPE: PRT
<213> ORGANISM: Homo sapiens
<220> FEATURE:
<223> OTHER INFORMATION: Individual Isolate: S18

<400> SEQUENCE: 57

Tyr Gln Val Arg Asn Ser Thr Gly Leu Tyr His Val Thr Asn Asp Cys
 1               5                  10                  15

Pro Asn Ser Ser Ile Val Tyr Glu Thr Ala Asp Thr Ile Leu His Ser
                20                  25                  30

Pro Gly Cys Val Pro Cys Val Arg Glu Gly Asn Ala Ser Arg Cys Trp
            35                  40                  45

Val Pro Val Ala Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
 65                  70                  75                  80

Cys Ser Ala Leu Tyr Val Gly Asp Leu Cys Gly Ser Val Phe Leu Val
                85                  90                  95

Ser Gln Leu Phe Thr Ile Ser Pro Arg Arg His Trp Thr Thr Gln Asp
                100                 105                 110

Cys Asn Cys Ser Ile Tyr Pro Gly His Ile Thr Gly His Arg Met Ala
            115                 120                 125

Trp Asp Met Met Met Asn Trp Ser Pro Thr Thr Ala Leu Val Ile Ala
    130                 135                 140
```

```
Gln Leu Leu Arg Val Pro Gln Ala Val Leu Asp Met Ile Ala Gly Ala
145                 150                 155                 160

His Trp Gly Val Leu Ala Gly Ile Ala Tyr Phe Ser Met Ala Gly Asn
                165                 170                 175

Trp Ala Lys Val Leu Leu Val Leu Leu Phe Ala Gly Val Asp Ala
            180                 185                 190

<210> SEQ ID NO 58
<211> LENGTH: 192
<212> TYPE: PRT
<213> ORGANISM: Homo sapiens
<220> FEATURE:
<223> OTHER INFORMATION: Individual Isolate:  SW1

<400> SEQUENCE: 58

Tyr Gln Val Arg Asn Ser Ser Gly Leu Tyr His Val Thr Asn Asp Cys
1               5                   10                  15

Pro Asn Ser Ser Ile Val Tyr Glu Thr Ala Asp Ala Ile Leu His Ser
            20                  25                  30

Pro Gly Cys Val Pro Cys Val Arg Glu Asp Gly Ala Pro Lys Cys Trp
        35                  40                  45

Val Ala Val Ala Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Ser Gln Leu Phe Thr Phe Ser Pro Arg Arg His Trp Thr Thr Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Val Ala
    130                 135                 140

Gln Leu Leu Arg Ile Pro Gln Ala Val Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Ile Val Leu Leu Phe Ser Gly Val Asp Ala
            180                 185                 190

<210> SEQ ID NO 59
<211> LENGTH: 192
<212> TYPE: PRT
<213> ORGANISM: Homo sapiens
<220> FEATURE:
<223> OTHER INFORMATION: Individual Isolate:  US11

<400> SEQUENCE: 59

Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Met Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80
```

```
Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Leu Val Val Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Phe Ala Gly Val Asp Ala
                180                 185                 190
```

<210> SEQ ID NO 60
<211> LENGTH: 192
<212> TYPE: PRT
<213> ORGANISM: Homo sapiens
<220> FEATURE:
<223> OTHER INFORMATION: Individual Isolate: D1

<400> SEQUENCE: 60

```
Tyr Glu Val Arg Asn Val Ser Gly Val Tyr His Val Thr Asn Asp Cys
 1               5                  10                  15

Ser Asn Ser Ser Ile Val Tyr Glu Thr Ala Asp Met Ile Met His Thr
            20                  25                  30

Pro Gly Cys Val Pro Cys Val Arg Glu Asp Asn Ser Ser Arg Cys Trp
        35                  40                  45

Val Ala Leu Thr Pro Thr Leu Ala Ala Arg Asn Gly Asn Val Pro Thr
    50                  55                  60

Thr Ala Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Ile
                85                  90                  95

Ser Gln Leu Phe Thr Leu Ser Pro Arg Arg His Glu Thr Val Gln Glu
            100                 105                 110

Cys Asn Cys Ser Ile Tyr Pro Gly His Val Thr Gly His Arg Met Ala
        115                 120                 125

Trp Asp Met Met Met Asn Trp Ser Pro Thr Thr Ala Leu Val Val Ser
    130                 135                 140

Gln Leu Leu Arg Ile Pro Gln Ala Val Met Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Phe Ala Gly Val Asp Gly
                180                 185                 190
```

<210> SEQ ID NO 61
<211> LENGTH: 192
<212> TYPE: PRT
<213> ORGANISM: Homo sapiens
<220> FEATURE:
<223> OTHER INFORMATION: Individual Isolate: D3

<400> SEQUENCE: 61

```
Tyr Glu Val Arg Asn Val Ser Gly Val Tyr Gln Val Thr Asn Asp Cys
```

```
                1               5                    10                   15
Ser Asn Ser Ser Ile Val Tyr Glu Thr Ala Asp Met Ile Met His Thr
                20                   25                   30

Pro Gly Cys Val Pro Cys Val Arg Glu Asp Asn Ser Ser Arg Cys Trp
                35                   40                   45

Val Ala Leu Thr Pro Thr Leu Ala Ala Arg Asn Ser Ser Val Pro Thr
                50                   55                   60

Thr Thr Ile Arg Arg His Val Asp Leu Leu Val Gly Ala Ala Ala Phe
 65                   70                   75                   80

Cys Ser Ala Met Tyr Val Gly Asp Leu Cys Gly Ser Val Phe Leu Val
                85                   90                   95

Ser Gln Leu Phe Thr Phe Ser Pro Arg Arg His Glu Thr Val Gln Glu
                100                  105                  110

Cys Asn Cys Ser Ile Tyr Pro Gly His Val Thr Gly His Arg Met Ala
                115                  120                  125

Trp Asp Met Met Met Asn Trp Ser Pro Thr Ala Leu Val Val Ser
                130                  135                  140

Gln Leu Leu Arg Ile Pro Gln Ala Val Val Asp Met Val Ala Gly Ala
145                  150                  155                  160

His Trp Gly Val Leu Ala Gly Leu Ala Tyr Tyr Ser Met Val Gly Asn
                165                  170                  175

Trp Ala Lys Val Leu Ile Val Met Leu Leu Phe Ala Gly Val Asp Gly
                180                  185                  190

<210> SEQ ID NO 62
<211> LENGTH: 192
<212> TYPE: PRT
<213> ORGANISM: Homo sapiens
<220> FEATURE:
<223> OTHER INFORMATION: Individual Isolate: DK1

<400> SEQUENCE: 62

Tyr Glu Val Arg Asn Val Ser Gly Val Tyr His Val Thr Asn Asp Cys
 1               5                    10                   15

Ser Asn Ser Ser Ile Val Tyr Glu Ala Val Asp Val Ile Met His Thr
                20                   25                   30

Pro Gly Cys Val Pro Cys Val Arg Glu Asn Asn His Ser Arg Cys Trp
                35                   40                   45

Val Ala Leu Thr Pro Thr Leu Ala Ala Arg Asn Ala Ser Ile Pro Thr
                50                   55                   60

Thr Thr Ile Arg Arg His Val Asp Leu Leu Val Gly Ala Ala Ala Phe
 65                   70                   75                   80

Cys Ser Ala Met Tyr Val Gly Asp Leu Cys Gly Ser Val Phe Leu Val
                85                   90                   95

Ser Gln Leu Phe Thr Phe Ser Pro Arg Arg His Glu Thr Ala Gln Asp
                100                  105                  110

Cys Asn Cys Ser Ile Tyr Pro Gly His Val Ser Gly His Arg Met Ala
                115                  120                  125

Trp Asp Met Met Met Asn Trp Ser Pro Thr Thr Ala Leu Val Leu Ser
                130                  135                  140

Gln Leu Leu Arg Ile Pro Gln Ala Val Val Asp Met Val Ala Gly Ala
145                  150                  155                  160

His Trp Gly Val Leu Ala Gly Leu Ala Tyr Tyr Ser Met Ala Gly Asn
                165                  170                  175

Trp Ala Lys Val Leu Ile Val Leu Leu Leu Phe Ala Gly Val Asp Gly
```

-continued

```
                  180                 185                 190

<210> SEQ ID NO 63
<211> LENGTH: 192
<212> TYPE: PRT
<213> ORGANISM: Homo sapiens
<220> FEATURE:
<223> OTHER INFORMATION: Individual Isolate: HK3

<400> SEQUENCE: 63

Tyr Glu Val Arg Asn Val Ser Gly Ile Tyr His Val Thr Asn Asp Cys
  1               5                  10                  15

Ser Asn Ser Ser Val Val Tyr Glu Thr Ala Asp Met Ile Met His Thr
                 20                  25                  30

Pro Gly Cys Val Pro Cys Val Arg Glu Asn Asn Ser Ser Arg Cys Trp
             35                  40                  45

Val Ala Leu Thr Pro Thr Leu Ala Ala Arg Asn Val Ser Val Pro Thr
         50                  55                  60

Thr Thr Ile Arg Arg His Val Asp Leu Leu Val Gly Ala Ala Ala Phe
 65                  70                  75                  80

Cys Ser Ala Met Tyr Val Gly Asp Leu Cys Gly Ser Val Phe Leu Val
                 85                  90                  95

Ser Gln Leu Phe Thr Phe Ser Pro Arg Arg His Glu Thr Val Gln Asp
                100                 105                 110

Cys Asn Cys Ser Leu Tyr Pro Gly His Val Ser Gly His Arg Met Ala
            115                 120                 125

Trp Asp Met Met Met Asn Trp Ser Pro Thr Ala Ala Leu Val Val Ser
130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
                180                 185                 190

<210> SEQ ID NO 64
<211> LENGTH: 192
<212> TYPE: PRT
<213> ORGANISM: Homo sapiens
<220> FEATURE:
<223> OTHER INFORMATION: Individual Isolate: HK4

<400> SEQUENCE: 64

His Glu Val His Asn Val Ser Gly Ile Tyr His Val Thr Asn Asp Cys
  1               5                  10                  15

Ser Asn Ser Ser Ile Val Tyr Glu Ala Ala Asp Met Ile Met His Thr
                 20                  25                  30

Pro Gly Cys Val Pro Cys Val Arg Glu Asn Asn Ser Ser Arg Cys Trp
             35                  40                  45

Val Ala Leu Thr Pro Thr Leu Ala Ala Arg Asn Ala Ser Ile Pro Thr
         50                  55                  60

Thr Thr Ile Arg Arg His Val Asp Leu Leu Val Gly Ala Ala Ala Phe
 65                  70                  75                  80

Cys Ser Ala Met Tyr Val Gly Asp Leu Cys Gly Ser Val Phe Leu Val
                 85                  90                  95

Ser Gln Leu Phe Thr Phe Ser Pro Arg Arg His Glu Thr Val Gln Asp
                100                 105                 110
```

```
Cys Asn Cys Ser Ile Tyr Pro Gly His Val Ser Gly His Arg Met Ala
            115                 120                 125

Trp Asp Met Met Asn Trp Ser Pro Thr Ala Ala Leu Val Val Ser
130                 135                 140

Gln Leu Leu Arg Leu Pro Gln Ala Val Met Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
                180                 185                 190

<210> SEQ ID NO 65
<211> LENGTH: 192
<212> TYPE: PRT
<213> ORGANISM: Homo sapiens
<220> FEATURE:
<223> OTHER INFORMATION: Individual Isolate: HK5

<400> SEQUENCE: 65

Tyr Glu Val Arg Asn Val Ser Gly Val Tyr His Val Thr Asn Asp Cys
  1               5                  10                  15

Ser Asn Leu Ser Ile Val Tyr Glu Thr Thr Asp Met Ile Met His Thr
                 20                  25                  30

Pro Gly Cys Val Pro Cys Val Arg Glu Asn Asn Ser Ser Arg Cys Trp
             35                  40                  45

Val Ala Leu Ala Pro Thr Leu Ala Ala Arg Asn Ala Ser Val Pro Thr
         50                  55                  60

Thr Ala Ile Arg Arg His Val Asp Leu Leu Val Gly Ala Ala Ala Phe
 65                  70                  75                  80

Cys Ser Ala Met Tyr Val Gly Asp Leu Cys Gly Ser Val Phe Leu Val
                 85                  90                  95

Ser Gln Leu Phe Thr Phe Ser Pro Arg Arg His Glu Thr Val Gln Asp
                100                 105                 110

Cys Asn Cys Ser Ile Tyr Pro Gly His Val Thr Gly His Arg Met Ala
            115                 120                 125

Trp Asp Met Met Asn Trp Ser Pro Thr Thr Ala Leu Val Val Ser
130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
                180                 185                 190

<210> SEQ ID NO 66
<211> LENGTH: 192
<212> TYPE: PRT
<213> ORGANISM: Homo sapiens
<220> FEATURE:
<223> OTHER INFORMATION: Individual Isolate: HK8

<400> SEQUENCE: 66

Tyr Glu Val Arg Asn Val Ser Gly Ile Tyr His Val Thr Asn Asp Cys
  1               5                  10                  15

Ser Asn Ser Ser Ile Val Tyr Glu Thr Ala Asp Met Ile Met His Thr
                 20                  25                  30

Pro Gly Cys Met Pro Cys Val Arg Glu Asn Asn Ser Ser Arg Cys Trp
             35                  40                  45
```

-continued

```
Val Ala Leu Thr Pro Thr Leu Ala Ala Arg Asn Val Ser Val Pro Thr
     50                  55                  60
Thr Thr Ile Arg Arg His Val Asp Leu Val Gly Ala Ala Ala Phe
 65                  70                  75                  80
Cys Ser Ala Met Tyr Val Gly Asp Leu Cys Gly Ser Val Phe Leu Val
                 85                  90                  95
Ser Gln Leu Phe Thr Phe Ser Pro Arg Arg His Glu Thr Val Gln Asp
                100                 105                 110
Cys Asn Cys Ser Ile Tyr Pro Gly His Val Ser Gly His Arg Met Ala
            115                 120                 125
Trp Asp Met Met Met Asn Trp Ser Pro Thr Ala Leu Val Val Ser
130                 135                 140
Gln Leu Leu Arg Ile Pro Gln Ala Ile Val Asp Met Val Ala Gly Ala
145                 150                 155                 160
His Trp Gly Val Leu Ala Gly Leu Ala Tyr Tyr Ser Met Val Gly Asn
                165                 170                 175
Trp Ala Lys Val Leu Ile Val Met Leu Leu Phe Ala Gly Val Asp Gly
                180                 185                 190

<210> SEQ ID NO 67
<211> LENGTH: 192
<212> TYPE: PRT
<213> ORGANISM: Homo sapiens
<220> FEATURE:
<223> OTHER INFORMATION: Individual Isolate: IND5

<400> SEQUENCE: 67

Tyr Glu Val Arg Asn Val Ser Gly Val Tyr His Val Thr Asn Asp Cys
 1               5                  10                  15
Ser Asn Ser Ser Ile Val Tyr Glu Ala Ala Asp Met Ile Met His Thr
                 20                  25                  30
Pro Gly Cys Val Pro Cys Val Arg Glu Gly Asn Ser Ser Arg Cys Trp
             35                  40                  45
Val Ala Leu Thr Pro Thr Leu Ala Ala Arg Asn Ala Ser Val Ser Thr
     50                  55                  60
Thr Thr Ile Arg His His Val Asp Leu Val Gly Ala Ala Ala Phe
 65                  70                  75                  80
Cys Ser Ala Met Tyr Val Gly Asp Leu Cys Gly Ser Val Phe Leu Val
                 85                  90                  95
Ser Gln Leu Phe Thr Phe Ser Pro Arg Arg His Glu Thr Val Gln Asp
                100                 105                 110
Cys Asn Cys Ser Ile Tyr Pro Gly His Val Ser Gly His Arg Met Ala
            115                 120                 125
Trp Asp Met Met Met Asn Trp Ser Pro Thr Ala Ala Leu Val Val Ser
130                 135                 140
Gln Leu Leu Arg Ile Pro Gln Ala Val Val Asp Met Val Ala Gly Ala
145                 150                 155                 160
His Trp Gly Ile Leu Ala Gly Leu Ala Tyr Tyr Ser Met Val Gly Asn
                165                 170                 175
Trp Ala Lys Val Leu Ile Val Met Leu Leu Phe Ala Gly Val Asp Gly
                180                 185                 190

<210> SEQ ID NO 68
<211> LENGTH: 192
<212> TYPE: PRT
<213> ORGANISM: Homo sapiens
```

```
<220> FEATURE:
<223> OTHER INFORMATION: Individual Isolate:   IND8

<400> SEQUENCE: 68
```

| Tyr | Glu | Val | Arg | Asn | Val | Ser | Gly | Val | Tyr | His | Val | Thr | Asn | Asp | Cys |
|---|---|---|---|---|---|---|---|---|---|---|---|---|---|---|---|
| 1 | | | | 5 | | | | | 10 | | | | | 15 | |

| Ser | Asn | Ser | Ser | Ile | Val | Tyr | Glu | Ala | Ala | Asp | Met | Ile | Met | His | Thr |
|---|---|---|---|---|---|---|---|---|---|---|---|---|---|---|---|
| | | | 20 | | | | | 25 | | | | | 30 | | |

| Pro | Gly | Cys | Val | Pro | Cys | Val | Arg | Glu | Gly | Asn | Phe | Ser | Ser | Cys | Trp |
|---|---|---|---|---|---|---|---|---|---|---|---|---|---|---|---|
| | | 35 | | | | | 40 | | | | | 45 | | | |

| Val | Ala | Leu | Thr | Pro | Thr | Leu | Ala | Ala | Arg | Asn | Ala | Ser | Val | Pro | Thr |
|---|---|---|---|---|---|---|---|---|---|---|---|---|---|---|---|
| | 50 | | | | | 55 | | | | | 60 | | | | |

| Thr | Thr | Ile | Arg | Arg | His | Val | Asp | Leu | Leu | Val | Gly | Ala | Ala | Ala | Phe |
|---|---|---|---|---|---|---|---|---|---|---|---|---|---|---|---|
| 65 | | | | | 70 | | | | | 75 | | | | | 80 |

| Cys | Ser | Ala | Met | Tyr | Val | Gly | Asp | Leu | Cys | Gly | Ser | Val | Phe | Leu | Val |
|---|---|---|---|---|---|---|---|---|---|---|---|---|---|---|---|
| | | | | 85 | | | | | 90 | | | | | 95 | |

| Ser | Gln | Leu | Phe | Thr | Phe | Ser | Pro | Arg | Arg | His | Glu | Thr | Val | Gln | Asp |
|---|---|---|---|---|---|---|---|---|---|---|---|---|---|---|---|
| | | | | 100 | | | | | 105 | | | | | 110 | |

| Cys | Asn | Cys | Ser | Ile | Tyr | Pro | Gly | His | Val | Ser | Gly | His | Arg | Met | Ala |
|---|---|---|---|---|---|---|---|---|---|---|---|---|---|---|---|
| | | | 115 | | | | | 120 | | | | | 125 | | |

| Trp | Asp | Met | Met | Met | Asn | Trp | Ser | Pro | Thr | Ala | Ala | Leu | Val | Val | Ser |
|---|---|---|---|---|---|---|---|---|---|---|---|---|---|---|---|
| | | 130 | | | | | 135 | | | | | 140 | | | |

| Gln | Leu | Leu | Arg | Ile | Pro | Gln | Ala | Val | Val | Asp | Met | Val | Ala | Gly | Ala |
|---|---|---|---|---|---|---|---|---|---|---|---|---|---|---|---|
| 145 | | | | | 150 | | | | | 155 | | | | | 160 |

| His | Trp | Gly | Ile | Leu | Ala | Gly | Leu | Ala | Tyr | Tyr | Ser | Met | Val | Gly | Asn |
|---|---|---|---|---|---|---|---|---|---|---|---|---|---|---|---|
| | | | | 165 | | | | | 170 | | | | | 175 | |

| Trp | Ala | Lys | Val | Leu | Ile | Val | Met | Leu | Leu | Phe | Ala | Gly | Val | Asp | Gly |
|---|---|---|---|---|---|---|---|---|---|---|---|---|---|---|---|
| | | | 180 | | | | | 185 | | | | | 190 | | |

```
<210> SEQ ID NO 69
<211> LENGTH: 192
<212> TYPE: PRT
<213> ORGANISM: Homo sapiens
<220> FEATURE:
<223> OTHER INFORMATION: Individual Isolate:   P10

<400> SEQUENCE: 69
```

| Tyr | Glu | Val | Arg | Asn | Val | Ser | Gly | Val | Tyr | His | Val | Thr | Asn | Asp | Cys |
|---|---|---|---|---|---|---|---|---|---|---|---|---|---|---|---|
| 1 | | | | 5 | | | | | 10 | | | | | 15 | |

| Ser | Asn | Ser | Ser | Ile | Val | Tyr | Glu | Ala | Ala | Asp | Met | Ile | Met | His | Thr |
|---|---|---|---|---|---|---|---|---|---|---|---|---|---|---|---|
| | | | 20 | | | | | 25 | | | | | 30 | | |

| Pro | Gly | Cys | Val | Pro | Cys | Val | Arg | Glu | Asn | Asn | Ser | Ser | Arg | Cys | Trp |
|---|---|---|---|---|---|---|---|---|---|---|---|---|---|---|---|
| | | 35 | | | | | 40 | | | | | 45 | | | |

| Val | Ala | Leu | Thr | Pro | Thr | Leu | Ala | Ala | Arg | Asn | Ser | Ser | Val | Pro | Thr |
|---|---|---|---|---|---|---|---|---|---|---|---|---|---|---|---|
| | 50 | | | | | 55 | | | | | 60 | | | | |

| Thr | Ala | Ile | Arg | Arg | His | Val | Asp | Leu | Leu | Val | Gly | Ala | Ala | Ala | Phe |
|---|---|---|---|---|---|---|---|---|---|---|---|---|---|---|---|
| 65 | | | | | 70 | | | | | 75 | | | | | 80 |

| Cys | Ser | Ala | Met | Tyr | Val | Gly | Asp | Leu | Cys | Gly | Ser | Val | Leu | Leu | Val |
|---|---|---|---|---|---|---|---|---|---|---|---|---|---|---|---|
| | | | | 85 | | | | | 90 | | | | | 95 | |

| Ser | Gln | Leu | Phe | Thr | Phe | Ser | Pro | Arg | Arg | His | Trp | Thr | Val | Gln | Asp |
|---|---|---|---|---|---|---|---|---|---|---|---|---|---|---|---|
| | | | | 100 | | | | | 105 | | | | | 110 | |

| Cys | Asn | Cys | Ser | Ile | Tyr | Pro | Gly | His | Val | Ser | Gly | His | Arg | Met | Ala |
|---|---|---|---|---|---|---|---|---|---|---|---|---|---|---|---|
| | | | 115 | | | | | 120 | | | | | 125 | | |

| Trp | Asp | Met | Met | Met | Asn | Trp | Ser | Pro | Thr | Ala | Ala | Leu | Val | Val | Ser |
|---|---|---|---|---|---|---|---|---|---|---|---|---|---|---|---|
| | | 130 | | | | | 135 | | | | | 140 | | | |

| Gln | Leu | Leu | Arg | Ile | Pro | Gln | Ala | Ile | Leu | Asp | Val | Val | Ala | Gly | Ala |
|---|---|---|---|---|---|---|---|---|---|---|---|---|---|---|---|

145              150              155              160

His Trp Gly Val Leu Ala Gly Leu Ala Tyr Tyr Ser Met Val Gly Asn
                165              170              175

Trp Ala Lys Val Leu Ile Val Met Leu Leu Phe Ala Gly Val Asp Gly
            180              185              190

<210> SEQ ID NO 70
<211> LENGTH: 192
<212> TYPE: PRT
<213> ORGANISM: Homo sapiens
<220> FEATURE:
<223> OTHER INFORMATION: Individual Isolate: S9

<400> SEQUENCE: 70

Tyr Glu Val Arg Asn Val Ser Gly Ala Tyr His Val Thr Asn Asp Cys
 1               5                  10                  15

Ser Asn Ser Ser Ile Val Tyr Glu Ala Ala Asp Val Ile Met His Thr
                20                  25                  30

Pro Gly Cys Val Pro Cys Val Gln Glu Gly Asn Ser Ser Gln Cys Trp
            35                  40                  45

Val Ala Leu Thr Pro Thr Leu Ala Ala Arg Asn Ala Thr Val Pro Thr
        50                  55                  60

Thr Thr Ile Arg Arg His Val Asp Leu Leu Val Gly Ala Ala Val Phe
65                  70                  75                  80

Cys Ser Ala Met Tyr Val Gly Asp Leu Cys Gly Ser Val Phe Leu Ile
                85                  90                  95

Ser Gln Leu Phe Thr Ile Ser Pro Arg Arg His Glu Thr Val Gln Asn
                100                 105                 110

Cys Asn Cys Ser Ile Tyr Pro Gly His Val Thr Gly His Arg Met Ala
            115                 120                 125

Trp Asp Met Met Met Asn Trp Ser Pro Thr Thr Ala Leu Val Val Ser
        130                 135                 140

Gln Leu Leu Arg Ile Pro Gln Ala Val Met Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
            180                 185                 190

<210> SEQ ID NO 71
<211> LENGTH: 192
<212> TYPE: PRT
<213> ORGANISM: Homo sapiens
<220> FEATURE:
<223> OTHER INFORMATION: Individual Isolate: S45

<400> SEQUENCE: 71

Tyr Glu Val Arg Asn Val Ser Gly Ala Tyr His Val Thr Asn Asp Cys
 1               5                  10                  15

Ser Asn Ser Ser Ile Val Tyr Glu Ala Val Asp Val Ile Leu His Thr
                20                  25                  30

Pro Gly Cys Val Pro Cys Val Arg Glu Asn Asn Ser Ser Arg Cys Trp
            35                  40                  45

Val Ala Leu Thr Pro Thr Leu Ala Ala Arg Asn Ser Ser Val Pro Thr
        50                  55                  60

Thr Thr Ile Arg Arg His Val Asp Leu Leu Val Gly Ala Ala Ala Phe
65                  70                  75                  80

```
Cys Ser Ala Met Tyr Val Gly Asp Leu Cys Gly Ser Val Phe Leu Val
                85                  90                  95

Ser Gln Leu Phe Thr Phe Ser Pro Arg Arg His Glu Thr Val Gln Asp
                100                 105                 110

Cys Asn Cys Ser Ile Tyr Pro Gly His Val Thr Gly His Arg Met Ala
                115                 120                 125

Trp Asp Met Met Met Asn Trp Ser Pro Thr Ala Ala Leu Val Val Ser
130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
                180                 185                 190

<210> SEQ ID NO 72
<211> LENGTH: 192
<212> TYPE: PRT
<213> ORGANISM: Homo sapiens
<220> FEATURE:
<223> OTHER INFORMATION: Individual Isolate: SA10

<400> SEQUENCE: 72

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
                20                  25                  30

Pro Gly Cys Val Pro Cys Val Arg Glu Asn Asn Ser Ser Arg Cys Trp
                35                  40                  45

Val Ala Leu Thr Pro Thr Leu Ala Ala Arg Asn Ser Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg Tyr Glu Thr Val Gln Asp
                100                 105                 110

Cys Asn Cys Ser Ile Tyr Pro Gly Arg Val Thr Gly His Arg Met Ala
                115                 120                 125

Trp Asp Met Met Met Asn Trp Ser Pro Thr Thr Ala Leu Val Val Ser
130                 135                 140

Gln Leu Leu Arg Ile Pro Gln Ala Ile Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
                180                 185                 190

<210> SEQ ID NO 73
<211> LENGTH: 192
<212> TYPE: PRT
<213> ORGANISM: Homo sapiens
<220> FEATURE:
<223> OTHER INFORMATION: Individual Isolate: SW2

<400> SEQUENCE: 73

Tyr Glu Val Arg Asn Val Ser Gly Val Tyr His Val Thr Asn Asp Cys
1               5                   10                  15
```

Ser Asn Ser Ser Ile Val Tyr Glu Thr Ala Asp Met Ile Met His Thr
            20                  25                  30

Pro Gly Cys Val Pro Cys Val Arg Glu Ala Asn Ser Ser Arg Cys Trp
        35                  40                  45

Val Ala Leu Thr Pro Thr Leu Ala Ala Arg Asn Thr Ser Val Pro Thr
    50                  55                  60

Thr Thr Ile Arg Arg His Val Asp Leu Leu Val Gly Ala Ala Ala Phe
65                  70                  75                  80

Cys Ser Val Met Tyr Val Gly Asp Leu Cys Gly Ser Val Phe Leu Val
                85                  90                  95

Ser Gln Leu Phe Thr Phe Ser Pro Arg Arg His Glu Thr Val Gln Asp
            100                 105                 110

Cys Asn Cys Ser Ile Tyr Pro Gly His Val Ser Gly His Arg Met Ala
        115                 120                 125

Trp Asp Met Met Met Asn Trp Ser Pro Thr Ala Ala Leu Val Val Ser
    130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
            180                 185                 190

<210> SEQ ID NO 74
<211> LENGTH: 192
<212> TYPE: PRT
<213> ORGANISM: Homo sapiens
<220> FEATURE:
<223> OTHER INFORMATION: Individual Isolate: T3

<400> SEQUENCE: 74

Tyr Glu Val Arg Asn Val Ser Gly Val Tyr Tyr Val Thr Asn Asp Cys
1               5                   10                  15

Ser Asn Ser Ser Ile Val Tyr Glu Thr Ala Asp Met Ile Met His Thr
            20                  25                  30

Pro Gly Cys Val Pro Cys Val Arg Glu Ser Asn Ser Ser Arg Cys Trp
        35                  40                  45

Val Ala Leu Thr Pro Thr Leu Ala Ala Arg Asn Ala Ser Val Pro Thr
    50                  55                  60

Lys Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg His Glu Thr Val Gln Asp
            100                 105                 110

Cys Asn Cys Ser Ile Tyr Pro Gly His Val Thr Gly His Arg Met Ala
        115                 120                 125

Trp Asp Met Met Met Asn Trp Ser Pro Thr Thr Ala Leu Val Val Ser
    130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Leu Leu Leu Phe Ala Gly Val Asp Gly
            180                 185                 190

```
<210> SEQ ID NO 75
<211> LENGTH: 192
<212> TYPE: PRT
<213> ORGANISM: Homo sapiens
<220> FEATURE:
<223> OTHER INFORMATION: Individual Isolate: T10

<400> SEQUENCE: 75

Tyr Glu Val Arg Asn Val Ser Gly Met Tyr His Val Thr Asn Asp Cys
  1               5                  10                  15

Ser Asn Ser Ser Ile Val Phe Glu Ala Ala Asp Leu Ile Met His Thr
             20                  25                  30

Pro Gly Cys Val Pro Cys Val Arg Glu Gly Asn Ser Ser Arg Cys Trp
         35                  40                  45

Val Ala Leu Thr Pro Thr Leu Ala Ala Arg Asn Thr Ser Val Pro Thr
     50                  55                  60

Thr Thr Ile Arg Arg His Val Asp Leu Leu Val Gly Ala Ala Ala Phe
 65                  70                  75                  80

Cys Ser Ala Met Tyr Val Gly Asp Leu Cys Gly Ser Val Phe Leu Val
                 85                  90                  95

Ser Gln Leu Phe Thr Phe Ser Pro Arg Arg His Glu Thr Leu Gln Asp
            100                 105                 110

Cys Asn Cys Ser Ile Tyr Pro Gly His Leu Ser Gly His Arg Met Ala
        115                 120                 125

Trp Asp Met Met Met Asn Trp Ser Pro Thr Thr Ala Leu Val Val Ser
130                 135                 140

Gln Leu Leu Arg Ile Pro Gln Ala Val Met Asp Met Val Thr Gly Ala
145                 150                 155                 160

His Trp Gly Val Leu Ala Gly Leu Ala Tyr Tyr Ser Met Ala Gly Asn
                165                 170                 175

Trp Ala Lys Val Leu Ile Val Met Leu Leu Phe Ala Gly Val Asp Gly
            180                 185                 190

<210> SEQ ID NO 76
<211> LENGTH: 192
<212> TYPE: PRT
<213> ORGANISM: Homo sapiens
<220> FEATURE:
<223> OTHER INFORMATION: Individual Isolate: US6

<400> SEQUENCE: 76

Tyr Glu Val Arg Asn Val Ser Gly Met Tyr His Val Thr Asn Asp Cys
  1               5                  10                  15

Ser Asn Ser Ser Ile Val Tyr Glu Ala Ala Asp Met Ile Met His Thr
             20                  25                  30

Pro Gly Cys Val Pro Cys Val Arg Glu Asn Asn Ser Ser Arg Cys Trp
         35                  40                  45

Val Ala Leu Thr Pro Thr Leu Ala Ala Arg Asn Ala Ser Val Pro Thr
     50                  55                  60

Thr Thr Ile Arg Arg His Val Asp Leu Leu Val Gly Ala Ala Thr Phe
 65                  70                  75                  80

Cys Ser Ala Met Tyr Val Gly Asp Leu Cys Gly Ser Val Phe Leu Ile
                 85                  90                  95

Ser Gln Leu Phe Thr Phe Ser Pro Arg Gln His Glu Thr Val Gln Asp
            100                 105                 110

Cys Asn Cys Ser Ile Tyr Pro Gly His Val Ser Gly His Arg Met Ala
```

```
                    115                 120                 125
Trp Asp Met Met Met Asn Trp Ser Pro Thr Ala Ala Leu Val Val Ser
    130                 135                 140

Gln Leu Leu Arg Ile Pro Gln Ala Val Met Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Leu Leu Phe Ala Gly Val Asp Gly
                180                 185                 190

<210> SEQ ID NO 77
<211> LENGTH: 192
<212> TYPE: PRT
<213> ORGANISM: Homo sapiens
<220> FEATURE:
<223> OTHER INFORMATION: Individual Isolate: T2

<400> SEQUENCE: 77

Ala Gln Val Arg Asn Thr Ser Arg Gly Tyr Met Val Thr Asn Asp Cys
1               5                   10                  15

Ser Asn Glu Ser Ile Thr Trp Gln Leu Gln Ala Ala Val Leu His Val
                20                  25                  30

Pro Gly Cys Ile Pro Cys Glu Arg Leu Gly Asn Thr Ser Arg Cys Trp
            35                  40                  45

Ile Pro Val Thr Pro Asn Val Ala Val Arg Gln Pro Gly Ala Leu Thr
        50                  55                  60

Gln Gly Leu Arg Thr His Ile Asp Met Val Val Met Ser Ala Thr Leu
65                  70                  75                  80

Cys Ser Ala Leu Tyr Val Gly Asp Leu Cys Gly Gly Val Met Leu Ala
                85                  90                  95

Ala Gln Met Phe Ile Val Ser Pro Arg Arg His Trp Phe Val Gln Glu
                100                 105                 110

Cys Asn Cys Ser Ile Tyr Pro Gly Thr Ile Thr Gly His Arg Met Ala
            115                 120                 125

Trp Asp Met Met Met Asn Trp Ser Pro Thr Ala Thr Met Ile Leu Ala
    130                 135                 140

Tyr Ala Met Arg Val Pro Glu Val Ile Asp Ile Ile Gly Gly Ala
145                 150                 155                 160

His Trp Gly Val Met Phe Gly Leu Ala Tyr Phe Ser Met Gln Gly Ala
                165                 170                 175

Trp Ala Lys Val Ile Val Ile Leu Leu Ala Ala Gly Val Asp Ala
                180                 185                 190

<210> SEQ ID NO 78
<211> LENGTH: 192
<212> TYPE: PRT
<213> ORGANISM: Homo sapiens
<220> FEATURE:
<223> OTHER INFORMATION: Individual Isolate: T4

<400> SEQUENCE: 78

Ala Gln Val Lys Asn Thr Thr Asn Ser Tyr Met Val Thr Asn Asp Cys
1               5                   10                  15

Ser Asn Asp Ser Ile Thr Trp Gln Leu Gln Ala Ala Val Leu His Val
                20                  25                  30

Pro Gly Cys Val Pro Cys Glu Lys Thr Gly Asn Thr Ser Arg Cys Trp
            35                  40                  45
```

```
Ile Pro Val Ser Pro Asn Val Ala Val Arg Gln Pro Gly Ala Leu Thr
         50                  55                  60

Gln Gly Leu Arg Thr His Ile Asp Met Val Val Met Ser Ala Thr Leu
 65                  70                  75                  80

Cys Ser Ala Leu Tyr Val Gly Asp Leu Cys Gly Gly Val Met Leu Ala
                 85                  90                  95

Ala Gln Met Phe Ile Val Ser Pro Gln His His Trp Phe Val Gln Asp
                100                 105                 110

Cys Asn Cys Ser Ile Tyr Pro Gly Thr Ile Thr Gly His Arg Met Ala
                115                 120                 125

Trp Asp Met Met Met Asn Trp Ser Pro Thr Ala Thr Met Ile Leu Ala
        130                 135                 140

Tyr Ala Met Arg Val Pro Glu Val Ile Leu Asp Ile Val Ser Gly Ala
145                 150                 155                 160

His Trp Gly Val Met Phe Gly Leu Ala Tyr Phe Ser Met Gln Gly Ala
                165                 170                 175

Trp Ala Lys Val Val Ile Leu Leu Leu Ala Ala Gly Val Asp Ala
                180                 185                 190

<210> SEQ ID NO 79
<211> LENGTH: 192
<212> TYPE: PRT
<213> ORGANISM: Homo sapiens
<220> FEATURE:
<223> OTHER INFORMATION: Individual Isolate: T9

<400> SEQUENCE: 79

Ala Glu Val Lys Asn Thr Ser Thr Ser Tyr Met Val Thr Asn Asp Cys
 1               5                  10                  15

Ser Asn Asp Ser Ile Thr Trp Gln Leu Gln Ala Ala Val Leu His Val
                 20                  25                  30

Pro Gly Cys Val Pro Cys Glu Arg Val Gly Asn Ala Ser Arg Cys Trp
             35                  40                  45

Ile Pro Val Ser Pro Asn Val Ala Val Gln Arg Pro Gly Ala Leu Thr
         50                  55                  60

Gln Gly Leu Arg Thr His Ile Asp Met Val Val Met Ser Ala Thr Leu
 65                  70                  75                  80

Cys Ser Ala Leu Tyr Val Gly Asp Leu Cys Gly Gly Val Met Leu Ala
                 85                  90                  95

Ala Gln Met Phe Ile Ile Ser Pro Gln His His Trp Phe Val Gln Glu
                100                 105                 110

Cys Asn Cys Ser Ile Tyr Pro Gly Thr Ile Thr Gly His Arg Met Ala
                115                 120                 125

Trp Asp Met Met Met Asn Trp Ser Pro Thr Thr Thr Met Ile Leu Ala
        130                 135                 140

Tyr Ala Met Arg Val Pro Glu Val Ile Ile Asp Ile Ser Gly Ala
145                 150                 155                 160

His Trp Gly Val Met Phe Gly Leu Ala Tyr Phe Ser Met Gln Gly Ala
                165                 170                 175

Trp Ala Lys Val Val Ile Leu Leu Leu Thr Ala Gly Val Asp Ala
                180                 185                 190

<210> SEQ ID NO 80
<211> LENGTH: 192
<212> TYPE: PRT
<213> ORGANISM: Homo sapiens
<220> FEATURE:
```

<223> OTHER INFORMATION: Individual Isolate: US10

<400> SEQUENCE: 80

| Val | Gln | Val | Lys | Asn | Thr | Ser | Thr | Ser | Tyr | Met | Val | Thr | Asn | Asp | Cys |
|---|---|---|---|---|---|---|---|---|---|---|---|---|---|---|---|
| 1 | | | | 5 | | | | | 10 | | | | | 15 | |

| Ser | Asn | Asp | Ser | Ile | Thr | Trp | Gln | Leu | Glu | Ala | Ala | Val | Leu | His | Val |
|---|---|---|---|---|---|---|---|---|---|---|---|---|---|---|---|
| | | | 20 | | | | | 25 | | | | | 30 | | |

| Pro | Gly | Cys | Val | Pro | Cys | Glu | Lys | Val | Gly | Asn | Thr | Ser | Arg | Cys | Trp |
|---|---|---|---|---|---|---|---|---|---|---|---|---|---|---|---|
| | | 35 | | | | | 40 | | | | | 45 | | | |

| Ile | Pro | Val | Ser | Pro | Asn | Val | Ala | Val | Gln | Arg | Pro | Gly | Ala | Leu | Thr |
|---|---|---|---|---|---|---|---|---|---|---|---|---|---|---|---|
| | 50 | | | | | 55 | | | | | 60 | | | | |

| Gln | Gly | Leu | Arg | Thr | His | Ile | Asp | Met | Val | Val | Met | Ser | Ala | Thr | Leu |
|---|---|---|---|---|---|---|---|---|---|---|---|---|---|---|---|
| 65 | | | | | 70 | | | | | 75 | | | | | 80 |

| Cys | Ser | Ala | Leu | Tyr | Val | Gly | Asp | Phe | Cys | Gly | Met | Met | Leu | Ala |
|---|---|---|---|---|---|---|---|---|---|---|---|---|---|---|
| | | | | 85 | | | | | 90 | | | | | 95 |

| Ala | Gln | Met | Phe | Ile | Val | Ser | Pro | Arg | His | His | Ser | Phe | Val | Gln | Glu |
|---|---|---|---|---|---|---|---|---|---|---|---|---|---|---|---|
| | | | | 100 | | | | | 105 | | | | | 110 | |

| Cys | Asn | Cys | Ser | Ile | Tyr | Pro | Gly | Thr | Ile | Thr | Gly | His | Arg | Met | Ala |
|---|---|---|---|---|---|---|---|---|---|---|---|---|---|---|---|
| | | | 115 | | | | | 120 | | | | | 125 | | |

| Trp | Asp | Met | Met | Met | Asn | Trp | Ser | Pro | Thr | Ala | Thr | Leu | Ile | Leu | Ala |
|---|---|---|---|---|---|---|---|---|---|---|---|---|---|---|---|
| | 130 | | | | | 135 | | | | | 140 | | | | |

| Tyr | Val | Met | Arg | Val | Pro | Glu | Val | Ile | Ile | Asp | Ile | Ile | Ser | Gly | Ala |
|---|---|---|---|---|---|---|---|---|---|---|---|---|---|---|---|
| 145 | | | | | 150 | | | | | 155 | | | | | 160 |

| His | Trp | Gly | Val | Leu | Phe | Gly | Leu | Ala | Tyr | Phe | Ser | Met | Gln | Gly | Ala |
|---|---|---|---|---|---|---|---|---|---|---|---|---|---|---|---|
| | | | | 165 | | | | | 170 | | | | | 175 | |

| Trp | Ala | Lys | Val | Val | Val | Ile | Leu | Leu | Leu | Ala | Ala | Gly | Val | Asp | Ala |
|---|---|---|---|---|---|---|---|---|---|---|---|---|---|---|---|
| | | | 180 | | | | | 185 | | | | | 190 | | |

<210> SEQ ID NO 81
<211> LENGTH: 192
<212> TYPE: PRT
<213> ORGANISM: Homo sapiens
<220> FEATURE:
<223> OTHER INFORMATION: Individual Isolate: DK8

<400> SEQUENCE: 81

| Val | Glu | Val | Arg | Asn | Ile | Ser | Ser | Tyr | Tyr | Ala | Thr | Asn | Asp | Cys |
|---|---|---|---|---|---|---|---|---|---|---|---|---|---|---|
| 1 | | | | 5 | | | | | 10 | | | | | 15 |

| Ser | Asn | Asn | Ser | Ile | Thr | Trp | Gln | Leu | Thr | Asp | Ala | Val | Leu | His | Leu |
|---|---|---|---|---|---|---|---|---|---|---|---|---|---|---|---|
| | | | 20 | | | | | 25 | | | | | 30 | | |

| Pro | Gly | Cys | Val | Pro | Cys | Glu | Asn | Asp | Asn | Gly | Thr | Leu | Arg | Cys | Trp |
|---|---|---|---|---|---|---|---|---|---|---|---|---|---|---|---|
| | | 35 | | | | | 40 | | | | | 45 | | | |

| Ile | Gln | Val | Thr | Pro | Asn | Val | Ala | Val | Lys | His | Arg | Gly | Ala | Leu | Thr |
|---|---|---|---|---|---|---|---|---|---|---|---|---|---|---|---|
| | 50 | | | | | 55 | | | | | 60 | | | | |

| His | Asn | Leu | Arg | Thr | His | Val | Asp | Val | Ile | Val | Met | Ala | Ala | Thr | Val |
|---|---|---|---|---|---|---|---|---|---|---|---|---|---|---|---|
| 65 | | | | | 70 | | | | | 75 | | | | | 80 |

| Cys | Ser | Ala | Leu | Tyr | Val | Gly | Asp | Val | Cys | Gly | Ala | Val | Met | Ile | Val |
|---|---|---|---|---|---|---|---|---|---|---|---|---|---|---|---|
| | | | | 85 | | | | | 90 | | | | | 95 | |

| Ser | Gln | Ala | Leu | Ile | Ile | Ser | Pro | Glu | Arg | His | Asn | Phe | Thr | Gln | Glu |
|---|---|---|---|---|---|---|---|---|---|---|---|---|---|---|---|
| | | | | 100 | | | | | 105 | | | | | 110 | |

| Cys | Asn | Cys | Ser | Ile | Tyr | Gln | Gly | His | Ile | Thr | Gly | His | Arg | Met | Ala |
|---|---|---|---|---|---|---|---|---|---|---|---|---|---|---|---|
| | | | 115 | | | | | 120 | | | | | 125 | | |

| Trp | Asp | Met | Met | Leu | Asn | Trp | Ser | Pro | Thr | Leu | Thr | Met | Ile | Leu | Ala |
|---|---|---|---|---|---|---|---|---|---|---|---|---|---|---|---|
| | 130 | | | | | 135 | | | | | 140 | | | | |

| Tyr | Ala | Ala | Arg | Val | Pro | Glu | Leu | Ala | Leu | Gln | Val | Val | Phe | Gly | Gly |
|---|---|---|---|---|---|---|---|---|---|---|---|---|---|---|---|
| 145 | | | | | 150 | | | | | 155 | | | | | 160 |

His Trp Gly Val Val Phe Gly Leu Ala Tyr Phe Ser Met Gln Gly Ala
                165                 170                 175

Trp Ala Lys Val Ile Ala Ile Leu Leu Leu Val Ala Gly Val Asp Ala
            180                 185                 190

<210> SEQ ID NO 82
<211> LENGTH: 192
<212> TYPE: PRT
<213> ORGANISM: Homo sapiens
<220> FEATURE:
<223> OTHER INFORMATION: Individual Isolate: DK11

<400> SEQUENCE: 82

Val Glu Val Arg Asn Thr Ser Ser Tyr Tyr Ala Thr Asn Asp Cys
 1               5                  10                  15

Ser Asn Asn Ser Ile Thr Trp Gln Leu Thr Asn Ala Val Leu His Leu
            20                  25                  30

Pro Gly Cys Val Pro Cys Glu Asn Asp Asn Gly Thr Leu His Cys Trp
        35                  40                  45

Ile Gln Val Thr Pro Asn Val Ala Val Lys His Arg Gly Ala Leu Thr
    50                  55                  60

His Asn Leu Arg Ala His Ile Asp Met Ile Val Met Ala Ala Thr Val
65                  70                  75                  80

Cys Ser Ala Leu Tyr Val Gly Asp Val Cys Gly Ala Val Met Ile Val
                85                  90                  95

Ser Gln Ala Phe Ile Val Ser Pro Glu His His Phe Thr Gln Glu
            100                 105                 110

Cys Asn Cys Ser Ile Tyr Gln Gly His Ile Thr Gly His Arg Met Ala
        115                 120                 125

Trp Asp Met Met Leu Asn Trp Ser Pro Thr Leu Thr Met Ile Leu Ala
    130                 135                 140

Tyr Ala Ala Arg Val Pro Glu Leu Val Leu Glu Val Val Phe Gly Gly
145                 150                 155                 160

His Trp Gly Val Val Phe Gly Leu Ala Tyr Phe Ser Met Gln Gly Ala
                165                 170                 175

Trp Ala Lys Val Ile Ala Ile Leu Leu Leu Val Ala Gly Val Asp Ala
            180                 185                 190

<210> SEQ ID NO 83
<211> LENGTH: 192
<212> TYPE: PRT
<213> ORGANISM: Homo sapiens
<220> FEATURE:
<223> OTHER INFORMATION: Individual Isolate: SW3

<400> SEQUENCE: 83

Val Glu Val Arg Asn Ile Ser Ser Tyr Tyr Ala Thr Asn Asp Cys
 1               5                  10                  15

Ser Asn Ser Ser Ile Thr Trp Gln Leu Thr Asn Ala Val Leu His Leu
            20                  25                  30

Pro Gly Cys Val Pro Cys Glu Asn Asp Asn Gly Thr Leu His Cys Trp
        35                  40                  45

Ile Gln Val Thr Pro Asn Val Ala Val Lys His Arg Gly Ala Leu Thr
    50                  55                  60

His Asn Leu Arg Ala His Val Asp Met Ile Val Met Ala Ala Thr Val
65                  70                  75                  80

Cys Ser Ala Leu Tyr Val Gly Asp Met Cys Gly Ala Val Met Ile Val

-continued

```
                85                  90                  95
Ser Gln Ala Phe Ile Ile Ser Pro Glu Arg His Asn Phe Thr Gln Glu
                100                 105                 110

Cys Asn Cys Ser Ile Tyr Gln Gly Arg Ile Thr Gly His Arg Met Ala
            115                 120                 125

Trp Asp Met Met Leu Asn Trp Ser Pro Thr Leu Thr Met Ile Leu Ala
    130                 135                 140

Tyr Ala Ala Arg Val Pro Glu Leu Val Leu Glu Val Val Phe Gly Gly
145                 150                 155                 160

His Trp Gly Val Val Phe Gly Leu Ala Tyr Phe Ser Met Gln Gly Ala
                165                 170                 175

Trp Ala Lys Val Ile Ala Ile Leu Leu Leu Val Ala Gly Val Asp Ala
                180                 185                 190

<210> SEQ ID NO 84
<211> LENGTH: 192
<212> TYPE: PRT
<213> ORGANISM: Homo sapiens
<220> FEATURE:
<223> OTHER INFORMATION: Individual Isolate:  T8

<400> SEQUENCE: 84

Val Glu Val Arg Asn Thr Ser Phe Ser Tyr Tyr Ala Thr Asn Asp Cys
1               5                   10                  15

Ser Asn Asn Ser Ile Thr Trp Gln Leu Thr Asn Ala Val Leu His Leu
                20                  25                  30

Pro Gly Cys Val Pro Cys Glu Asn Asp Asn Gly Thr Leu Arg Cys Trp
            35                  40                  45

Ile Gln Val Thr Pro Asn Val Ala Val Lys His Arg Gly Ala Leu Thr
    50                  55                  60

His Asn Leu Arg Thr His Val Asp Val Ile Val Met Ala Ala Thr Val
65                  70                  75                  80

Cys Ser Ala Leu Tyr Val Gly Asp Val Cys Gly Ala Val Met Ile Ala
                85                  90                  95

Ser Gln Ala Phe Ile Ile Ser Pro Glu Arg His Asn Phe Thr Gln Glu
                100                 105                 110

Cys Asn Cys Ser Ile Tyr Gln Gly His Ile Thr Gly His Arg Met Ala
            115                 120                 125

Trp Asp Met Met Leu Asn Trp Ser Pro Thr Leu Thr Met Ile Leu Ala
    130                 135                 140

Tyr Ala Ala Arg Val Pro Glu Leu Val Leu Glu Val Val Phe Gly Gly
145                 150                 155                 160

His Trp Gly Val Val Phe Gly Leu Ala Tyr Phe Ser Met Gln Gly Ala
                165                 170                 175

Trp Ala Lys Val Ile Ala Ile Leu Leu Leu Val Ala Gly Val Asp Ala
                180                 185                 190

<210> SEQ ID NO 85
<211> LENGTH: 192
<212> TYPE: PRT
<213> ORGANISM: Homo sapiens
<220> FEATURE:
<223> OTHER INFORMATION: Individual Isolate:  S83

<400> SEQUENCE: 85

Val Glu Val Lys Asp Thr Gly Asp Ser Tyr Met Pro Thr Asn Asp Cys
1               5                   10                  15
```

-continued

```
Ser Asn Ser Ser Ile Val Trp Gln Leu Glu Gly Ala Val Leu His Thr
            20                  25                  30

Pro Gly Cys Val Pro Cys Glu Arg Thr Ala Asn Val Ser Arg Cys Trp
            35                  40                  45

Val Pro Val Ala Pro Asn Leu Ala Ile Ser Gln Pro Gly Ala Leu Thr
 50                  55                  60

Lys Gly Leu Arg Ala His Ile Asp Ile Val Met Ser Ala Thr Val
 65                  70                  75                  80

Cys Ser Ala Leu Tyr Val Gly Asp Val Cys Gly Ala Leu Met Leu Ala
            85                  90                  95

Ala Gln Val Val Val Ser Pro Gln His His Thr Phe Val Gln Glu
           100                 105                 110

Cys Asn Cys Ser Ile Tyr Pro Gly Arg Ile Thr Gly His Arg Met Ala
           115                 120                 125

Trp Asp Met Met Met Asn Trp Ser Pro Thr Thr Thr Met Leu Leu Ala
130                 135                 140

Tyr Leu Val Arg Ile Pro Glu Val Ile Leu Asp Ile Val Thr Gly Gly
145                 150                 155                 160

His Trp Gly Val Met Phe Gly Leu Ala Tyr Phe Ser Met Gln Gly Ser
           165                 170                 175

Trp Ala Lys Val Ile Val Ile Leu Leu Leu Thr Ala Gly Val Glu Ala
           180                 185                 190
```

<210> SEQ ID NO 86
<211> LENGTH: 192
<212> TYPE: PRT
<213> ORGANISM: Homo sapiens
<220> FEATURE:
<223> OTHER INFORMATION: Individual Isolate: DK12

<400> SEQUENCE: 86

```
Leu Glu Trp Arg Asn Val Ser Gly Leu Tyr Val Leu Thr Asn Asp Cys
 1               5                  10                  15

Ser Asn Ser Ser Ile Val Tyr Glu Ala Asp Asp Val Ile Leu His Thr
            20                  25                  30

Pro Gly Cys Val Pro Cys Val Gln Asp Gly Asn Thr Ser Thr Cys Trp
            35                  40                  45

Thr Ser Val Thr Pro Thr Val Ala Val Arg Tyr Val Gly Ala Thr Thr
 50                  55                  60

Ala Ser Ile Arg Ser His Val Asp Leu Leu Val Gly Ala Ala Thr Met
 65                  70                  75                  80

Cys Ser Ala Leu Tyr Val Gly Asp Val Cys Gly Ala Val Phe Leu Val
            85                  90                  95

Gly Gln Ala Phe Thr Phe Arg Pro Arg Arg His Gln Thr Val Gln Thr
           100                 105                 110

Cys Asn Cys Ser Leu Tyr Pro Gly His Leu Ser Gly His Arg Met Ala
           115                 120                 125

Trp Asp Met Met Met Asn Trp Ser Pro Ala Val Gly Met Val Val Ala
130                 135                 140

His Val Leu Arg Leu Pro Gln Thr Leu Phe Asp Ile Ile Ala Gly Ala
145                 150                 155                 160

His Trp Gly Ile Met Ala Gly Leu Ala Tyr Tyr Ser Met Gln Gly Asn
           165                 170                 175

Trp Ala Lys Val Ala Ile Ile Met Val Met Phe Ser Gly Val Asp Ala
           180                 185                 190
```

-continued

<210> SEQ ID NO 87
<211> LENGTH: 192
<212> TYPE: PRT
<213> ORGANISM: Homo sapiens
<220> FEATURE:
<223> OTHER INFORMATION: Individual Isolate: HK10

<400> SEQUENCE: 87

```
Leu Glu Trp Arg Asn Val Ser Gly Leu Tyr Val Leu Thr Asn Asp Cys
  1               5                  10                  15

Pro Asn Ser Ser Ile Val Tyr Glu Ala Asp Asp Val Ile Leu His Thr
             20                  25                  30

Pro Gly Cys Val Pro Cys Val Gln Asp Gly Asn Thr Ser Thr Cys Trp
         35                  40                  45

Thr Ser Val Thr Pro Thr Val Ala Val Arg Tyr Val Gly Ala Thr Thr
     50                  55                  60

Ala Ser Ile Arg Ser His Val Asp Leu Leu Val Gly Ala Ala Thr Met
 65                  70                  75                  80

Cys Ser Ala Leu Tyr Val Gly Asp Met Cys Gly Ala Val Phe Leu Val
                 85                  90                  95

Gly Gln Ala Phe Thr Phe Arg Pro Arg Arg His Gln Thr Val Gln Thr
            100                 105                 110

Cys Asn Cys Ser Leu Tyr Pro Gly His Leu Ser Gly His Arg Met Ala
        115                 120                 125

Trp Asp Met Met Met Asn Trp Ser Pro Ala Val Gly Met Val Val Ala
    130                 135                 140

His Val Leu Arg Leu Pro Gln Thr Leu Phe Asp Ile Ile Ala Gly Ala
145                 150                 155                 160

His Trp Gly Ile Leu Ala Gly Leu Ala Tyr Tyr Ser Met Gln Gly Asn
                165                 170                 175

Trp Ala Lys Val Ala Ile Ile Met Val Met Phe Ser Gly Val Asp Ala
            180                 185                 190
```

<210> SEQ ID NO 88
<211> LENGTH: 192
<212> TYPE: PRT
<213> ORGANISM: Homo sapiens
<220> FEATURE:
<223> OTHER INFORMATION: Individual Isolate: S2

<400> SEQUENCE: 88

```
Leu Glu Trp Arg Asn Thr Ser Gly Leu Tyr Val Leu Thr Asn Asp Cys
  1               5                  10                  15

Ser Asn Ser Ser Ile Val Tyr Glu Ala Asp Asp Val Ile Leu His Thr
             20                  25                  30

Pro Gly Cys Val Pro Cys Val Gln Asp Gly Asn Thr Ser Thr Cys Trp
         35                  40                  45

Thr Pro Val Thr Pro Thr Val Ala Val Arg Tyr Val Gly Ala Thr Thr
     50                  55                  60

Ala Ser Ile Arg Ser His Val Asp Leu Leu Val Gly Ala Ala Thr Met
 65                  70                  75                  80

Cys Ser Ala Leu Tyr Val Gly Asp Met Cys Gly Ala Val Phe Leu Val
                 85                  90                  95

Gly Gln Ala Phe Thr Phe Arg Pro Arg Arg His Gln Thr Val Gln Thr
            100                 105                 110

Cys Asn Cys Ser Leu Tyr Pro Gly His Leu Ser Gly His Arg Met Ala
        115                 120                 125
```

Trp Asp Met Met Met Asn Trp Ser Pro Ala Val Gly Met Val Val Ala
            130                 135                 140

His Val Leu Arg Leu Pro Gln Thr Val Phe Asp Ile Ile Ala Gly Ala
145                 150                 155                 160

His Trp Gly Ile Leu Ala Gly Leu Ala Tyr Tyr Ser Met Gln Gly Asn
                165                 170                 175

Trp Ala Lys Val Ala Ile Ile Met Val Met Phe Ser Gly Val Asp Ala
            180                 185                 190

<210> SEQ ID NO 89
<211> LENGTH: 192
<212> TYPE: PRT
<213> ORGANISM: Homo sapiens
<220> FEATURE:
<223> OTHER INFORMATION: Individual Isolate: S52

<400> SEQUENCE: 89

Leu Glu Trp Arg Asn Thr Ser Gly Leu Tyr Val Leu Thr Asn Asp Cys
  1               5                  10                  15

Ser Asn Ser Ser Ile Val Tyr Glu Ala Asp Asp Val Ile Leu His Thr
            20                  25                  30

Pro Gly Cys Val Pro Cys Val Gln Asp Gly Asn Thr Ser Met Cys Trp
        35                  40                  45

Thr Pro Val Thr Pro Thr Val Ala Val Arg Tyr Val Gly Ala Thr Thr
    50                  55                  60

Ala Ser Ile Arg Ser His Val Asp Leu Leu Val Gly Ala Ala Thr Leu
65                  70                  75                  80

Cys Ser Ala Leu Tyr Val Gly Asp Met Cys Gly Ala Val Phe Leu Val
                85                  90                  95

Gly Gln Ala Phe Thr Phe Arg Pro Arg Arg His Gln Thr Val Gln Thr
            100                 105                 110

Cys Asn Cys Ser Leu Tyr Pro Gly His Val Ser Gly His Arg Met Ala
        115                 120                 125

Trp Asp Met Met Met Asn Trp Ser Pro Ala Val Gly Met Val Val Ala
    130                 135                 140

His Ile Leu Arg Leu Pro Gln Thr Leu Phe Asp Ile Leu Ala Gly Ala
145                 150                 155                 160

His Trp Gly Ile Leu Ala Gly Leu Ala Tyr Tyr Ser Met Gln Gly Asn
                165                 170                 175

Trp Ala Lys Val Ala Ile Val Met Ile Met Phe Ser Gly Val Asp Ala
            180                 185                 190

<210> SEQ ID NO 90
<211> LENGTH: 192
<212> TYPE: PRT
<213> ORGANISM: Homo sapiens
<220> FEATURE:
<223> OTHER INFORMATION: Individual Isolate: S54

<400> SEQUENCE: 90

Leu Glu Trp Arg Asn Thr Ser Gly Leu Tyr Ile Leu Thr Asn Asp Cys
  1               5                  10                  15

Ser Asn Ser Ser Ile Val Tyr Glu Ala Asp Asp Val Ile Leu His Thr
            20                  25                  30

Pro Gly Cys Val Pro Cys Val Gln Asp Gly Asn Thr Ser Thr Cys Trp
        35                  40                  45

Thr Pro Val Thr Pro Thr Val Ala Val Arg Tyr Val Gly Ala Thr Thr

```
                  50                  55                  60

Ala Ser Ile Arg Ser His Val Asp Leu Leu Val Gly Ala Ala Thr Leu
 65                  70                  75                  80

Cys Ser Ala Leu Tyr Val Gly Asp Met Cys Gly Ala Val Phe Leu Val
                 85                  90                  95

Gly Gln Ala Phe Thr Phe Arg Pro Arg His Gln Thr Val Gln Thr
            100                 105                 110

Cys Asn Cys Ser Leu Tyr Pro Gly His Leu Ser Gly His Arg Met Ala
            115                 120                 125

Trp Asp Met Met Met Asn Trp Ser Pro Ala Val Gly Met Val Val Ala
130                 135                 140

His Ile Leu Arg Leu Pro Gln Thr Leu Phe Asp Ile Leu Ala Gly Ala
145                 150                 155                 160

His Trp Gly Ile Leu Ala Gly Leu Ala Tyr Tyr Ser Met Gln Gly Asn
                165                 170                 175

Trp Ala Lys Val Ala Ile Ile Met Ile Met Phe Ser Gly Val Asp Ala
                180                 185                 190

<210> SEQ ID NO 91
<211> LENGTH: 192
<212> TYPE: PRT
<213> ORGANISM: Homo sapiens
<220> FEATURE:
<223> OTHER INFORMATION: Individual Isolate:  Z4

<400> SEQUENCE: 91

Glu His Tyr Arg Asn Ala Ser Gly Ile Tyr His Ile Thr Asn Asp Cys
  1               5                  10                  15

Pro Asn Ser Ser Ile Val Tyr Glu Ala Asp His His Ile Leu His Leu
                 20                  25                  30

Pro Gly Cys Val Pro Cys Val Met Thr Gly Asn Thr Ser Arg Cys Trp
             35                  40                  45

Thr Pro Val Thr Pro Thr Val Ala Val Ala His Pro Gly Ala Pro Leu
 50                  55                  60

Glu Ser Phe Arg Arg His Val Asp Leu Met Val Gly Ala Ala Thr Leu
 65                  70                  75                  80

Cys Ser Ala Leu Tyr Val Gly Asp Leu Cys Gly Ala Phe Leu Met
                 85                  90                  95

Gly Gln Met Ile Thr Phe Arg Pro Arg His Trp Thr Thr Gln Glu
            100                 105                 110

Cys Asn Cys Ser Ile Tyr Thr Gly His Ile Thr Gly His Arg Met Ala
            115                 120                 125

Trp Asp Met Met Met Asn Trp Ser Pro Thr Thr Thr Leu Leu Leu Ala
130                 135                 140

Gln Ile Met Arg Val Pro Thr Ala Phe Leu Asp Met Val Ala Gly Gly
145                 150                 155                 160

His Trp Gly Val Leu Ala Gly Leu Ala Tyr Phe Ser Met Gln Gly Asn
                165                 170                 175

Trp Ala Lys Val Val Leu Val Leu Phe Leu Phe Ala Gly Val Asp Ala
                180                 185                 190

<210> SEQ ID NO 92
<211> LENGTH: 192
<212> TYPE: PRT
<213> ORGANISM: Homo sapiens
<220> FEATURE:
<223> OTHER INFORMATION: Individual Isolate:  Z1
```

```
<400> SEQUENCE: 92

Val His Tyr Arg Asn Ala Ser Gly Val Tyr His Val Thr Asn Asp Cys
 1               5                  10                  15

Pro Asn Thr Ser Ile Val Tyr Glu Thr Glu His Ile Met His Leu
             20                  25                  30

Pro Gly Cys Val Pro Cys Val Arg Thr Glu Asn Thr Ser Arg Cys Trp
             35                  40                  45

Val Pro Leu Thr Pro Thr Val Ala Ala Pro Tyr Pro Asn Ala Pro Leu
         50                  55                  60

Glu Ser Met Arg Arg His Val Asp Leu Met Val Gly Ala Ala Thr Met
 65                  70                  75                  80

Cys Ser Ala Phe Tyr Ile Gly Asp Leu Cys Gly Gly Val Phe Leu Val
                 85                  90                  95

Gly Gln Leu Phe Asp Phe Arg Pro Arg Arg His Trp Thr Thr Gln Asp
            100                 105                 110

Cys Asn Cys Ser Ile Tyr Pro Gly His Val Ser Gly His Arg Met Ala
            115                 120                 125

Trp Asp Met Met Met Asn Trp Ser Pro Thr Ser Ala Leu Ile Met Ala
130                 135                 140

Gln Ile Leu Arg Ile Pro Ser Ile Leu Gly Asp Leu Leu Thr Gly Gly
145                 150                 155                 160

His Trp Gly Val Leu Ala Gly Leu Ala Phe Phe Ser Met Gln Ser Asn
                165                 170                 175

Trp Ala Lys Val Ile Leu Val Leu Phe Leu Phe Ala Gly Val Glu Gly
            180                 185                 190

<210> SEQ ID NO 93
<211> LENGTH: 192
<212> TYPE: PRT
<213> ORGANISM: Homo sapiens
<220> FEATURE:
<223> OTHER INFORMATION: Individual Isolate:  Z6

<400> SEQUENCE: 93

Val Asn Tyr Arg Asn Ala Ser Gly Val Tyr His Val Thr Asn Asp Cys
 1               5                  10                  15

Pro Asn Ser Ser Ile Val Tyr Glu Ala Glu His Gln Ile Leu His Leu
             20                  25                  30

Pro Gly Cys Leu Pro Cys Val Arg Val Gly Asn Gln Ser Arg Cys Trp
             35                  40                  45

Val Ala Leu Thr Pro Thr Val Ala Val Ser Tyr Ile Gly Ala Pro Leu
         50                  55                  60

Asp Ser Leu Arg Arg His Val Asp Leu Met Val Gly Ala Ala Thr Val
 65                  70                  75                  80

Cys Ser Ala Leu Tyr Val Gly Asp Leu Cys Gly Gly Ala Phe Leu Val
                 85                  90                  95

Gly Gln Met Phe Ser Phe Gln Pro Arg Arg His Trp Thr Thr Gln Asp
            100                 105                 110

Cys Asn Cys Ser Ile Tyr Ala Gly His Ile Thr Gly His Arg Met Ala
            115                 120                 125

Trp Asp Met Met Met Asn Trp Ser Pro Thr Thr Leu Leu Leu Ala
130                 135                 140

Gln Val Met Arg Ile Pro Ser Thr Leu Val Asp Leu Leu Ala Gly Gly
145                 150                 155                 160
```

-continued

His Trp Gly Val Leu Val Gly Leu Ala Tyr Phe Ser Met Gln Ala Asn
            165                 170                 175

Trp Ala Lys Val Ile Leu Val Leu Phe Leu Phe Ala Gly Val Asp Ala
            180                 185                 190

<210> SEQ ID NO 94
<211> LENGTH: 192
<212> TYPE: PRT
<213> ORGANISM: Homo sapiens
<220> FEATURE:
<223> OTHER INFORMATION: Individual Isolate: Z7

<400> SEQUENCE: 94

Val Asn Tyr His Asn Ala Ser Gly Val Tyr His Ile Thr Asn Asp Cys
 1               5                  10                  15

Pro Asn Ser Ser Ile Met Tyr Glu Ala Glu His His Ile Leu His Leu
            20                  25                  30

Pro Gly Cys Val Pro Cys Val Arg Glu Gly Asn Gln Ser Arg Cys Trp
         35                  40                  45

Val Ala Leu Thr Pro Thr Val Ala Ala Pro Tyr Ile Gly Ala Pro Leu
     50                  55                  60

Glu Ser Ile Arg Arg His Val Asp Leu Met Val Gly Ala Ala Thr Val
 65                  70                  75                  80

Cys Ser Ala Leu Tyr Ile Gly Asp Leu Cys Gly Gly Val Phe Leu Val
                 85                  90                  95

Gly Gln Met Phe Ser Phe Gln Pro Arg Arg His Trp Thr Thr Gln Asp
            100                 105                 110

Cys Asn Cys Ser Ile Tyr Ala Gly His Val Thr Gly His Arg Met Ala
        115                 120                 125

Trp Asp Met Met Met Asn Trp Ser Pro Thr Thr Thr Leu Val Leu Ala
    130                 135                 140

Gln Val Met Arg Ile Pro Ser Thr Leu Val Asp Leu Leu Thr Gly Gly
145                 150                 155                 160

His Trp Gly Ile Leu Ile Gly Val Ala Tyr Phe Cys Met Gln Ala Asn
            165                 170                 175

Trp Ala Lys Val Ile Leu Val Leu Phe Leu Tyr Ala Gly Val Asp Ala
            180                 185                 190

<210> SEQ ID NO 95
<211> LENGTH: 192
<212> TYPE: PRT
<213> ORGANISM: Homo sapiens
<220> FEATURE:
<223> OTHER INFORMATION: Individual Isolate: DK13

<400> SEQUENCE: 95

Tyr Asn Tyr Arg Asn Ser Ser Gly Val Tyr His Val Thr Asn Asp Cys
 1               5                  10                  15

Pro Asn Ser Ser Ile Val Tyr Glu Thr Asp Tyr His Ile Leu His Leu
            20                  25                  30

Pro Gly Cys Val Pro Cys Val Arg Glu Gly Asn Lys Ser Thr Cys Trp
         35                  40                  45

Val Ser Leu Thr Pro Thr Val Ala Ala Gln His Leu Asn Ala Pro Leu
     50                  55                  60

Glu Ser Leu Arg Arg His Val Asp Leu Met Val Gly Ala Thr Leu
 65                  70                  75                  80

Cys Ser Ala Leu Tyr Ile Gly Asp Val Cys Gly Gly Val Phe Leu Val
                 85                  90                  95

```
Gly Gln Leu Phe Thr Phe Gln Pro Arg Arg His Trp Thr Thr Gln Asp
                100                 105                 110

Cys Asn Cys Ser Ile Tyr Thr Gly His Ile Thr Gly His Arg Met Ala
            115                 120                 125

Trp Asp Met Met Met Asn Trp Ser Pro Thr Ala Thr Leu Val Leu Ala
        130                 135                 140

Gln Leu Met Arg Ile Pro Gly Ala Met Val Asp Leu Leu Ala Gly Gly
145                 150                 155                 160

His Trp Gly Ile Leu Val Gly Ile Ala Tyr Phe Ser Met Gln Ala Asn
                165                 170                 175

Trp Ala Lys Val Ile Leu Val Leu Phe Leu Phe Ala Gly Val Asp Ala
                180                 185                 190

<210> SEQ ID NO 96
<211> LENGTH: 192
<212> TYPE: PRT
<213> ORGANISM: Homo sapiens
<220> FEATURE:
<223> OTHER INFORMATION: Individual Isolate:  SA1

<400> SEQUENCE: 96

Val Pro Tyr Arg Asn Ala Ser Gly Val Tyr His Val Thr Asn Asp Cys
  1               5                  10                  15

Pro Asn Ser Ser Ile Val Tyr Glu Ala Asp Ser Leu Ile Leu His Ala
                20                  25                  30

Pro Gly Cys Val Pro Cys Val Arg Gln Asp Asn Val Ser Arg Cys Trp
            35                  40                  45

Val Gln Ile Thr Pro Thr Leu Ser Ala Pro Thr Phe Gly Ala Val Thr
     50                  55                  60

Ala Pro Leu Arg Arg Ala Val Asp Tyr Leu Ala Gly Ala Ala Leu
 65                 70                  75                  80

Cys Ser Ala Leu Tyr Val Gly Asp Ala Cys Gly Ala Val Phe Leu Val
                85                  90                  95

Gly Gln Met Phe Thr Tyr Arg Pro Arg Gln His Thr Thr Val Gln Asp
                100                 105                 110

Cys Asn Cys Ser Ile Tyr Ser Gly His Ile Thr Gly His Arg Met Ala
            115                 120                 125

Trp Asp Met Met Met Asn Trp Ser Pro Thr Thr Ala Leu Leu Met Ala
        130                 135                 140

Gln Met Leu Arg Ile Pro Gln Val Val Ile Asp Ile Ile Ala Gly Gly
145                 150                 155                 160

His Trp Gly Val Leu Phe Ala Ala Ala Tyr Phe Ala Ser Ala Ala Asn
                165                 170                 175

Trp Ala Lys Val Val Leu Val Leu Phe Leu Phe Ala Gly Val Asp Gly
                180                 185                 190

<210> SEQ ID NO 97
<211> LENGTH: 192
<212> TYPE: PRT
<213> ORGANISM: Homo sapiens
<220> FEATURE:
<223> OTHER INFORMATION: Individual Isolate:  SA4

<400> SEQUENCE: 97

Val Pro Tyr Arg Asn Ala Ser Gly Val Tyr His Val Thr Asn Asp Cys
  1               5                  10                  15

Pro Asn Ser Ser Ile Val Tyr Glu Ala Asp Asn Leu Ile Leu His Ala
```

-continued

```
                20                  25                  30
Pro Gly Cys Val Pro Cys Val Arg Gln Asp Asn Val Ser Lys Cys Trp
            35                  40                  45
Val Gln Ile Thr Pro Thr Leu Ser Ala Pro Asn Leu Gly Ala Val Thr
         50                  55                  60
Ala Pro Leu Arg Arg Ala Val Asp Tyr Leu Ala Gly Ala Ala Leu
 65                  70                  75                  80
Cys Ser Ala Leu Tyr Val Gly Asp Ala Cys Gly Ala Val Phe Leu Val
                 85                  90                  95
Gly Gln Met Phe Thr Tyr Arg Pro Arg Gln His Thr Thr Val Gln Asp
            100                 105                 110
Cys Asn Cys Ser Ile Tyr Ser Gly His Ile Thr Gly His Arg Met Ala
            115                 120                 125
Trp Asp Met Met Met Asn Trp Ser Pro Thr Thr Ala Leu Leu Met Ala
            130                 135                 140
Gln Leu Leu Arg Ile Pro Gln Val Val Ile Asp Ile Ala Gly Gly
145                 150                 155                 160
His Trp Gly Val Leu Phe Ala Ala Ala Tyr Phe Ala Ser Ala Ala Asn
                165                 170                 175
Trp Ala Lys Val Ile Leu Val Leu Phe Leu Phe Ala Gly Val Asp Ala
            180                 185                 190

<210> SEQ ID NO 98
<211> LENGTH: 192
<212> TYPE: PRT
<213> ORGANISM: Homo sapiens
<220> FEATURE:
<223> OTHER INFORMATION: Individual Isolate: SA5

<400> SEQUENCE: 98

Val Pro Tyr Arg Asn Ala Ser Gly Val Tyr His Val Thr Asn Asp Cys
  1               5                  10                  15
Pro Asn Ser Ser Ile Val Tyr Glu Ala Asp Asn Leu Ile Leu His Ala
            20                  25                  30
Pro Gly Cys Val Pro Cys Val Lys Glu Gly Asn Val Ser Arg Cys Trp
            35                  40                  45
Val Gln Ile Thr Pro Thr Leu Ser Ala Pro Asn Leu Gly Ala Val Thr
         50                  55                  60
Ala Pro Leu Arg Arg Val Val Asp Tyr Leu Ala Gly Ala Ala Leu
 65                  70                  75                  80
Cys Ser Ala Leu Tyr Val Gly Asp Ala Cys Gly Ala Val Phe Leu Val
                 85                  90                  95
Gly Gln Met Phe Thr Tyr Arg Pro Arg Gln His Thr Thr Val Gln Asp
            100                 105                 110
Cys Asn Cys Ser Ile Tyr Ser Gly His Ile Thr Gly His Arg Met Ala
            115                 120                 125
Trp Asp Met Met Met Asn Trp Ser Pro Thr Thr Ala Leu Val Met Ala
            130                 135                 140
Gln Val Leu Arg Ile Pro Gln Val Val Ile Asp Ile Ala Gly Gly
145                 150                 155                 160
His Trp Gly Val Leu Phe Ala Val Ala Tyr Phe Ala Ser Ala Ala Asn
                165                 170                 175
Trp Ala Lys Val Val Leu Val Leu Phe Leu Phe Ala Gly Val Asp Gly
            180                 185                 190
```

-continued

```
<210> SEQ ID NO 99
<211> LENGTH: 192
<212> TYPE: PRT
<213> ORGANISM: Homo sapiens
<220> FEATURE:
<223> OTHER INFORMATION: Individual Isolate:  SA6

<400> SEQUENCE: 99

Val Pro Tyr Arg Asn Ala Ser Gly Val Tyr His Val Thr Asn Asp Cys
  1               5                  10                  15

Pro Asn Ser Ser Ile Val Tyr Glu Ala Asp Asp Leu Ile Leu His Ala
             20                  25                  30

Pro Gly Cys Val Pro Cys Val Arg Lys Asp Asn Val Ser Arg Cys Trp
         35                  40                  45

Val His Ile Thr Pro Thr Leu Ser Ala Pro Ser Leu Gly Ala Val Thr
     50                  55                  60

Ala Pro Leu Arg Arg Ala Val Asp Tyr Leu Ala Gly Ala Ala Leu
 65                  70                  75                  80

Cys Ser Ala Leu Tyr Val Gly Asp Val Cys Gly Ala Leu Phe Leu Val
                 85                  90                  95

Gly Gln Met Phe Thr Tyr Arg Pro Arg Gln His Ala Thr Val Gln Asp
            100                 105                 110

Cys Asn Cys Ser Ile Tyr Ser Gly His Ile Thr Gly His Arg Met Ala
        115                 120                 125

Trp Asp Met Met Met Asn Trp Ser Pro Ala Thr Ala Leu Val Met Ala
    130                 135                 140

Gln Met Leu Arg Ile Pro Gln Val Val Ile Asp Ile Ile Ala Gly Gly
145                 150                 155                 160

His Trp Gly Val Leu Phe Ala Ala Ala Tyr Phe Ala Ser Ala Ala Asn
                165                 170                 175

Trp Ala Lys Val Val Leu Val Leu Phe Leu Phe Ala Gly Val Asp Ala
            180                 185                 190

<210> SEQ ID NO 100
<211> LENGTH: 192
<212> TYPE: PRT
<213> ORGANISM: Homo sapiens
<220> FEATURE:
<223> OTHER INFORMATION: Individual Isolate:  SA7

<400> SEQUENCE: 100

Val Pro Tyr Arg Asn Ala Ser Gly Val Tyr His Val Thr Asn Asp Cys
  1               5                  10                  15

Pro Asn Ser Ser Ile Val Tyr Glu Ala Asp Asn Leu Ile Leu His Ala
             20                  25                  30

Pro Gly Cys Val Pro Cys Val Arg Gln Asn Asn Val Ser Arg Cys Trp
         35                  40                  45

Val Gln Ile Thr Pro Thr Leu Ser Ala Pro Asn Leu Gly Ala Val Thr
     50                  55                  60

Ala Pro Leu Arg Arg Ala Val Asp Tyr Leu Ala Gly Ala Ala Leu
 65                  70                  75                  80

Cys Ser Ala Leu Tyr Val Gly Asp Ala Cys Gly Ala Val Phe Leu Val
                 85                  90                  95

Gly Gln Met Phe Ser Tyr Arg Pro Arg Gln His Thr Thr Val Gln Asp
            100                 105                 110

Cys Asn Cys Ser Ile Tyr Ser Gly His Ile Thr Gly His Arg Met Ala
        115                 120                 125
```

```
Trp Asp Met Met Met Asn Trp Ser Pro Thr Thr Ala Leu Val Met Ala
        130                 135                 140

Gln Leu Leu Arg Ile Pro Gln Val Val Ile Asp Ile Ile Ala Gly Gly
145                 150                 155                 160

His Trp Gly Val Leu Phe Ala Ala Ala Tyr Phe Ala Ser Ala Ala Asn
                165                 170                 175

Trp Ala Lys Val Val Leu Val Leu Phe Leu Phe Ala Gly Val Asp Ala
                180                 185                 190

<210> SEQ ID NO 101
<211> LENGTH: 192
<212> TYPE: PRT
<213> ORGANISM: Homo sapiens
<220> FEATURE:
<223> OTHER INFORMATION: Individual Isolate:  SA13

<400> SEQUENCE: 101

Val Pro Tyr Arg Asn Ala Ser Gly Val Tyr His Val Thr Asn Asp Cys
  1               5                  10                  15

Pro Asn Ser Ser Ile Val Tyr Glu Ala Asp Asp Leu Ile Leu His Ala
                 20                  25                  30

Pro Gly Cys Val Pro Cys Val Arg Gln Gly Asn Val Ser Arg Cys Trp
             35                  40                  45

Val Gln Ile Thr Pro Thr Leu Ser Ala Pro Ser Leu Gly Ala Val Thr
         50                  55                  60

Ala Pro Leu Arg Arg Ala Val Asp Tyr Leu Ala Gly Ala Ala Ala Leu
 65                  70                  75                  80

Cys Ser Ala Leu Tyr Val Gly Asp Ala Cys Gly Ala Val Phe Leu Val
                 85                  90                  95

Gly Gln Met Phe Thr Tyr Ser Pro Arg Arg His Asn Val Val Gln Asp
                100                 105                 110

Cys Asn Cys Ser Ile Tyr Ser Gly His Ile Thr Gly His Arg Met Ala
            115                 120                 125

Trp Asp Met Met Met Asn Trp Ser Pro Thr Thr Ala Leu Val Met Ala
        130                 135                 140

Gln Leu Leu Arg Ile Pro Gln Val Val Ile Asp Ile Ile Ala Gly Ala
145                 150                 155                 160

His Trp Gly Val Leu Phe Ala Ala Ala Tyr Tyr Ala Ser Ala Ala Asn
                165                 170                 175

Trp Ala Lys Val Val Leu Val Leu Phe Leu Phe Ala Gly Val Asp Ala
                180                 185                 190

<210> SEQ ID NO 102
<211> LENGTH: 192
<212> TYPE: PRT
<213> ORGANISM: Homo sapiens
<220> FEATURE:
<223> OTHER INFORMATION: Individual Isolate:  HK2

<400> SEQUENCE: 102

Leu Thr Tyr Gln Asn Ser Ser Gln Leu Tyr His Leu Thr Asn Asp Cys
  1               5                  10                  15

Pro Asn Ser Ser Ile Val Leu Glu Ala Asp Ala Met Ile Leu His Leu
                 20                  25                  30

Pro Gln Cys Leu Pro Cys Val Arg Val Asp Asp Arg Ser Thr Cys Trp
             35                  40                  45

His Ala Val Thr Pro Thr Leu Ala Ile Pro Asn Ala Ser Thr Pro Ala
         50                  55                  60
```

```
Thr Gln Phe Arg Arg His Val Asp Leu Leu Ala Gln Ala Ala Val Val
 65                  70                  75                  80

Cys Ser Ser Leu Tyr Ile Gln Asp Leu Cys Gln Ser Leu Phe Leu Ala
             85                  90                  95

Gln Gln Leu Phe Thr Phe Gln Pro Arg Arg His Trp Thr Val Gln Asp
            100                 105                 110

Cys Asn Cys Ser Ile Tyr Thr Gln His Val Thr Gln His Arg Met Ala
            115                 120                 125

Trp Asp Met Met Asn Trp Ser Pro Thr Thr Leu Val Leu Ser
130                 135                 140

Ser Ile Leu Arg Val Pro Glu Ile Cys Ala Ser Val Ile Phe Gln Gln
145                 150                 155                 160

His Trp Gln Ile Leu Leu Ala Val Ala Tyr Phe Gln Met Ala Gln Asn
                165                 170                 175

Trp Leu Lys Val Leu Ala Val Leu Phe Leu Phe Ala Gln Val Glu Ala
            180                 185                 190

<210> SEQ ID NO 103
<211> LENGTH: 573
<212> TYPE: DNA
<213> ORGANISM: Homo sapiens
<220> FEATURE:
<223> OTHER INFORMATION: Individual Isolate: DK7

<400> SEQUENCE: 103
atgagcacga atcctaaacc tcaaagaaaa accaaacgta acaccaaccg tcgcccacag        60
gacgtcaagt tcccgggtgg cggtcagatc gttggtggag tttacttgtt gccgcgcagg      120
ggccctagat tgggtgtgcg cgcgccgagg aagacttccg agcggtcgca acctcgaggt      180
agacgtcagc ctatccccaa ggcacgtcgg cccgagggca ggacctgggc tcagcccggg      240 taccccttggc ccctctatgg caatgagggc tgcgggtggg cgggatggct cctgtctccc     300
cgtggctctc ggcctagctg ggccccaca gaccccggc gcaggtcgcg caatttgggt       360
aaagtcatcg atacccttac gtgcggcttc gccgacctca tggggtacat accgtcgtc       420 ggcgcccctc ttggaggcgc tgccagggcc ctggcgcatg gcgtccgggt tctggaagac     480
ggcgtgaact atgcaacagg gaaccttcct ggttgctctt tctctatctt ccttttggcc      540
ctgctctctt gcctgaccgt gcccgcttcg gcc                                  573

<210> SEQ ID NO 104
<211> LENGTH: 573
<212> TYPE: DNA
<213> ORGANISM: Homo sapiens
<220> FEATURE:
<223> OTHER INFORMATION: Individual Isolate: US11

<400> SEQUENCE: 104
atgagcacga atcctaaacc tcaaagaaaa accaaacgta acaccaaccg tcgcccacag        60
gacgtcaagt tcccgggtgg cggtcagatc gttggtggag tttacttgtt gccgcgcagg      120
ggccctagat tgggtgtgcg cgcgacgagg aagacttccg agcggtcgca acctcgaggt      180
agacgtcagc ctatccccaa ggcacgtcgg cccgagggca ggacctgggc tcagcccggg      240 taccccttggc ccctctatgg caatgagggc tgcgggtggg cgggatggct cctgtctccc     300
cgtggctctc ggcctagctg ggccccacg gaccccggc gtaggtcgcg caatttgggt       360
aaagtcatcg atacccttac gtgcggcttc gccgacctca tggggtacat accgtcgtc       420
```

| | |
|---|---|
| ggcgcccctc tcggaggcgc tgccagggcc ctggcgcatg gcgtccgggt tctggaagac | 480 |
| ggcgtgaact atgcaacagg gaaccttcct ggttgctctt tctctatctt ccttctggcc | 540 |
| ctgctctctt gcctgactgt gcccgcttca gcc | 573 |

<210> SEQ ID NO 105
<211> LENGTH: 573
<212> TYPE: DNA
<213> ORGANISM: Homo sapiens
<220> FEATURE:
<223> OTHER INFORMATION: Individual Isolate: S14

<400> SEQUENCE: 105

| | |
|---|---|
| atgagcacga atcctaaacc tcaaagaaaa accaaacgta acaccaaccg tcgcccacag | 60 |
| gacgtcaagt tcccgggtgg cggtcagatc gttggtggag tttacttgtt gccgcgcagg | 120 |
| ggccctagat tgggtgtgcg cgcgacgagg aagacttccg agcggtcgca acctcgaggt | 180 |
| agacgtcagc ctatccccaa ggcacgtcgg cccgagggca ggacctgggc tcagcccggg | 240 |
| tatccttggc ccctctatgg caatgagggc tgcgggtggg cgggatggct cctgtctccc | 300 |
| cgtggctctc ggcctagctg ggccccaca gaccccggc gtaggtcgcg caatttgggt | 360 |
| aaggtcatcg ataccctcac gtgcggcttc gccgacctca tggggtacat accgctcgtc | 420 |
| ggcgccccc tcggggcgc tgccagggcc ctggcgcatg gcgtccgggt tctggaagac | 480 |
| ggcgtgaact atgcaacagg gaaccttcct ggttgctctt tctctatctt cctcctagcc | 540 |
| ctgctttctt gcctgactgt gcccgcttca gcc | 573 |

<210> SEQ ID NO 106
<211> LENGTH: 573
<212> TYPE: DNA
<213> ORGANISM: Homo sapiens
<220> FEATURE:
<223> OTHER INFORMATION: Individual Isolate: SW1

<400> SEQUENCE: 106

| | |
|---|---|
| atgagcacga atcctaaacc tcaaagaaaa accaaacgta acaccaaccg tcgcccacag | 60 |
| gacgtcaagt tcccgggtgg cggtcagatc gttggtggag tttacttgtt gccgcgcagg | 120 |
| ggccctagat tgggtgtgcg cgcgacgagg aagacttccg agcggtcgca acctcgaggt | 180 |
| agacgtcagc ctatccccaa ggcgcgtcgg cccgagggca ggacctgggc tcagcccggg | 240 |
| tatccttggc ccctctatgg caatgagggc tgcggatggg cgggatggct cctgtccccc | 300 |
| cgtggctctc ggcctagctg ggccctaca gaccccggc gtaggtcgcg caatttgggt | 360 |
| aaggtcatcg ataccctcac gtgcggcttc gccgacctca tggggtacat tccgctcgtc | 420 |
| ggcgcccctc ttggaggcgc tgccagggcc ctggcgcatg gcgtccgggt tctggaagac | 480 |
| ggcgtgaact atgcaacagg gaaccttcct ggttgctctt tctctatctt ccttctggcc | 540 |
| ctgctttctt gcctgacagt gcccgcgtca gcc | 573 |

<210> SEQ ID NO 107
<211> LENGTH: 573
<212> TYPE: DNA
<213> ORGANISM: Homo sapiens
<220> FEATURE:
<223> OTHER INFORMATION: Individual Isolate: S18

<400> SEQUENCE: 107

| | |
|---|---|
| atgagcacaa atcctaaacc tcaaagaaaa accaaacgta acaccaaccg tcgcccacag | 60 |
| gacgttaagt tcccgggtgg cggtcagatc gttggtggag tttacttgtt gccgcgcagg | 120 |

-continued

```
ggccctagat tgggtgtgcg cgcgacgagg aagacttccg agcggtcgca acctcgcggt    180
agacgtcagc ctatccccaa ggcgcgtcgg cccgagggca ggacctgggc tcagcccggg    240 taccttggc ccctctatgg caatgagggc tgcgggtggg cgggatggct cctgtccccc    300
cgtggctccc ggcctagctg gggccctaca accccggc gtaggtcgcg caatttgggc     360
aaagtcatcg ataccctcac gtgcggcttc gccgacctca tggggtacat ccgctcgtc    420 ggcgcccctc tcggaggcgc tgccagggcc ctggcgcatg cgtccgggt tctggaagac    480 ggcgtgaact atgcaacagg gaaccttcct ggttgctctt tctctatctt ccttctggcc    540
ctgctctctt gtctgactgt gcccgcgtca gct                                 573
```

<210> SEQ ID NO 108
<211> LENGTH: 573
<212> TYPE: DNA
<213> ORGANISM: Homo sapiens
<220> FEATURE:
<223> OTHER INFORMATION: Individual Isolate: DR4

<400> SEQUENCE: 108

```
atgagcacga atcctaaacc tcaaagaaaa accaaacgta acaccaaccg tcgcccacag    60
gacgtcaagt tcccgggtgg cggtcagatc gttggtggag tttacttgtt gccgcgcagg   120
ggccctagat tgggtgtgcg cgcgacgagg aagacttccg agcggtcgca acctcgaggt   180
agacgtcagc ctatccccaa ggcgcgtcgg cccgagggca ggacctgggc tcagcccggg   240 taccttggc ccctctatgg caatgagggc tgcgggtggg cgggatggct cctgtccccc    300
cgtggctctc ggcctagctg gggcccaca accccggc gtaggtcgcg caatttgggt     360
aaggtcatcg acaccctcac gtgcggcttc gccgacctca tggggtacat cccgctcgtc   420 ggcgccccc ttggggcgc tgccagggcc ctggcgcatg cgtccgagt tctggaagac      480 ggcgtgaact atgcaacagg gaatcttcct ggttgctctt tctctatctt ccttttggct   540
ttgctctctt gcttgaccgt gcccgcatcg gcc                                 573
```

<210> SEQ ID NO 109
<211> LENGTH: 573
<212> TYPE: DNA
<213> ORGANISM: Homo sapiens
<220> FEATURE:
<223> OTHER INFORMATION: Individual Isolate: SA10

<400> SEQUENCE: 109

```
atgagcacga atcctaaacc tcaaagaaaa accaaacgta acaccaaccg ccgcccacag    60
gacgtcaagt tcccgggcgg tggtcagatc gttggtggag tctatctgtt gccgcgcagg   120
ggccccaggt tgggtgtgcg cgcgacgagg aagacttccg agcggtcgca acctcgtgga   180
aggcgacaac ctatccccaa ggctcgccag cccgagggca ggacctgggc ccagcccggg   240 taccttggc ccctctatgg caatgagggc ttggggtggg caggatggct cctgtcaccc    300
cgtggctctc ggcctagttg gggccccacg accccggc gtaggtcgcg taatttgggt     360
aaggtcatcg ataccctcac atgcggcttc gccgacctca tggggtacat ccgctcgtc    420 ggcgcccctt tagggggcgc tgccagggcc ttggcgcatg cgtccgggt tctggaagac    480 ggcgtgaact atgcaacagg gaatttgccc ggttgccctt tctctatctt cctcttggct   540
ttgctgtcct gttttaaccat cccagcttcc gct                                573
```

<210> SEQ ID NO 110

<211> LENGTH: 573
<212> TYPE: DNA
<213> ORGANISM: Homo sapiens
<220> FEATURE:
<223> OTHER INFORMATION: Individual Isolate: S45

<400> SEQUENCE: 110

| | | | | |
|---|---|---|---|---|
| atgagcacga | atcctaaacc | tcaaagacaa | accaaacgta | acaccaaccg | ccgcccacag | 60 |
| gacgtcaagt | tcccgggtgg | cggtcagatc | gttggtggag | tttacctgtt | gccgcgcagg | 120 |
| ggccccaggt | tgggtgtgcg | cgcgactagg | aagacttccg | agcggtcaca | acctcgtgga | 180 |
| cggcgacaac | ctatccccaa | ggctcgccgg | cccgagggca | gggcctgggc | ccagcccggg | 240 |
| catccttggc | ccctctatgg | caatgagggc | ttggggtggg | caggatggct | cctgtcaccc | 300 |
| cgtggctccc | ggcctagttg | gggccccacg | gaccccggc | gtaggtcgcg | caatttgggt | 360 |
| aaggtcatcg | ataccctcac | gtgcggcttc | gccgacctca | tggggtacat | tccgctcgtc | 420 |
| ggcgccccc | taggggcgc | tgccagagcc | ttggcgcatg | gcgtccgggt | tctggaggac | 480 |
| ggcgtgaact | atgcaacagg | gaatctgccc | ggttgctctt | tctctatctt | cctcttggct | 540 |
| ctgctgtcct | gcttgaccat | cccagcttcc | gct | | | 573 |

<210> SEQ ID NO 111
<211> LENGTH: 573
<212> TYPE: DNA
<213> ORGANISM: Homo sapiens
<220> FEATURE:
<223> OTHER INFORMATION: Individual Isolate: D1

<400> SEQUENCE: 111

| | | | | | | |
|---|---|---|---|---|---|---|
| atgagcacga | atcctaaacc | tcaaagaaaa | accaaacgta | acaccaaccg | ccgcccacag | 60 |
| gacgtcaagt | tcccgggcgg | tggtcagatc | gttggtggag | tttacctgtt | gccgcgcagg | 120 |
| ggccccaggt | tgggtgtgcg | cgcgactagg | aagacttccg | agcggtcgca | acctcgtgga | 180 |
| aggcgacaac | ctatccccaa | ggctcgccgg | cccgaggggta | gggcctgggc | tcagcccggg | 240 |
| taccccttggc | ccctctatgg | caacgagggc | ttggggtggg | caggatggct | cctgtcaccc | 300 |
| cgcggctccc | ggcctagttg | gggccccacc | gaccccggc | gtaggtcgcg | taatttgggt | 360 |
| aaggtcatcg | ataccctcac | atgcggcttc | gccgacctca | tggggtacat | cccgctcgtc | 420 |
| ggcgccccc | tagggggtgc | tgccagggcc | ctggcgcatg | gcgtccgggt | tctggaggac | 480 |
| ggcgtgaatt | atgcaacagg | gaatttgccc | ggttgctctt | tctctatctt | cctcttggct | 540 |
| ttgctgtcct | gtttgaccat | cccagcttcc | gct | | | 573 |

<210> SEQ ID NO 112
<211> LENGTH: 573
<212> TYPE: DNA
<213> ORGANISM: Homo sapiens
<220> FEATURE:
<223> OTHER INFORMATION: Individual Isolate: US6

<400> SEQUENCE: 112

| | | | | | | |
|---|---|---|---|---|---|---|
| atgagcacga | atcctaaacc | tcaaagaaaa | accaaacgta | acaccaaccg | ccgcccacag | 60 |
| gacgtcaagt | tcccgggcgg | tggtcagatc | gttggtggag | tttacctgtt | gccgcgcagg | 120 |
| ggccccaggt | tgggtgtgcg | cgcgactagg | aagacttccg | agcggtcgca | acctcgtgga | 180 |
| aggcgacaac | ctatccccaa | ggctcgccgg | cccgagggca | gggcctgggc | tcagcccggg | 240 |
| taccccttggc | ccctctatgg | caacgagggc | atggggtggg | caggatggct | cctgtcaccc | 300 |
| cgtggctccc | ggcctagttg | gggccccacg | gaccccggc | gtaggtcgcg | taatttgggt | 360 |

```
aaggtcatcg ataccctcac atgcggcttc gccgacctca tggggtacat tccgctcgtc    420 ggcgccccc tagggggcgc tgccagggcc ttggcgcatg gcgtccgggt tctggaggac     480
ggcgtgaact atgcaacagg gaacttgccc ggttgctctt tctctatctt cctcttggct   540
ttgctgtcct gtttgaccat tccagcttcc gct                                 573
```

<210> SEQ ID NO 113
<211> LENGTH: 573
<212> TYPE: DNA
<213> ORGANISM: Homo sapiens
<220> FEATURE:
<223> OTHER INFORMATION: Individual Isolate: P10

<400> SEQUENCE: 113

```
atgagcacga atcctaaacc tcaaagaaaa accaaacgta acaccaaccg ccgcccacag     60
gacgtcaagt tcccgggcgg tggtcagatc gttggtggag tttacctgtt gccgcgcagg   120
ggccccaggt tgggtgtgcg cgcgactagg aagacttccg agcggtcgca acctcgtgga   180
aggcgacaac ctatcccaa ggctcgccgg cccgagggca gggcctgggc tcagcccggg    240 taccctggc ccctctatgg caatgagggc ttggggtggg caggatggct cctgtcaccc    300
cgtggctctc ggcctagttg gggccccacg gaccccggc gtaggtcgcg taatttgggt    360
aaggtcatcg ataccctcac atgcggcttc gccgacctca tggggtacat tccgctcgtc   420 ggcgccccc tagggggcgc tgccagggcc ctggcgcatg gcgtccgggt tctggaggac   480
ggcgtgaact atgcaacagg gaatctgccc ggttgctctt tctctatctt cctcttggct   540
ttgctgtcct gcctgaccat cccagcgtcc gct                                 573
```

<210> SEQ ID NO 114
<211> LENGTH: 573
<212> TYPE: DNA
<213> ORGANISM: Homo sapiens
<220> FEATURE:
<223> OTHER INFORMATION: Individual Isolate: DK1

<400> SEQUENCE: 114

```
atgagcacga atcctaaacc tcaaagaaaa accaaacgta acaccaaccg ccgcccacag     60
gacgtcaagt tcccgggcgg tggtcagatc gttggtggag tttacctgtt gccgcgcagg   120
ggccccaggt tgggtgtgcg cgcgactagg aagacttccg agcggtcgca acctcgtgga   180
aggcgacaac ctatcccaa ggctcgccgg cccgagggca gggcctgggc tcagcccggg    240 taccctggc ccctctatgg caatgagggc atggggtggg caggatggct cctgtcaccc    300
cgcggctctc ggcctagttg gggccccaac gaccccggc gtaggtcgcg taatttgggt    360
aaggtcatcg ataccctcac atgcggcttc gccgacctca tggggtacat tccgctcgtc   420 ggcgccccc tagggggcgc tgccagggcc ctggcgcatg gcgtccgggt tctggaggac   480
ggcgtgaact acgcaacagg gaatttgccc ggttgctctt tctctatctt cctcttggct   540
ctgttgtcct gtttgaccat cccagcttcc gcc                                 573
```

<210> SEQ ID NO 115
<211> LENGTH: 573
<212> TYPE: DNA
<213> ORGANISM: Homo sapiens
<220> FEATURE:
<223> OTHER INFORMATION: Individual Isolate: T10

<400> SEQUENCE: 115

-continued

```
atgagcacga atcctaaacc tcaaagaaaa accaaacgta acaccaaccg ccgcccacag      60
gacgtcaagt tcccgggcgg tggtcagatc gttggtggag tttacctgtt gccgcgcagg     120
ggccccaggt tgggtgtgcg cgcgactagg aagacttccg agcggtcgca acctcgtgga     180
aggcgacagc ctatccccaa ggctcgccag cccgagggca gggcctgggc tcagcccggg     240 taccctggc ccctctatgg caatgagggc atggggtggg caggatggct cctgtcaccc      300
cgtggctccc ggcctagttg gggccccaca gaccccggc gtaggtcgcg taatttgggt      360
aaggtcatcg ataccctcac atgcggcttc gccgacctca tggggtacat tccgctcgtc    420
ggcgcccccc tagggggcgc tgccagggct ctggcacatg gtgtccgggt tctggaggac    480
ggcgtgaact atgcaacagg gaatttgccc ggttgctctt tttctatctt cctcttggct   540
ctgctgtctt gtctgaccat cccagcttcc gct                                 573
```

<210> SEQ ID NO 116
<211> LENGTH: 573
<212> TYPE: DNA
<213> ORGANISM: Homo sapiens
<220> FEATURE:
<223> OTHER INFORMATION: Individual Isolate: SW2

<400> SEQUENCE: 116

```
atgagcacga atcctaaacc tcaaagaaaa accaaacgta acaccaaccg ccgcccacag      60
gacgtcaagt tcccgggcgg tggccagatc gttggtggag tttacctgtt gccgcgcagg     120 ggccccggt tgggtgtgcg cgcgactagg aagacttccg agcggtcgca acctcgtgga      180
aggcgacaac ctatccccaa ggctcgccag cccgagggca gggcctgggc tcagcctggg    240 taccctggc ccctctatgg caatgagggc atgggatggg caggatggct cctgtccccc     300
cgcggctctc ggcctagttg gggcccact gaccccggc gtaggtcgcg taatttgggt       360
aaggtcatcg ataccctcac atgcggcttc gccgacctca tggggtacat tccgctcgtc    420
ggcgcccccc tagggggcgc tgccagggcc ctggcgcatg gcgtccgggt cctggaggac    480
ggcgtgaact atgcaacagg gaatctgccc ggttgctcct tttctatctt cctcttggct    540
ttgctgtcct gtctgaccat cccagcttcc gct                                 573
```

<210> SEQ ID NO 117
<211> LENGTH: 573
<212> TYPE: DNA
<213> ORGANISM: Homo sapiens
<220> FEATURE:
<223> OTHER INFORMATION: Individual Isolate: IND3

<400> SEQUENCE: 117

```
atgagcacga atcctaaacc tcaaagaaaa accaaacgta acaccaaccg ccgcccacag      60
gacgtcaagt tcccgggcgg tggccagatc gttggtggag tttacctgtt gccgcgcagg     120
ggccccaggt tgggtgtgcg cgcgactagg aagacttccg agcggtcgca acctcgtgga    180
aggcgacaac ctatccccaa ggctcgccgg cccgagggta gggcctgggc tcagcccggg    240 taccctggc ccctctatgg caatgagggc ttggggtggg caggatggct cctgtcaccc     300
cgcggttctc ggcctagttg gggccccaca gaccccggc gtaggtcgcg taatttgggt     360
aaagtcatcg ataccctcac atgcggcttc gccgacctca tggggtacat cccgctcgtc    420
ggcgcccccc tagggggcgc tgccagggcc ctggcgcatg gcgtccgggt cctggaggac    480
ggcgtgaact atgcaacagg gaacttgccc ggttgctctt tctctatctt cctttagct    540 ttgctatcct gtttgaccat cccagcttcc gct                                 573
```

<210> SEQ ID NO 118
<211> LENGTH: 573
<212> TYPE: DNA
<213> ORGANISM: Homo sapiens
<220> FEATURE:
<223> OTHER INFORMATION: Individual Isolate: IND8

<400> SEQUENCE: 118

```
atgagcacga atcctaaacc tcaaagaaaa accaaacgta acaccaaccg ccgcccacag      60
gacgtcaagt tcccgggcgg tggccagatc gttggtggag tttacctgtt gccgcgcagg     120
ggccccaggt tgggtgtgcg cgcgactagg aagacttccg agcggtcgca acctcgtgga    180
aggcgacaac ctatccccaa ggctcgccgg cccgagggta gggcctgggc tcagcccggg    240
caccttggc ccctctatgg caatgagggc ttggggtggg caggatggct cctgtcaccc      300
cgcggctctc ggcctagttg ggccccaca gaccccggc gtaggtcgcg taatttgggt       360
aaggtcatcg ataccctcac atgcggcttc gccgacctca tggggtacat cccgctcgtc    420
ggcgccccc taggggtgc tgccagggcc ctggcgcatg gcgtccgggt cctggaggac       480
ggcgtgaact atgcaacagg gaacttgccc ggttgctctt tctctatctt ccttttggct    540
ttgctatcct gtttgaccgt cccagcttcc gct                                 573
```

<210> SEQ ID NO 119
<211> LENGTH: 573
<212> TYPE: DNA
<213> ORGANISM: Homo sapiens
<220> FEATURE:
<223> OTHER INFORMATION: Individual Isolate: S9

<400> SEQUENCE: 119

```
atgagcacga atcctaaacc tcaaagaaaa accaaacgta acaccaaccg ccgcccacag      60
gacgttaagt tcccgggcgg tggtcagatc gtcggtggag tttacctgtt gccgcgcagg    120
ggccccaggt tgggtgtgcg cgcaactagg aagacttccg agcggtcgca acctcgtgga    180
aggcgacaac ctatccccaa ggctcgccat cccgagggca gggcctgggc tcagcccggg    240
taccttggc ccctctacgg caatgagggc ttggggtggg caggatggct cctgtcaccc      300
cgtggctctc ggcctagttg ggccccaat gaccccggc gtaggtcgcg taatttgggt       360
aaggtcatcg ataccctcac atgcggcttt gccgacctca tggggtacat ccgctcgtc     420
ggcgccccc taggggcgc tgccagggct ctggcgcatg gcgtccgggt tctggaggac       480
ggcgtgaact atgcaacagg gaacctcccc ggttgctctt tctctatctt ccttctggct    540
ttgctgtcct gtttgaccat cccagcttcc gct                                 573
```

<210> SEQ ID NO 120
<211> LENGTH: 573
<212> TYPE: DNA
<213> ORGANISM: Homo sapiens
<220> FEATURE:
<223> OTHER INFORMATION: Individual Isolate: HK3

<400> SEQUENCE: 120

```
atgagcacga atcctaaacc tcaaagaaaa accaaacgta acaccaaccg ccgcccacag      60
gacgtcaagt tcccgggcgg tggtcagatc gttggtggag tttacctgtt gccgcgcagg    120
ggccccaggt tgggtgtgcg cgcgaccagg aagacttcag agcggtcgca acctcgtgga    180
aggcgacaac ctatccccaa ggctcgccaa cccgagggca ggacctgggc tcagcccggg    240
```

```
tatccttggc ccctctatgg caacgagggc atggggtggg caggatggct cctgtcaccc     300
cgcggctctc ggcctaattg gggccccacg accccggc gtaggtcgcg caatttgggt       360
aaggtcatcg ataccctcac gtgcggcttc gccgacctca tggggtacat cccgctcgtc    420 ggtgccccc taggggggcgt tgccagagcc ttggcacatg gtgtccgggt tctggaggac     480
ggcgtgaact atgcaacagg gaatttaccc ggttgctctt tctctatctt cctcttggct    540
ttgctgtcct gcttgaccac cccagcttcc gct                                  573

<210> SEQ ID NO 121
<211> LENGTH: 573
<212> TYPE: DNA
<213> ORGANISM: Homo sapiens
<220> FEATURE:
<223> OTHER INFORMATION: Individual Isolate:  HK5

<400> SEQUENCE: 121
atgagcacga atcctaaacc tcaaagaaaa accaaacgta acaccaaccg ccgcccacag     60
gacgtcaagt tcccgggcgg tggtcagatc gttggtggag tttacctgtt gccgcgcagg   120
ggccccaggt tgggtgtgcg cgcgaccagg aagacttccg agcggtcgca acctcgtgga   180
aggcgacaac ctatccccaa ggctcgccga cccgagggca ggacctgggc tcagcccggg   240
tatccttggc ccctctatgg caatgagggc atggggtggg caggatggct cctgtcaccc    300
catggctctc ggcctagttg gggccccacg accccggc gtaggtcgcg taatttgggt      360
aaggtcatcg ataccctcac gtgcggcttc gccgacctca tggggtacat cccgctcgtc   420 ggcgccccc taggggggcgt tgccagagcc ctggcacacg gtgtccgggt tctggaggac    480
ggcgtgaact acgcaacagg gaatataccc ggttgctctt tctctatctt cctttttggct  540 ttgctgtcct gtctgaccac cccagtttcc gct                                  573

<210> SEQ ID NO 122
<211> LENGTH: 573
<212> TYPE: DNA
<213> ORGANISM: Homo sapiens
<220> FEATURE:
<223> OTHER INFORMATION: Individual Isolate:  HK4

<400> SEQUENCE: 122
atgagcacga atcctaaacc tcaaagaaag accaaacgta acaccaaccg ccgcccacag    60
gacgttaagt tcccgggcgg tggccagatc gtcggtggag tttacctgtt gccgcgcagg  120
ggccccaggt tgggtgtgcg cgcgactagg aagacttccg agcggtcgca acctcgtgga   180
aggcgacaac ctatccccaa ggctcgccaa cccgagggca ggacctgggc tcagcccggg    240 taccttggc ccctctatgg caatgagggc atggggtggg caggatggct cctgtcaccc     300
cgcggctctc ggcctagttg gggccccacg accccggc gtaggtcgcg caatttgggt     360
aaggtcatcg ataccctcac atgcggcttc gccgacctca tggggtacat cccgctcgtc   420
ggcgccccct taggggggcgt tgccagagcc ctggcacatg gtgtccgggt tgtggaggac   480
ggcgtgaact atgcaacagg gaatttgccc ggttgctctt tctctatctt cctcttggct   540
ctgctgtcct gttttgaccat cccagcttcc gct                                573

<210> SEQ ID NO 123
<211> LENGTH: 573
<212> TYPE: DNA
<213> ORGANISM: Homo sapiens
<220> FEATURE:
<223> OTHER INFORMATION: Individual Isolate:  P8
```

<400> SEQUENCE: 123

```
atgagcacga ctcctaaacc tcaaagaaaa accaaacgta acaccagccg ccgcccacag    60
gacgttaagt tcccgggcgg tggtcagatc gttggtggag tttacctgtt gccgcgcagg   120
ggccccaggt tgggtgtgcg cgcgactagg aagacttccg agcgatcgca acctcgtggc   180
aggcgacaac ctatccccaa ggctcgccgg cccgagggta gggcctgggc tcagcccggg   240
caccccttggc ccctctatgc caatgagggc ttggggtggg cgggatggct cctgtcaccc   300
cgcggctccc ggcctagttg ggcccacg accccggc gtaggtcgcg caatttgggt        360
aaggtcatcg ataccctcac atgcggcttc gccgacctca tggggtacat tccgctcgtc   420
ggcggccccc taggggggcgt tgccaggggcc ctggcgcatg gcgtccgggt tgtggaggac  480
ggcgtgaact atgcaacagg gaatctgcct ggttgctctt tctctatctt ccttttggct   540
ttgctgtctt gtctgaccat cccagcttcc gct                                573
```

<210> SEQ ID NO 124
<211> LENGTH: 573
<212> TYPE: DNA
<213> ORGANISM: Homo sapiens
<220> FEATURE:
<223> OTHER INFORMATION: Individual Isolate: T3

<400> SEQUENCE: 124

```
atgagcacga atcctaaacc tcaaagaaaa accaaacgta acaccaaccg ccgcccacag    60
gacgttaagt tcccgggcgg tggtcagatc gttggtggag tttacctgtt gccgcgcagg   120
ggccccaggt tgggtgtgcg cgcgactagg aagacttccg agcggtcgca acctcgtgga   180
aggcgacaac ctatccccaa ggctcgccgg cccgagggta gggcctgggc tcagcccggg   240
taccccttggc ccctctatgg cgacgagggc atggggtggg caggatggct cctgtcaccc   300
cgcggctccc ggcctaattg ggcccccaca accccggc gtaggtcgcg taatctgggt     360
aaggtcatcg ataccctcac atgcggcttc gccgacctca tggggtacat tccgctcgtc   420
ggcgctccct taggggggcgt tgccaggggcc ctggcgcatg gcgtccgggt tctggaggac  480
ggcgtgaatt acgcaacagg gaatttgcct ggttgctctt tctctatctt cctcttggct   540
ttgctgtcct gcttgaccat cccagcttcc gct                                573
```

<210> SEQ ID NO 125
<211> LENGTH: 573
<212> TYPE: DNA
<213> ORGANISM: Homo sapiens
<220> FEATURE:
<223> OTHER INFORMATION: Individual Isolate: T4

<400> SEQUENCE: 125

```
atgagcacaa atcctaaacc tcaaagaaaa accaaaagaa acaccaaccg tcgcccacag    60
gacgttaagt tcccgggcgg cggccagatc gttggcggag tatacttgtt gccgcgcagg   120
ggccccaggt tgggtgtgcg cgcgacaagg aagacttcgg agcgatccca gccacgtggg   180
aggcgccagc ccatccccaa agatcggcgc tccactggca agtcctgggg aaaaccagga   240
tatccctggc ccctgtatgg gaatgaggga ctcggctggg caggatggct cctgtccccc   300
cgaggttccc gtccctcctg gggccccaat gaccccggc ataggtcgcg caacgtgggt    360
aaggtcatcg ataccctaac gtgcagcctt gccgacctca tggggtacgt ccccgtcgta   420
ggcggcccgt tgggtggcgt cgccagagct ctcgcgcatg gcgtgagagt cctggaggac  480
```

```
ggggttaatt atgcaacagg gaacttacct ggttgctcct tttctatttt cttgctggcc    540
ctactgtcct gcatcaccat tccagtctcc gct                                 573
```

<210> SEQ ID NO 126
<211> LENGTH: 573
<212> TYPE: DNA
<213> ORGANISM: Homo sapiens
<220> FEATURE:
<223> OTHER INFORMATION: Individual Isolate:  US10

<400> SEQUENCE: 126

```
atgagcacaa atcctaaacc tcaaagaaaa accaaaagaa acactaaccg tcgcccacaa     60
gacgttaagt ttccgggcgg cggccagatc gttggcggag tatacttgtt gccgcgcagg    120
ggccccaggt tgggtgtgcg cgcgacaagg aagacttcgg agcggtccca gccacgtggg    180
aggcgccagc ccatccccaa agatcggcgc cccactggca agtcctgggg aaaaccagga    240
tacccttggc ccctatatgg gaatgaggga ctcggctggg caggatggct cctgtccccc    300
cgaggttccc gtccctcttg ggccccact  gatccccggc ataggtcgcg caacgtgggt    360
aaggtcatcg atacctaac  gtgcggcttt gccgacctca tgggatacat ccccgtcgtg    420
ggcgctccgc ttggtggcgt cgccagagct ctcgcgcatg gcgtgagggt cctggaggac    480
ggggttaatt atgcaacagg gaacttaccc ggttgctcct tttctatctt cttgctggcc    540
ttactgtcct gcatcaccat tccagtctct gct                                 573
```

<210> SEQ ID NO 127
<211> LENGTH: 573
<212> TYPE: DNA
<213> ORGANISM: Homo sapiens
<220> FEATURE:
<223> OTHER INFORMATION: Individual Isolate:  T9

<400> SEQUENCE: 127

```
atgagcacaa atccaaaacc ccaaagaaaa accataagaa acaccaaccg tcgcccacag     60
gacgttaagt tcccgggcgg cggccagatc gttggcggag tatacttgtt gccgcgcagg    120
ggccctaggt tgggtgtgcg cacgacaagg aagacttcgg agcggtccca gccacgtggg    180
aggcgccagc ccatccccaa agatcggcgc tccactggca agtcctgggg aaaaccagga    240 taccccctggc ctctatatgg gaatgaggga ctcggctggg cgggatggct cctgtccccc   300
cgaggttccc gtccctcttg ggccccagt  gaccccggc  ataggtcgcg caacgtgggt    360
aaggtcatcg atacctaac  gtgcggcttt gccgacctca tggggtacat ccccgtcgta    420
ggcgccccgc ttggtggcgt tgccagagct ctcgcgcacg gcgtgagagt cctggaggac    480
ggggttaatt atgcaacagg gaacctacct ggttgctctt tttctatctt cttgctggcc    540
ctactgtcct gcatcaccac tccggcctct gct                                 573
```

<210> SEQ ID NO 128
<211> LENGTH: 573
<212> TYPE: DNA
<213> ORGANISM: Homo sapiens
<220> FEATURE:
<223> OTHER INFORMATION: Individual Isolate:  T2

<400> SEQUENCE: 128

```
atgagcacaa ttcctaaacc tcaaagaaaa accaaaagaa acactaaccg tcgcccacaa     60
gacgttaagt ttccgggcgg cggccagatc gttggcggag tatacttgct gccgcgcagg    120
ggccccaggt tgggtgtgcg cgcgacaagg aagacttcgg agcggtccca gcctcgtgga    180
```

```
aggcgccagc ccatccctaa agatcggcgc tccactggca agtcctgggg aaaaccagga      240
tacccctggc ccctgtatgg gaatgagggg ctcggctggg caggatggct cctgtccccc      300
cgaggttctc gtccctcttg ggccccaat gaccccggc ataggtcgcg caatgtgggt        360
aaagtcatcg ataccctaac gtgcggcttt gccgacctca tggggtacat ccccgtcgta     420
ggcgccccgc ttggtggtgt cgccagagct cttgcgcatg cgtgagagt cctgaggac       480 ggagttaatt atgcaacagg taacttaccc ggttgctcct tttctatctt cttgctagcc      540
ctgctgtcct gcatcactat tccggtttca gct                                   573
```

<210> SEQ ID NO 129
<211> LENGTH: 573
<212> TYPE: DNA
<213> ORGANISM: Homo sapiens
<220> FEATURE:
<223> OTHER INFORMATION: Individual Isolate: T8

<400> SEQUENCE: 129

```
atgagcacaa atcctaaacc tcaaagaaaa accaaaagaa acacaaaccg ccgcccacag      60
gacgtcaagt tcccgggtgg cggccagatc gttggcggag tttacttgct gccgcgcagg     120
ggccctaggt tgggtgtgcg cgcgacaagg aagacttccg agcgatccca gccgcgtggg    180
agacgccagc ccatcccgaa agatcggcgc tccaccggca agtcctgggg aaaaccagga    240
tatccttggc ctctttacgg aaacgagggc tgcggttggg caggttggct cctgtccccc    300
cgcgggtctc gtcctacttg ggccccact gaccccggc atagatcacg taatttgggc      360
agagtcatcg ataccattac atgtggtttt gccgacctca tggggtacat ccctgtcgtt    420
ggcgccccgg tcggaggcgt cgccagagct ctggcacatg gtgttagggt cctggaagac   480 gggataaaact atgcaacagg gaatttgcct ggttgctctt tttctatctt cttgcttgct    540
cttctgtcat gcttcacagt gccagtgtct gca                                   573
```

<210> SEQ ID NO 130
<211> LENGTH: 573
<212> TYPE: DNA
<213> ORGANISM: Homo sapiens
<220> FEATURE:
<223> OTHER INFORMATION: Individual Isolate: US1

<400> SEQUENCE: 130

```
atgagcacaa atcctaaacc tcaaagaaaa accaaaagaa acacaaaccg ccgcccacag      60
gacgtcaagt tcccgggtgg cggtcagatc gttggcggag tttacttgct gccgcgcagg    120
ggccccaggt tgggtgtgcg cgcgacaagg aagacttccg agcgatccca gccgcgtggg    180
agacgccagc ccatcccgaa agatcggcgc tccaccggca agtcctgggg aaagccagga   240
tatccttggc ctctgtacgg aaacgagggc tgcggctggg caggttggct cctgtccccc   300
cgcgggtctc gtcctacttg ggccccact gaccccggc acagatcacg taacttgggc     360
aaggtcatcg ataccattac gtgtggtttt gccgacctca tggggtacat ccctgtcgtt   420
ggcgccccgg tcggaggcgt cgccagagct ctggcacacg gtgttagggt cctggaagac  480
gggataaatt acgcaacagg gaatctgcct ggttgctcct tttctatctt cttacttgct    540
cttctgtcgt gcgccacggt gccggtgtct gca                                   573
```

<210> SEQ ID NO 131
<211> LENGTH: 573
<212> TYPE: DNA

<213> ORGANISM: Homo sapiens
<220> FEATURE:
<223> OTHER INFORMATION: Individual Isolate: DK11

<400> SEQUENCE: 131

| | |
|---|---|
| atgagcacaa atcctaaacc tcaaagaaaa accaaaagaa atacaaaccg ccgcccacag | 60 |
| gacgttaagt tcccgggtgg cggccagatc gttggcggag tttacttgct gccgcgcagg | 120 |
| ggccccaggt tgggtgtgcg cacgacaagg aagacttccg agcgatccca gccgcgtggg | 180 |
| agacgccagc ccatcccgaa agatcggcgc tccaccggca agccctgggg aaagccagga | 240 |
| tatccttggc ccctgtatgg aaacgagggc tgcggctggg caggttggct cctgtccccc | 300 |
| cgcgggtctc atcctaattg gggccccact gaccccggc ataaatcacg caatttgggt | 360 |
| aaagtcatcg acaccattac gtgtggtttt gccgacctca tggggtacat ccctgtcgtc | 420 |
| ggcgccccgg tcggaggcgt cgccagagct ctggcacacg tgttagagt cctggaagac | 480 |
| gggataaatt acgcaacagg gaatctgcct ggttgctctt tttctatctt cttacttgct | 540 |
| cttctgtcat gctgcacagt gccagtgtct gcg | 573 |

<210> SEQ ID NO 132
<211> LENGTH: 573
<212> TYPE: DNA
<213> ORGANISM: Homo sapiens
<220> FEATURE:
<223> OTHER INFORMATION: Individual Isolate: SW3

<400> SEQUENCE: 132

| | |
|---|---|
| atgagcacaa atcctaaacc tcaaagaaaa accaaaagaa atacaaaccg ccgcccacag | 60 |
| gacgttaagt tcccgggtgg cggccagatc gttggcggag tttacttgct gccgcgcagg | 120 |
| ggccccaggt tgggtgtgcg cgcgacaagg aagacttccg agcgatccca gccgcgtggg | 180 |
| agacgccagc ccatcccgaa agatcggcgc tccaccggca agtcctgggg aaagccagga | 240 |
| tatccttggc ccctgtatgg aaacgagggc tgcggctggg caggttggct cctgtccccc | 300 |
| cgcgggtctc atcctaattg gggccccact gaccccggc atagatcacg caatttgggc | 360 |
| aaagtcatcg acaccattac gtgtggtttt gccgacctca tggggtacat ccctgtcgtt | 420 |
| ggcgccccgg tcggaggcgt cgccagagct ctggcacacg tgttagagt cctggaagac | 480 |
| gggataaatt acgcaacagg gaatctgcct ggttgctctt tttctatctt cttacttgct | 540 |
| cttctgtcgt gcttcacagt gccagtgtct gcg | 573 |

<210> SEQ ID NO 133
<211> LENGTH: 573
<212> TYPE: DNA
<213> ORGANISM: Homo sapiens
<220> FEATURE:
<223> OTHER INFORMATION: Individual Isolate: DK8

<400> SEQUENCE: 133

| | |
|---|---|
| atgagcacaa atcctaaacc tcaaagaaaa accaaaagaa acacaaaccg ccgcccacag | 60 |
| gacgttaagt tcccgggtgg cggccagatc gttggcggag tttacttgct gccgcgcagg | 120 |
| ggccccaggt tgggtgtgcg cgcgacaagg aagtcttccg agcgatccca gccgcgtggg | 180 |
| aggcgccagc ccatcccgaa agatcggcgc tccaccggca agtcctgggg aaaaccggga | 240 |
| tatccttggc ccctgtatgg aaacgagggc tgcggctggg caggttggct cctgtccccc | 300 |
| cgcgggtctc gtcctacttg gggccccact gaccccggc atagatcacg caatttgggc | 360 |
| aaagtcatcg acaccattac gtgtggtttt gccgacctca tggggtacat ccctgtcgtt | 420 |

```
ggcgccccgg ttggaggcgt cgccagagct ctggcacacg gtgttagggt cctggaagac    480
gggataaatt acgcaacagg gaatttgcct ggttgctctt tttctatctt cttgcttgct    540
cttctgtcgt gctgcacagt gccagtgtct gcg                                 573

<210> SEQ ID NO 134
<211> LENGTH: 573
<212> TYPE: DNA
<213> ORGANISM: Homo sapiens
<220> FEATURE:
<223> OTHER INFORMATION: Individual Isolate:  S83

<400> SEQUENCE: 134
atgagcacaa atcctaaacc tcaaagaaaa accaaaagaa acactaaccg ccgcccacag     60
gacgtcaagt tcccgggcgg tggccagatc gttggcggag tatacttgct gccgcgcagg    120
ggcccgagat tgggtgtgcg cgcgacgagg aaaacttccg aacggtccca gccacgtggg    180
aggcgccagc ccatccctaa agatcggcgc accactggca agtcctgggg aaggccagga    240 taccttggc  ccctgtatgg gaatgagggc ctcggctggg cagggtggct cctgtccccc    300
cgcggttctc gccccttcatg gggccccacc gaccccggc ataaatcgcg caacttgggt     360
aaggtcatcg ataccctaac gtgcggtttt gccgacctca tggggtacat acccgtcgtt    420
ggcgctcccg ttggcggcgt tgccagagcc ctcgcccatg gggtgagggt tctggaggac    480
gggataaatt atgcaacggg gaatttgccc ggttgctctt tctctatctt tctcttggcc    540
ctcttgtctt gcatctctgt gccagtttcc gcc                                 573

<210> SEQ ID NO 135
<211> LENGTH: 573
<212> TYPE: DNA
<213> ORGANISM: Homo sapiens
<220> FEATURE:
<223> OTHER INFORMATION: Individual Isolate:  HK10

<400> SEQUENCE: 135
atgagcacac ttcctaaacc tcaaagaaaa accaaaagaa acaccatccg tcgcccacag     60
gacgttaagt tcccgggtgg cggacagatc gttggtggag tatacgtgtt gccgcgcagg    120
ggcccacgat tgggtgtgcg cgcgacgcgt aaaacttctg aacggtcgca gcctcgcgga    180
cgacgacagc ctatccccaa ggcgcgtcgg agcgaaggcc ggtcctgggc tcagcccggg    240 taccttggc  ccctctatgg taacgagggc tgcgggtggg caggatggct cctgtcccca    300
cgcggctccc gtccatcttg gggcccaaac gaccccggc gacggtcccg caatttgggt    360
aaagtcatcg ataccttac  gtgcggattc gccgacctca tggggtacat cccgctcgtc    420
ggcgctcccg taggaggcgt cgcaagagcc ctcgcgcatg gcgtgagggc ccttgaagac    480
gggataaatt tcgcaacagg gaacttgccc ggttgctcct tttctatctt ccttcttgct    540
ctgttctctt gcttaattca tccagcagct agt                                 573

<210> SEQ ID NO 136
<211> LENGTH: 573
<212> TYPE: DNA
<213> ORGANISM: Homo sapiens
<220> FEATURE:
<223> OTHER INFORMATION: Individual Isolate:  S52

<400> SEQUENCE: 136
atgagcacac ttcctaaacc tcaaagaaaa accaaaagaa acaccatccg tcgcccacag     60
```

```
gacgttaagt tcccgggtgg cggacagatc gttggtggag tatacgtgtt gccgcgcagg    120
ggcccacgat tgggtgtgcg cgcgacgcgt aaaacttctg aacggtcaca gcctcgcgga    180 cgacgcagc  ctatcccaa  ggcgcgtcgg agcgaaggcc ggtcctgggc tcagcccggg    240 taccctttggc ccctctatgg taatgagggc tgcgggtggg cagggtggct cctgtcccca   300
cgcggctccc gtccatcttg gggcccaaac gaccccggc  ggaggtcccg caatttgggt    360
aaagtcatcg ataccttac  gtgcggattc gccgacctca tggggtacat cccgctcgtc    420
ggcgctcccg taggaggcgt cgcaagagcc ctcgcgcatg gcgtgagggc ccttgaagac    480
gggataaatt ttgcaacagg gaacttgccc ggttgctcct tttctatctt ccttcttgct    540
ctgttctcct gcttagttca tcctgcagct agt                                 573
```

<210> SEQ ID NO 137
<211> LENGTH: 573
<212> TYPE: DNA
<213> ORGANISM: Homo sapiens
<220> FEATURE:
<223> OTHER INFORMATION: Individual Isolate:  S2

<400> SEQUENCE: 137

```
atgagcacac ttcctaaacc tcaaagaaaa accaaaagaa acaccatccg tcgcccacag     60
gacatcaagt tcccgggtgg cggacagatc gttggtggag tatacgtgtt gccgcgcagg    120
ggcccacgat tgggtgtgcg cgcgacgcgt aaaacttctg aacggtcaca gcctcgcgga    180
cggcgacagc ctatcccaa  ggcgcgtcgg agcgaaggcc gatcctgggc tcagcccggg    240 taccttggc  ccctctatgg taacgagggc tgcgggtggg cagggtggct cctgtcccca    300
cgcggctccc gtccatcttg gggcccaaat gaccccggc  ggaggtcccg caatttgggt    360
aaagtcatcg ataccttac  gtgcggcttc gccgacctca tggggtacat cccgctcgtc    420
ggcgctcccg taggaggcgt cgcaagagcc ctcgcgcatg gcgtgagggc ccttgaagac    480
gggataaatt ttgcaacagg gaacttgccc ggttgctctt tttctatctt ccttcttgcc    540
ctgttctctt gcttaattca tccagcagct agt                                 573
```

<210> SEQ ID NO 138
<211> LENGTH: 573
<212> TYPE: DNA
<213> ORGANISM: Homo sapiens
<220> FEATURE:
<223> OTHER INFORMATION: Individual Isolate:  DK12

<400> SEQUENCE: 138

```
atgagcacac ttcctaaacc tcaaagaaaa accaaaagaa acaccatccg tcgcccacag     60
gacgtcaagt tcccgggtgg cggacagatc gttggtggag tatacgtgtt gccgcgcagg    120
ggcccacgat tgggtgtgcg cgcgacgcgt aaaacttctg aacggtcaca gcctcgcgga    180
cggcgacagc ctatcccaa  ggcgcgtcgg agcgaaggcc ggtcctgggc tcagcctggg    240 taccctttggc ccctctatgg taacgagggc tgcgggtggg cagggtggct cctgtcccca   300
cgcggctccc gtccatcttg gggcccaaac gaccccggc  ggaggtcccg caatttgggt    360
aaggtcatcg ataccctcac gtgcggattc gccgacctca tggggtacat cccgctcgtc    420
ggcgctcctg taggggggcgt cgcaagagcc ctcgcgcatg gcgtgagggc ccttgaagac   480
gggataaatt tcgcaacagg gaacttgccc ggttgctcct tttctatctt ccttcttgct    540
ctgttctctt gcctaattca tccagcagct agt                                 573
```

-continued

<210> SEQ ID NO 139
<211> LENGTH: 573
<212> TYPE: DNA
<213> ORGANISM: Homo sapiens
<220> FEATURE:
<223> OTHER INFORMATION: Individual Isolate: Z4

<400> SEQUENCE: 139

| | | | | | |
|---|---|---|---|---|---|
| atgagcacga | atcctaaacc | tcaaagaaaa | accaaacgta | acaccaaccg | ccgcccatg | 60 |
| gacgtaaagt | tcccgggtgg | tggccagatc | gttggcggag | tttacttgtt | gccgcgcagg | 120 |
| ggccccaggt | tgggtgtgcg | cgcgactcga | aagacttcgg | agcggtcgca | acctcgtggc | 180 |
| aggcgtcaac | ctatccccaa | ggcgcgccag | ccagagggca | gatcctgggc | gcagcccggg | 240 |
| taccttggc | ccctctatgg | caatgagggc | tgcgggtggg | cagggtggct | cctgtctcct | 300 |
| cgcggctctc | ggccatcttg | gggcccaaat | gatccccggc | ggagatcgcg | caatctgggt | 360 |
| aaggtcatcg | ataccctgac | gtgcggcttc | gccgacctca | tgggatacat | cccgatcgtg | 420 |
| ggcgcccccg | tgggggggcgt | cgccagggct | ctggcgcatg | gcgtcagggc | tgtggaggac | 480 |
| gggattaact | atgcaacagg | gaatcttccc | ggttgctctt | tctctatctt | ccttttggca | 540 |
| cttctttcgt | gcctcactgt | tccagcgtcg | gct | | | 573 |

<210> SEQ ID NO 140
<211> LENGTH: 573
<212> TYPE: DNA
<213> ORGANISM: Homo sapiens
<220> FEATURE:
<223> OTHER INFORMATION: Individual Isolate: Z8

<400> SEQUENCE: 140

| | | | | | |
|---|---|---|---|---|---|
| atgagcacga | atcctaaacc | tcaaagaaaa | accaaacgta | acaccaaccg | ccgccctatg | 60 |
| gatgtaaaat | tcccaggcgg | cggccagatc | gttggcggag | tttacttgtt | gccgcgcagg | 120 |
| ggccccaggt | tgggtgtgcg | cgcgactcgg | aagacttcgg | agcggtcgca | acctcgtggc | 180 |
| aggcgtcagc | ctatccccaa | ggcacgtcgg | tccgagggta | ggtcctgggc | tcagcccggg | 240 |
| tacccatggc | ctcttttacgg | taatgaaggc | tgtgggtggg | caggttggct | cctgtccccc | 300 |
| cgcggctctc | gaccgtcttg | gggcccaaat | gatccccggc | ggaggtcgcg | caatttgggt | 360 |
| aaggtcatcg | ataccctcac | gtgcggcttc | gccgacctca | tgggatacat | cccgctcgtg | 420 |
| ggcgcccccag | taggaggcgt | cgccagagcc | ctggcgcatg | gcgtcagggc | tgtggaggac | 480 |
| gggatcaact | atgcaacagg | gaaccttcct | ggttgctctt | tctctatctt | cctcttggca | 540 |
| cttctctcgt | gcctaaccgt | cccagcgtct | gct | | | 573 |

<210> SEQ ID NO 141
<211> LENGTH: 573
<212> TYPE: DNA
<213> ORGANISM: Homo sapiens
<220> FEATURE:
<223> OTHER INFORMATION: Individual Isolate: Z1

<400> SEQUENCE: 141

| | | | | | |
|---|---|---|---|---|---|
| atgagcacaa | atcctaaacc | tcaaagaaaa | accaaacgta | acaccaaccg | tcgcccatg | 60 |
| gatgtgaaat | tcccgggcgg | cggccagatc | gttggcggag | tttacttgct | gccgcgcagg | 120 |
| ggccccggt | tgggtgtgcg | cgcagctcgg | aagacttcgg | agcggtcaca | acctcgtggc | 180 |
| aggcgtcagc | ctatccccaa | ggcgcgccgg | tccgagggca | ggtcctgggc | tcagcccggg | 240 |
| taccctttggc | cccttttacgg | caatgagggc | tgtgggtggg | cagggtggct | cctgtccccc | 300 |

-continued

```
cgcggttcca ggccgtcttg gggccccaat gatccccggc gtaggtcccg taatctgggt    360
aaagtcatcg ataccctgac gtgtggcttc gccgacctca tgggatacat tccgctcgta    420
ggcgcccctg tgggtggcgt cgccagggcc ctggcgcatg gcgtcagggc cgtggaggac    480
ggaattaact acgcaacagg gaaccttcct ggttgctctt tctctatctt tcttcttgca    540
cttctctcgt gcctgacaac accagcatct gcc                                 573
```

<210> SEQ ID NO 142
<211> LENGTH: 573
<212> TYPE: DNA
<213> ORGANISM: Homo sapiens
<220> FEATURE:
<223> OTHER INFORMATION: Individual Isolate: Z5

<400> SEQUENCE: 142

```
atgagcacga atcctaaacc tcaaagaaaa accaaacgta acaccaaccg ccgccccatg    60
gatgtaaaat tcccgggtgg tggtcagatc gttggcggag tttacttgtt gccgcgcagg    120
ggccccaggt tgggtgtgcg cgcgactcgg aagacttcgg agcggtcgca acctcgcggc    180
aggcgtcagc ctatccccca ggcacgtcgg tccgagggca ggtcctgggc tcagcccggg    240 taccctttggc ctctttatgg caatgagggc tgtgggtggg cagggtggct cctgtccccc    300
cgcggatctc ggccatcttg gggccaaaat gatccccggc gtaggtcccg caatctgggt    360
aaggtcatcg ataccctgac gtgtggcttc gccgacctca tgggatacat tccgctcgtc    420
ggcgccccag taggtggcgt cgccagggcc ttggcgcatg gcgtcagggc cctggaggac    480
ggaatcaact atgcaacagg gaatcttcct ggttgctcct tttctatctt cctacttgca    540
cttttctcgt gcttgacaac accggcatcc gct                                 573
```

<210> SEQ ID NO 143
<211> LENGTH: 573
<212> TYPE: DNA
<213> ORGANISM: Homo sapiens
<220> FEATURE:
<223> OTHER INFORMATION: Individual Isolate: Z6

<400> SEQUENCE: 143

```
atgagcacga atcctaaacc tcaaagaaaa accaaacgta acaccaaccg ccgccccatg    60
gacgttaagt tcccgggtgg tggccagatc gttggcggag tttacttgtt gccgcgcagg    120
ggccccaggt tgggtgtgcg cgcgactagg aagacttcgg agcggtcgca acctcgtggg    180
agacgccagc ctatccccaa ggcacgtcga tctgagggaa ggtcctgggc tcagcccggg    240
tatccatggc ctctttacgg taatgagggt tgcgggtggg cgggatggct cctgtcaccc    300
cgtggctctc gaccgtcttg gggtccaaat gatccccggc gaaggtcccg caacttgggt    360
aaggtcatcg atactctaac ttgcggtttc gccgatctca tgggatacat cccgctcgta    420
ggcgcccccg tgggcggcgt cgccagggcc ctggcacatg gtgttagggc tgtggaggac    480
gggatcaatt atgcaacagg gaatcttccc ggttgctctt tctctatctt cctcttggca    540
cttctttcgt gcctaactgt tcccacctcg gcc                                 573
```

<210> SEQ ID NO 144
<211> LENGTH: 573
<212> TYPE: DNA
<213> ORGANISM: Homo sapiens
<220> FEATURE:
<223> OTHER INFORMATION: Individual Isolate: Z7

<400> SEQUENCE: 144

-continued

| | |
|---|---|
| atgagcacga atcctaaacc tcaaagaaaa accaaacgta acaccaaccg ccgcccatg | 60 |
| gacgttaagt tcccgggcgg tggccagatc gttggcggag tttacttgtt gccgcgcagg | 120 |
| ggccccagat tgggtgtgcg cacaactagg aagacttcgg agcggtcgca acctcgtggg | 180 |
| agacgtcagc ctatccccaa ggcacgtcga tctgagggaa ggtcctgggc tcaacccggg | 240 |
| tacccatggc tctttacgg taacgagggt tgcgggtggg caggatggct cttgtcaccc | 300 |
| cgtggctctc gaccgtcttg gggcccaaat gatccccggc gaaggtcccg caacttgggt | 360 |
| aaggtcatcg atacccta ac ctgcggcttt gccgacctca tgggatacat cccgctcgta | 420 |
| ggcgccccg tgggcggcgt cgccagggcc ctagcgcatg gcgttagggc tctggaggac | 480 |
| gggattaatt atgcaacagg gaaccttccc ggttgctctt tttctatctt cctcttggca | 540 |
| cttctttcgt gcctgactgt tcccgcctcg gcc | 573 |

<210> SEQ ID NO 145
<211> LENGTH: 573
<212> TYPE: DNA
<213> ORGANISM: Homo sapiens
<220> FEATURE:
<223> OTHER INFORMATION: Individual Isolate: DK13

<400> SEQUENCE: 145

| | |
|---|---|
| atgagcacga atcctaaacc tcaaagaaaa accaaacgta acaccaaccg ccgcccaatg | 60 |
| gacgttaagt tcccgggtgg cggccagatc gttggcggag tttacttgtt gccgcgcagg | 120 |
| ggccctagat tgggtgtgcg cgcgactagg aagacttcgg agcggtcgca acctcgtggg | 180 |
| aggcgccagc ctatccccaa ggcgcgccaa ctcgagggta ggtcctgggc tcagcctggg | 240 |
| tatccttggc ccctttacgg caatgagggc tgcgggtggg cgggatggct cctgtcaccc | 300 |
| cgtggctctc ggccgtcttg gggcccgaat gatccccggc ggaggtcccg caacttgggt | 360 |
| aaggtcatcg atacccta ac ttgcggcttc gccgacctca tgggatacat cccggtcgta | 420 |
| ggcgccccg tgggtggcgt cgccagagcc ctggcgcatg gcgtcaggct tctggaggac | 480 |
| ggggtcaatt atgcaacagg gaatcttccc ggttgctctt tctctatctt cctcttggca | 540 |
| ctgctctcgt gcctgactgt tcccgcttcg gcc | 573 |

<210> SEQ ID NO 146
<211> LENGTH: 573
<212> TYPE: DNA
<213> ORGANISM: Homo sapiens
<220> FEATURE:
<223> OTHER INFORMATION: Individual Isolate: SA4

<400> SEQUENCE: 146

| | |
|---|---|
| atgagcacga atcctaaacc tcaaagaaaa accaaaagaa acaccaaccg ccgcccacag | 60 |
| gacgttaagt tcccgggcgg tggtcagatc gttggtggag tctacttgtt gccgcgcagg | 120 |
| ggccctaggt tgggtgtgcg cgcgactcgg aagacttcag aacggtcgca accccgtggg | 180 |
| cggcgccagc ctattcccaa ggcgcgccaa cccacgggcc ggtcctgggg tcaacccggg | 240 |
| taccctttggc cccctttacgc caatgagggc ctcgggtggg caggtggtt gctctccccc | 300 |
| cgaggctctc ggcctaattg gggcccaat gaccccggc gaaagtcgcg caatttgggt | 360 |
| aaggtcatcg atacccta ac gtgcggattc gccgacctca tggggtacat cccgctcgta | 420 |
| ggcgccccg ttgggggcgt cgcaagggcc cttgcacatg gtgtgagggt tcttgaggac | 480 |
| ggggtaaact atgcaacggg gaatttgccc ggttgctctt tctctatctt tatccttgca | 540 |

-continued cttctctcgt gcctgaccgt cccggcctct gca 573

<210> SEQ ID NO 147
<211> LENGTH: 573
<212> TYPE: DNA
<213> ORGANISM: Homo sapiens
<220> FEATURE:
<223> OTHER INFORMATION: Individual Isolate: SA5

<400> SEQUENCE: 147

| | |
|---|---|
| atgagcacga atcctaaacc tcaaagaaaa accaaaagaa acaccaaccg ccgcccacag | 60 |
| gacgtcaagt tcccgggcgg tggtcagatc gttggtggag tttacttgtt gccgcgcagg | 120 |
| ggccctagat tgggtgtgcg cgcgactcgg aagacttcag aacggtcgca accccgtggg | 180 |
| cggcgccagc ctattcccaa ggcgcgccaa cccacgggcc ggtcctgggg tcaacccggg | 240 |
| taccctnggc ccctttacgc caatgagggc ctcgggtggg cagggtggtt gctctccccc | 300 |
| cgaggctctc ggcctaattg ggccccaat gaccccggc gaaaatcgcg caatttgggt | 360 |
| aaggtcatcg ataccctaac gtgcggattc gccgacctca tggggtacat cccgctcgta | 420 |
| ggcggccccg ttgggggcgt cgcaagggcc ctcgcacatg gtgtgagggt tcttgaggac | 480 |
| ggggtaaact atgcaacagg gaatttgccc ggttgctctt tctctatctt tatccttgca | 540 |
| cttctctcgt gcttgaccgt cccagcctct gca | 573 |

<210> SEQ ID NO 148
<211> LENGTH: 573
<212> TYPE: DNA
<213> ORGANISM: Homo sapiens
<220> FEATURE:
<223> OTHER INFORMATION: Individual Isolate: SA7

<400> SEQUENCE: 148

| | |
|---|---|
| atgagcacga atcctaaacc tcaaagaaaa accaaaagaa acaccaaccg ccgcccacag | 60 |
| gacgtcaagt tcccgggcgg tggtcagatc gttggtggag tttacttgtt gccgcgcagg | 120 |
| ggccctaggt tgggtgtgcg cgcgactcgg aagacttcag aacggtcgca accccgtggg | 180 |
| cggcgccagc ctattcccaa ggcgcgccaa cccacgggcc ggtcctgggg tcaacccggg | 240 |
| taccctnggc ccctttacgc caatgagggc ctcgggtggg cagggtggtt gctctccccc | 300 |
| cgaggctctc ggcctaattg ggccccaat gaccccggc gaaagtcgcg caatttgggt | 360 |
| aaggtcatcg acaccctaac atgcggattc gccgacctca tggggtacat cccgctcgta | 420 |
| ggcggccccg ttgggggcgt cgcaagggct ctcgcacacg gtgtgagggt tcttgaggac | 480 |
| ggggtaaatt acgcaacagg gaatctgccc ggttgctctt tctctatctt tatccttgca | 540 |
| cttctctcgt gcctgaccgt cccagcctcc gca | 573 |

<210> SEQ ID NO 149
<211> LENGTH: 573
<212> TYPE: DNA
<213> ORGANISM: Homo sapiens
<220> FEATURE:
<223> OTHER INFORMATION: Individual Isolate: SA1

<400> SEQUENCE: 149

| | |
|---|---|
| atgagcacga atcctaaacc tcaaagaaaa accaaaagaa acaccaacct ccgcccacag | 60 |
| gacgtcaagt tcccgggcgg tggtcagatc gttggtggag tttacttgtt gccgcgcagg | 120 |
| ggccccaggt tgggtgtgcg cgcgactcgg aagacttcgg aacggtcgca accccgtggg | 180 |
| cggcgccagc ctattcccaa ggcgcgccaa cccacgggcc ggtcctgggg tcaacccggg | 240 |

```
tacccttggc ccctttacgc caatgagggc ctcgggtggg cagggtggtt gctctccccc        300
cgaggctctc ggcctaattg gggccccaat gaccccggc ggaagtcgcg caatttgggt         360
aaggtcatcg atacectaac gtgcggattc gccgacctca tggggtacat cccgctcgta        420
ggcggccccg ttgggggcgt cgcaagggct ctcgcacacg gtgtgagggt tcttgaggac        480
ggggtaaact acgcaacagg gaatttgccc ggttgctctt tctctatctt tatccttgca       540
cttctttcct gtctgatcat cccggcctct gca                                    573

<210> SEQ ID NO 150
<211> LENGTH: 573
<212> TYPE: DNA
<213> ORGANISM: Homo sapiens
<220> FEATURE:
<223> OTHER INFORMATION: Individual Isolate:  SA3

<400> SEQUENCE: 150
atgagcacga atcctaaacc tcaaagaaaa accaaaagaa acaccaaccg ccgcccacag         60
gacgtcaagt tcccgggcgg tggtcagatc gttggtggag tttacttgtt gccgcgcagg       120
ggccccaggt tgggtgtgcg cgcgactcgg aagacttcag aacggtcgca accccgtgga       180
cggcgccagc ctattcccaa ggctcgccag cccacgggcc ggtcctgggg tcaacccggg       240
tacccttggc ccctttacgc caatgagggc ctcgagtggg cagggtggtt gctctccccc       300
cgaggctctc ggcctagttg gggcccaac gaccccggc ggaaatcgcg caatttgggt        360
aaggtcatcg atacectaac gtgcggattc gccgatctca tggggtacat cccgctcgta      420
ggcggccccg ttggggggcgt cgcaagggct ctcgcacatg gtgtgagggt tcttgaggac    480
ggggtaaact acgcaacagg gaatttaccc ggttgctctt tctctatctt tatccttgca    540
cttctttcat gcctgaccgt cccggcctct gca                                    573

<210> SEQ ID NO 151
<211> LENGTH: 573
<212> TYPE: DNA
<213> ORGANISM: Homo sapiens
<220> FEATURE:
<223> OTHER INFORMATION: Individual Isolate:  SA13

<400> SEQUENCE: 151
atgagcacga atcctaaacc tcaaagaaaa accaaaagaa acaccaaccg ccgcccacag         60
gacgtcaagt tcccgggcgg tggtcagatc gttggtggag tttacttgtt gccgcgcagg       120
ggccctaggt tgggtgtgcg cgcaactcgg aagacttcag aacggtcgca accccgtgga       180
cggcgtcagc ctatcccaa ggcgcgccag cccacgggcc ggtcctgggg tcaacccggg       240
tacccttggc ccctttatgc caatgagggc ctcgggtggg cagggtggtt gctctccccc       300
cgaggctctc ggcctaattg gggccccaat gaccccggc ggaaatcgcg caacttgggt        360
aaggtcatcg atacectgac gtgcggattc gccgacctca tggggtacat cccgctcgta      420
ggcggccccg ttgggggcgt cgcaagggct ctcgcacacg gtgtgagggt ccttgaggac       480
ggggtaaact atgcaacagg gaatttaccc ggttgctctt tctctatctt tatccttgca      540
cttctttcat gcctgactgt cccgacctct gcc                                    573

<210> SEQ ID NO 152
<211> LENGTH: 573
<212> TYPE: DNA
<213> ORGANISM: Homo sapiens
<220> FEATURE:
```

<223> OTHER INFORMATION: Individual Isolate: SA6

<400> SEQUENCE: 152

| | | |
|---|---|---|
| atgagcacga atcctaaacc tcaaagaaaa acccaaagaa acaccaaccg ccgcccacag | 60 |
| gacgtcaagt tcccgggcgg tggtcagatc gttggtggag tttacttgtt gccgcgcagg | 120 |
| ggccctcgta tgggtgtgcg cgcgactcgg aagacttcgg aacggtcgca accccgtgga | 180 |
| cggcgtcagc ctattcccaa ggcgcgccaa tccgcgggtc ggtcctgggg tcaacccggg | 240 |
| taccccttggc cccttttacgc caatgagggc ctcgggtggg cagggtggtt gctctccccc | 300 |
| cgaggctctc ggcctaattg ggccccaat accccccggc gaaaatcgcg caatttgggt | 360 |
| aaggtcatcg ataccctaac gtgcggattc gccgacctca tggggtacat cccgctcgta | 420 |
| ggcggccccg ttggggggcgt cgcaagggct ctcgcacacg gtgtgagggt tcttgaggac | 480 |
| ggggtaaact atgcaacagg gaatttgccc ggttgctctt tctctatctt tgtccttgca | 540 |
| cttctctcgt gcctaaccgt ccctgcctct gca | 573 |

<210> SEQ ID NO 153
<211> LENGTH: 573
<212> TYPE: DNA
<213> ORGANISM: Homo sapiens
<220> FEATURE:
<223> OTHER INFORMATION: Individual Isolate: SA11

<400> SEQUENCE: 153

| | | |
|---|---|---|
| atgagcacga atcctaaacc tcaaagaaaa accaaaagaa acaccaaccg ccgcccacag | 60 |
| gacgtcaagt tcccgggcgg tggtcagatc gttggtggag tttacttgtt gccgcgcagg | 120 |
| ggccctaggt tgggtgtgcg cgcgactcgg aagacttcag aacggtcgca accccgtggg | 180 |
| cggcgtcagc ctattcccaa ggcgcgccaa cccacgggcc ggtcctgggg tcaacccggg | 240 |
| taccccttggc cctttttacgc caatgagggc ctcgggtggg cagggtggct gctctcccct | 300 |
| cgaggctctc ggcctaactg ggccccaat accccccggc gaagatcgcg caatttgggc | 360 |
| aaggtcatcg ataccctaac gtgcggattc gccgacctca tggggtacat cccgctcgta | 420 |
| ggcggccccg ttggggggcgt cgcaagggcc ctcgcacacg gtgtgagagc tcttgaggac | 480 |
| ggggtaaatt atgcaacagg gaatcttccc ggttgctctt tctccatctt tatccttgca | 540 |
| cttctctcgt gcttgaccgt cccggccact gca | 573 |

<210> SEQ ID NO 154
<211> LENGTH: 573
<212> TYPE: DNA
<213> ORGANISM: Homo sapiens
<220> FEATURE:
<223> OTHER INFORMATION: Individual Isolate: HK2

<400> SEQUENCE: 154

| | | |
|---|---|---|
| atgagcacac ttccaaaacc ccaaagaaaa accaaaagaa acaccaaccg tcgcccaacg | 60 |
| gacgtcaagt tcccgggtgg cggtcagatc gttggcggag tttacttgtt gccgcgcagg | 120 |
| ggcccccggt tgggtgtgcg cgcgacgaga aagacttccg agcgatccca gcccagaggc | 180 |
| aggcgccaac ctataccaaa ggcgcgccag ccccagggca ggcactgggc tcagcccgga | 240 |
| taccccttggc ctcttatgg aaacgagggc tgtgggtggg caggttggct cctgtccccc | 300 |
| cgcggctccc ggccacattg ggccccaat accccccggc gtcgatcccg gaatttgggt | 360 |
| aaggtcatcg ataccctaac gtgtgggttc gccgatctca tggggtacat tccgtcgtg | 420 |
| ggcgcgcctt tgggcggcgt cgcggctgcg ctcgcacatg gcgtgagggc aatcgaggac | 480 |

-continued

```
gggatcaatt atgcaacagg gaatctcccc ggttgctctt tctctatctt ccttttggca    540
ctactctcgt gcctcacaac gccagcttcg gct                                 573
```

<210> SEQ ID NO 155
<211> LENGTH: 191
<212> TYPE: PRT
<213> ORGANISM: Homo sapiens
<220> FEATURE:
<223> OTHER INFORMATION: Individual Isolate: DK7

<400> SEQUENCE: 155

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```

<210> SEQ ID NO 156
<211> LENGTH: 191
<212> TYPE: PRT
<213> ORGANISM: Homo sapiens
<220> FEATURE:
<223> OTHER INFORMATION: Individual Isolate: US11

<400> SEQUENCE: 156

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95
```

```
Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 157
<211> LENGTH: 191
<212> TYPE: PRT
<213> ORGANISM: Homo sapiens
<220> FEATURE:
<223> OTHER INFORMATION: Individual Isolate:  S14

<400> SEQUENCE: 157

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 158
<211> LENGTH: 191
<212> TYPE: PRT
<213> ORGANISM: Homo sapiens
<220> FEATURE:
<223> OTHER INFORMATION: Individual Isolate:  SW1

<400> SEQUENCE: 158

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                20                  25                  30
```

```
Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
                180                 185                 190

<210> SEQ ID NO 159
<211> LENGTH: 191
<212> TYPE: PRT
<213> ORGANISM: Homo sapiens
<220> FEATURE:
<223> OTHER INFORMATION: Individual Isolate:  S18

<400> SEQUENCE: 159

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
                180                 185                 190

<210> SEQ ID NO 160
```

-continued

```
<211> LENGTH: 191
<212> TYPE: PRT
<213> ORGANISM: Homo sapiens
<220> FEATURE:
<223> OTHER INFORMATION: Individual Isolate: DR4

<400> SEQUENCE: 160
```

Met Ser Thr Asn Pro Lys Pro Gln Arg Lys Thr Lys Arg Asn Thr Asn
 1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

```
<210> SEQ ID NO 161
<211> LENGTH: 191
<212> TYPE: PRT
<213> ORGANISM: Homo sapiens
<220> FEATURE:
<223> OTHER INFORMATION: Individual Isolate: SA10

<400> SEQUENCE: 161
```

Met Ser Thr Asn Pro Lys Pro Gln Arg Lys Thr Lys Arg Asn Thr Asn
 1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
 50                  55                  60

Ile Pro Lys Ala Arg Gln Pro Glu Gly Arg Thr Trp Ala Gln Pro Gly
 65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu

```
                130             135             140
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Pro Phe Ser Ile
                165                 170                 175

Phe Leu Leu Ala Leu Leu Ser Cys Leu Thr Ile Pro Ala Ser Ala
                180                 185                 190

<210> SEQ ID NO 162
<211> LENGTH: 191
<212> TYPE: PRT
<213> ORGANISM: Homo sapiens
<220> FEATURE:
<223> OTHER INFORMATION: Individual Isolate: S45

<400> SEQUENCE: 162

Met Ser Thr Asn Pro Lys Pro Gln Arg Ala Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ala Trp Ala Gln Pro Gly
65                  70                  75                  80

His Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130             135             140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190

<210> SEQ ID NO 163
<211> LENGTH: 191
<212> TYPE: PRT
<213> ORGANISM: Homo sapiens
<220> FEATURE:
<223> OTHER INFORMATION: Individual Isolate: D1

<400> SEQUENCE: 163

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
50                  55                  60
```

```
Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
            180                 185                 190
```

<210> SEQ ID NO 164
<211> LENGTH: 191
<212> TYPE: PRT
<213> ORGANISM: Homo sapiens
<220> FEATURE:
<223> OTHER INFORMATION: Individual Isolate: US6

<400> SEQUENCE: 164

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
            180                 185                 190
```

<210> SEQ ID NO 165
<211> LENGTH: 191
<212> TYPE: PRT
<213> ORGANISM: Homo sapiens
<220> FEATURE:
<223> OTHER INFORMATION: Individual Isolate: P10

<400> SEQUENCE: 165

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190
```

<210> SEQ ID NO 166
<211> LENGTH: 191
<212> TYPE: PRT
<213> ORGANISM: Homo sapiens
<220> FEATURE:
<223> OTHER INFORMATION: Individual Isolate: DK1

<400> SEQUENCE: 166

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

```
Phe Leu Leu Ala Leu Leu Ser Cys Leu Thr Ile Pro Ala Ser Ala
            180                 185                 190

<210> SEQ ID NO 167
<211> LENGTH: 191
<212> TYPE: PRT
<213> ORGANISM: Homo sapiens
<220> FEATURE:
<223> OTHER INFORMATION: Individual Isolate:  T10

<400> SEQUENCE: 167

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Gln Pro Glu Gly Arg Ala Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
            180                 185                 190

<210> SEQ ID NO 168
<211> LENGTH: 191
<212> TYPE: PRT
<213> ORGANISM: Homo sapiens
<220> FEATURE:
<223> OTHER INFORMATION: Individual Isolate:  SW2

<400> SEQUENCE: 168

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Gln Pro Glu Gly Arg Ala Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Ser Trp Gly Pro Thr Asp Pro
```

```
                    100                 105                 110
Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
            180                 185                 190

<210> SEQ ID NO 169
<211> LENGTH: 191
<212> TYPE: PRT
<213> ORGANISM: Homo sapiens
<220> FEATURE:
<223> OTHER INFORMATION: Individual Isolate:   IND3

<400> SEQUENCE: 169

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
            180                 185                 190

<210> SEQ ID NO 170
<211> LENGTH: 191
<212> TYPE: PRT
<213> ORGANISM: Homo sapiens
<220> FEATURE:
<223> OTHER INFORMATION: Individual Isolate:   IND8

<400> SEQUENCE: 170

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                20                  25                  30
```

```
Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Ala Trp Ala Gln Pro Gly
 65                  70                  75                  80

His Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
                180                 185                 190

<210> SEQ ID NO 171
<211> LENGTH: 191
<212> TYPE: PRT
<213> ORGANISM: Homo sapiens
<220> FEATURE:
<223> OTHER INFORMATION: Individual Isolate: S9

<400> SEQUENCE: 171

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg His Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190

<210> SEQ ID NO 172
<211> LENGTH: 191
```

```
<212> TYPE: PRT
<213> ORGANISM: Homo sapiens
<220> FEATURE:
<223> OTHER INFORMATION: Individual Isolate:  HK3

<400> SEQUENCE: 172

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Gln Pro Glu Gly Arg Thr Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro Arg Gly Ser Arg Pro Asn Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala
                180                 185                 190

<210> SEQ ID NO 173
<211> LENGTH: 191
<212> TYPE: PRT
<213> ORGANISM: Homo sapiens
<220> FEATURE:
<223> OTHER INFORMATION: Individual Isolate:  HK5

<400> SEQUENCE: 173

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Met Gly Trp Ala Gly Trp
                 85                  90                  95

Leu Leu Ser Pro His Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140
```

```
Gly Gly Val Ala Arg Ala Leu Ala His Gly Val Arg Val Leu Glu Asp
145                 150                 155                 160

Gly Val Asn Tyr Ala Thr Gly Asn Ile Pro Gly Cys Ser Phe Ser Ile
            165                 170                 175

Phe Leu Leu Ala Leu Leu Ser Cys Leu Thr Thr Pro Val Ser Ala
            180                 185                 190
```

<210> SEQ ID NO 174
<211> LENGTH: 191
<212> TYPE: PRT
<213> ORGANISM: Homo sapiens
<220> FEATURE:
<223> OTHER INFORMATION: Individual Isolate: HK4

<400> SEQUENCE: 174

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Gln Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Val Val Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Ile Pro Ala Ser Ala
            180                 185                 190
```

<210> SEQ ID NO 175
<211> LENGTH: 191
<212> TYPE: PRT
<213> ORGANISM: Homo sapiens
<220> FEATURE:
<223> OTHER INFORMATION: Individual Isolate: P8

<400> SEQUENCE: 175

```
Met Ser Thr Thr Pro Lys Pro Gln Arg Lys Thr Lys Arg Asn Thr Ser
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ala Trp Ala Gln Pro Gly
```

```
         65                  70                  75                  80
His Pro Trp Pro Leu Tyr Ala Asn Glu Gly Leu Gly Trp Ala Gly Trp
                    85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Gly Pro Leu
        130                 135                 140

Gly Gly Val Ala Arg Ala Leu Ala His Gly Val Arg Val Val Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190

<210> SEQ ID NO 176
<211> LENGTH: 191
<212> TYPE: PRT
<213> ORGANISM: Homo sapiens
<220> FEATURE:
<223> OTHER INFORMATION: Individual Isolate: T3

<400> SEQUENCE: 176

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asp Glu Gly Met Gly Trp Ala Gly Trp
                    85                  90                  95

Leu Leu Ser Pro Arg Gly Ser Arg Pro Asn Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190

<210> SEQ ID NO 177
<211> LENGTH: 191
<212> TYPE: PRT
<213> ORGANISM: Homo sapiens
<220> FEATURE:
<223> OTHER INFORMATION: Individual Isolate: T4

<400> SEQUENCE: 177
```

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
                100                 105                 110

Arg His Arg Ser Arg Asn Val Gly Lys Val Ile Asp Thr Leu Thr Cys
                115                 120                 125

Ser Leu Ala Asp Leu Met Gly Tyr Val Pro Val Val Gly Gly Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Ile Pro Val Ser Ala
                180                 185                 190

<210> SEQ ID NO 178
<211> LENGTH: 191
<212> TYPE: PRT
<213> ORGANISM: Homo sapiens
<220> FEATURE:
<223> OTHER INFORMATION: Individual Isolate: US10

<400> SEQUENCE: 178

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Pro Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Thr Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

```
Phe Leu Leu Ala Leu Leu Ser Cys Ile Thr Ile Pro Val Ser Ala
                180                 185                 190
```

<210> SEQ ID NO 179
<211> LENGTH: 191
<212> TYPE: PRT
<213> ORGANISM: Homo sapiens
<220> FEATURE:
<223> OTHER INFORMATION: Individual Isolate: T9

<400> SEQUENCE: 179

```
Met Ser Thr Asn Pro Lys Pro Gln Arg Lys Thr Ile Arg Asn Thr Asn
 1               5                  10                  15

Arg Arg Pro Gln Asp Val Lys Phe Pro Gly Gly Gln Ile Val Gly
                20                  25                  30

Gly Val Tyr Leu Leu Pro Arg Arg Gly Pro Arg Leu Gly Val Arg Thr
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Ser Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Thr Pro Ala Ser Ala
            180                 185                 190
```

<210> SEQ ID NO 180
<211> LENGTH: 191
<212> TYPE: PRT
<213> ORGANISM: Homo sapiens
<220> FEATURE:
<223> OTHER INFORMATION: Individual Isolate: T2

<400> SEQUENCE: 180

```
Met Ser Thr Ile Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110
```

-continued

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Ile Pro Val Ser Ala
            180                 185                 190

<210> SEQ ID NO 181
<211> LENGTH: 191
<212> TYPE: PRT
<213> ORGANISM: Homo sapiens
<220> FEATURE:
<223> OTHER INFORMATION: Individual Isolate: T8

<400> SEQUENCE: 181

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Phe Thr Val Pro Val Ser Ala
            180                 185                 190

<210> SEQ ID NO 182
<211> LENGTH: 191
<212> TYPE: PRT
<213> ORGANISM: Homo sapiens
<220> FEATURE:
<223> OTHER INFORMATION: Individual Isolate: US1

<400> SEQUENCE: 182

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala

```
                  35                   40                  45
Thr Arg Lys Thr Ser Glu Arg Ser Gln Pro Arg Gly Arg Gln Pro
 50                      55                      60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                   90                   95

Leu Leu Ser Pro Arg Gly Ser Arg Pro Thr Trp Gly Pro Thr Asp Pro
                100                  105                  110

Arg His Arg Ser Arg Asn Leu Gly Lys Val Ile Asp Thr Ile Thr Cys
                115                  120                  125

Gly Phe Ala Asp Leu Met Gly Tyr Ile Pro Val Val Gly Ala Pro Val
            130                  135                  140

Gly Gly Val Ala Arg Ala Leu Ala His Gly Val Arg Val Leu Glu Asp
145                 150                  155                  160

Gly Ile Asn Tyr Ala Thr Gly Asn Leu Pro Gly Cys Ser Phe Ser Ile
                165                  170                  175

Phe Leu Leu Ala Leu Leu Ser Cys Ala Thr Val Pro Val Ser Ala
                180                  185                  190
```

<210> SEQ ID NO 183
<211> LENGTH: 191
<212> TYPE: PRT
<213> ORGANISM: Homo sapiens
<220> FEATURE:
<223> OTHER INFORMATION: Individual Isolate: DK11

<400> SEQUENCE: 183

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Thr
             35                   40                  45

Thr Arg Lys Thr Ser Glu Arg Ser Gln Pro Arg Gly Arg Arg Gln Pro
 50                      55                      60

Ile Pro Lys Asp Arg Arg Ser Thr Gly Lys Pro Trp Gly Lys Pro Gly
 65                  70                  75                  80

Tyr Pro Trp Pro Leu Tyr Gly Asn Glu Gly Cys Gly Trp Ala Gly Trp
                 85                   90                   95

Leu Leu Ser Pro Arg Gly Ser His Pro Asn Trp Gly Pro Thr Asp Pro
                100                  105                  110

Arg His Lys Ser Arg Asn Leu Gly Lys Val Ile Asp Thr Ile Thr Cys
                115                  120                  125

Gly Phe Ala Asp Leu Met Gly Tyr Ile Pro Val Val Gly Ala Pro Val
            130                  135                  140

Gly Gly Val Ala Arg Ala Leu Ala His Gly Val Arg Val Leu Glu Asp
145                 150                  155                  160

Gly Ile Asn Tyr Ala Thr Gly Asn Leu Pro Gly Cys Ser Phe Ser Ile
                165                  170                  175

Phe Leu Leu Ala Leu Leu Ser Cys Cys Thr Val Pro Val Ser Ala
                180                  185                  190
```

<210> SEQ ID NO 184
<211> LENGTH: 191
<212> TYPE: PRT

```
<213> ORGANISM: Homo sapiens
<220> FEATURE:
<223> OTHER INFORMATION: Individual Isolate:   SW3

<400> SEQUENCE: 184

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser His Pro Asn Trp Gly Pro Thr Asp Pro
                100                 105                 110

Arg His Arg Ser Arg Asn Leu Gly Lys Val Ile Asp Thr Ile Thr Cys
            115                 120                 125

Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Phe Thr Val Pro Val Ser Ala
                180                 185                 190

<210> SEQ ID NO 185
<211> LENGTH: 191
<212> TYPE: PRT
<213> ORGANISM: Homo sapiens
<220> FEATURE:
<223> OTHER INFORMATION: Individual Isolate:   DK8

<400> SEQUENCE: 185

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Ser Ser Glu Arg Ser Gln Pro Arg Gly Arg Arg Gln Pro
 50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Thr Trp Gly Pro Thr Asp Pro
                100                 105                 110

Arg His Arg Ser Arg Asn Leu Gly Lys Val Ile Asp Thr Ile Thr Cys
            115                 120                 125

Gly Phe Ala Asp Leu Met Gly Tyr Ile Pro Val Val Gly Ala Pro Val
130                 135                 140
```

```
Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Cys Thr Val Pro Val Ser Ala
            180                 185                 190

<210> SEQ ID NO 186
<211> LENGTH: 191
<212> TYPE: PRT
<213> ORGANISM: Homo sapiens
<220> FEATURE:
<223> OTHER INFORMATION: Individual Isolate:  S83

<400> SEQUENCE: 186

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Asp Arg Arg Thr Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Lys Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Ser Val Pro Val Ser Ala
            180                 185                 190

<210> SEQ ID NO 187
<211> LENGTH: 191
<212> TYPE: PRT
<213> ORGANISM: Homo sapiens
<220> FEATURE:
<223> OTHER INFORMATION: Individual Isolate:  HK10

<400> SEQUENCE: 187

Met Ser Thr Leu Pro Lys Pro Gln Arg Lys Thr Lys Arg Asn Thr Ile
 1               5                  10                  15

Arg Arg Pro Gln Asp Val Lys Phe Pro Gly Gly Gly Gln Ile Val Gly
             20                  25                  30

Gly Val Tyr Val Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Ser Glu Gly Arg Ser Trp Ala Gln Pro Gly
65                  70                  75                  80
```

```
Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
            165                 170                 175

Phe Leu Ala Leu Phe Ser Cys Leu Ile His Pro Ala Ala Ser
        180                 185                 190

<210> SEQ ID NO 188
<211> LENGTH: 191
<212> TYPE: PRT
<213> ORGANISM: Homo sapiens
<220> FEATURE:
<223> OTHER INFORMATION: Individual Isolate: S52

<400> SEQUENCE: 188

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
            165                 170                 175

Phe Leu Ala Leu Phe Ser Cys Leu Val His Pro Ala Ala Ser
        180                 185                 190

<210> SEQ ID NO 189
<211> LENGTH: 191
<212> TYPE: PRT
<213> ORGANISM: Homo sapiens
<220> FEATURE:
<223> OTHER INFORMATION: Individual Isolate: S2

<400> SEQUENCE: 189

Met Ser Thr Leu Pro Lys Pro Gln Arg Lys Thr Lys Arg Asn Thr Ile
```

```
                1               5              10              15
Arg Arg Pro Gln Asp Ile Lys Phe Pro Gly Gly Gln Ile Val Gly
                   20              25              30
Gly Val Tyr Val Leu Pro Arg Arg Gly Pro Arg Leu Gly Val Arg Ala
                35              40              45
Thr Arg Lys Thr Ser Glu Arg Ser Gln Pro Arg Gly Arg Arg Gln Pro
           50              55              60
Ile Pro Lys Ala Arg Arg Ser Glu Gly Arg Ser Trp Ala Gln Pro Gly
 65              70              75              80
Tyr Pro Trp Pro Leu Tyr Gly Asn Glu Gly Cys Gly Trp Ala Gly Trp
               85              90              95
Leu Leu Ser Pro Arg Gly Ser Arg Pro Ser Trp Gly Pro Asn Asp Pro
              100             105             110
Arg Arg Arg Ser Arg Asn Leu Gly Lys Val Ile Asp Thr Leu Thr Cys
              115             120             125
Gly Phe Ala Asp Leu Met Gly Tyr Ile Pro Leu Val Gly Ala Pro Val
              130             135             140
Gly Gly Val Ala Arg Ala Leu Ala His Gly Val Arg Ala Leu Glu Asp
145             150             155             160
Gly Ile Asn Phe Ala Thr Gly Asn Leu Pro Gly Cys Ser Phe Ser Ile
              165             170             175
Phe Leu Leu Ala Leu Phe Ser Cys Leu Ile His Pro Ala Ala Ser
              180             185             190
```

<210> SEQ ID NO 190
<211> LENGTH: 191
<212> TYPE: PRT
<213> ORGANISM: Homo sapiens
<220> FEATURE:
<223> OTHER INFORMATION: Individual Isolate: DK12

<400> SEQUENCE: 190

```
Met Ser Thr Leu Pro Lys Pro Gln Arg Lys Thr Lys Arg Asn Thr Ile
 1               5              10              15
Arg Arg Pro Gln Asp Val Lys Phe Pro Gly Gly Gly Gln Ile Val Gly
                   20              25              30
Gly Val Tyr Val Leu Pro Arg Arg Gly Pro Arg Leu Gly Val Arg Ala
                35              40              45
Thr Arg Lys Thr Ser Glu Arg Ser Gln Pro Arg Gly Arg Arg Gln Pro
           50              55              60
Ile Pro Lys Ala Arg Arg Ser Glu Gly Arg Ser Trp Ala Gln Pro Gly
 65              70              75              80
Tyr Pro Trp Pro Leu Tyr Gly Asn Glu Gly Cys Gly Trp Ala Gly Trp
               85              90              95
Leu Leu Ser Pro Arg Gly Ser Arg Pro Ser Trp Gly Pro Asn Asp Pro
              100             105             110
Arg Arg Arg Ser Arg Asn Leu Gly Lys Val Ile Asp Thr Leu Thr Cys
              115             120             125
Gly Phe Ala Asp Leu Met Gly Tyr Ile Pro Leu Val Gly Ala Pro Val
              130             135             140
Gly Gly Val Ala Arg Ala Leu Ala His Gly Val Arg Ala Leu Glu Asp
145             150             155             160
Gly Ile Asn Phe Ala Thr Gly Asn Leu Pro Gly Cys Ser Phe Ser Ile
              165             170             175
Phe Leu Leu Ala Leu Phe Ser Cys Leu Ile His Pro Ala Ala Ser
```

```
<210> SEQ ID NO 191
<211> LENGTH: 191
<212> TYPE: PRT
<213> ORGANISM: Homo sapiens
<220> FEATURE:
<223> OTHER INFORMATION: Individual Isolate: Z4

<400> SEQUENCE: 191
```

Met Ser Thr Asn Pro Lys Pro Gln Arg Lys Thr Lys Arg Asn Thr Asn
 1               5                  10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Ile Val Gly Ala Pro Val
    130                 135                 140

Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

```
<210> SEQ ID NO 192
<211> LENGTH: 191
<212> TYPE: PRT
<213> ORGANISM: Homo sapiens
<220> FEATURE:
<223> OTHER INFORMATION: Individual Isolate: Z8

<400> SEQUENCE: 192
```

Met Ser Thr Asn Pro Lys Pro Gln Arg Lys Thr Lys Arg Asn Thr Asn
 1               5                  10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

```
Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 193
<211> LENGTH: 191
<212> TYPE: PRT
<213> ORGANISM: Homo sapiens
<220> FEATURE:
<223> OTHER INFORMATION: Individual Isolate: Z1

<400> SEQUENCE: 193

Met Ser Thr Asn Pro Lys Pro Gln Arg Lys Thr Lys Arg Asn Thr Asn
  1                 5                  10                  15

Arg Arg Pro Met Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Ala Arg Lys Thr Ser Glu Arg Ser Gln Pro Arg Gly Arg Arg Gln Pro
         50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala
            180                 185                 190

<210> SEQ ID NO 194
<211> LENGTH: 191
<212> TYPE: PRT
<213> ORGANISM: Homo sapiens
<220> FEATURE:
<223> OTHER INFORMATION: Individual Isolate: Z5

<400> SEQUENCE: 194

Met Ser Thr Asn Pro Lys Pro Gln Arg Lys Thr Lys Arg Asn Thr Asn
  1                 5                  10                  15

Arg Arg Pro Met Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45
```

```
Thr Arg Lys Thr Ser Glu Arg Ser Gln Pro Arg Gly Arg Arg Gln Pro
 50                  55                  60

Ile Pro Gln Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Phe Ser Cys Leu Thr Thr Pro Ala Ser Ala
            180                 185                 190

<210> SEQ ID NO 195
<211> LENGTH: 191
<212> TYPE: PRT
<213> ORGANISM: Homo sapiens
<220> FEATURE:
<223> OTHER INFORMATION: Individual Isolate: Z6

<400> SEQUENCE: 195

Met Ser Thr Asn Pro Lys Pro Gln Arg Lys Thr Lys Arg Asn Thr Asn
  1               5                  10                  15

Arg Arg Pro Met Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Thr Ser Ala
            180                 185                 190

<210> SEQ ID NO 196
<211> LENGTH: 191
<212> TYPE: PRT
<213> ORGANISM: Homo sapiens
```

-continued

```
<220> FEATURE:
<223> OTHER INFORMATION: Individual Isolate: Z7

<400> SEQUENCE: 196

Met Ser Thr Asn Pro Lys Pro Gln Arg Lys Thr Lys Arg Asn Thr Asn
  1               5                  10                  15

Arg Arg Pro Met Asp Val Lys Phe Pro Gly Gly Gln Ile Val Gly
             20                  25                  30

Gly Val Tyr Leu Leu Pro Arg Arg Gly Pro Arg Leu Gly Val Arg Thr
         35                  40                  45

Thr Arg Lys Thr Ser Glu Arg Ser Gln Pro Arg Gly Arg Arg Gln Pro
     50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
                180                 185                 190

<210> SEQ ID NO 197
<211> LENGTH: 191
<212> TYPE: PRT
<213> ORGANISM: Homo sapiens
<220> FEATURE:
<223> OTHER INFORMATION: Individual Isolate: DK13

<400> SEQUENCE: 197

Met Ser Thr Asn Pro Lys Pro Gln Arg Lys Thr Lys Arg Asn Thr Asn
  1               5                  10                  15

Arg Arg Pro Met Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Gln Leu Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Val
        130                 135                 140

Gly Gly Val Ala Arg Ala Leu Ala His Gly Val Arg Leu Leu Glu Asp
```

-continued

```
               145                 150                 155                 160
Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 198
<211> LENGTH: 191
<212> TYPE: PRT
<213> ORGANISM: Homo sapiens
<220> FEATURE:
<223> OTHER INFORMATION: Individual Isolate: SA4

<400> SEQUENCE: 198

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Ser Ala
            180                 185                 190

<210> SEQ ID NO 199
<211> LENGTH: 191
<212> TYPE: PRT
<213> ORGANISM: Homo sapiens
<220> FEATURE:
<223> OTHER INFORMATION: Individual Isolate: SA5

<400> SEQUENCE: 199

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80
```

```
Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Ser Ala
            180                 185                 190
```

<210> SEQ ID NO 200
<211> LENGTH: 191
<212> TYPE: PRT
<213> ORGANISM: Homo sapiens
<220> FEATURE:
<223> OTHER INFORMATION: Individual Isolate: SA7

<400> SEQUENCE: 200

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Ser Ala
            180                 185                 190
```

<210> SEQ ID NO 201
<211> LENGTH: 191
<212> TYPE: PRT
<213> ORGANISM: Homo sapiens
<220> FEATURE:
<223> OTHER INFORMATION: Individual Isolate: SA1

<400> SEQUENCE: 201

```
Met Ser Thr Asn Pro Lys Pro Gln Arg Lys Thr Lys Arg Asn Thr Asn
1               5                   10                  15
```

-continued

```
Leu Arg Pro Gln Asp Val Lys Phe Pro Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Gln Pro Thr Gly Arg Ser Trp Gly Gln Pro Gly
 65                  70                  75                  80

Tyr Pro Trp Pro Leu Tyr Ala Asn Glu Gly Leu Gly Trp Ala Gly Trp
                 85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Ile Ile Pro Ala Ser Ala
            180                 185                 190

<210> SEQ ID NO 202
<211> LENGTH: 191
<212> TYPE: PRT
<213> ORGANISM: Homo sapiens
<220> FEATURE:
<223> OTHER INFORMATION: Individual Isolate: SA3

<400> SEQUENCE: 202

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Gln Pro Thr Gly Arg Ser Trp Gly Gln Pro Gly
 65                  70                  75                  80

Tyr Pro Trp Pro Leu Tyr Ala Asn Glu Gly Leu Glu Trp Ala Gly Trp
                 85                  90                  95

Leu Leu Ser Pro Arg Gly Ser Arg Pro Ser Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Ser Ala
            180                 185                 190
```

```
<210> SEQ ID NO 203
<211> LENGTH: 191
<212> TYPE: PRT
<213> ORGANISM: Homo sapiens
<220> FEATURE:
<223> OTHER INFORMATION: Individual Isolate:  SA13

<400> SEQUENCE: 203

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Thr Ser Ala
            180                 185                 190

<210> SEQ ID NO 204
<211> LENGTH: 191
<212> TYPE: PRT
<213> ORGANISM: Homo sapiens
<220> FEATURE:
<223> OTHER INFORMATION: Individual Isolate:  SA6

<400> SEQUENCE: 204

Met Ser Thr Asn Pro Lys Pro Gln Arg Lys Thr Gln Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Ser Ala Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
```

-continued

```
                115                 120                 125
Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Val Leu Ala Leu Leu Ser Cys Leu Thr Val Pro Ala Ser Ala
                180                 185                 190

<210> SEQ ID NO 205
<211> LENGTH: 191
<212> TYPE: PRT
<213> ORGANISM: Homo sapiens
<220> FEATURE:
<223> OTHER INFORMATION: Individual Isolate:  SA11

<400> SEQUENCE: 205

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Gln Pro Thr Gly Arg Ser Trp Gly Gln Pro Gly
 65                  70                  75                  80

Tyr Pro Trp Pro Phe Tyr Ala Asn Glu Gly Leu Gly Trp Ala Gly Trp
                 85                  90                  95

Leu Leu Ser Pro Arg Gly Ser Arg Pro Asn Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Ala Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Thr Ala
                180                 185                 190

<210> SEQ ID NO 206
<211> LENGTH: 191
<212> TYPE: PRT
<213> ORGANISM: Homo sapiens
<220> FEATURE:
<223> OTHER INFORMATION: Individual Isolate:  HK2

<400> SEQUENCE: 206

Met Ser Thr Leu Pro Lys Pro Gln Arg Lys Thr Lys Arg Asn Thr Asn
  1               5                  10                  15

Arg Arg Pro Thr Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45
```

-continued

```
Thr Arg Lys Thr Ser Glu Arg Ser Gln Pro Arg Gly Arg Arg Gln Pro
 50                  55                  60
Ile Pro Lys Ala Arg Gln Pro Gln Gly Arg His Trp Ala Gln Pro Gly
 65                  70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro His Trp Gly Pro Asn Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Val Val Gly Ala Pro Leu
130                 135                 140
Gly Gly Val Ala Ala Leu Ala His Gly Val Arg Ala Ile Glu Asp
145                 150                 155                 160
Gly Ile Asn Tyr Ala Thr Gly Asn Leu Pro Gly Cys Ser Phe Ser Ile
                165                 170                 175
Phe Leu Leu Ala Leu Leu Ser Cys Leu Thr Thr Pro Ala Ser Ala
                180                 185                 190
```

<210> SEQ ID NO 207
<211> LENGTH: 40
<212> TYPE: DNA
<213> ORGANISM: Homo sapiens

<400> SEQUENCE: 207
gcgtccgggt tctggaagac ggcgtgaact atgcaacagg                40

<210> SEQ ID NO 208
<211> LENGTH: 40
<212> TYPE: DNA
<213> ORGANISM: Homo sapiens

<400> SEQUENCE: 208
aggctttcat tgcagttcaa ggccgtgcta ttgatgtgcc                40

<210> SEQ ID NO 209
<211> LENGTH: 40
<212> TYPE: DNA
<213> ORGANISM: Homo sapiens

<400> SEQUENCE: 209
aagacggcgt gaactatgca acagggaacc ttcctggttg                40

<210> SEQ ID NO 210
<211> LENGTH: 40
<212> TYPE: DNA
<213> ORGANISM: Homo sapiens

<400> SEQUENCE: 210
agttcaaggc cgtgctattg atgtgccaac tgccgttggt                40

<210> SEQ ID NO 211
<211> LENGTH: 40
<212> TYPE: DNA
<213> ORGANISM: Homo sapiens

<400> SEQUENCE: 211
aagacggcgt gaattctgca acagggaacc ttcctggttg                40

<210> SEQ ID NO 212

```
<211> LENGTH: 40
<212> TYPE: DNA
<213> ORGANISM: Homo sapiens

<400> SEQUENCE: 212
agttcaaggc cgtggaattc atgtgccaac tgccgttggt                              40

<210> SEQ ID NO 213
<211> LENGTH: 42
<212> TYPE: DNA
<213> ORGANISM: Homo sapiens

<400> SEQUENCE: 213
arctycgacg tyacatcgay ctgctygtyg gragygccac cc                           42

<210> SEQ ID NO 214
<211> LENGTH: 31
<212> TYPE: DNA
<213> ORGANISM: Homo sapiens

<400> SEQUENCE: 214
rcargccrtc ttggayatga tcgctggwgc y                                       31

<210> SEQ ID NO 215
<211> LENGTH: 42
<212> TYPE: DNA
<213> ORGANISM: Homo sapiens

<400> SEQUENCE: 215
cratacgacr ycaygtcgay ttgctcgttg gggcggctry yt                           42

<210> SEQ ID NO 216
<211> LENGTH: 31
<212> TYPE: DNA
<213> ORGANISM: Homo sapiens

<400> SEQUENCE: 216
rcaagctrtc rtggayrtgg trrcrggrgc c                                       31

<210> SEQ ID NO 217
<211> LENGTH: 40
<212> TYPE: DNA
<213> ORGANISM: Homo sapiens

<400> SEQUENCE: 217
ttgcggackc acatygacat ggtygtgatg tccgccacgc                              40

<210> SEQ ID NO 218
<211> LENGTH: 43
<212> TYPE: DNA
<213> ORGANISM: Homo sapiens

<400> SEQUENCE: 218
gatgcgcgtt cccgaggtca tcwtagacat crtyrgcggr gcd                          43

<210> SEQ ID NO 219
<211> LENGTH: 54
<212> TYPE: DNA
<213> ORGANISM: Homo sapiens

<400> SEQUENCE: 219
aatggcaccy tgcrctgctg gatacaagtr acacctaatg tggctgtgaa acac              54
```

<210> SEQ ID NO 220
<211> LENGTH: 31
<212> TYPE: DNA
<213> ORGANISM: Homo sapiens

<400> SEQUENCE: 220
tgarctagyc ctysargtyg tcttcggygg y                            31

<210> SEQ ID NO 221
<211> LENGTH: 54
<212> TYPE: DNA
<213> ORGANISM: Homo sapiens

<400> SEQUENCE: 221
gccaacgtct ctcgatgttg ggtgccggtt gcccccaatc tcgccataag tcaa   54

<210> SEQ ID NO 222
<211> LENGTH: 46
<212> TYPE: DNA
<213> ORGANISM: Homo sapiens

<400> SEQUENCE: 222
aagggcctgc gagcacacat cgatatcatc gtgatgtctg ctacgg            46

<210> SEQ ID NO 223
<211> LENGTH: 45
<212> TYPE: DNA
<213> ORGANISM: Homo sapiens

<400> SEQUENCE: 223
ttggtgcgca tcccggaagt catcttggat attgttacag gaggt             45

<210> SEQ ID NO 224
<211> LENGTH: 40
<212> TYPE: DNA
<213> ORGANISM: Homo sapiens

<400> SEQUENCE: 224
agtcaggtay gtcggagcaa ccaccgcytc gatacgcagt                   40

<210> SEQ ID NO 225
<211> LENGTH: 46
<212> TYPE: DNA
<213> ORGANISM: Homo sapiens

<400> SEQUENCE: 225
agccttcacg ttcagacckc gtcgccatca aacrgtccag acctgt            46

<210> SEQ ID NO 226
<211> LENGTH: 75
<212> TYPE: DNA
<213> ORGANISM: Homo sapiens

<400> SEQUENCE: 226
tcccccgcyg tgggtatggt ggtrgcgcac rtyctgcgdy tgcccagac cktgttygac   60 atamtrgcyg gggcc                                              75

<210> SEQ ID NO 227
<211> LENGTH: 39
<212> TYPE: DNA
<213> ORGANISM: Homo sapiens

<400> SEQUENCE: 227

```
acgccggtga cgcctacagt ggctgtcgca cacccgggc                        39
```

<210> SEQ ID NO 228
<211> LENGTH: 42
<212> TYPE: DNA
<213> ORGANISM: Homo sapiens

<400> SEQUENCE: 228

```
atgagggtcc ccacagcctt tctcgacatg gttgccggag gc                    42
```

<210> SEQ ID NO 229
<211> LENGTH: 40
<212> TYPE: DNA
<213> ORGANISM: Homo sapiens

<400> SEQUENCE: 229

```
cgcgccctat cccaacgcac cgttagagtc catgcgcagg                       40
```

<210> SEQ ID NO 230
<211> LENGTH: 49
<212> TYPE: DNA
<213> ORGANISM: Homo sapiens

<400> SEQUENCE: 230

```
tcagatctta cggatcccct ctatcctagg tgacttgctc accgggggt             49
```

<210> SEQ ID NO 231
<211> LENGTH: 54
<212> TYPE: DNA
<213> ORGANISM: Homo sapiens

<400> SEQUENCE: 231

```
cagtcacgct gctgggtggc ccttactccc accgtggcgg ygycttatat cggt       54
```

<210> SEQ ID NO 232
<211> LENGTH: 31
<212> TYPE: DNA
<213> ORGANISM: Homo sapiens

<400> SEQUENCE: 232

```
tagcactctg gtrgayctac tcrctggagg g                                31
```

<210> SEQ ID NO 233
<211> LENGTH: 54
<212> TYPE: DNA
<213> ORGANISM: Homo sapiens

<400> SEQUENCE: 233

```
aagtctacat gctgggtgtc tctcaccccc accgtggctg cgcaacatct gaat       54
```

<210> SEQ ID NO 234
<211> LENGTH: 31
<212> TYPE: DNA
<213> ORGANISM: Homo sapiens

<400> SEQUENCE: 234

```
aggcgccatg gtcgacctgc ttgcaggcgg c                                31
```

<210> SEQ ID NO 235
<211> LENGTH: 43
<212> TYPE: DNA
<213> ORGANISM: Homo sapiens

<400> SEQUENCE: 235

```
tcagccccga vyytcggagc ggtcacggct cctcttcgga ggg         43

<210> SEQ ID NO 236
<211> LENGTH: 44
<212> TYPE: DNA
<213> ORGANISM: Homo sapiens

<400> SEQUENCE: 236
tgytacggat yccccargtg gtcathgaca tcatwgccgg ggsc         44

<210> SEQ ID NO 237
<211> LENGTH: 40
<212> TYPE: DNA
<213> ORGANISM: Homo sapiens

<400> SEQUENCE: 237
cataccaaat gcttccacgc ccgcaacggg attccgcagg              40

<210> SEQ ID NO 238
<211> LENGTH: 37
<212> TYPE: DNA
<213> ORGANISM: Homo sapiens

<400> SEQUENCE: 238
tcttcttgcg ggcgccgcag tggtttgctc atccctg                 37

<210> SEQ ID NO 239
<211> LENGTH: 52
<212> TYPE: DNA
<213> ORGANISM: Homo sapiens

<400> SEQUENCE: 239
atctagcatc ttgagggtac ctgagatttg tgcgagtgtg atatttggtg gc    52

<210> SEQ ID NO 240
<211> LENGTH: 33
<212> TYPE: PRT
<213> ORGANISM: Homo sapiens
<220> FEATURE:
<221> NAME/KEY: SITE
<222> LOCATION: (22)..
<223> OTHER INFORMATION: "Ala" or "Thr"
<221> NAME/KEY: SITE
<222> LOCATION: (24)..
<223> OTHER INFORMATION: "Val" or "Ile"
<221> NAME/KEY: SITE
<222> LOCATION: (26)
<223> OTHER INFORMATION: "Val" or "Met"

<400> SEQUENCE: 240

Trp Ile Gln Val Thr Pro Asn Val Ala Val Lys His Arg Gly Ala Leu
  1               5                  10                  15
Thr His Asn Leu Arg Xaa His Xaa Asp Xaa Ile Val Met Ala Ala Thr
              20                  25                  30
Val

<210> SEQ ID NO 241
<211> LENGTH: 33
<212> TYPE: PRT
<213> ORGANISM: Homo sapiens

<400> SEQUENCE: 241

Trp Val Pro Val Ala Pro Asn Leu Ala Ile Ser Gln Pro Gly Ala Leu
  1               5                  10                  15
```

```
Thr Lys Gly Leu Arg Ala His Ile Asp Ile Ile Val Met Ser Ala Thr
            20                  25                  30

Val
```

<210> SEQ ID NO 242
<211> LENGTH: 33
<212> TYPE: PRT
<213> ORGANISM: Homo sapiens
<220> FEATURE:
<221> NAME/KEY: SITE
<222> LOCATION: (5)
<223> OTHER INFORMATION: "Ser" or "Thr"
<221> NAME/KEY: SITE
<222> LOCATION: (11)
<223> OTHER INFORMATION: "Arg" or "Gln"
<221> NAME/KEY: SITE
<222> LOCATION: (12)
<223> OTHER INFORMATION: "Arg" or "Gln"

<400> SEQUENCE: 242

```
Trp Ile Pro Val Xaa Pro Asn Val Ala Val Xaa Xaa Pro Gly Ala Leu
 1               5                  10                  15

Thr Gln Gly Leu Arg Thr His Ile Asp Met Val Val Met Ser Ala Thr
            20                  25                  30

Leu
```

<210> SEQ ID NO 243
<211> LENGTH: 33
<212> TYPE: PRT
<213> ORGANISM: Homo sapiens
<220> FEATURE:
<221> NAME/KEY: SITE
<222> LOCATION: (3)
<223> OTHER INFORMATION: "Pro" or "Ser"
<221> NAME/KEY: SITE
<222> LOCATION: (33)
<223> OTHER INFORMATION: "Leu" or "Met"

<400> SEQUENCE: 243

```
Trp Thr Xaa Val Thr Pro Thr Val Ala Val Arg Tyr Val Gly Ala Thr
 1               5                  10                  15

Thr Ala Ser Ile Arg Ser His Val Asp Leu Leu Val Gly Ala Ala Thr
            20                  25                  30

Xaa
```

<210> SEQ ID NO 244
<211> LENGTH: 33
<212> TYPE: PRT
<213> ORGANISM: Homo sapiens
<220> FEATURE:
<221> NAME/KEY: SITE
<222> LOCATION: (5)
<223> OTHER INFORMATION: "Thr" or "Ala"
<221> NAME/KEY: SITE
<222> LOCATION: (13)
<223> OTHER INFORMATION: "Gly" or "Ala" or "Ser" or "Val" or "Thr"
<221> NAME/KEY: SITE
<222> LOCATION: (14)
<223> OTHER INFORMATION: "Ser" or "Thr" or "Asn"
<221> NAME/KEY: SITE
<222> LOCATION: (15)
<223> OTHER INFORMATION: "Val" or "Ile"
<221> NAME/KEY: SITE
<222> LOCATION: (16)
<223> OTHER INFORMATION: "Pro" or "Ser"
<221> NAME/KEY: SITE
<222> LOCATION: (18)
<223> OTHER INFORMATION: "Thr" or "Lys"

```
<221> NAME/KEY: SITE
<222> LOCATION: (19)
<223> OTHER INFORMATION: "Thr" or "Ala"
<221> NAME/KEY: SITE
<222> LOCATION: (22)
<223> OTHER INFORMATION: "Arg" or "His"
<221> NAME/KEY: SITE
<222> LOCATION: (32)
<223> OTHER INFORMATION: "Ala" or "Val" or "Thr"

<400> SEQUENCE: 244

Trp Val Ala Leu Xaa Pro Thr Leu Ala Ala Arg Asn Xaa Xaa Xaa Xaa
 1               5                  10                  15

Thr Xaa Xaa Ile Arg Xaa His Val Asp Leu Leu Val Gly Ala Ala Xaa
            20                  25                  30

Phe

<210> SEQ ID NO 245
<211> LENGTH: 33
<212> TYPE: PRT
<213> ORGANISM: Homo sapiens
<220> FEATURE:
<221> NAME/KEY: SITE
<222> LOCATION: (3)
<223> OTHER INFORMATION: "Ala" or "Pro"
<221> NAME/KEY: SITE
<222> LOCATION: (4)
<223> OTHER INFORMATION: "Val" or "Met"
<221> NAME/KEY: SITE
<222> LOCATION: (5)
<223> OTHER INFORMATION: "Thr" or "Ala"
<221> NAME/KEY: SITE
<222> LOCATION: (17)
<223> OTHER INFORMATION: "Thr" or "Ala"
<221> NAME/KEY: SITE
<222> LOCATION: (18)
<223> OTHER INFORMATION: "Thr" or "Ala"
<221> NAME/KEY: SITE
<222> LOCATION: (23)
<223> OTHER INFORMATION: "His" or "Tyr"

<400> SEQUENCE: 245

Trp Val Xaa Xaa Xaa Pro Thr Val Ala Thr Arg Asp Gly Lys Leu Pro
 1               5                  10                  15

Xaa Xaa Gln Leu Arg Arg Xaa Ile Asp Leu Leu Val Gly Ser Ala Thr
            20                  25                  30

Leu

<210> SEQ ID NO 246
<211> LENGTH: 33
<212> TYPE: PRT
<213> ORGANISM: Homo sapiens

<400> SEQUENCE: 246

Trp Thr Pro Val Thr Pro Thr Val Ala Val Ala His Pro Gly Ala Pro
 1               5                  10                  15

Leu Glu Ser Phe Arg Arg His Val Asp Leu Met Val Gly Ala Ala Thr
            20                  25                  30

Leu

<210> SEQ ID NO 247
<211> LENGTH: 33
<212> TYPE: PRT
<213> ORGANISM: Homo sapiens
<220> FEATURE:
<221> NAME/KEY: SITE
<222> LOCATION: (10)
```

```
<223> OTHER INFORMATION: "Val" or "Ala"
<221> NAME/KEY: SITE
<222> LOCATION: (11)
<223> OTHER INFORMATION: "Ser" or "Pro"
<221> NAME/KEY: SITE
<222> LOCATION: (18)
<223> OTHER INFORMATION: "Asp" or "Glu"
<221> NAME/KEY: SITE
<222> LOCATION: (20)
<223> OTHER INFORMATION: "Leu" or "Ile"

<400> SEQUENCE: 247

Trp Val Ala Leu Thr Pro Thr Val Ala Xaa Xaa Tyr Ile Gly Ala Pro
 1               5                  10                  15

Leu Xaa Ser Xaa Arg Arg His Val Asp Leu Met Val Gly Ala Ala Thr
            20                  25                  30

Val

<210> SEQ ID NO 248
<211> LENGTH: 33
<212> TYPE: PRT
<213> ORGANISM: Homo sapiens

<400> SEQUENCE: 248

Trp Val Ser Leu Thr Pro Thr Val Ala Ala Gln His Leu Asn Ala Pro
 1               5                  10                  15

Leu Glu Ser Leu Arg Arg His Val Asp Leu Met Val Gly Gly Ala Thr
            20                  25                  30

Leu

<210> SEQ ID NO 249
<211> LENGTH: 33
<212> TYPE: PRT
<213> ORGANISM: Homo sapiens

<400> SEQUENCE: 249

Trp Val Pro Leu Thr Pro Thr Val Ala Ala Pro Tyr Pro Asn Ala Pro
 1               5                  10                  15

Leu Glu Ser Met Arg Arg His Val Asp Leu Met Val Gly Ala Ala Thr
            20                  25                  30

Met

<210> SEQ ID NO 250
<211> LENGTH: 33
<212> TYPE: PRT
<213> ORGANISM: Homo sapiens
<220> FEATURE:
<221> NAME/KEY: SITE
<222> LOCATION: (3)
<223> OTHER INFORMATION: "Gln" or "His"
<221> NAME/KEY: SITE
<222> LOCATION: (12)
<223> OTHER INFORMATION: "Asn" or "Ser" or "Thr"
<221> NAME/KEY: SITE
<222> LOCATION: (13)
<223> OTHER INFORMATION: "Leu" or "Phe"
<221> NAME/KEY: SITE
<222> LOCATION: (23)
<223> OTHER INFORMATION: "Ala" or "Val"

<400> SEQUENCE: 250

Trp Val Xaa Ile Thr Pro Thr Leu Ser Ala Pro Xaa Xaa Gly Ala Val
 1               5                  10                  15

Thr Ala Pro Leu Arg Arg Xaa Val Asp Tyr Leu Ala Gly Gly Ala Ala
            20                  25                  30
```

Leu

<210> SEQ ID NO 251
<211> LENGTH: 33
<212> TYPE: PRT
<213> ORGANISM: Homo sapiens

<400> SEQUENCE: 251

Trp His Ala Val Thr Pro Thr Leu Ala Ile Pro Asn Ala Ser Thr Pro
 1               5                  10                  15

Ala Thr Gly Phe Arg Arg His Val Asp Leu Leu Ala Gly Ala Ala Val
            20                  25                  30

Val

<210> SEQ ID NO 252
<211> LENGTH: 23
<212> TYPE: PRT
<213> ORGANISM: Homo sapiens
<220> FEATURE:
<221> NAME/KEY: SITE
<222> LOCATION: (16)
<223> OTHER INFORMATION: "Val" or "Ala"
<221> NAME/KEY: SITE
<222> LOCATION: (18)
<223> OTHER INFORMATION: "Glu" or "Gln"

<400> SEQUENCE: 252

Thr Leu Thr Met Ile Leu Ala Tyr Ala Ala Arg Val Pro Glu Leu Xaa
 1               5                  10                  15

Leu Xaa Val Val Phe Gly Gly
            20

<210> SEQ ID NO 253
<211> LENGTH: 23
<212> TYPE: PRT
<213> ORGANISM: Homo sapiens

<400> SEQUENCE: 253

Thr Thr Thr Met Leu Leu Ala Tyr Leu Val Arg Ile Pro Glu Val Ile
 1               5                  10                  15

Leu Asp Ile Val Thr Gly Gly
            20

<210> SEQ ID NO 254
<211> LENGTH: 23
<212> TYPE: PRT
<213> ORGANISM: Homo sapiens
<220> FEATURE:
<221> NAME/KEY: SITE
<222> LOCATION: (2)
<223> OTHER INFORMATION: "Ala" or "Thr"
<221> NAME/KEY: SITE
<222> LOCATION: (4)
<223> OTHER INFORMATION: "Met" or "Leu"
<221> NAME/KEY: SITE
<222> LOCATION: (9)
<223> OTHER INFORMATION: "Ala" or "Val"
<221> NAME/KEY: SITE
<222> LOCATION: (17)
<223> OTHER INFORMATION: "Ile" or "Leu"
<221> NAME/KEY: SITE
<222> LOCATION: (20)
<223> OTHER INFORMATION: "Ile" or "Val"
<221> NAME/KEY: SITE
<222> LOCATION: (21)
<223> OTHER INFORMATION: "Ser" or "Gly"

```
<400> SEQUENCE: 254

Thr Xaa Thr Xaa Ile Leu Ala Tyr Xaa Met Arg Val Pro Glu Val Ile
 1               5                  10                  15

Xaa Asp Ile Xaa Xaa Gly Ala
            20

<210> SEQ ID NO 255
<211> LENGTH: 23
<212> TYPE: PRT
<213> ORGANISM: Homo sapiens
<220> FEATURE:
<221> NAME/KEY: SITE
<222> LOCATION: (9)
<223> OTHER INFORMATION: "Val" or "Ile"
<221> NAME/KEY: SITE
<222> LOCATION: (16)
<223> OTHER INFORMATION: "Leu" or "Val"
<221> NAME/KEY: SITE
<222> LOCATION: (20)
<223> OTHER INFORMATION: "Ile" or "Leu"

<400> SEQUENCE: 255

Ala Val Gly Met Val Val Ala His Xaa Leu Arg Leu Pro Gln Thr Xaa
 1               5                  10                  15

Phe Asp Ile Xaa Ala Gly Ala
            20

<210> SEQ ID NO 256
<211> LENGTH: 23
<212> TYPE: PRT
<213> ORGANISM: Homo sapiens
<220> FEATURE:
<221> NAME/KEY: SITE
<222> LOCATION: (2)
<223> OTHER INFORMATION: "Ala" or "Thr"
<221> NAME/KEY: SITE
<222> LOCATION: (6)
<223> OTHER INFORMATION: "Val" or "Leu"
<221> NAME/KEY: SITE
<222> LOCATION: (12)
<223> OTHER INFORMATION: "Ile" or "Leu"
<221> NAME/KEY: SITE
<222> LOCATION: (16)
<223> OTHER INFORMATION: "Val" or "Ile"
<221> NAME/KEY: SITE
<222> LOCATION: (17)
<223> OTHER INFORMATION: "Val" or "Leu" or "Met"
<221> NAME/KEY: SITE
<222> LOCATION: (19)
<223> OTHER INFORMATION: "Met" or "Val"
<221> NAME/KEY: SITE
<222> LOCATION: (21)
<223> OTHER INFORMATION: "Ala" or "Thr"

<400> SEQUENCE: 256

Thr Xaa Ala Leu Val Xaa Ser Gln Leu Leu Arg Xaa Pro Gln Ala Xaa
 1               5                  10                  15

Xaa Asp Xaa Val Xaa Gly Ala
            20

<210> SEQ ID NO 257
<211> LENGTH: 23
<212> TYPE: PRT
<213> ORGANISM: Homo sapiens
<220> FEATURE:
<221> NAME/KEY: SITE
<222> LOCATION: (2)
<223> OTHER INFORMATION: "Thr" or "Ala"
<221> NAME/KEY: SITE
<222> LOCATION: (6)
```

-continued

```
<223> OTHER INFORMATION: "Val" or "Ile" or "Met"
<221> NAME/KEY: SITE
<222> LOCATION: (12)
<223> OTHER INFORMATION: "Ile" or "Val"
<221> NAME/KEY: SITE
<222> LOCATION: (16)
<223> OTHER INFORMATION: "Ile" or "Val"

<400> SEQUENCE: 257

Thr Xaa Ala Leu Val Xaa Ala Gln Leu Leu Arg Xaa Pro Gln Ala Xaa
 1               5                  10                  15

Leu Asp Met Ile Ala Gly Ala
            20

<210> SEQ ID NO 258
<211> LENGTH: 23
<212> TYPE: PRT
<213> ORGANISM: Homo sapiens

<400> SEQUENCE: 258

Thr Thr Thr Leu Leu Leu Ala Gln Ile Met Arg Val Pro Thr Ala Phe
 1               5                  10                  15

Leu Asp Met Val Ala Gly Gly
            20

<210> SEQ ID NO 259
<211> LENGTH: 23
<212> TYPE: PRT
<213> ORGANISM: Homo sapiens
<220> FEATURE:
<221> NAME/KEY: SITE
<222> LOCATION: (5)
<223> OTHER INFORMATION: "Leu" or "Val"
<221> NAME/KEY: SITE
<222> LOCATION: (21)
<223> OTHER INFORMATION: "Thr" or "Ala"

<400> SEQUENCE: 259

Thr Thr Thr Leu Xaa Leu Ala Gln Val Met Arg Ile Pro Ser Thr Leu
 1               5                  10                  15

Val Asp Leu Leu Xaa Gly Gly
            20

<210> SEQ ID NO 260
<211> LENGTH: 23
<212> TYPE: PRT
<213> ORGANISM: Homo sapiens

<400> SEQUENCE: 260

Thr Ala Thr Leu Val Leu Ala Gln Leu Met Arg Ile Pro Gly Ala Met
 1               5                  10                  15

Val Asp Leu Leu Ala Gly Gly
            20

<210> SEQ ID NO 261
<211> LENGTH: 23
<212> TYPE: PRT
<213> ORGANISM: Homo sapiens

<400> SEQUENCE: 261

Thr Ser Ala Leu Ile Met Ala Gln Ile Leu Arg Ile Pro Ser Ile Leu
 1               5                  10                  15

Gly Asp Leu Leu Thr Gly Gly
            20
```

```
<210> SEQ ID NO 262
<211> LENGTH: 23
<212> TYPE: PRT
<213> ORGANISM: Homo sapiens
<220> FEATURE:
<221> NAME/KEY: SITE
<222> LOCATION: (1)
<223> OTHER INFORMATION: "Thr" or "Ala"
<221> NAME/KEY: SITE
<222> LOCATION: (5)
<223> OTHER INFORMATION: "Val" or "Leu"
<221> NAME/KEY: SITE
<222> LOCATION: (9)
<223> OTHER INFORMATION: "Leu" or "Met" or "Val"
<221> NAME/KEY: SITE
<222> LOCATION: (23)
<223> OTHER INFORMATION: "Gly" or "Ala"

<400> SEQUENCE: 262

Xaa Thr Ala Leu Xaa Met Ala Gln Xaa Leu Arg Ile Pro Gln Val Val
 1               5                  10                  15

Ile Asp Ile Ile Ala Gly Xaa
                20

<210> SEQ ID NO 263
<211> LENGTH: 23
<212> TYPE: PRT
<213> ORGANISM: Homo sapiens

<400> SEQUENCE: 263

Thr Thr Thr Leu Val Leu Ser Ser Ile Leu Arg Val Pro Glu Ile Cys
 1               5                  10                  15

Ala Ser Val Ile Phe Gly Gly
                20

<210> SEQ ID NO 264
<211> LENGTH: 191
<212> TYPE: PRT
<213> ORGANISM: Homo sapiens
<220> FEATURE:
<221> NAME/KEY: SITE
<222> LOCATION: (49)
<223> OTHER INFORMATION: "Thr" or "Pro"

<400> SEQUENCE: 264

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Xaa Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140
```

-continued

```
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 265
<211> LENGTH: 191
<212> TYPE: PRT
<213> ORGANISM: Homo sapiens
<220> FEATURE:
<221> NAME/KEY: SITE
<222> LOCATION: (4)
<223> OTHER INFORMATION: "Thr" or "Asn"
<221> NAME/KEY: SITE
<222> LOCATION: (10)
<223> OTHER INFORMATION: "Lys" or "Gln"
<221> NAME/KEY: SITE
<222> LOCATION: (16)
<223> OTHER INFORMATION: "Ser" or "Asn"
<221> NAME/KEY: SITE
<222> LOCATION: (70)
<223> OTHER INFORMATION: "Arg" or "His" or "Gln"
<221> NAME/KEY: SITE
<222> LOCATION: (75)
<223> OTHER INFORMATION: "Ala" or "Thr"
<221> NAME/KEY: SITE
<222> LOCATION: (81)
<223> OTHER INFORMATION: "His" or "Tyr"
<221> NAME/KEY: SITE
<222> LOCATION: (87)
<223> OTHER INFORMATION: "Ala" or "Gly"
<221> NAME/KEY: SITE
<222> LOCATION: (88)
<223> OTHER INFORMATION: "Asn" or "Asp"
<221> NAME/KEY: SITE
<222> LOCATION: (91)
<223> OTHER INFORMATION: "Leu" or "Met"
<221> NAME/KEY: SITE
<222> LOCATION: (101)
<223> OTHER INFORMATION: "Arg" or "His"
<221> NAME/KEY: SITE
<222> LOCATION: (106)
<223> OTHER INFORMATION: "Ser" or "Asn"
<221> NAME/KEY: SITE
<222> LOCATION: (110)
<223> OTHER INFORMATION: "Thr" or "Asn"
<221> NAME/KEY: SITE
<222> LOCATION: (142)
<223> OTHER INFORMATION: "Gly" or "Ala"
<221> NAME/KEY: SITE
<222> LOCATION: (147)
<223> OTHER INFORMATION: "Val" or "Ala"
<221> NAME/KEY: SITE
<222> LOCATION: (158)
<223> OTHER INFORMATION: "Val" or "Leu"
<221> NAME/KEY: SITE
<222> LOCATION: (169)
<223> OTHER INFORMATION: "Leu" or "Ile"
<221> NAME/KEY: SITE
<222> LOCATION: (173)
<223> OTHER INFORMATION: "Ser" or "Pro"
<221> NAME/KEY: SITE
<222> LOCATION: (187)
<223> OTHER INFORMATION: "Ile" or "Val" or "Thr"
<221> NAME/KEY: SITE
<222> LOCATION: (189)
<223> OTHER INFORMATION: "Ala" or "Val"

<400> SEQUENCE: 265

Met Ser Thr Xaa Pro Lys Pro Gln Arg Xaa Thr Lys Arg Asn Thr Xaa
1               5                   10                  15
```

-continued

```
Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Xaa Pro Glu Gly Arg Xaa Trp Ala Gln Pro Gly
65                  70                  75                  80

Xaa Pro Trp Pro Leu Tyr Xaa Xaa Glu Gly Xaa Gly Trp Ala Gly Trp
                85                  90                  95

Leu Leu Ser Pro Xaa Gly Ser Arg Pro Xaa Trp Gly Pro Xaa Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Xaa Pro Leu
130                 135                 140

Gly Gly Xaa Ala Arg Ala Leu Ala His Gly Val Arg Val Xaa Glu Asp
145                 150                 155                 160

Gly Val Asn Tyr Ala Thr Gly Asn Xaa Pro Gly Cys Xaa Phe Ser Ile
                165                 170                 175

Phe Leu Leu Ala Leu Leu Ser Cys Leu Thr Xaa Pro Xaa Ser Ala
            180                 185                 190
```

<210> SEQ ID NO 266
<211> LENGTH: 191
<212> TYPE: PRT
<213> ORGANISM: Homo sapiens
<220> FEATURE:
<221> NAME/KEY: SITE
<222> LOCATION: (4)
<223> OTHER INFORMATION: "Asn" or "Thr"
<221> NAME/KEY: SITE
<222> LOCATION: (10)
<223> OTHER INFORMATION: "Lys" or "Gln"
<221> NAME/KEY: SITE
<222> LOCATION: (16)
<223> OTHER INFORMATION: "Asn" or "Ser"
<221> NAME/KEY: SITE
<222> LOCATION: (49)
<223> OTHER INFORMATION: "Thr" or "Pro"
<221> NAME/KEY: SITE
<222> LOCATION: (70)
<223> OTHER INFORMATION: "Arg" or "Gln" or "His"
<221> NAME/KEY: SITE
<222> LOCATION: (75)
<223> OTHER INFORMATION: "Thr" or "Ala"
<221> NAME/KEY: SITE
<222> LOCATION: (81)
<223> OTHER INFORMATION: "Tyr" or "His"
<221> NAME/KEY: SITE
<222> LOCATION: (87)
<223> OTHER INFORMATION: "Gly" or "Ala"
<221> NAME/KEY: SITE
<222> LOCATION: (88)
<223> OTHER INFORMATION: "Asn" or "Asp"
<221> NAME/KEY: SITE
<222> LOCATION: (91)
<223> OTHER INFORMATION: "Met" or "Leu" or "Cys"
<221> NAME/KEY: SITE
<222> LOCATION: (101)
<223> OTHER INFORMATION: "His" or "Arg"
<221> NAME/KEY: SITE
<222> LOCATION: (106)
<223> OTHER INFORMATION: "Ser" or "Asn"
<221> NAME/KEY: SITE
<222> LOCATION: (110)
<223> OTHER INFORMATION: "Thr" or "Asn"
<221> NAME/KEY: SITE

```
<222> LOCATION: (142)
<223> OTHER INFORMATION: "Ala" or "Gly"
<221> NAME/KEY: SITE
<222> LOCATION: (147)
<223> OTHER INFORMATION: "Val" or "Ala"
<221> NAME/KEY: SITE
<222> LOCATION: (158)
<223> OTHER INFORMATION: "Leu" or "Val"
<221> NAME/KEY: SITE
<222> LOCATION: (169)
<223> OTHER INFORMATION: "Ile" or "Leu"
<221> NAME/KEY: SITE
<222> LOCATION: (173)
<223> OTHER INFORMATION: "Ser" or "Pro"
<221> NAME/KEY: SITE
<222> LOCATION: (187)
<223> OTHER INFORMATION: "Thr" or "Ile" or "Val"
<221> NAME/KEY: SITE
<222> LOCATION: (189)
<223> OTHER INFORMATION: "Val" or "Ala"

<400> SEQUENCE: 266

Met Ser Thr Xaa Pro Lys Pro Gln Arg Xaa Thr Lys Arg Asn Thr Xaa
 1               5                  10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Xaa Arg Lys Thr Ser Glu Arg Ser Gln Pro Arg Gly Arg Arg Gln Pro
 50                  55                  60

Ile Pro Lys Ala Arg Xaa Pro Glu Gly Arg Xaa Trp Ala Gln Pro Gly
 65                  70                  75                  80

Xaa Pro Trp Pro Leu Tyr Xaa Xaa Glu Gly Xaa Gly Trp Ala Gly Trp
                85                  90                  95

Leu Leu Ser Pro Xaa Gly Ser Arg Pro Xaa Trp Gly Pro Xaa Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Xaa Pro Leu
130                 135                 140

Gly Gly Xaa Ala Arg Ala Leu Ala His Gly Val Arg Val Xaa Glu Asp
145                 150                 155                 160

Gly Val Asn Tyr Ala Thr Gly Asn Xaa Pro Gly Cys Xaa Phe Ser Ile
                165                 170                 175

Phe Leu Leu Ala Leu Leu Ser Cys Leu Thr Xaa Pro Xaa Ser Ala
                180                 185                 190

<210> SEQ ID NO 267
<211> LENGTH: 191
<212> TYPE: PRT
<213> ORGANISM: Homo sapiens
<220> FEATURE:
<221> NAME/KEY: SITE
<222> LOCATION: (4)
<223> OTHER INFORMATION: "Asn" or "Ile"
<221> NAME/KEY: SITE
<222> LOCATION: (12)
<223> OTHER INFORMATION: "Ile" or "Lys"
<221> NAME/KEY: SITE
<222> LOCATION: (48)
<223> OTHER INFORMATION: "Thr" or "Ala"
<221> NAME/KEY: SITE
<222> LOCATION: (71)
<223> OTHER INFORMATION: "Ser" or "Pro"
<221> NAME/KEY: SITE
<222> LOCATION: (110)
```

<223> OTHER INFORMATION: "Ser" or "Thr" or "Asn"
<221> NAME/KEY: SITE
<222> LOCATION: (129)
<223> OTHER INFORMATION: "Gly" or "Ser"
<221> NAME/KEY: SITE
<222> LOCATION: (130)
<223> OTHER INFORMATION: "Phe" or "Leu"
<221> NAME/KEY: SITE
<222> LOCATION: (137)
<223> OTHER INFORMATION: "Ile" or "Val"
<221> NAME/KEY: SITE
<222> LOCATION: (142)
<223> OTHER INFORMATION: "Ala" or "Gly"
<221> NAME/KEY: SITE
<222> LOCATION: (187)
<223> OTHER INFORMATION: "Thr" or "Ile"
<221> NAME/KEY: SITE
<222> LOCATION: (189)
<223> OTHER INFORMATION: "Ala" or "Val"

<400> SEQUENCE: 267

```
Met Ser Thr Xaa Pro Lys Pro Gln Arg Lys Thr Xaa Arg Asn Thr Asn
  1               5                  10                  15

Arg Arg Pro Gln Asp Val Lys Phe Pro Gly Gly Gln Ile Val Gly
             20                  25                  30

Gly Val Tyr Leu Leu Pro Arg Arg Gly Pro Arg Leu Gly Val Arg Xaa
         35                  40                  45

Thr Arg Lys Thr Ser Glu Arg Ser Gln Pro Arg Gly Arg Arg Gln Pro
 50                  55                  60

Ile Pro Lys Asp Arg Arg Xaa Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Xaa Asp Pro
                100                 105                 110

Arg His Arg Ser Arg Asn Val Gly Lys Val Ile Asp Thr Leu Thr Cys
            115                 120                 125

Xaa Xaa Ala Asp Leu Met Gly Tyr Xaa Pro Val Val Gly Xaa Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Xaa Pro Xaa Ser Ala
                180                 185                 190
```

<210> SEQ ID NO 268
<211> LENGTH: 191
<212> TYPE: PRT
<213> ORGANISM: Homo sapiens
<220> FEATURE:
<221> NAME/KEY: SITE
<222> LOCATION: (48)
<223> OTHER INFORMATION: "Thr" or "Ala"
<221> NAME/KEY: SITE
<222> LOCATION: (52)
<223> OTHER INFORMATION: "Thr" or "Ser"
<221> NAME/KEY: SITE
<222> LOCATION: (75)
<223> OTHER INFORMATION: "Pro" or "Ser"
<221> NAME/KEY: SITE
<222> LOCATION: (104)
<223> OTHER INFORMATION: "His" or "Arg"
<221> NAME/KEY: SITE
<222> LOCATION: (106)
<223> OTHER INFORMATION: "Asn" or "Thr"

```
<221> NAME/KEY: SITE
<222> LOCATION: (115)
<223> OTHER INFORMATION: "Lys" or "Arg"
<221> NAME/KEY: SITE
<222> LOCATION: (121)
<223> OTHER INFORMATION: "Lys" or "Arg"
<221> NAME/KEY: SITE
<222> LOCATION: (185)
<223> OTHER INFORMATION: "Cys" or "Phe" or "Ala"

<400> SEQUENCE: 268
```

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Xaa
                35                  40                  45

Thr Arg Lys Xaa Ser Glu Arg Ser Gln Pro Arg Gly Arg Arg Gln Pro
        50                  55                  60

Ile Pro Lys Asp Arg Arg Ser Thr Gly Lys Xaa Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Xaa Pro Xaa Trp Gly Pro Thr Asp Pro
            100                 105                 110

Arg His Xaa Ser Arg Asn Leu Gly Xaa Val Ile Asp Thr Ile Thr Cys
        115                 120                 125

Gly Phe Ala Asp Leu Met Gly Tyr Ile Pro Val Val Gly Ala Pro Val
130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Xaa Thr Val Pro Val Ser Ala
            180                 185                 190

```
<210> SEQ ID NO 269
<211> LENGTH: 191
<212> TYPE: PRT
<213> ORGANISM: Homo sapiens
<220> FEATURE:
<221> NAME/KEY: SITE
<222> LOCATION: (4)
<223> OTHER INFORMATION: "Asn" or "Ile"
<221> NAME/KEY: SITE
<222> LOCATION: (12)
<223> OTHER INFORMATION: "Lys" or "Ile"
<221> NAME/KEY: SITE
<222> LOCATION: (48)
<223> OTHER INFORMATION: "Thr" or "Ala"
<221> NAME/KEY: SITE
<222> LOCATION: (52)
<223> OTHER INFORMATION: "Thr" or "Ser"
<221> NAME/KEY: SITE
<222> LOCATION: (71)
<223> OTHER INFORMATION: "Ser" "Thr" or "Pro"
<221> NAME/KEY: SITE
<222> LOCATION: (75)
<223> OTHER INFORMATION: "Pro" or "Ser"
<221> NAME/KEY: SITE
<222> LOCATION: (78)
<223> OTHER INFORMATION: "Lys" or "Arg"
<221> NAME/KEY: SITE
<222> LOCATION: (91)
<223> OTHER INFORMATION: "Cys" or "Leu"
<221> NAME/KEY: SITE
```

-continued

```
<222> LOCATION: (104)
<223> OTHER INFORMATION: "His" or "Arg"
<221> NAME/KEY: SITE
<222> LOCATION: (106)
<223> OTHER INFORMATION: "Asn" or "Thr" or "Ser"
<221> NAME/KEY: SITE
<222> LOCATION: (110)
<223> OTHER INFORMATION: "Thr" or "Asn" or "Ser"
<221> NAME/KEY: SITE
<222> LOCATION: (115)
<223> OTHER INFORMATION: "Lys" or "Arg"
<221> NAME/KEY: SITE
<222> LOCATION: (119)
<223> OTHER INFORMATION: "Leu" or "Val"
<221> NAME/KEY: SITE
<222> LOCATION: (121)
<223> OTHER INFORMATION: "Lys" or "Arg"
<221> NAME/KEY: SITE
<222> LOCATION: (126)
<223> OTHER INFORMATION: "Ile" or "Leu"
<221> NAME/KEY: SITE
<222> LOCATION: (129)
<223> OTHER INFORMATION: "Gly" or "Ser"
<221> NAME/KEY: SITE
<222> LOCATION: (130)
<223> OTHER INFORMATION: "Phe" or "Leu"
<221> NAME/KEY: SITE
<222> LOCATION: (137)
<223> OTHER INFORMATION: "Ile" or "Val"
<221> NAME/KEY: SITE
<222> LOCATION: (142)
<223> OTHER INFORMATION: "Ala" or "Gly"
<221> NAME/KEY: SITE
<222> LOCATION: (144)
<223> OTHER INFORMATION: "Val" or "Leu"
<221> NAME/KEY: SITE
<222> LOCATION: (162)
<223> OTHER INFORMATION: "Ile" or "Val"
<221> NAME/KEY: SITE
<222> LOCATION: (185)
<223> OTHER INFORMATION: "Cys" or "Phe" or "Ala" or "Ile"
<221> NAME/KEY: SITE
<222> LOCATION: (186)
<223> OTHER INFORMATION: "Thr" or "Ser"
<221> NAME/KEY: SITE
<222> LOCATION: (187)
<223> OTHER INFORMATION: "Val" or "Ile" or "Thr"
<221> NAME/KEY: SITE
<222> LOCATION: (189)
<223> OTHER INFORMATION: "Val" or "Ala"

<400> SEQUENCE: 269

Met Ser Thr Xaa Pro Lys Pro Gln Arg Lys Thr Xaa Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Xaa
         35                  40                  45

Thr Arg Lys Xaa Ser Glu Arg Ser Gln Pro Arg Gly Arg Arg Gln Pro
 50                  55                  60

Ile Pro Lys Asp Arg Arg Xaa Thr Gly Lys Xaa Trp Gly Xaa Pro Gly
 65                  70                  75                  80

Tyr Pro Trp Pro Leu Tyr Gly Asn Glu Gly Xaa Gly Trp Ala Gly Trp
                 85                  90                  95

Leu Leu Ser Pro Arg Gly Ser Xaa Pro Xaa Trp Gly Pro Xaa Asp Pro
            100                 105                 110

Arg His Xaa Ser Arg Asn Xaa Gly Xaa Val Ile Asp Thr Xaa Thr Cys
        115                 120                 125

Xaa Xaa Ala Asp Leu Met Gly Tyr Xaa Pro Val Val Gly Xaa Pro Xaa
130                 135                 140
```

-continued

```
Gly Gly Val Ala Arg Ala Leu Ala His Gly Val Arg Val Leu Glu Asp
145                 150                 155                 160

Gly Xaa Asn Tyr Ala Thr Gly Asn Leu Pro Gly Cys Ser Phe Ser Ile
                165                 170                 175

Phe Leu Leu Ala Leu Leu Ser Cys Xaa Xaa Xaa Pro Xaa Ser Ala
            180                 185                 190

<210> SEQ ID NO 270
<211> LENGTH: 191
<212> TYPE: PRT
<213> ORGANISM: Homo sapiens
<220> FEATURE:
<221> NAME/KEY: SITE
<222> LOCATION: (22)
<223> OTHER INFORMATION: "Ile" or "Val"
<221> NAME/KEY: SITE
<222> LOCATION: (186)
<223> OTHER INFORMATION: "Ile" or "Val"

<400> SEQUENCE: 270

Met Ser Thr Leu Pro Lys Pro Gln Arg Lys Thr Lys Arg Asn Thr Ile
1               5                   10                  15

Arg Arg Pro Gln Asp Xaa Lys Phe Pro Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Xaa His Pro Ala Ala Ser
            180                 185                 190

<210> SEQ ID NO 271
<211> LENGTH: 191
<212> TYPE: PRT
<213> ORGANISM: Homo sapiens
<220> FEATURE:
<221> NAME/KEY: SITE
<222> LOCATION: (48)
<223> OTHER INFORMATION: "Ala" or "Thr"
<221> NAME/KEY: SITE
<222> LOCATION: (49)
<223> OTHER INFORMATION: "Thr" or "Ala"
<221> NAME/KEY: SITE
<222> LOCATION: (67)
<223> OTHER INFORMATION: "Gln" or "Lys"
<221> NAME/KEY: SITE
<222> LOCATION: (70)
<223> OTHER INFORMATION: "Arg" or "Gln"
```

```
<221> NAME/KEY: SITE
<222> LOCATION: (71)
<223> OTHER INFORMATION: "Ser" or "Pro" or "Leu"
<221> NAME/KEY: SITE
<222> LOCATION: (109)
<223> OTHER INFORMATION: "Gln" or "Pro"
<221> NAME/KEY: SITE
<222> LOCATION: (139)
<223> OTHER INFORMATION: "Leu" or "Ile" or "Val"
<221> NAME/KEY: SITE
<222> LOCATION: (157)
<223> OTHER INFORMATION: "Ala" or "Leu"
<221> NAME/KEY: SITE
<222> LOCATION: (158)
<223> OTHER INFORMATION: "Leu" or "Val"
<221> NAME/KEY: SITE
<222> LOCATION: (162)
<223> OTHER INFORMATION: "Ile" or "Val"
<221> NAME/KEY: SITE
<222> LOCATION: (182)
<223> OTHER INFORMATION: "Phe" or "Leu"
<221> NAME/KEY: SITE
<222> LOCATION: (187)
<223> OTHER INFORMATION: "Thr" or "Val"
<221> NAME/KEY: SITE
<222> LOCATION: (189)
<223> OTHER INFORMATION: "Ala" or "Thr"

<400> SEQUENCE: 271

Met Ser Thr Asn Pro Lys Pro Gln Arg Lys Thr Lys Arg Asn Thr Asn
 1               5                  10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Xaa
        35                  40                  45

Xaa Arg Lys Thr Ser Glu Arg Ser Gln Pro Arg Gly Arg Arg Gln Pro
     50                  55                  60

Ile Pro Xaa Ala Arg Xaa Xaa Glu Gly Arg Ser Trp Ala Gln Pro Gly
 65                  70                  75                  80

Tyr Pro Trp Pro Leu Tyr Gly Asn Glu Gly Cys Gly Trp Ala Gly
                85                  90                  95

Leu Leu Ser Pro Arg Gly Ser Arg Pro Ser Trp Gly Xaa Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Xaa Val Gly Ala Pro Val
130                 135                 140

Gly Gly Val Ala Arg Ala Leu Ala His Gly Val Arg Xaa Xaa Glu Asp
145                 150                 155                 160

Gly Xaa Asn Tyr Ala Thr Gly Asn Leu Pro Gly Cys Ser Phe Ser Ile
                165                 170                 175

Phe Leu Leu Ala Leu Xaa Ser Cys Leu Thr Xaa Pro Xaa Ser Ala
            180                 185                 190

<210> SEQ ID NO 272
<211> LENGTH: 191
<212> TYPE: PRT
<213> ORGANISM: Homo sapiens
<220> FEATURE:
<221> NAME/KEY: SITE
<222> LOCATION: (12)
<223> OTHER INFORMATION: "Lys" or "Gln"
<221> NAME/KEY: SITE
<222> LOCATION: (17)
<223> OTHER INFORMATION: "Arg" or "Leu"
<221> NAME/KEY: SITE
```

-continued

```
<222> LOCATION: (44)
<223> OTHER INFORMATION: "Leu" or "Met"
<221> NAME/KEY: SITE
<222> LOCATION: (71)
<223> OTHER INFORMATION: "Pro" or "Ser"
<221> NAME/KEY: SITE
<222> LOCATION: (72)
<223> OTHER INFORMATION: "Thr" or "Ala"
<221> NAME/KEY: SITE
<222> LOCATION: (85)
<223> OTHER INFORMATION: "Phe" or "Leu"
<221> NAME/KEY: SITE
<222> LOCATION: (92)
<223> OTHER INFORMATION: "Gly" or "Glu"
<221> NAME/KEY: SITE
<222> LOCATION: (106)
<223> OTHER INFORMATION: "Asn" or "Ser"
<221> NAME/KEY: SITE
<222> LOCATION: (115)
<223> OTHER INFORMATION: "Arg" or "Lys"
<221> NAME/KEY: SITE
<222> LOCATION: (157)
<223> OTHER INFORMATION: "Ala" or "Val"
<221> NAME/KEY: SITE
<222> LOCATION: (178)
<223> OTHER INFORMATION: "Ile" or "Val"
<221> NAME/KEY: SITE
<222> LOCATION: (186)
<223> OTHER INFORMATION: "Thr" or "Ile"
<221> NAME/KEY: SITE
<222> LOCATION: (187)
<223> OTHER INFORMATION: "Val" or "Ile"
<221> NAME/KEY: SITE
<222> LOCATION: (189)
<223> OTHER INFORMATION: "Ala" or "Thr"
<221> NAME/KEY: SITE
<222> LOCATION: (190)
<223> OTHER INFORMATION: "Thr" or "Ser"

<400> SEQUENCE: 272

Met Ser Thr Asn Pro Lys Pro Gln Arg Lys Thr Xaa Arg Asn Thr Asn
  1               5                  10                  15

Xaa Arg Pro Gln Asp Val Lys Phe Pro Gly Gly Gln Ile Val Gly
             20                  25                  30

Gly Val Tyr Leu Leu Pro Arg Arg Gly Pro Arg Xaa Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Gln Xaa Xaa Gly Arg Ser Trp Gly Gln Pro Gly
 65                  70                  75                  80

Tyr Pro Trp Pro Xaa Tyr Ala Asn Glu Gly Leu Xaa Trp Ala Gly Trp
                 85                  90                  95

Leu Leu Ser Pro Arg Gly Ser Arg Pro Xaa Trp Gly Pro Asn Asp Pro
            100                 105                 110

Arg Arg Xaa Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Xaa Leu Glu Asp
145                 150                 155                 160

Gly Val Asn Tyr Ala Thr Gly Asn Leu Pro Gly Cys Ser Phe Ser Ile
                165                 170                 175

Phe Xaa Leu Ala Leu Leu Ser Cys Leu Xaa Xaa Pro Xaa Xaa Ala
            180                 185                 190

<210> SEQ ID NO 273
```

```
<211> LENGTH: 191
<212> TYPE: PRT
<213> ORGANISM: Homo sapiens
<220> FEATURE:
<221> NAME/KEY: SITE
<222> LOCATION: (4)
<223> OTHER INFORMATION: "Asn" or "Leu"
<221> NAME/KEY: SITE
<222> LOCATION: (10)
<223> OTHER INFORMATION: "Lys"
<221> NAME/KEY: SITE
<222> LOCATION: (12)
<223> OTHER INFORMATION: "Lys"
<221> NAME/KEY: SITE
<222> LOCATION: (16)
<223> OTHER INFORMATION: "Asn" or "Ile"
<221> NAME/KEY: SITE
<222> LOCATION: (17)
<223> OTHER INFORMATION: "Arg"
<221> NAME/KEY: SITE
<222> LOCATION: (20)
<223> OTHER INFORMATION: "Gln" or "Met" or "Thr"
<221> NAME/KEY: SITE
<222> LOCATION: (22)
<223> OTHER INFORMATION: "Val"
<221> NAME/KEY: SITE
<222> LOCATION: (36)
<223> OTHER INFORMATION: "Leu" or "Val"
<221> NAME/KEY: SITE
<222> LOCATION: (44)
<223> OTHER INFORMATION: "Leu"
<221> NAME/KEY: SITE
<222> LOCATION: (48)
<223> OTHER INFORMATION: "Ala"
<221> NAME/KEY: SITE
<222> LOCATION: (49)
<223> OTHER INFORMATION: "Thr"
<221> NAME/KEY: SITE
<222> LOCATION: (52)
<223> OTHER INFORMATION: "Thr"
<221> NAME/KEY: SITE
<222> LOCATION: (67)
<223> OTHER INFORMATION: "Lys"
<221> NAME/KEY: SITE
<222> LOCATION: (68)
<223> OTHER INFORMATION: "Ala" or "Asp"
<221> NAME/KEY: SITE
<222> LOCATION: (70)
<223> OTHER INFORMATION: "Arg" or "Gln"
<221> NAME/KEY: SITE
<222> LOCATION: (71)
<223> OTHER INFORMATION: "Pro" or "Ser"
<221> NAME/KEY: SITE
<222> LOCATION: (72)
<223> OTHER INFORMATION: "Glu" or "Thr" or "Gln"
<221> NAME/KEY: SITE
<222> LOCATION: (74)
<223> OTHER INFORMATION: "Arg" or "Lys"
<221> NAME/KEY: SITE
<222> LOCATION: (75)
<223> OTHER INFORMATION: "Ala" or "Ser" or "His"
<221> NAME/KEY: SITE
<222> LOCATION: (77)
<223> OTHER INFORMATION: "Ala" or "Gly"
<221> NAME/KEY: SITE
<222> LOCATION: (78)
<223> OTHER INFORMATION: "Gln" or "Lys"
<221> NAME/KEY: SITE
<222> LOCATION: (81)
<223> OTHER INFORMATION: "Tyr"
<221> NAME/KEY: SITE
<222> LOCATION: (85)
<223> OTHER INFORMATION: "Leu"
<221> NAME/KEY: SITE
<222> LOCATION: (87)
<223> OTHER INFORMATION: "Gly" or "Ala"
<221> NAME/KEY: SITE
<222> LOCATION: (88)
<223> OTHER INFORMATION: "Asn"
```

-continued

```
<221> NAME/KEY: SITE
<222> LOCATION: (91)
<223> OTHER INFORMATION: "Leu" or "Cys"
<221> NAME/KEY: SITE
<222> LOCATION: (92)
<223> OTHER INFORMATION: "Gly"
<221> NAME/KEY: SITE
<222> LOCATION: (101)
<223> OTHER INFORMATION: "Arg"
<221> NAME/KEY: SITE
<222> LOCATION: (104)
<223> OTHER INFORMATION: "Arg"
<221> NAME/KEY: SITE
<222> LOCATION: (106)
<223> OTHER INFORMATION: "Ser" or "Asn" or "His"
<221> NAME/KEY: SITE
<222> LOCATION: (109)
<223> OTHER INFORMATION: "Pro"
<221> NAME/KEY: SITE
<222> LOCATION: (110)
<223> OTHER INFORMATION: "Thr" or "Asn"
<221> NAME/KEY: SITE
<222> LOCATION: (114)
<223> OTHER INFORMATION: "Arg" or "His"
<221> NAME/KEY: SITE
<222> LOCATION: (115)
<223> OTHER INFORMATION: "Arg" or "Lys"
<221> NAME/KEY: SITE
<222> LOCATION: (119)
<223> OTHER INFORMATION: "Leu"
<221> NAME/KEY: SITE
<222> LOCATION: (121)
<223> OTHER INFORMATION: "Lys"
<221> NAME/KEY: SITE
<222> LOCATION: (126)
<223> OTHER INFORMATION: "Leu"
<221> NAME/KEY: SITE
<222> LOCATION: (129)
<223> OTHER INFORMATION: "Gly"
<221> NAME/KEY: SITE
<222> LOCATION: (130)
<223> OTHER INFORMATION: "Phe"
<221> NAME/KEY: SITE
<222> LOCATION: (137)
<223> OTHER INFORMATION: "Ile"
<221> NAME/KEY: SITE
<222> LOCATION: (139)
<223> OTHER INFORMATION: "Leu" or "Val"
<221> NAME/KEY: SITE
<222> LOCATION: (142)
<223> OTHER INFORMATION: "Ala" or "Gly"
<221> NAME/KEY: SITE
<222> LOCATION: (144)
<223> OTHER INFORMATION: "Leu" or "Val"
<221> NAME/KEY: SITE
<222> LOCATION: (147)
<223> OTHER INFORMATION: "Ala" or "Val"
<221> NAME/KEY: SITE
<222> LOCATION: (149)
<223> OTHER INFORMATION: "Arg" or "Ala"
<221> NAME/KEY: SITE
<222> LOCATION: (157)
<223> OTHER INFORMATION: "Val" or "Ala"
<221> NAME/KEY: SITE
<222> LOCATION: (158)
<223> OTHER INFORMATION: "Leu" or "Val" or "Ile"
<221> NAME/KEY: SITE
<222> LOCATION: (162)
<223> OTHER INFORMATION: "Val" or "Ile"
<221> NAME/KEY: SITE
<222> LOCATION: (164)
<223> OTHER INFORMATION: "Tyr" or "Phe"
<221> NAME/KEY: SITE
<222> LOCATION: (169)
<223> OTHER INFORMATION: "Leu"
<221> NAME/KEY: SITE
<222> LOCATION: (173)
<223> OTHER INFORMATION: "Ser"
<221> NAME/KEY: SITE
```

```
<222> LOCATION: (178)
<223> OTHER INFORMATION: "Leu" or "Ile"
<221> NAME/KEY: SITE
<222> LOCATION: (182)
<223> OTHER INFORMATION: "Leu" or "Phe"
<221> NAME/KEY: SITE
<222> LOCATION: (185)
<223> OTHER INFORMATION: "Leu" or "Ile"
<221> NAME/KEY: SITE
<222> LOCATION: (186)
<223> OTHER INFORMATION: "Thr" or "Ile"
<221> NAME/KEY: SITE
<222> LOCATION: (187)
<223> OTHER INFORMATION: "Ile" or "Val" or "His" or "Thr"
<221> NAME/KEY: SITE
<222> LOCATION: (189)
<223> OTHER INFORMATION: "Ala" or "Val"
<221> NAME/KEY: SITE
<222> LOCATION: (190)
<223> OTHER INFORMATION: "Ser" or "Ala"
<221> NAME/KEY: SITE
<222> LOCATION: (191)
<223> OTHER INFORMATION: "Ala" or "Ser"

<400> SEQUENCE: 273
```

Met Ser Thr Xaa Pro Lys Pro Gln Arg Xaa Thr Xaa Arg Asn Thr Xaa
 1               5                  10                  15

Xaa Arg Pro Xaa Asp Xaa Lys Phe Pro Gly Gly Gln Ile Val Gly
            20                  25                  30

Gly Val Tyr Xaa Leu Pro Arg Arg Gly Pro Arg Xaa Gly Val Arg Xaa
             35                  40                  45

Xaa Arg Lys Xaa Ser Glu Arg Ser Gln Pro Arg Gly Arg Arg Gln Pro
 50                  55                  60

Ile Pro Xaa Xaa Arg Xaa Xaa Xaa Gly Xaa Xaa Trp Xaa Xaa Pro Gly
 65                  70                  75                  80

Xaa Pro Trp Pro Xaa Tyr Xaa Xaa Glu Gly Xaa Xaa Trp Ala Gly Trp
                 85                  90                  95

Leu Leu Ser Pro Xaa Gly Ser Xaa Pro Xaa Trp Gly Xaa Xaa Asp Pro
                100                 105                 110

Arg Xaa Xaa Ser Arg Asn Xaa Gly Xaa Val Ile Asp Thr Xaa Thr Cys
        115                 120                 125

Xaa Xaa Ala Asp Leu Met Gly Tyr Xaa Pro Xaa Val Gly Xaa Pro Xaa
130                 135                 140

Gly Gly Xaa Ala Xaa Ala Leu Ala His Gly Val Arg Xaa Xaa Glu Asp
145                 150                 155                 160

Gly Xaa Asn Xaa Ala Thr Gly Asn Xaa Pro Gly Cys Xaa Phe Ser Ile
            165                 170                 175

Phe Xaa Leu Ala Leu Xaa Ser Cys Xaa Xaa Xaa Pro Xaa Xaa Xaa
        180                 185                 190

```
<210> SEQ ID NO 274
<211> LENGTH: 191
<212> TYPE: PRT
<213> ORGANISM: Homo sapiens
<220> FEATURE:
<221> NAME/KEY: SITE
<222> LOCATION: (4)
<223> OTHER INFORMATION: "Asn" or "Leu"
<221> NAME/KEY: SITE
<222> LOCATION: (10)
<223> OTHER INFORMATION: "Lys"
<221> NAME/KEY: SITE
<222> LOCATION: (12)
<223> OTHER INFORMATION: "Lys"
<221> NAME/KEY: SITE
<222> LOCATION: (16)
```

-continued

```
<223> OTHER INFORMATION: "Asn" or "Ile"
<221> NAME/KEY: SITE
<222> LOCATION: (17)
<223> OTHER INFORMATION: "Arg"
<221> NAME/KEY: SITE
<222> LOCATION: (20)
<223> OTHER INFORMATION: "Gln" or "Met" or "Thr"
<221> NAME/KEY: SITE
<222> LOCATION: (22)
<223> OTHER INFORMATION: "Val"
<221> NAME/KEY: SITE
<222> LOCATION: (36)
<223> OTHER INFORMATION: "Leu" or "Val"
<221> NAME/KEY: SITE
<222> LOCATION: (44)
<223> OTHER INFORMATION: "Leu"
<221> NAME/KEY: SITE
<222> LOCATION: (48)
<223> OTHER INFORMATION: "Ala"
<221> NAME/KEY: SITE
<222> LOCATION: (49)
<223> OTHER INFORMATION: "Thr" or "Ala"
<221> NAME/KEY: SITE
<222> LOCATION: (52)
<223> OTHER INFORMATION: "Thr"
<221> NAME/KEY: SITE
<222> LOCATION: (67)
<223> OTHER INFORMATION: "Lys" or "Gln"
<221> NAME/KEY: SITE
<222> LOCATION: (68)
<223> OTHER INFORMATION: "Ala" or "Asp"
<221> NAME/KEY: SITE
<222> LOCATION: (70)
<223> OTHER INFORMATION: "Arg" or "Gln"
<221> NAME/KEY: SITE
<222> LOCATION: (71)
<223> OTHER INFORMATION: "Pro" or "Ser" or "Thr" or "Leu"
<221> NAME/KEY: SITE
<222> LOCATION: (72)
<223> OTHER INFORMATION: "Glu" or "Thr" or "Gln"
<221> NAME/KEY: SITE
<222> LOCATION: (74)
<223> OTHER INFORMATION: "Arg" or "Lys"
<221> NAME/KEY: SITE
<222> LOCATION: (75)
<223> OTHER INFORMATION: "Thr" or "Ala or "Ser" or "His"
<221> NAME/KEY: SITE
<222> LOCATION: (77)
<223> OTHER INFORMATION: "Ala" or "Gly"
<221> NAME/KEY: SITE
<222> LOCATION: (78)
<223> OTHER INFORMATION: "Gln" or "Lys" or "Arg"
<221> NAME/KEY: SITE
<222> LOCATION: (81)
<223> OTHER INFORMATION: "Tyr"
<221> NAME/KEY: SITE
<222> LOCATION: (85)
<223> OTHER INFORMATION: "Leu"
<221> NAME/KEY: SITE
<222> LOCATION: (87)
<223> OTHER INFORMATION: "Gly" or "Ala"
<221> NAME/KEY: SITE
<222> LOCATION: (88)
<223> OTHER INFORMATION: "Asn"
<221> NAME/KEY: SITE
<222> LOCATION: (91)
<223> OTHER INFORMATION: "Cys" or "Met" or "Leu"
<221> NAME/KEY: SITE
<222> LOCATION: (92)
<223> OTHER INFORMATION: "Gly"
<221> NAME/KEY: SITE
<222> LOCATION: (101)
<223> OTHER INFORMATION: "Arg"
<221> NAME/KEY: SITE
<222> LOCATION: (104)
<223> OTHER INFORMATION: "Arg"
<221> NAME/KEY: SITE
<222> LOCATION: (106)
<223> OTHER INFORMATION: "Ser" or "Thr" or "Asn" or "His"
```

-continued

```
<221> NAME/KEY: SITE
<222> LOCATION: (109)
<223> OTHER INFORMATION: "Pro" or "Gln"
<221> NAME/KEY: SITE
<222> LOCATION: (110)
<223> OTHER INFORMATION: "Thr" or "Asn"
<221> NAME/KEY: SITE
<222> LOCATION: (114)
<223> OTHER INFORMATION: "Arg" or "His"
<221> NAME/KEY: SITE
<222> LOCATION: (115)
<223> OTHER INFORMATION: "Arg" or "Lys"
<221> NAME/KEY: SITE
<222> LOCATION: (119)
<223> OTHER INFORMATION: "Leu" or "Val"
<221> NAME/KEY: SITE
<222> LOCATION: (121)
<223> OTHER INFORMATION: "Lys"
<221> NAME/KEY: SITE
<222> LOCATION: (126)
<223> OTHER INFORMATION: "Leu" or "Ile"
<221> NAME/KEY: SITE
<222> LOCATION: (129)
<223> OTHER INFORMATION: "Gly"
<221> NAME/KEY: SITE
<222> LOCATION: (130)
<223> OTHER INFORMATION: "Phe"
<221> NAME/KEY: SITE
<222> LOCATION: (137)
<223> OTHER INFORMATION: "Ile"
<221> NAME/KEY: SITE
<222> LOCATION: (139)
<223> OTHER INFORMATION: "Leu" or "Val" or "Ile"
<221> NAME/KEY: SITE
<222> LOCATION: (142)
<223> OTHER INFORMATION: "Ala" or "Gly"
<221> NAME/KEY: SITE
<222> LOCATION: (144)
<223> OTHER INFORMATION: "Leu" or "Val"
<221> NAME/KEY: SITE
<222> LOCATION: (147)
<223> OTHER INFORMATION: "Ala" or "Val"
<221> NAME/KEY: SITE
<222> LOCATION: (149)
<223> OTHER INFORMATION: "Arg" or "Ala"
<221> NAME/KEY: SITE
<222> LOCATION: (157)
<223> OTHER INFORMATION: "Val" or "Ala" or "Leu"
<221> NAME/KEY: SITE
<222> LOCATION: (158)
<223> OTHER INFORMATION: "Leu" or "Val" or "Ile"
<221> NAME/KEY: SITE
<222> LOCATION: (162)
<223> OTHER INFORMATION: "Val" or "Ile"
<221> NAME/KEY: SITE
<222> LOCATION: (164)
<223> OTHER INFORMATION: "Tyr" or "Phe"
<221> NAME/KEY: SITE
<222> LOCATION: (169)
<223> OTHER INFORMATION: "Leu"
<221> NAME/KEY: SITE
<222> LOCATION: (173)
<223> OTHER INFORMATION: "Ser"
<221> NAME/KEY: SITE
<222> LOCATION: (178)
<223> OTHER INFORMATION: "Leu" or "Ile"
<221> NAME/KEY: SITE
<222> LOCATION: (182)
<223> OTHER INFORMATION: "Leu" or "Phe"
<221> NAME/KEY: SITE
<222> LOCATION: (185)
<223> OTHER INFORMATION: "Leu" or "Ile" or "Phe"
<221> NAME/KEY: SITE
<222> LOCATION: (186)
<223> OTHER INFORMATION: "Thr" or "Ser" or "Ile"
<221> NAME/KEY: SITE
<222> LOCATION: (187)
<223> OTHER INFORMATION: "Val" or "Ile" or "His" or "Thr"
<221> NAME/KEY: SITE
```

-continued

```
<222> LOCATION: (189)
<223> OTHER INFORMATION: "Ala" or "Val" or "Thr"
<221> NAME/KEY: SITE
<222> LOCATION: (190)
<223> OTHER INFORMATION: "Ser" or "Ala"
<221> NAME/KEY: SITE
<222> LOCATION: (191)
<223> OTHER INFORMATION: "Ala" or "Ser"

<400> SEQUENCE: 274

Met Ser Thr Xaa Pro Lys Pro Gln Arg Xaa Thr Xaa Arg Asn Thr Xaa
 1               5                  10                  15

Xaa Arg Pro Xaa Asp Xaa Lys Phe Pro Gly Gly Gly Gln Ile Val Gly
            20                  25                  30

Gly Val Tyr Xaa Leu Pro Arg Arg Gly Pro Arg Xaa Gly Val Arg Xaa
            35                  40                  45

Xaa Arg Lys Xaa Ser Glu Arg Ser Gln Pro Arg Gly Arg Arg Gln Pro
        50                  55                  60

Ile Pro Xaa Xaa Arg Xaa Xaa Gly Xaa Xaa Trp Xaa Xaa Pro Gly
 65                  70                  75                  80

Xaa Pro Trp Pro Xaa Tyr Xaa Xaa Glu Gly Xaa Xaa Trp Ala Gly Trp
                85                  90                  95

Leu Leu Ser Pro Xaa Gly Ser Xaa Pro Xaa Trp Gly Xaa Xaa Asp Pro
                100                 105                 110

Arg Xaa Xaa Ser Arg Asn Xaa Gly Xaa Val Ile Asp Thr Xaa Thr Cys
        115                 120                 125

Xaa Xaa Ala Asp Leu Met Gly Tyr Xaa Pro Xaa Val Gly Xaa Pro Xaa
    130                 135                 140

Gly Gly Xaa Ala Xaa Ala Leu Ala His Gly Val Arg Xaa Xaa Glu Asp
145                 150                 155                 160

Gly Xaa Asn Xaa Ala Thr Gly Asn Xaa Pro Gly Cys Xaa Phe Ser Ile
            165                 170                 175

Phe Xaa Leu Ala Leu Xaa Ser Cys Xaa Xaa Xaa Pro Xaa Xaa Xaa
            180                 185                 190
```

NUCLEOTIDE AND DEDUCED AMINO ACID SEQUENCES OF THE ENVELOPE 1 AND CORE GENES OF ISOLATES OF HEPATITIS C VIRUS AND THE USE OF REAGENTS DERIVED FROM THESE SEQUENCES IN DIAGNOSTIC METHODS AND VACCINES

The present application is a divisional application of U.S. application Ser. No. 08/290,665, filed Aug. 15, 1994, now U.S. Pat. No. 5,882,852, which is a continuation-in-part of U.S. application Ser. No. 08/086,428, filed on Jun. 29, 1993, now U.S. Pat. No. 5,514,539.

FIELD OF INVENTION

The present invention is in the field of hepatitis virology. The invention relates to the complete nucleotide and deduced amino acid sequences of the envelope 1 (E1) and core genes of hepatitis C virus (HCV) isolates from around the world and the grouping of these isolates into fourteen distinct HCV genotypes. More specifically, this invention relates to oligonucleotides, peptides and recombinant proteins derived from the envelope 1 and core gene sequences of these isolates of hepatitis C virus and to diagnostic methods and vaccines which employ these reagents.

BACKGROUND OF INVENTION

Hepatitis C, originally called non-A, non-B hepatitis, was first described in 1975 as a disease serologically distinct from hepatitis A and hepatitis B (Feinstone, S. M. et al. (1975) N. Engl. J. Med. 292:767–770). Although hepatitis C was (and is) the leading type of transfusion-associated hepatitis as well as an important part of community-acquired hepatitis, little progress was made in understanding the disease until the recent identification of hepatitis C virus (HCV) as the causative agent of hepatitis C via the cloning and sequencing of the HCV genome (Choo, A. L. et al. (1989) Science 288:359–362). The sequence information generated by this study resulted in the characterization of HCV as a small, enveloped, positive-stranded RNA virus and led to the demonstration that HCV is a major cause of both acute and chronic hepatitis worldwide (Weiner, A. J. et al. (1990) Lancet 335:1–3). These observations, combined with studies showing that over 50% of acute cases of hepatitis C progress to chronicity with 20% of these resulting in cirrhosis and an undetermined proportion progressing to liver cancer, have led to tremendous efforts by investigators within the hepatitis C field to develop diagnostic assays and vaccines which can detect and prevent hepatitis C infection.

The cloning and sequencing of the HCV genome by Choo et al. (1989) has permitted the development of serologic tests which can detect HCV or antibody to HCV (Kuo, G. et al. (1989) Science 244:362–364). In addition, the work of Choo et al. has also allowed the development of methods for detecting HCV infection via amplification of HCV RNA sequences by reverse transcription and cDNA polymerase chain reaction (RT-PCR) using primers derived from the HCV genomic sequence (Weiner, A. J. et al.). However, although the development of these diagnostic methods has resulted in improved diagnosis of HCV infection, only approximately 60% of cases of hepatitis C are associated with a factor identified as contributing to transmission of HCV (Alter, M. J. et al. (1989) JAMA 262:1201–1205). This observation suggests that effective control of hepatitis C transmission is likely to occur only via universal pediatric vaccination as has been initiated recently for hepatitis B virus. Unfortunately, attempts to date to protect chimpanzees from hepatitis C infection via administration of recombinant vaccines have had only limited success. Moreover, the apparent genetic heterogeneity of HCV, as indicated by the recent assignment of all available HCV isolates to one of four genotypes, I–IV (Okamoto, H. et al. (1992) J. Gen. Virol; 73:673–679), presents additional hurdles which must be overcome in order to develop accurate and effective diagnostic assays and vaccines.

For example, one possible obstacle to the development of effective hepatitis C vaccines would arise if the observed genetic heterogeneity of HCV reflects serologic heterogeneity. In such a case, the most genetically diverse strains of HCV may then represent different serotypes of HCV with the result being that infection with one strain may not protect against infection with another. Indeed, the inability of one strain to protect against infection with another strain was recently noted by both Farci et al. (Farci, P. et al. (1992) Science 258:135–140) and Prince et al. (Prince, A. M. et al. (1992) J. Infect. Dis. 165:438–443), each of whom presented evidence that while infection with one strain of HCV does modify the degree of the hepatitis C associated with the reinfection, it does not protect against reinfection with a closely related strain. The genetic heterogeneity among different HCV strains also increases the difficulty encountered in developing RT-PCR assays to detect HCV infection since such heterogeneity often results in false-negative results because of primer and template mismatch. In addition, currently used serologic tests for detection of HCV or for detection of antibody to HCV are not sufficiently well developed to detect all of the HCV genotypes which might exist in a given blood sample. Finally, in terms of choosing the proper treatment modality to combat hepatitis infection, the inability of presently available serologic assays to distinguish among the various genotypes of HCV represents a significant shortcoming in that recent reports suggest that an HCV-infected patient's response to therapy might be related to the genotype of the infectious virus (Yoshioka, K. et al. (1992) Hepatology 16:293–299; Kanai, K. et al. (1992) Lancet 339:1543; Lan, J. Y. N. et al. (1992) Hepatology 16:209A). Indeed, the data presented in the above studies suggest that the closely related genotypes I and II are less responsive to interferon therapy than are the closely related genotypes III and IV. Moreover, preliminary data by Pozzato et al. (Pozzato, G. et al. (1991) Lancet 338:509) suggests that different genotypes may be associated with different types or degrees of clinical disease. Taken together, these studies suggest that before effective vaccines against HCV infection can be developed, and indeed, before more accurate and effective methods for diagnosis and treatment of HCV infection can be produced, one must obtain a greater knowledge about the genetic and serologic diversity of HCV isolates.

In a recent attempt to gain an understanding of the extent of genetic heterogeneity among HCV strains, Bukh et al. carried out a detailed analysis of HCV isolates via the use of PCR technology to amplify different regions of the HCV genome (Bukh, J. et al. (1992a) Proc. Natl. Acad. Sci. 89:187–191). Following PCR amplification, the 5'-noncoding (5' NC) portion of the genomes of various HCV isolates were sequenced and it was found that primer pairs designed from conserved regions of the 5' NC region of the HCV genome were more sensitive for detecting the presence of HCV than were primer pairs representing other portions of the genome (Bukh, J. et al. (1992b) Proc. Natl. Acad. Sci. U.S.A. 89:4942–4946). In addition, the authors noted that although many of the HCV isolates examined could be classified into the four genotypes described by Okamoto et al. (1992), other previously undescribed genotypes emerged based on genetic heterogeneity observed in the 5' NC region of the various isolates. One of the most prominent of these newly noted genotypes comprised a group of related viruses that contained the most genetically divergent 5' NC regions of those studied. This group of viruses, tentatively classified as a fifth genotype, are very similar to strains recently described by others (Cha, T.-A et al. (1992) Proc. Natl. Acad. Sci. U.S.A. 89:7144–7148; Chan, S-W. et al. (1992) J. Gen. Virol., 73:1131–1141 and Lee, C-H et al. (1992) J. Clin. Microbio. 30:1602–1604). In addition, at least four more putative genotypes were identified thereby providing evidence that the genetic heterogeneity of HCV was more extensive than previously appreciated.

However, while the studies of Bukh et al. (1992a and b) provided new and useful information on the genetic heterogeneity of HCV, it is widely appreciated by those skilled in the art that the three structural genes of HCV, core (C), envelope (E1) and envelope 2/nonstructural 1 (E2/NS1) are the most important for the development of serologic diagnostics and vaccines since it is the product of these genes that constitutes the hepatitis C virion. Thus, a determination of the nucleotide sequence of one or all of the structural genes of a variety of HCV isolates would be useful in designing reagents for use in diagnostic assays and vaccines since a demonstration of genetic heterogeneity in a structural gene(s) of HCV isolates might suggest that some of the HCV genotypes represent distinct serotypes of HCV based upon the previously observed relationship between genetic heterogeneity and serologic heterogeneity among another group of single-stranded, positive-sense RNA viruses, the picornaviruses (Ruechert, R. R. "Picornaviridae and their replication", in Fields, B. N. et al., eds. Virology, New York: Raven Press, Ltd. (1990) 507–548).

SUMMARY OF INVENTION

The present invention relates to cDNAs encoding the complete nucleotide sequence of either the envelope 1 (E1) gene or the core (C) gene of an isolate of human hepatitis C virus (HCV).

The present invention also relates to the nucleic acid and deduced amino acid sequences of these E1 and core cDNAs.

It is an object of this invention to provide synthetic nucleic acid sequences capable of directing production of recombinant E1 and core proteins, as well as equivalent natural nucleic acid sequences. Such natural nucleic acid sequences may be isolated from a cDNA or genomic library from which the gene capable of directing synthesis of the E1 or core proteins may be identified and isolated. For purposes of this application, nucleic acid sequence refers to RNA, DNA, cDNA or any synthetic variant thereof which encodes for peptides.

The invention also relates to the method of preparing recombinant E1 and core proteins derived from E1 and core cDNA sequences respectively by cloning the nucleic acid encoding either the recombinant E1 or core protein and inserting the cDNA into an expression vector and expressing the recombinant protein in a host cell.

The invention also relates to isolated and substantially purified recombinant E1 and core proteins and analogs thereof encoded by E1 and core cDNAs respectively.

The invention further relates to the use of recombinant E1 and core proteins, either alone, or in combination with each other, as diagnostic agents and as vaccines.

The present invention also relates to the recombinant production of the core protein of the present invention to contain a second protein on its surface and therefore serve as a carrier in a multivalent vaccine preparation. Further, the present invention relates to the use of the self aggregating core or envelope proteins as a drug delivery system for anti-virals.

The invention also relates to the use of single- stranded antisense poly- or oligonucleotides derived from E1 or core cDNAs, or from both E1 and core cDNAs, to inhibit expression of hepatitis C E1 and/or core genes.

The invention further relates to multiple computer-generated alignments of the nucleotide and deduced amino acid sequences of the E1 and core cDNAs. These multiple sequence alignments produce consensus sequences which serve to highlight regions of homology and non-homology between sequences found within the same genotype or in different genotypes and hence, these alignments can be used by one skilled in the art to design peptides and oligonucleotides useful as reagents in diagnostic assays and vaccines.

The invention therefore also relates to purified and isolated peptides and analogs thereof derived from E1 and core cDNA sequences.

The invention further relates to the use of these peptides as diagnostic agents and vaccines.

The present invention also encompasses methods of detecting antibodies specific for hepatitis C virus in biological samples. The methods of detecting HCV or antibodies to HCV disclosed in the present invention are useful for diagnosis of infection and disease caused by HCV and for monitoring the progression of such disease. Such methods are also useful for monitoring the efficacy of therapeutic agents during the course of treatment of HCV infection and disease in a mammal.

The invention also provides a kit for the detection of antibodies specific for HCV in a biological sample where said kit contains at least one purified and isolated peptide derived from the E1 or core cDNA sequences. In addition, the invention provides for a kit containing at least one purified and isolated peptide derived from the E1 cDNA sequences and at least one purified and isolated peptide derived from the core cDNA sequences.

The invention further provides isolated and purified genotype-specific oligonucleotides and analogs thereof derived from E1 and core cDNA sequences.

The invention also relates to methods for detecting the presence of hepatitis C virus in a mammal, said methods comprising analyzing the RNA of a mammal for the presence of hepatitis C virus. The invention further relates to methods for determining the genotype of hepatitis C virus present in a mammal. This method is useful in determining the proper course of treatment for an HCV-infected patient.

The invention also provides a diagnostic kit for the detection of hepatitis C virus in a biological sample. The kit comprises purified and isolated nucleic acid sequences useful as primers for reverse-transcription polymerase chain reaction (RT-PCR) analysis of RNA for the presence of hepatitis C virus genomic RNA.

The invention further provides a diagnostic kit for the determination of the genotype of a hepatitis C virus present in a mammal. The kit comprises purified and isolated nucleic acid sequences useful as primers for RT-PCR analysis of RNA for the presence of HCV in a biological sample and purified and isolated nucleic acid sequences useful as hybridization probes in determining the genotype of the HCV isolate detected in PCR analysis.

This invention also relates to pharmaceutical compositions useful in prevention or treatment of hepatitis C in a mammal.

DESCRIPTION OF FIGURES

FIGS. 1 A–H show computer generated sequence alignments of the nucleotide sequences of 51 HCV E1 cDNAs. The single letter abbreviations used for the nucleotides shown in FIGS. 1A–H are those standardly used in the art. FIG. 1A shows the alignment of SEQ ID NOs:1–8 to produce a consensus sequence for genotype I/1a. FIG. 1B shows the alignment of SEQ ID NOs:9–25 to produce a consensus sequence for genotype II/1b. FIG. 1C shows the alignment of SEQ ID NOs:26–29 to produce a consensus sequence for genotype III/2a. FIG. 1D shows the alignment of SEQ ID NOs:30–33 to produce a consensus sequence for genotype IV/2b. FIG. 1E shows the alignment of SEQ ID NOs:35–39 to produce a consensus sequence for genotype V/3a. FIG. 1F shows the computer alignment of SEQ ID NOs:42–43 to produce a "consensus" sequence for genotype 4C where the "consensus" sequence given is that of SEQ ID NO:42. FIG. 1G shows the alignment of SEQ ID NOs:45–50 to produce a consensus sequence for genotype 5a. The nucleotides shown in capital letters in the consensus sequences of FIGS. 1A–G are those conserved within a genotype while nucleotides shown in lower case letters in the consensus sequences are those variable within a genotype. In addition, in FIGS. 1A–E and 1G, when the lower case letter is shown in a consensus sequence, the lower case letter represents the nucleotide found most frequently in the sequences aligned to produce the consensus sequence. In FIG. 1F, the lower case letters shown in the consensus sequence are nucleotides in SEQ ID NO:42 which differ from nucleotides found in the same positions in SEQ ID NO:43. Finally, a hyphen at a nucleotide position in the consensus sequences in FIGS. 1A–G indicates that two nucleotides were found in equal numbers at that position in the aligned sequences. In the aligned sequences, nucleotides are shown in lower case letters if they differed from the nucleotides of both adjacent isolates. FIG. 1H shows the alignment of the consensus sequences of FIGS. 1A–G with SEQ ID NO:34 (genotype 2c), SEQ ID NO:40 (genotype 4a), SEQ ID NO:41 (genotype 4b), SEQ ID NO:44 (genotype 4d) and SEQ ID NO:51 (genotype 6a) to produce a consensus sequence for all twelve genotypes. This consensus sequence is shown as the bottom line of FIG. 1H where the nucleotides shown in capital letters are conserved among all genotypes and a blank space indicates that the nucleotide at that position is not conserved among all genotypes.

FIG. 2A shows the alignment of SEQ ID NOs:52–59 to produce a consensus sequence for genotype I/1a. FIG. 2B shows the alignment of SEQ ID NOs:60–76 to produce a consensus sequence for genotype II/1b. FIG. 2C shows the alignment of SEQ ID NOs:77–80 to produce a consensus sequence for genotype III/2a. FIG. 2D shows the alignment of SEQ ID NOs:81–84 to produce a consensus sequence for genotype IV/2b. FIG. 2E shows the alignment of SEQ ID NOs:86–90 to produce a consensus sequence for genotype V/3a. FIG. 2F shows the computer alignment of SEQ ID NOs:93–94 to produce a consensus sequence for genotype 4c. FIG. 2G shows the alignment of SEQ ID NOs:96–101 to produce a consensus sequence for genotype 5a. The amino acids shown in capital letters in the consensus sequences of FIGS. 2A–G are those conserved within a genotype while amino acids shown in lower case letters in the consensus sequences are those variable within a genotype. In addition, in FIGS. 2A–E and 2G when the lower case letter is shown in a consensus sequence, the letter represents the amino acid found most frequently in the sequences aligned to produce the consensus sequence. In FIG. 2F, the lower case letters shown in the consensus sequence are amino acids in SEQ ID NO:93 which differ from amino acids found in the same positions in SEQ ID NO:94. Finally, a hyphen at an amino acid position in the consensus sequences of FIGS. 2A–G indicates that two amino acids were found in equal numbers at that position in the aligned sequences. In the aligned sequences, amino acids are shown in lower case letters if they differed from the amino acids of both adjacent isolates. FIG. 2H shows the alignment of the consensus sequences of FIGS. 2A–G with SEQ ID NO:85 (genotype 2c), SEQ ID NO:91 (genotype 4a), SEQ ID NO:92 (genotype 4b), SEQ ID NO:95 (genotype 4d) and SEQ ID NO:102 (genotype 6a) to produce a consensus sequence for all twelve genotypes. This consensus sequence is shown as the bottom line of FIG. 2H where the amino acids shown in capital letters are conserved among all genotypes and a blank space indicates that the amino acid at that position is not conserved among all genotypes.

FIG. 3 shows multiple sequence alignment of the deduced amino acid sequence of the E1 gene of 51 HCV isolates collected worldwide. The consensus sequence of the E1 protein is shown in boldface (top). In the consensus sequence cysteine residues are highlighted with stars, potential N-linked glycosylation sites are underlined, and invariant amino acids are capitalized, whereas variable amino acids are shown in lower case letters. In the alignment, amino acids are shown in lower case letters if they differed from the amino acid of both adjacent isolates. Amino acid residues shown in bold print in the alignment represent residues which at that position in the amino acid sequence are genotype-specific. Amino acids that were invariant among all HCV isolates are shown as hyphens (–) in the alignment. Amino acid positions correspond to those of the HCV prototype sequence (HCV-1, Choo, L. et al. (1991) Proc. Natl. Acad. Sci. USA 88:2451–2455) with the first amino acid of the E1 protein at position 192. The grouping of isolates into 12 genotypes (I/1a, II/1b, III/2a, IV/2b, V/3a, 2c, 4a, 4b, 4c, 4d, 5a and 6a) is indicated.

Figures 2, 6K:
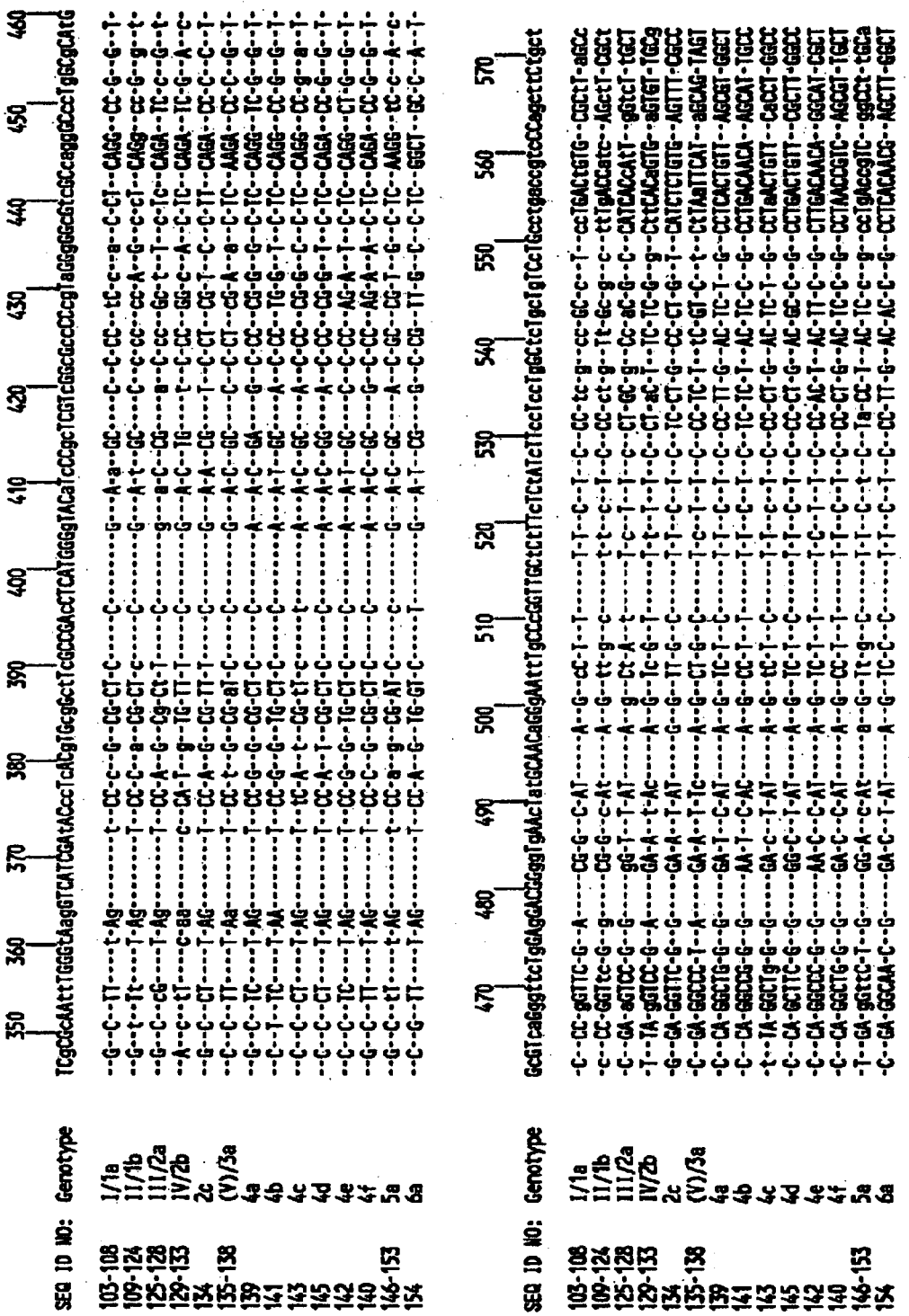
FIGS. 2A–H show computer alignments of the deduced amino acid sequences of 51 HCV E1 cDNAs. The single letter abbreviations used for the amino acids shown in FIGS. 2A–H follow the conventional amino acid shorthand for the twenty naturally occurring amino acids.

FIGS. 6A–K show computer generated sequence alignments of the nucleotide sequences of 52 HCV core cDNAs. Single letter abbreviations used for the nucleotides shown in FIGS. 6A–J are those standardly used in the art. FIG. 6A shows the alignment of SEQ ID NOs: 103–108 to produce a consensus sequence for genotype I/Ia. FIG. 6B shows the alignment of SEQ ID NOs: 109–124 to produce a consensus sequence for genotype II/1b. FIG. 6C shows the alignments of the sequences comprising minor genotypes I/1a (SEQ ID NOS: 103–108) and II/1b (SEQ ID NOs: 109–124) to produce a consensus sequence for the major genotype, genotype 1. FIG. 6D shows the alignment of SEQ ID NOs: 125–128 to produce a consensus sequence for genotype III/2a. FIG. 6E shows the alignment of SEQ ID NOs: 129–133 to produce a consensus sequence for genotype IV/2b. FIG. 6F shows the alignment of the sequences of minor genotypes III/2a (SEQ ID NOs: 125–128), IV/2b (SEQ ID NOs: 129–133) and 2c (SEQ ID NO: 134) to produce a consensus sequence for the major genotype, genotype 2. FIG. 6G shows the alignment of SEQ ID NOs: 135–138 to produce a consensus sequence for genotype V/3a. FIG. 6H shows the computer alignment of the sequences of minor genotypes 4a–4f (SEQ ID NOs: 139–145) to produce a consensus sequence for the major genotype, genotype 4. FIG. 6I shows the alignment of SEQ ID NOs: 146–153 to produce a consensus sequence for genotype 5a. The nucleotides shown in capital letters in the consensus sequences in FIGS. 6A–I are those conserved within the genotype while nucleotides shown in lower case letters in the consensus sequences are those variable within a genotype. In addition, when the lower case letter is shown in the consensus sequence, the lower case letter represents the nucleotide found most frequently in the sequences aligned to produce that consensus sequence. Moreover, a hyphen at a nucleotide position in the consensus sequences in FIGS. 6A–6I indicates that two nucleotides were found in equal numbers at that position in the sequences aligned to produce the consensus sequence. Finally, nucleotides are shown in lower case letters in the sequences aligned to produce each consensus sequence shown in FIGS. 6A–6I, if they differed from the nucleotides of both adjacent isolates. FIG. 6J shows the alignment of the consensus sequences of major genotypes 1 (FIG. 6C), 2 (FIG. 6F), 3 (FIG. 6G), 4 (FIG. 6H), 5 (FIG. 6I) and 6 (SEQ ID NO: 154) to produce a consensus sequence for all genotypes and FIG. 6K shows the alignment of consensus sequences of FIGS. 6A, 6B, 6D, 6E, 6G and 6I with SEQ ID NO:134 (genotype 2c), SEQ ID NO:139 (genotype 4a), SEQ ID NO:141 (genotype 4b), SEQ ID NO:143 (genotype 4c), SEQ ID NO:145 (genotype 4d), SEQ ID NO:142 (genotype 4e), SEQ ID NO:140 (genotype 4f) and SEQ ID NO:154 (genotype 6a) to produce a consensus sequence for all fourteen genotypes. The nucleotides shown in capital letters in the consensus sequences of FIGS. 6J and 6K are conserved among all genotypes and the nucleotide shown in lower case letter represent the nucleotides found most frequently in the sequences aligned to produce this consensus sequence. In addition, the presence of a hyphen at a nucleotide position in all fourteen sequences aligned in FIG. 6K indicates that the nucleotide found at that position in the aligned sequences is the same as nucleotide shown at the corresponding position in the consensus sequences of FIG. 6K.

FIGS. 7A–7J show computer alignments of the deduced amino acid sequences of the 52 HCV core cDNAs. The single letter abbreviations used for the amino acids shown in FIGS. 7A–7J follow the conventional amino acid short hand for the twenty natural occurring amino acids. FIG. 7A shows the alignment of SEQ ID NOs: 155–160 to produce a consensus sequence for genotype I/1a. FIG. 7B shows the alignment of SEQ ID NOs: 161–176 to produce a consensus sequence for genotype II/1b. FIG. 7C shows the alignment of the sequences comprising minor genotypes I/a (SEQ ID NOS: 155–160) and II/1b (SEQ ID NOS: 161–176) to produce a consensus sequence for the major genotype, genotype 1. FIG. 7D shows the alignment of SEQ ID NOs: 177–180 to produce a consensus sequence for genotype III/2a. FIG. 7E shows the alignment of SEQ ID NOs: 181–185 to produce a consensus sequence for genotype IV/2b. FIG. 7F shows the alignment of the sequences of minor genotypes III/2a (SEQ ID NOS: 177–180), IV/2b (SEQ ID NOS: 181–185) and 2c (SEQ ID NO: 186) to produce a consensus sequence for the major genotype, genotype 2. FIG. 7G shows the alignment of SEQ ID NOs: 187–190 to produce a consensus sequence for genotype V/3a. FIG. 7H shows the computer alignment of the sequences of minor genotypes 4a–4f (SEQ ID NOs: 191–197) to produce a consensus sequence for the major genotype, genotype 4. FIG. 7I shows the alignment of SEQ ID NOs: 198–205 to produce a consensus sequence for genotype 5a. The amino acids shown in capital letters in the consensus sequences of FIGS. 7A–7I are those conserved within the genotype while amino acids shown in lower case letters in the consensus sequences are those variable within the genotype. In addition, when a lower case letter is found in the consensus sequences shown in FIGS. 7A–7I, the letter represents the amino acid found most frequently in the sequences aligned to produce that consensus sequence. Moreover, a hyphen in an amino acid position in the consensus sequences of FIGS. 7A–7I indicates that two amino acids were found in equal numbers at that position in the sequences aligned to produce that consensus sequence. Finally, amino acids are shown in lower case letters in the sequences aligned to produce the consensus sequences shown in FIGS. 7A–7I if these amino acids differed from the amino acids of both adjacent isolates. FIG. 7J shows the alignment of the consensus sequences of major genotypes 1 (FIG. 7C), 2 (FIG. 7F), 3 (FIG. 7G), 4 (FIG. 7H), 5 (FIG. 7I) and 6 (SEQ ID NO: 154) to produce a consensus sequence for all genotypes and FIG. 7K shows the alignment of the consensus sequences of FIGS. 7A, 7B, 7D, 7E, 7G and 7I with SEQ ID NO:186 (genotype 2c), SEQ ID NO:191 (genotype 4a), SEQ ID NO:193 (genotype 4b), SEQ ID NO:195 (genotype 4c), SEQ ID NO:197 (genotype 4d), SEQ ID NO:194 (genotype 4e), SEQ ID NO:192 (genotype 4f) and SEQ ID NO:206 (genotype 6a) to produce a consensus sequence for all fourteen genotypes. The amino acids shown in capital letters in the consensus sequences shown in FIGS. 7J and 7K are conserved among all genotypes while the amino acids shown in lower case letters represent amino acids found most frequently in the sequences aligned to produce this consensus sequence. In addition, the presence of a hyphen at an amino acid position in all fourteen sequences aligned in FIG. 7K indicates that the amino acid found at that position in the aligned sequences is the same as the amino acid shown at the corresponding position in the consensus sequence of FIG. 7K.

Figure 8A:
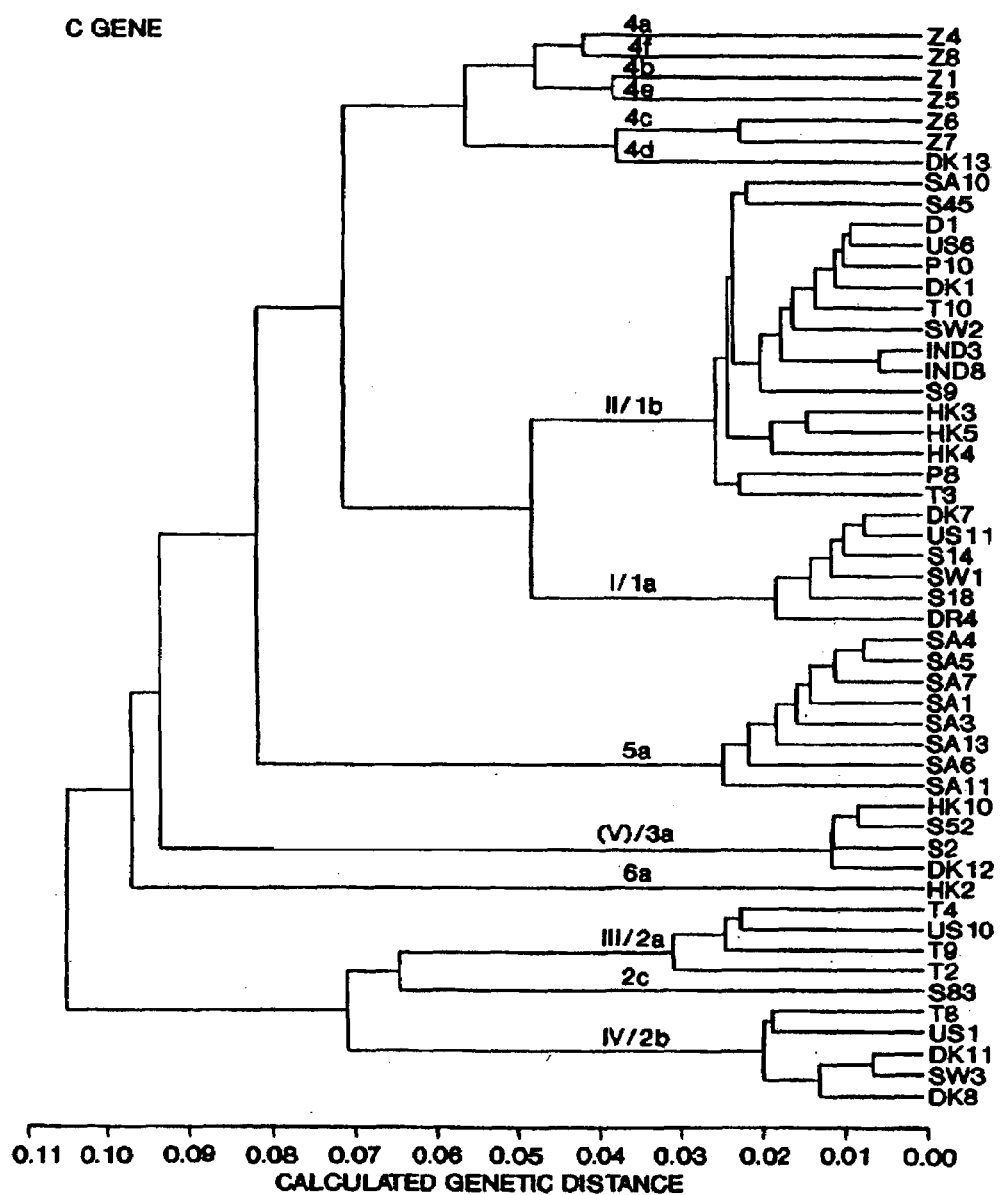
Figure 8B:
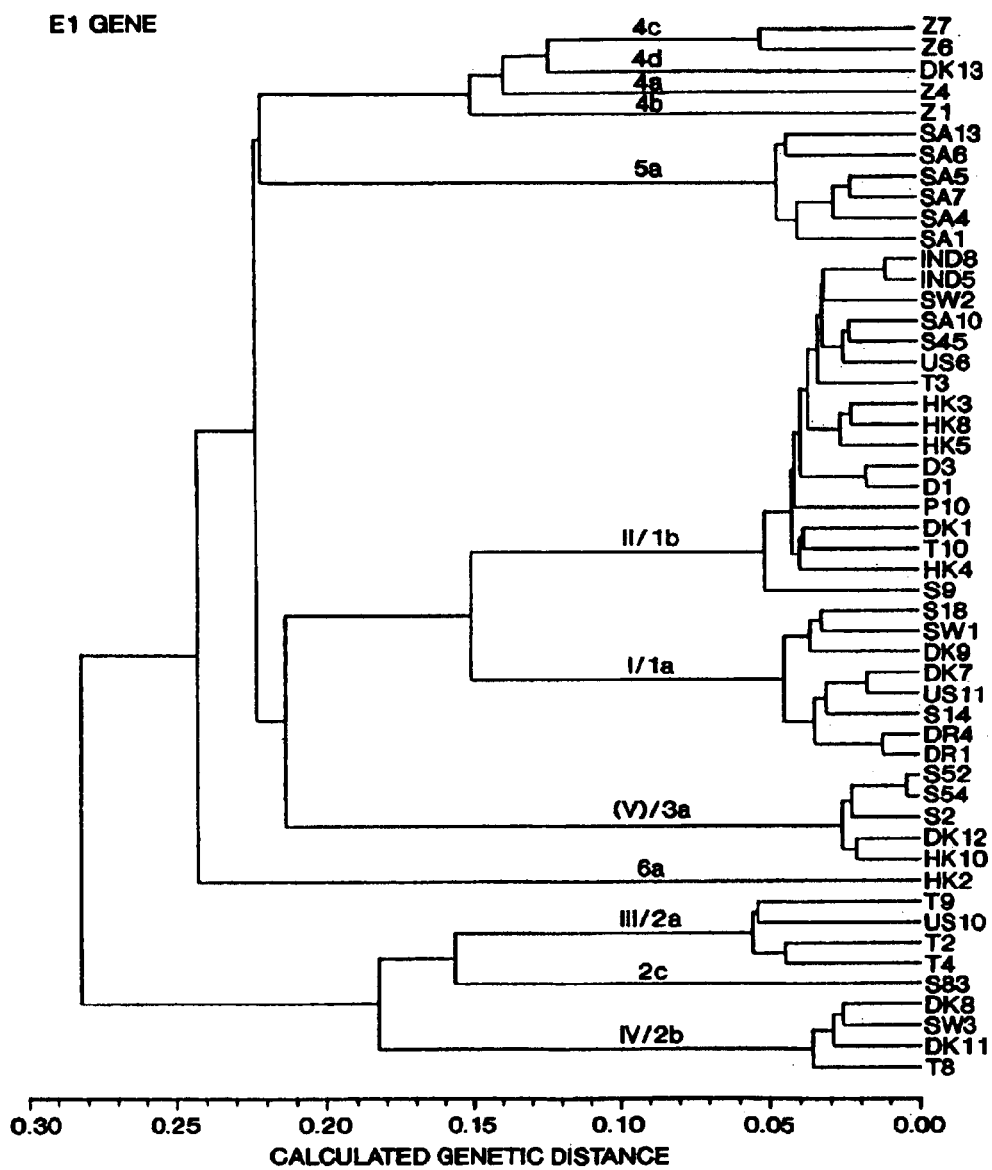

FIG. 8 shows phylogenetic trees illustrating the calculated evolutionary relationships of the different HCV isolates based upon the C gene sequence of 52 HCV isolates and the E1 gene sequence of 51 HCV isolates, respectively. The phylogenetic trees were constructed by the unweighted pair-group method with arithmetic mean (Nei, M. (1987) *Molecular Evolutionary Genetics* (Columbia University Press, New York, N.Y.), pp 287–326) using the computer software package "Gene Works" from IntelliGenetics. The lengths of the horizontal lines connecting the sequences, given in absolute values from 0 to 1, are proportional to the estimated genetic distances between the sequences. Genotype designations of HCV isolates are indicated. In 45 HCV isolates, both the C and the E1 gene sequences were determined.

DETAILED DESCRIPTION OF INVENTION

The present invention relates to cDNAs encoding the complete nucleotide sequence of the envelope 1 (E1) and core genes of isolates of human hepatitis C virus (HCV). The E1 cDNAs of the present invention were obtained as follows. Viral RNA was extracted from serum collected from humans infected with hepatitis C virus and the viral RNA was then reverse transcribed and amplified by polymerase chain reaction using primers deduced from the sequence of the HCV strain H-77 (Ogata, N. et al. (1991) Proc. Natl. Acad. Sci. U.S.A. 88:3392–3396). The amplified cDNA was then isolated by gel electrophoresis and sequenced.

The present invention further relates to the nucleotide sequences of the cDNAs encoding the E1 gene of 51 HCV isolates. These nucleotide sequences are shown in the sequence listing as SEQ ID NO:1 through SEQ ID NO:51.

The abbreviations used for the nucleotides are those standardly used in the art.

The deduced amino acid sequence of each of SEQ ID NO:1 through SEQ ID NO:51 are presented in the sequence listing as SEQ ID NO:52 through SEQ ID NO:102 where the amino acid sequence in SEQ ID NO:52 is deduced from the nucleotide sequence shown in SEQ ID NO:1, the amino acid sequence shown in SEQ ID NO:53 is deduced from the nucleotide sequence shown in SEQ ID NO:2 and so on. The deduced amino acid sequence of each of SEQ ID Nos: 52–102 starts at nucleotide 1 of the corresponding nucleic acid sequence shown in SEQ ID NOs:1–51 and extends 575 nucleotides to a total length of 576 nucleotides.

The three letter abbreviations used in SEQ ID Nos: 52–102 follow the conventional amino acid shorthand for the twenty naturally occurring amino acids.

The present invention also relates to the nucleotide sequences of the cDNAs encoding the core gene of 52 HCV isolates. These nucleotide sequences are shown in the sequence listing as SEQ ID NO:103 through SEQ ID NO:154.

The core cDNAs of the present invention were obtained as follows. Viral RNA was extracted from serum and reversed transcribed as described above for cloning of the E1 cDNAs. The core cDNAs of the present invention were then amplified by polymerase chain reaction using primers deduced from previously determined sequences that flank the core gene (Bukh et al. (1992)) *Proc. Natl. Acad. Sci. U.S.A.*, 89: 4942–4946; Bukh et al. (1993) *Proc. Natl. Acad. Sci. U.S.A.*, 90: 8234–8238).

The deduced amino acid sequence of each of SEQ ID NO:103 through SEQ ID NO:154 are presented in the sequence listing as SEQ ID NO:155 through SEQ ID NO:206 where the amino acid sequence in SEQ ID NO:155 is deduced from the nucleotide sequence shown in SEQ ID NO:103, the amino acid sequence shown in SEQ ID NO:156 is deduced from the nucleotide sequence shown in SEQ ID NO:104 and so on. The deduced amino acid sequence of each of SEQ ID NOs: 155–206 starts at nucleotide 1 of the corresponding nucleotide sequence shown in SEQ ID NOs: 103–154 and extends 572 nucleotides to a total length of 573 nucleotides.

Preferably, the E1 and core proteins and peptides of the present invention are substantially homologous to, and most preferably biologically equivalent to, native HCV E1 and core proteins and peptides. By "biologically equivalent" as used throughout the specification and claims, it is meant that the compositions are immunogenically equivalent to the native E1 and core proteins and peptides. The E1 and core proteins and peptides of the present invention may also stimulate the production of protective antibodies upon injection into a mammal that would serve to protect the mammal upon challenge with HCV. By "substantially homologous" as used throughout the ensuing specification and claims to describe E1 and core proteins and peptides, it is meant a degree of homology in the amino acid sequence of the E1 and core proteins and peptides to the native E1 and core proteins and peptides respectively. Preferably the degree of homology is in excess of 90, preferably in excess of 95, with a particularly preferred group of proteins being in excess of 99 homologous with the native E1 or core proteins and peptides.

Variations are contemplated in the cDNA sequences shown in SEQ ID NO:1 through SEQ ID NO:51 and in SEQ ID NO:103 through SEQ ID NO:154 which will result in a nucleic acid sequence that is capable of directing production of analogs of the corresponding protein shown in SEQ ID NO:52 through SEQ ID NO:102 and in SEQ ID NO:155 through SEQ ID NO:206. It should be noted that the cDNA sequences set forth above represent a preferred embodiment of the present invention. Due to the degeneracy of the genetic code, it is to be understood that numerous choices of nucleotides may be made that will lead to a DNA sequence capable of directing production of the instant protein or its analogs. As such, DNA sequences which are functionally equivalent to the sequence set forth above or which are functionally equivalent to sequences that would direct production of analogs of the E1 and core proteins produced pursuant to the amino acid sequences set forth above, are intended to be encompassed within the present invention.

The term analog as used throughout the specification or claims to describe the E1 and core proteins and peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the native E1 or core protein or peptide.

"Chemical derivative" refers to an E1 or core protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The E1 and core proteins and peptide of the present invention also includes any protein or peptide having one or more additions and/or deletions of residues relative to the sequence of a peptide whose sequence is shown herein, so long as the peptide is biologically equivalent to the native E1 or core protein or peptide.

The present invention also includes a recombinant DNA method for the manufacture of HCV E1 and core proteins. In this method, natural or synthetic nucleic acid sequences may be used to direct the production of E1 and core proteins.

In one embodiment of the invention, the method comprises:
  (a) preparation of a nucleic acid sequence capable of directing a host organism to produce HCV E1 or core protein;
  (b) cloning the nucleic acid sequence into a vector capable of being transferred into and replicated in a host organism, such vector containing operational elements for the nucleic acid sequence;
  (c) transferring the vector containing the nucleic acid and operational elements into a host organism capable of expressing the protein;
  (d) culturing the host organism under conditions appropriate for amplification of the vector and expression of the protein; and
  (e) harvesting the protein.

In another embodiment of the invention, the method for the recombinant DNA synthesis of an HCV E1 protein encoded by any one of the nucleic acid sequences shown in SEQ ID NOs:1–51 comprises:
  (a) culturing a transformed or transfected host organism containing a nucleic acid sequence capable of directing the host organism to produce a protein, under conditions such that the protein is produced, said protein exhibiting substantial homology to a native E1 protein isolated from HCV having the amino acid sequence according to any one of the amino acid sequences shown in SEQ ID NOs:52–102 or combinations thereof.

In one embodiment, the RNA sequence of an HCV isolate was isolated and converted to cDNA as follows. Viral RNA is extracted from a biological sample collected from human subjects infected with hepatitis C and the viral RNA is then reverse transcribed and amplified by polymerase chain reaction using primers deduced from the sequence of HCV strain H-77 (Ogata et al. (1991)). Preferred primer sequences are shown as SEQ ID NOs:207–212 in the sequence listing.

Once amplified, the PCR fragments are isolated by gel electrophoresis and sequenced.

In an alternative embodiment, the above method may be utilized for the recombinant DNA synthesis of an HCV core protein encoded by any one of the nucleic acid sequences shown in SEQ ID NOS: 103–154, where the protein produced by this method exhibits substantial homology to a native core protein isolated from HCV having amino acid sequence according to any one of the amino acid sequences shown in SEQ ID NOS: 155–206 or combinations thereof.

The vectors contemplated for use in the present invention include any vectors into which a nucleic acid sequence as described above can be inserted, along with any preferred or required operational elements, and which vector can then be subsequently transferred into a host organism and replicated in such organisms. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

In construction of the recombinant expression vectors of the present invention, it should additionally be noted that multiple copies of the nucleic acid sequence of interest (either E1 or core) and its attendant operational elements may be inserted into each vector. In such an embodiment, the host organism would produce greater amounts per vector of the desired E1 or core protein. The number of multiple copies of the nucleic acid sequence which may be inserted into the vector is limited only by the ability of the resultant vector due to its size, to be transferred into and replicated and transcribed in an appropriate host microorganism.

Of course, those skilled in the art would readily understand that copies of both core and E1 nucleic acid sequence may be inserted into single vector such that a host organism transformed or transfected with said vector would produce both the desired E1 and core proteins. For example, a polysistronic vector in which multiple different E1 and/or core proteins may be expressed from a single vector is created by placing expression of each protein under control of an internal ribosomal entry site (IRES)(Molla, A. et al. *Nature*, 356:255–257 (1992); Gong, S. K. et al. *J. of Virol.*, 263:1651–1660 (1989)).

In another embodiment, restriction digest fragments containing a coding sequence for E1 or core proteins can be inserted into a suitable expression vector that functions in prokaryotic or eukaryotic cells. By suitable is meant that the vector is capable of carrying and expressing a complete nucleic acid sequence coding for an E1 or core protein. Preferred expression vectors are those that function in a eukaryotic cell. Examples of such vectors include but are not limited to, vaccinia virus vectors, adenovirus or herpes viruses. A preferred vector is the baculovirus transfer vector, pBlueBac.

In yet another embodiment, the selected recombinant expression vector may then be transfected into a suitable eukaryotic cell system for purposes of expressing the recombinant protein. Such eukaryotic cell systems include but are not limited to cell lines such as HeLa, MRC-5 or CV-1. A preferred eukaryotic cell system is SF9 insect cells.

The expressed recombinant protein may be detected by methods known in the art including, but not limited to, Coomassie blue staining and Western blotting.

The present invention also relates to substantially purified and isolated recombinant E1 and core proteins. In one embodiment, the recombinant protein expressed by the SF9 cells can be obtained as a crude lysate or it can be purified by standard protein purification procedures known in the art which may include differential precipitation, molecular sieve chromatography, ion-exchange chromatography, isoelectric focusing, gel electrophoresis and affinity and immunoaffinity chromatography. The recombinant protein may be purified by passage through a column containing a resin which has bound thereto antibodies specific for the open reading frame (ORF) protein.

The present invention further relates to the use of recombinant E1 and core proteins as diagnostic agents and vaccines. In one embodiment, the expressed recombinant proteins of this invention can be used in immunoassays for diagnosing or prognosing hepatitis C in a mammal. For the purposes of the present invention, "mammal" as used throughout the specification and claims, includes, but is not limited to humans, chimpanzees, other primates and the like. In a preferred embodiment, the immunoassay is useful in diagnosing hepatitis C infection in humans.

Immunoassays of the present invention may be those commonly used by those skilled in the art including, but not limited to, radioimmunoassay, Western blot assay, immunofluorescent assay, enzyme immunoassay, chemiluminescent assay, immunohistochemical assay, immunoprecipitation and the like. Standard techniques known in the art for ELISA are described in *Methods in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art (Oellerich, M. 1984. *J. Clin. Chem. Clin. BioChem* 22:895–904) Biological samples appropriate for such detection assays include, but are not limited to serum, liver, saliva, lymphocytes or other mononuclear cells.

In a preferred embodiment, test serum is reacted with a solid phase reagent having surface-bound recombinant HCV E1 and/or core protein(s) as antigen(s). The solid surface reagent can be prepared by known techniques for attaching protein to solid support material. These attachment methods include non-specific adsorption of the protein to the support or covalent attachment of the protein to a reactive group on the support. After reaction of the antigen with anti-HCV antibody, unbound serum components are removed by washing and the antigen-antibody complex is reacted with a secondary antibody such as labelled anti-human antibody. The label may be an enzyme which is detected by incubating the solid support in the presence of a suitable fluorimetric or calorimetric reagent. Other detectable labels may also be used, such as radiolabels or colloidal gold, and the like.

The HCV E1 and/or core proteins and analogs thereof may be prepared in the form of a kit, alone, or in combinations with other reagents such as secondary antibodies, for use in immunoassays.

In yet another embodiment the recombinant E1 and core proteins or analogs thereof can be used as a vaccine to protect mammals against challenge with hepatitis C. The vaccine, which acts as an immunogen, may be a cell, cell lysate from cells transfected with a recombinant expression vector or a culture supernatant containing the expressed protein. Alternatively, the immunogen is a partially or substantially purified recombinant protein. In yet another embodiment, the immunogen may be a fusion protein comprising core protein and a second, non-core protein joined together such that the core portion of the fusion protein will aggregate and "trap" the second protein on the surface of the particle produced by aggregation of the core protein. (Molecular Biology of the Hepatitis B Virus", McLachlan, A. (1991) CRC Press, Boca Raton, Fla.). Alternatively, the core protein could be mixed with the second protein in vitro to produce particles in which all or part of the second protein was exposed on the surface of the particle. Such particles would then serve as a carrier in a multi-valent vaccine preparation. Second proteins or parts thereof which could be mixed with or fused to the core protein include, but are not limited to, HCV E1 and hepatitis B surface antigen.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving the solid active ingredient in water containing physiologically compatible substances such as sodium chloride (e.g. 0.1–2.0m), glycine, and the like, and having a buffered pH compatible with physiological conditions to produce an aqueous solution, and rendering said solution sterile. These may be present in unit or multi-dose containers, for example, sealed ampules or vials.

The formulations of the present invention may incorporate a stabilizer. Illustrative stabilizers are preferably incorporated in an amount of 0.10–10,000 parts by weight per part by weight of immunogens. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, an anti-adsorption agent may be used.

Additional pharmaceutical methods may be employed to control the duration of action. Controlled release preparations may be achieved through the use of polymer to complex or adsorb the proteins or their derivatives. The controlled delivery may be exercised by selecting appropriate macromolecules (for example polyester, polyamino acids, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

The E1 and core proteins of the present invention may also be used as a delivery system for anti-virals to prevent or attenuate HCV infection in a mammal by utilizing the property of both proteins to self-aggregate in vitro to "trap" the antiviral within the particles produced via aggregation of the core and E1 proteins. Examples of anti-virals which could be delivered by such a system include, but are not limited to antisense DNA or RNAs.

Vaccination can be conducted by conventional methods. For example, the immunogen or immunogens (e.g. the E1 protein may be administered alone or in combination with the E1 proteins derived from other isolates of HCV) can be used in a suitable diluent such as saline or water, or complete or incomplete adjuvants. Further, the immunogen(s) may or may not be bound to a carrier to make the protein(s) immunogenic. Examples of such carrier molecules include but are not limited to bovine serum albumin (BSA), keyhole limpet hemocyanin (KLH), tetanus toxoid, and the like. The immunogen(s) can be administered by any route appropriate for antibody production such as intravenous, intraperitoneal, intramuscular, subcutaneous, and the like. The immunogen(s) may be administered once or at periodic intervals until a significant titer of anti-HCV antibody is produced. The antibody may be detected in the serum using an immunoassay.

In yet another embodiment, the immunogen may be nucleic acid sequence capable of directing host organism synthesis of E1 and/or core protein(s). Such nucleic acid sequence may be inserted into a suitable expression vector by methods known to those skilled in the art. Expression vectors suitable for producing high efficiency gene transfer in vivo include retroviral, adenoviral and vaccinia viral vectors. Operational elements of such expression vectors are disclosed previously in the present specification and are known to one skilled in the art. Such expression vectors can be administered intravenously, intramuscularly, subcutaneously, intraperitoneally or orally.

In an alternative embodiment, direct gene transfer may be accomplished via intramuscular injection of, for example, plasmid-based eukaryotic expression vectors containing a nucleic acid sequence capable of directing host organism synthesis of E1 and/or core protein(s). Such an approach has previously been utilized to produce the hepatitis B surface antigen in vivo and resulted in an antibody response to the surface antigen (Davis, H. L. et al. (1993) Human molecular Genetics, 2:1847–1851; see also Davis et al. (1993) Human Gene Therapy, 4:151–159 and 733–740).

Doses of E1 and/or core protein(s)-encoding nucleic acid sequence effective to elicit a protective antibody response against HCV infection range from about 1 to about 500 µg. A more preferred range being about 1 to about 500 µg.

The E1 and/or core proteins and expression vectors containing a nucleic acid sequence capable of directing host organism synthesis of E1 and/or core protein(s) may be supplied in the form of a kit, alone, or in the form of a pharmaceutical composition as described above.

The administration of the immunogen(s) of the present invention may be for either a prophylactic or therapeutic purpose. When provided prophylactically, the immunogen(s) is provided in advance of any exposure to HCV or in advance of any symptom of any symptoms due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV. The therapeutic administration of the immunogen(s) serves to attenuate the infection or disease.

In addition to use as a vaccine, the compositions can be used to prepare antibodies to HCV E1 and core proteins. The antibodies can be used directly as antiviral agents or they may be used in immunoassays disclosed herein to detect HCV E1 and core proteins present in patient sera. To prepare antibodies, a host animal is immunized using the E1 and/or core proteins native to the virus particle bound to a carrier as described above for vaccines. The host serum or plasma is collected following an appropriate time interval to provide a composition comprising antibodies reactive with the E1 or core protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen-binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res.

47:999; Wood et al., 1985 Nature 314:446; Shaw et al., 1988 J. Natl. Cancer Inst. 80:15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedleret al. 1988 J. Immunol. 141:4053, all incorporated herein by reference).

The antibodies or antigen binding fragments may also be produced by genetic engineering. The technology for expression of both heavy and light cain genes in *E. coli* is the subject of the PCT patent applications; publication number WO 901443, WO901443, and WO 9014424 and in Huse et al., 1989 Science 246:1275–1281.

The antibodies can also be used as a means of enhancing the immune response. The antibodies can be administered in amount similar to those used for other therapeutic administrations of antibody. For example, normal immune globulin is administered at 0.02–0.1 ml/1b body weight during the early incubation period of other viral diseases such as rabies, measles, and hepatitis B to interfere with viral entry into cells. Thus, antibodies reactive with the HCV E1 and/or core proteins can be passively administered alone or in conjunction with another anti-viral agent to a host infected with an HCV to enhance the immune response and/or the effectiveness of an antiviral drug.

Alternatively, anti-HCV E1 antibodies and anti-HCV core antibodies can be induced by administered anti-idiotype antibodies as immunogens. Conveniently, a purified anti-HCV E1 or anti-HCV core antibody preparation prepared as described above is used to induce anti-idiotype antibody in a host animal, the composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-HCV E1 and anti-HCV core antibodies, or by affinity chromatography using anti-HCV E1 or anti-HCV core antibodies bound to the affinity matrix. The anti-idiotype antibodies produced are similar in conformation to the authentic HCV E1 or core protein and may be used to prepare an HCV vaccine rather than using an HCV E1 or core protein.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

The HCV E1 and core proteins of the invention are also intended for use in producing antiserum designed for pre- or post-exposure prophylaxis. Here an E1 or core protein, or mixture of E1 and/or core proteins is formulated with a suitable adjuvant and administered by injection to human volunteers, according to known methods for producing human antisera. Antibody response to the injected proteins is monitored, during a several-week period following immunization, by periodic serum sampling to detect the presence of anti-HCV E1 and/or anti-HCV core serum antibodies, using an immunoassay as described herein.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

For both in vivo use of antibodies to HCV virus-like particles and proteins and anti-idiotype antibodies and diagnostic use, it may be preferable to use monoclonal antibodies. Monoclonal anti-HCV E1 and anti-HCV core protein antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., NY, N.Y., pp. 56–97). To produce a human-human hybridoma, a human lymphocyte donor is selected. A donor known to be infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-E1 and anti-core antibodies, the antibodies must bind to HCV E1 and core proteins respectively. For monoclonal anti-idiotype antibodies, the antibodies must bind to anti-E1 and anti-core protein antibodies respectively. Cells producing antibodies of the desired specificity are selected.

The present invention also relates to the use of single-stranded antisense poly- or oligonucleotides derived from nucleotide sequences substantially homologous to those shown in SEQ ID NOs:1–51 to inhibit the expression of hepatitis C E1 genes. The present invention further relates to the use of single-stranded anti-sense poly- or oligo-nucleotides derived from nucleotide sequences substantially homologous to those shown in SEQ ID NOs:103–154 to inhibit the expression of hepatitis C core genes. Alternatively, the anti-sense poly- or oligo-nucleotides may be complementary to both the E1 and core genes and hence, inhibit the expression of both hepatitis C E1 and core genes. By substantially homologous as used throughout the specification and claims to describe the nucleic acid sequences of the present invention, is meant a level of homology between the nucleic acid sequence and the SEQ ID NOs. referred to in the above sentence. Preferably, the level of homology is in excess of 80%, more preferably in excess of 90%, with a preferred nucleic acid sequence being in excess of 95% homologous with the DNA sequence shown in the indicated SEQ ID NO. These anti-sense poly- or oligonucleotides can be either DNA or RNA. The targeted sequence is typically messenger RNA and more preferably, a single sequence required for processing or translation of the RNA. The anti-sense poly- or oligonucleotides can be conjugated to a polycation such as polylysine as disclosed in Lemaitre, M. et al. ((1989) Proc. Natl. Acad. Sci. USA 84:648–652) and this conjugate can be administered to a mammal in an amount sufficient to hybridize to and inhibit the function of the messenger RNA.

The present invention further relates to multiple computer-generated alignments of the nucleotide and deduced amino acid sequences shown in SEQ ID NOs:1–206. Computer analysis of the nucleotide sequences shown in SEQ ID NOs:1–51 and 103–154 and of the deduced amino acid sequences shown in SEQ ID NOs:52–102 and 155–206 can be carried out using commercially available computer programs known to one skilled in the art.

In one embodiment, computer analysis of SEQ ID NOs:1–51 by the program GENALIGN (Intelligenetics, Inc. Mountainview, Calif.) results in distribution of the 51 HCV E1 sequences into twelve genotypes based upon the degree of variation of the sequences. For the purposes of the present invention, the nucleotide sequence identity of E1 cDNAs of HCV isolates of the same genotype is in the range of about 85% to about 100% whereas the identity of E1 cDNA sequences of different genotypes is in the range of about 50% to about 80%.

The grouping of SEQ ID NOs:1–51 into twelve HCV genotypes is shown below.

| SEQ ID NOs: | Genotypes |
| --- | --- |
| 1–8 | I/1a |
| 9–25 | II/1b |
| 26–29 | III/2a |
| 30–33 | IV/2b |
| 34 | 2c |
| 35–39 | V/3a |
| 40 | 4a |
| 41 | 4b |
| 42–43 | 4c |
| 44 | 4d |
| 45–50 | 5a |
| 51 | 6a |

Figure 1A-4:
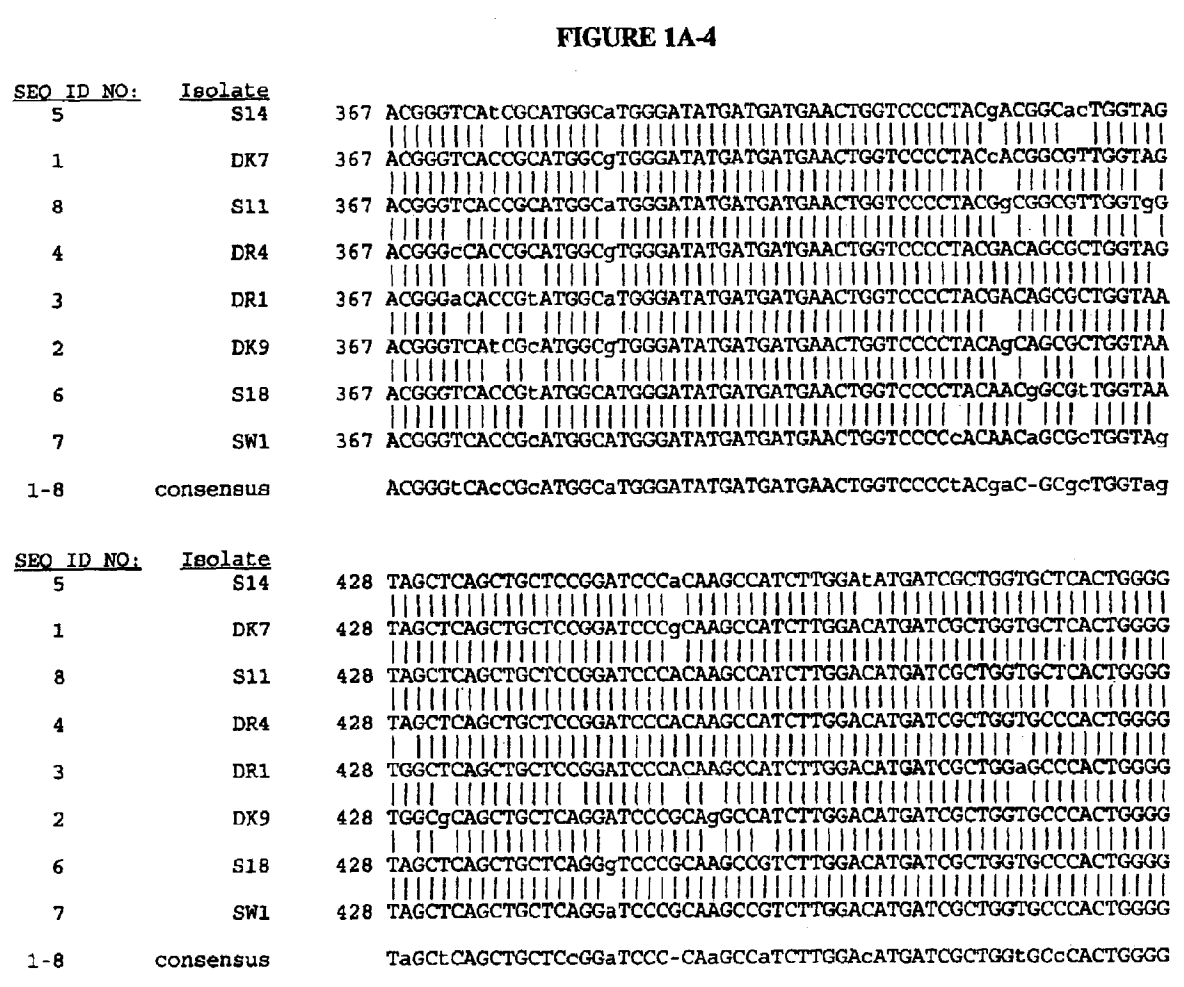

For those genotypes containing more than one E1 nucleotide sequence, computer alignment of the constituent nucleotide sequences of the genotype was conducted using GENALIGN in order to produce a consensus sequence for each genotype. These alignments and their resultant consensus sequences are shown in FIGS. 1A–G for the seven genotypes (I/1a, II/1b, III/2a, IV/2b, V/3a, 4c and 5a) which comprise more than one nucleotide sequence. Further alignment of the consensus sequences of FIGS. 1A–G with SEQ ID NO:34 (genotype 2c), SEQ ID NO:40 (genotype 4a), SEQ ID NO:41 (genotype 4b), SEQ ID NO:44 (genotype 4d) and SEQ ID NO:51 (genotype 6a) produces a consensus sequence for all twelve genotypes as shown in FIG. 1H. The multiple alignments of nucleotide sequences shown in FIGS. 1A–H produce consensus sequences which serve to highlight regions of homology and non-homology between sequences found within the same genotype or in different genotypes and hence, these alignments can be used by one skilled in the art to design oligonucleotides useful as reagents in diagnostic assays for HCV.

Examples of purified and isolated oligonucleotide sequences derived from the consensus sequences shown in FIGS. 1A–H include, but are not limited to, SEQ ID NOs:213–239 where these oligonucleotides are useful as "genotype-specific" primers and probes since these oligonucleotides can hybridize specifically to the nucleotide sequence of the E1 gene of HCV isolates belonging to a single genotype. The genotype-specificity of the oligonucleotides shown in SEQ ID NOs:213–239 is as follows: SEQ ID NOs:213–214 are specific for genotype I/1a; SEQ ID NOs:215–216 are specific for genotype II/1b; SEQ ID NOs:217–218 are specific for genotype III/2a; SEQ ID NOs:219–220 are specific for genotype IV/2b; SEQ ID NOs:221–223 are specific for genotype 2c; SEQ ID NOs:224–226 are specific for genotype V/3a; SEQ ID NOs:227–228 are specific for genotype 4a; SEQ ID NOs:229–230 are specific for genotype 4b; SEQ ID NOs:231–232 are specific for genotype 4c; SEQ ID NOs:233–234 are specific for genotype 4d; SEQ ID NOs:235–236 are specific for genotype 5a and SEQ ID NOs:237–239 are specific for genotype 6a.

In another embodiment, the computer analysis of SEQ ID NOs:103–154 by the program GENALIGN results in distribution of the 52 HCV core sequences into 14 genotypes based upon the degree of variation of the sequences.

The grouping of SEQ ID NOs:103–154 into 14 HCV genotypes is shown below.

| SEQ ID NOs: | Genotypes |
| --- | --- |
| 103–108 | I/1a |
| 109–124 | II/1b |
| 125–128 | III/2a |
| 129–133 | IV/2b |
| 134 | 2c |
| 135–138 | V/3a |
| 139 | 4a |
| 141 | 4b |
| 143 | 4c |
| 144 | 4c |
| 145 | 4d |
| 142 | 4e |
| 140 | 4f |
| 146–153 | 5a |
| 154 | 6a |

These 14 genotypes can be further grouped into 6 major genotypes designated genotypes 1–6 where genotype 1 comprises the sequences contained in minor genotypes I/1a and II/1b; genotype 2 comprises the sequences contained in minor genotypes III/2a, IV/2b and 2c; genotype 3 comprises sequences contained in genotype V/3a; genotype 4 comprises sequences contained in minor genotypes 4a–4f; genotype 5 comprises the sequences contained in genotype 5a and genotype 6 comprises the sequence contained in genotype 6a. Computer alignment of the constituent nucleotide sequences of the core cDNAs falling within genotypes I/1a, II/1b, III/2a, IV/2b, V/3a and 5a, to produce a consensus sequence for each of these genotypes is shown in FIGS. 6A (I/1a), 6B (II/1b), 6D (III/2a), 6E (IV/2b), 6G (V/3a) and 6I (5a). The alignment of the sequences found in minor genotypes I/1a and II/1b to produce a consensus sequence for major genotype 1 is shown in FIG. 6C. The alignment of the sequences contained in minor genotypes III/2a, IV/2b and 2c to produce a consensus sequence for major genotype 2 is shown in FIG. 6F. The alignment of the nucleotide sequences contained in minor genotypes 4a–4f to produce a consensus sequence for major genotype 4 is shown in FIG. 6H. Further alignment of the consensus sequences shown in FIGS. 6C, 6F, 6G, 6H and 6I with SEQ ID NO:154 (genotype 6a/major genotype 6) to produce a consensus sequence for all genotypes is shown in FIG. 6J and alignment of the consensus sequences shown in FIGS. 6A, 6B, 6D, 6E, 6G and 6I with 4a), SEQ ID NO:141 (genotype 4b), SEQ ID NO:143 (genotype 4c), SEQ ID NO:145 (genotype 4d), SEQ ID NO:142 (genotype 4e), SEQ ID NO:140 (genotype 4f)

and SEQ ID NO:154 (genotype 6a) to produce a consensus sequence for all fourteen genotypes is shown in FIG. 6K. As with the alignments of the envelope (E1) nucleotide sequences, the consensus sequences shown in FIGS. 6A–6K serve to highlight regions of homology and non-homology between sequences found within the same genotype or in different genotypes and hence, can be used by one skilled in the art to design oligonucleotides useful as reagents in diagnostic assays for HCV.

For example, purified and isolated oligonucleotide sequences derived from the consensus sequences shown in FIGS. 6A–6K may be useful as genotype-specific primers and probes since these oligonucleotides can hybridize specifically to the nucleotide sequence of the core gene of HCV isolates belonging to a given genotype. Examples of regions of the consensus sequence of the core gene of a given genotype from which primers specific for that genotype may be deduced include but are not limited to, the nucleotide domains shown below for each genotype. The sequence in which the indicated nucleotide domains are found are indicated in parentheses to the right of each genotype.

Genotype 1 (Consensus Sequence of FIG. 6C)
427–466, 444–483, 447–486 (5'-3', sense)
505–466, 522–483, 525–486 (5'-3', antisense)

Genotype 1a (Consensus Sequence of FIG. 6A)
141–180, 279–318 (5'-3', sense)
219–180, 246–207 (5'-3', antisense)

Genotype 1b (Consensus Sequence of FIG. 6B)
67–106, 127–186, 234–273 (5'-3', sense)
144–106, 225–186, 311–272, 312–273 (5'-3', antisense)

Genotype 2 (Consensus Sequence of FIG. 6F)
153–192, 162–201, 164–203, 168–207, 171–210, 182–221, 192–231, 193–232, 302–341 (5'-3', sense)
231–192, 240–201, 242–203, 246–207, 249–210, 260–221, 270–231, 271–232, 380–341 (5'-3', antisense)

Genotype III/2a (Consensus Sequence of FIG. 6D)
276–315, 306–355 (5'-3', sense)
309–270, 354–315, 394–355, 571–532 (5'-3', antisense)

Genotype IV/2b (Consensus Sequence of FIG. 6E)
6–45, 135–174, 177–216, 309–348, 337–376, 375–414, 501–540 (5'-3', sense)
84–45, 213–174, 255–216, 387–348, 415–376, 453–414, 571–532, 573–540 (5'-3', antisense)

Genotype 2c (SEQ ID NO:134)
194–233, 273–312, 279–318, 417–456, 423–462, 504–543, 505–544, 517–556 (5'-3', sense)
272–233, 351–312, 354–315, 357–318, 450–411, 495–456, 501–462, 573–543, 556–573 (5'-3', antisense)

Genotype 3 or Genotype V/3a (Consensus Sequence of FIG. 6G)
8–47, 45–84, 68–107, 87–126, 88–127, 90–129, 111–150, 142–181, 173–212, 177–216, 261–300,
276–315, 452–491, 520–559, 521–560, 529–568, 532–571, 533–572. (5'-3', sense)
86–47, 123–84, 146–107, 165–126, 186–147, 189–150, 219–180, 250–211, 251–212, 255–216,
339–300, 530–491, 573–543, 573–557, 573–559, 573–560. (5'-3', antisense)

Genotype 4 (Consensus Sequence of FIG. 6H)
20–59 (5'-3', sense)
97–58, 98–59 (5'-3', antisense)

Genotype 4a (SEQ ID NO:139)
111–150, 150–189, 174–213, 183–222, 192–231, 261–300, 376–415, 396–435, 531–570 (5'-3', sense)
186–147, 252–213, 270–231, 339–300, 454–415 (5'-3', antisense)

Genotype 4b (SEQ ID NO:141)
27–66, 30–69, 106–145, 271–310, 433–472, 447–486, 453–492 (5'-3', sense)
105–66, 183–144, 184–145, 345–306, 348–309, 349–310, 468–429, 510–471, 522–483, 570–531 (5'-3', antisense)

Genotype 4c (SEQ ID NO:143)
174–213, 180–219, 207–246, 231–270 (5'-3', sense)
249–210, 252–213, 258–219, 309–270, 504–465 (5'-3', antisense)

Genotype 4d (SEQ ID NO:145)
173–212, 188–327, 430–469 (5'-3', sense)
248–209, 249–210, 250–211, 251–212, 366–327, 508–469 (5'-3', antisense)

Genotype 4e (SEQ ID NO:142)
160–199, 267–306, 287–326, 288–327, 524–564 (5'-3', sense)
238–199, 345–306, 365–326, 216–177, 522–483 (5'-3', antisense)

Genotype 4f (SEQ ID NO:140)
18–57, 36–75, 228–267, 396–435 (5'-3', sense)
96–57, 114–75, 306–267 (5'-3', antisense)

Genotype 5 or 5a (Consensus Sequence of FIG. 6I)
176–215, 177–216, 181–220, 195–234, 221–260, 252–291, 255–294, 396–435, 435–474, 447–486, 498–537 (5'-3', sense)
254–215, 299–260, 310–271, 330–291, 333–294, 354–315, 464–425, 471–432, 483–444, 570–531 (5'-3', antisense)

Genotype 6 or 6a (SEQ ID NO:154)
20–59, 136–175, 156–195, 159–198, 175–214, 185–224, 277–316, 278–317, 312–351, 348–387, 405–444, 406–445, 407–446, 408–447, 411–450, 432–471, 433–472, 435–474, 522–561 (5'-3', sense).
98–59, 214–175, 234–195, 237–198, 253–214, 262–223, 263–224, 354–315, 355–316, 382–343, 390–351, 426–387, 468–429, 483–444, 484–445, 485–446, 486–447, 489–450, 510–471, 511–472, 513–474 (5'-3', antisense)

Such nucleotide domains may range from about 15 to about 100 bases in length with a more preferred range being about 30 to about 60 bases in length.

In an alternative embodiment, universal primers able to hybridize to the nucleotide sequences of the core gene of HCV isolates belonging to all of the genotypes disclosed herein may be deduced from universally conserved nucleotide domains of the consensus sequence shown in FIGS. 6J and 6K. Examples of such nucleotide domains include, but are not limited to, those shown below:

nucleotides 1–20, 1–25, 1–26, 1–27, 1–33, 50–89, 51–90, 52–91, 53–92, 61–100, 62–101, 77–116, 78–117, 79–118, 80–119, 81–120, 82–121, 83–122, 84–123, 85–124, 86–125, 97–136, 98–137, 99–138, 100–139, 101–140, 102–141, 329–368, 330–369, 331–370, 332–371, 354–393, 355–394, 356–395, 362–401, 363–402, 364–403, 365–404, 369–408, 442–481, 443–482, 457–496, 458–497, 475–514, 476–515, 477–516 (5'-3, sense); and nucleotides 40–1, 41–2, 42–3, 43–4, 51–12, 52–13, 55–16, 56–17, 57–18, 58–19, 61–22, 62–23, 63–24, 64–25, 70–31, 124–85, 125–86, 126–87, 127–88, 128–89, 129–90, 136–97, 137–98, 138–99, 149–110, 150–111, 151–112, 152–113, 153–114, 154–115, 155–116, 156–117, 157–118, 158–119, 159–120, 170–131, 171–132, 172–133, 173–134, 174–135, 175–136, 403–364, 405–365, 406–366, 406–367, 430–391, 431–392, 432–393, 436–397, 437–398, 438–399, 439–400, 517–478, 518–479, 519–480, 532–493, 533–494, 550–511, 551–512 (5'-3', antisense)

Those skilled in the art would readily understand that the term "antisense" as used herein refers to primer sequences which are the complementary sequence of the indicated consensus sequence or SEQ ID NO:. Further, provided with the above examples of regions of the consensus sequences or indicated SEQ ID NOS: from which to deduce universal and genotype-specific primers, those skilled in the art would readily be able to select pairs of primers, one sense and one antisense, which would be useful in the detection of HCV genotypes via the PCR methods described herein.

In yet another embodiment, the sequences shown in SEQ ID NO.:103–154 and the resultant consensus sequences produced by alignment of these SEQ ID NOs as shown in FIGS. 6A–6K may also be useful in the design of hybridization probes specific for a given HCV genotype. Examples of nucleotide domains of the consensus sequence or SEQ ID NO of a given genotype from which genotype-specific hybridization probes may be deduced include, but are not limited to, those shown below where the sequence from which the domains are found is indicated in parentheses to the right of each genotype.

| Genotype | Position |
| --- | --- |
| 1a (Consensus sequence of FIG. 6A) | 50–85 |
|  | 155–205 |
|  | 207–277 |
|  | 281–333 |
|  | 429–477 |
|  | 530–573 |
| 1b (Consensus sequence of FIG. 6B) | 81–131 |
|  | 159–225 |
|  | 252–318 |
|  | 411–472 |
|  | 530–573 |
| 2a (Consensus sequence of FIG. 6D) | 35–75 |
|  | 200–276 |
|  | 290–340 |
|  | 330–380 |
|  | 410–472 |
|  | 530–573 |
| 2b (Consensus sequence of FIG. 6E) | 20–70 |
|  | 149–199 |
|  | 191–241 |
|  | 240–285 |
|  | 261–318 |
|  | 323–373 |
|  | 351–401 |
|  | 389–439 |
|  | 429–477 |
|  | 530–573 |
| 2c (SEQ ID NO:134) | 208–258 |
|  | 230–276 |
|  | 290–345 |
|  | 411–460 |
|  | 430–490 |
|  | 530–573 |
| 3a (Consensus sequence of FIG. 6G) | 1–50 |
|  | 40–100 |
|  | 100–160 |
|  | 145–190 |
|  | 190–240 |

-continued

| Genotype | Position |
| --- | --- |
|  | 275–325 |
|  | 411–455 |
|  | 466–516 |
|  | 530–573 |
| 4a (SEQ ID NO:139) | 35–85 |
|  | 145–195 |
|  | 200–250 |
|  | 255–305 |
|  | 341–390 |
|  | 390–440 |
|  | 530–573 |
| 4b (SEQ ID NO:141) | 35–85 |
|  | 120–170 |
|  | 180–225 |
|  | 230–275 |
|  | 285–335 |
|  | 405–455 |
|  | 462–492 |
|  | 530–573 |
| 4c (SEQ ID NO:143) | 35–85 |
|  | 190–246 |
|  | 245–295 |
|  | 282–318 |
|  | 372–415 |
|  | 440–480 |
|  | 530–573 |
| 4d (SEQ ID NO:145) | 35–85 |
|  | 187–237 |
|  | 302–352 |
|  | 405–455 |
|  | 444–494 |
|  | 530–573 |
| 4e (SEQ ID NO:142) | 35–85 |
|  | 57–84 |
|  | 174–224 |
|  | 230–275 |
|  | 290–340 |
|  | 422–472 |
|  | 530–573 |
| 4f (SEQ ID NO:140) | 35–85 |
|  | 174–224 |
|  | 242–292 |
|  | 290–340 |
|  | 422–472 |
|  | 530–573 |
| 5a (Consensus sequence of FIG. 6I) | 180–234 |
|  | 265–315 |
|  | 315–355 |
|  | 420–486 |
|  | 530–573 |
| 6a (SEQ ID NO:154) | 34–84 |
|  | 150–200 |
|  | 180–230 |
|  | 230–290 |
|  | 291–333 |
|  | 341–395 |
|  | 429–490 |
|  | 530–573 |
| 1 (Consensus sequence of FIG. 6C) | 192–241 |
|  | 435–495 |
| 2 (Consensus sequence of FIG. 6F) | 186–240 |
|  | 320–360 |
|  | 440–475 |
| 4 (Consensus sequence of FIG. 6H) | 40–80 |

In yet another embodiment, universal hybridization probes may be derived from the consensus sequences shown in FIGS. 6J and 6K. Examples of nucleotide domains of the consensus sequences shown in FIGS. 6J and 6K from which universal hybridization probes may be derived include, but are not limited to, 1–33; 85–141; 364–408; 478–516.

The oligonucleotides of this invention can be synthesized using any of the known methods of oligonucleotide synthesis (e.g., the phosphodiester method of Agarwal et al. 1972, Agnew. Chem. Int. Ed. Engl. 11:451, the phosphotriester method of Hsiung et al. 1979, Nucleic Acids Res 6:1371, or the automated diethylphosphoramidite method of Baeucage et al. 1981, Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In a preferred embodiment, the oligonucleotides of the present invention are synthetic oligonucleotides. The oligonucleotides of the present invention may range from about 15 to about 100 nucleotides; with the preferred sizes being about 20 to about 60 nucleotides; a more preferred size being about 25 to about 50 nucleotides; and a most preferred size being about 30 to about 40 nucleotides.

The present invention also relates to methods for detecting the presence of HCV in a mammal, said methods comprising analyzing the RNA of a mammal for the presence of hepatitis C virus.

The RNA to be analyzed can be isolated from serum, liver, saliva, lymphocytes or other mononuclear cells as viral RNA, whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412). A preferred method of isolating RNA is extraction of viral RNA by the guanidinium-phenol-chloroform method of Bukh et al. (1992a).

The methods for analyzing the RNA for the presence of HCV include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W.H. Freeman and Company, New York).

A preferred method for analyzing the RNA is RT-PCR. In this method, the RNA can be reverse transcribed to first strand cDNA using a primer or primers derived from the nucleotide sequences shown in SEQ ID NOs:1–51 or SEQ ID NOs:103–154 or sequences complementary to those described. Once the cDNAs are synthesized, PCR amplification is carried out using pairs of primers designed to hybridize with sequences in the HCV E1 or core cDNA which are an appropriate distance apart (at least about 50 nucleotides) to permit amplification of the cDNA and subsequent detection of the amplification product. Alternatively, one can amplify both E1 and core cDNA sequences by using a primer pair where one primer hybridizes with the E1 cDNA sequence and the other primer hybridizes with the core cDNA sequence. Each primer of a pair is a single-stranded oligonucleotide of about 20 to about 60 bases in length with a more preferred range being about 30 to about 50 bases in length where one primer (the "upstream" primer) is complementary to the original RNA and the second primer (the "downstream" primer) is complementary to the first strand of cDNA generated by reverse transcription of the RNA. The target sequence is generally about 100 to about 300 base pairs long but can be as large as 500–1500 base pairs. Optimization of the amplification reaction to obtain sufficiently specific hybridization to the nucleotide sequence of interest (either E1 or core or both E1 and core) is well within the skill in the art and is preferably achieved by adjusting the annealing temperature.

In one embodiment, the primer pairs selected to amplify E1 and core cDNAs are universal primers. By "universal", as used to describe primers throughout the claims and specification, is meant those primer pairs which can amplify E1 and/or core gene fragments derived from an HCV isolate belonging to any one of the genotypes of HCV described herein. Purified and isolated universal primers for E1 cDNAs are used in Example 1 of the present invention and are shown as SEQ ID NOs:207–212 where SEQ ID NOs: 207 and 208 represent one pair of primers, SEQ ID NOs:209 and 210 represent a second pair of primers and SEQ ID NOs:211–212 represent a third pair of primers. Nucleotide domains of the consensus sequence shown in FIG. 6J from which universal primers for core cDNAs may be deduced have previously been disclosed within the present specification. Alternatively, a universal primer for E1 cDNA sequence and a universal primer for core cDNA sequence may be used as a universal primer pair to amplify both E1 and core cDNAs.

In an alternative embodiment, primer pairs selected to amplify E1 and/or core cDNAs are genotype-specific primers. In the present invention, genotype-specific primer pairs can readily be derived from the following genotype-specific E1 nucleotide domains: nucleotides 197–238 and 450–480 of the consensus sequence of genotype I/1a shown in FIG. 1A; nucleotides 197–238 and 450–480 of the consensus sequence of genotype II/1b shown in FIG. 1B; nucleotides 199–238 and 438–480 of the consensus sequence of genotype III/2a shown in Figure C; nucleotides 124–177 and 450–480 of the consensus sequence of genotype IV/2b shown in FIG. 1D; nucleotides 124–177, 193–238 and 436–480 of SEQ ID NO:34 (genotype 2C); nucleotides 168–207, 294–339 and 406–480 of the consensus sequence of genotype V/3a shown in FIG. 1E; nucleotides 145–183 and 439–480 of SEQ ID NO:40 (genotype 4a); nucleotides 168–207 and 432–480 of SEQ ID NO:41 (genotype 4b); nucleotides 130–183 and 450–480 of the consensus sequence of genotype 4c shown in FIG. 1F; nucleotides 130–183 and 450–480 of SEQ ID NO:44 (genotype 4d); nucleotides 166–208 and 437–480 of the consensus sequence of genotype 5a shown in FIG. 1*b* and nucleotides 168–207, 216–252 and 429–480 of SEQ ID NO:51 (genotype 6a). Genotype-specific HCV core nucleotide domains from which genotype-specific primers may be deduced have previously been described herein. Those skilled in the art would readily appreciate that in a pair of genotype-specific primers, each primer is derived from different nucleotide domains specific for a given genotype. Also, it is understood by those skilled in the art that each pair of primers comprises one primer which is complementary to the original viral RNA and the other which is complementary to the first strand of cDNA generated by reverse transcription of the viral RNA. For example, in a pair of genotype-specific primers for genotype 4b, one primer would have a nucleotide sequence derived from region 168–207 of SEQ ID NO:40 and the other primer would have a nucleotide sequence which is the complement of region 432–480 of SEQ ID NO:40. One skilled in the art would readily recognize that such genotype-specific domains would also be useful in designing oligonucleotides for use as genotype-specific hybridization probes. Indeed, genotype-specific hybridization probes deduced from the E1 and core sequences of the present invention have been previously disclosed herein.

The amplification products of PCR can be detected either directly or indirectly. In one embodiment, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be detected by agarose gel electrophoresis followed by ethidum bromide staining and visualization under ultraviolet light or via direct sequencing of the PCR-products. Thus, in one embodiment, the present invention relates to a method for determining the genotype of a hepatitis C virus present in a mammal where said method comprises: amplifying RNA of a mammal via RT-PCR using labelled genotype-specific primers for the amplification step of the cDNA produced by reverse transcription.

In yet another embodiment, unlabelled amplification products can be detected via hybridization with labelled nucleic acid probes radioactively labelled or, labelled with biotin, in methods known to one skilled in the art such as dot and slot blot hybridization (Kafatos, F. C. et al. (1979) or filter hybridization (Hollander, M. C. et al. (1990)).

In one embodiment, the nucleic acid sequences used as probes are selected from, and substantially homologous to, SEQ ID NOs:1–51 and/or SEQ ID NOs:103–154. Such probes are useful as universal probes in that they can detect PCR-amplification products of E1 and/or core cDNAs of an HCV isolate belonging to any of the HCV genotypes disclosed herein. The size of these probes can range from about 200 to about 500 nucleotides. In an alternative embodiment, the sequence alignments shown in FIGS. 1A–1H and 6A–6J may be used to design oligonucleotides useful as universal hybridization probes. Examples of core and envelope nucleotide domains from which such universal oligonucleotides may be deduced are disclosed herein.

In yet another embodiment, the present invention relates to a method for determining the genotype of a hepatitis C virus present in a mammal where said method comprises:

(a) amplifying RNA of a mammal via RT-PCR to produce amplification products;

(b) contacting said products with at least one genotype-specific oligonucleotide; and (c) detecting complexes of said products which bind to said oligonucleotide(s).

In this method, one embodiment of said amplification step is carried out using the universal primers for E1 or core cDNAs as disclosed above. In step (b) of this method, the genotype-specific sequences used as probes may be deduced from the genotype-specific E1 and core nucleotide domains disclosed herein. These probes are useful in specifically detecting PCR-amplification products of E1 or core cDNAs of HCV isolates belonging to one of the HCV genotypes disclosed herein. In a preferred embodiment, these probes are used alone or in combination with other probes specific to the same genotype.

For example, a probe having a sequence according to SEQ ID NO:213 can be used alone or in combination with a probe having a sequence according to SEQ ID NO:214. The probes used in this method can range in size from about 15 to about 100 nucleotides with a more preferred range being about 30 to about 70 nucleotides. Such probes can be synthesized as described earlier.

In an alternative embodiment, the genotype of the amplification product of step (a) may be determined by using the nucleic acid sequences shown in SEQ ID NOs: 1–51 and 103–154 as probes (Delwart, E. et al. (1993)) *Science,* 262: 1257–1261). Probes utilized in the method of Delwart et al. may range in size from about 100 to about 1,000 nucleotides with a more preferred probe size being about 200 to about 800 base pairs and a most preferred probe size being about 300 to about 700 nucleotides.

The nucleic acid sequence used as a probe to detect PCR amplification products of the present invention can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.,* 70:2238–2242; Heck, R. F. (1968) *S. Am. Chem. Soc.,* 90:5518–5523), methods which allow detection by chemiluminescence (Barton, S. K. et al. (1992) *J. Am. Chem. Soc.,* 114:8736–8740) and methods utilizing biotinylated nucleic acid probes (Johnson, T. K. et al. (1983) *Anal. Biochem.,* 133:126–131; Erickson, P. F. et al. (1982) *J. of Immunology Methods,* 51:241–249; Matthaei, F. S. et al. (1986) *Anal. Biochem.,* 157:123–128) and methods which allow detection by fluorescence using commercially available products.

The present invention also relates to computer analysis of the amino acid sequences shown in SEQ ID NOs:52–102 by the program GENALIGN. This analysis groups the 51 amino acid sequences shown in SEQ ID NOs:52–102 into twelve genotypes based upon the degree of variation of the amino acid sequences. For the purposes of the present invention, the amino acid sequence identity of E1 amino acid sequences of the same genotype ranges from about 85% to about 100% whereas the identity of E1 amino acid sequences of different genotypes ranges from about 45% to about 80%.

The grouping of SEQ ID NOs:52–102 into twelve HCV genotypes is shown below:

| SEQ ID NOs: | Genotypes |
| --- | --- |
| 52–59 | I/1a |
| 60–76 | II/1b |
| 77–80 | III/2a |
| 81–84 | IV/2b |
| 85 | 2c |
| 86–90 | V/3a |
| 91 | 4a |
| 92 | 4b |
| 93–94 | 4c |
| 95 | 4d |

-continued

| SEQ ID NOs: | Genotypes |
|---|---|
| 96–101 | 5a |
| 102 | 6a |

For those genotypes containing more than one E1 amino acid sequence, computer alignment of the constituent sequences of each genotype was conducted using the computer program GENALIGN in order to produce a consensus sequence for each genotype. These alignments and their resultant consensus sequences are shown in FIGS. 2A–G for the seven genotypes (I/1a, II/1b, III/2a, IV/2b, V/3a, 4c and 5a) which comprise more than one sequence. Further alignment of the consensus sequences shown in FIGS. 2A–G with the amino acid sequences of SEQ ID NO:85 (genotype 2c); SEQ ID NO:91 (genotype 4a); SEQ ID NO:92 (genotype 4b); SEQ ID NO:95 (genotype 4d) and SEQ ID NO:102 (genotype 6a) to produce a consensus amino acid sequence for all twelve genotypes is shown in FIG. 2H. The multiple alignment of E1 amino acid sequences shown in FIGS. 2A–H produces consensus sequences which serve to highlight regions of homology and non-homology between E1 amino acid sequences of the same genotype and of different genotypes and hence, these alignments can readily be used by those skilled in the art to design peptides useful in assays and vaccines for the diagnosis and prevention of HCV infection.

In another embodiment, the computer analysis of SEQ ID NOS: 155–206 by the probe genome results in distribution of the 52 HCV core sequences into 14 genotypes based upon identification of genotype-specific amino acid sequences.

The grouping of SEQ ID NOS: 155–206 into 14 HCV genotypes is shown below:

| SEQ ID NOS: | Genotypes |
|---|---|
| 155–160 | I/1a |
| 161–176 | II/1b |
| 177–180 | III/2a |
| 181–185 | IV/2b |
| 186 | 2c |
| 187–190 | V/3a |
| 191 | 4a |
| 193 | 4b |
| 195 | 4c |
| 196 | 4c |
| 197 | 4d |
| 194 | 4e |
| 192 | 4f |
| 198–205 | 5a |
| 206 | 6a |

These fourteen genotypes can be further grouped into six major genotypes designated genotypes 1–6 as described earlier for the core nucleotide sequences of the present application. Computer alignment of the amino acid sequences disclosed in SEQ ID NOS: 155–206 are shown in FIGS. 7A–7J. As with the multiple alignments of the E-1 amino acid sequences, the consensus sequences shown in FIGS. 7A–7J serve to highlight regions of homology and nonhomology between core amino acid sequences of the same genotype and of different genotypes and hence, these alignments can readily be used by those skilled in the art to design peptides useful in assays and vaccines for the diagnosis and prevention of HCV infection.

Examples of purified and isolated peptides deduced from the alignments shown in FIGS. 2A–2H include, but are not limited to, SEQ ID NOs:240–263 wherein these peptides are derived from two regions of the amino acid sequences shown in FIGS. 2A–H, amino acids 48–80 and amino acids 138–160. The peptides shown in SEQ ID NOs. 240–263 are useful as genotype-specific diagnostic reagents since they are capable of detecting an immune response specific to HCV isolates belonging to a single genotype. The genotype-specificity of the peptides shown in SEQ ID NOs:240–263 are as follows: SEQ ID NOs:240 and 252 are specific for genotype IV/2b; SEQ ID NOs:241 and 253 are specific for genotype 2c; SEQ ID NOs:242 and 254 are specific for genotype III/2a; SEQ ID NOs:243 and 255 are specific for genotype V/a; SEQ ID NOs:244 and 256 are specific for genotype II/1b; SEQ ID NOs:245 and 257 are specific for genotype I/1a; SEQ ID NOs:246 and 258 are specific for genotype 4a; SEQ ID NOs:247 and 259 are specific for genotype 4c; SEQ ID NOs:248 and 260 are specific for genotype 4d; SEQ ID NOs:249 and 261 are specific for genotype 4b; SEQ ID NOs:250 and 262 are specific for genotype 5a and SEQ ID NOs:251 and 263 are specific for genotype 6a. In SEQ ID NO:240, Xaa at position 22 is a residue of Ala or Thr, Xaa at position 24 is a residue of Val or Ile, Xaa at position 26 is a residue of Val or Met; in SEQ ID NO:242, Xaa at position 5 is a Ser or Thr residue, Xaa at position 11 is an Arg or Gln residue, Xaa at position 12 is an Arg or Gln residue; in SEQ ID NO:243, Xaa at position 3 is a Pro or Ser residue, Xaa at position 33 is a Leu or Met residue; in SEQ ID NO:244, Xaa at position 5 is a Thr or Ala residue, Xaa at position 13 is a Gly, Ala, Ser, Val or Thr residue, Xaa at position 14 is a Ser, Thr or Asn residue, Xaa at position 15 is a Val or Ile residue, Xaa at position 16 is a Pro or Ser residue, Xaa at position 18 is a Thr or Lys residue, Xaa at position 19 is a Thr or Ala residue, Xaa at position 22 is an Arg or His residue, Xaa at position 32 is an Ala, Val or Thr residue; in SEQ ID NO:245, Xaa at position 3 is an Ala or Pro residue, Xaa at position 4 is a Val or Met residue, Xaa at position 5 is a Thr or Ala residue, Xaa at position 17 is a Thr or Ala residue, Xaa at position 18 is a Thr or Ala residue, Xaa at position 23 is a His or Tyr residue; in SEQ ID NO:247, Xaa at position 10 is a Val or Ala residue, Xaa at position 11 is a Ser or Pro residue, Xaa at position 18 is an Asp or Glu residue Xaa at position 20 is a Leu or Ile residue; in SEQ ID NO:250, Xaa at position 3 is a Gln or His residue, Xaa at position 12 is an Asn, Ser or Thr residue, Xaa at position 13 is a Leu or Phe residue, Xaa at position 23 is an Ala or Val residue; in SEQ ID NO:252, Xaa at position 16 is a Val or Ala residue, Xaa at position 18 is a Glu or Gln residue; in SEQ ID NO:254, Xaa at position 2 is an Ala or Thr residue, Xaa at position 4 is a Met or Leu residue, Xaa at position 9 is an Ala or Val residue, Xaa at position 17 is an Ile or Leu residue, Xaa at position 20 is an Ile or Val residue, Xaa at position 21 is a Ser or Gly residue; in SEQ ID NO:151, Xaa at position 9 is a Val or Ile residue, Xaa at position 16 is a Leu or Val residue, Xaa at position 20 is an Ile or Leu residue; in SEQ ID NO:256, Xaa at position 2 is an Ala or Thr residue, Xaa at position 6 is a Val or Leu residue, Xaa at position 12 is an Ile or Leu residue, Xaa at position 16 is a Val or Ile residue, Xaa at position 17 is a Val, Leu or Met residue, Xaa at position 19 is a Met or Val residue, Xaa at position 21 is an Ala or Thr residue; in SEQ ID NO:257, Xaa at position 2 is a Thr or Ala residue, Xaa at position 6 is a Val, Ile or Met residue, Xaa at position 12 is an Ile or Val residue, Xaa at position 16 is a Ile or Val residue; in SEQ ID NO:155, Xaa at position 5 is a Leu or Val residue, Xaa at position 21 is a Thr or Ala residue; in SEQ ID NO:262, Xaa at position 1 is a Thr or Ala residue, Xaa at position 5 is a Val or Leu residue, Xaa at position 9 is a Leu, Met or Val residue, Xaa at position 23 is a Gly or Ala residue.

Examples of core amino acid domains from which genotype-specific peptides may be deduced, include but are not limited to, those shown below where the sequence in which the indicated domains are found is given in parentheses to the right of each genotype:

| Genotype | Amino Acid Domains |
| --- | --- |
| 1a (consensus sequence of FIG. 7A) | 67–78 |
| 1b (consensus sequence of FIG. 7B) | 67–78 |
| 2 (consensus sequence of FIG. 7F) | 66–81 |
|  | 110–119 |
| 2a (consensus sequence of FIG. 7D) | 67–78 |
|  | 115–125 |
| 2b (consensus sequence of FIG. 7E) | 67–78 |
|  | 123–133 |
| 2c (SEQ ID NO:186) | 67–78 |
|  | 75–81 |
|  | 184–191 |
| 3a (consensus sequence of FIG. 7G) | 8–22 |
|  | 32–46 |
|  | 67–78 |
|  | 158–170 |
|  | 180–191 |
| 4 (consensus sequence of FIG. 7H) | 14–23 |
| 4a (SEQ ID NO:191) | 67–78 |
| 4b (SEQ ID NO:193) | 45–57 |
|  | 67–78 |
| 4c (SEQ ID NO:195) | 67–78 |
| 4d (SEQ ID NO:197) | 67–78 |
| 4e (SEQ ID NO:194) | 67–78 |
| 4f (SEQ ID NO:192) | 67–78 |
| 5a (consensus sequence of FIG. 7J) | 67–78 |
| 6a (SEQ ID NO:206) | 67–78 |
|  | 101–108 |
|  | 144–155 |
|  | 157–163 |

Those skilled in the art would be aware that the peptides of the present invention or analogs thereof can be synthesized by automated instruments sold by a variety of manufacturers or can be commercially custom-ordered and prepared. The term analog has been described earlier in the specification and for purposes of describing the peptides of the present invention, analogs can further include branched, cyclic or other non-linear arrangements of the peptide sequences of the present invention.

Alternatively, peptides can be expressed from nucleic acid sequences where such sequences can be DNA, cDNA, RNA or any variant thereof which is capable of directing protein synthesis. In one embodiment, restriction digest fragments containing a coding sequence for a peptide can be inserted into a suitable expression vector that functions in prokaryotic or eukaryotic cells. Such restriction digest fragments may be obtained from clones isolated from prokaryotic or eukaryotic sources which encode the peptide sequence.

Suitable expression vectors and methods of isolating clones encoding the peptide sequences of the present invention have previously been described. In yet another embodiment, an oligonucleotide capable of directing host organism synthesis of the given peptide may be synthesized and inserted into the expression vector.

The preferred size of the peptides of the present invention is from about 8 to about 100 amino acids in length when the peptides are chemically synthesized with a more preferred size being about 8 to about 30 amino acids and a most preferred size being about 10 to about 20 amino acids in length. For recombinantly expressed peptides, the size may range from about 20 to about 190 amino acids in length with a more preferred size being about 70 amino acids.

The present invention further relates to the use of genotype-specific peptides in methods of detecting antibodies against a specific genotype of HCV in biological samples. In one embodiment, at least one genotype-specific peptide deduced from a genotype-specific core or E1 amino acid domain may be used in any of immunoassays described herein to detect antibodies specific for a single genotype of HCV. In another embodiment, at least one genotype-specific peptide deduced from a genotype-specific core nucleotide domain and at least one genotype-specific peptide deduced from an E1 amino acid domain may be used in an immunoassay to detect antibodies against a single genotype of HCV. A preferred immunoassay is ELISA.

It is understood by those skilled in the art that the diagnostic assays described herein using genotype-specific oligonucleotides or genotype-specific peptides can be useful in assisting one skilled in the art to choose a course of therapy for the HCV-infected individual.

In an alternative embodiment, a mixture of genotype-specific peptides can be used in an immunoassay to detect antibodies against multiple genotypes of HCV disclosed herein. For example, a mixture of genotype-specific peptides deduced from E1 amino acid sequences may comprise at least one peptide selected from SEQ ID NOs:244–245 and 256–257; one peptide selected from SEQ ID NOs:240, 242, 252 and 254; one peptide selected from SEQ ID NOs: 246–249 and 258–261; one peptide selected from SEQ ID NOs:250 and 262; one peptide selected from SEQ ID NOs:243 and 255; one peptide selected from SEQ ID NOs:242 and 254 and one peptide selected from SEQ ID NOs:244 and 263. In a preferred embodiment, the peptides of the present invention can be used in an ELISA assay as described previously for recombinant E1 and core proteins.

In an alternative embodiment, the peptide(s) utilized in an immunoassay to detect all the genotypes of HCV disclosed herein may be a universal peptide deduced from universally conserved amino acid domains of the E1 or core proteins disclosed herein.

Examples of universally conserved core amino acid domains within the consensus sequence shown in FIG. 7J from which universal peptides may be deduced include, but are not limited to amino acid domains 23–35, 53–66, 93–108, 122–138, 150–156, and 165–181 of the consensus sequence. Examples of universally conserved E1 amino acid domains within the HCV E1 protein are located within the consensus sequence for the 51 HCV E1 proteins shown in FIG. 2H of the present application. Examples of universally conserved domains within the consensus sequence shown in FIG. 2H include, but are not limited to, amino acid domains 10–20, 111–120, and 124–137 of the consensus sequence. The universal peptides of the present invention may be used in an immunoassay to detect antibodies in patient sera specific for any of the genotypes of HCV disclosed herein.

The peptides of the present invention or analogs thereof may be prepared in the form of a kit, alone or in combinations with other reagents such as secondary antibodies, for use in immunoassay.

In another embodiment, the genotype-specific and universal peptides of the present invention may be used to produce antibodies that will react against HCV E1 or core proteins in immunoassays. In one embodiment, a genotype-specific E1 or core peptide can be used alone or in combination with other E1 or core peptides specific to the same genotype as immunogens to produce antibodies specific to HCV proteins of a single genotype.

In another embodiment, a mixture of peptides specific for different genotypes may be used to produce antibodies that will react with HCV proteins of any genotype disclosed herein. More preferably, antibodies reactive with HCV proteins of any genotype may be produced by immunizing an animal with universal peptide(s) of the present invention. Examples of immunoassays in which such antibodies could be utilized to detect HCV E1 and core proteins in biological samples include, but are not limited to, radioimmunoassays and ELISAs. Examples of biological samples in which HCV E1 and core proteins could be detected includes, but it is not limited to, serum, saliva and liver.

Of course, those skilled in the art would readily understand that the genotype-specific and universal peptides of the present invention and expression vectors containing nucleic acid sequence capable of directing host organism synthesis of these peptides could also be used as vaccines against hepatitis C. Formulations suitable for administering the peptide(s) and expression vectors of the present invention as immunogen, routes of administration, pharmaceutical compositions comprising the peptides expression vectors and so forth are the same as those previously described for recombinant E1 and core proteins.

The genotype-specific and universal peptides of the present invention and expression vectors containing nucleic acid sequence capable of direct host organism synthesis of these peptides may also be supplied in the form of a kit, alone, or in the form of a pharmaceutical composition as described above for recombinant E1 and core proteins.

Any articles or patents referenced herein are incorporated by reference. The following examples illustrate various aspects of the invention but are in no way intended to limit the scope thereof.

MATERIALS

Serum used in these examples was obtained from 84 anti-HCV positive individuals who were previously found to be positive for HCV RNA in a cDNA PCR assay with primer set a from the 5′ NC region of the HCV genome (Bukh, J. et al. (1992 (b)) Proc. Natl. Acad. Sci. USA 89:4942–4946). These samples were from 12 countries: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z).

EXAMPLE 1

Identification of the cDNA Sequence of the E1 Gene of 51 Isolates of HCV via RT-PCR Analysis of Viral RNA Using Universal Primers Viral RNA was extracted from 100 µl of serum by the guanidinium-phenol-chloroform method and the final RNA solution was divided into 10 equal aliquots and stored at −80° C. as described (Bukh, et al. (1992 (a)). The sequences of the synthetic oligonucleotides used in the RT-PCR assay, deduced from the sequence of HCV strain H-77 (Ogata, N. et al. (1991) Proc. Natl. Acad. Sci. USA 88:3392–3396), are shown as SEQ ID NOs:207–212. One aliquot of the final RNA solution, equivalent to 10 µl of serum, was used for cDNA synthesis that was performed in a 20 µl reaction mixture using avian myeloblastosis virus reverse transcriptase (Promega, Madison, Wis.) and SEQ ID NO:208 as a primer. The resulting cDNA was amplified in a "nested" PCR assay by Taq DNA polymerase (Amplitaq, Perkin-Elmer/Cetus) as described previously (Bukh et al. (1992a)) with primer set e (SEQ ID NOs:207–210). Precautions were taken to avoid contamination with exogenous HCV nucleic acid (Bukh et al. 1992a)), and negative controls (normal, uninfected serum) were interspersed between every test sample in both the RNA extraction and cDNA PCR procedures. No false positive results were observed in the analysis. In most instances, amplified DNA (first or second PCR products) was reamplified with primers SEQ ID NO:211 and SEQ ID NO:212 prior to sequencing since these two primers contained EcoR1 sites which would facilitate future cloning of the E1 gene. Amplified DNA was purified by gel electrophoresis followed by glass-milk extraction (Geneclean, BIO 101, LaJolla, Calif.) and both strands were sequenced directly by the dideoxy-nucleotide chain termination method (Bachman, B. et al. (1990) Nucl. Acids Res. 18:1309)) with phage T7 DNA polymerase (Sequenase, United States Biochemicals, Cleveland, Ohio), [alpha $^{35}$S]DATP (Amersham, Arlington Heights, Ill.) or [alpha $^{33}$P] DATP (Amersham or DuPont, Wilmington, Del.) and sequencing primers. RNA extracted from serum containing HCV strain H-77, previously sequenced by Ogata, N. et al. (1991), was amplified with primer set e (SEQ ID NOs:207–210) and sequenced in parallel as a control. The nucleotide sequences of the envelope 1 (E1) gene of all 51 HCV isolates are shown as SEQ ID NOs:1–51. In all 51 HCV isolates, the E1 gene was exactly 576 nucleotides in length and did not have any in-frame stop codons.

EXAMPLE 2

Computer Analysis of the Nucleotide and Deduced Amino Acid Sequences of the E1 Gene of 51 HCV Isolates Multiple computer-generated alignments of the nucleotide (SEQ ID NOs:1–51, FIGS. 1A–H) and deduced amino acid sequences (SEQ ID NOs:52–102, FIGS. 2A–H) of the cDNAs of the 51 HCV isolates constructed using the computer program GENALIGN (Miller, R. H. et al. (1990) Proc. Natl. Acad. Sci. USA 87:2057–2061) resulted in the 51 HCV isolates being divided into twelve genotypes based upon the degree of variation of the E1 gene sequence as shown in table 1.

Biochemistry: Bukh et al.

TABLE 1

Percent nucleotide (nt) and amino acid (aa) sequence identify of the E1 gene among the 12 HCV genotypes.

| | I/1a | II/1b | III/2a | IV/2b | 2c | (V)/3a | 4a | 4b | 4c | 4d | 5a | 6a | nt: |
|---|---|---|---|---|---|---|---|---|---|---|---|---|---|
| | 89.9–97.6 | 72.0–76.2 | 59.2–63.7 | 56.1–58.3 | 60.8–62.8 | 63.0–66.3 | 63.9–67.2 | 64.9–66.8 | 62.7–64.4 | 67.7–69.4 | 62.3–67.2 | 62.2–63.9 | I/1a |
| aa: | | 88.9–97.9 | 58.3–62.2 | 53.8–57.5 | 60.1–61.5 | 63.9–67.2 | 60.9–63.7 | 63.4–65.8 | 61.6–65.1 | 63.0–65.5 | 62.2–66.5 | 61.6–63.0 | II/1b |

TABLE 1-continued

Percent nucleotide (nt) and amino acid (aa) sequence identify of the E1 gene among the 12 HCV genotypes.

| | I/1a | II/1b | III/2a | IV/2b | 2c | (V)/3a | 4a | 4b | 4c | 4d | 5a | 6a | nt: |
|---|---|---|---|---|---|---|---|---|---|---|---|---|---|
| I/1a | 91.1–98.4 | | 88.0–91.3 | 69.1–71.0 | 72.7–73.6 | 58.0–60.8 | 61.5–62.7 | 58.9–60.4 | 59.7–63.4 | 58.7–61.3 | 56.6–60.8 | 55.0–56.8 | III/2a |
| II/1b | 75.5–80.7 | 90.1–97.9 | | 92.7–95.0 | 67.5–68.9 | 56.3–58.3 | 58.9–60.8 | 56.4–57.6 | 57.1–59.9 | 57.5–59.0 | 53.5–56.6 | 53.6–55.2 | IV/2b |
| III/2a | 58.3–64.6 | 52.6–56.8 | 89.1–92.7 | | — | 57.5–58.2 | 59.2 | 58.5 | 58.0–58.3 | 58.9 | 56.9–57.1 | 57.6 | 2c |
| IV/2b | 54.2–56.8 | 51.0–54.2 | 69.3–72.9 | 93.8–96.4 | | 93.8–99.1 | 64.4–65.3 | 62.7–64.1 | 60.9–62.5 | 62.3–63.9 | 61.8–64.4 | 58.0–58.9 | (V)/3a |
| 2c | 56.3–60.4 | 52.6–55.7 | 74.5–77.1 | 67.7–69.8 | — | | — | 74.8 | 75.5–78.0 | 74.8 | 62.8–64.6 | 62.0 | 4a |
| (V)/3a | 64.1–68.8 | 66.7–70.8 | 54.7–58.9 | 54.2–56.8 | 52.1–53.6 | 94.3–98.4 | | — | 74.0–74.8 | 72.0 | 63.9–64.6 | 62.7 | 4b |
| 4a | 69.3–73.4 | 64.6–67.2 | 62.0–63.0 | 58.9–60.4 | 58.3 | 66.1–68.8 | — | | 90.1 | 77.6–78.6 | 62.7–64.8 | 63.0–64.4 | 4c |
| 4b | 66.7–69.3 | 66.1–70.3 | 53.6–56.3 | 52.1–53.1 | 53.6 | 62.0–64.6 | 76.0 | — | | — | 64.4–66.1 | 64.1 | 4d |
| 4c | 66.1–72.9 | 64.6–69.3 | 55.2–61.5 | 54.2–58.3 | 54.7–58.3 | 63.0–65.6 | 77.1–81.3 | 79.2–80.2 | 89.6 | | 90.1–95.7 | 60.6–63.2 | 5a |
| 4d | 73.4–75.5 | 66.7–70.3 | 56.3–58.9 | 55.2–55.7 | 54.2 | 63.5–64.6 | 78.1 | 77.6 | 82.8 | — | | — | 6a |
| 5a | 66.1–73.4 | 64.1–70.3 | 52.6–57.3 | 50.5–53.1 | 54.2–56.3 | 60.4–64.1 | 67.2–68.2 | 65.1–67.2 | 67.7–71.4 | 69.3–71.4 | 92.7–97.4 | | |
| 6a | 64.6–65.6 | 62.5–65.6 | 49.0–51.0 | 49.0–50.5 | 50.5 | 57.8–58.9 | 66.1 | 62.5 | 66.1–67.2 | 66.7 | 62.0–63.5 | — | |

Nucleotide sequences analyzed in compiling the above table are shown in SEQ ID NOs: 1–51 while the amino acid sequences analyzed are shown in SEQ ID NOs: 52–102. The grouping of SEQ ID NOs: into genotypes is previously described in the specification.

The nucleotide and amino acid sequence identity of HCV isolates of the same genotype was in the range of 88.0–99.1% and 89.1–98.4%, respectively, whereas that of HCV isolates of different genotypes was in the range of 53.5–78.6% and 49.0–82.8%, respectively. The latter differences are similar to those found when comparing the envelope gene sequences of the various serotypes of the related flaviviruses, as well as other RNA viruses. When microheterogeneity in a sequence was observed, defined as more than one prominent nucleotide at a specific position, the nucleotide that was identical to that of the HCV prototype (HCV1, Choo et al. (1989)) was reported if possible. Alternatively, the nucleotide that was identical to the most closely related isolate is shown.

Figure 3A:
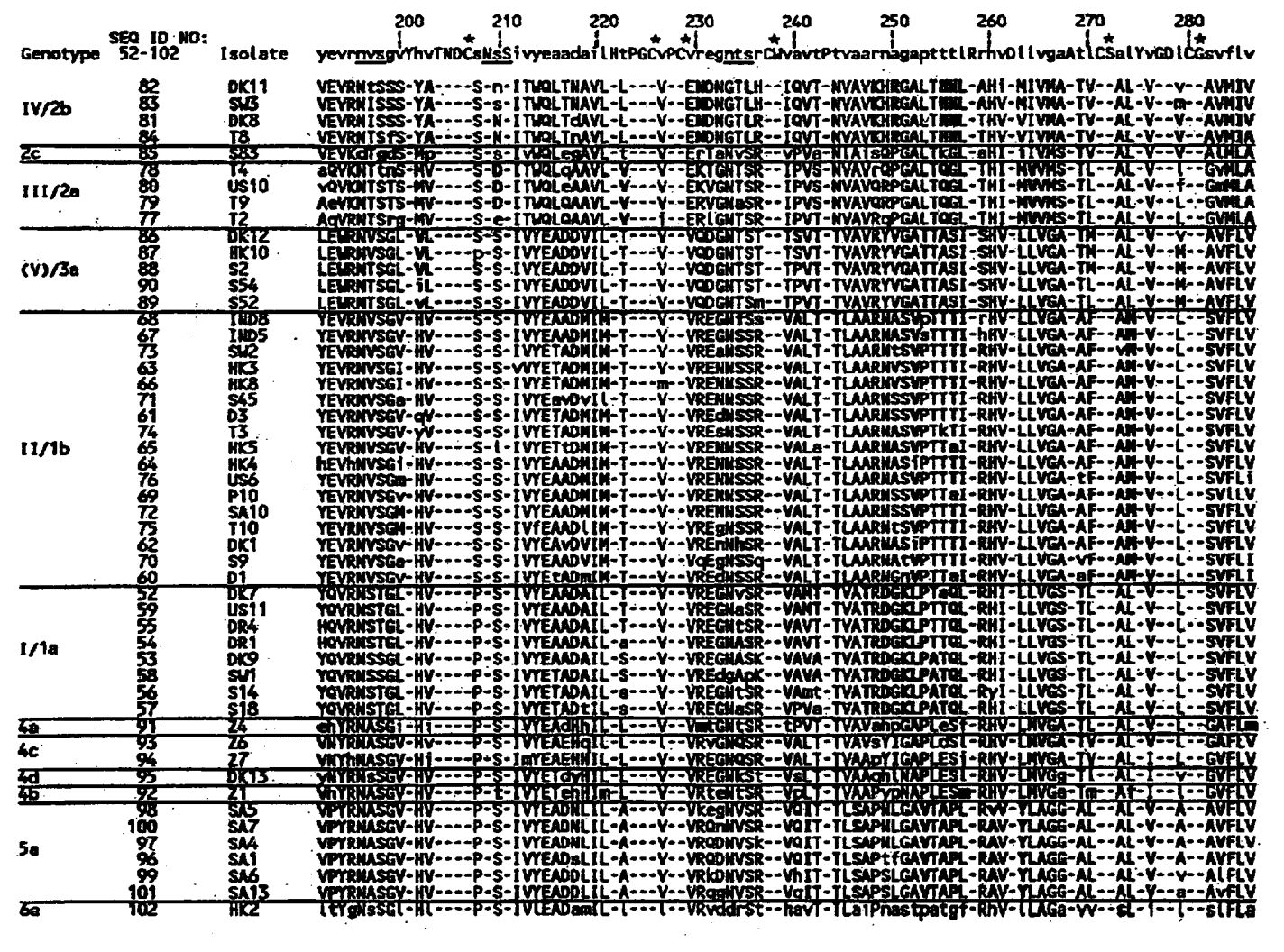
Figure 3B:
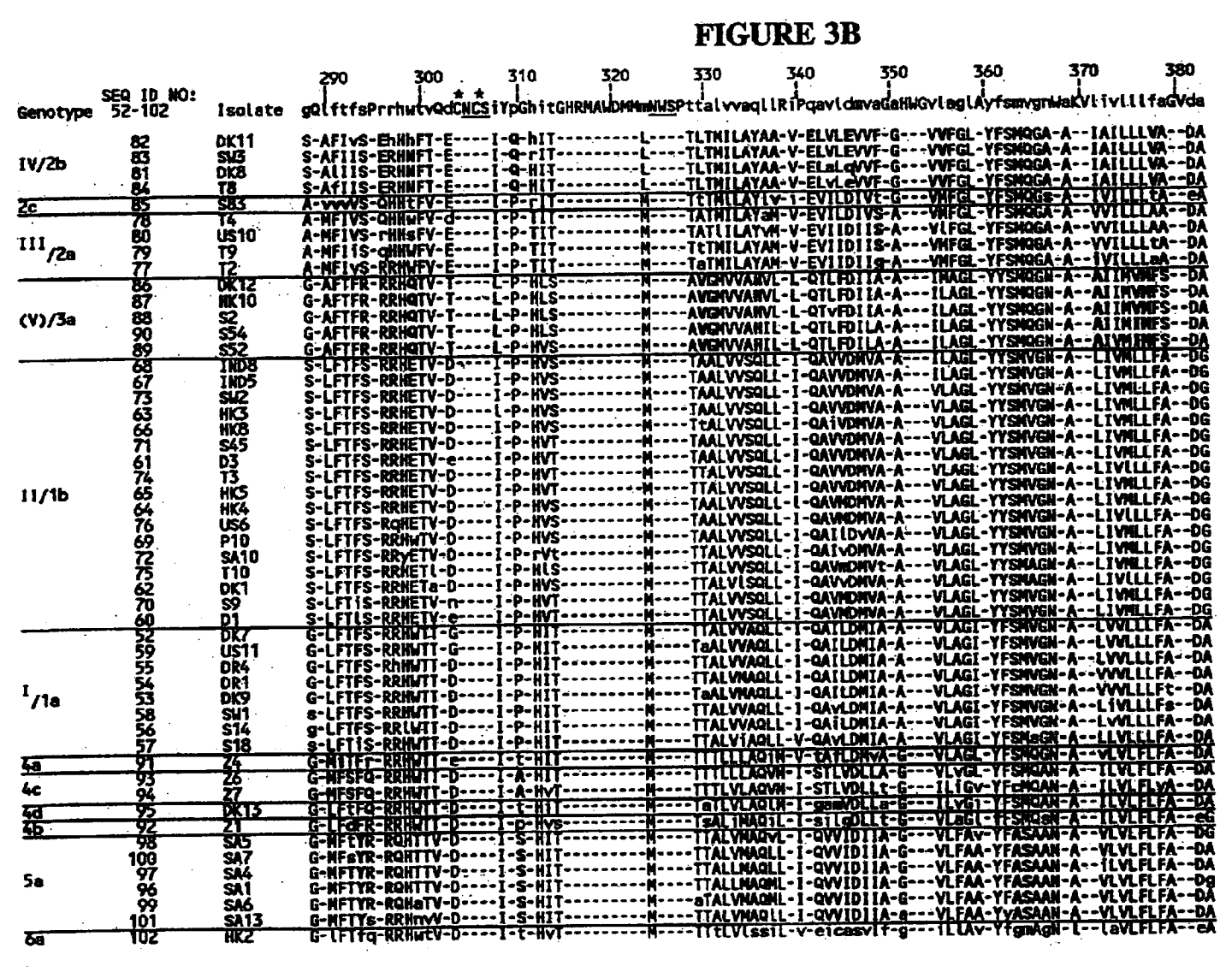

Analysis of the consensus sequence of the E1 protein of the 51 HCV isolates from this study demonstrated that a total of 60 (30.3%) of the 192 amino acids of the E1 protein were invariant among these isolates (FIG. 3). Most impressive, all 8 cysteine residues as well as 6 of 8 proline residues were invariant. The most abundant amino acids (e.g. alanine, valine and leucine) showed a very low degree of conservation. The consensus sequence of the E1 protein contained 5 potential N-linked glycosylation sites. Three sites at positions 209, 305 and 325 were maintained in all 51 HCV isolates. A site at position 196 was maintained in all isolates except the sole isolate of genotype 2c. Also, a site at position 234 was maintained in all isolates except one isolate of genotype I/1a, all four isolates of genotype IV/2b and the sole isolate of genotype 6a. Conversely, only genotype IV/2b isolates had a potential glycosylation site at position 233. Further analysis revealed a highly conserved amino acid domain (aa 302–328) in the E1 protein with 20 (74.1%) of 27 amino acids invariant among all 51 HCV isolates. It is possible that the 5' and 3' ends of this domain are conserved due to important cysteine residues and N-linked glycosylation sites. The central sequence, 5'-GHRMAWDMM-3' (aa 315–323), may be conserved due to additional functional constraints on the protein structure. Finally, although the amino acid sequence surrounding the putative E1 protein cleavage site was variable, an amino acid doublet (GV) at position 380 was invariant among all HCV isolates.

Figure 4:
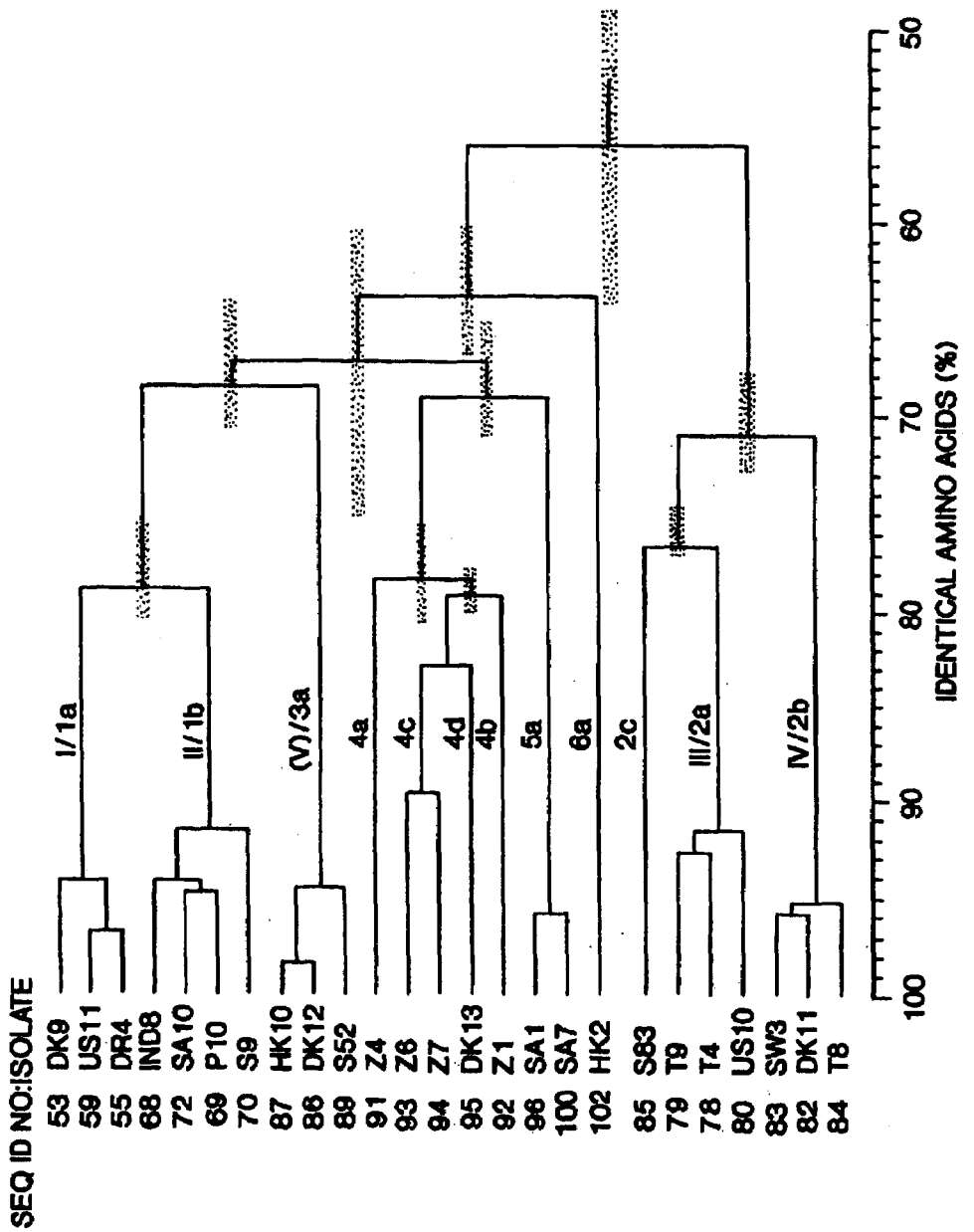
FIG. 4 shows a dendrogram of the genetic relatedness of the twelve genotypes of HCV based on the percent amino acid identity of the E1 gene of the HCV genome. The twelve genotypes shown are designated as I/1a, II/1b, III/2a, IV/2b, V/3a, 2c, 4a, 4b, 4c, 4d, 5a and 6a. The shaded bars represent a range showing the maximum and minimum homology between the amino acid sequence of any one isolate of the genotype indicated and the amino acid sequence of any other isolate.

A dendrogram of the genetic relatedness of the E1 protein of selected HCV isolates representing the 12 genotypes is shown in FIG. 4. This dendrogram was constructed using the program CLUSTAL (Higgins, D. G. et al. (1988) Gene, 73:237–244) and had a limit of 25 sequences. The scale showing percent identity was added based upon manual calculation. From the 51 HCV isolates for which the complete sequence of the E1 gene region was obtained, 25 isolates representing the twelve genotypes were selected for analysis. This dendrogram in combination with the analysis of the E1 gene sequence of 51 HCV isolates in Table 1 demonstrates extensive heterogeneity of this important gene.

Figure 5:
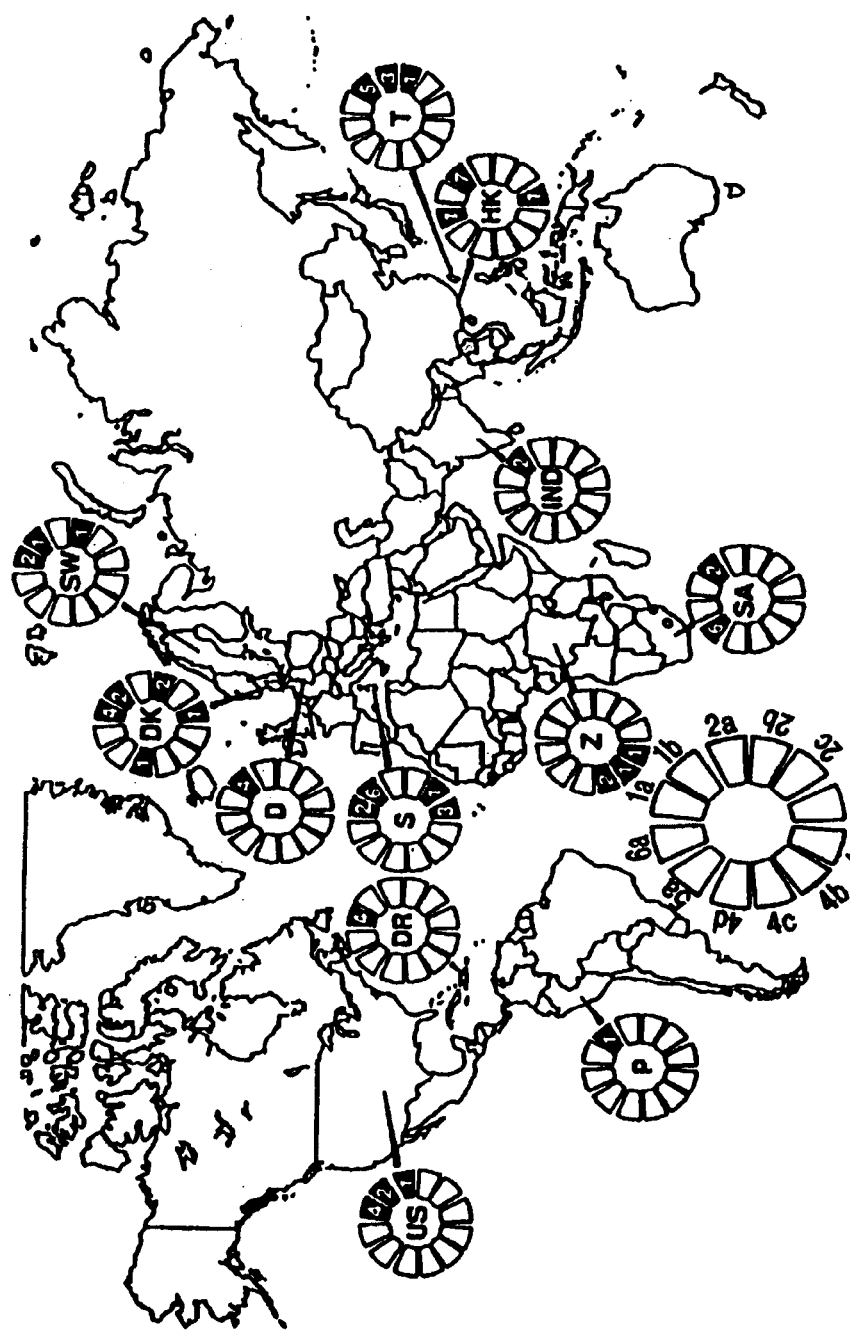
FIG. 5 shows the distribution of the complete E1 gene sequence of 74 HCV isolates into the twelve HCV genotypes in the 12 countries studied. For 51 of these HCV isolates, including 8 isolates of genotype I/1a, 17 isolates of genotype II/1b and 26 isolates comprising the additional 10 genotypes, the complete E1 gene sequence was determined. In the remaining 23 isolates, all of genotypes I/1a and II/1b, the genotype assignment was based on only a partial E1 gene sequence. The partially sequenced isolates did not represent additional genotypes in any of the 12 countries. The number of isolates of a particular genotype is given in each of the 12 countries studied. For ease of viewing, those genotypes designated by two terms (e.g., I/1a) are indicated by the latter term (e.g. 1a). The designations used for each country are: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z). National borders depicted in this figure represent those existing at the time of sampling.

The worldwide distribution of the 12 genotypes among 74 HCV isolates is depicted in FIG. 5. The complete E1 gene sequence was determined in 51 of these HCV isolates (SEQ ID NOs:1–51), including 8 isolates of genotype I/1a, 17 isolates of genotype II/1b and 26 isolates comprising genotypes III/2a, IV/2b, 2c, 3a, 4a–4d, 5a and 6a. In the remaining 23 isolates, all of genotypes I/1a and II/1b, the genotype assignment was based on a partial E1 gene sequence since they did not represent additional genotypes in any of the 12 countries. The number of isolates of a particular genotype is given in each of the 12 countries studied. Of the twelve genotypes, genotypes I/1a and II/1b were the most common accounting for 48 (65%) of the 74 isolates. Analysis of the E1 gene sequences available in the GenBank data base at the time of this study revealed that all 44 such sequences were of genotypes I/1a, II/1b, III/2a and IV/2b. Thus, based upon E1 gene analysis, 8 new genotypes of HCV have been identified.

Also of interest, different HCV genotypes were frequently found in the same country, with the highest number of genotypes (five) being detected in Denmark. Of the twelve genotypes, genotypes I/1a, II/1b, III/2a, IV/2b and V/3a were widely distributed with genotype II/1b being identified in 11 of 12 countries studied (Zaire was the only exception). In addition, while genotypes I/1a and II/1b were predominant in the Americas, Europe and Asia, several new genotypes were predominant in Africa.

It was also found that genotypes I/1a, II/1b, III/2a, IV/2b and V/3a of HCV were widely distributed around the world, whereas genotypes 2c, 4a, 4b, 4d, 5a and 6a were identified only in discreet geographical regions. For example, the majority of isolates in South Africa comprised a new genotype (5a) and all isolates in Zaire comprised 3 new closely related genotypes (4a, 4b, 4c). These genotypes were not identified outside Africa.

EXAMPLE 3

Identification of the cDNA Sequence of the Core Gene of 52 Isolates of HCV

Viral RNA extraction, cDNA synthesis and "nested" PCR were carried out as in Example 1. For the cDNA PCR assay HCV-specific synthetic oligonucleotides deduced from previously determined sequences that flank the C gene were used. Amplified DNA was purified by gel electrophoresis followed by glass-milk extraction as described in Example 1 or by electroelution and both strands were sequenced directly. In 44 of the 52 HCV isolates studied the procedures for direct sequencing described in Example 1 were utilized. For a number of the HCV isolates confirmatory sequencing was performed with the Applied Biosystems 373A automated DNA sequencer and 8 HCV isolates of genotype I/1a or II/1b were sequenced exclusively by this method. All 73 negative control samples interspersed among the test samples were negative for HCV RNA.

The amplified DNA fragment obtained in 50 of the 52 HCV isolates was specifically designed to overlap with previously obtained 5'NC sequences (Bukh et al. (1992b) Proc. Natl. Acad. Sci. U.S.A. 89:4942–4946) and with the E1 sequences disclosed herein at approximately 80 nucleotide positions each. A complete match was observed in 6033 of 6035 overlapping nucleotides. Two discrepancies were observed in isolate US6 at nt 552 (C and T) and nt 561 (C and T) respectively. This may have been due to microheterogeneity at these nucleotide positions, since the remaining overlapping sequence was unique for isolate US6. In addition, there were 3 confirmed instances of microheterogeneity: nt 33 in isolate SA11 (C,T and T), nt 36 in isolate S45 (A,C and A), and nt 552 in isolate P10 (C,T and T). Overall, the excellent agreement in these overlapping sequences in this study with the NC sequences disclosed in Bukh et al. and with the E1 sequences disclosed herein definitively ruled out contamination as a source of non-authentic HCV sequences. Furthermore, this analysis proved that the sequences obtained were from a single population, and not from different populations as could happen in mixed infections.

The core (C) gene was exactly 573 nucleotides in length in all 52 HCV isolates with an amino terminal start codon and no in-frame stop codons. Microheterogeneity was observed in 26 of the 52 HCV isolates at 0.2–1.4% of the 573 nucleotide positions of the C gene, and resulted in changes in 0.5–1.0% of the 191 predicted amino acids in 12 of these isolates. A multiple sequence alignment was performed and it showed that the nucleotide identities of the C gene among these HCV isolates were in the range of 79.4–99.0%. In order to compare the genetic relatedness of HCV isolates in different gene regions, phylogenetic trees of the C gene of all 52 HCV isolates and the E1 gene of 51 HCV isolates were constructed using the unweighted pair-group method with arithmetic mean (Nei, M. (1987) Molecular Evolutionary Genetics (Columbia University Press, New York, N.Y., pp. 287–326) (FIG. 8). In both dendrograms a division of the 45 HCV isolates from which C and E1 genes had been cloned into at least six major genetic groups (genotypes 1–6) and 12 minor genetic groups (genotypes I/1a, II/1b, III/2a, IV/2b, 2c, V/3a, 4a–4d, 5a, and 6a) was observed. It is noteworthy that a major division in genetic distance between HCV isolates of genotype 2 and those of the other genotypes in the phylogenetic analyses of both gene sequences was observed. Furthermore, the divergence of the minor genotypes within genotype 2 exhibited a degree of heterogeneity that is equivalent to that observed among the major genotypes. Analysis of the C gene from isolates Z5 and Z8, which had a unique 5' NC sequence (Bukh et al. (1992)) but from which the E1 gene could not be amplified, revealed that these isolates represented two additional genotypes. The designations 4e and 4f are assigned to these genotypes that have not been described previously. Overall, the present specification demonstrates that the genetic relatedness of HCV isolates is equivalent when analyzing the most conserved gene (C) and one of the most variable genes (E1) of the HCV genome, thereby providing strong evidence for the suggested division into major and minor genotypes.

EXAMPLE 4

Computer Analysis of the Nucleotide and Deduced Amino Acid Sequences of the Core Gene Of 52 HCV Isolates In order to study further the heterogeneity of the C gene, a consensus sequence of the core gene from the 52 HCV isolates (FIG. 6J) was obtained. A total of 335 (58.5%) of the 573 nucleotides of the C gene were invariant among these HCV isolates. Nucleotides at the 1st and 2nd codon positions were invariant at 70.7% and 81.7% of these positions, respectively, while nucleotides at the 3rd position were invariant at only 23.0% of such positions. Stretches of 6 or more invariant nucleotides were observed from nucleotides 1–8, 22–27, 85–92, 110–125, 131–141, 334–340, 364–371, 397–404, and 511–516 and may be suitable for anchoring primers for amplification of HCV RNA in cDNA PCR assays.

Genotype-specific nucleotide positions of the core gene of hepatitis C virus were also noted for each of the genotypes. These genotype-specific nucleotides are shown below where each genotype-specific nucleotide is given in parentheses next to the nucleotide position in which it is found.

Genotype 1: 460 (C), 466 (C), 483 (C), 486 (G).

Genotype I/1a: 180 (T).

Genotype II/1b: 106 (C), 273 (G).

Genotype 2: 192 (C), 201 (A), 203 (A), 207 (G), 210 (C), 221 (A), 231 (A), 232 (A), 341(A).

Genotype III/2a: 315 (C), 355 (G).

Genotype IV/2b: 45 (A), 174 (G), 216 (C), 348 (A), 376 (A), 414 (T).

Genotype 2c: 233 (G), 312 (C), 318 (A), 456 (C), 462 (G), 543 (C), 556 (T).

Genotype V/3a: 47 (T), 84 (A), 106 (G), 126 (A), 150 (T), 212 (G), 216 (A), 300 (A), 491 (T), 559 (C), 560 (A), 568 (G), 571 (A), 572 (G)

Genotype 4: 59 (T).

Genotype 4a: 213 (A), 231 (G), 415 (A).

Genotype 4b: 66 (G), 145 (G), 310 (A).

Genotype 4c: 213 (T), 219 (A), 270 (T).

Genotype 4d: 212 (T), 327 (G), 469 (C)

Genotype 4e: 199 (C), 306 (A), 326 (A).

Genotype 4f: 57 (T), 75 (A), 267 (A).

Genotype 5a: 291 (G), 294 (C).

Genotype 6a: 59 (C), 175 (A), 195 (A), 198 (A), 214 (C), 224 (A), 316 (C), 351 (G), 387 (G), 444–447 (GGCT), 450 (G), 471–472 (AA), 474 (C).

These genotype-specific nucleotides are of utility in designing the genotype-specific PCR primers and hybridization probes.

Finally, although the full length nucleic acid sequence of the C gene of isolates representing genotypes I/1a, II/1b, III/2a, IV/2b and V/3a have been reported by others, those of 9 of the 14 genotypes (i.e., 2c, 4a–4f, 5a and 6a) have not been reported previously. In sum, by aligning the consensus sequences of the major genotypes, the present application enables those skilled in the art to map universally conserved sequences as well as genotype-specific sequences of the C gene among 14 genotypes of HCV.

In order to study the heterogeneity of the deduced C protein, a multiple sequence alignment of the predicted amino acids for all 52 HCV isolates was performed, and a consensus sequence was obtained (FIG. 7J). The identities of the predicted 191 amino acids of the C protein among these HCV isolates were in the range of 85.3–100.0%. A total of 132 (69.1%) of the 191 amino acids of the C protein were invariant. The most prevalent amino acids in the consensus sequence were glycine (13.6%), arginine (12.6%), proline (11.0%), and leucine (9.9%). The most conserved amino acids were tryptophan (5 of 5 amino acids invariant), aspartic acid (5 of 5 amino acids invariant), proline (19 of 21 amino acids invariant) and glycine (23 of 26 amino acids invariant). Previous analyses indicated that HCV is evolutionarily related to pestiviruses (Miller et al. (1990) *Proc. Natl. Acad. Sci. U.S.A.* 87:2057–2061). In this regard, it is of interest to note that the C proteins of both viruses have a high content of proline residues (Collette M. S. et al. (1988) *Virology* 165:200–208), which are likely to be important in maintaining the structure of this protein. As is characteristic for a protein that binds to nucleic acid, the C protein has conserved amino acids that are basic and positively charged, and these are capable of neutralizing the negative charge of the HCV RNA encapsidated by this protein (Rice, C. M. et al. (1986) in Togaviridae and Flaviviridae, eds Schleinger, S. & Schlensinger, M. J. (Plenum Press, New York, N.Y.) pp. 279–326). Specifically, over 16% of the amino acids in the consensus sequence of the C protein of HCV are arginine and lysine that are located primarily in three clusters (i.e., from amino acids 6–23, 39–74 and 101–121) (Shih, C. M. et al. (1993) *J. Gen. Virol.* 67:5823–5832) (FIG. 7J). The 10 arginine and lysine residues within amino acids 39–62 are invariant among all 52 HCV isolates, suggesting that this domain may represent an important RNA-binding site. The capsid proteins of the related flavi-and pestiviruses (Miller et al. (1990)) also have a high content of arginine and lysine (Rice et al. (1986); Collette et al. (1988). Although there are three major hydrophilic regions (i.e., amino acids 2–23, 39–74 and 101–121) that are conserved in all 52 HCV isolates, the remainder of the C protein is hydrophobic. Interestingly, one such highly conserved hydrophobic domain from aa 24–39 is flanked by proline residues. The hydrophobic domains are likely to be involved in protein—protein and/or protein-RNA interactions during assembly of the nucleocapsid, as well as in interaction with the lipoprotein envelope, as has been suggested for flaviviruses (Rice et al. (1986)). Other significant observations are: (i) a cluster of 5 invariant tryptophan residues from aa 76–107; (ii) the lack of an N-linked glycosylation site (N-X-T/S); (iii) two potential nuclear localization signals (i.e., PRRGPR at amino acids 38–43 and PRGRRQP at amino acids 58–64) that are present in all 52 HCV isolates (Shih et al. (1993)); and (iv) a putative DNA-binding motif SPRG at amino acids 99–102, found in 51 of the 52 HCV isolates, with SP present in all 52 isolates. This study demonstrates that the C protein has features that are highly conserved among the various genotypes of HCV, and that are known to be characteristic of capsid proteins of other related viruses.

It should also be noted that the phylogenetic analysis of the amino acid sequence of the C proteins was not capable of resolving the minor groups within genotypes 1 and 4 because of the conservation of this protein (data not shown). Indeed, only a few type-specific amino acids were identified. One striking example was that isolates of genotype 4 have an additional methionine at position 20 that is specific for this major genetic group. Finally, the conservation of the sequences surrounding the cleavage site between the C and the E1 proteins of the different genotypes, which has been determined to be between amino acid 191 (alanine) and aa 192 (tyrosine) in HCV isolates of genotype 1 was analyzed (Hijikata, M., et al. (1991) *Proc. Natl. Acad. Sci. USA* 88:5547–5551). The C-terminal sequence of C is serine-alanine in all but one of the 48 HCV isolates comprising genotypes 1, 2, 4, 5 and 6. However, all 4 HCV isolates of genotype 3 in this study, as well as isolates of genotype 3 published previously (Okamoto, H., et al. (1993) *J. Gen. Virol.* 74:2385–2390, Stuyver, L., et al. (1993) *Biochem. Biophys. Res. Comm.* 192:635–641), contain alanine-serine at this position. Thus, studies will be needed to determine the C/E1 cleavage site in genotype 3 isolates. Overall, the present invention application discloses the mapping of universally conserved sequences, as well as genotype-specific sequences, of the C protein among 14 genotypes of HCV.

Implications of the Mapping of Universally Conserved and Genotype-Specific Core Nucleotide and Amino Acid Core Sequences for Diagnosis of HCV Infection and for Determination of HCV Genotypes Detection of antibodies directed against the HCV core protein is important in the diagnosis of HCV infection. The recombinant C22-3 protein, spanning amino acids 2–120 of the C gene, is a major component of the commercially available second-generation anti-HCV tests. Several studies have indicated that the three major hydrophilic regions of the C protein contain linear immunogenic epitopes (summarized in *J. Clin. Microbiol,* 30:1989–1994) (Sällberg, M. et al. (1992). For example, antibodies against synthetic peptides from amino acids 1–18, 51–68 and 101–118 were detected in infected patients (Sällberg, M. et al. (1992)). The present application demonstrates that, while these immunogenic regions are highly conserved, genotype-specific differences are observed at several amino acid positions that may influence the specificity and sensitivity of the serological tests. One such example is that a single amino acid substitution at amino acid 110 has been demonstrated to affect sero-reactivity (Sällberg, et al. (1992)). Despite the high degree of conservation in the immunodominant regions of the C protein among the different genotypes, it is possible that genetic heterogeneity of the C protein could lead to false negative results in current serological tests.

With respect to genotype analysis, several methods have been used to determine the genotype of HCV isolates without resorting to sequence analysis. These include PCR followed by: (i) amplification with type-specific primers (Okamoto, H. et al. (1992) *J. Gen. Virol.*, 73:673–679); (ii) determination of restriction-length polymorphism (Simmons, P. et al. (1993) *J. Gen. Virol.*, 74:661–668); and (iii) specific hybridization (Stuyver, L. (1993) *J. Gen. Virol.*, 74:1093–1102). The proposed methods have primarily been based on 5' NC and C sequences. Previous studies suggested that 5' NC-based genotyping systems would only be predictive of the major genetic groups of HCV (Bukh, J., et al. (1992) *Proc. Natl. Acad. Sci. USA* 89:4942–4946, Bukh, J., et al. (1993) *Proc. Natl. Acad. Sci. USA* 90:8234–8238). The most widely used C-based genotype system has been the PCR assay with type-specific primers that was designed for distinguishing HCV isolates of genotypes I/1a, II/1b, III/2a, IV/2b and V/3a (Okamoto, H., et al. (1993) *J. Gen. Virol.* 74:2385–2390, Okamoto, H. et al. (1992) *J. Gen. Virol.* 73:673–679). Since this system was developed prior to the identification of genotypes 2c, 4a–4f, 5a and 6a there are significant limitations to this typing system. For example, the primers specific for genotype IV/2b (nt 270–251) are as highly conserved within isolates of genotype 4c and 6a as within the isolates of genotype IV/2b. Thus, this assay probably can not distinguish among these genotypes. Another C-based approach involves distinguishing between genotypes 1 and 2 by type-specific antibody responses (Machida et al (1992) *Hepatology*, 16:886–891). Synthetic peptides composed of amino acids 65–81 were found to be genotype-specific for genotypes 1 and 2 in ELISA assays. The present analysis of amino acid sequences demonstrated significant variation within isolates of genotypes 1 and 2. Thus it is likely that these peptides will not identify all isolates of genotypes 1 and 2. Furthermore, the peptide for genotype 1 was highly conserved within isolates of genotypes 3 and 4 and might detect antibodies against these genotypes as well. Finally, it should be pointed out that most isolates of genotypes 3 and 4 had an identical amino acid sequence at positions 65–81.

EXAMPLE 5

Detection by ELISA Based on Antigen from Insect Cells Expressing Complete E1 or Core Protein Expression of E1 or Core protein in SF9 cells. A cDNA (eg SEQ ID NO:1) encoding a complete E1 protein (eg SEQ ID NO:52) or a cDNA (eg SEQ ID NO:103) encoding a complete core protein (e.g. SEQ ID NO:155) is subcloned into pBlueBac-Transfer vector (Invitrogen) using standard subcloning procedures. The resultant recombinant expression vector is cotransfected into SF9 insect cells (Invitrogen) by the Ca precipitation method according to the Invitrogen protocol.

ELISA Based on Infected SF9 cells. $5 \times 10^6$ SF9 cells infected with the above-described recombinant expression vector are resuspended in 1 ml of 10 mM Tris-HCl, pH 7.5, 0.15M NaCl and are then frozen and thawed 3 times. 10 ul of this suspension is dissolved in 10 ml of carbonate buffer (pH 9.6) and used to cover one flexible microtiter assay plate (Falcon). Serum samples are diluted 1:20, 1:400 and 1:8000, or 1:100, 1:1000 and 1:10000. Blocking and washing solutions for use in the ELISA assay are PBS containing 10' fetal calf serum and 0.5% gelatin (blocking solution) and PBS with 0.05% Tween –20 (Sigma, St. Louis, Mo.) (washing solution). As a secondary antibody, peroxidase-conjugated goat IgG fraction to human IgG or horse radish peroxidase-labelled goat anti-Old or anti-New World monkey immunoglobulin is used. The results are determined by measuring the optical density (O.D.) at 405 nm.

To determine if insect cells-derived E1 or core protein representing genotype I/a of HCV could detect anti-HCV antibody in chimpanzees infected with genotype I/1a of HCV, three infected chimpanzees are examined. The serum of all 3 chimpanzees are found to seroconvert to anti-HCV.

EXAMPLE 6

Use of the Complete E1 Protein as a Vaccine

Mammals are immunized with purified or partially purified E1 protein in an amount sufficient to stimulate the production of protective antibodies. The immunized mammals challenged with various genotypes of HCV are protected.

It is understood by one skilled in the art that the recombinant E1 protein used in the above vaccine can also be used in combination with other recombinant E1 proteins having an amino acid sequence shown in SEQ ID NOs:52–102. In addition, recombinant core proteins having an amino acid sequence shown in SEQ ID NOs:155–206 could also be used in the above vaccine, either alone, in combination with other recombinant core proteins of the present invention, or in combination with recombinant E1 proteins having an amino acid sequence shown in SEQ ID NOs:52–102.

EXAMPLE 7

Determination of the Genotype of an HCV Isolate Via Hybridization of Genotype-Specific Oligonucleotides to RT-PCR Amplification Products Viral RNA is isolated from serum obtained from a mammal and is subjected to RT-PCR as in Example 1 or Example 3. Following amplification, the amplified DNA is purified as described in Example 1 or Example 3 and aliquots of 100 ul of amplification product are applied to dots on a nitrocellulose filter set in a dot blot apparatus. The dots are then cut into separate dots and each dot is hybridized to a $^{32}$P-labelled oligonucleotide specific for a single genotype of HCV. The oligonucleotides to be used as hybridization probes are deduced from the consensus sequences shown in FIGS. 1A–1H or 6A–6J or from the SEQ ID NOs: representing E1 or core sequences comprising genotypes 4a–4f, 2c and 6a.

EXAMPLE 8

ELISA Based on Synthetic Peptides Derived from E1 cDNA Sequences

E1 peptide(s) specific for genotype I/1a is placed in 0.1% PBS buffer and 50 ul of a 1 mg/ml solution of peptide is used to cover each well of the microtiter assay plate. Serum samples from two mammals infected with genotype I/1a HCV and from one mammal infected with genotype 5a HCV are diluted as in Example 3 and the ELISA is carried out as in Example 3. Both mammals infected with genotype I HCV react positively with peptides while the mammal infected with genotype 5a HCV exhibits no reactivity. One skilled in the art would readily understand that in the above experiment, core peptides specific for genotype I/1a could be used in place of, or in combination with the E1 genotype-specific peptide(s).

EXAMPLE 9

Use of E1 Peptides as a Vaccine

Since the E1 genotype-specific peptides of the present invention are derived from two variable regions in the complete E1 protein, there exists support for the use of these peptides as a vaccine to protect against a variety of HCV genotypes. Mammals are immunized with peptide(s) selected from SEQ ID NOs: 136–159 in an amount sufficient to stimulate production of protective antibodies. The immunized mammals challenged with various genotypes of HCV are protected. One skilled in the art would readily understand that genotype-specific core peptides of the present invention could also be used either alone, in combination with each other, or in combination with the genotype-specific E1 peptides, as a vaccine to protect against a variety of HCV genotypes. In addition, the above vaccines may also be formulated using the universal core and/or E1 peptides of the present invention.

The invention claimed is:

1. A purified and isolated protein encoded by the gene sequence of SEQ ID NO: 154.

2. A purified and isolated protein having the amino acid sequence of SEQ ID NO: 206.

3. A method of detecting antibodies against HCV, said method comprising:
   (a) contacting a biological sample with the protein of claim 2 to form an immune complex with the antibodies; and
   (b) detecting the presence of the immune complex.

4. The method of claim 3, wherein the biological sample is selected from the group consisting of serum, saliva or lymphocytes or other mononuclear cells.

5. The method of claim 3, wherein the protein is bound to a solid support.

6. The method of claim 3, wherein the immune complex is detected using a labeled antibody.

7. A hepatitis C virus kit comprising: at least one protein comprising an the amino acid sequence of SEQ ID NO: 206.

8. A composition comprising the protein of claim 2 and an excipient, diluent or carrier.

9. An immunogenic composition for inducing an immune response in a mammal against hepatitis C virus, comprising the protein according to claim 2 in a pharmacologically acceptable carrier.

10. An isolated genotype-specific peptide comprising an amino acid sequence of at least 8 contiguous amino acids from SEQ ID NO: 206, said peptide having at least one of the following residues: Q72, H75, H106, A149, and I158; and wherein genotype-specific is defined as belonging to the single genotype 6a (type 6) of HCV.

11. A method of detecting antibodies specific for the single genotype 6a (type 6) of HCV, said method comprising:
   (a) contacting a biological sample with at least one peptide of claim 10 to form an immune complex with the antibodies, and
   (b) detecting the presence of the immune complex.

12. The method of claim 11, wherein the biological sample is selected from the group consisting of serum, saliva or lymphocytes or other mononuclear cells.

13. The method of claim 11, wherein said peptide is bound to a solid support.

14. The method of claim 11, wherein the immune complex is detected using a labelled antibody or antigen.

15. A kit for use in detecting antibodies specific for a single genotype of HCV, said kit comprising: at least one genotype-specific peptide of claim 10.

16. An isolated universally conserved peptide consisting of an amino acid sequence of at least 8 amino acids deduced from universally conserved amino acid domains found in SEQ ID NO: 206, wherein universally conserved is defined as belonging to all genotypes of HCV with reference to FIG. 7K.

17. A method of detecting antibodies against all genotypes of HCV, said method comprising:
  (a) contacting a biological sample with at least one peptide of claim 16 to form an immune complex with the antibodies, and
  (b) detecting the presence of the immune complex.

18. The method of claim 17, wherein the biological sample is selected from the group consisting of serum, saliva or lymphocytes or other mononuclear cells.

19. The method of claim 17, wherein said peptide is bound to a solid support.

20. The method of claim 17, wherein the immune complex is detected using a labelled antibody or antigen.

21. A composition comprising at least one peptide of claim 10 and an excipient, diluent or carrier.

22. A composition comprising at least one peptide of claim 16 and an excipient, diluent or carrier.

23. An immunogenic composition for inducing an immune response in a mammal against hepatitis C virus, comprising at least one peptide according to claims 10 or 16 in a pharmaceutically acceptable carrier.

* * * * *

UNITED STATES PATENT AND TRADEMARK OFFICE
CERTIFICATE OF CORRECTION

PATENT NO. : 7,070,790 B1
APPLICATION NO. : 09/084691
DATED : July 4, 2006
INVENTOR(S) : Bukh et al.

It is certified that error appears in the above-identified patent and that said Letters Patent is hereby corrected as shown below:

Col. 293, Line 64 (approx.), Claim 7, after "comprising" delete "an".

Col. 295, Line 7 (approx.), Claim 16, after "least 8" insert -- consecutive --.

Signed and Sealed this

Twentieth Day of February, 2007

JON W. DUDAS
*Director of the United States Patent and Trademark Office*